United States Patent
Kruse

(10) Patent No.: US 12,054,528 B2
(45) Date of Patent: Aug. 6, 2024

(54) CO-AGONISTS OF THE GLP-1 AND AMYLIN RECEPTORS

(71) Applicant: Novo Nordisk A/S, Bagsvaerd (DK)

(72) Inventor: Thomas Kruse, Herlev (DK)

(73) Assignee: Novo Nordisk A/S, Bagsvaerd (DK)

(*) Notice: Subject to any disclaimer, the term of this patent is extended or adjusted under 35 U.S.C. 154(b) by 0 days.

(21) Appl. No.: 18/084,088

(22) Filed: Dec. 19, 2022

(65) Prior Publication Data

US 2023/0331803 A1   Oct. 19, 2023

Related U.S. Application Data

(63) Continuation of application No. PCT/EP2021/086494, filed on Dec. 17, 2021.

(30) Foreign Application Priority Data

| Dec. 18, 2020 | (EP) | 20215291 |
| Feb. 2, 2021 | (EP) | 21154668 |
| Jun. 16, 2021 | (EP) | 21179810 |

(51) Int. Cl.
| C07K 14/605 | (2006.01) |
| A61K 47/54 | (2017.01) |
| A61P 3/04 | (2006.01) |
| C07K 14/575 | (2006.01) |

(52) U.S. Cl.
CPC .......... *C07K 14/605* (2013.01); *A61K 47/542* (2017.08); *A61P 3/04* (2018.01); *C07K 14/575* (2013.01); *C07K 2319/00* (2013.01)

(58) Field of Classification Search
CPC . C07K 14/605; C07K 2319/00; A61K 47/542
See application file for complete search history.

(56) References Cited

U.S. PATENT DOCUMENTS

| 2006/0094652 A1 | 5/2006 | Levy et al. |
| 2010/0292172 A1 | 11/2010 | Ghosh et al. |
| 2013/0288958 A1* | 10/2013 | Lau .......................... A61P 3/10 514/5.3 |

FOREIGN PATENT DOCUMENTS

| CN | 104558198 A | 4/2015 |
| CN | 105367664 | * 3/2016 |
| CN | 108424460 A | 8/2018 |
| WO | 05/027978 A2 | 3/2005 |
| WO | 2006097537 | 9/2006 |
| WO | 2007022123 A2 | 2/2007 |
| WO | 09030771 A1 | 3/2009 |
| WO | 2009030738 A1 | 3/2009 |
| WO | 10118384 A2 | 10/2010 |
| WO | 11063414 A1 | 5/2011 |
| WO | 11084808 A2 | 7/2011 |
| WO | WO 2011/080102 | * 7/2011 |
| WO | 12160212 A1 | 11/2012 |
| WO | 12162547 A2 | 11/2012 |
| WO | 12168431 A2 | 12/2012 |
| WO | 2014202727 A1 | 12/2014 |
| WO | 16034604 A1 | 3/2016 |
| WO | 2016083499 A1 | 6/2016 |
| WO | 2016097108 A1 | 6/2016 |
| WO | 17100896 A1 | 6/2017 |
| WO | 18083335 A1 | 5/2018 |

OTHER PUBLICATIONS

Bower et al., "Molecular Signature for Receptor Engagement in the Metabolic Peptide Hormone Amylin," ACS Pharmacol. Transl. Sci., 2018, vol. 1, pp. 32-49.
Enebo et al., "Safety, tolerability, pharmacokinetics, and pharmacodynamics of concomitant administration of multiple doses of cagrilintide with semaglutide 2•4 mg for weight management: a randomised, controlled, phase 1b trial", The Lancet, May 2021, vol. 397, No. 10286, pp. 1736-1748.
Finan et al., Emerging opportunities for the treatment of metabolic diseases: Glucagon-like peptide-1 based multi-agonists, "Molecular and Cellular Endocrinology., Dec. 2015, vol. 418, pp. 42-54".
Roberts et al., "Molecular and functional characterization of amylin, a peptide associated with type 2 diabetes mellitus," PNAS, Dec. 1989, vol. 86, pp. 9662-9666.
Sun et al., "Bifunctional PEGylated Exenatide-Amylinomimetic Hybrids to Treat Metabolic Disorders: An Example of Long-Acting Dual Hormonal Therapeutics," Journal of Medicinal Chemistry, 2013, vol. 56, pp. 9328-9341.
Trevaskis et al., "Improved Glucose Control and Reduced Body Weight in Rodents with Dual Mechanism of Action Peptide Hybrids," PLOS One, Oct. 2013, vol. 8, No. 10, e78154, 12 pages.

* cited by examiner

Primary Examiner — Gyan Chandra
(74) Attorney, Agent, or Firm — Jianjie Hu

(57) ABSTRACT

The invention relates to a compound comprising a GLP-1 receptor agonist and an amylin receptor agonist. The invention also relates to a pharmaceutical formulation, suitable for but not limited to oral administration, which comprises such a compound. The compound and pharmaceutical formulation comprising it may be used for the medical treatment of subjects with overweight, obesity and associated co-morbidities.

24 Claims, 183 Drawing Sheets

Figure 1:
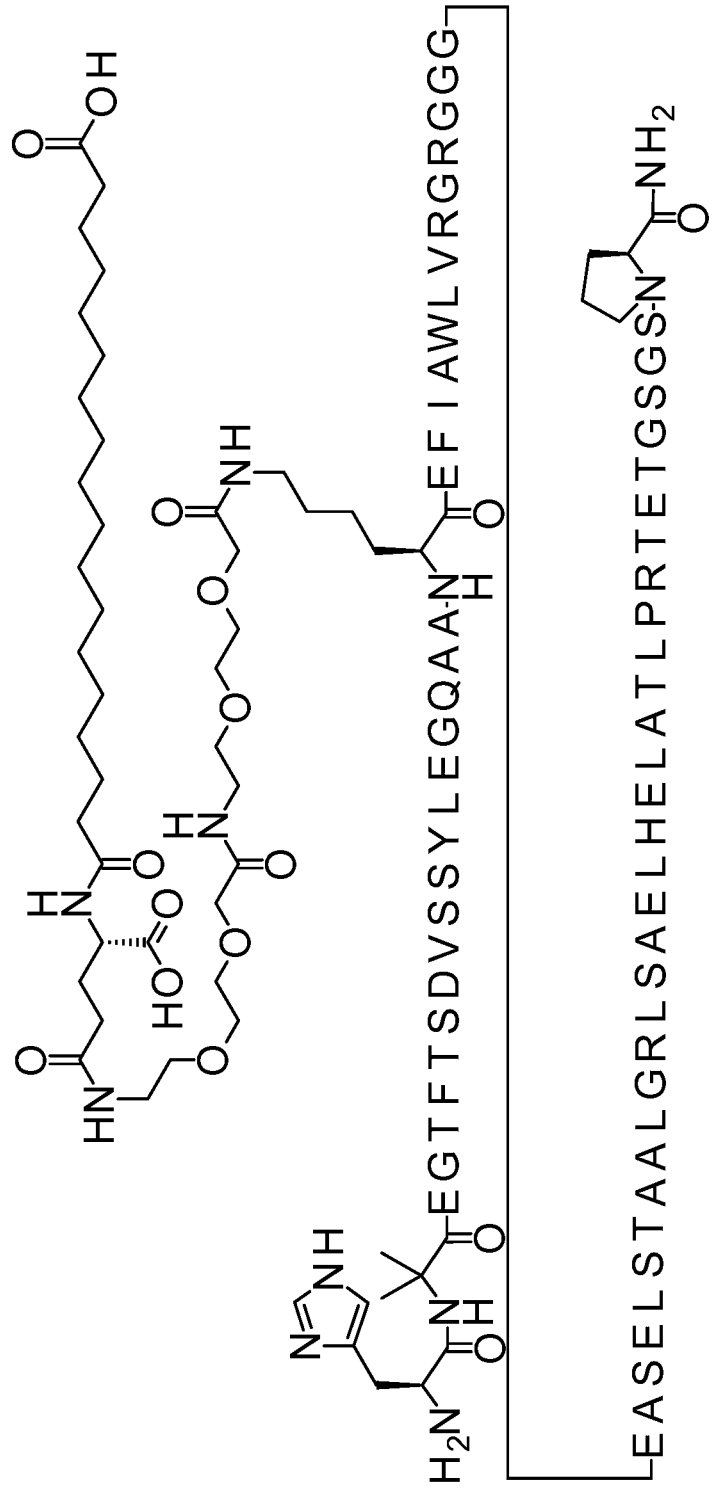

Specification includes a Sequence Listing.

Compound 0007

H-Aib-EGTFTSDVSSYLEGQAA-K[(2-[2-[2-[2-[2-[[(4S)-4-carboxy-4-(17-carboxyheptadecanoylamino)butanoyl]amino]ethoxy]ethoxy]acetyl]amino]ethoxy]ethoxy]acetyl])-EFIAWLVRGRGGGEASELSTAALGRLSAELHELATLPRTETGSGSP-amide Compound 0009

H-Aib-EGTFTSDVSSYLEGQAAREFIAWLVRG-K([2-[2-[2-[2-[2-[[(4S)-4-carboxy-4-(17-carboxyheptadecanoylamino)butanoyl]amino]ethoxy]ethoxy]acetyl]amino]ethoxy]ethoxy]acetyl])-GEGEGEEASELSTAALGRLSAELHELATLPRTETGSGSP-amide Compound 0010

H-Aib-EGTFTSDVSSYLEGQAAREFIAWLVRGRGEGEGE-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-EASELSTAALGRLSAELHELATLPRTETGSGSP-amide Compound 0019

H-Aib-EGTFTSDVSSYLEGQAA-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-EFIAWLVRGRGGQEPGQEPEASELSTAALGRLSAELHELATLPRTETGSSGSP-amide Compound 0026

H-Aib-EGTFTSDVSSYLEGQAA-K([2-[2-[2-[2-[[(4S)-4-carboxy-4-(17-carboxyheptadecanoylamino)butanoyl]amino]ethoxy]ethoxy]acetyl]amino]ethoxy]ethoxy]acetyl])-EFIAWLVRGRGQEPGQAPEASELSTAALGRLSAELHELATLPRTETGSSGSP-amide 0035
Imp-AEGTFTSDVSSYLEEQAAREFIAWLVRGR-K([2-[2-[2-[2-[2-[[(4S)-4-carboxy-4-[[4-[(19-carboxynonadecanoyl)amino)methyl]cyclohexanecarbonyl]amino]butanoyl]amino]ethoxy]acetyl]amino]ethoxy]ethoxy]acetyl])-EASELSTAALGRLSAELHELATLPRTETGSGSP-amide Compound 0039
HGEGTFTSDVSSYLEEQAAR-K([2-[2-[2-[[2-[2-[2-[[(4S)-4-carboxy-4-(13-carboxytridecanoyl-amino)butanoyl]amino]ethoxy]ethoxy]acetyl]amino]ethoxy]ethoxy]acetyl])-FIEWLVRG-K([2-[2-[2-[[2-[2-[2-[[(4S)-4-carboxy-4-(13-carboxytridecanoylamino)butanoyl]amino]ethoxy]ethoxy]acetyl]-amino]ethoxy]ethoxy]acetyl])-GEASELSTAALGRLSAELHELATLPRTETGSGSP-amide Compound 0040

H-Aib-EGTFTSDVSSYLEGQAA-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-EFIAWLVRGRGGGGEASELSTAALGRLSAELHELATLPRTETGSGSP-amide Compound 0042
H-Aib-EGTFTSDVSSYLEGQAAKEFIAWLVRGR-K([2-[2-[2-[2-[2-[[(4S)-4-carboxy-4-(17-carboxyheptadecanoylamino)butanoyl]amino]ethoxy]ethoxy]acetyl]amino]ethoxy]ethoxy]acetyl])-GGEASELSTAALGRLSAELHELATLPRTETGSGSP-amide Compound 0044

H-Aib-EGTFTSDVSSYLEGQAA-K[((2S)-2-amino-6-[[2-[2-[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]hexanoyl]-EFIAWLVRGRGGGEASELSTAALGRLSAELHELATLPRTETGSSGSP-amide Compound 0045

H-Aib-EGTFTSDVSSYLEGQAAKEFIAWLVRGR-K([(2S)-2-amino-6-[[2-[2-[2-[[2-[2-[2-[[(4S)-4-carboxy-4-(17-carboxyheptadecanoyl)amino]butanoyl]amino]ethoxy]acetyl]amino]ethoxy]acetyl]amino]hexanoyl])-GGEASELSTAALGRLSAELHELATLPRTETGSGSP-amide Compound 0051
Imp-AEGTFTSDVSSYLEEQAAAREFIAWLVRGR-K([2-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-EASELSTAALGRLSAELHELATLPRTETGSSGSP-amide Compound 0052

H-Aib-EGTFTSDVSSYLEGQAA-K[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-EFIAWLVRGRGGGGGGGGEASELSTAALGRLSAELHELATLPRTETGSGSP-amide Compound 0056

H-Aib-EGTFTSDVSSYLEGQAA-K[(2-[2-[2-[2-[[(4S)-4-carboxy-4-(17-carboxyheptadecano-ylamino)butanoyl]amino]ethoxy]acetyl]amino]ethoxy]ethoxy]acetyl])-EFIAWLVRGRG-K((2-[2-[2-[2-[[(4S)-4-carboxy-4-(17-carboxyheptadecanoylamino)butanoyl]amino]ethoxy]ethoxy]acetyl]amino]ethoxy]ethoxy]acetyl])-QEPGQEPEASELSTAALGRLSAELHELATLPRTETGSGSP-amide Compound 0057

H-Aib-EGTFTSDVSSYLEGQAA-K([2-[2-[2-[2-[2-[[(4S)-4-carboxy-4-(17-carboxyheptadecano-ylamino)butanoyl]amino]ethoxy]ethoxy]acetyl]amino]ethoxy]ethoxy]acetyl])-EFIAWLVRGRGGQ-E-K([2-[2-[2-[2-[2-[[(4S)-4-carboxy-4-(17-carboxyheptadecanoylamino)butanoyl]amino]ethoxy]ethoxy]acetyl]amino]ethoxy]ethoxy]acetyl])-GQEPEASELSTAALGRLSAELHELATLPRTETGSSGSP-amide Compound 0071

H-Aib-EGTFTSDVSSYLEGQAA-K([2-[2-[2-[2-[[(4S)-4-carboxy-4-(17-carboxyheptadecano-ylamino)butanoyl]amino]ethoxy]acetyl]amino]ethoxy]ethoxy]acetyl])-EFIAWLVRGRGGQ-EPGQEP-K([2-[2-[2-[2-[[(4S)-4-carboxy-4-(17-carboxyheptadecanoylamino)butanoyl]amino]ethoxy]ethoxy]acetyl]amino]ethoxy]acetyl])-EASELSTAALGRLSAELHELATLPRTETGSGSP-amide Compound 0072

H-Aib-EGTFTSDVSSYLEGQAA-K([2-[2-[2-[2-[2-[2-[[(4S)-4-carboxy-4-(15-carboxypentadecanoylamino)butanoyl]amino]ethoxy]ethoxy]acetyl]amino]ethoxy]ethoxy]acetyl])-EFIAWLVRGRGG-K([2-[2-[2-[2-[2-[2-[[(4S)-4-carboxy-4-(15-carboxypentadecanoylamino)butanoyl]amino]ethoxy]ethoxy]acetyl]amino]ethoxy]ethoxy]acetyl])-EASELSTAALGRLSAELHELATLPRTETGSGSP-amide Compound 0073

H-Aib-EGTFTSDVSSYLEGQAAR-K([2-[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-FIAWLVRGRGG-K([2-[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-EASELSTAALGRLSAELHELATLPRTETGSGSP-amide Compound 0074

H-Aib-EGTFTSDVSSYLEEQAAR-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-FIAWLVRGRGG-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-EASELSTAALGRLSAELHELATLPRTETGSSGSP-amide Compound 0075

H-Aib-EGTFTSDVSSYLEGQAA-K([2-[2-[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-EFIAWLVRG-K([2-[2-[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-GGGEASELSTAALGRLSAELHELATLPRTETGSGSP-amide Compound 0076

H-Aib-EGTFTSDVSSYLEEQAAR-K([2-[2-[2-[2-[2-[[(4S)-4-carboxy-4-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-FIAWLVRG-K([2-[2-[2-[2-[[(4S)-4-carboxy-4-(15-carboxypentadecanoylamino)butanoyl]amino]ethoxy]ethoxy]acetyl]amino]ethoxy]ethoxy]acetyl])-GGGEASELSTAALGRLSAELHELATLPRTETGSGSP-amide Compound 0077

H-Aib-EGTFTSDVSSYLEEQAAR-K([2-[2-[2-[[2-[2-[2-[[(4S)-4-carboxy-4-[(15-carboxypentadecanoylamino)butanoyl]amino]ethoxy]ethoxy]acetyl]amino]ethoxy]ethoxy]acetyl])-FIAWLV-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-GRGGGEASELSTAALGRLSAELHELATLPRTETGSGSP-amide Compound 0083

H-Aib-EGTFTSDVSSYLEGQAAREFIAWLVRGR-K([2-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]ethoxy]acetyl]amino]ethoxy]acetyl]amino)butanoyl]amino]-GQEPGQAPEASELSTAALGRLSAELHELATLPRTETGSGSP-amide Compound 0084

H-Aib-EGTFTSDVSSYLEGQAAAREFIAWLVRGRGQEP-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-GQAPEASELSTAALGRLSAELHELATLPRTETGSGSP-amide Fig. 25
Compound 0085
H-Aib-EGTFTSDVSSYLEGQAAREFIAWLVRGRGQEPGQAP-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-EASELSTAALGRLSAELHELATLPRTETGSSGSP-amide
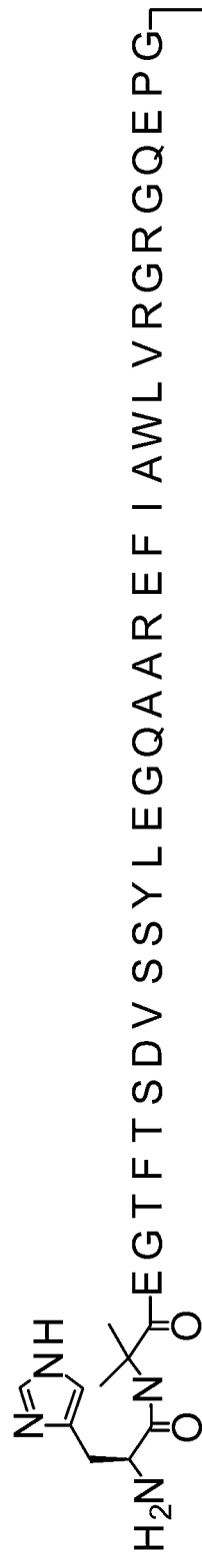
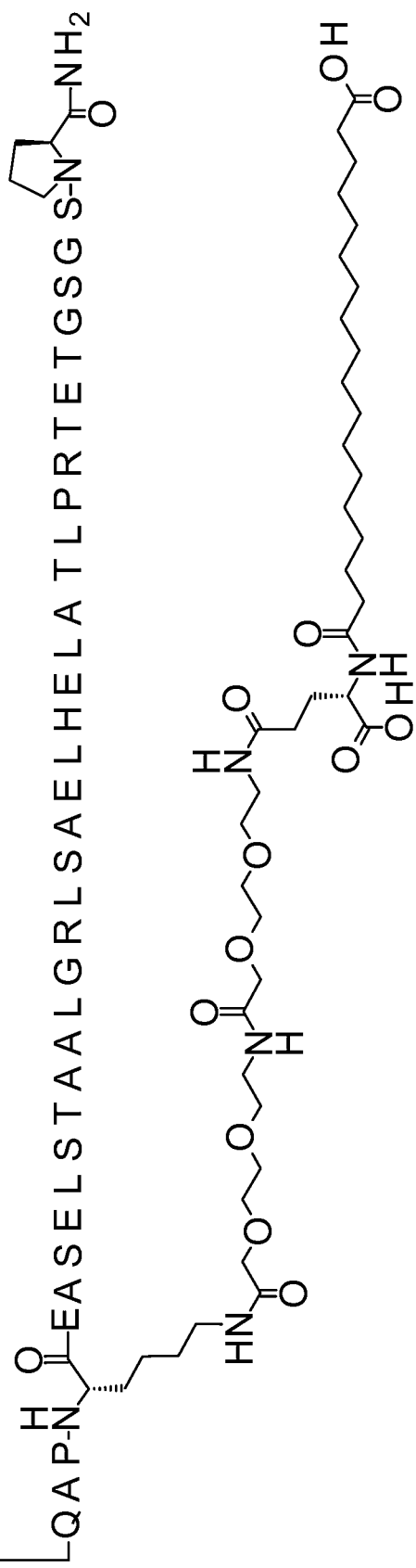

Compound 0086

H-Aib-EGTFTSDVSSYLEEQAAR-K([2-[2-[2-[2-[2-[2-[[(4S)-4-carboxy-4-(15-carboxypentadecanoylamino)butanoyl]amino]ethoxy]ethoxy]acetyl]amino]ethoxy]ethoxy]acetyl])-FIEWLVRG-K([2-[2-[2-[2-[2-[2-[[(4S)-4-carboxy-4-(15-carboxypentadecanoylamino)butanoyl]amino]ethoxy]ethoxy]acetyl]amino]ethoxy]ethoxy]acetyl])-GEGGEASELSTAALGRLSAELHELATLPRTETGSGSP-amide Compound 0087
HGEGTFTSDVSSYLEEQAAR-K([2-[2-[2-[2-[2-[[(4S)-4-carboxy-4-(15-carboxypentadecanoylamino)butanoyl]amino]ethoxy]ethoxy]acetyl]amino]ethoxy]ethoxy]acetyl])-FIEWLVRG-K([2-[2-[2-[2-[2-[[(4S)-4-carboxy-4-(15-carboxypentadecanoylamino)butanoyl]amino]ethoxy]ethoxy]acetyl]amino]ethoxy]ethoxy]acetyl])-GEGGEASELSTAALGRLSAELHELATLPRTETGSGSP-amide Compound 0089

H-Aib-EGTFTSDVSSYLEEQAAR-K([2-[2-[2-[2-[2-[[(4S)-4-carboxy-4-(17-carboxyheptadecanoylamino)butanoyl]amino]ethoxy]ethoxy]acetyl]amino]ethoxy]acetyl])-FIEWLVRG-K([2-[2-[2-[2-[2-[[(4S)-4-carboxy-4-(17-carboxyheptadecanoylamino)butanoyl]amino]ethoxy]ethoxy]acetyl]amino]ethoxy]ethoxy]acetyl])-GEGGEASELSTAALGRLSAELHELATLPRTETGSGSP-amide Compound 0090

HGEGTFTSDVSSYLEEQAAR-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-FIEWLVRG-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-GEGGEASELSTAALGRLSAELHELATLPRTETGSGSP-amide Compound 0092

H-Aib-EGTFTSDVSSYLEGQAA-K([(2-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-EFIAWLVRGRGGGGGGGGGGGGGGEASELSTAALGRLSAELHELATLPRTETGSGSP-amide Compound 0093
H-Aib-EGTFTSDVSSYLEGQAA-K[(2-[2-[2-[2-[2-[2-[[(4S)-4-carboxy-4-(17-carboxyheptadecanoylamino)butanoyl]amino]ethoxy]ethoxy]acetyl]amino]ethoxy]ethoxy]acetyl)-EFIAWLVRGRGGGGGGGGGGEASELSTAALGRLSAELHELATLPRTETGSSGSP-amide Compound 0094

H-Aib-EGTFTSDVSSYLEGQAA-K[(2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl])-EFIAWLVRGRGGGGGGEASELSTAALGRLSAELHELATLPRTETGSGSP-amide

Fig. 33
Compound 0095
H-Aib-EGTFTSDVSSYLEGQAA-K((2-[2-[2-[2-[2-[2-[[(4S)-4-carboxy-4-[[4-[(19-carboxynonadecanoyl)amino]methyl]cyclohexanecarbonyl]amino]butanoyl]amino]ethoxy]ethoxy]acetyl]amino]ethoxy]ethoxy]acetyl)-EFIAWLVRGRGGGGGGGGGEASELSTAALGRLSAELHELATLPRTETGSGSP-amide
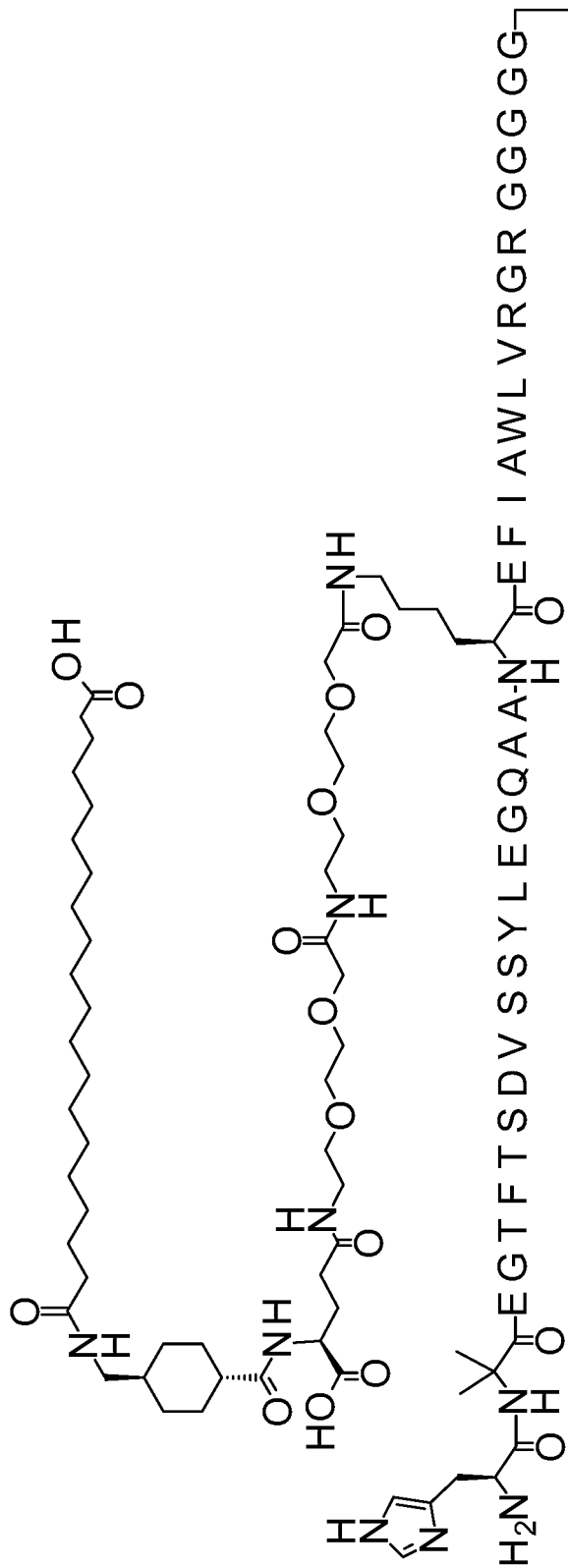

Compound 0096

HGEGTFTSDVSSYLEEQAAR-K([2-[2-[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl])-FIEWLVRG-K([2-[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl])-GEGEASELSTAALGRLSAELHELATLPRTETGSGSP-amide Compound 0097

HGEGTFTSDVSSYLEEQAAR-K([2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl])-FIEWLVRG-K([2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl])-GEGGGGEASELSTAALGRLSAELHELATLPRTETGSSGSP-amide Compound 0098

HGEGTFTSDVSSYLEEQAAR-K([2-[2-[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl])-FIEWLVRG-K([2-[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl])-GEGGGGGGGEASELSTAALGRLSAELHELATLPRTETGSSGSP-amide Compound 0099
HWEGTFTSDVSSYLEEQAAR-K([2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl])-FIEWLVRG-K([2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl])-GEGEASELSTAALGRLSAELHELATLPRTETGSSGSP-amide Compound 0100

HWEGTFTSDVSSYLEEQAAR-K([2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl])-FIEWLVRG-K([2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl])-GEGGGGEASELSTAALGRLSAELHELATLPRTETGSGSP-amide Compound 0101

HWEGTFTSDVSSYLEEQAAR-K([2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl])-FIEWLVRG-K([2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl])-GEGGGGGGGEASELSTAALGRLSAELHELATLPRTETGSGSP-amide Compound 0102

H-Aib-EGTFTSDVSSYLEEQAAREFIAWLVRGR-K((4-[17-(1H-tetrazol-5-yl)heptadecanoylsulfamoyl]butanoyl)-ELSTAALGRLSAELHELATLPRTETGSGSP-amide Compound 0103

H-Aib-EGTFTSDVSSYLEEQAAAREFIAWLVRGR-K(4-[17-(1H-tetrazol-5-yl)heptadecanoylsulfamoyl]butanoyl)-EASELSTAALGRLSAELHELATLPRTETGSSGSP-amide Compound 0105

H-Aib-EGTFTSDVSSYLEEQAAR-K([2-[2-[2-[2-[[(4S)-4-carboxy-4-(15-carboxypentadecanoylamino)butanoyl]amino]ethoxy]ethoxy]acetyl]amino]ethoxy]ethoxy]acetyl])-FIEWLVRG-K([2-[2-[2-[2-[[(4S)-4-carboxy-4-(15-carboxypentadecanoylamino)butanoyl]amino]ethoxy]ethoxy]acetyl]amino]ethoxy]ethoxy]acetyl])-GEGQEPGGASELSTAALGRLSAELHELATLPRTETGSGSP-amide Compound 0106

H-Aib-EGTFTSDVSSYLEEQAAR-K([2-[2-[2-[2-[2-[[(4S)-4-carboxy-4-(17-carboxyheptadecanoylamino)butanoyl]amino]ethoxy]ethoxy]acetyl]amino]ethoxy]ethoxy]acetyl])-FIEWLVRG-K([2-[2-[2-[2-[2-[[(4S)-4-carboxy-4-(17-carboxyheptadecanoylamino)butanoyl]amino]ethoxy]ethoxy]acetyl]amino]ethoxy]ethoxy]acetyl])-GEGQEPGGASELSTAALGRLSAELHELATLPRTETGSGSP-amide Compound 0109

H-Aib-EGTFTSDVSSYLEEQAAR-K([2-[2-[2-[2-[2-[[(4S)-4-carboxy-4-(17-carboxyheptadecanoylamino)butanoyl]amino]ethoxy]ethoxy]acetyl]amino]ethoxy]ethoxy]acetyl])-FIAWLVRG-K([2-[2-[2-[2-[2-[[(4S)-4-carboxy-4-(17-carboxyheptadecanoylamino)butanoyl]amino]ethoxy]ethoxy]acetyl]amino]ethoxy]ethoxy]acetyl])-GGGGGGGGEASELSTAALGRLSAELHELATLPRTETGSSGSP-amide Compound 0110

H-Aib-EGTFTSDVSSYLEEQAAR-K[[(2S)-2-amino-6-[[2-[2-[2-[[(4S)-4-carboxy-4-(17-carboxyheptadecanoylamino)butanoyl]amino]ethoxy]ethoxy]acetyl]amino]hexanoyl])-FIAWLVRG-K[[(2S)-2-amino-6-[[2-[2-[2-[2-[[(4S)-4-carboxy-4-(17-carboxyheptadecanoylamino)butanoyl]amino]ethoxy]ethoxy]acetyl]amino]ethoxy]acetyl]amino]hexanoyl])-GGGGGGGGEASELSTAALGRLSAELHELATLPRTETGSGSP-amide Compound 0111

H-Aib-EGTFTSDVSSYLEEQAAAREFIAWLVRGR-K([2-[2-[2-[2-[[2-[2-[[(4S)-4-carboxy-4-(17-carboxyheptadecanoylamino)butanoyl]amino]ethoxy]acetyl]amino]ethoxy]ethoxy]acetyl])-GGGGEASELSTAALGRLSAELHELATLPRTETGSSGSP-amide Compound 0114
H-Aib-EGTFTSDVSSYLEEQAAREFIAWLVRGR-K([2-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-GGEASELSTAALGRLSAELHELATLPRTETGSGSP-amide Compound 0115

H-Aib-EGTFTSDVSSYLEEQAAREFIAWLVRGR-K((2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-EASELSTAALGRLSAELHELATLPRTETGSGSP-amide Compound 0116

H-Aib-EGTFTSDVSSYLEEQAAR-K([2-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-FIAWLVRGR-K([2-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-GGEASELSTAALGRLSAELHELATLPRTETGSGSP-amide Compound 0120

H-Aib-EGTFTSDVSSYLEEQAAREFIAWLVRGR-K(([2-[2-[2-[[(4S)-4-carboxy-4-[[4-[(19-carboxynonadecanoyl)amino]methyl]cyclohexanecarbonyl]amino]butanoyl]amino]ethoxy]ethoxy]acetyl]amino]ethoxy]ethoxy]acetyl])-GGGGEASELSTAALGRLSAELHELATLPRTETGSGSP-amide Compound 0124

Imp-Aib-EGTFTSDVSSYLEEQAAREFIAWLVRGR-K(4-[17-(1H-tetrazol-5-yl)heptadecanoylsulfamoyl)butanoyl)-EASELSTAALGRLSAELHELATLPRTETGSGSP-amide Compound 0125

H-Aib-EGTFTSDVSSYLEEQAAR-K(4-[17-(1H-tetrazol-5-yl)heptadecanoylsulfamoyl]butanoyl)-FIAWLVRGRGEASELSTAALGRLSAELHELATLPRTETGSGSP-amide Compound 0127

H-Aib-EGTFTSDVSSYLEEQAAR-K([2-[2-[2-[[2-[2-[2-[[(4S)-4-carboxy-4-((17-carboxyheptadecanoylamino)butanoyl]amino]ethoxy]ethoxy]acetyl]amino]ethoxy]ethoxy]acetyl])-FIAWLVRG-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-GGEASELSTAALGRLSAELHELATLPRTETGSSGSP-amide Compound 0128
H-Aib-EGTFTSDVSSYLEEQAAR-K([2-[2-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-FIEWLVRG-K([2-[2-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-GGEASELSTAALGRLSAELHELATLPRTETGSGSP-amide Compound 0129

H-Aib-EGTFTSDVSSYLEEQAAR-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-FIEWLVRGR-K([2-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-GGEASELSTAALGRLSAELHELATLPRTETGSGSP-amide Compound 0131
H-Aib-EGTFTSDVSSYLEEQAAR-K[[(4S)-4-carboxy-4-(17-carboxyheptadecanoylamino)butanoyl])-FIAWLVRGR-K[[(4S)-4-carboxy-4-(17-carboxyheptadecanoylamino)butanoyl])-EASELSTAALGRLSAELHELATLPRTETGSGSP-amide Compound 0132

H-Aib-EGTFTSDVSSYLEEQAAREFIAWLVRG-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-GGEASELSTAALGRLSAELHELATLPRTETGSGSP-amide Compound 0141
H-Aib-EGTFTSDVSSYLEEQAAREFIAWLVRGR-K[((4S)-4-carboxy-4-(19-carboxynonadecanoylamino)butanoyl])-
EASELSTAALGRLSAELHELATLPRTETGSGSP-amide Compound 0142
Imp-Aib-EGTFTSDVSSYLEEQAAREFIAWLVRGR-K([(4S)-4-carboxy-4-(19-carboxynonadecanoylamino)butanoyl])-EASELSTAALGRLSAELHELATLPRTETGSGSP-amide Compound 0144

H-Aib-EGTFTSDVSSYLEEQAAREFIAWLV-K([2-[2-[2-[2-[2-[[(4S)-4-carboxy-4-(17-carboxyheptadecanoylamino)butanoyl]amino]ethoxy]ethoxy]acetyl]amino]ethoxy]ethoxy]acetyl])-GRGGGGEASELSTAALGRLSAELHELATLPRTETGSGSP-amide Compound 0145

H-Aib-EGTFTSDVSSYLEEQAAREFIAWLVRGRG-K(4-[17-(1H-tetrazol-5-yl)heptadecanoylsulfamoyl]butanoyl)-GGGASELSTAALGRLSAELHELATLPRTETGSGSP-amide Compound 0146

H-Aib-EGTFTSDVSSYLEEQAAREFIEWLVRG-K(4-[17-(1H-tetrazol-5-yl)heptadecanoylsulfamoyl]butanoyl)-GGGASELSTAALGRLSAELHELATLPRTETGSSGSP-amide Compound 0147
H-Aib-EGTFTSDVSSYLEEQAAAREFIEWLVRG-K((4-[17-(1H-tetrazol-5-yl)heptadecanoylsulfamoyl]butanoyl)-ASELSTAALGRLSAELHELATLPRTETGSGSP-amide Compound 0151

H-Aib-EGTFTSDVSSYLEGQAAAREFIAWLVRGR-K((2-[2-[2-[2-[2-[[(4S)-4-carboxy-4-(17-carboxyheptadecanoylamino)butanoyl]amino]ethoxy]ethoxy]acetyl]amino]ethoxy]ethoxy]acetyl])-GGGGEASELSTAALGRLSAELHELATLPRTETGSGSP-amide Compound 0156

H-Aib-EGTFTSDVSSYLEGQAA-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-EFIAWLVRGRGQAPGQEPEASELSTAALGRLSAELHELATLPRTETGSGSP-amide Compound 0157

H-Aib-EGTFTSDVSSYLEGQAA-K([2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl])-EFIAWLVRGRGQAPGQEPEASELSTAALGRLSAELHELATLPRTETGSGSP-amide Compound 0159

H-Aib-EGTFTSDVSSYLEGQAA-K{[(2S)-2-amino-6-[[2-[2-[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]hexanoyl]}-EFIAWLVRGRGGGGGGGGGGEASELSTAALGRLSAELHELATLPRTETGSSGSP-amide Compound 0160
H-Aib-EGTFTSDVSSYLEEQAAR-K([(4S)-4-carboxy-4-(17-carboxyheptadecanoylamino)butanoyl])-FIAWLVRGRGGGGGGG-K([(4S)-4-carboxy-4-(17-carboxyheptadecanoylamino)butanoyl])-EASELSTAALGRLSAELHELATLPRTETGSGSP-amide Compound 0179

H-Aib-EGTFTSDVSSYLEEQAAREFIEWLVRGR-K[(2-[2-[2-[2-[2-[[(4S)-4-carboxy-4-[[4-[(19-carboxynonadecanoyl)amino]cyclohexanecarbonyl]amino]butanoyl]amino]ethoxy]ethoxy]acetyl]amino]ethoxy]ethoxy]acetyl])-EAEAEASELSTAALGRLSAELHELATLPRTETGSSGSP-amide Compound 0180

H-Aib-EGTFTSDVSSYLEEQAAREFIEWLVRGR-K(((2S)-2-amino-6-[[2-[2-[2-[[2-[2-[2-[[(4S)-4-carboxy-4-[[4-[(19-carboxynonadecanoyl)amino]methyl]cyclohexanecarbonyl]amino]butanoyl]amino]ethoxy]ethoxy]acetyl]amino]ethoxy]ethoxy]acetyl]amino]hexanoyl])-EAEAEASELSTAALGRLSAELHELATLPRTETGSGSP-amide Compound 0191
H-Aib-EGTFTSDVSSYLEGQAAREFIAWLVRGRGQEP-K(([2-[2-[2-[2-[2-[[2-[2-[[(4S)-4-carboxy-4-(17-carboxyheptadecanoylamino)butanoyl]amino]ethoxy]ethoxy]acetyl]amino]ethoxy]ethoxy]acetyl])-GQAPASRLSTEALGRLSAELHELATLPRTETGSSGSP-amide Compound 0202

H-Aib-EGTFTSDVSSYLEGQAA-K([2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl])-EFIAWLVRGRGQEPGQAPEASELSTAALGRLSAELHELATLPRTETGSGSP-amide

Fig. 73
Compound 0231
HWEGTFTSDVSSYLEEQAAR-K([2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl])-FIEWLVRGRGEGGGGASELSTAALGRLS-K([2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl])-ELHELATLPRTETGSGSP-amide
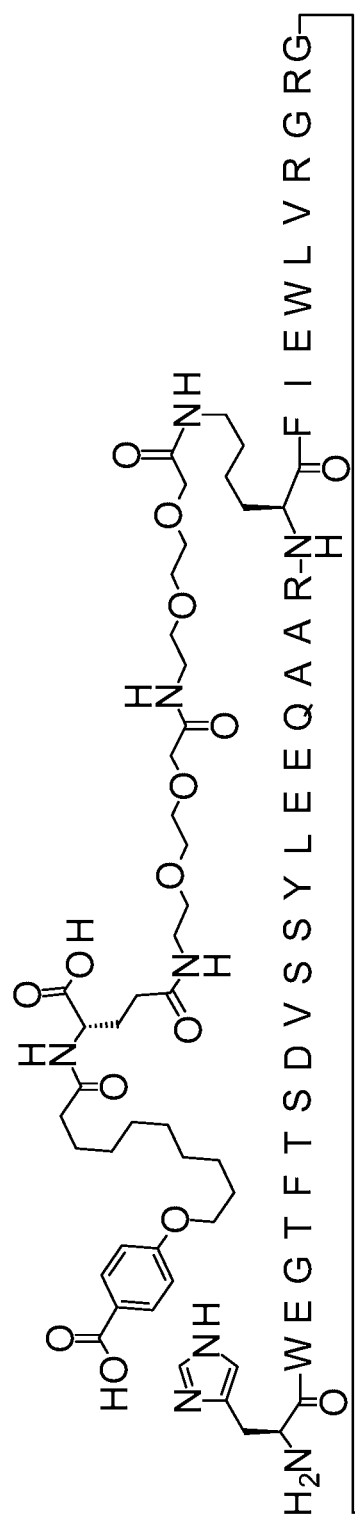
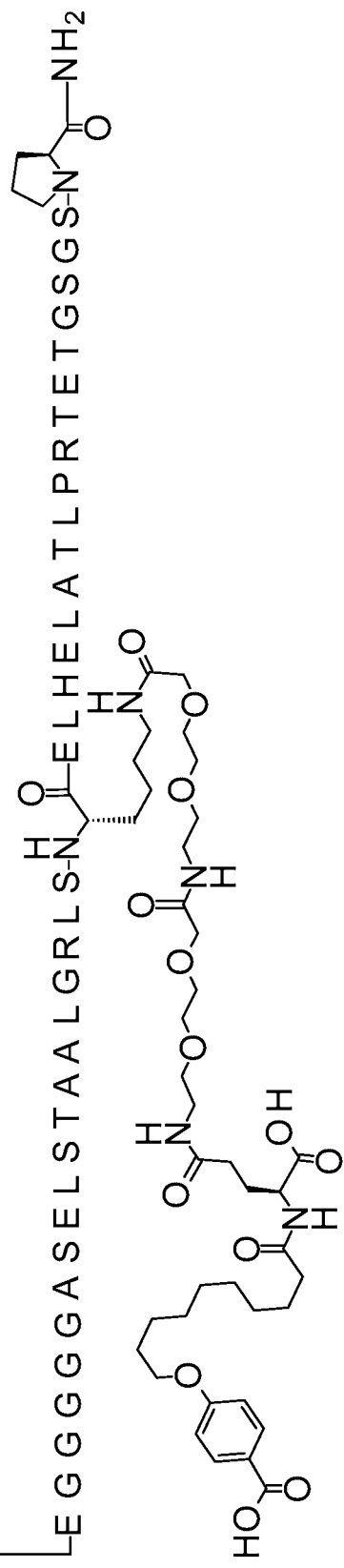

Compound 0232

HWEGTFTSDVSSYLEEQAAR-K([2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl])-FIEWLVRGRGEGGGGASELSTAALGRLSAELHEL-K([2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl])-TLPRTETGSSGSP-amide Fig. 75
Compound 0233
HWEGTFTSDVSSYLEEQAAREFIEWLVRG-K([2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl])-GEGGGGASELSTAALGRLS-K([2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl])-ELHELATLPRTETGSGSP-amide
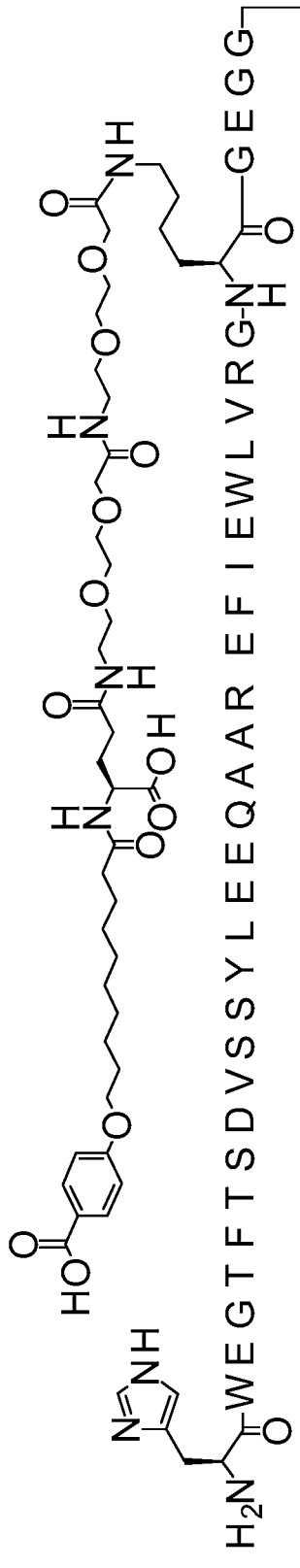
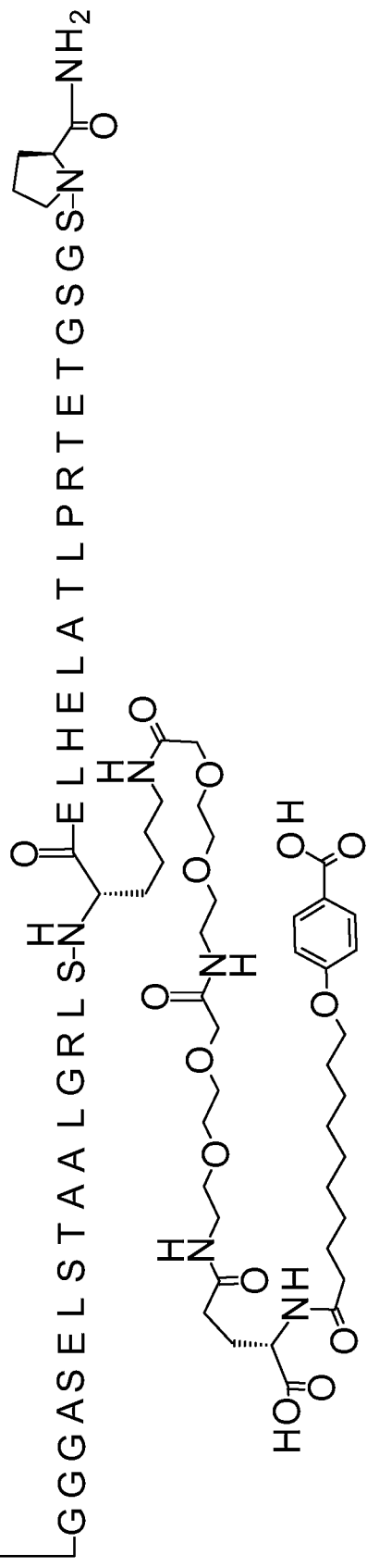

Compound 0234

HWEGTFTSDVSSYLEEQAAREFIEWLVRG-K([2-[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl])-GEGGGGASELSTAALGRLSAELHEL-K([2-[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl])-TLPRTETGSSGSP-amide Compound 0235

H-Aib-EGTFTSDVSSYLEEQAAREFIAWLVRG-K([2-[2-[2-[2-[[(4S)-4-carboxy-4-[10-(3-carboxyphenoxy)decanoylamino]butanoyl]amino]ethoxy]ethoxy]acetyl]amino]ethoxy]ethoxy]acetyl])-K([2-[2-[2-[2-[[(4S)-4-carboxy-4-[10-(3-carboxyphenoxy)decanoylamino]butanoyl]amino]ethoxy]ethoxy]acetyl]amino]ethoxy]ethoxy]acetyl])-GGGGASELSTAALGRLSAELHELATLPRTETGSGSP-amide Compound 0254

HWEGTFTSDVSSYLEEQAAR-K{[2-[2-[2-[[2-[2-[2-[[(4S)-4-carboxy-4-[[4-[(19-carboxynonadecanoyl)amino]methyl]cyclohexanecarbonyl]amino]butanoyl]amino]ethoxy]ethoxy]acetyl]amino]ethoxy]ethoxy]acetyl]}-FIEWLVRGRGEGGGGGASELSTAALGRLSAELHELATLPRTETGSGSP-amide Fig. 79
Compound 0255
HWEGTFTSDVSSYLEEQAAR-K([2-[2-[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl])-FIEWLVRGRGEGGGGASELSTAALGRLS-K([2-[2-[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl])-ELHELATLPRTETGSGSP-amide
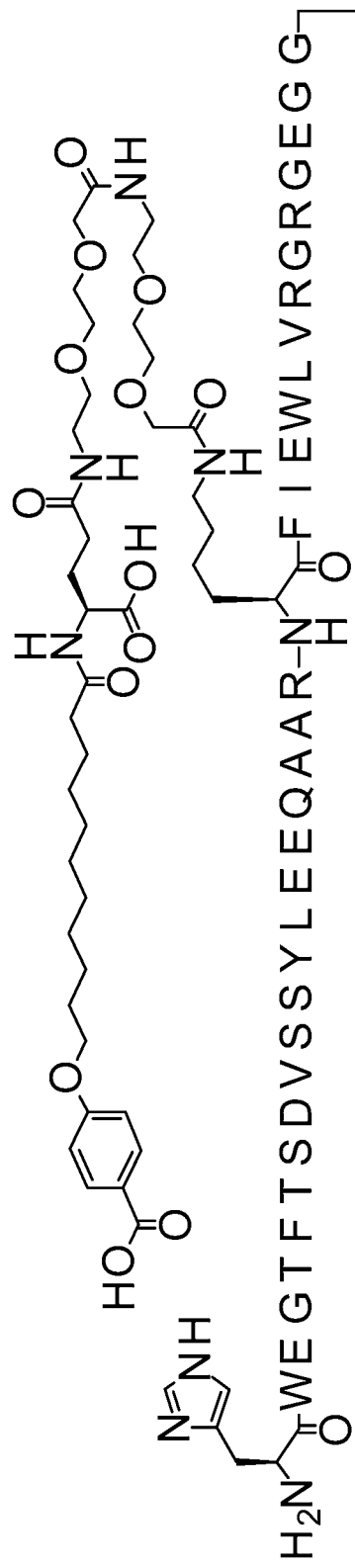
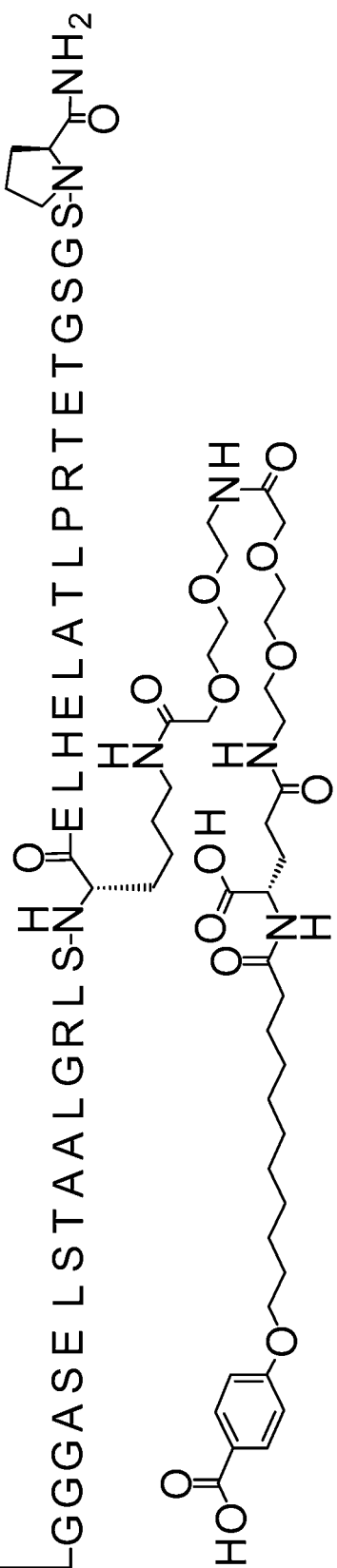

Compound 0259

H-Aib-EGTFTSD-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-SSYLEEQAAREFIAWLVRGRGGGGEASELSTAALGRLSAELH-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-LATLPRTETGSSGSP-amide Compound 0260

H-Aib-EGTFTSD-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-SSYLEEQAAREFIAWLVRGRGGGGGEASELSTAALGRLSAELHEL-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-TLPRTETGSSGSP-amide Compound 0261

H-Aib-EGTFTSD-K([2-[2-[2-[2-[2-[[(4S)-4-carboxy-4-(15-carboxypentadecanoylamino)butanoyl]amino]ethoxy]ethoxy]acetyl]amino]ethoxy]ethoxy]acetyl])-SSYLEEQAAREFIAWLVRGRGGGGGEASELSTAALGRLSAELHELATL-K([2-[2-[2-[2-[2-[[(4S)-4-carboxy-4-(15-carboxypentadecanoylamino)butanoyl]amino]ethoxy]ethoxy]acetyl]amino]ethoxy]ethoxy]acetyl])-RTETGSSGSP-amide Compound 0263

H-Aib-EGTFTSDVSSYLEEQAAREFIAWLVRGR-K[[2-[2-[2-[2-[[2-[2-[2-[[(4S)-4-carboxy-4-[[4-[(19-carboxynonadecanoyl]amino)methyl]cyclohexanecarbonyl]amino]butanoyl]amino]ethoxy]ethoxy]acetyl]amino]ethoxy]ethoxy]acetyl])-EASELSTAALGRLSAELHELATLPRTETGSGSP-amide Compound 0264

H-Aib-EGTFTSDVSSYLEEQAAREFIAWLVRG-K([2-[2-[2-[[2-[2-[2-[[(4S)-4-carboxy-4-[[4-[[(19-carboxynonadecanoyl)amino]methyl]cyclohexanecarbonyl]amino]butanoyl]amino]ethoxy]ethoxy]acetyl]amino]ethoxy]ethoxy]acetyl])-GGGGEASELSTAALGRLSAELHELATLPRTETGSGSP-amide Compound 0265

H-Aib-EGTFTSDVSSYLEE-K([2-[2-[2-[2-[2-[2-[[(4S)-4-carboxy-4-[[4-[[(19-carboxynonadecanoylamino)methyl]cyclohexanecarbonyl]amino]butanoyl]amino]ethoxy]ethoxy]acetyl]amino]ethoxy]ethoxy]acetyl])-AAREFIAWLVRGRGGGGEASELSTAALGRLSAELHELATLPRTETGSGSP-amide Compound 0266

H-Aib-EGTFTSD-K([2-[2-[2-[2-[2-[2-[[2-[[(4S)-4-carboxy-4-[[4-[(19-carboxynonadecanoyl)amino]methyl]cyclohexanecarbonyl]amino]butanoyl]amino]ethoxy]ethoxy]acetyl]amino]ethoxy]ethoxy]acetyl])-SSYLEEQAAREFIAWLVRGRGGGGEASELSTAALGRLSAELHELATLPRTETGSSGSP-amide Compound 0267
HWEGTFTSDVSSYLEEQAAREFIEWLVRG-K([2-[2-[2-[2-[[2-[2-[2-[[(4S)-4-carboxy-4-[[4-[(19-carboxynonadecanoyl)amino]methyl]cyclohexanecarbonyl]amino]butanoyl]amino]ethoxy]ethoxy]acetyl]amino]ethoxy]ethoxy]acetyl])-GEASELSTAALGRLSAELHELATLPRTETGSGSP-amide Compound 0268

HWEGTFTSDVSSYLEEQAAREFIAWLVRGR-K([2-[2-[2-[2-[2-[[(4S)-4-carboxy-4-[[4-[(19-carboxynonadecanoyl)amino]methyl]cyclohexanecarbonyl]amino]butanoyl]amino]ethoxy]ethoxy]acetyl]amino]ethoxy]ethoxy]acetyl])-GGGGEASELSTAALGRLSAELHELATLPRTETGSGSP-amide Compound 0269

HWEGTFTSDVSSYLEEQAAREFIEWLVRGR-K([2-[2-[2-[2-[[(4S)-4-carboxy-4-[[4-[[(19-carboxynonadecanoyl)amino]methyl]cyclohexanecarbonyl]amino]butanoyl]amino]ethoxy]ethoxy]acetyl]amino]ethoxy]ethoxy]acetyl])-GGGGEASELSTAALGRLSAELHELATLPRTETGSSGSP-amide Compound 0270

HWEGTFTSDVSSYLEE-K([2-[2-[2-[2-[2-[[2-[2-[2-[[(4S)-4-carboxy-4-[[4-[[(19-carboxynonadecanoylamino)methyl]cyclohexanecarbonyl]amino]butanoyl]amino]ethoxy]ethoxy]acetyl]amino]ethoxy]ethoxy]acetyl])-AAREFIEWLVRGRGEASELSTAALGRLSAELHELATLPRTETGSGSP-amide Compound 0271

HWEGTFTSDVSSYLEE-K([2-[2-[2-[2-[2-[2-[[(4S)-4-carboxy-4-(17-carboxyheptadecanoylamino)butanoyl]amino]ethoxy]ethoxy]acetyl]amino]ethoxy]ethoxy]acetyl])-AAREFIEWLVRGRGEASELSTAALGRLSAELHELATLPRTETGSGSP-amide Compound 0272

HWEGTFTSD-K([2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl])-SSYLEEQAAREFIEWLVRGRGEASELSTAALGRLSAELHELATLPRTETGSSGSP-amide Fig. 93
Compound 0273
HWEGTFTSD-K([2-[2-[2-[2-[2-[2-[[(4S)-4-carboxy-4-(17-carboxyheptadecanoylamino)butanoyl]amino]ethoxy]ethoxy]acetyl]amino]ethoxy]ethoxy]acetyl])-SSYLEEQAAAREFIEWLVRGRGEASELSTAALGRLSAELHELATLPRTETGSGSP-amide
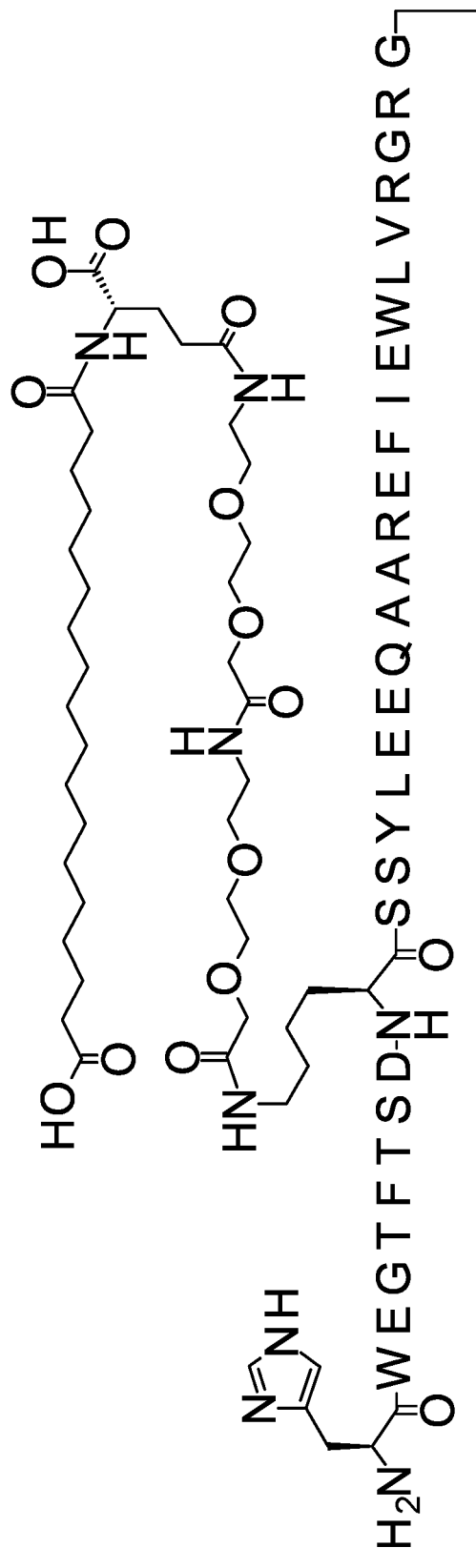
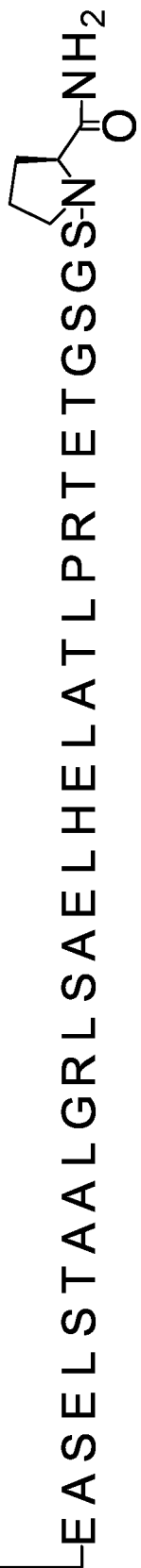

Compound 0280

H-Aib-EGTFTSDVSSYLEEQAAREFIAWLVRG-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-GGGGGEASELSTAALGRLSAELH-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-LATLPRTETGSGSP-amide Compound 0281

H-Aib-EGTFTSDVSSYLEEQAAREFIAWLVRG-K([2-[2-[2-[2-[[(4S)-4-carboxy-4-(15-carboxypentadecanoylamino)butanoyl]amino]ethoxy]acetyl]amino]ethoxy]acetyl])-GGGGGEASELSTAALGRLSAELHEL-K([2-[2-[2-[2-[2-[[(4S)-4-carboxy-4-(15-carboxypentadecanoylamino)butanoyl]amino]ethoxy]acetyl]amino]ethoxy]acetyl])-TLPRTETGSGSP-amide Compound 0284

H-Aib-EGTFTSDVSSYLEEQAAREFIAWLVRG-K{[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]}-GGGGGEASELSTAALGRLSAELHELATL-K{[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]}-RTETGSGSP-amide Compound 0285

H-Aib-EGTFTSDVSSYLEEQAAREFIAWLVRG-K([2-[2-[2-[2-[2-[[(4S)-4-carboxy-4-(15-carboxypentadecanoylamino)butanoyl]amino]ethoxy]ethoxy]acetyl]amino]ethoxy]ethoxy]acetyl])-GGGGGEASELSTAALGRLSAELHELATLPRTETG-K([2-[2-[2-[2-[2-[[(4S)-4-carboxy-4-(15-carboxypentadecanoylamino)butanoyl]amino]ethoxy]ethoxy]acetyl]amino]ethoxy]ethoxy]acetyl])-GSP-amide Fig. 98
Compound 0292
H-Aib-EGTFTSD-K([2-[2-[2-[2-[[(4S)-4-carboxy-4-(15-carboxypentadecanoylamino)butanoyl]amino]ethoxy]ethoxy]acetyl]amino]ethoxy]acetyl])-SSYLEEQAAREFIAWLVRGRGGGGASELSTAALGRLS-K([2-[2-[2-[2-[[(4S)-4-carboxy-4-(15-carboxypentadecanoylamino)butanoyl]amino]ethoxy]ethoxy]acetyl]amino]ethoxy]acetyl])-ELHELATLPRTETGSGSP-amide
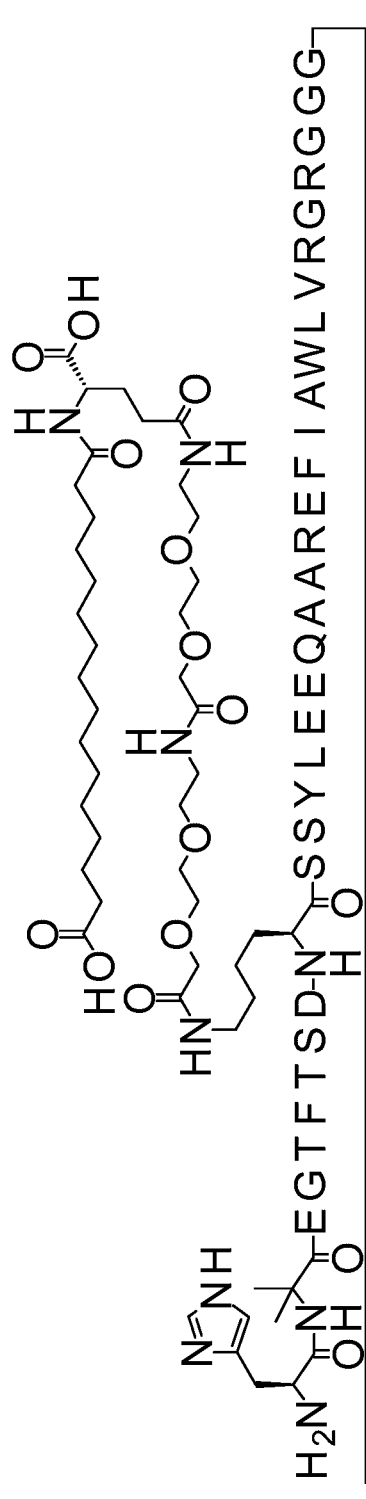
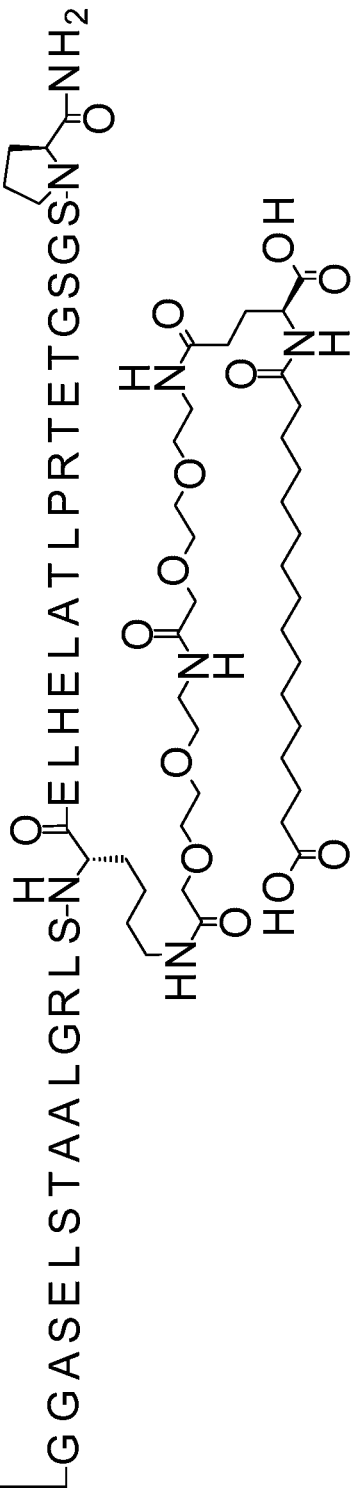

Compound 0294

H-Aib-EGTFTSDVSSYLE-K([2-[2-[2-[2-[2-[[(4S)-4-carboxy-4-(15-carboxypentadecanoylamino)butanoyl]amino]ethoxy]ethoxy]acetyl]amino]ethoxy]ethoxy]acetyl])-QAAREFIAWLVRGRGGGGASELSTAALGRLS-K([2-[2-[2-[2-[2-[[(4S)-4-carboxy-4-(15-carboxypentadecanoylamino)butanoyl]amino]ethoxy]ethoxy]acetyl]amino]ethoxy]ethoxy]acetyl])-ELHELATLPRTETGSSGSP-amide Compound 0295

H-Aib-EGTFTSDVSSYLEE-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-AAREFIAWLVRGRGGGGASELSTAALGRLS-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-ELHELATLPRTETGSGSP-amide

Fig. 101
Compound 0296
H-Aib-EGTFTSDVSSYLEEQAAR-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-FIAWLVRGRGGGGGASELSTAALGRLS-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-ELHELATLPRTETGSSGSP-amide
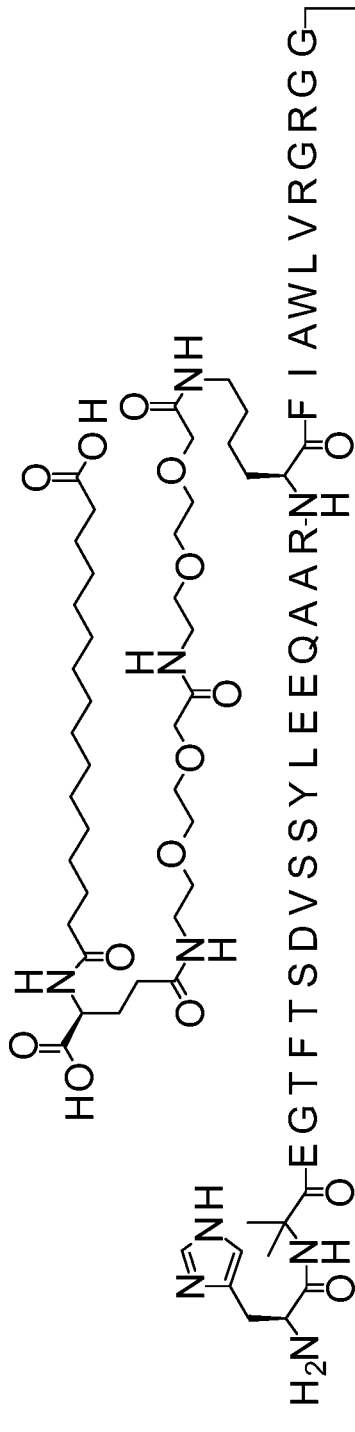
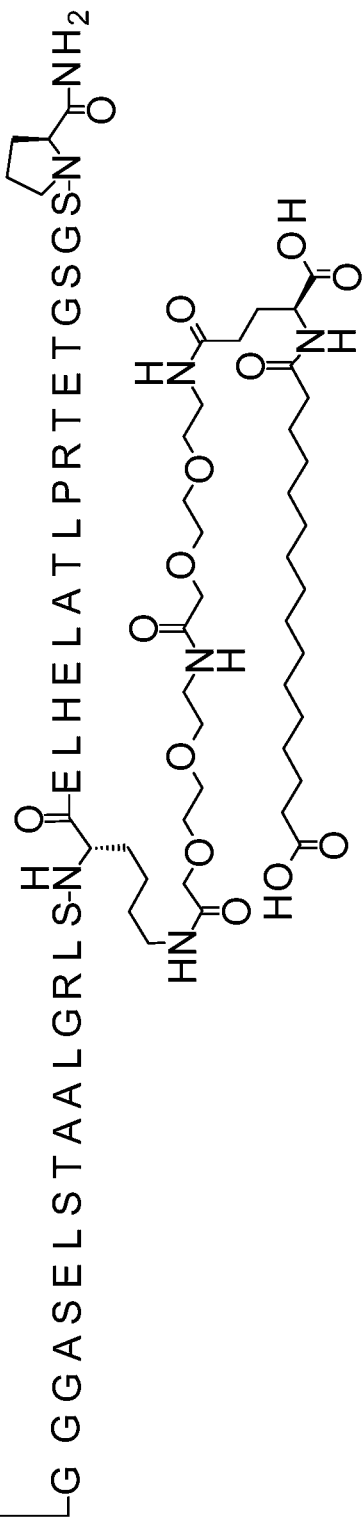

Compound 0297
H-Aib-EGTFTSDVSSYLEEQAAREFIAWLVR-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-RGGGGGASELSTAALGRLS-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-ELHELATLPRTETGSGSP-amide

Fig. 103
Compound 0299
H-Aib-EGTFTSDVSSYLEE-K([2-[2-[2-[2-[2-[2-[[(4S)-4-carboxy-4-(15-carboxypentadecanoylamino)butanoyl]amino]ethoxy]ethoxy]acetyl]amino]ethoxy]ethoxy]acetyl])-AAREFIAWLVRGRGGGGGEASELSTAALGRLSAELH-K([2-[2-[2-[2-[2-[2-[[(4S)-4-carboxy-4-(15-carboxypentadecanoylamino)butanoyl]amino]ethoxy]ethoxy]acetyl]amino]ethoxy]ethoxy]acetyl])-LATLPRTETGSGSP-amide
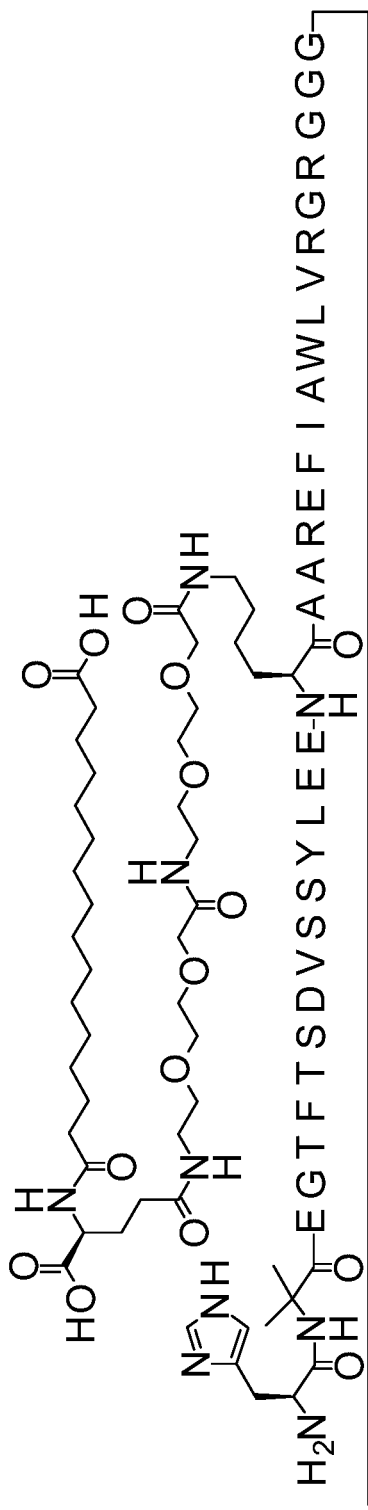
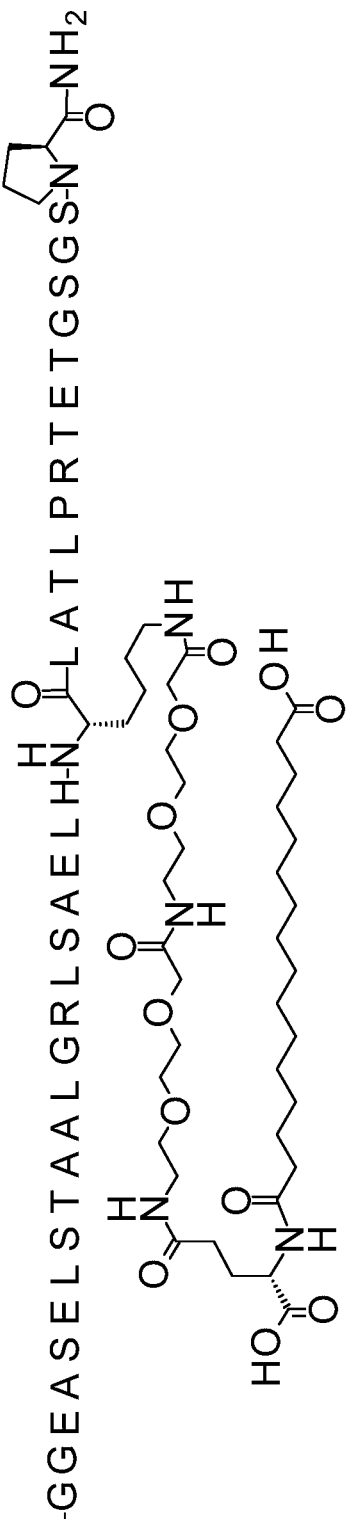

Fig. 104
Compound 0396
H-Aib-EGTFTSDVSSYLEE-K([2-[2-[2-[[2-[2-[2-[[(4S)-4-carboxy-4-[(15-carboxypentadecanoylamino)butanoyl]amino]ethoxy]ethoxy]acetyl]amino]ethoxy]ethoxy]acetyl])-AAREFIAWLVRGRGGGGEASELSTAALGRLSAELHEL-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-TLPRTETGSGSP-amide
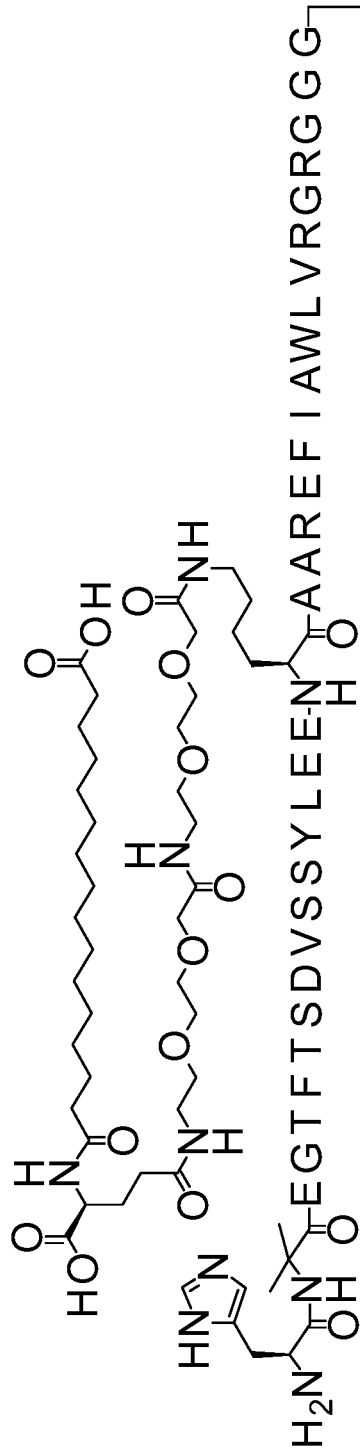
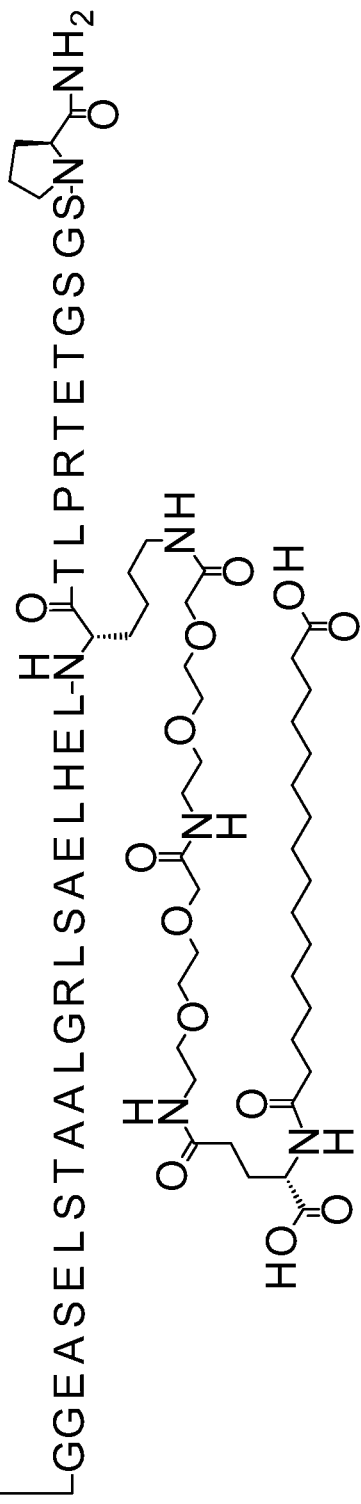

Compound 0397

H-Aib-EGTFTSDVSSYLEE-K([2-[2-[2-[[2-[2-[2-[[(4S)-4-carboxy-4-((15-carboxypentadecanoylamino)butanoyl]amino]ethoxy]ethoxy]acetyl]amino]ethoxy]ethoxy]acetyl])-AAREFIAWLVRGRGGGGEASELSTAALGRLSAELHELATL-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-RTETGSGSP-amide Compound 0411

H-Aib-EGTFTSDVSSYLEE-K([2-[2-[2-[2-[[(4S)-4-carboxy-4-(15-carboxypentadecanoylamino)butanoyl]amino]ethoxy]ethoxy]acetyl]amino]ethoxy]ethoxy]acetyl])-AAREFIAWLVRGRGGGGEASELSTAALGRLSAELHELATLPRTETG-K([2-[2-[2-[2-[[(4S)-4-carboxy-4-(15-carboxypentadecanoylamino)butanoyl]amino]ethoxy]ethoxy]acetyl]amino]ethoxy]ethoxy]acetyl])-GSP-amide Compound 0414

HAEGTFTSDVSSYLEE-K([2-[2-[2-[2-[2-[2-[[(4S)-4-carboxy-4-[[4-[(19-carboxynonadecanoylamino)methyl]cyclohexanecarbonyl]amino]butanoyl]amino]ethoxy]acetyl]amino]ethoxy]ethoxy]acetyl])-AAREFIEWLVRGREGEASELSTAALGRLSAELHELATLPRTETGSSGSP-amide Compound 0415

H-Aib-EGTFTSDVSSYLEE-K([2-[2-[2-[[2-[2-[[(4S)-4-carboxy-4-[[4-[(19-carboxynonadecanoyl)amino]butanoyl]amino]ethoxy]acetyl]amino]ethoxy]ethoxy]acetyl])-AAREFIEWLVRGRGEASELSTAAALGRLSAELHELATLPRTETGSGSP-amide Compound 0416

HAEGTFTS-K([2-[2-[2-[2-[[2-[2-[2-[[(4S)-4-carboxy-4-[[4-[[(19-carboxynonadecanoylamino)methyl]cyclohexanecarbonyl]amino]butanoyl]amino]ethoxy]acetyl]amino]ethoxy]acetyl])-VSSYLEEQAAREFIEWLVRGRGEASELSTAALGRLSAELHELATLPRTETGSGSP-amide Compound 0417

H-Aib-EGTFTS-K{[2-[2-[2-[2-[[(4S)-4-carboxy-4-[[4-[(19-carboxynonadecanoyl)amino]methyl]cyclohexanecarbonyl]amino]butanoyl]amino]ethoxy]ethoxy]acetyl]amino]ethoxy]acetyl]}-VSSYLEEQAAREFIEWLVRGRGEASELSTAALGRLSAELHELATLPRTETGSGSP-amide Compound 0431

HAEGTFTSD-K([2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]acetyl]amino]ethoxy]ethoxy]acetyl])-SSYLEEQAAREFIEWLVRGRGEASELSTAALGRLSAELHELATLPRTETGSSGSP-amide Compound 0433

HWEGTFTSD-K(I[(2S)-2-amino-6-[[2-[2-[2-[[2-[2-[2-[[(4S)-4-carboxy-4-[[4-[[(19-carboxynonadecanoyl)amino]butanoyl]amino]ethoxy]acetyl]amino]ethoxy]ethoxy]acetyl]amino]hexanoyl])-SSYLEEQAAREFIEWLVRGRGEASELSTAALGRLSAELHELATLPRTETGSGSP-amide Compound 0434

HWEGTFTSDVSSYLEE-K([((2S)-2-amino-6-[[2-[2-[2-[2-[2-[[(4S)-4-carboxy-4-[[4-[((19-carboxynonadecanoylamino)methyl]cyclohexanecarbonyl]amino]butanoyl]amino]ethoxy]ethoxy]acetyl]amino]ethoxy]ethoxy]acetyl]amino]hexanoyl])-AAREFIEWLVRGRGEASELSTAALGRLSAELHELATLPRTETGSSGSP-amide Compound 0435

HWEGTFTSDVSSYLEEQAA-K([[(2S)-2-amino-6-[[2-[2-[2-[2-[[2-[2-[[(4S)-4-carboxy-4-[[4-[[(19-carboxynonadecanoyl)amino]butanoyl]amino]ethoxy]acetyl]amino]ethoxy]ethoxy]acetyl]amino]hexanoyl])-EFIEWLVRGRGEASELSTAALGRLSAELHELATLPRTETGSSGSP-amide Compound 0436

H-Aib-EGTFTSDVSSYLEEQAA-K[[(2S)-2-amino-6-[[2-[2-[2-[[2-[2-[2-[[(4S)-4-carboxy-4-[[4-[(19-carboxynonadecanoyl]amino]methyl]cyclohexanecarbonyl]amino]butanoyl]amino]ethoxy]ethoxy]acetyl]amino]ethoxy]ethoxy]acetyl]amino]hexanoyl])-EFIEWLVRGRGEASELSTAALGRLSAELHELATLPRTETGSGSP-amide Compound 0437

HWEGTFTSDVSSYLEEQAAR-K{[(2S)-2-amino-6-[[2-[2-[2-[2-[2-[[(4S)-4-carboxy-4-[[4-[(19-carboxynonadecanoylamino)methyl]cyclohexanecarbonyl]amino]butanoyl]amino]ethoxy]acetyl]amino]ethoxy]acetyl]amino]hexanoyl]}-FIEWLVRGRGEASELSTAALGRLSAELHELATLPRTETGSGSP-amide Compound 0438

H-Aib-EGTFTSDVSSYLEEQAAREFIEWLVRGR-K([(2S)-2-amino-6-[[2-[2-[2-[[2-[2-[[(4S)-4-carboxy-4-[[4-[[(19-carboxynonadecanoyl)amino]methyl]cyclohexanecarbonyl]amino]butanoyl]amino]ethoxy]acetyl]amino]ethoxy]ethoxy]acetyl]amino]hexanoyl])-EASELSTAALGRLSAELHELATLPRTETGSGSP-amide Compound 0439

H-Aib-EGTFTSDVSSYLEEQAAR-K([(2S)-2-amino-6-[[2-[2-[2-[2-[[(4S)-4-carboxy-4-[[4-[(19-carboxynonadecanoylamino)methyl]cyclohexanecarbonyl]amino]butanoyl]amino]ethoxy]acetyl]amino]ethoxy]ethoxy]acetyl]amino]hexanoyl])-FIEWLVRGRGEASELSTAALGRLSAELHELATLPRTETGSSGSP-amide Compound 0440

H-Aib-EGTFTSD-K([2-[2-[2-[2-[2-[[2-[2-[[(4S)-4-carboxy-4-[[4-[(19-carboxynonadecanoyl)amino]methyl]cyclohexanecarbonyl]amino]butanoyl]amino]ethoxy]acetyl]amino]ethoxy]ethoxy]acetyl])-SSYLEEQAAREFIEWLVRGRGEASELSTAALGRLSAELHELATLPRTETGSGSP-amide Compound 0472
HAEGTFTSDVSSYLEE-K(([2-[2-[2-[[2-[2-[2-[[(4S)-4-carboxy-4-((17-carboxyheptadecanoylamino)butanoyl]amino]ethoxy]ethoxy]acetyl]amino]ethoxy]ethoxy]acetyl])-AAREFIEWLVRGRGEASELSTAALGRLSAELHELATLPRTETGSSGSP-amide Compound 0474

HAEGTFTSDVSSYLEE-K{[2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl]}-AAREFIEWLVRGRGEASELSTAALGRLSAELHELATLPRTETGSGSP-amide Compound 0475
HAEGTFTSD-K([2-[2-[2-[[2-[2-[2-[[(4S)-4-carboxy-4-((15-carboxypentadecanoylamino)butanoyl]amino]ethoxy]ethoxy]acetyl]amino]ethoxy]ethoxy]acetyl])-SSYLEE-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-AAREFIEWLVRGRGEASELSTAALGRLSAELHELATLPRTETGSGSP-amide Compound 0482

HAEGTFTSDVS-K([2-[2-[2-[[2-[2-[2-[[(4S)-4-carboxy-4-((15-carboxypentadecanoylamino)butanoyl]amino]ethoxy]ethoxy]acetyl]amino]ethoxy]ethoxy]acetyl)-YLEEQAVREFIA-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-LVRGRGGGEASELSTAALGRLSAELHELATLPRTETGSGSP-amide Compound 0483

H-Aib-EGTFTSDVS-K([2-[2-[2-[2-[2-[2-[[(4S)-4-carboxy-4-(15-carboxypentadecanoylamino)butanoyl]amino]ethoxy]ethoxy]acetyl]amino]ethoxy]acetyl])-YLEEQAVREFIA-K([2-[2-[2-[2-[2-[2-[[(4S)-4-carboxy-4-(15-carboxypentadecanoylamino)butanoyl]amino]ethoxy]ethoxy]acetyl]amino]ethoxy]acetyl])-LVRGRGGGEASELSTAALGRLSAELHELATLPRTETGSSGSP-amide Compound 0484

H-Aib-EGTFTSDVS-K([2-[2-[2-[[2-[2-[2-[2-[[(4S)-4-carboxy-4-[[(4S)-4-carboxy-4-(13-carboxytridecanoylamino)butanoyl]amino]butanoyl]amino]ethoxy]ethoxy]acetyl]amino]ethoxy]ethoxy]acetyl])-YLEEQAVREFIA-K([2-[2-[2-[[2-[2-[2-[2-[[(4S)-4-carboxy-4-(13-carboxytridecanoylamino)butanoyl]amino]ethoxy]ethoxy]acetyl]amino]ethoxy]ethoxy]acetyl])-LVRGRGGGEASELSTAALGRLSAELHELATLPRTETGSGSP-amide Compound 0502

H-Aib-EGTFTSDVSSYLEEQAAREFIAWLVRGR-K([2-[2-[2-[2-[2-[2-[[(4S)-4-carboxy-4-(19-carboxynonadecanoylamino)butanoyl]amino]ethoxy]ethoxy]acetyl]amino]ethoxy]ethoxy]acetyl])-GGGGEASELSTAALGRLSAELHELATLPRTETGSGSP-amide Compound 0503

H-Aib-EGTFTSDVSSYLEEQAAREFIEWLVRGR-K([2-[2-[2-[2-[2-[[(4S)-4-carboxy-4-[[4-[[(19-carboxynonadecanoylamino)methyl]cyclohexanecarbonyl]amino]butanoyl]amino]ethoxy]ethoxy]acetyl]amino]ethoxy]ethoxy]acetyl)-GGGGEASELSTAALGRLSAELHELATLPRTETGSSGSP-amide Compound 0504

H-Aib-EGTFTSDVSSYLEEQAAREFIAWLVRGRP-K[(2-[2-[2-[2-[[(4S)-4-carboxy-4-[[4-[(19-carboxynonadecanoyl)amino]methyl]cyclohexanecarbonyl]amino]butanoyl]amino]ethoxy]acetyl]amino]ethoxy]ethoxy]acetyl)]-GGGGEASELSTAALGRLSAELHELATLPRTETGSSGSP-amide Compound 0506

H-Aib-EGTFTSDVSSYLEEQAAREFIAWLVRGR-K[((2S)-2-amino-6-[[2-[2-[2-[2-[2-[[(4S)-4-carboxy-4-[[4-[(19-carboxynonadecanoyl)amino]butanoyl]amino]ethoxy]acetyl]amino]ethoxy]ethoxy]acetyl]amino]hexanoyl])-GGGGEASELSTAALGRLSAELHELATLPRTETGSGSP-amide Compound 0509

H-Aib-EGTFTSDVSSYLEEQAAR-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-FIAWLVRGRGGGGEASELSTAALGRLSAELH-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-LATLPRTETGSGSP-amide Compound 0511

H-Aib-EGTFTSDVSRYLEEQAAREFIEWLVRGR-K((2-[2-[2-[2-[2-[2-[[(4S)-4-carboxy-4-[[4-[(19-carboxynonadecanoyl)amino]methyl]cyclohexanecarbonyl]amino]butanoyl]amino]ethoxy]ethoxy]acetyl]amino]ethoxy]ethoxy]acetyl)-GGGGEASELSTAALGRLSAELHELATLPRTETGSGSP-amide Compound 0512

H-Aib-EGTFTSDVSSYLEEQAAREFIAWLVRGR-K[(2-[2-[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl])-GGEASELSTAALGRLSAELHELATLPRTETGSGSP-amide Compound 0516

H-Aib-EGTFTSDVS-K([2-[2-[2-[2-[2-[2-[[(4S)-4-carboxy-4-((15-carboxypentadecanoylamino)butanoyl]amino]ethoxy]ethoxy]acetyl]amino]ethoxy]acetyl])-YLEEQAAR-K([2-[2-[2-[2-[[(4S)-4-carboxy-4-(15-carboxypentadecanoylamino)butanoyl]amino]ethoxy]ethoxy]amino]ethoxy]ethoxy]acetyl]amino]ethoxy]ethoxy]acetyl])-FIAWLVRGRGGGGEASELSTAALGRLSAELHELATLPRTETGSSGSP-amide Compound 0518

H-Aib-EGTFTSDVS-K([2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl])-YLEEQAAREFIAWLVRGRGGGGEASELSTAALGRLSAELHELATLPRTETGSSGSP-amide Compound 0528

H-Aib-EGTFTSDVS-K([2-[2-[2-[2-[2-[[(4S)-4-carboxy-4-(15-carboxypentadecanoylamino)butanoyl]amino]ethoxy]ethoxy]acetyl]amino]ethoxy]ethoxy]acetyl])-YLEEQAAREFIAWLVRGR-K([2-[2-[2-[2-[2-[[(4S)-4-carboxy-4-(15-carboxypentadecanoylamino)butanoyl]amino]ethoxy]ethoxy]acetyl]amino]ethoxy]ethoxy]acetyl])-GGGGEASELSTAALGRLSAELHELATLPRTETGSSGSP-amide Compound 0529

H-Aib-EGTFTSDVSSYLEGQAAAREFIAWLVRGRGQEP-K([2-[2-[2-[2-[2-[[(4S)-4-carboxy-4-(19-carboxynonadecanoylamino)butanoyl]amino]ethoxy]ethoxy]acetyl]amino]ethoxy]ethoxy]acetyl])-GQAPEASELSTAALGRLSAELHELATLPRTETGSSGSP-amide Compound 0539

H-Aib-EGTFTSDVSSYLEGQAAREFIAWLVRGRGQEP-K([2-[2-[2-[[2-[2-[2-[[(4S)-4-carboxy-4-[[4-[(19-carboxynonadecanoyl)amino]methyl]cyclohexanecarbonyl]amino]butanoyl]amino]ethoxy]ethoxy]acetyl]amino]ethoxy]ethoxy]acetyl])-GQAPEASELSTAALGRLSAELHELATLPRTETGSGSP-amide Compound 0552

H-Aib-EGTFTSDVSSYLEEQAAREFIAWLVRGR-K([(2S)-2-amino-6-[2-[2-[2-[2-[2-[[(4S)-4-carboxy-4-(19-carboxynonadecanoylamino)butanoyl]amino]ethoxy]ethoxy]acetyl]amino]ethoxy]ethoxy]acetyl]amino]hexanoyl])-GGGGEASELSTAALGRLSAELHELATLPRTETGSSGSP-amide Compound 0560

HGEGTFTSDVSSYLEGQAA-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-EFIAWLVRGRGEASELSTAALGRLSAELHELATLPRTETGSSGSP-amide Compound 0561

H-Aib-EGTFTSDVSSYLEEQAAR-K([2-[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl])-FIAWLVRGRGGGGGEASELSTAALGRLSAELHELATLPRTETGSGSP-amide Compound 0562

H-Aib-EGTFTSDVSSYLEEQAAR-K([2-[2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl])-FIAWLVRGRGGGGGEASELSTAALGRLSAELHELATLPRTETGSGSP-amide Compound 0564

H-Aib-EGTFTSDVS-K([2-[2-[2-[[(2S)-2,6-bis[[2-[2-[2-[[2-[2-[2-[[(4S)-4-carboxy-4-(15-carboxypentadecanoyl)amino]butanoyl]amino]ethoxy]ethoxy]acetyl]amino]ethoxy]ethoxy]acetyl]amino]hexanoyl]amino]ethoxy]ethoxy]acetyl])-YLEEQAAREFIAWLVRGRGGGGEASELSTAALGRLSAELHELATLPRTETGSSGSP-amide Compound 0565

H-Aib-EGTFTSDVS-K([2-[2-[2-[2-[2-[2-[[(4S)-4-carboxy-4-(19-carboxynonadecanoylamino)butanoyl]amino]ethoxy]ethoxy]acetyl]amino]ethoxy]ethoxy]acetyl])-YLEEQAAREFIAWLVRGRGGGGEASELSTAALGRLSAELHELATLPRTETGSGSP-amide Compound 0575

H-Aib-EGTFTSDVS-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-YLEEQAAR-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-FIAWLVRGRQEGGGGASELSTAALGRLSAELHELATLPRTETGSGSP-amide Compound 0576

H-Aib-EGTFTSDVS-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-YLEEQAAR-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-FIEWLVRGRGEGGGGGASELSTAALGRLSAELHELATLPRTETGSGSP-amide Compound 0577

H-Aib-EGTFTSDVS-K([2-[2-[2-[2-[2-[[(4S)-4-carboxy-4-(15-carboxypentadecanoylamino)butanoyl]amino]ethoxy]ethoxy]acetyl]amino]ethoxy]acetyl])-YLEEQAAR-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-FIEWLVRGRGEASELSTAALGRLSAELHELATLPRTETGSGSP-amide Compound 0578

H-Aib-EGTFTSDVS-K([2-[2-[2-[2-[2-[2-[[(4S)-4-carboxy-4-(15-carboxypentadecanoylamino)butanoyl]amino]ethoxy]ethoxy]acetyl]amino]ethoxy]acetyl])-YLEEQAAR-K([2-[2-[2-[2-[2-[2-[[(4S)-4-carboxy-4-(15-carboxypentadecanoylamino)butanoyl]amino]ethoxy]ethoxy]acetyl]amino]ethoxy]acetyl])-FIAWLVRGRQEASELSTAALGRLSAELHELATLPRTETGSGSP-amide Compound 0580

H-Aib-EGTFTSDVSSYLEEQAAR-K([2-[2-[2-[2-[2-[2-[[(4S)-4-carboxy-4-(19-carboxynonadecanoylamino)butanoyl]amino]ethoxy]ethoxy]acetyl]amino]ethoxy]ethoxy]acetyl])-FIAWLVRGGASELSTAALGRLSAELHELATLPRTETGSSGSP-amide Compound 0581

H-Aib-EGTFTSDVSSYLEEQAAR-K([2-[2-[2-[2-[2-[[2-[2-[[(4S)-4-carboxy-4-(19-carboxynonadecanoylamino)butanoyl]amino]ethoxy]ethoxy]acetyl]amino]ethoxy]ethoxy]acetyl])-FIEWLVRGASELSTAALGRLSAELHELATLPRTETGSGSP-amide Compound 0629

H-Aib-EGTFTSDVS-K([2-[2-[2-[2-[2-[2-[[(4S)-4-carboxy-4-(15-carboxypentadecanoylamino)butanoyl]amino]ethoxy]ethoxy]acetyl]amino]ethoxy]ethoxy]acetyl])-YLEEQAAR-K([2-[2-[2-[[(4S)-4-carboxy-4-(15-carboxypentadecanoylamino)butanoyl]amino]ethoxy]ethoxy]acetyl]amino]ethoxy]ethoxy]acetyl])-FIEWLVRGAAEASELSTAALGRLSAELHELATLPRTETGSGSP-amide Compound 0630

H-Aib-EGTFTSDVS-K(6-[[(4S)-4-carboxy-4-[[(4S)-4-carboxy-4-(15-carboxypentadecanoylamino)butanoyl]amino]butanoyl]amino]hexanoyl)-YLEEQAAR-K(6-[[(4S)-4-carboxy-4-[[(4S)-4-carboxy-4-(15-carboxypentadecanoylamino)butanoyl]amino]butanoyl]amino]hexanoyl)-FIEWLVRGAAEASELSTAALGRLSAELHELATLPRTETGSGSP-amide Compound 0631

H-Aib-EGTFTSDVS-K[[(4S)-4-carboxy-4-[[(4S)-4-carboxy-4-[[(4S)-4-carboxy-4-(15-carboxypentadecanoylamino)butanoyl]amino]butanoyl]amino]butanoyl]-YLEEQAAR-K([[(4S)-4-carboxy-4-[[(4S)-4-carboxy-4-[[(4S)-4-carboxy-4-(15-carboxypentadecanoylamino)butanoyl]amino]butanoyl]amino]butanoyl])-FIEWLVRGAAEASELSTAALGRLSAELHELATLPRTETGSGSP-amide Compound 0632

H-Aib-EGTFTSDVS-K([(4S)-4-carboxy-4-[[(4S)-4-carboxy-4-[[(4S)-4-carboxy-4-(19-carboxynonadecanoylamino)butanoyl]amino]butanoyl]amino]butanoyl])-YLEEQAAREFIEWLVRGAAEASELSTAALGRLSAELHELATLPRTETGSGSP-amide Compound 0633

H-Aib-EGTFTSDVSSYLEEQAAR-K([(4S)-4-carboxy-4-[[(4S)-4-carboxy-4-[[(4S)-4-carboxy-4-(19-carboxynonadecanoylamino)butanoyl]amino]butanoyl]amino]butanoyl])-FIAWLVRGRGGGGGEASELSTAALGRLSAELHELATLPRTETGSGSP-amide Compound 0634

H-Aib-EGTFTSDVS-K[[(4S)-4-carboxy-4-[[(4S)-4-carboxy-4-[[(4S)-4-carboxy-4-(15-carboxypentadecanoylamino)butanoyl]amino]butanoyl]amino]butanoyl]-YLEEQAAR-K[[(4S)-4-carboxy-4-[[(4S)-4-carboxy-4-[[(4S)-4-carboxy-4-(15-carboxypentadecanoylamino)butanoyl]amino]butanoyl]amino]butanoyl])-FIAWLVRGRGEASELSTAALGRLSAELHELATLPRTETGSGSP-amide

Fig. 157

Compound 0635

H-Aib-EGTFTSDVS-K([2-[2-[2-[[2-[2-[2-[[(4S)-4-carboxy-4-((13-carboxytridecanoylamino)butanoyl]amino]ethoxy]ethoxy]acetyl]amino]ethoxy]ethoxy]acetyl])-YLEEQAAR-K([2-[2-[2-[[2-[2-[2-[[(4R)-4-carboxy-4-((13-carboxytridecanoylamino)butanoyl]amino]ethoxy]ethoxy]acetyl]amino]ethoxy]ethoxy]acetyl])-FIAWLVRGR-K([2-[2-[2-[[2-[2-[2-[[(4S)-4-carboxy-4-((13-carboxytridecanoylamino)butanoyl]amino]ethoxy]ethoxy]acetyl]amino]ethoxy]ethoxy]acetyl])-GGEASELSTAALGRLSAELHELATLPRTETGSGSP-amide

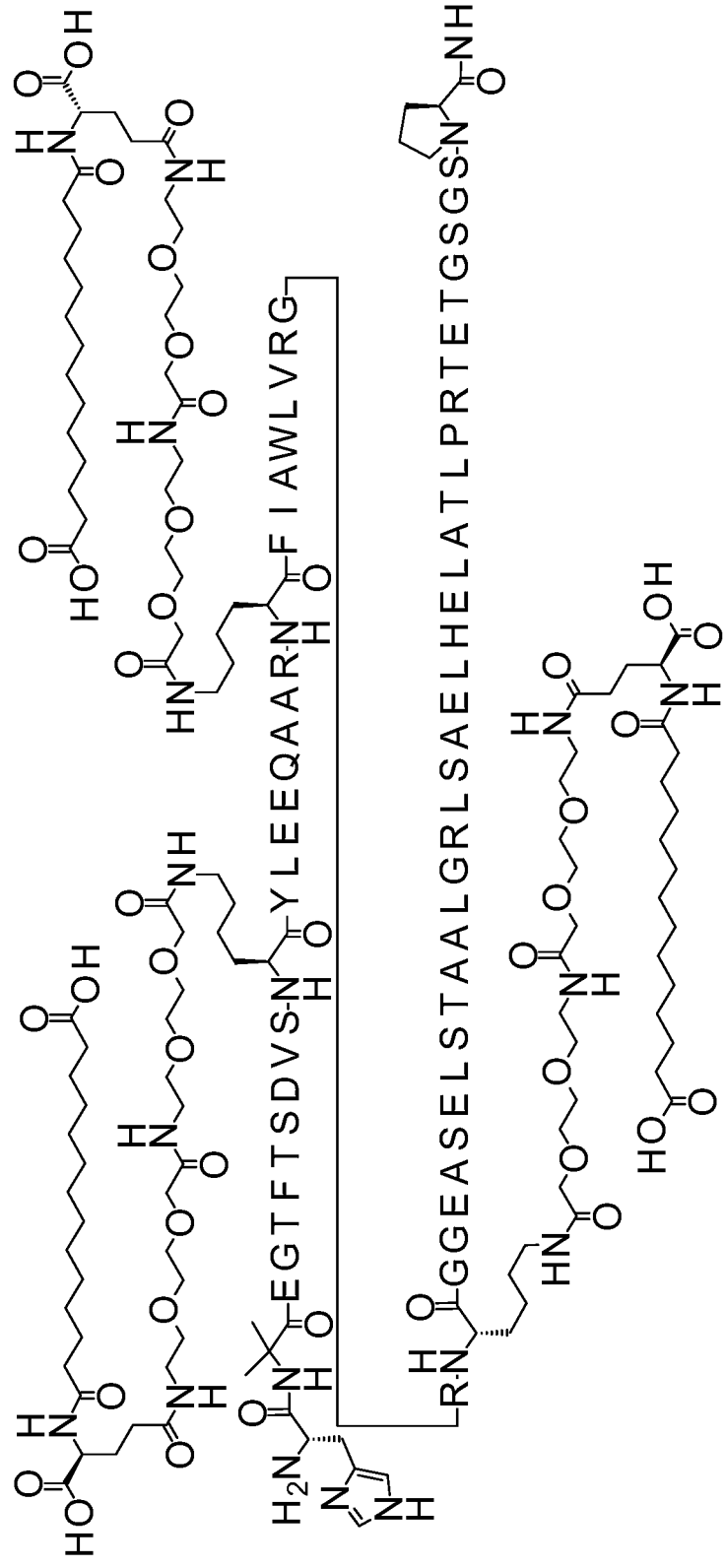

Compound 0636

H-Aib-EGTFTSDVSSYLEEQAAR-K([2-[2-[2-[[2-[2-[2-[[(4S)-4-carboxy-4-[[(4S)-4-carboxy-4-[[(4S)-4-carboxy-4-(19-carboxynonadecanoylamino)butanoyl]amino]butanoyl]amino]ethoxy]acetyl]amino]ethoxy]ethoxy]acetyl)-FIEWLVRGRQEAASELSTAALGRLSAELHQLATLPRTETGSGSP-amide Compound 0637

H-Aib-EGTFTSDVSSYLEEQAAREFIAWLVRGR-K([2-[2-[2-[2-[2-[2-[[(4S)-4-carboxy-4-(17-carboxyheptadecanoylamino)butanoyl]amino]ethoxy]ethoxy]acetyl]amino]ethoxy]ethoxy]acetyl])-GGGGSGGGEASELSTAALGRLSAELHELATLPRTETGSGSP-amide Compound 0638

H-Aib-EGTFTSDVSSYLEEQAAREFIAWLVRGR-K([2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl])-GGGGSGGGEASELSTAALGRLSAELHELATLPRTETGSGSP-amide Compound 0639

H-Aib-EGTFTSDVSSYLEEQAAR-K([2-[2-[2-[2-[2-[[(4S)-4-carboxy-4-(17-carboxyheptadecanoylamino)butanoyl]amino]ethoxy]ethoxy]acetyl]amino]ethoxy]ethoxy]acetyl])-FIAWLVRGRGGGGEASELSTAALGRLSAELHELATLPRTETGSSGSP-amide Compound 0640

H-Aib-EGTFTSDVS-K([2-[2-[2-[2-[2-[2-[[(4S)-4-carboxy-4-((17-carboxyheptadecanoylamino)butanoyl]amino]ethoxy]ethoxy]acetyl]amino]ethoxy]ethoxy]acetyl])-YLEEQAAREFIAWLVRGRGRGGGGEASELSTAALGRLSAELHELATLPRTETGSGSP-amide Compound 0648

HWEGTFTSDVSSYLEEQAAREFIAWLVRGR-K([2-[2-[2-[2-[[(4S)-4-carboxy-4-(17-carboxyheptadecanoylamino)butanoyl]amino]ethoxy]ethoxy]amino]ethoxy]ethoxy]acetyl])-GGGGEASELSTAALGRLSAELHELATLPRTETGSGSP-amide Compound 0654

H-Aib-EGTFTSDVSSYLEEQAAREFIAWLVRGR-K([2-[2-[2-[2-[[(4S)-4-carboxy-4-(16-sulfohexadecanoylamino)butanoyl]amino]ethoxy]ethoxy]acetyl]amino]ethoxy]ethoxy]acetyl])-GGGGEASELSTAALGRLSAELHELATLPRTETGSGSP-amide Compound 0655

H-Aib-EGTFTSDVSSYLEEQAAREFIAWLVRGR-K[(2-[2-[2-[2-[2-[[(4S)-4-carboxy-4-[17-(1H-tetrazol-5-yl)heptadecanoylamino]butanoyl]amino]ethoxy]ethoxy]acetyl]amino]ethoxy]ethoxy]acetyl])-GGGGEASELSTAALGRLSAELHELATLPRTETGSSGSP-amide Compound 0656

H-Aib-EGTFTSDVSSYLEEQAAREFIAWLVRGR-K[[(2S)-2-amino-6-[[(2S)-2-amino-6-[[(4S)-4-carboxy-4-(17-carboxyheptadecanoylamino)butanoyl]amino]hexanoyl]amino]hexanoyl])-GGGGEASELSTAALGRLSAELHELATLPRTETGSGSP-amide Compound 0657

H-Aib-EGTFTSDVSSYLEEQAAREFIAWLVRGR-K[[(2S)-2-amino-6-[[(2S)-2-amino-6-[[(4S)-4-carboxy-4-(19-carboxynonadecanoylamino)butanoyl]amino]hexanoyl]amino]hexanoyl])-GGGGEASELSTAALGRLSAELHELATLPRTETGSGSP-amide Compound 0658

H-Aib-EGTFTSDVSSYLEEQAAREFIAWLVRGR-K(6-[6-[[(4S)-4-carboxy-4-(17-carboxyheptadecanoylamino)butanoyl]amino]hexanoylamino]hexanoyl)-GGGGEASELSTAALGRLSAELHELATLPRTETGSGSP-amide Compound 0659

H-Aib-EGTFTSDVSSYLEEQAAREFIAWLVRGR-K(6-[[(4S)-4-carboxy-4-(19-carboxynonadecanoylamino)butanoyl]amino]hexanoylamino]hexanoyl)-GGGGEASELSTAALGRLSAELHELATLPRTETGSGSP-amide Compound 0660

H-Aib-EGTFTSDVSSYLEEQAAREFIAWLVRGR-K[(2-[2-[2-[[(4S)-4-carboxy-4-(17-carboxyheptadecanoylamino)butanoyl]amino]ethoxy]ethoxy]acetyl])-GGGGEASELSTAALGRLSAELHELATLPRTETGSGSP-amide Compound 0661

H-Aib-EGTFTSDVSSYLEEQAAREFIAWLVRGR-K([2-[2-[2-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]ethoxy]ethoxy]acetyl])-GGGGEASELSTAALGRLSAELHELATLPRTETGSGSP-amide Compound 0662

H-Aib-EGTFTSDVSSYLEEQAAREFIAWLVRGR-K([2-[2-[2-[2-[2-[2-[2-[[2-[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]ethoxy]ethoxy]acetyl])-GGGGEASELSTAALGRLSAELHELATLPRTETGSGSP-amide Compound 0663

H-Aib-EGTFTSDVSSYLEEQAAREFIAWLVRGR-K([2-[2-[2-[2-[[2-[2-[2-[2-[[2-[2-[2-[[(4S)-4-carboxy-4-(19-carboxynonadecanoylamino)butanoyl]amino]ethoxy]acetyl]amino]ethoxy]ethoxy]acetyl]amino]ethoxy]ethoxy]acetyl]amino]ethoxy]ethoxy]acetyl])-GGGGEASELSTAALGRLSAELHELATLPRTETGSGSP-amide Comparator compound 0164

H-Aib-EGTFTSDVSSYLEGQAAKEIFAWLVRGR-K(([(2S)-2-amino-6-[[2-[2-[2-[[(4S)-4-carboxy-4-(17-carboxyheptadecanoylamino)butanoyl]amino]ethoxy]acetyl]amino]ethoxy]ethoxy]acetyl]amino]hexanoyl])-GGEASELSTAALGRLSAELHELATLPRTETGSSGSP-amide Comparator compound 0185

H-Aib-EGTFTSDVSSYLEGQAAKEFIAWLVRGR-K(([(2S)-2-amino-6-[[2-[2-[2-[2-[2-[[(4S)-4-carboxy-4-(17-carboxyheptadecanoylamino)butanoyl]amino]ethoxy]acetyl]amino]ethoxy]acetyl]amino]hexanoyl])-GGEASELSTAALGRPSAELHELATLPRTETGSSGSP-amide

Fig. 176
Comparator compound 0015
H-Aib-EGTFTSDVSSYLEGQAA-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-EFIAWLVRGRGGQEPGQEPCNTATCATQRLAEFLRHSSNNFGPILPPTNVGSNTP-amide
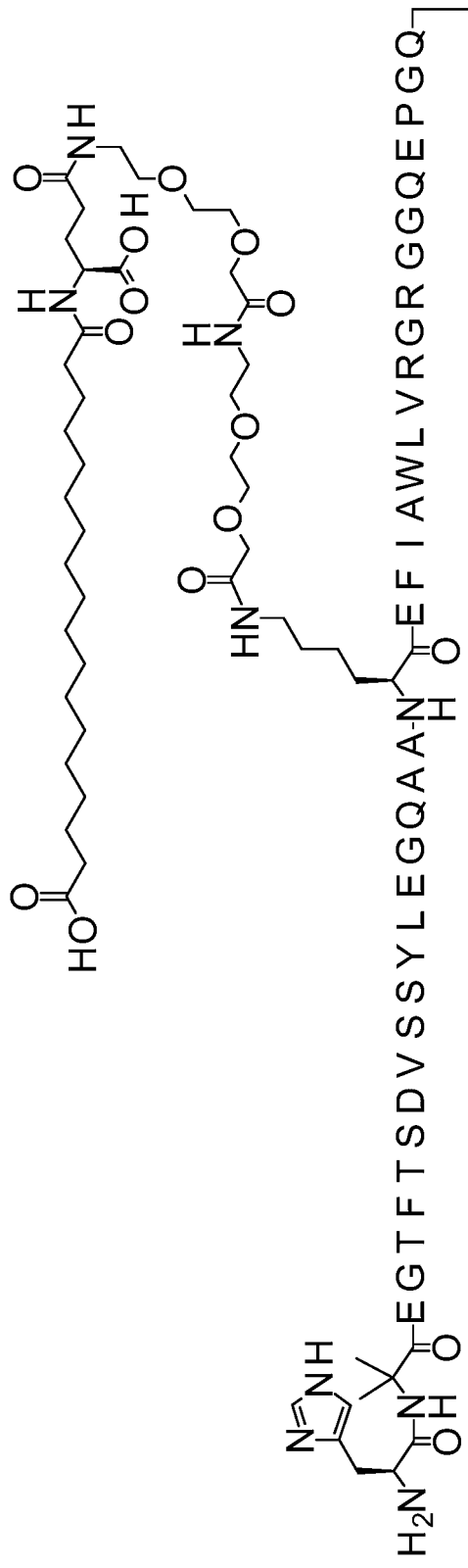
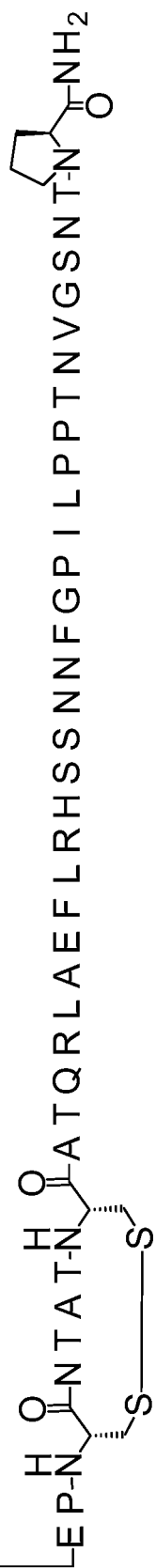

Comparator compound 0016

H-Aib-EGTFTSDVSSYLEGQAA-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-EFIAWLVRGRGGQEPGQEP-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-CNTATCATQRLAEFLRHSSNNFGPILPPTNVGSNTP-amide Comparator compound 0668

H-Aib-EGTFTSDVSSYLEGQAA-K([2-[2-[2-[[2-[2-[[(4S)-4-carboxy-4-(17-carboxyheptadecanoylamino)butanoyl]amino]ethoxy]ethoxy]acetyl]amino]ethoxy]ethoxy]acetyl)-EFIAWLVRGRGGQEPGQEP-K([[(4S)-4-carboxy-4-[[(4S)-4-carboxy-4-(19-carboxynonadecanoylamino)butanoyl]amino]butanoyl])-CNTATCATQRLADFLRHSSPNFGAIPSSTNVGSRTY-amide Comparator compound 0671

H-Aib-EGTFTSDVSSYLEEQAAAREFIAWLVRGR-K([2-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-GGGGEKCNTATCATQRLANFLVHSSNNFGPILPPTNVGSNTY-amide

Fig. 180
Comparator compound 0672
H-Aib-EGTFTSDVSSYLEEQAAREFIAWLVRGR-K[(2-[2-[2-[(2-[2-[2-[[(4S)-4-carboxy-4-(17-carboxyheptadecanoylamino)butanoyl]amino]ethoxy]ethoxy]acetyl]amino]ethoxy]ethoxy]acetyl])-GGGGEKCNTATCATQRLAEFLRHSSNNFGPILPPTNVGSNTP-amide
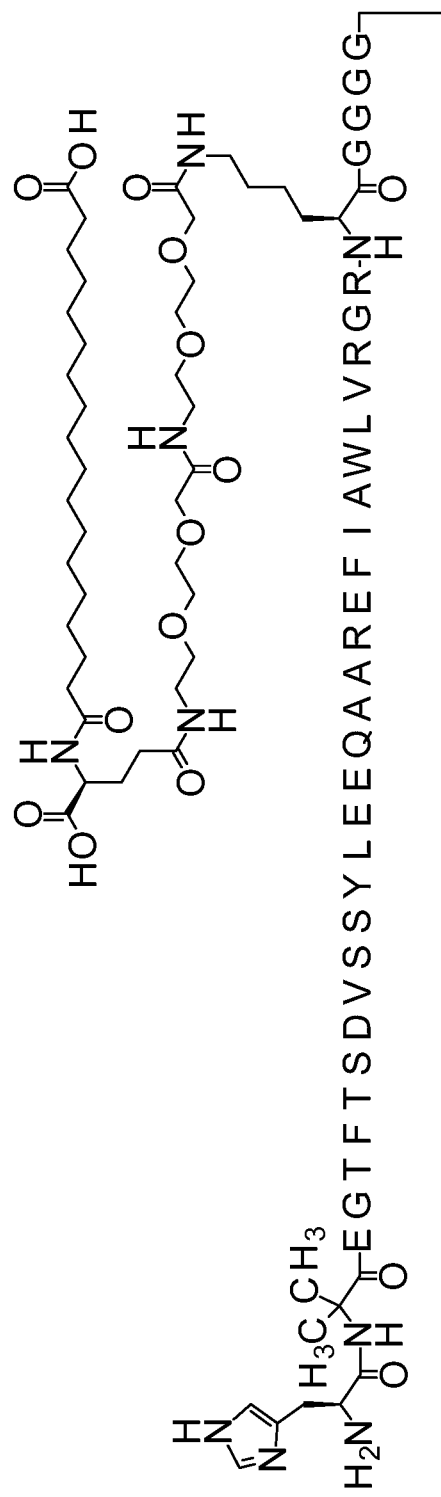
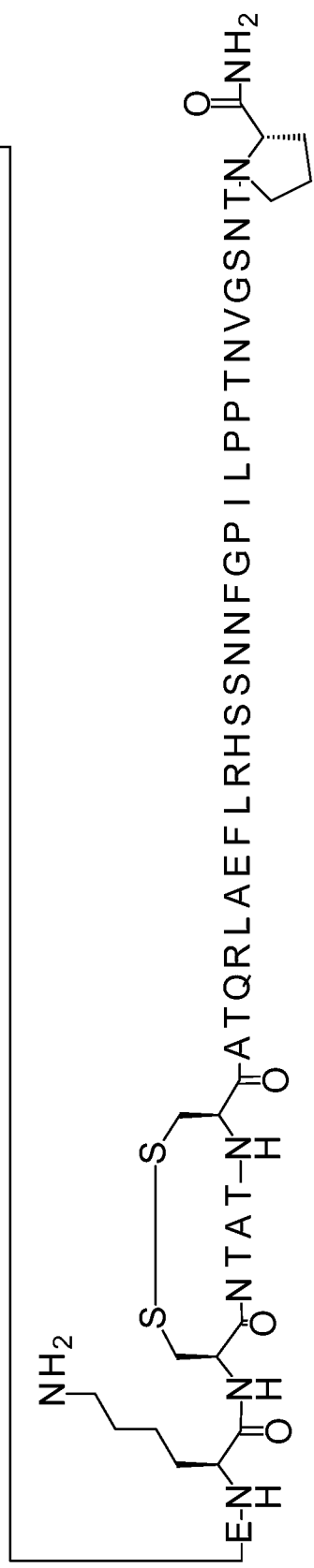

Comparator compound 0167

H-Aib-EGTFTSDVSSYLEEQAAREIFAWLVRGR-K([2-[2-[2-[2-[[2-[2-[[(4S)-4-carboxy-4-[[4-[(19-carboxynonadecanoyl)amino]methyl]cyclohexanecarbonyl]amino]butanoyl]amino]ethoxy]ethoxy]acetyl]amino]ethoxy]ethoxy]acetyl])-GGGGEASELSTAALGRLSAELHELATLPRTETGSGSP-amide Comparator compound 0192

H-Aib-EGTFTSDVSSYLEEQAAAREFIAWLVRGR-K([2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]acetyl]amino]ethoxy]ethoxy]acetyl])-GGGGEASELSTAALGRPSAELHELATLPRTETGSGSP-amide Amylin receptor agonist 1806
EASELSTAALGRLSAELHELATLPRTETGSGSP-amide

```
                            SEQUENCE LISTING

Sequence total quantity: 256
SEQ ID NO: 1            moltype = AA  length = 31
FEATURE                 Location/Qualifiers
source                  1..31
                        mol_type = protein
                        organism = Homo sapiens
SEQUENCE: 1
HAEGTFTSDV SSYLEGQAAK EFIAWLVKGR G                                 31

SEQ ID NO: 2            moltype = AA  length = 31
FEATURE                 Location/Qualifiers
REGION                  1..31
                        note = GLP-1 receptor agonist
MOD_RES                 2
                        note = Xaa is Aib (alpha-aminoisobutyryl)
source                  1..31
                        mol_type = protein
                        organism = synthetic construct
SEQUENCE: 2
HXEGTFTSDV SSYLEGQAAK EFIAWLVRGR G                                 31

SEQ ID NO: 3            moltype = AA  length = 31
FEATURE                 Location/Qualifiers
REGION                  1..31
                        note = GLP-1 receptor agonist
MOD_RES                 2
                        note = Xaa is Aib (alpha-aminoisobutyryl)
source                  1..31
                        mol_type = protein
                        organism = synthetic construct
SEQUENCE: 3
HXEGTFTSDV SSYLEGQAAR EFIAWLVRGK G                                 31

SEQ ID NO: 4            moltype = AA  length = 31
FEATURE                 Location/Qualifiers
REGION                  1..31
                        note = GLP-1 receptor agonist
MOD_RES                 2
                        note = Xaa is Aib (alpha-aminoisobutyryl)
source                  1..31
                        mol_type = protein
                        organism = synthetic construct
SEQUENCE: 4
HXEGTFTSDV SSYLEGQAAR EFIAWLVRGR G                                 31

SEQ ID NO: 5            moltype = AA  length = 31
FEATURE                 Location/Qualifiers
REGION                  1..31
                        note = GLP-1 receptor agonist
MOD_RES                 1
                        note = Xaa is Imp (imidazole propionyl)
source                  1..31
                        mol_type = protein
                        organism = synthetic construct
SEQUENCE: 5
XAEGTFTSDV SSYLEEQAAR EFIAWLVRGR K                                 31

SEQ ID NO: 6            moltype = AA  length = 31
FEATURE                 Location/Qualifiers
REGION                  1..31
                        note = GLP-1 receptor agonist
source                  1..31
                        mol_type = protein
```

```
                                organism = synthetic construct
SEQUENCE: 6
HGEGTFTSDV SSYLEEQAAR KFIEWLVRGK G                                         31

SEQ ID NO: 7              moltype = AA   length = 31
FEATURE                   Location/Qualifiers
REGION                    1..31
                          note = GLP-1 receptor agonist
MOD_RES                   2
                          note = Xaa is Aib (alpha-aminoisobutyryl)
source                    1..31
                          mol_type = protein
                          organism = synthetic construct
SEQUENCE: 7
HXEGTFTSDV SSYLEGQAAK EFIAWLVRGR K                                         31

SEQ ID NO: 8              moltype = AA   length = 31
FEATURE                   Location/Qualifiers
REGION                    1..31
                          note = GLP-1 receptor agonist
MOD_RES                   2
                          note = Xaa is Aib (alpha-aminoisobutyryl)
source                    1..31
                          mol_type = protein
                          organism = synthetic construct
SEQUENCE: 8
HXEGTFTSDV SSYLEGQAAR KFIAWLVRGR G                                         31

SEQ ID NO: 9              moltype = AA   length = 31
FEATURE                   Location/Qualifiers
REGION                    1..31
                          note = GLP-1 receptor agonist
MOD_RES                   2
                          note = Xaa is Aib (alpha-aminoisobutyryl)
source                    1..31
                          mol_type = protein
                          organism = synthetic construct
SEQUENCE: 9
HXEGTFTSDV SSYLEEQAAR KFIAWLVRGR G                                         31

SEQ ID NO: 10             moltype = AA   length = 31
FEATURE                   Location/Qualifiers
REGION                    1..31
                          note = GLP-1 receptor agonist
MOD_RES                   2
                          note = Xaa is Aib (alpha-aminoisobutyryl)
source                    1..31
                          mol_type = protein
                          organism = synthetic construct
SEQUENCE: 10
HXEGTFTSDV SSYLEGQAAK EFIAWLVRGK G                                         31

SEQ ID NO: 11             moltype = AA   length = 31
FEATURE                   Location/Qualifiers
REGION                    1..31
                          note = GLP-1 receptor agonist
MOD_RES                   2
                          note = Xaa is Aib (alpha-aminoisobutyryl)
source                    1..31
                          mol_type = protein
                          organism = synthetic construct
SEQUENCE: 11
HXEGTFTSDV SSYLEEQAAR KFIAWLVRGK G                                         31

SEQ ID NO: 12             moltype = AA   length = 31
FEATURE                   Location/Qualifiers
REGION                    1..31
                          note = GLP-1 receptor agonist
MOD_RES                   2
                          note = Xaa is Aib (alpha-aminoisobutyryl)
source                    1..31
                          mol_type = protein
                          organism = synthetic construct
SEQUENCE: 12
HXEGTFTSDV SSYLEEQAAR KFIAWLVKGR G                                         31

SEQ ID NO: 13             moltype = AA   length = 31
FEATURE                   Location/Qualifiers
REGION                    1..31
```

```
                         note = GLP-1 receptor agonist
MOD_RES                  2
                         note = Xaa is Aib (alpha-aminoisobutyryl)
source                   1..31
                         mol_type = protein
                         organism = synthetic construct
SEQUENCE: 13
HXEGTFTSDV SSYLEGQAAR EFIAWLVRGR K                                       31

SEQ ID NO: 14            moltype = AA   length = 31
FEATURE                  Location/Qualifiers
REGION                   1..31
                         note = GLP-1 receptor agonist
MOD_RES                  2
                         note = Xaa is Aib (alpha-aminoisobutyryl)
source                   1..31
                         mol_type = protein
                         organism = synthetic construct
SEQUENCE: 14
HXEGTFTSDV SSYLEEQAAR KFIEWLVRGK G                                       31

SEQ ID NO: 15            moltype = AA   length = 31
FEATURE                  Location/Qualifiers
REGION                   1..31
                         note = GLP-1 receptor agonist
source                   1..31
                         mol_type = protein
                         organism = synthetic construct
SEQUENCE: 15
HWEGTFTSDV SSYLEEQAAR KFIEWLVRGK G                                       31

SEQ ID NO: 16            moltype = AA   length = 29
FEATURE                  Location/Qualifiers
REGION                   1..29
                         note = GLP-1 receptor agonist
MOD_RES                  2
                         note = Xaa is Aib (alpha-aminoisobutyryl)
source                   1..29
                         mol_type = protein
                         organism = synthetic construct
SEQUENCE: 16
HXEGTFTSDV SSYLEEQAAR EFIAWLVRG                                          29

SEQ ID NO: 17            moltype = AA   length = 31
FEATURE                  Location/Qualifiers
REGION                   1..31
                         note = GLP-1 receptor agonist
MOD_RES                  2
                         note = Xaa is Aib (alpha-aminoisobutyryl)
source                   1..31
                         mol_type = protein
                         organism = synthetic construct
SEQUENCE: 17
HXEGTFTSDV SSYLEEQAAR EFIAWLVRGR K                                       31

SEQ ID NO: 18            moltype = AA   length = 31
FEATURE                  Location/Qualifiers
REGION                   1..31
                         note = GLP-1 receptor agonist
MOD_RES                  2
                         note = Xaa is Aib (alpha-aminoisobutyryl)
source                   1..31
                         mol_type = protein
                         organism = synthetic construct
SEQUENCE: 18
HXEGTFTSDV SSYLEEQAAR KFIAWLVRGR K                                       31

SEQ ID NO: 19            moltype = AA   length = 31
FEATURE                  Location/Qualifiers
REGION                   1..31
                         note = GLP-1 receptor agonist
MOD_RES                  1
                         note = Xaa is Imp (imidazole propionyl)
MOD_RES                  2
                         note = Xaa is Aib (alpha-aminoisobutyryl)
source                   1..31
                         mol_type = protein
                         organism = synthetic construct
SEQUENCE: 19
```

```
XXEGTFTSDV SSYLEEQAAR EFIAWLVRGR K                                    31

SEQ ID NO: 20           moltype = AA   length = 31
FEATURE                 Location/Qualifiers
REGION                  1..31
                        note = GLP-1 receptor agonist
MOD_RES                 2
                        note = Xaa is Aib (alpha-aminoisobutyryl)
source                  1..31
                        mol_type = protein
                        organism = synthetic construct
SEQUENCE: 20
HXEGTFTSDV SSYLEEQAAR KFIEWLVRGR K                                    31

SEQ ID NO: 21           moltype = AA   length = 31
FEATURE                 Location/Qualifiers
REGION                  1..31
                        note = GLP-1 receptor agonist
MOD_RES                 2
                        note = Xaa is Aib (alpha-aminoisobutyryl)
source                  1..31
                        mol_type = protein
                        organism = synthetic construct
SEQUENCE: 21
HXEGTFTSDV SSYLEEQAAR EFIAWLVRGK G                                    31

SEQ ID NO: 22           moltype = AA   length = 31
FEATURE                 Location/Qualifiers
REGION                  1..31
                        note = GLP-1 receptor agonist
MOD_RES                 2
                        note = Xaa is Aib (alpha-aminoisobutyryl)
source                  1..31
                        mol_type = protein
                        organism = synthetic construct
SEQUENCE: 22
HXEGTFTSDV SSYLEEQAAR EFIAWLVKGR G                                    31

SEQ ID NO: 23           moltype = AA   length = 31
FEATURE                 Location/Qualifiers
REGION                  1..31
                        note = GLP-1 receptor agonist
MOD_RES                 2
                        note = Xaa is Aib (alpha-aminoisobutyryl)
source                  1..31
                        mol_type = protein
                        organism = synthetic construct
SEQUENCE: 23
HXEGTFTSDV SSYLEEQAAR EFIAWLVRGR G                                    31

SEQ ID NO: 24           moltype = AA   length = 31
FEATURE                 Location/Qualifiers
REGION                  1..31
                        note = GLP-1 receptor agonist
MOD_RES                 2
                        note = Xaa is Aib (alpha-aminoisobutyryl)
source                  1..31
                        mol_type = protein
                        organism = synthetic construct
SEQUENCE: 24
HXEGTFTSDV SSYLEEQAAR EFIEWLVRGK G                                    31

SEQ ID NO: 25           moltype = AA   length = 30
FEATURE                 Location/Qualifiers
REGION                  1..30
                        note = GLP-1 receptor agonist
MOD_RES                 2
                        note = Xaa is Aib (alpha-aminoisobutyryl)
source                  1..30
                        mol_type = protein
                        organism = synthetic construct
SEQUENCE: 25
HXEGTFTSDV SSYLEEQAAR EFIEWLVRGK                                      30

SEQ ID NO: 26           moltype = AA   length = 31
FEATURE                 Location/Qualifiers
REGION                  1..31
                        note = GLP-1 receptor agonist
MOD_RES                 2
```

```
                             note = Xaa is Aib (alpha-aminoisobutyryl)
source                       1..31
                             mol_type = protein
                             organism = synthetic construct
SEQUENCE: 26
HXEGTFTSDV SSYLEEQAAR EFIEWLVRGR K                                          31

SEQ ID NO: 27                moltype = AA  length = 31
FEATURE                      Location/Qualifiers
REGION                       1..31
                             note = GLP-1 receptor agonist
source                       1..31
                             mol_type = protein
                             organism = synthetic construct
SEQUENCE: 27
HWEGTFTSDV SSYLEEQAAR KFIEWLVRGR G                                          31

SEQ ID NO: 28                moltype = AA  length = 31
FEATURE                      Location/Qualifiers
REGION                       1..31
                             note = GLP-1 receptor agonist
source                       1..31
                             mol_type = protein
                             organism = synthetic construct
SEQUENCE: 28
HWEGTFTSDV SSYLEEQAAR EFIEWLVRGK G                                          31

SEQ ID NO: 29                moltype = AA  length = 31
FEATURE                      Location/Qualifiers
REGION                       1..31
                             note = GLP-1 receptor agonist
source                       1..31
                             mol_type = protein
                             organism = synthetic construct
MOD_RES                      2
                             note = Xaa is Aib (alpha-aminoisobutyryl)
SEQUENCE: 29
HXEGTFTSDV SSYLEEQAAR EFIAWLVRGK K                                          31

SEQ ID NO: 30                moltype = AA  length = 31
FEATURE                      Location/Qualifiers
REGION                       1..31
                             note = GLP-1 receptor agonist
MOD_RES                      2
                             note = Xaa is Aib (alpha-aminoisobutyryl)
source                       1..31
                             mol_type = protein
                             organism = synthetic construct
SEQUENCE: 30
HXEGTFTSDK SSYLEEQAAR EFIAWLVRGR G                                          31

SEQ ID NO: 31                moltype = AA  length = 31
FEATURE                      Location/Qualifiers
REGION                       1..31
                             note = GLP-1 receptor agonist
source                       1..31
                             mol_type = protein
                             organism = synthetic construct
MOD_RES                      2
                             note = Xaa is Aib (alpha-aminoisobutyryl)
SEQUENCE: 31
HXEGTFTSDV SSYLEEKAAR EFIAWLVRGR G                                          31

SEQ ID NO: 32                moltype = AA  length = 31
FEATURE                      Location/Qualifiers
REGION                       1..31
                             note = GLP-1 receptor agonist
source                       1..31
                             mol_type = protein
                             organism = synthetic construct
SEQUENCE: 32
HWEGTFTSDV SSYLEEQAAR EFIAWLVRGR K                                          31

SEQ ID NO: 33                moltype = AA  length = 31
FEATURE                      Location/Qualifiers
REGION                       1..31
                             note = GLP-1 receptor agonist
source                       1..31
                             mol_type = protein
```

-continued

```
                        organism = synthetic construct
SEQUENCE: 33
HWEGTFTSDV SSYLEEQAAR EFIEWLVRGR K                                              31

SEQ ID NO: 34           moltype = AA   length = 31
FEATURE                 Location/Qualifiers
REGION                  1..31
                        note = GLP-1 receptor agonist
source                  1..31
                        mol_type = protein
                        organism = synthetic construct
SEQUENCE: 34
HWEGTFTSDV SSYLEEKAAR EFIEWLVRGR G                                              31

SEQ ID NO: 35           moltype = AA   length = 31
FEATURE                 Location/Qualifiers
REGION                  1..31
                        note = GLP-1 receptor agonist
source                  1..31
                        mol_type = protein
                        organism = synthetic construct
SEQUENCE: 35
HWEGTFTSDK SSYLEEQAAR EFIEWLVRGR G                                              31

SEQ ID NO: 36           moltype = AA   length = 31
FEATURE                 Location/Qualifiers
REGION                  1..31
                        note = GLP-1 receptor agonist
MOD_RES                 2
                        note = Xaa is Aib (alpha-aminoisobutyryl)
source                  1..31
                        mol_type = protein
                        organism = synthetic construct
SEQUENCE: 36
HXEGTFTSDV SSYLEKQAAR EFIAWLVRGR G                                              31

SEQ ID NO: 37           moltype = AA   length = 31
FEATURE                 Location/Qualifiers
REGION                  1..31
                        note = GLP-1 receptor agonist
source                  1..31
                        mol_type = protein
                        organism = synthetic construct
MOD_RES                 2
                        note = Xaa is Aib (alpha-aminoisobutyryl)
SEQUENCE: 37
HXEGTFTSDV SSYLEEQAAR EFIAWLVRKR G                                              31

SEQ ID NO: 38           moltype = AA   length = 31
FEATURE                 Location/Qualifiers
REGION                  1..31
                        note = GLP-1 receptor agonist
source                  1..31
                        mol_type = protein
                        organism = synthetic construct
SEQUENCE: 38
HAEGTFTSDV SSYLEEKAAR EFIEWLVRGR G                                              31

SEQ ID NO: 39           moltype = AA   length = 31
FEATURE                 Location/Qualifiers
REGION                  1..31
                        note = GLP-1 receptor agonist
MOD_RES                 2
                        note = Xaa is Aib (alpha-aminoisobutyryl)
source                  1..31
                        mol_type = protein
                        organism = synthetic construct
SEQUENCE: 39
HXEGTFTSDV SSYLEEKAAR EFIEWLVRGR G                                              31

SEQ ID NO: 40           moltype = AA   length = 31
FEATURE                 Location/Qualifiers
REGION                  1..31
                        note = GLP-1 receptor agonist
source                  1..31
                        mol_type = protein
                        organism = synthetic construct
SEQUENCE: 40
HAEGTFTSKV SSYLEEQAAR EFIEWLVRGR G                                              31
```

```
SEQ ID NO: 41              moltype = AA   length = 31
FEATURE                    Location/Qualifiers
REGION                     1..31
                           note = GLP-1 receptor agonist
MOD_RES                    2
                           note = Xaa is Aib (alpha-aminoisobutyryl)
source                     1..31
                           mol_type = protein
                           organism = synthetic construct
SEQUENCE: 41
HXEGTFTSKV SSYLEEQAAR EFIEWLVRGR G                                31

SEQ ID NO: 42              moltype = AA   length = 31
FEATURE                    Location/Qualifiers
REGION                     1..31
                           note = GLP-1 receptor agonist
source                     1..31
                           mol_type = protein
                           organism = synthetic construct
SEQUENCE: 42
HAEGTFTSDK SSYLEEQAAR EFIEWLVRGR G                                31

SEQ ID NO: 43              moltype = AA   length = 31
FEATURE                    Location/Qualifiers
REGION                     1..31
                           note = GLP-1 receptor agonist
source                     1..31
                           mol_type = protein
                           organism = synthetic construct
SEQUENCE: 43
HWEGTFTSDV SSYLEEQAAK EFIEWLVRGR G                                31

SEQ ID NO: 44              moltype = AA   length = 31
FEATURE                    Location/Qualifiers
REGION                     1..31
                           note = GLP-1 receptor agonist
source                     1..31
                           mol_type = protein
                           organism = synthetic construct
MOD_RES                    2
                           note = Xaa is Aib (alpha-aminoisobutyryl)
SEQUENCE: 44
HXEGTFTSDV SSYLEEQAAK EFIEWLVRGR G                                31

SEQ ID NO: 45              moltype = AA   length = 31
FEATURE                    Location/Qualifiers
REGION                     1..31
                           note = GLP-1 receptor agonist
MOD_RES                    2
                           note = Xaa is Aib (alpha-aminoisobutyryl)
source                     1..31
                           mol_type = protein
                           organism = synthetic construct
SEQUENCE: 45
HXEGTFTSDV SSYLEEQAAR KFIEWLVRGR G                                31

SEQ ID NO: 46              moltype = AA   length = 31
FEATURE                    Location/Qualifiers
REGION                     1..31
                           note = GLP-1 receptor agonist
MOD_RES                    2
                           note = Xaa is Aib (alpha-aminoisobutyryl)
source                     1..31
                           mol_type = protein
                           organism = synthetic construct
SEQUENCE: 46
HXEGTFTSDK SSYLEEQAAR EFIEWLVRGR G                                31

SEQ ID NO: 47              moltype = AA   length = 31
FEATURE                    Location/Qualifiers
REGION                     1..31
                           note = GLP-1 receptor agonist
source                     1..31
                           mol_type = protein
                           organism = synthetic construct
SEQUENCE: 47
HAEGTFTSDK SSYLEEKAAR EFIEWLVRGR G                                31
```

```
SEQ ID NO: 48              moltype = AA  length = 31
FEATURE                    Location/Qualifiers
REGION                     1..31
                           note = GLP-1 receptor agonist
source                     1..31
                           mol_type = protein
                           organism = synthetic construct
SEQUENCE: 48
HAEGTFTSDV SKYLEEQAVR EFIAKLVRGR G                                    31

SEQ ID NO: 49              moltype = AA  length = 31
FEATURE                    Location/Qualifiers
REGION                     1..31
                           note = GLP-1 receptor agonist
source                     1..31
                           mol_type = protein
                           organism = synthetic construct
MOD_RES                    2
                           note = Xaa is Aib (alpha-aminoisobutyryl)
SEQUENCE: 49
HXEGTFTSDV SKYLEEQAVR EFIAKLVRGR G                                    31

SEQ ID NO: 50              moltype = AA  length = 31
FEATURE                    Location/Qualifiers
REGION                     1..31
                           note = GLP-1 receptor agonist
MOD_RES                    2
                           note = Xaa is Aib (alpha-aminoisobutyryl)
source                     1..31
                           mol_type = protein
                           organism = synthetic construct
SEQUENCE: 50
HXEGTFTSDV SSYLEEQAAR EFIAWLVRGR P                                    31

SEQ ID NO: 51              moltype = AA  length = 31
FEATURE                    Location/Qualifiers
REGION                     1..31
                           note = GLP-1 receptor agonist
MOD_RES                    2
                           note = Xaa is Aib (alpha-aminoisobutyryl)
source                     1..31
                           mol_type = protein
                           organism = synthetic construct
SEQUENCE: 51
HXEGTFTSDV SRYLEEQAAR EFIEWLVRGR K                                    31

SEQ ID NO: 52              moltype = AA  length = 31
FEATURE                    Location/Qualifiers
REGION                     1..31
                           note = GLP-1 receptor agonist
MOD_RES                    2
                           note = Xaa is Aib (alpha-aminoisobutyryl)
source                     1..31
                           mol_type = protein
                           organism = synthetic construct
SEQUENCE: 52
HXEGTFTSDV SKYLEEQAAR KFIAWLVRGR G                                    31

SEQ ID NO: 53              moltype = AA  length = 31
FEATURE                    Location/Qualifiers
REGION                     1..31
                           note = GLP-1 receptor agonist
MOD_RES                    2
                           note = Xaa is Aib (alpha-aminoisobutyryl)
source                     1..31
                           mol_type = protein
                           organism = synthetic construct
SEQUENCE: 53
HXEGTFTSDV SKYLEEQAAR EFIAWLVRGR G                                    31

SEQ ID NO: 54              moltype = AA  length = 31
FEATURE                    Location/Qualifiers
REGION                     1..31
                           note = GLP-1 receptor agonist
source                     1..31
                           mol_type = protein
                           organism = synthetic construct
MOD_RES                    2
                           note = Xaa is Aib (alpha-aminoisobutyryl)
```

```
SEQUENCE: 54
HXEGTFTSDV SKYLEEQAAR EFIAWLVRGR K                                31

SEQ ID NO: 55           moltype = AA  length = 31
FEATURE                 Location/Qualifiers
REGION                  1..31
                        note = GLP-1 receptor agonist
source                  1..31
                        mol_type = protein
                        organism = synthetic construct
SEQUENCE: 55
HGEGTFTSDV SSYLEGQAAK EFIAWLVRGR G                                31

SEQ ID NO: 56           moltype = AA  length = 31
FEATURE                 Location/Qualifiers
REGION                  1..31
                        note = GLP-1 receptor agonist
MOD_RES                 2
                        note = Xaa is Aib (alpha-aminoisobutyryl)
source                  1..31
                        mol_type = protein
                        organism = synthetic construct
SEQUENCE: 56
HXEGTFTSDV SKYLEEQAAR KFIAWLVRGR Q                                31

SEQ ID NO: 57           moltype = AA  length = 31
FEATURE                 Location/Qualifiers
REGION                  1..31
                        note = GLP-1 receptor agonist
MOD_RES                 2
                        note = Xaa is Aib (alpha-aminoisobutyryl)
source                  1..31
                        mol_type = protein
                        organism = synthetic construct
SEQUENCE: 57
HXEGTFTSDV SKYLEEQAAR KFIEWLVRGR G                                31

SEQ ID NO: 58           moltype = AA  length = 30
FEATURE                 Location/Qualifiers
REGION                  1..30
                        note = GLP-1 receptor agonist
MOD_RES                 2
                        note = Xaa is Aib (alpha-aminoisobutyryl)
source                  1..30
                        mol_type = protein
                        organism = synthetic construct
SEQUENCE: 58
HXEGTFTSDV SSYLEEQAAR KFIAWLVRGG                                  30

SEQ ID NO: 59           moltype = AA  length = 29
FEATURE                 Location/Qualifiers
REGION                  1..29
                        note = GLP-1 receptor agonist
MOD_RES                 2
                        note = Xaa is Aib (alpha-aminoisobutyryl)
source                  1..29
                        mol_type = protein
                        organism = synthetic construct
SEQUENCE: 59
HXEGTFTSDV SSYLEEQAAR KFIEWLVRG                                   29

SEQ ID NO: 60           moltype = AA  length = 31
FEATURE                 Location/Qualifiers
REGION                  1..31
                        note = GLP-1 receptor agonist
MOD_RES                 2
                        note = Xaa is Aib (alpha-aminoisobutyryl)
source                  1..31
                        mol_type = protein
                        organism = synthetic construct
SEQUENCE: 60
HXEGTFTSDV SKYLEEQAAR KFIEWLVRGA A                                31

SEQ ID NO: 61           moltype = AA  length = 31
FEATURE                 Location/Qualifiers
REGION                  1..31
                        note = GLP-1 receptor agonist
MOD_RES                 2
                        note = Xaa is Aib (alpha-aminoisobutyryl)
```

```
source                  1..31
                        mol_type = protein
                        organism = synthetic construct
SEQUENCE: 61
HXEGTFTSDV SKYLEEQAAR EFIEWLVRGA A                              31

SEQ ID NO: 62           moltype = AA  length = 31
FEATURE                 Location/Qualifiers
REGION                  1..31
                        note = GLP-1 receptor agonist
source                  1..31
                        mol_type = protein
                        organism = synthetic construct
MOD_RES                 2
                        note = Xaa is Aib (alpha-aminoisobutyryl)
SEQUENCE: 62
HXEGTFTSDV SKYLEEQAAR KFIAWLVRGR K                              31

SEQ ID NO: 63           moltype = AA  length = 31
FEATURE                 Location/Qualifiers
REGION                  1..31
                        note = GLP-1 receptor agonist
MOD_RES                 2
                        note = Xaa is Aib (alpha-aminoisobutyryl)
source                  1..31
                        mol_type = protein
                        organism = synthetic construct
SEQUENCE: 63
HXEGTFTSDV SSYLEEQAAR KFIEWLVRGR Q                              31

SEQ ID NO: 64           moltype = AA  length = 31
FEATURE                 Location/Qualifiers
REGION                  1..31
                        note = GLP-1 receptor agonist
MOD_RES                 2
                        note = Xaa is Aib (alpha-aminoisobutyryl)
source                  1..31
                        mol_type = protein
                        organism = synthetic construct
SEQUENCE: 64
HXEGTFTSDV SSYLEGQAAK EIFAWLVRGR G                              31

SEQ ID NO: 65           moltype = AA  length = 31
FEATURE                 Location/Qualifiers
REGION                  1..31
                        note = GLP-1 receptor agonist
MOD_RES                 2
                        note = Xaa is Aib (alpha-aminoisobutyryl)
source                  1..31
                        mol_type = protein
                        organism = synthetic construct
SEQUENCE: 65
HXEGTFTSDV SSYLEGQAAK EIFAWLVRGR K                              31

SEQ ID NO: 66           moltype = AA  length = 31
FEATURE                 Location/Qualifiers
REGION                  1..31
                        note = GLP-1 receptor agonist
MOD_RES                 2
                        note = Xaa is Aib (alpha-aminoisobutyryl)
source                  1..31
                        mol_type = protein
                        organism = synthetic construct
SEQUENCE: 66
HXEGTFTSDV SSYLEEQAAR EIFAWLVRGR K                              31

SEQ ID NO: 67           moltype = AA  length = 31
FEATURE                 Location/Qualifiers
REGION                  1..31
                        note = GLP-1 receptor agonist
source                  1..31
                        mol_type = protein
                        organism = synthetic construct
SEQUENCE: 67
HWEGTFTSDV SSYLEEQAAR KIFEWLVRGK G                              31

SEQ ID NO: 68           moltype = AA  length = 31
FEATURE                 Location/Qualifiers
REGION                  1..31
```

```
                        note = GLP-1 receptor agonist
MOD_RES                 2
                        note = Xaa is Aib (alpha-aminoisobutyryl)
source                  1..31
                        mol_type = protein
                        organism = synthetic construct
SEQUENCE: 68
HXEGTFTSDV SSYLEEQAAR KIFEWLVRGK G                              31

SEQ ID NO: 69           moltype = AA  length = 31
FEATURE                 Location/Qualifiers
REGION                  1..31
                        note = GLP-1 receptor agonist
MOD_RES                 2
                        note = Xaa is Aib (alpha-aminoisobutyryl)
source                  1..31
                        mol_type = protein
                        organism = synthetic construct
SEQUENCE: 69
HXEGTFTSDV SSYLEEQAAR KIFAWLVRGK G                              31

SEQ ID NO: 70           moltype = AA  length = 31
FEATURE                 Location/Qualifiers
REGION                  1..31
                        note = GLP-1 receptor agonist
MOD_RES                 2
                        note = Xaa is Aib (alpha-aminoisobutyryl)
source                  1..31
                        mol_type = protein
                        organism = synthetic construct
SEQUENCE: 70
HXEGTFTSDV SSYLEEQAAR KIFAWLVRGR K                              31

SEQ ID NO: 71           moltype = AA  length = 31
FEATURE                 Location/Qualifiers
REGION                  1..31
                        note = GLP-1 receptor agonist
MOD_RES                 2
                        note = Xaa is Aib (alpha-aminoisobutyryl)
source                  1..31
                        mol_type = protein
                        organism = synthetic construct
SEQUENCE: 71
HXEGTFTSDV SSYLEEQAAR KIFAWLVRGR G                              31

SEQ ID NO: 72           moltype = AA  length = 31
FEATURE                 Location/Qualifiers
REGION                  1..31
                        note = GLP-1 receptor agonist
source                  1..31
                        mol_type = protein
                        organism = synthetic construct
SEQUENCE: 72
HAEGTFTSDK SSYLEEQAAR EIFEWLVRGR G                              31

SEQ ID NO: 73           moltype = AA  length = 31
FEATURE                 Location/Qualifiers
REGION                  1..31
                        note = GLP-1 receptor agonist
MOD_RES                 2
                        note = Xaa is Aib (alpha-aminoisobutyryl)
source                  1..31
                        mol_type = protein
                        organism = synthetic construct
SEQUENCE: 73
HXEGTFTSDK SSYLEEQAAR EIFEWLVRGR G                              31

SEQ ID NO: 74           moltype = AA  length = 31
FEATURE                 Location/Qualifiers
REGION                  1..31
                        note = GLP-1 receptor agonist
source                  1..31
                        mol_type = protein
                        organism = synthetic construct
SEQUENCE: 74
HWEGTFTSDV SSYLEEQAAR KIFEWLVRGR G                              31

SEQ ID NO: 75           moltype = AA  length = 31
FEATURE                 Location/Qualifiers
```

```
                        REGION          1..31
                                        note = GLP-1 receptor agonist
                        MOD_RES         2
                                        note = Xaa is Aib (alpha-aminoisobutyryl)
                        source          1..31
                                        mol_type = protein
                                        organism = synthetic construct
SEQUENCE: 75
HXEGTFTSDV SSYLEGQAAR EIFAWLVRGR G                                              31

SEQ ID NO: 76           moltype = AA  length = 31
FEATURE                 Location/Qualifiers
REGION                  1..31
                        note = GLP-1 receptor agonist
source                  1..31
                        mol_type = protein
                        organism = synthetic construct
MOD_RES                 2
                        note = Xaa is Aib (alpha-aminoisobutyryl)
SEQUENCE: 76
HXEGTFTSDV SKYLEEQAAR KIFAWLVRGR G                                              31

SEQ ID NO: 77           moltype = AA  length = 31
FEATURE                 Location/Qualifiers
REGION                  1..31
                        note = GLP-1 receptor agonist
MOD_RES                 2
                        note = Xaa is Aib (alpha-aminoisobutyryl)
source                  1..31
                        mol_type = protein
                        organism = synthetic construct
SEQUENCE: 77
HXEGTFTSDV SKYLEEQAAR EIFAWLVRGR G                                              31

SEQ ID NO: 78           moltype = AA  length = 31
FEATURE                 Location/Qualifiers
REGION                  1..31
                        note = GLP-1 receptor agonist
source                  1..31
                        mol_type = protein
                        organism = synthetic construct
SEQUENCE: 78
HWEGTFTSDV SSYLEEQAAR EIFAWLVRGR K                                              31

SEQ ID NO: 79           moltype = AA  length = 32
FEATURE                 Location/Qualifiers
REGION                  1..32
                        note = Amylin receptor agonist
source                  1..32
                        mol_type = protein
                        organism = synthetic construct
SEQUENCE: 79
ASELSTAALG RLSAELHELA TLPRTETGSG SP                                             32

SEQ ID NO: 80           moltype = AA  length = 32
FEATURE                 Location/Qualifiers
REGION                  1..32
                        note = Amylin receptor agonist
source                  1..32
                        mol_type = protein
                        organism = synthetic construct
SEQUENCE: 80
RKELSTAALG RLSAELHELA TLPRTETGSG SP                                             32

SEQ ID NO: 81           moltype = AA  length = 32
FEATURE                 Location/Qualifiers
REGION                  1..32
                        note = Amylin receptor agonist
source                  1..32
                        mol_type = protein
                        organism = synthetic construct
SEQUENCE: 81
ASRLSTEALG RLSAELHELA TLPRTETGSG SP                                             32

SEQ ID NO: 82           moltype = AA  length = 32
FEATURE                 Location/Qualifiers
REGION                  1..32
                        note = Amylin receptor agonist
source                  1..32
```

```
                        mol_type = protein
                        organism = synthetic construct
SEQUENCE: 82
ASELSTAALG RLSKELHELA TLPRTETGSG SP                              32

SEQ ID NO: 83           moltype = AA   length = 32
FEATURE                 Location/Qualifiers
REGION                  1..32
                        note = Amylin receptor agonist
source                  1..32
                        mol_type = protein
                        organism = synthetic construct
SEQUENCE: 83
ASELSTAALG RLSAELHELK TLPRTETGSG SP                              32

SEQ ID NO: 84           moltype = AA   length = 32
FEATURE                 Location/Qualifiers
REGION                  1..32
                        note = Amylin receptor agonist
source                  1..32
                        mol_type = protein
                        organism = synthetic construct
SEQUENCE: 84
ASELSTAALG RLSAELHKLA TLPRTETGSG SP                              32

SEQ ID NO: 85           moltype = AA   length = 32
FEATURE                 Location/Qualifiers
REGION                  1..32
                        note = Amylin receptor agonist
source                  1..32
                        mol_type = protein
                        organism = synthetic construct
SEQUENCE: 85
ASELSTAALG RLSAELHELA TLKRTETGSG SP                              32

SEQ ID NO: 86           moltype = AA   length = 32
FEATURE                 Location/Qualifiers
REGION                  1..32
                        note = Amylin receptor agonist
source                  1..32
                        mol_type = protein
                        organism = synthetic construct
SEQUENCE: 86
ASELSTAALG RLSAELHELA TLPRTETGKG SP                              32

SEQ ID NO: 87           moltype = AA   length = 32
FEATURE                 Location/Qualifiers
REGION                  1..32
                        note = Amylin receptor agonist
source                  1..32
                        mol_type = protein
                        organism = synthetic construct
SEQUENCE: 87
ASELSTAALG RLSAELHQLA TLPRTETGSG SP                              32

SEQ ID NO: 88           moltype = AA   length = 32
FEATURE                 Location/Qualifiers
REGION                  1..32
                        note = Amylin receptor agonist
source                  1..32
                        mol_type = protein
                        organism = synthetic construct
SEQUENCE: 88
ASELSTAALG RPSAELHELA TLPRTETGSG SP                              32

SEQ ID NO: 89           moltype = AA   length = 4
FEATURE                 Location/Qualifiers
REGION                  1..4
                        note = Optional peptide linker
source                  1..4
                        mol_type = protein
                        organism = synthetic construct
SEQUENCE: 89
EGGE                                                             4

SEQ ID NO: 90           moltype = AA   length = 4
FEATURE                 Location/Qualifiers
REGION                  1..4
                        note = Optional peptide linker
```

```
source                     1..4
                           mol_type = protein
                           organism = synthetic construct
SEQUENCE: 90
GGGE                                                                    4

SEQ ID NO: 91              moltype = AA  length = 4
FEATURE                    Location/Qualifiers
REGION                     1..4
                           note = Optional peptide linker
source                     1..4
                           mol_type = protein
                           organism = synthetic construct
SEQUENCE: 91
GGGG                                                                    4

SEQ ID NO: 92              moltype = AA  length = 4
FEATURE                    Location/Qualifiers
REGION                     1..4
                           note = Optional peptide linker
source                     1..4
                           mol_type = protein
                           organism = synthetic construct
SEQUENCE: 92
KGGG                                                                    4

SEQ ID NO: 93              moltype = AA  length = 5
FEATURE                    Location/Qualifiers
REGION                     1..5
                           note = Optional peptide linker
source                     1..5
                           mol_type = protein
                           organism = synthetic construct
SEQUENCE: 93
EAEAE                                                                   5

SEQ ID NO: 94              moltype = AA  length = 5
FEATURE                    Location/Qualifiers
REGION                     1..5
                           note = Optional peptide linker
source                     1..5
                           mol_type = protein
                           organism = synthetic construct
SEQUENCE: 94
GGGGE                                                                   5

SEQ ID NO: 95              moltype = AA  length = 6
FEATURE                    Location/Qualifiers
REGION                     1..6
                           note = Optional peptide linker
source                     1..6
                           mol_type = protein
                           organism = synthetic construct
SEQUENCE: 95
EGEGEE                                                                  6

SEQ ID NO: 96              moltype = AA  length = 6
FEATURE                    Location/Qualifiers
REGION                     1..6
                           note = Optional peptide linker
source                     1..6
                           mol_type = protein
                           organism = synthetic construct
SEQUENCE: 96
EGGGGG                                                                  6

SEQ ID NO: 97              moltype = AA  length = 6
FEATURE                    Location/Qualifiers
REGION                     1..6
                           note = Optional peptide linker
source                     1..6
                           mol_type = protein
                           organism = synthetic construct
SEQUENCE: 97
KGGGGE                                                                  6

SEQ ID NO: 98              moltype = AA  length = 7
FEATURE                    Location/Qualifiers
REGION                     1..7
```

```
                        note = Optional peptide linker
source                  1..7
                        mol_type = protein
                        organism = synthetic construct
SEQUENCE: 98
EGEGEKE                                                                        7

SEQ ID NO: 99           moltype = AA  length = 7
FEATURE                 Location/Qualifiers
REGION                  1..7
                        note = Optional peptide linker
source                  1..7
                        mol_type = protein
                        organism = synthetic construct
SEQUENCE: 99
EGGGGGE                                                                        7

SEQ ID NO: 100          moltype = AA  length = 7
FEATURE                 Location/Qualifiers
REGION                  1..7
                        note = Optional peptide linker
source                  1..7
                        mol_type = protein
                        organism = synthetic construct
SEQUENCE: 100
EGQEPGG                                                                        7

SEQ ID NO: 101          moltype = AA  length = 8
FEATURE                 Location/Qualifiers
REGION                  1..8
                        note = Optional peptide linker
source                  1..8
                        mol_type = protein
                        organism = synthetic construct
SEQUENCE: 101
QEPGQAPE                                                                       8

SEQ ID NO: 102          moltype = AA  length = 8
FEATURE                 Location/Qualifiers
REGION                  1..8
                        note = Optional peptide linker
source                  1..8
                        mol_type = protein
                        organism = synthetic construct
SEQUENCE: 102
QAPGQEPE                                                                       8

SEQ ID NO: 103          moltype = AA  length = 8
FEATURE                 Location/Qualifiers
REGION                  1..8
                        note = Optional peptide linker
source                  1..8
                        mol_type = protein
                        organism = synthetic construct
SEQUENCE: 103
QEPKGQAP                                                                       8

SEQ ID NO: 104          moltype = AA  length = 8
FEATURE                 Location/Qualifiers
REGION                  1..8
                        note = Optional peptide linker
source                  1..8
                        mol_type = protein
                        organism = synthetic construct
SEQUENCE: 104
GGGGGGGK                                                                       8

SEQ ID NO: 105          moltype = AA  length = 9
FEATURE                 Location/Qualifiers
REGION                  1..9
                        note = Optional peptide linker
source                  1..9
                        mol_type = protein
                        organism = synthetic construct
SEQUENCE: 105
GGGGSGGGE                                                                      9

SEQ ID NO: 106          moltype = AA  length = 9
FEATURE                 Location/Qualifiers
```

```
REGION                  1..9
                        note = Optional peptide linker
source                  1..9
                        mol_type = protein
                        organism = synthetic construct
SEQUENCE: 106
GQEPGQEPE                                                                       9

SEQ ID NO: 107          moltype = AA   length = 9
FEATURE                 Location/Qualifiers
REGION                  1..9
                        note = Optional peptide linker
source                  1..9
                        mol_type = protein
                        organism = synthetic construct
SEQUENCE: 107
KQEPGQEPE                                                                       9

SEQ ID NO: 108          moltype = AA   length = 9
FEATURE                 Location/Qualifiers
REGION                  1..9
                        note = Optional peptide linker
source                  1..9
                        mol_type = protein
                        organism = synthetic construct
SEQUENCE: 108
GQEKGQEPE                                                                       9

SEQ ID NO: 109          moltype = AA   length = 9
FEATURE                 Location/Qualifiers
REGION                  1..9
                        note = Optional peptide linker
source                  1..9
                        mol_type = protein
                        organism = synthetic construct
SEQUENCE: 109
QEPGQAPKE                                                                       9

SEQ ID NO: 110          moltype = AA   length = 9
FEATURE                 Location/Qualifiers
REGION                  1..9
                        note = Optional peptide linker
source                  1..9
                        mol_type = protein
                        organism = synthetic construct
SEQUENCE: 110
QEPKGQAPE                                                                       9

SEQ ID NO: 111          moltype = AA   length = 9
FEATURE                 Location/Qualifiers
REGION                  1..9
                        note = GLP-1 receptor agonist
source                  1..9
                        mol_type = protein
                        organism = synthetic construct
SEQUENCE: 111
GGGGGGGGE                                                                       9

SEQ ID NO: 112          moltype = AA   length = 10
FEATURE                 Location/Qualifiers
REGION                  1..10
                        note = Optional peptide linker
source                  1..10
                        mol_type = protein
                        organism = synthetic construct
SEQUENCE: 112
GQEPGQEPKE                                                                     10

SEQ ID NO: 113          moltype = AA   length = 10
FEATURE                 Location/Qualifiers
REGION                  1..10
                        note = Optional peptide linker
source                  1..10
                        mol_type = protein
                        organism = synthetic construct
SEQUENCE: 113
KGQEPGQAPE                                                                     10

SEQ ID NO: 114          moltype = AA   length = 11
```

```
FEATURE                 Location/Qualifiers
REGION                  1..11
                        note = Optional peptide linker
source                  1..11
                        mol_type = protein
                        organism = synthetic construct
SEQUENCE: 114
EGGGGGGGGG E                                                              11

SEQ ID NO: 115          moltype = AA  length = 13
FEATURE                 Location/Qualifiers
REGION                  1..13
                        note = Optional peptide linker
source                  1..13
                        mol_type = protein
                        organism = synthetic construct
SEQUENCE: 115
GGGGGGGGGG GGE                                                            13

SEQ ID NO: 116          moltype = AA  length = 17
FEATURE                 Location/Qualifiers
REGION                  1..17
                        note = Optional peptide linker
source                  1..17
                        mol_type = protein
                        organism = synthetic construct
SEQUENCE: 116
GGGGGGGGGG GGGGGGE                                                        17

SEQ ID NO: 117          moltype = AA  length = 66
FEATURE                 Location/Qualifiers
REGION                  1..66
                        note = GLP-1-amylin receptor co-agonist
MOD_RES                 2
                        note = Xaa is Aib (alpha-aminoisobutyryl)
source                  1..66
                        mol_type = protein
                        organism = synthetic construct
SEQUENCE: 117
HXEGTFTSDV SSYLEGQAAK EFIAWLVRGR GGGEASELST AALGRLSAEL HELATLPRTE         60
TGSGSP                                                                    66

SEQ ID NO: 118          moltype = AA  length = 69
FEATURE                 Location/Qualifiers
REGION                  1..69
                        note = GLP-1-amylin receptor co-agonist
MOD_RES                 2
                        note = Xaa is Aib (alpha-aminoisobutyryl)
source                  1..69
                        mol_type = protein
                        organism = synthetic construct
SEQUENCE: 118
HXEGTFTSDV SSYLEGQAAR EFIAWLVRGK GEGEGEEASE LSTAALGRLS AELHELATLP         60
RTETGSGSP                                                                 69

SEQ ID NO: 119          moltype = AA  length = 70
FEATURE                 Location/Qualifiers
REGION                  1..70
                        note = GLP-1-amylin receptor co-agonist
MOD_RES                 2
                        note = Xaa is Aib (alpha-aminoisobutyryl)
source                  1..70
                        mol_type = protein
                        organism = synthetic construct
SEQUENCE: 119
HXEGTFTSDV SSYLEGQAAR EFIAWLVRGR GEGEGEKEAS ELSTAALGRL SAELHELATL         60
PRTETGSGSP                                                                70

SEQ ID NO: 120          moltype = AA  length = 72
FEATURE                 Location/Qualifiers
REGION                  1..72
                        note = GLP-1-amylin receptor co-agonist
MOD_RES                 2
                        note = Xaa is Aib (alpha-aminoisobutyryl)
source                  1..72
                        mol_type = protein
                        organism = synthetic construct
SEQUENCE: 120
HXEGTFTSDV SSYLEGQAAK EFIAWLVRGR GGQEPGQEPE ASELSTAALG RLSAELHELA         60
```

```
TLPRTETGSG SP                                                              72

SEQ ID NO: 121          moltype = AA  length = 71
FEATURE                 Location/Qualifiers
REGION                  1..71
                        note = GLP-1-amylin receptor co-agonist
MOD_RES                 2
                        note = Xaa is Aib (alpha-aminoisobutyryl)
source                  1..71
                        mol_type = protein
                        organism = synthetic construct
SEQUENCE: 121
HXEGTFTSDV SSYLEGQAAK EFIAWLVRGR GQEPGQAPEA SELSTAALGR LSAELHELAT   60
LPRTETGSGS P                                                        71

SEQ ID NO: 122          moltype = AA  length = 64
FEATURE                 Location/Qualifiers
REGION                  1..64
                        note = GLP-1-amylin receptor co-agonist
MOD_RES                 1
                        note = Xaa is Imp (imidazole propionyl)
source                  1..64
                        mol_type = protein
                        organism = synthetic construct
SEQUENCE: 122
XAEGTFTSDV SSYLEEQAAR EFIAWLVRGR KEASELSTAA LGRLSAELHE LATLPRTETG   60
SGSP                                                                64

SEQ ID NO: 123          moltype = AA  length = 64
FEATURE                 Location/Qualifiers
REGION                  1..64
                        note = GLP-1-amylin receptor co-agonist
source                  1..64
                        mol_type = protein
                        organism = synthetic construct
SEQUENCE: 123
HGEGTFTSDV SSYLEEQAAR KFIEWLVRGK GEASELSTAA LGRLSAELHE LATLPRTETG   60
SGSP                                                                64

SEQ ID NO: 124          moltype = AA  length = 67
FEATURE                 Location/Qualifiers
REGION                  1..67
                        note = GLP-1-amylin receptor co-agonist
MOD_RES                 2
                        note = Xaa is Aib (alpha-aminoisobutyryl)
source                  1..67
                        mol_type = protein
                        organism = synthetic construct
SEQUENCE: 124
HXEGTFTSDV SSYLEGQAAK EFIAWLVRGR GGGGEASELS TAALGRLSAE LHELATLPRT   60
ETGSGSP                                                             67

SEQ ID NO: 125          moltype = AA  length = 66
FEATURE                 Location/Qualifiers
REGION                  1..66
                        note = GLP-1-amylin receptor co-agonist
MOD_RES                 2
                        note = Xaa is Aib (alpha-aminoisobutyryl)
source                  1..66
                        mol_type = protein
                        organism = synthetic construct
SEQUENCE: 125
HXEGTFTSDV SSYLEGQAAK EFIAWLVRGR KGGEASELST AALGRLSAEL HELATLPRTE   60
TGSGSP                                                              66

SEQ ID NO: 126          moltype = AA  length = 72
FEATURE                 Location/Qualifiers
REGION                  1..72
                        note = GLP-1-amylin receptor co-agonist
MOD_RES                 2
                        note = Xaa is Aib (alpha-aminoisobutyryl)
source                  1..72
                        mol_type = protein
                        organism = synthetic construct
SEQUENCE: 126
HXEGTFTSDV SSYLEGQAAK EFIAWLVRGR GGGGGGGGGE ASELSTAALG RLSAELHELA   60
TLPRTETGSG SP                                                       72

SEQ ID NO: 127          moltype = AA  length = 72
```

```
FEATURE                 Location/Qualifiers
REGION                  1..72
                        note = GLP-1-amylin receptor co-agonist
source                  1..72
                        mol_type = protein
                        organism = synthetic construct
MOD_RES                 2
                        note = Xaa is Aib (alpha-aminoisobutyryl)
SEQUENCE: 127
HXEGTFTSDV SSYLEGQAAK EFIAWLVRGR GKQEPGQEPE ASELSTAALG RLSAELHELA    60
TLPRTETGSG SP                                                       72

SEQ ID NO: 128          moltype = AA  length = 72
FEATURE                 Location/Qualifiers
REGION                  1..72
                        note = GLP-1-amylin receptor co-agonist
MOD_RES                 2
                        note = Xaa is Aib (alpha-aminoisobutyryl)
source                  1..72
                        mol_type = protein
                        organism = synthetic construct
SEQUENCE: 128
HXEGTFTSDV SSYLEGQAAK EFIAWLVRGR GGQEKGQEPE ASELSTAALG RLSAELHELA    60
TLPRTETGSG SP                                                       72

SEQ ID NO: 129          moltype = AA  length = 73
FEATURE                 Location/Qualifiers
REGION                  1..73
                        note = GLP-1-amylin receptor co-agonist
MOD_RES                 2
                        note = Xaa is Aib (alpha-aminoisobutyryl)
source                  1..73
                        mol_type = protein
                        organism = synthetic construct
SEQUENCE: 129
HXEGTFTSDV SSYLEGQAAK EFIAWLVRGR GGQEPGQEPK EASELSTAAL GRLSAELHEL    60
ATLPRTETGS GSP                                                      73

SEQ ID NO: 130          moltype = AA  length = 66
FEATURE                 Location/Qualifiers
REGION                  1..66
                        note = GLP-1-amylin receptor co-agonist
MOD_RES                 2
                        note = Xaa is Aib (alpha-aminoisobutyryl)
source                  1..66
                        mol_type = protein
                        organism = synthetic construct
SEQUENCE: 130
HXEGTFTSDV SSYLEGQAAK EFIAWLVRGR GGKEASELST AALGRLSAEL HELATLPRTE    60
TGSGSP                                                              66

SEQ ID NO: 131          moltype = AA  length = 66
FEATURE                 Location/Qualifiers
REGION                  1..66
                        note = GLP-1-amylin receptor co-agonist
MOD_RES                 2
                        note = Xaa is Aib (alpha-aminoisobutyryl)
source                  1..66
                        mol_type = protein
                        organism = synthetic construct
SEQUENCE: 131
HXEGTFTSDV SSYLEGQAAR KFIAWLVRGR GGKEASELST AALGRLSAEL HELATLPRTE    60
TGSGSP                                                              66

SEQ ID NO: 132          moltype = AA  length = 66
FEATURE                 Location/Qualifiers
REGION                  1..66
                        note = GLP-1-amylin receptor co-agonist
MOD_RES                 2
                        note = Xaa is Aib (alpha-aminoisobutyryl)
source                  1..66
                        mol_type = protein
                        organism = synthetic construct
SEQUENCE: 132
HXEGTFTSDV SSYLEEQAAR KFIAWLVRGR GGKEASELST AALGRLSAEL HELATLPRTE    60
TGSGSP                                                              66

SEQ ID NO: 133          moltype = AA  length = 66
FEATURE                 Location/Qualifiers
```

```
REGION                  1..66
                        note = GLP-1-amylin receptor co-agonist
MOD_RES                 2
                        note = Xaa is Aib (alpha-aminoisobutyryl)
source                  1..66
                        mol_type = protein
                        organism = synthetic construct
SEQUENCE: 133
HXEGTFTSDV SSYLEGQAAK EFIAWLVRGK GGGEASELST AALGRLSAEL HELATLPRTE    60
TGSGSP                                                               66

SEQ ID NO: 134          moltype = AA  length = 66
FEATURE                 Location/Qualifiers
REGION                  1..66
                        note = GLP-1-amylin receptor co-agonist
MOD_RES                 2
                        note = Xaa is Aib (alpha-aminoisobutyryl)
source                  1..66
                        mol_type = protein
                        organism = synthetic construct
SEQUENCE: 134
HXEGTFTSDV SSYLEEQAAR KFIAWLVRGK GGGEASELST AALGRLSAEL HELATLPRTE    60
TGSGSP                                                               66

SEQ ID NO: 135          moltype = AA  length = 66
FEATURE                 Location/Qualifiers
REGION                  1..66
                        note = GLP-1-amylin receptor co-agonist
MOD_RES                 2
                        note = Xaa is Aib (alpha-aminoisobutyryl)
source                  1..66
                        mol_type = protein
                        organism = synthetic construct
SEQUENCE: 135
HXEGTFTSDV SSYLEEQAAR KFIAWLVKGR GGGEASELST AALGRLSAEL HELATLPRTE    60
TGSGSP                                                               66

SEQ ID NO: 136          moltype = AA  length = 72
FEATURE                 Location/Qualifiers
REGION                  1..72
                        note = GLP-1-amylin receptor co-agonist
MOD_RES                 2
                        note = Xaa is Aib (alpha-aminoisobutyryl)
source                  1..72
                        mol_type = protein
                        organism = synthetic construct
SEQUENCE: 136
HXEGTFTSDV SSYLEGQAAR EFIAWLVRGR KGQEPGQAPE ASELSTAALG RLSAELHELA    60
TLPRTETGSG SP                                                        72

SEQ ID NO: 137          moltype = AA  length = 72
FEATURE                 Location/Qualifiers
REGION                  1..72
                        note = GLP-1-amylin receptor co-agonist
MOD_RES                 2
                        note = Xaa is Aib (alpha-aminoisobutyryl)
source                  1..72
                        mol_type = protein
                        organism = synthetic construct
SEQUENCE: 137
HXEGTFTSDV SSYLEGQAAR EFIAWLVRGR GQEPKGQAPE ASELSTAALG RLSAELHELA    60
TLPRTETGSG SP                                                        72

SEQ ID NO: 138          moltype = AA  length = 72
FEATURE                 Location/Qualifiers
REGION                  1..72
                        note = GLP-1-amylin receptor co-agonist
MOD_RES                 2
                        note = Xaa is Aib (alpha-aminoisobutyryl)
source                  1..72
                        mol_type = protein
                        organism = synthetic construct
SEQUENCE: 138
HXEGTFTSDV SSYLEGQAAR EFIAWLVRGR GQEPGQAPKE ASELSTAALG RLSAELHELA    60
TLPRTETGSG SP                                                        72

SEQ ID NO: 139          moltype = AA  length = 67
FEATURE                 Location/Qualifiers
REGION                  1..67
```

```
                    note = GLP-1-amylin receptor co-agonist
MOD_RES             2
                    note = Xaa is Aib (alpha-aminoisobutyryl)
source              1..67
                    mol_type = protein
                    organism = synthetic construct
SEQUENCE: 139
HXEGTFTSDV SSYLEEQAAR KFIEWLVRGK GEGGEASELS TAALGRLSAE LHELATLPRT    60
ETGSGSP                                                              67

SEQ ID NO: 140      moltype = AA   length = 67
FEATURE             Location/Qualifiers
REGION              1..67
                    note = GLP-1-amylin receptor co-agonist
source              1..67
                    mol_type = protein
                    organism = synthetic construct
SEQUENCE: 140
HGEGTFTSDV SSYLEEQAAR KFIEWLVRGK GEGGEASELS TAALGRLSAE LHELATLPRT    60
ETGSGSP                                                              67

SEQ ID NO: 141      moltype = AA   length = 76
FEATURE             Location/Qualifiers
REGION              1..76
                    note = GLP-1 receptor agonist
MOD_RES             2
                    note = Xaa is Aib (alpha-aminoisobutyryl)
source              1..76
                    mol_type = protein
                    organism = synthetic construct
SEQUENCE: 141
HXEGTFTSDV SSYLEGQAAK EFIAWLVRGR GGGGGGGGGG GGGEASELST AALGRLSAEL    60
HELATLPRTE TGSGSP                                                    76

SEQ ID NO: 142      moltype = AA   length = 80
FEATURE             Location/Qualifiers
REGION              1..80
                    note = GLP-1-amylin receptor co-agonist
MOD_RES             2
                    note = Xaa is Aib (alpha-aminoisobutyryl)
source              1..80
                    mol_type = protein
                    organism = synthetic construct
SEQUENCE: 142
HXEGTFTSDV SSYLEGQAAK EFIAWLVRGR GGGGGGGGGG GGGGGGGEAS ELSTAALGRL    60
SAELHELATL PRTETGSGSP                                                80

SEQ ID NO: 143      moltype = AA   length = 66
FEATURE             Location/Qualifiers
REGION              1..66
                    note = GLP-1-amylin receptor co-agonist
source              1..66
                    mol_type = protein
                    organism = synthetic construct
SEQUENCE: 143
HGEGTFTSDV SSYLEEQAAR KFIEWLVRGK GEGEASELST AALGRLSAEL HELATLPRTE    60
TGSGSP                                                               66

SEQ ID NO: 144      moltype = AA   length = 70
FEATURE             Location/Qualifiers
REGION              1..70
                    note = GLP-1-amylin receptor co-agonist
source              1..70
                    mol_type = protein
                    organism = synthetic construct
SEQUENCE: 144
HGEGTFTSDV SSYLEEQAAR KFIEWLVRGK GEGGGGGEAS ELSTAALGRL SAELHELATL    60
PRTETGSGSP                                                           70

SEQ ID NO: 145      moltype = AA   length = 74
FEATURE             Location/Qualifiers
REGION              1..74
                    note = GLP-1-amylin receptor co-agonist
source              1..74
                    mol_type = protein
                    organism = synthetic construct
SEQUENCE: 145
HGEGTFTSDV SSYLEEQAAR KFIEWLVRGK GEGGGGGGGG GEASELSTAA LGRLSAELHE    60
LATLPRTETG SGSP                                                      74
```

```
SEQ ID NO: 146          moltype = AA   length = 66
FEATURE                 Location/Qualifiers
REGION                  1..66
                        note = GLP-1-amylin receptor co-agonist
source                  1..66
                        mol_type = protein
                        organism = synthetic construct
SEQUENCE: 146
HWEGTFTSDV SSYLEEQAAR KFIEWLVRGK GEGEASELST AALGRLSAEL HELATLPRTE   60
TGSGSP                                                             66

SEQ ID NO: 147          moltype = AA   length = 70
FEATURE                 Location/Qualifiers
REGION                  1..70
                        note = GLP-1-amylin receptor co-agonist
source                  1..70
                        mol_type = protein
                        organism = synthetic construct
SEQUENCE: 147
HWEGTFTSDV SSYLEEQAAR KFIEWLVRGK GEGGGGGEAS ELSTAALGRL SAELHELATL   60
PRTETGSGSP                                                         70

SEQ ID NO: 148          moltype = AA   length = 74
FEATURE                 Location/Qualifiers
REGION                  1..74
                        note = GLP-1-amylin receptor co-agonist
source                  1..74
                        mol_type = protein
                        organism = synthetic construct
SEQUENCE: 148
HWEGTFTSDV SSYLEEQAAR KFIEWLVRGK GEGGGGGGGG GEASELSTAA LGRLSAELHE   60
LATLPRTETG SGSP                                                    74

SEQ ID NO: 149          moltype = AA   length = 61
FEATURE                 Location/Qualifiers
REGION                  1..61
                        note = GLP-1-amylin receptor co-agonist
MOD_RES                 2
                        note = Xaa is Aib (alpha-aminoisobutyryl)
source                  1..61
                        mol_type = protein
                        organism = synthetic construct
SEQUENCE: 149
HXEGTFTSDV SSYLEEQAAR EFIAWLVRGR KELSTAALGR LSAELHELAT LPRTETGSGS   60
P                                                                  61

SEQ ID NO: 150          moltype = AA   length = 64
FEATURE                 Location/Qualifiers
REGION                  1..64
                        note = GLP-1-amylin receptor co-agonist
MOD_RES                 2
                        note = Xaa is Aib (alpha-aminoisobutyryl)
source                  1..64
                        mol_type = protein
                        organism = synthetic construct
SEQUENCE: 150
HXEGTFTSDV SSYLEEQAAR EFIAWLVRGR KEASELSTAA LGRLSAELHE LATLPRTETG   60
SGSP                                                               64

SEQ ID NO: 151          moltype = AA   length = 70
FEATURE                 Location/Qualifiers
REGION                  1..70
                        note = GLP-1-amylin receptor co-agonist
MOD_RES                 2
                        note = Xaa is Aib (alpha-aminoisobutyryl)
source                  1..70
                        mol_type = protein
                        organism = synthetic construct
SEQUENCE: 151
HXEGTFTSDV SSYLEEQAAR KFIEWLVRGK GEGQEPGGAS ELSTAALGRL SAELHELATL   60
PRTETGSGSP                                                         70

SEQ ID NO: 152          moltype = AA   length = 72
FEATURE                 Location/Qualifiers
REGION                  1..72
                        note = GLP-1-amylin receptor co-agonist
MOD_RES                 2
                        note = Xaa is Aib (alpha-aminoisobutyryl)
```

```
source                   1..72
                         mol_type = protein
                         organism = synthetic construct
SEQUENCE: 152
HXEGTFTSDV SSYLEEQAAR KFIAWLVRGK GGGGGGGGGE ASELSTAALG RLSAELHELA    60
TLPRTETGSG SP                                                       72

SEQ ID NO: 153           moltype = AA  length = 68
FEATURE                  Location/Qualifiers
REGION                   1..68
                         note = GLP-1-amylin receptor co-agonist
MOD_RES                  2
                         note = Xaa is Aib (alpha-aminoisobutyryl)
source                   1..68
                         mol_type = protein
                         organism = synthetic construct
SEQUENCE: 153
HXEGTFTSDV SSYLEEQAAR EFIAWLVRGR KGGGGEASEL STAALGRLSA ELHELATLPR    60
TETGSGSP                                                            68

SEQ ID NO: 154           moltype = AA  length = 66
FEATURE                  Location/Qualifiers
REGION                   1..66
                         note = GLP-1-amylin receptor co-agonist
source                   1..66
                         mol_type = protein
                         organism = synthetic construct
MOD_RES                  2
                         note = Xaa is Aib (alpha-aminoisobutyryl)
SEQUENCE: 154
HXEGTFTSDV SSYLEEQAAR EFIAWLVRGR KGGEASELST AALGRLSAEL HELATLPRTE    60
TGSGSP                                                              66

SEQ ID NO: 155           moltype = AA  length = 66
FEATURE                  Location/Qualifiers
REGION                   1..66
                         note = GLP-1-amylin receptor co-agonist
MOD_RES                  2
                         note = Xaa is Aib (alpha-aminoisobutyryl)
source                   1..66
                         mol_type = protein
                         organism = synthetic construct
SEQUENCE: 155
HXEGTFTSDV SSYLEEQAAR KFIAWLVRGR KGGEASELST AALGRLSAEL HELATLPRTE    60
TGSGSP                                                              66

SEQ ID NO: 156           moltype = AA  length = 64
FEATURE                  Location/Qualifiers
REGION                   1..64
                         note = GLP-1-amylin receptor co-agonist
MOD_RES                  1
                         note = Xaa is Imp (imidazole propionyl)
MOD_RES                  2
                         note = Xaa is Aib (alpha-aminoisobutyryl)
source                   1..64
                         mol_type = protein
                         organism = synthetic construct
SEQUENCE: 156
XXEGTFTSDV SSYLEEQAAR EFIAWLVRGR KEASELSTAA LGRLSAELHE LATLPRTETG    60
SGSP                                                                64

SEQ ID NO: 157           moltype = AA  length = 64
FEATURE                  Location/Qualifiers
REGION                   1..64
                         note = GLP-1-amylin receptor co-agonist
MOD_RES                  2
                         note = Xaa is Aib (alpha-aminoisobutyryl)
source                   1..64
                         mol_type = protein
                         organism = synthetic construct
SEQUENCE: 157
HXEGTFTSDV SSYLEEQAAR KFIAWLVRGR GEASELSTAA LGRLSAELHE LATLPRTETG    60
SGSP                                                                64

SEQ ID NO: 158           moltype = AA  length = 65
FEATURE                  Location/Qualifiers
REGION                   1..65
                         note = GLP-1-amylin receptor co-agonist
MOD_RES                  2
```

```
                        note = Xaa is Aib (alpha-aminoisobutyryl)
source                  1..65
                        mol_type = protein
                        organism = synthetic construct
SEQUENCE: 158
HXEGTFTSDV SSYLEEQAAR KFIAWLVRGK GGEASELSTA ALGRLSAELH ELATLPRTET    60
GSGSP                                                                65

SEQ ID NO: 159          moltype = AA  length = 65
FEATURE                 Location/Qualifiers
REGION                  1..65
                        note = GLP-1-amylin receptor co-agonist
source                  1..65
                        mol_type = protein
                        organism = synthetic construct
MOD_RES                 2
                        note = Xaa is Aib (alpha-aminoisobutyryl)
SEQUENCE: 159
HXEGTFTSDV SSYLEEQAAR KFIEWLVRGK GGEASELSTA ALGRLSAELH ELATLPRTET    60
GSGSP                                                                65

SEQ ID NO: 160          moltype = AA  length = 66
FEATURE                 Location/Qualifiers
REGION                  1..66
                        note = GLP-1-amylin receptor co-agonist
MOD_RES                 2
                        note = Xaa is Aib (alpha-aminoisobutyryl)
source                  1..66
                        mol_type = protein
                        organism = synthetic construct
SEQUENCE: 160
HXEGTFTSDV SSYLEEQAAR KFIEWLVRGR KGGEASELST AALGRLSAEL HELATLPRTE    60
TGSGSP                                                               66

SEQ ID NO: 161          moltype = AA  length = 64
FEATURE                 Location/Qualifiers
REGION                  1..64
                        note = GLP-1-amylin receptor co-agonist
MOD_RES                 2
                        note = Xaa is Aib (alpha-aminoisobutyryl)
source                  1..64
                        mol_type = protein
                        organism = synthetic construct
SEQUENCE: 161
HXEGTFTSDV SSYLEEQAAR KFIAWLVRGR KEASELSTAA LGRLSAELHE LATLPRTETG    60
SGSP                                                                 64

SEQ ID NO: 162          moltype = AA  length = 65
FEATURE                 Location/Qualifiers
REGION                  1..65
                        note = GLP-1-amylin receptor co-agonist
MOD_RES                 2
                        note = Xaa is Aib (alpha-aminoisobutyryl)
source                  1..65
                        mol_type = protein
                        organism = synthetic construct
SEQUENCE: 162
HXEGTFTSDV SSYLEEQAAR EFIAWLVRGK GGEASELSTA ALGRLSAELH ELATLPRTET    60
GSGSP                                                                65

SEQ ID NO: 163          moltype = AA  length = 68
FEATURE                 Location/Qualifiers
REGION                  1..68
                        note = GLP-1-amylin receptor co-agonist
source                  1..68
                        mol_type = protein
                        organism = synthetic construct
MOD_RES                 2
                        note = Xaa is Aib (alpha-aminoisobutyryl)
SEQUENCE: 163
HXEGTFTSDV SSYLEEQAAR EFIAWLVKGR GGGGEASEL STAALGRLSA ELHELATLPR    60
TETGSGSP                                                             68

SEQ ID NO: 164          moltype = AA  length = 67
FEATURE                 Location/Qualifiers
REGION                  1..67
                        note = GLP-1-amylin receptor co-agonist
source                  1..67
                        mol_type = protein
```

```
                        organism = synthetic construct
MOD_RES                 2
                        note = Xaa is Aib (alpha-aminoisobutyryl)
SEQUENCE: 164
HXEGTFTSDV SSYLEEQAAR EFIAWLVRGR GKGGGASELS TAALGRLSAE LHELATLPRT    60
ETGSGSP                                                              67

SEQ ID NO: 165          moltype = AA  length = 65
FEATURE                 Location/Qualifiers
REGION                  1..65
                        note = GLP-1-amylin receptor co-agonist
source                  1..65
                        mol_type = protein
                        organism = synthetic construct
MOD_RES                 2
                        note = Xaa is Aib (alpha-aminoisobutyryl)
SEQUENCE: 165
HXEGTFTSDV SSYLEEQAAR EFIEWLVRGK GGGASELSTA ALGRLSAELH ELATLPRTET    60
GSGSP                                                                65

SEQ ID NO: 166          moltype = AA  length = 62
FEATURE                 Location/Qualifiers
REGION                  1..62
                        note = GLP-1-amylin receptor co-agonist
source                  1..62
                        mol_type = protein
                        organism = synthetic construct
MOD_RES                 2
                        note = Xaa is Aib (alpha-aminoisobutyryl)
SEQUENCE: 166
HXEGTFTSDV SSYLEEQAAR EFIEWLVRGK ASELSTAALG RLSAELHELA TLPRTETGSG    60
SP                                                                   62

SEQ ID NO: 167          moltype = AA  length = 68
FEATURE                 Location/Qualifiers
REGION                  1..68
                        note = GLP-1-amylin receptor co-agonist
source                  1..68
                        mol_type = protein
                        organism = synthetic construct
MOD_RES                 2
                        note = Xaa is Aib (alpha-aminoisobutyryl)
SEQUENCE: 167
HXEGTFTSDV SSYLEGQAAR EFIAWLVRGR KGGGGEASEL STAALGRLSA ELHELATLPR    60
TETGSGSP                                                             68

SEQ ID NO: 168          moltype = AA  length = 71
FEATURE                 Location/Qualifiers
REGION                  1..71
                        note = GLP-1-amylin receptor co-agonist
MOD_RES                 2
                        note = Xaa is Aib (alpha-aminoisobutyryl)
source                  1..71
                        mol_type = protein
                        organism = synthetic construct
SEQUENCE: 168
HXEGTFTSDV SSYLEGQAAK EFIAWLVRGR GQAPGQEPEA SELSTAALGR LSAELHELAT    60
LPRTETGSGS P                                                         71

SEQ ID NO: 169          moltype = AA  length = 72
FEATURE                 Location/Qualifiers
REGION                  1..72
                        note = GLP-1-amylin receptor co-agonist
source                  1..72
                        mol_type = protein
                        organism = synthetic construct
MOD_RES                 2
                        note = Xaa is Aib (alpha-aminoisobutyryl)
SEQUENCE: 169
HXEGTFTSDV SSYLEEQAAR KFIAWLVRGR GGGGGGGGKE ASELSTAALG RLSAELHELA    60
TLPRTETGSG SP                                                        72

SEQ ID NO: 170          moltype = AA  length = 68
FEATURE                 Location/Qualifiers
REGION                  1..68
                        note = GLP-1-amylin receptor co-agonist
MOD_RES                 2
                        note = Xaa is Aib (alpha-aminoisobutyryl)
source                  1..68
```

```
                          mol_type = protein
                          organism = synthetic construct
SEQUENCE: 170
HXEGTFTSDV SSYLEEQAAR EFIEWLVRGR KEAEAEASEL STAALGRLSA ELHELATLPR    60
TETGSGSP                                                             68

SEQ ID NO: 171            moltype = AA  length = 71
FEATURE                   Location/Qualifiers
REGION                    1..71
                          note = GLP-1-amylin receptor co-agonist
MOD_RES                   2
                          note = Xaa is Aib (alpha-aminoisobutyryl)
source                    1..71
                          mol_type = protein
                          organism = synthetic construct
SEQUENCE: 171
HXEGTFTSDV SSYLEGQAAR EFIAWLVRGR GQEPKGQAPA SRLSTEALGR LSAELHELAT    60
LPRTETGSGS P                                                         71

SEQ ID NO: 172            moltype = AA  length = 69
FEATURE                   Location/Qualifiers
REGION                    1..69
                          note = GLP-1-amylin receptor co-agonist
source                    1..69
                          mol_type = protein
                          organism = synthetic construct
SEQUENCE: 172
HWEGTFTSDV SSYLEEQAAR KFIEWLVRGR GEGGGGGASE LSTAALGRLS KELHELATLP    60
RTETGSGSP                                                            69

SEQ ID NO: 173            moltype = AA  length = 69
FEATURE                   Location/Qualifiers
REGION                    1..69
                          note = GLP-1-amylin receptor co-agonist
source                    1..69
                          mol_type = protein
                          organism = synthetic construct
SEQUENCE: 173
HWEGTFTSDV SSYLEEQAAR KFIEWLVRGR GEGGGGGASE LSTAALGRLS AELHELKTLP    60
RTETGSGSP                                                            69

SEQ ID NO: 174            moltype = AA  length = 69
FEATURE                   Location/Qualifiers
REGION                    1..69
                          note = GLP-1-amylin receptor co-agonist
source                    1..69
                          mol_type = protein
                          organism = synthetic construct
SEQUENCE: 174
HWEGTFTSDV SSYLEEQAAR EFIEWLVRGK GEGGGGGASE LSTAALGRLS KELHELATLP    60
RTETGSGSP                                                            69

SEQ ID NO: 175            moltype = AA  length = 69
FEATURE                   Location/Qualifiers
REGION                    1..69
                          note = GLP-1-amylin receptor co-agonist
source                    1..69
                          mol_type = protein
                          organism = synthetic construct
SEQUENCE: 175
HWEGTFTSDV SSYLEEQAAR EFIEWLVRGK GEGGGGGASE LSTAALGRLS AELHELKTLP    60
RTETGSGSP                                                            69

SEQ ID NO: 176            moltype = AA  length = 67
FEATURE                   Location/Qualifiers
REGION                    1..67
                          note = GLP-1-amylin receptor co-agonist
source                    1..67
                          mol_type = protein
                          organism = synthetic construct
MOD_RES                   2
                          note = Xaa is Aib (alpha-aminoisobutyryl)
SEQUENCE: 176
HXEGTFTSDV SSYLEEQAAR EFIAWLVRGK KGGGGASELS TAALGRLSAE LHELATLPRT    60
ETGSGSP                                                              67

SEQ ID NO: 177            moltype = AA  length = 69
FEATURE                   Location/Qualifiers
REGION                    1..69
```

```
                        note = GLP-1-amylin receptor co-agonist
source                  1..69
                        mol_type = protein
                        organism = synthetic construct
SEQUENCE: 177
HWEGTFTSDV SSYLEEQAAR KFIEWLVRGR GEGGGGGASE LSTAALGRLS AELHELATLP   60
RTETGSGSP                                                          69

SEQ ID NO: 178          moltype = AA  length = 68
FEATURE                 Location/Qualifiers
REGION                  1..68
                        note = GLP-1-amylin receptor co-agonist
MOD_RES                 2
                        note = Xaa is Aib (alpha-aminoisobutyryl)
source                  1..68
                        mol_type = protein
                        organism = synthetic construct
SEQUENCE: 178
HXEGTFTSDK SSYLEEQAAR EFIAWLVRGR GGGGGEASEL STAALGRLSA ELHKLATLPR   60
TETGSGSP                                                           68

SEQ ID NO: 179          moltype = AA  length = 68
FEATURE                 Location/Qualifiers
REGION                  1..68
                        note = GLP-1-amylin receptor co-agonist
MOD_RES                 2
                        note = Xaa is Aib (alpha-aminoisobutyryl)
source                  1..68
                        mol_type = protein
                        organism = synthetic construct
SEQUENCE: 179
HXEGTFTSDK SSYLEEQAAR EFIAWLVRGR GGGGGEASEL STAALGRLSA ELHELKTLPR   60
TETGSGSP                                                           68

SEQ ID NO: 180          moltype = AA  length = 68
FEATURE                 Location/Qualifiers
REGION                  1..68
                        note = GLP-1-amylin receptor co-agonist
MOD_RES                 2
                        note = Xaa is Aib (alpha-aminoisobutyryl)
source                  1..68
                        mol_type = protein
                        organism = synthetic construct
SEQUENCE: 180
HXEGTFTSDK SSYLEEQAAR EFIAWLVRGR GGGGGEASEL STAALGRLSA ELHELATLKR   60
TETGSGSP                                                           68

SEQ ID NO: 181          moltype = AA  length = 67
FEATURE                 Location/Qualifiers
REGION                  1..67
                        note = GLP-1-amylin receptor co-agonist
MOD_RES                 2
                        note = Xaa is Aib (alpha-aminoisobutyryl)
source                  1..67
                        mol_type = protein
                        organism = synthetic construct
SEQUENCE: 181
HXEGTFTSDV SSYLEEQAAR EFIAWLVRGK GGGGEASELS TAALGRLSAE LHELATLPRT   60
ETGSGSP                                                            67

SEQ ID NO: 182          moltype = AA  length = 67
FEATURE                 Location/Qualifiers
REGION                  1..67
                        note = GLP-1-amylin receptor co-agonist
MOD_RES                 2
                        note = Xaa is Aib (alpha-aminoisobutyryl)
source                  1..67
                        mol_type = protein
                        organism = synthetic construct
SEQUENCE: 182
HXEGTFTSDV SSYLEEKAAR EFIAWLVRGR GGGGEASELS TAALGRLSAE LHELATLPRT   60
ETGSGSP                                                            67

SEQ ID NO: 183          moltype = AA  length = 67
FEATURE                 Location/Qualifiers
REGION                  1..67
                        note = GLP-1-amylin receptor co-agonist
MOD_RES                 2
                        note = Xaa is Aib (alpha-aminoisobutyryl)
```

```
source                  1..67
                        mol_type = protein
                        organism = synthetic construct
SEQUENCE: 183
HXEGTFTSDK SSYLEEQAAR EFIAWLVRGR GGGGEASELS TAALGRLSAE LHELATLPRT    60
ETGSGSP                                                              67

SEQ ID NO: 184          moltype = AA   length = 64
FEATURE                 Location/Qualifiers
REGION                  1..64
                        note = GLP-1-amylin receptor co-agonist
source                  1..64
                        mol_type = protein
                        organism = synthetic construct
SEQUENCE: 184
HWEGTFTSDV SSYLEEQAAR EFIEWLVRGK GEASELSTAA LGRLSAELHE LATLPRTETG    60
SGSP                                                                 64

SEQ ID NO: 185          moltype = AA   length = 68
FEATURE                 Location/Qualifiers
REGION                  1..68
                        note = GLP-1-amylin receptor co-agonist
source                  1..68
                        mol_type = protein
                        organism = synthetic construct
SEQUENCE: 185
HWEGTFTSDV SSYLEEQAAR EFIAWLVRGR KGGGGEASEL STAALGRLSA ELHELATLPR    60
TETGSGSP                                                             68

SEQ ID NO: 186          moltype = AA   length = 68
FEATURE                 Location/Qualifiers
REGION                  1..68
                        note = GLP-1-amylin receptor co-agonist
source                  1..68
                        mol_type = protein
                        organism = synthetic construct
SEQUENCE: 186
HWEGTFTSDV SSYLEEQAAR EFIEWLVRGR KGGGGEASEL STAALGRLSA ELHELATLPR    60
TETGSGSP                                                             68

SEQ ID NO: 187          moltype = AA   length = 64
FEATURE                 Location/Qualifiers
REGION                  1..64
                        note = GLP-1-amylin receptor co-agonist
source                  1..64
                        mol_type = protein
                        organism = synthetic construct
SEQUENCE: 187
HWEGTFTSDV SSYLEEKAAR EFIEWLVRGR GEASELSTAA LGRLSAELHE LATLPRTETG    60
SGSP                                                                 64

SEQ ID NO: 188          moltype = AA   length = 64
FEATURE                 Location/Qualifiers
REGION                  1..64
                        note = GLP-1-amylin receptor co-agonist
source                  1..64
                        mol_type = protein
                        organism = synthetic construct
SEQUENCE: 188
HWEGTFTSDK SSYLEEQAAR EFIEWLVRGR GEASELSTAA LGRLSAELHE LATLPRTETG    60
SGSP                                                                 64

SEQ ID NO: 189          moltype = AA   length = 68
FEATURE                 Location/Qualifiers
REGION                  1..68
                        note = GLP-1-amylin receptor co-agonist
MOD_RES                 2
                        note = Xaa is Aib (alpha-aminoisobutyryl)
source                  1..68
                        mol_type = protein
                        organism = synthetic construct
SEQUENCE: 189
HXEGTFTSDV SSYLEEQAAR EFIAWLVRGK GGGGEASEL STAALGRLSA ELHKLATLPR     60
TETGSGSP                                                             68

SEQ ID NO: 190          moltype = AA   length = 68
FEATURE                 Location/Qualifiers
REGION                  1..68
                        note = GLP-1-amylin receptor co-agonist
```

```
MOD_RES                     2
                            note = Xaa is Aib (alpha-aminoisobutyryl)
source                      1..68
                            mol_type = protein
                            organism = synthetic construct
SEQUENCE: 190
HXEGTFTSDV SSYLEEQAAR EFIAWLVRGK GGGGGEASEL STAALGRLSA ELHELKTLPR    60
TETGSGSP                                                             68

SEQ ID NO: 191              moltype = AA   length = 68
FEATURE                     Location/Qualifiers
REGION                      1..68
                            note = GLP-1-amylin receptor co-agonist
MOD_RES                     2
                            note = Xaa is Aib (alpha-aminoisobutyryl)
source                      1..68
                            mol_type = protein
                            organism = synthetic construct
SEQUENCE: 191
HXEGTFTSDV SSYLEEQAAR EFIAWLVRGK GGGGGEASEL STAALGRLSA ELHELATLKR    60
TETGSGSP                                                             68

SEQ ID NO: 192              moltype = AA   length = 68
FEATURE                     Location/Qualifiers
REGION                      1..68
                            note = GLP-1-amylin receptor co-agonist
MOD_RES                     2
                            note = Xaa is Aib (alpha-aminoisobutyryl)
source                      1..68
                            mol_type = protein
                            organism = synthetic construct
SEQUENCE: 192
HXEGTFTSDV SSYLEEQAAR EFIAWLVRGK GGGGGEASEL STAALGRLSA ELHELATLPR    60
TETGKGSP                                                             68

SEQ ID NO: 193              moltype = AA   length = 67
FEATURE                     Location/Qualifiers
REGION                      1..67
                            note = GLP-1-amylin receptor co-agonist
source                      1..67
                            mol_type = protein
                            organism = synthetic construct
MOD_RES                     2
                            note = Xaa is Aib (alpha-aminoisobutyryl)
SEQUENCE: 193
HXEGTFTSDK SSYLEEQAAR EFIAWLVRGR GGGGGASELS TAALGRLSKE LHELATLPRT    60
ETGSGSP                                                              67

SEQ ID NO: 194              moltype = AA   length = 67
FEATURE                     Location/Qualifiers
REGION                      1..67
                            note = GLP-1-amylin receptor co-agonist
MOD_RES                     2
                            note = Xaa is Aib (alpha-aminoisobutyryl)
source                      1..67
                            mol_type = protein
                            organism = synthetic construct
SEQUENCE: 194
HXEGTFTSDV SSYLEKQAAR EFIAWLVRGR GGGGGASELS TAALGRLSKE LHELATLPRT    60
ETGSGSP                                                              67

SEQ ID NO: 195              moltype = AA   length = 67
FEATURE                     Location/Qualifiers
REGION                      1..67
                            note = GLP-1-amylin receptor co-agonist
source                      1..67
                            mol_type = protein
                            organism = synthetic construct
MOD_RES                     2
                            note = Xaa is Aib (alpha-aminoisobutyryl)
SEQUENCE: 195
HXEGTFTSDV SSYLEEKAAR EFIAWLVRGR GGGGGASELS TAALGRLSKE LHELATLPRT    60
ETGSGSP                                                              67

SEQ ID NO: 196              moltype = AA   length = 67
FEATURE                     Location/Qualifiers
REGION                      1..67
                            note = GLP-1-amylin receptor co-agonist
source                      1..67
```

```
                        mol_type = protein
                        organism = synthetic construct
MOD_RES                 2
                        note = Xaa is Aib (alpha-aminoisobutyryl)
SEQUENCE: 196
HXEGTFTSDV SSYLEEQAAR KFIAWLVRGR GGGGGASELS TAALGRLSKE LHELATLPRT    60
ETGSGSP                                                              67

SEQ ID NO: 197          moltype = AA  length = 67
FEATURE                 Location/Qualifiers
REGION                  1..67
                        note = GLP-1-amylin receptor co-agonist
MOD_RES                 2
                        note = Xaa is Aib (alpha-aminoisobutyryl)
source                  1..67
                        mol_type = protein
                        organism = synthetic construct
SEQUENCE: 197
HXEGTFTSDV SSYLEEQAAR EFIAWLVRKR GGGGGASELS TAALGRLSKE LHELATLPRT    60
ETGSGSP                                                              67

SEQ ID NO: 198          moltype = AA  length = 68
FEATURE                 Location/Qualifiers
REGION                  1..68
                        note = GLP-1-amylin receptor co-agonist
MOD_RES                 2
                        note = Xaa is Aib (alpha-aminoisobutyryl)
source                  1..68
                        mol_type = protein
                        organism = synthetic construct
SEQUENCE: 198
HXEGTFTSDV SSYLEEKAAR EFIAWLVRGR GGGGGEASEL STAALGRLSA ELHKLATLPR    60
TETGSGSP                                                             68

SEQ ID NO: 199          moltype = AA  length = 68
FEATURE                 Location/Qualifiers
REGION                  1..68
                        note = GLP-1-amylin receptor co-agonist
MOD_RES                 2
                        note = Xaa is Aib (alpha-aminoisobutyryl)
source                  1..68
                        mol_type = protein
                        organism = synthetic construct
SEQUENCE: 199
HXEGTFTSDV SSYLEEKAAR EFIAWLVRGR GGGGGEASEL STAALGRLSA ELHELKTLPR    60
TETGSGSP                                                             68

SEQ ID NO: 200          moltype = AA  length = 68
FEATURE                 Location/Qualifiers
REGION                  1..68
                        note = GLP-1-amylin receptor co-agonist
MOD_RES                 2
                        note = Xaa is Aib (alpha-aminoisobutyryl)
source                  1..68
                        mol_type = protein
                        organism = synthetic construct
SEQUENCE: 200
HXEGTFTSDV SSYLEEKAAR EFIAWLVRGR GGGGGEASEL STAALGRLSA ELHELATLKR    60
TETGSGSP                                                             68

SEQ ID NO: 201          moltype = AA  length = 68
FEATURE                 Location/Qualifiers
REGION                  1..68
                        note = GLP-1-amylin receptor co-agonist
MOD_RES                 2
                        note = Xaa is Aib (alpha-aminoisobutyryl)
source                  1..68
                        mol_type = protein
                        organism = synthetic construct
SEQUENCE: 201
HXEGTFTSDV SSYLEEKAAR EFIAWLVRGR GGGGGEASEL STAALGRLSA ELHELATLPR    60
TETGKGSP                                                             68

SEQ ID NO: 202          moltype = AA  length = 64
FEATURE                 Location/Qualifiers
REGION                  1..64
                        note = GLP-1-amylin receptor co-agonist
source                  1..64
                        mol_type = protein
```

```
                              organism = synthetic construct
SEQUENCE: 202
HAEGTFTSDV SSYLEEKAAR EFIEWLVRGR GEASELSTAA LGRLSAELHE LATLPRTETG   60
SGSP                                                               64

SEQ ID NO: 203            moltype = AA  length = 64
FEATURE                   Location/Qualifiers
REGION                    1..64
                          note = GLP-1-amylin receptor co-agonist
source                    1..64
                          mol_type = protein
                          organism = synthetic construct
MOD_RES                   2
                          note = Xaa is Aib (alpha-aminoisobutyryl)
SEQUENCE: 203
HXEGTFTSDV SSYLEEKAAR EFIEWLVRGR GEASELSTAA LGRLSAELHE LATLPRTETG   60
SGSP                                                               64

SEQ ID NO: 204            moltype = AA  length = 64
FEATURE                   Location/Qualifiers
REGION                    1..64
                          note = GLP-1-amylin receptor co-agonist
source                    1..64
                          mol_type = protein
                          organism = synthetic construct
SEQUENCE: 204
HAEGTFTSKV SSYLEEQAAR EFIEWLVRGR GEASELSTAA LGRLSAELHE LATLPRTETG   60
SGSP                                                               64

SEQ ID NO: 205            moltype = AA  length = 64
FEATURE                   Location/Qualifiers
REGION                    1..64
                          note = GLP-1-amylin receptor co-agonist
MOD_RES                   2
                          note = Xaa is Aib (alpha-aminoisobutyryl)
source                    1..64
                          mol_type = protein
                          organism = synthetic construct
SEQUENCE: 205
HXEGTFTSKV SSYLEEQAAR EFIEWLVRGR GEASELSTAA LGRLSAELHE LATLPRTETG   60
SGSP                                                               64

SEQ ID NO: 206            moltype = AA  length = 64
FEATURE                   Location/Qualifiers
REGION                    1..64
                          note = GLP-1-amylin receptor co-agonist
source                    1..64
                          mol_type = protein
                          organism = synthetic construct
SEQUENCE: 206
HAEGTFTSDK SSYLEEQAAR EFIEWLVRGR GEASELSTAA LGRLSAELHE LATLPRTETG   60
SGSP                                                               64

SEQ ID NO: 207            moltype = AA  length = 64
FEATURE                   Location/Qualifiers
REGION                    1..64
                          note = GLP-1-amylin receptor co-agonist
source                    1..64
                          mol_type = protein
                          organism = synthetic construct
SEQUENCE: 207
HWEGTFTSDV SSYLEEQAAK EFIEWLVRGR GEASELSTAA LGRLSAELHE LATLPRTETG   60
SGSP                                                               64

SEQ ID NO: 208            moltype = AA  length = 64
FEATURE                   Location/Qualifiers
REGION                    1..64
                          note = GLP-1-amylin receptor co-agonist
source                    1..64
                          mol_type = protein
                          organism = synthetic construct
MOD_RES                   2
                          note = Xaa is Aib (alpha-aminoisobutyryl)
SEQUENCE: 208
HXEGTFTSDV SSYLEEQAAK EFIEWLVRGR GEASELSTAA LGRLSAELHE LATLPRTETG   60
SGSP                                                               64

SEQ ID NO: 209            moltype = AA  length = 64
FEATURE                   Location/Qualifiers
```

```
REGION                      1..64
                            note = GLP-1-amylin receptor co-agonist
source                      1..64
                            mol_type = protein
                            organism = synthetic construct
SEQUENCE: 209
HWEGTFTSDV SSYLEEQAAR KFIEWLVRGR GEASELSTAA LGRLSAELHE LATLPRTETG   60
SGSP                                                               64

SEQ ID NO: 210              moltype = AA  length = 64
FEATURE                     Location/Qualifiers
REGION                      1..64
                            note = GLP-1-amylin receptor co-agonist
MOD_RES                     2
                            note = Xaa is Aib (alpha-aminoisobutyryl)
source                      1..64
                            mol_type = protein
                            organism = synthetic construct
SEQUENCE: 210
HXEGTFTSDV SSYLEEQAAR EFIEWLVRGR KEASELSTAA LGRLSAELHE LATLPRTETG   60
SGSP                                                               64

SEQ ID NO: 211              moltype = AA  length = 64
FEATURE                     Location/Qualifiers
REGION                      1..64
                            note = GLP-1-amylin receptor co-agonist
source                      1..64
                            mol_type = protein
                            organism = synthetic construct
MOD_RES                     2
                            note = Xaa is Aib (alpha-aminoisobutyryl)
SEQUENCE: 211
HXEGTFTSDV SSYLEEQAAR KFIEWLVRGR GEASELSTAA LGRLSAELHE LATLPRTETG   60
SGSP                                                               64

SEQ ID NO: 212              moltype = AA  length = 64
FEATURE                     Location/Qualifiers
REGION                      1..64
                            note = GLP-1-amylin receptor co-agonist
MOD_RES                     2
                            note = Xaa is Aib (alpha-aminoisobutyryl)
source                      1..64
                            mol_type = protein
                            organism = synthetic construct
SEQUENCE: 212
HXEGTFTSDK SSYLEEQAAR EFIEWLVRGR GEASELSTAA LGRLSAELHE LATLPRTETG   60
SGSP                                                               64

SEQ ID NO: 213              moltype = AA  length = 64
FEATURE                     Location/Qualifiers
REGION                      1..64
                            note = GLP-1-amylin receptor co-agonist
source                      1..64
                            mol_type = protein
                            organism = synthetic construct
SEQUENCE: 213
HAEGTFTSDK SSYLEEKAAR EFIEWLVRGR GEASELSTAA LGRLSAELHE LATLPRTETG   60
SGSP                                                               64

SEQ ID NO: 214              moltype = AA  length = 66
FEATURE                     Location/Qualifiers
REGION                      1..66
                            note = GLP-1-amylin receptor co-agonist
source                      1..66
                            mol_type = protein
                            organism = synthetic construct
SEQUENCE: 214
HAEGTFTSDV SKYLEEQAVR EFIAKLVRGR GGGEASELST AALGRLSAEL HELATLPRTE   60
TGSGSP                                                             66

SEQ ID NO: 215              moltype = AA  length = 66
FEATURE                     Location/Qualifiers
REGION                      1..66
                            note = GLP-1-amylin receptor co-agonist
MOD_RES                     2
                            note = Xaa is Aib (alpha-aminoisobutyryl)
source                      1..66
                            mol_type = protein
                            organism = synthetic construct
```

```
SEQUENCE: 215
HXEGTFTSDV SKYLEEQAVR EFIAKLVRGR GGGEASELST AALGRLSAEL HELATLPRTE    60
TGSGSP                                                              66

SEQ ID NO: 216          moltype = AA   length = 68
FEATURE                 Location/Qualifiers
REGION                  1..68
                        note = GLP-1-amylin receptor co-agonist
MOD_RES                 2
                        note = Xaa is Aib (alpha-aminoisobutyryl)
source                  1..68
                        mol_type = protein
                        organism = synthetic construct
SEQUENCE: 216
HXEGTFTSDV SSYLEEQAAR EFIEWLVRGR KGGGGEASEL STAALGRLSA ELHELATLPR    60
TETGSGSP                                                            68

SEQ ID NO: 217          moltype = AA   length = 69
FEATURE                 Location/Qualifiers
REGION                  1..69
                        note = GLP-1-amylin receptor co-agonist
MOD_RES                 2
                        note = Xaa is Aib (alpha-aminoisobutyryl)
source                  1..69
                        mol_type = protein
                        organism = synthetic construct
SEQUENCE: 217
HXEGTFTSDV SSYLEEQAAR EFIAWLVRGR PKGGGGEASE LSTAALGRLS AELHELATLP    60
RTETGSGSP                                                           69

SEQ ID NO: 218          moltype = AA   length = 68
FEATURE                 Location/Qualifiers
REGION                  1..68
                        note = GLP-1-amylin receptor co-agonist
MOD_RES                 2
                        note = Xaa is Aib (alpha-aminoisobutyryl)
source                  1..68
                        mol_type = protein
                        organism = synthetic construct
SEQUENCE: 218
HXEGTFTSDV SSYLEEQAAR KFIAWLVRGR GGGGGEASEL STAALGRLSA ELHKLATLPR    60
TETGSGSP                                                            68

SEQ ID NO: 219          moltype = AA   length = 68
FEATURE                 Location/Qualifiers
REGION                  1..68
                        note = GLP-1-amylin receptor co-agonist
MOD_RES                 2
                        note = Xaa is Aib (alpha-aminoisobutyryl)
source                  1..68
                        mol_type = protein
                        organism = synthetic construct
SEQUENCE: 219
HXEGTFTSDV SRYLEEQAAR EFIEWLVRGR KGGGGEASEL STAALGRLSA ELHELATLPR    60
TETGSGSP                                                            68

SEQ ID NO: 220          moltype = AA   length = 68
FEATURE                 Location/Qualifiers
REGION                  1..68
                        note = GLP-1-amylin receptor co-agonist
MOD_RES                 2
                        note = Xaa is Aib (alpha-aminoisobutyryl)
source                  1..68
                        mol_type = protein
                        organism = synthetic construct
SEQUENCE: 220
HXEGTFTSDV SKYLEEQAAR KFIAWLVRGR GGGGGEASEL STAALGRLSA ELHELATLPR    60
TETGSGSP                                                            68

SEQ ID NO: 221          moltype = AA   length = 68
FEATURE                 Location/Qualifiers
REGION                  1..68
                        note = GLP-1-amylin receptor co-agonist
MOD_RES                 2
                        note = Xaa is Aib (alpha-aminoisobutyryl)
source                  1..68
                        mol_type = protein
                        organism = synthetic construct
SEQUENCE: 221
```

```
HXEGTFTSDV SKYLEEQAAR EFIAWLVRGR GGGGGEASEL STAALGRLSA ELHELATLPR    60
TETGSGSP                                                             68

SEQ ID NO: 222          moltype = AA  length = 68
FEATURE                 Location/Qualifiers
REGION                  1..68
                        note = GLP-1-amylin receptor co-agonist
MOD_RES                 2
                        note = Xaa is Aib (alpha-aminoisobutyryl)
source                  1..68
                        mol_type = protein
                        organism = synthetic construct
SEQUENCE: 222
HXEGTFTSDV SKYLEEQAAR EFIAWLVRGR KGGGGEASEL STAALGRLSA ELHELATLPR    60
TETGSGSP                                                             68

SEQ ID NO: 223          moltype = AA  length = 64
FEATURE                 Location/Qualifiers
REGION                  1..64
                        note = GLP-1-amylin receptor co-agonist
source                  1..64
                        mol_type = protein
                        organism = synthetic construct
SEQUENCE: 223
HGEGTFTSDV SSYLEGQAAK EFIAWLVRGR GEASELSTAA LGRLSAELHE LATLPRTETG    60
SGSP                                                                 64

SEQ ID NO: 224          moltype = AA  length = 68
FEATURE                 Location/Qualifiers
REGION                  1..68
                        note = GLP-1-amylin receptor co-agonist
source                  1..68
                        mol_type = protein
                        organism = synthetic construct
MOD_RES                 2
                        note = Xaa is Aib (alpha-aminoisobutyryl)
SEQUENCE: 224
HXEGTFTSDV SSYLEEQAAR KFIAWLVRGR GGGGGEASEL STAALGRLSA ELHELATLPR    60
TETGSGSP                                                             68

SEQ ID NO: 225          moltype = AA  length = 69
FEATURE                 Location/Qualifiers
REGION                  1..69
                        note = GLP-1-amylin receptor co-agonist
MOD_RES                 2
                        note = Xaa is Aib (alpha-aminoisobutyryl)
source                  1..69
                        mol_type = protein
                        organism = synthetic construct
SEQUENCE: 225
HXEGTFTSDV SKYLEEQAAR KFIAWLVRGR QEGGGGGASE LSTAALGRLS AELHELATLP    60
RTETGSGSP                                                            69

SEQ ID NO: 226          moltype = AA  length = 69
FEATURE                 Location/Qualifiers
REGION                  1..69
                        note = GLP-1-amylin receptor co-agonist
MOD_RES                 2
                        note = Xaa is Aib (alpha-aminoisobutyryl)
source                  1..69
                        mol_type = protein
                        organism = synthetic construct
SEQUENCE: 226
HXEGTFTSDV SKYLEEQAAR KFIEWLVRGR GEGGGGGASE LSTAALGRLS AELHELATLP    60
RTETGSGSP                                                            69

SEQ ID NO: 227          moltype = AA  length = 64
FEATURE                 Location/Qualifiers
REGION                  1..64
                        note = GLP-1-amylin receptor co-agonist
MOD_RES                 2
                        note = Xaa is Aib (alpha-aminoisobutyryl)
source                  1..64
                        mol_type = protein
                        organism = synthetic construct
SEQUENCE: 227
HXEGTFTSDV SKYLEEQAAR KFIEWLVRGR GEASELSTAA LGRLSAELHE LATLPRTETG    60
SGSP                                                                 64
```

```
SEQ ID NO: 228          moltype = AA  length = 64
FEATURE                 Location/Qualifiers
REGION                  1..64
                        note = GLP-1-amylin receptor co-agonist
MOD_RES                 2
                        note = Xaa is Aib (alpha-aminoisobutyryl)
source                  1..64
                        mol_type = protein
                        organism = synthetic construct
SEQUENCE: 228
HXEGTFTSDV SKYLEEQAAR KFIAWLVRGR QEASELSTAA LGRLSAELHE LATLPRTETG    60
SGSP                                                                 64

SEQ ID NO: 229          moltype = AA  length = 62
FEATURE                 Location/Qualifiers
REGION                  1..62
                        note = GLP-1-amylin receptor co-agonist
source                  1..62
                        mol_type = protein
                        organism = synthetic construct
MOD_RES                 2
                        note = Xaa is Aib (alpha-aminoisobutyryl)
SEQUENCE: 229
HXEGTFTSDV SSYLEEQAAR KFIAWLVRGG ASELSTAALG RLSAELHELA TLPRTETGSG    60
SP                                                                   62

SEQ ID NO: 230          moltype = AA  length = 61
FEATURE                 Location/Qualifiers
REGION                  1..61
                        note = GLP-1-amylin receptor co-agonist
source                  1..61
                        mol_type = protein
                        organism = synthetic construct
MOD_RES                 2
                        note = Xaa is Aib (alpha-aminoisobutyryl)
SEQUENCE: 230
HXEGTFTSDV SSYLEEQAAR KFIEWLVRGA SELSTAALGR LSAELHELAT LPRTETGSGS    60
P                                                                    61

SEQ ID NO: 231          moltype = AA  length = 64
FEATURE                 Location/Qualifiers
REGION                  1..64
                        note = GLP-1-amylin receptor co-agonist
MOD_RES                 2
                        note = Xaa is Aib (alpha-aminoisobutyryl)
source                  1..64
                        mol_type = protein
                        organism = synthetic construct
SEQUENCE: 231
HXEGTFTSDV SKYLEEQAAR KFIEWLVRGA AEASELSTAA LGRLSAELHE LATLPRTETG    60
SGSP                                                                 64

SEQ ID NO: 232          moltype = AA  length = 64
FEATURE                 Location/Qualifiers
REGION                  1..64
                        note = GLP-1-amylin receptor co-agonist
MOD_RES                 2
                        note = Xaa is Aib (alpha-aminoisobutyryl)
source                  1..64
                        mol_type = protein
                        organism = synthetic construct
SEQUENCE: 232
HXEGTFTSDV SKYLEEQAAR EFIEWLVRGA AEASELSTAA LGRLSAELHE LATLPRTETG    60
SGSP                                                                 64

SEQ ID NO: 233          moltype = AA  length = 64
FEATURE                 Location/Qualifiers
REGION                  1..64
                        note = GLP-1-amylin receptor co-agonist
source                  1..64
                        mol_type = protein
                        organism = synthetic construct
MOD_RES                 2
                        note = Xaa is Aib (alpha-aminoisobutyryl)
SEQUENCE: 233
HXEGTFTSDV SKYLEEQAAR KFIAWLVRGR GEASELSTAA LGRLSAELHE LATLPRTETG    60
SGSP                                                                 64

SEQ ID NO: 234          moltype = AA  length = 66
```

```
FEATURE                 Location/Qualifiers
REGION                  1..66
                        note = GLP-1-amylin receptor co-agonist
source                  1..66
                        mol_type = protein
                        organism = synthetic construct
MOD_RES                 2
                        note = Xaa is Aib (alpha-aminoisobutyryl)
SEQUENCE: 234
HXEGTFTSDV SKYLEEQAAR KFIAWLVRGR KGGEASELST AALGRLSAEL HELATLPRTE    60
TGSGSP                                                                66

SEQ ID NO: 235          moltype = AA  length = 65
FEATURE                 Location/Qualifiers
REGION                  1..65
                        note = GLP-1-amylin receptor co-agonist
MOD_RES                 2
                        note = Xaa is Aib (alpha-aminoisobutyryl)
source                  1..65
                        mol_type = protein
                        organism = synthetic construct
SEQUENCE: 235
HXEGTFTSDV SSYLEEQAAR KFIEWLVRGR QEAASELSTA ALGRLSAELH QLATLPRTET    60
GSGSP                                                                 65

SEQ ID NO: 236          moltype = AA  length = 72
FEATURE                 Location/Qualifiers
REGION                  1..72
                        note = GLP-1-amylin receptor co-agonist
MOD_RES                 2
                        note = Xaa is Aib (alpha-aminoisobutyryl)
source                  1..72
                        mol_type = protein
                        organism = synthetic construct
SEQUENCE: 236
HXEGTFTSDV SSYLEEQAAR EFIAWLVRGR KGGGGSGGGE ASELSTAALG RLSAELHELA    60
TLPRTETGSG SP                                                         72

SEQ ID NO: 237          moltype = AA  length = 29
FEATURE                 Location/Qualifiers
source                  1..29
                        mol_type = protein
                        organism = Homo sapiens
SEQUENCE: 237
HSQGTFTSDY SKYLDSRRAQ DFVQWLMNT                                       29

SEQ ID NO: 238          moltype = AA  length = 31
FEATURE                 Location/Qualifiers
REGION                  1..31
                        note = GLP-1 receptor agonist peptide (Z1)
source                  1..31
                        mol_type = protein
                        organism = synthetic construct
VAR_SEQ                 1
                        note = Xaa can be His (H) or Imp
VAR_SEQ                 2
                        note = Xaa can be Aib, Ala (A), Gly (G) or Trp (W)
VAR_SEQ                 30
                        note = Xaa can be Ala (A), Cys (C), Gly (G), Lys (K), Arg
                         (R) or absent
VAR_SEQ                 22
                        note = Xaa can be Phe (F), Trp (W) or Tyr (Y)
VAR_SEQ                 12
                        note = Xaa can be Cys (C), Lys (K), Arg (R) or Ser (S)
VAR_SEQ                 29
                        note = Xaa can be Cys (C), Lys (K) or Gly (G)
VAR_SEQ                 17
                        note = Xaa can be Cys (C), Gln (Q) or Lys (K)
VAR_SEQ                 10
                        note = Xaa can be Cys (C), Lys (K) or Val (V)
VAR_SEQ                 31
                        note = Xaa can be Ala (A), Cys (C), Lys (K), Gly (G), Gln
                         (Q) or absent
VAR_SEQ                 9
                        note = Xaa can be Cys (C), Asp (D) or Lys (K)
VAR_SEQ                 19
                        note = Xaa can be Ala (A) or Val (V)
VAR_SEQ                 16
                        note = Xaa can be Cys (C), Glu (E), Gly (G) or Lys (K)
```

```
VAR_SEQ                    24
                           note = Xaa can be Ala (A), Cys (C), Glu (E) or Leu (L)
VAR_SEQ                    23
                           note = Xaa can be Ile (I), Leu (L) or Val (V)
VAR_SEQ                    28
                           note = Xaa can be Cys (C), Lys (K) or Arg (R)
VAR_SEQ                    25
                           note = Xaa can be Cys (C), Lys (K) or Trp (W)
VAR_SEQ                    20
                           note = Xaa can be Cys (C), Lys (K) or Arg (R)
VAR_SEQ                    21
                           note = Xaa can be Cys (C), Glu (E) or Lys (K)
SEQUENCE: 238
XXEGTFTSXX SXYLEXXAXX XXXXXLVXXX X                                    31

SEQ ID NO: 239             moltype =    length =
SEQUENCE: 239
000

SEQ ID NO: 240             moltype = AA  length = 32
FEATURE                    Location/Qualifiers
REGION                     1..32
                           note = Amylin receptor agonist peptide (Z3)
source                     1..32
                           mol_type = protein
                           organism = synthetic construct
VAR_SEQ                    18
                           note = Xaa can be Cys (C), Glu (E), Lys (K) or Gln (Q)
VAR_SEQ                    7
                           note = Xaa can be Ala (A), Cys (C), Glu (E) or Lys (K)
VAR_SEQ                    23
                           note = Xaa can be Cys (C), Lys (K) or Pro (P)
VAR_SEQ                    3
                           note = Xaa can be Cys (C), Glu (E), Lys (K) or Arg (R)
VAR_SEQ                    29
                           note = Xaa can be Cys (C), Ser (S) or Lys (K)
VAR_SEQ                    1
                           note = Xaa can be Ala (A), Cys (C), Lys (K) or absent
VAR_SEQ                    2
                           note = Xaa can be Cys (C), Lys (K) or Ser (S)
VAR_SEQ                    32
                           note = Xaa can be Pro (P) or Tyr (Y)
VAR_SEQ                    20
                           note = Xaa can be Ala (A), Cys (C) or Lys (K)
VAR_SEQ                    14
                           note = Xaa can be Ala (A), Cys (C) or Lys (K)
SEQUENCE: 240
XXXLSTXALG RLSXELHXLX TLXRTETGXG SX                                   32

SEQ ID NO: 241             moltype = AA  length = 66
FEATURE                    Location/Qualifiers
REGION                     1..66
                           note = Peptide backbone in comparator compound
MOD_RES                    2
                           note = Xaa is Aib (alpha-aminoisobutyryl)
source                     1..66
                           mol_type = protein
                           organism = synthetic construct
SEQUENCE: 241
HXEGTFTSDV SSYLEGQAAK EIFAWLVRGR KGGEASELST AALGRLSAEL HELATLPRTE     60
TGSGSP                                                                66

SEQ ID NO: 242             moltype = AA  length = 66
FEATURE                    Location/Qualifiers
REGION                     1..66
                           note = Peptide backbone in comparator compound
MOD_RES                    2
                           note = Xaa is Aib (alpha-aminoisobutyryl)
source                     1..66
                           mol_type = protein
                           organism = synthetic construct
SEQUENCE: 242
HXEGTFTSDV SSYLEGQAAK EFIAWLVRGR KGGEASELST AALGRPSAEL HELATLPRTE     60
TGSGSP                                                                66

SEQ ID NO: 243             moltype = AA  length = 75
FEATURE                    Location/Qualifiers
REGION                     1..75
                           note = Peptide backbone in comparator compound
```

```
MOD_RES                 2
                        note = Xaa is Aib (alpha-aminoisobutyryl)
source                  1..75
                        mol_type = protein
                        organism = synthetic construct
SEQUENCE: 243
HXEGTFTSDV SSYLEGQAAK EFIAWLVRGR GGQEPGQEPC NTATCATQRL AEFLRHSSNN    60
FGPILPPTNV GSNTP                                                    75

SEQ ID NO: 244          moltype = AA  length = 76
FEATURE                 Location/Qualifiers
REGION                  1..76
                        note = Peptide backbone in comparator compound
MOD_RES                 2
                        note = Xaa is Aib (alpha-aminoisobutyryl)
source                  1..76
                        mol_type = protein
                        organism = synthetic construct
SEQUENCE: 244
HXEGTFTSDV SSYLEGQAAK EFIAWLVRGR GGQEPGQEPK CNTATCATQR LAEFLRHSSN    60
NFGPILPPTN VGSNTP                                                   76

SEQ ID NO: 245          moltype = AA  length = 76
FEATURE                 Location/Qualifiers
REGION                  1..76
                        note = Peptide backbone in comparator compound
MOD_RES                 2
                        note = Xaa is Aib (alpha-aminoisobutyryl)
source                  1..76
                        mol_type = protein
                        organism = synthetic construct
SEQUENCE: 245
HXEGTFTSDV SSYLEGQAAK EFIAWLVRGR GGQEPGQEPK CNTATCATQR LADFLRHSSP    60
NFGAIPSSTN VGSRTY                                                   76

SEQ ID NO: 246          moltype = AA  length = 31
FEATURE                 Location/Qualifiers
REGION                  1..31
                        note = Peptide backbone in semaglutide
source                  1..31
                        mol_type = protein
                        organism = synthetic construct
MOD_RES                 2
                        note = Xaa is Aib (alpha-aminoisobutyryl)
MOD_RES                 2
                        note = Xaa is Aib
SEQUENCE: 246
HXEGTFTSDV SSYLEGQAAK EFIAWLVRGR G                                   31

SEQ ID NO: 247          moltype = AA  length = 37
FEATURE                 Location/Qualifiers
REGION                  1..37
                        note = Peptide backbone in pramlintide
source                  1..37
                        mol_type = protein
                        organism = synthetic construct
SEQUENCE: 247
KCNTATCATQ RLANFLVHSS NNFGPILPPT NVGSNTY                             37

SEQ ID NO: 248          moltype = AA  length = 37
FEATURE                 Location/Qualifiers
REGION                  1..37
                        note = Peptide backbone in cagrilintide
source                  1..37
                        mol_type = protein
                        organism = synthetic construct
SEQUENCE: 248
KCNTATCATQ RLAEFLRHSS NNFGPILPPT NVGSNTP                             37

SEQ ID NO: 249          moltype = AA  length = 32
FEATURE                 Location/Qualifiers
source                  1..32
                        mol_type = protein
                        organism = Salmo salar
SEQUENCE: 249
CSNLSTCVLG KLSQELHKLQ TYPRTNTGSG TP                                  32

SEQ ID NO: 250          moltype = AA  length = 33
FEATURE                 Location/Qualifiers
```

```
REGION              1..33
                    note = Compound 1806
source              1..33
                    mol_type = protein
                    organism = synthetic construct
SEQUENCE: 250
EASELSTAAL GRLSAELHEL ATLPRTETGS GSP                              33

SEQ ID NO: 251      moltype = AA  length = 73
FEATURE             Location/Qualifiers
REGION              1..73
                    note = Peptide backbone in comparator compound 0671
source              1..73
                    mol_type = protein
                    organism = synthetic construct
MOD_RES             2
                    note = Xaa is Aib (alpha-aminoisobutyryl)
SEQUENCE: 251
HXEGTFTSDV SSYLEEQAAR EFIAWLVRGR KGGGGEKCNT ATCATQRLAN FLVHSSNNFG 60
PILPPTNVGS NTY                                                    73

SEQ ID NO: 252      moltype = AA  length = 73
FEATURE             Location/Qualifiers
REGION              1..73
                    note = Peptide backbone in comparator compound 0672
source              1..73
                    mol_type = protein
                    organism = synthetic construct
MOD_RES             2
                    note = Xaa is Aib (alpha-aminoisobutyryl)
SEQUENCE: 252
HXEGTFTSDV SSYLEEQAAR EFIAWLVRGR KGGGGEKCNT ATCATQRLAE FLRHSSNNFG 60
PILPPTNVGS NTP                                                    73

SEQ ID NO: 253      moltype = AA  length = 68
FEATURE             Location/Qualifiers
REGION              1..68
                    note = Peptide backbone in comparator compound 0167
MOD_RES             2
                    note = Xaa is Aib (alpha-aminoisobutyryl)
source              1..68
                    mol_type = protein
                    organism = synthetic construct
SEQUENCE: 253
HXEGTFTSDV SSYLEEQAAR EIFAWLVRGR KGGGGEASEL STAALGRLSA ELHELATLPR 60
TETGSGSP                                                          68

SEQ ID NO: 254      moltype = AA  length = 68
FEATURE             Location/Qualifiers
REGION              1..68
                    note = Peptide backbone in comparator compound 0192
MOD_RES             2
                    note = Xaa is Aib (alpha-aminoisobutyryl)
source              1..68
                    mol_type = protein
                    organism = synthetic construct
SEQUENCE: 254
HXEGTFTSDV SSYLEEQAAR EFIAWLVRGR KGGGGEASEL STAALGRPSA ELHELATLPR 60
TETGSGSP                                                          68

SEQ ID NO: 255      moltype = AA  length = 31
FEATURE             Location/Qualifiers
REGION              1..31
                    note = GLP-1 receptor agonist peptide (Z1)
source              1..31
                    mol_type = protein
                    organism = synthetic construct
VAR_SEQ             29
                    note = Xaa can be Lys (K) or Gly (G)
VAR_SEQ             21
```

```
                         note = Xaa can be Glu (E) or Lys (K)
VAR_SEQ                  20
                         note = Xaa can be Lys (K) or Arg (R)
VAR_SEQ                  24
                         note = Xaa can be Ala (A), Glu (E) or Leu (L)
VAR_SEQ                  31
                         note = Xaa can be Ala (A), Lys (K), Gly (G), Gln (Q) or
                          absent
VAR_SEQ                  22
                         note = Xaa can be Phe (F), Trp (W) or Tyr (Y)
VAR_SEQ                  23
                         note = Xaa can be Ile (I), Leu (L) or Val (V)
VAR_SEQ                  17
                         note = Xaa can be Gln (Q) or Lys (K)
VAR_SEQ                  9
                         note = Xaa can be Asp (D) or Lys (K)
VAR_SEQ                  16
                         note = Xaa can be Glu (E), Gly (G) or Lys (K)
VAR_SEQ                  19
                         note = Xaa can be Ala (A) or Val (V)
VAR_SEQ                  10
                         note = Xaa can be Lys (K) or Val (V)
VAR_SEQ                  1
                         note = Xaa can be His (H) or Imp
VAR_SEQ                  30
                         note = Xaa can be Ala (A), Gly (G), Lys (K), Arg (R) or
                          absent
VAR_SEQ                  25
                         note = Xaa can be Lys (K) or Trp (W)
VAR_SEQ                  2
                         note = Xaa can be Aib, Ala (A), Gly (G) or Trp (W)
VAR_SEQ                  12
                         note = Xaa can be Lys (K), Arg (R) or Ser (S)
VAR_SEQ                  28
                         note = Xaa can be Lys (K) or Arg (R)
SEQUENCE: 255
XXEGTFTSXX SXYLEXXAXX XXXXXLVXXX X                                           31

SEQ ID NO: 256           moltype = AA  length = 32
FEATURE                  Location/Qualifiers
REGION                   1..32
                         note = Amylin receptor agonist peptide (Z3)
source                   1..32
                         mol_type = protein
                         organism = synthetic construct
VAR_SEQ                  7
                         note = Xaa can be Ala (A), Glu (E) or Lys (K)
VAR_SEQ                  3
                         note = Xaa can be Glu (E), Lys (K) or Arg (R)
VAR_SEQ                  20
                         note = Xaa can be Ala (A) or Lys (K)
VAR_SEQ                  14
                         note = Xaa can be Ala (A) or Lys (K)
VAR_SEQ                  29
                         note = Xaa can be Ser (S) or Lys (K)
VAR_SEQ                  18
                         note = Xaa can be Glu (E), Lys (K) or Gln (Q)
VAR_SEQ                  32
                         note = Xaa can be Pro (P) or Tyr (Y)
VAR_SEQ                  2
                         note = Xaa can be Lys (K) or Ser (S)
VAR_SEQ                  1
                         note = Xaa can be Ala (A), Lys (K) or absent
VAR_SEQ                  23
                         note = Xaa can be Lys (K) or Pro (P)
SEQUENCE: 256
XXXLSTXALG RLSXELHXLX TLXRTETGXG SX                                          32
```

CO-AGONISTS OF THE GLP-1 AND AMYLIN RECEPTORS

CROSS-REFERENCE TO RELATED APPLICATIONS

This application is a continuation of International Application PCT/EP2021/086494, filed Dec. 17, 2021, which claims priority to European Patent Applications 20215291.4, filed Dec. 18, 2020, 21154668.4, filed Feb. 2, 2021, and 21179810.3, filed Jun. 16, 2021; the contents of which are incorporated by reference in their entirety.

INCORPORATION-BY-REFERENCE OF THE SEQUENCE LISTING

The instant application contains a Sequence Listing which has been submitted in XML format via the USPTO patent electronic filing system and is hereby incorporated by reference in its entirety. Said XML file, created on Nov. 8, 2022, is named 200062US01.xml and is 408 kilobytes in size.

TECHNICAL FIELD

The invention relates to a compound comprising a GLP-1 receptor agonist and an amylin receptor agonist. The invention also relates to a pharmaceutical formulation, suitable for but not limited to oral administration, which comprises such a compound. The compound and pharmaceutical formulation comprising it may be used for the medical treatment of subjects with overweight or obesity, with or without associated comorbidities; diabetes with or without associated comorbidities; cardiovascular diseases, non-alcoholic steatohepatitis (NASH) and cognitive impairment, such as that caused by Alzheimer's disease.

BACKGROUND

Overweight and obesity are the abnormal or excessive accumulation of body fat that present a risk to an individual's overall health. A body mass index (BMI) over 25 is considered overweight, and a BMI of over 30 is considered obese. Obesity is a leading risk factor in a large number of serious conditions, including type 2 diabetes and its associated co-morbidities, and cardiovascular diseases such as heart disease and stroke, which are the leading causes of death worldwide. Obesity is now recognised by the World Health Organization (WHO) as an issue that has grown to epidemic proportion, even in children: in 2016, 1.9 billion adults worldwide were reportedly obese; in 2019, 38.3 million children under the age of 5 worldwide were reportedly obese. According to the WHO, 422 million people worldwide have diabetes and 1.6 million deaths are directly attributed to diabetes each year. There is, therefore, a huge incentive for the individual, as well as society, to try to prevent and/or treat obesity.

When diet and exercise alone do not suffice in reducing the body mass index (BMI) of an obese individual to an acceptable level, treatment with pharmaceutical drugs such as liraglutide, orlistat and naltrexone-bupropion have been shown to cause some weight loss. Nonetheless, bariatric surgery has proven necessary in many cases. While bariatric surgery is currently the most effective treatment in terms of obtaining long-term weight loss, it is an invasive procedure associated with high risk to the patient and high cost. Therefore, an efficacious and minimally invasive treatment would be a significant improvement in the treatment of obesity.

Amylin is a 37-amino acid long polypeptide hormone that is produced in and co-secreted with insulin from the pancreatic beta (β)-cell. Endogenous amylin has a half-life of approximately 15-20 minutes. It produces its effects in several different organ systems, primarily acting via amylin receptors 1-3 (AMYR1-3). Amylin is an important regulator of energy metabolism in health and disease, inhibiting glucagon secretion, delaying gastric emptying, signalling satiety and suppressing appetite. Other amylin actions have also been reported, such as on the cardiovascular system and on bone.

Clinical studies have shown that amylin receptor agonists may be useful for the treatment of overweight, obesity, type 1 diabetes and/or type 2 diabetes. Currently, there is one product on the market (Symlin®) which contains an amylin receptor agonist (pramlintide acetate) as the active pharmaceutical ingredient. Symlin®, a liquid pharmaceutical formulation for subcutaneous administration, is approved for use in patients with type 1 or type 2 diabetes who use basal and mealtime insulin and have failed to achieve desired glycemic control, despite optimal insulin therapy. Pramlintide for use in overweight and obese patients was also investigated in the clinic. Pramlintide has a short biological half-life (less than 1 hour), necessitating administration thrice daily. Consequently, there is a large diurnal difference in the pramlintide plasma levels of patients treated with it.

GLP-1 is a 30 or 31-amino acid polypeptide hormone that is synthesised and secreted from enteroendocrine L-cells. GLP-1 is an incretin, decreasing blood sugar levels in a glucose-dependent manner by enhancing the secretion of insulin. Endogenous GLP-1 is rapidly degraded, primarily by dipeptidyl peptidase-4 (DPP-4), resulting in a half-life of approximately 2 minutes.

Several marketed products containing a GLP-1 receptor agonist as the active pharmaceutical ingredient are approved for use in individuals with type 2 diabetes. These include dulaglutide (Trulicity®), exenatide (Byetta®, Bydureon®), liraglutide (Victoza®), lixisenatide (Lyxumia®) and semaglutide (Ozempic®).

Semaglutide is the first GLP-1 receptor agonist to be approved in the form of a tablet (Rybelsus®). It is safe and effective as a monotherapy, and as add-on pharmacological therapy, for the treatment of type 2 diabetes mellitus.

Two marketed products containing a GLP-1 receptor agonist as the active pharmaceutical ingredient are approved for use in individuals who are overweight or obese and have at least one weight-related co-morbidity: liraglutide (Saxenda®) and semaglutide (Wegovy®). The maximum efficacy that can be achieved with a GLP-1 receptor agonist is limited by tolerability. At increasing doses, side-effects such as nausea and vomiting become increasingly pronounced. Amylin receptor agonist therapy is limited by tolerability in much the same way as GLP-1 receptor agonist therapy (and by similar side-effects such as nausea and vomiting). There has been a similar desire to be able to prolong the action of amylin.

A fixed-dose combination of an amylin receptor agonist, cagrilintide, and a GLP-1 receptor agonist, semaglutide, is currently under investigation for the treatment of overweight and obesity (Lancet 2021; 397: 1736-48). The drug products being investigated are separate liquid pharmaceutical formulations for subcutaneous use. A clinical trial has demonstrated that a combination of semaglutide and cagrilintide induced a greater weight loss in obese patients than the maximal approved dose of semaglutide monotherapy, without resulting in a significant worsening of the side-effect profile.

Whilst current therapy options and investigatory drugs provide promise, individuals with overweight, obesity and/or associated comorbidities can, at best, hope to be treated with injectable pharmaceutical formulations or medications with modest efficacy. There still remains a need in the art for a more efficacious medicament, which does not simultaneously result in a proportionally increased level of side-effects and which is suitable for oral administration.

SUMMARY OF THE INVENTION

Disclosed herein is a GLP-1 receptor-amylin receptor co-agonist comprising a polypeptide (R1) according to Formula I:

Z1-Z2-Z3, comprising 1-3 lysine (Lys, K) residues and no disulfide bridge; wherein:

Z1 is a GLP-1 receptor agonist peptide comprising a maximum of 9 amino acid modifications, relative to SEQ ID NO: 1 (human GLP-1(7-37), with the proviso that Z1 does not comprise an isoleucine (Ile, 1) at position 22, relative to SEQ ID NO: 1 or SEQ ID NO: 255;

Z2 is an optional peptide linker;

Z3 is an amylin receptor agonist peptide comprising a C-terminal amide and a maximum of 4 amino acid modifications, relative to SEQ ID NO: 79, with the proviso that Z3 does not comprise a proline (Pro, P) at position 12 (relative to SEQ ID NO: 79 or SEQ ID NO: 256).

Disclosed herein is a GLP-1 receptor-amylin receptor co-agonist comprising a polypeptide (R1) according to Formula I:

Z1-Z2-Z3, comprising 1-3 lysine (Lys, K) residues and no disulfide bridge;

wherein:

Z1 is a GLP-1 receptor agonist peptide comprising a maximum of 9 amino acid modifications, relative to SEQ ID NO: 1 (human GLP-1(7-37);

Z2 is an optional peptide linker;

Z3 is an amylin receptor agonist peptide comprising a C-terminal amide and a maximum of 7 amino acid modifications, relative to SEQ ID NO: 79.

Disclosed herein is said GLP-1 receptor-amylin receptor co-agonist, further comprising 1-3 protraction moieties attached via the 1-3 lysine residues.

One preferred compound is "compound 0111", that is: H-Aib-EGTFTSDVSSYLEEQAAREFIAWLVRGR-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-GGGGEASELSTAALGRLSAELHELATLPRTETGSGSP-amide (see FIG. 46):

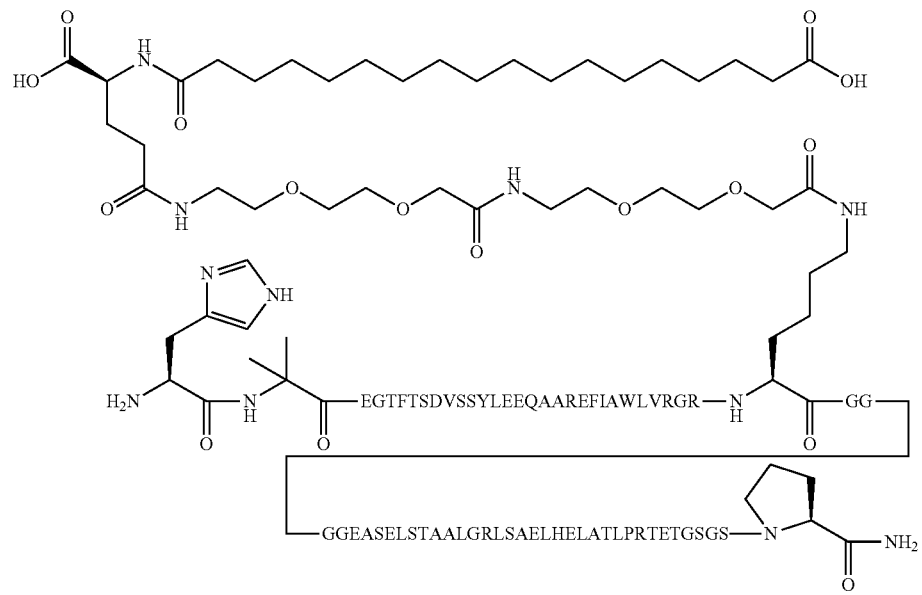

Disclosed herein is a GLP-1 receptor-amylin receptor co-agonist for use as a medicament. Disclosed herein is a GLP-1 receptor-amylin receptor co-agonist for use in the treatment of subjects with; an initial body mass index (BMI) of 27 or more, such as 30 or more, optionally in the presence of at least one weight-related comorbidity; diabetes, optionally in the presence of at least one comorbidity, cardiovascular disease, non-steroidal steatohepatitis and/or cognitive impairment, such as that caused by Alzheimer's disease.

Disclosed herein is a pharmaceutical formulation comprising a GLP-1 receptor-amylin receptor co-agonist and pharmaceutically acceptable excipients.

SEQUENCE LISTING

SEQ ID NO: 1 represents the amino acid sequence of human GLP-1(7-37).

SEQ ID NOs: 2-78 represent the amino acid sequences of exemplified GLP-1 receptor agonist peptide backbones.

SEQ ID NOs: 79-88 represent the amino acid sequences of exemplified amylin receptor agonist peptide backbones.

SEQ ID NOs: 89-116 represent the amino acid sequences of exemplified optional peptide linkers.

SEQ ID NOs: 117-236 represent the amino acid sequences of exemplified GLP-1 receptor-amylin receptor co-agonist polypeptide backbones.

SEQ ID NO: 237 represents the amino acid sequence of human glucagon.

SEQ ID NO: 238 represents the amino acid sequence of a GLP-1 receptor agonist (peptide Z1) according to Formula II.

SEQ ID NO: 239 represents the amino acid sequence of optional peptide linker Z2.

SEQ ID NO: 240 represents the amino acid sequence of an amylin receptor agonist (peptide Z3) according to Formula III.

SEQ ID NOs: 241-245 represent the amino acid sequences of the polypeptide backbones within exemplified comparator compounds.

SEQ ID NO: 246 represents the amino acid sequence of the polypeptide backbone within semaglutide.

SEQ ID NO: 247 represents the amino acid sequence of the polypeptide backbone within pramlintide.

SEQ ID NO: 248 represents the amino acid sequence of the polypeptide backbone within cagrilintide.

SEQ ID NO: 249 represents the amino acid sequence of salmon calcitonin.

SEQ ID NO: 250 represents the amino acid sequence of the polypeptide backbone within compound 1806.

SEQ ID NOs: 251-254 represent the amino acid sequences of the polypeptide backbones within exemplified comparator compounds.

SEQ ID NO: 255 represents the amino acid sequence of a GLP-1 receptor agonist (peptide Z1) according to Formula II.

SEQ ID NO: 256 represents the amino acid sequence of an amylin receptor agonist (peptide Z3) according to Formula III.

DRAWINGS

Figure 173:
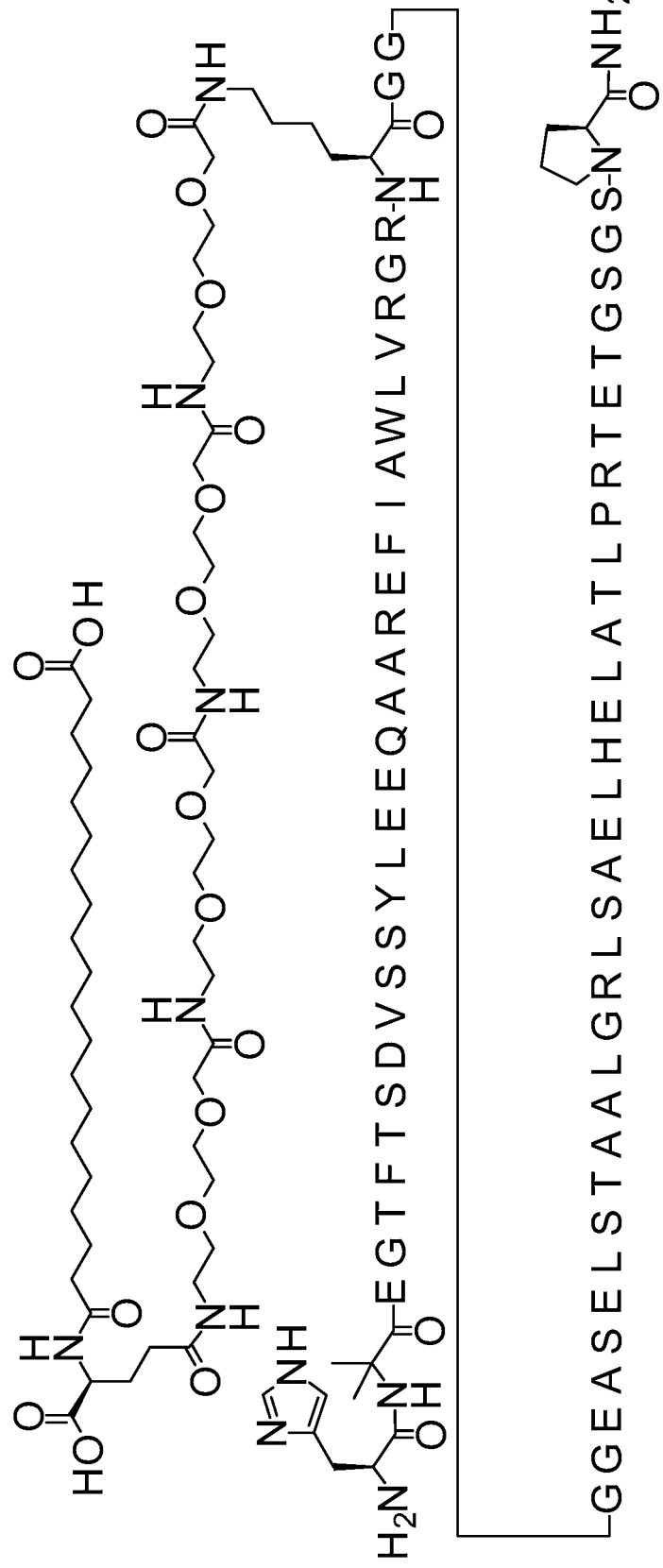

FIGS. 1-173 depict the manufactured compounds according to the invention that are further described in Example 1.

Figure 2:
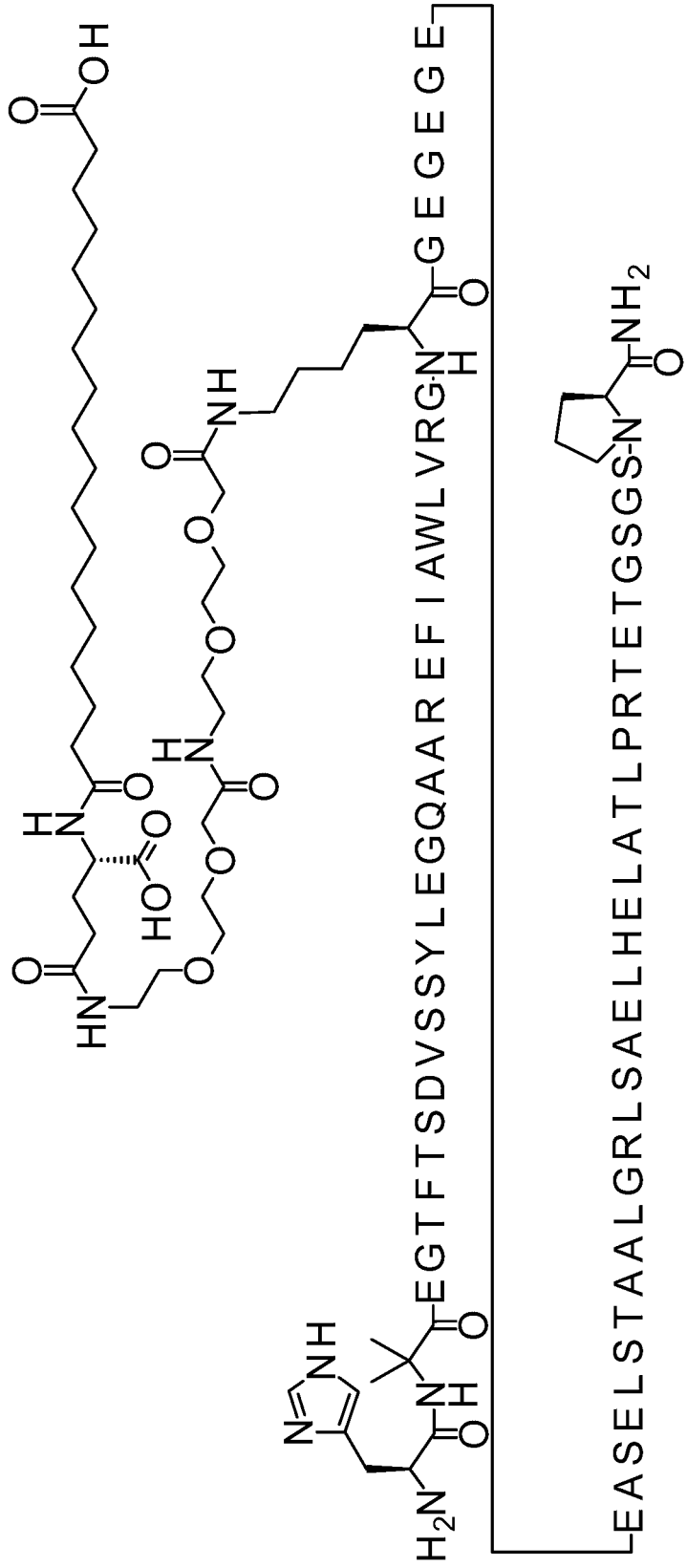
Figure 3:
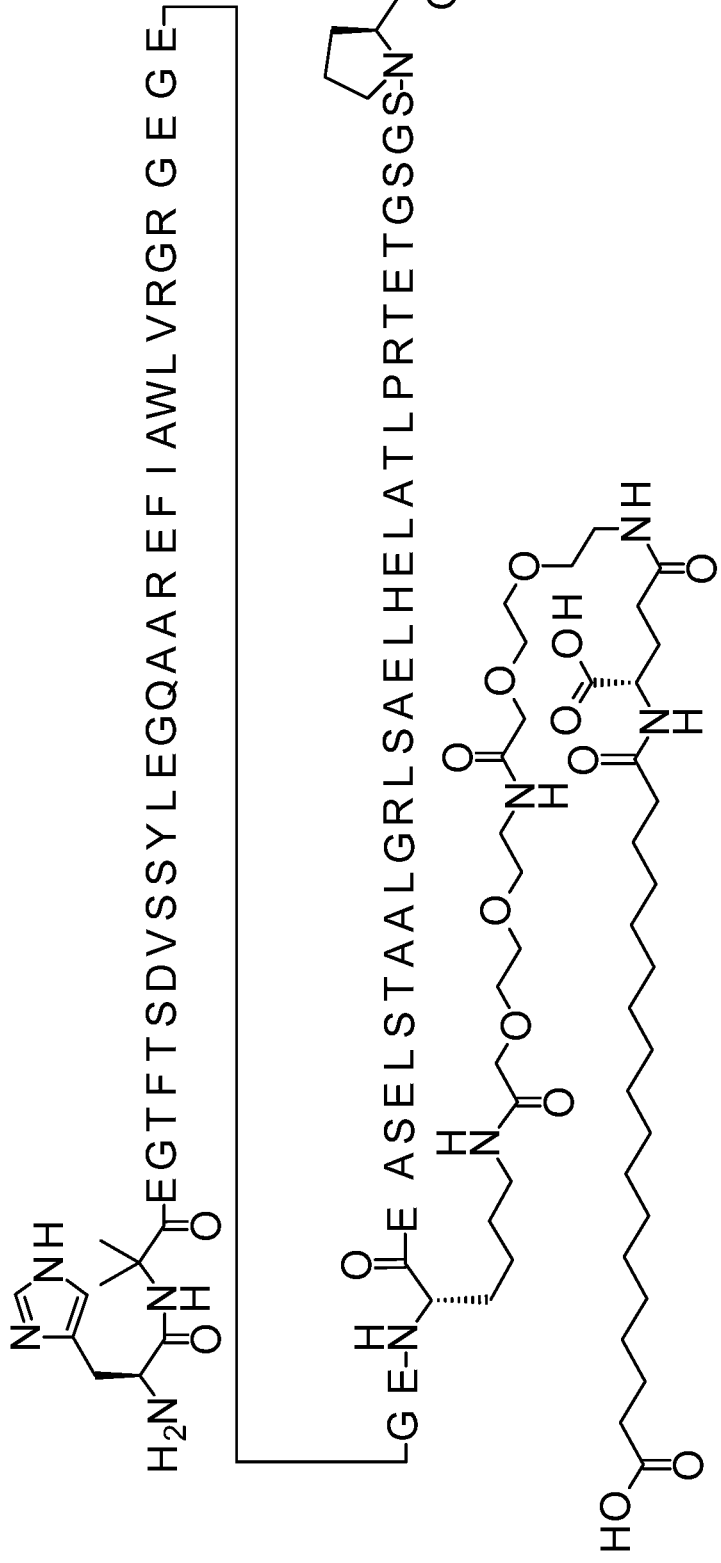
Figure 4:
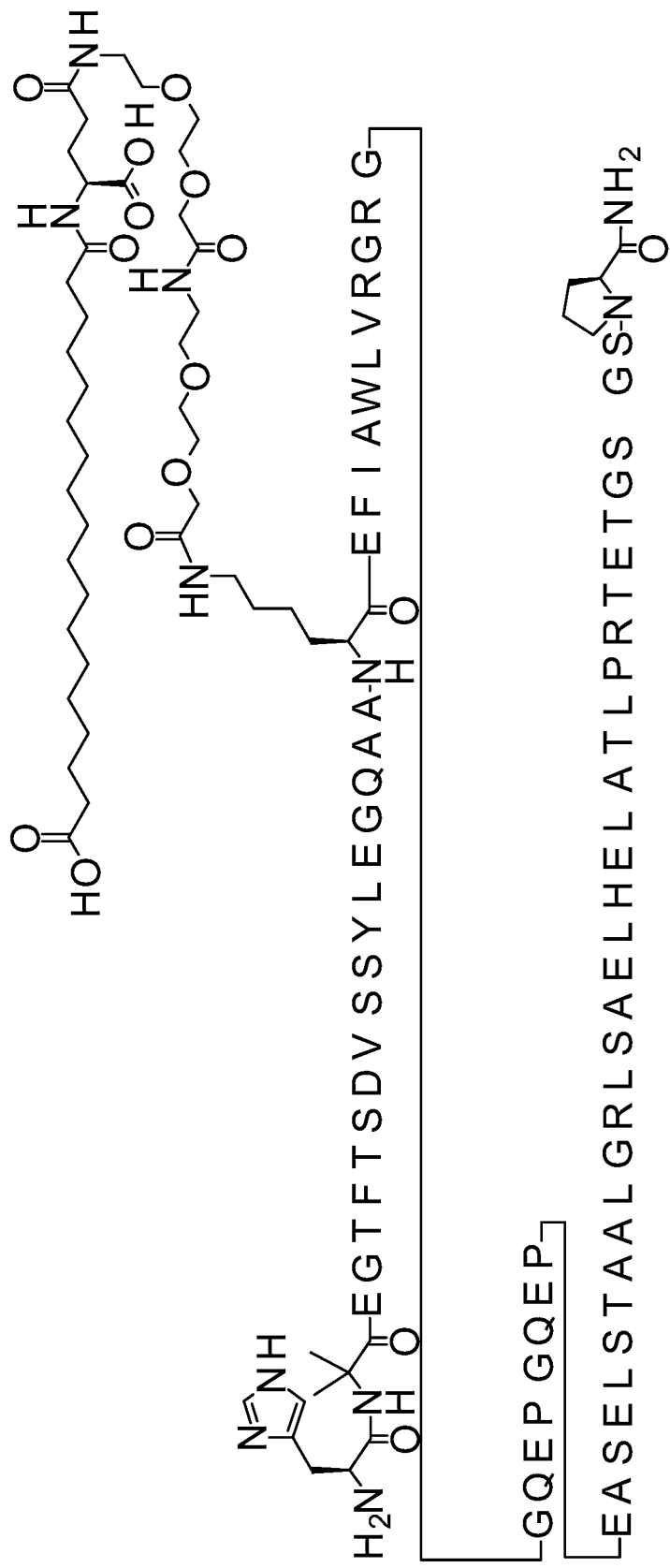
Figure 5:
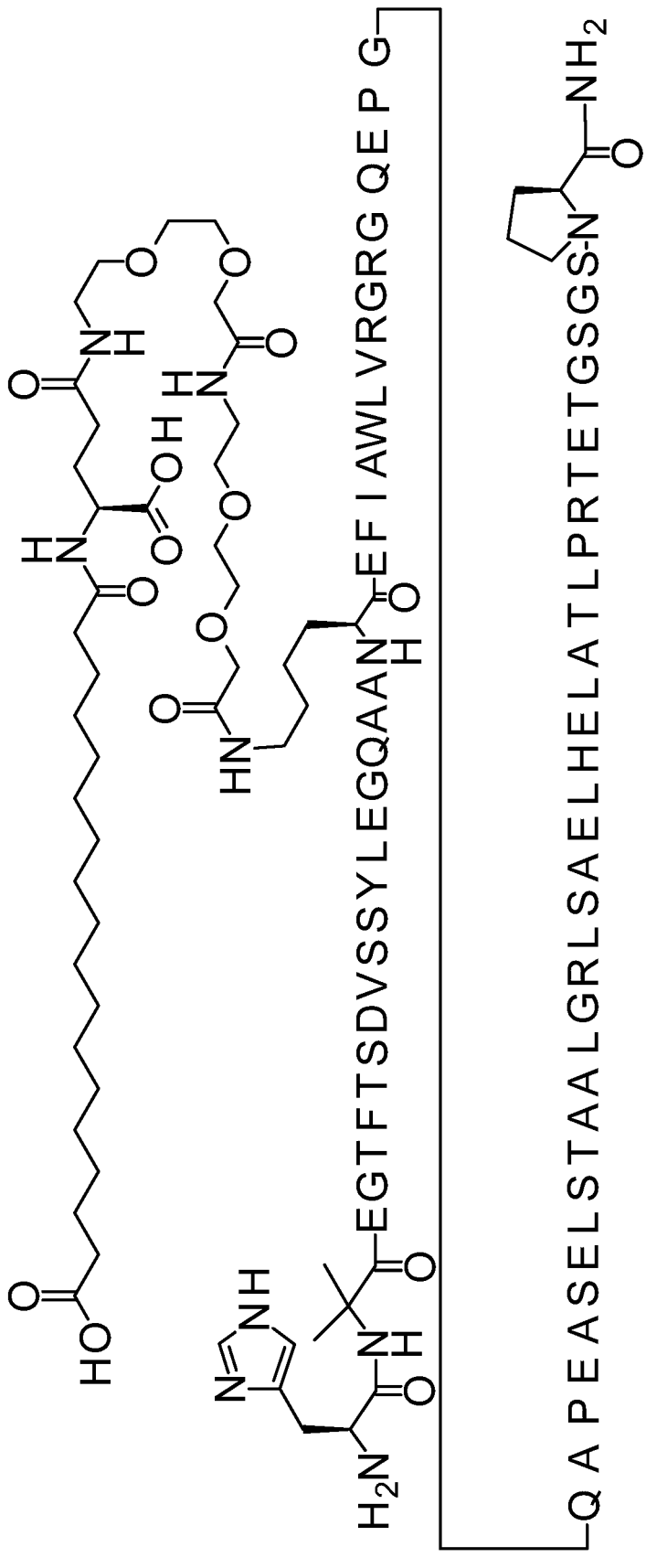
Figure 6:
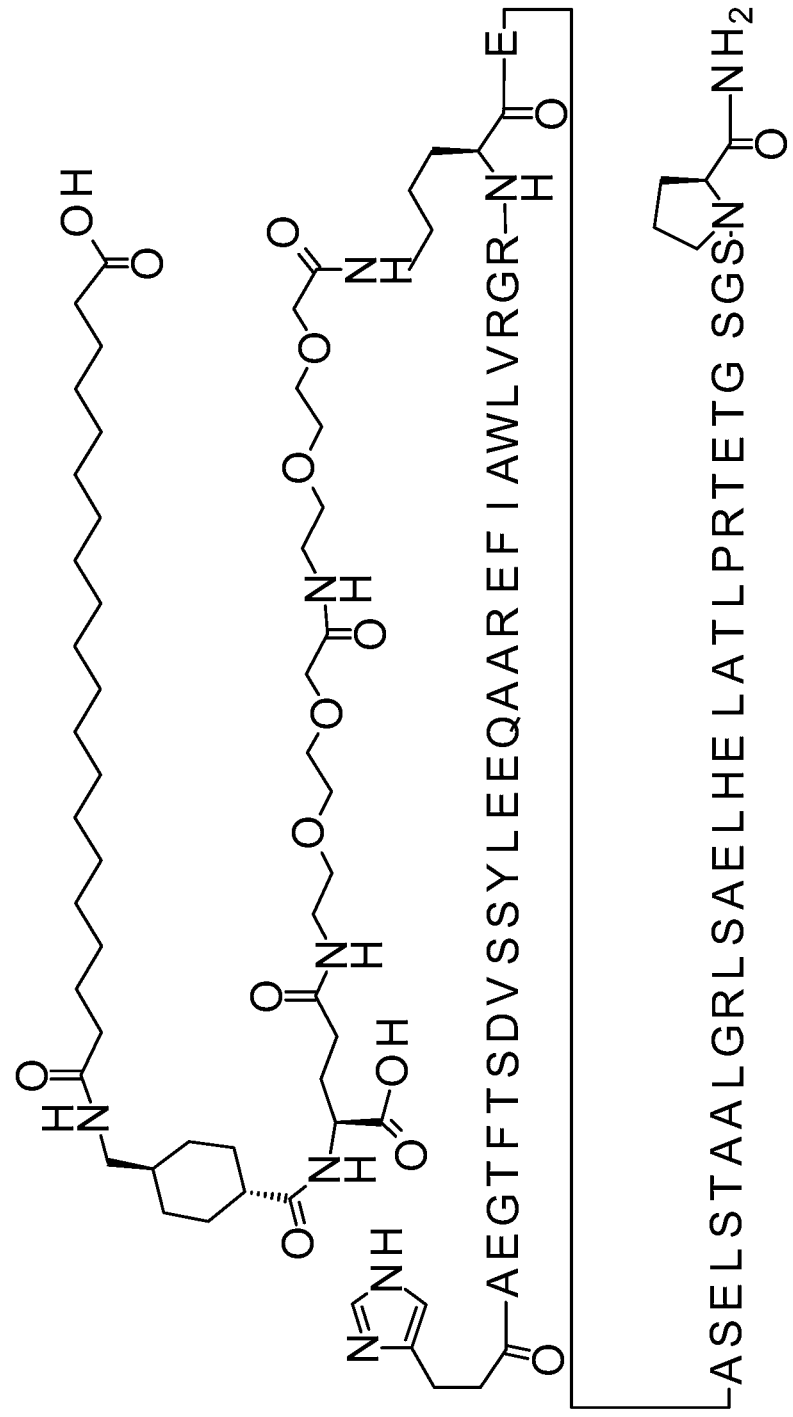
Figure 7:
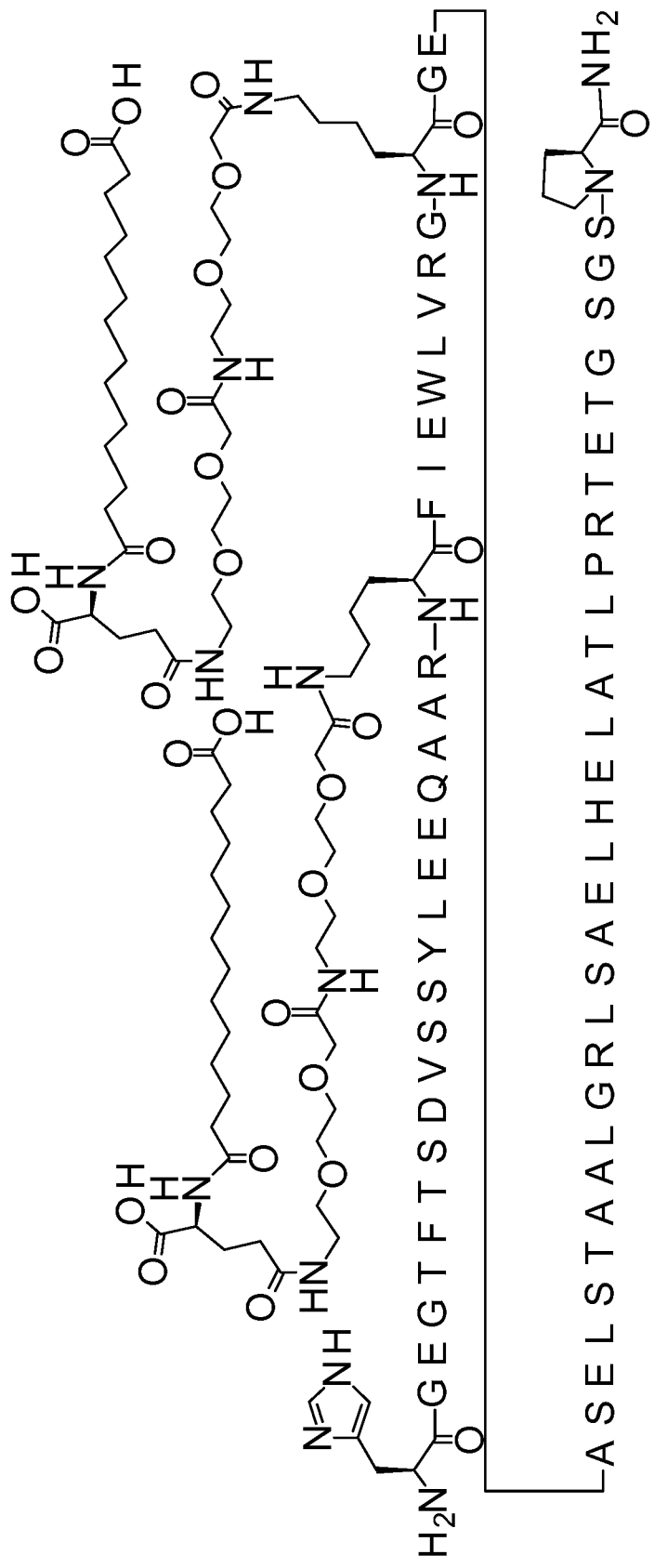
Figure 8:
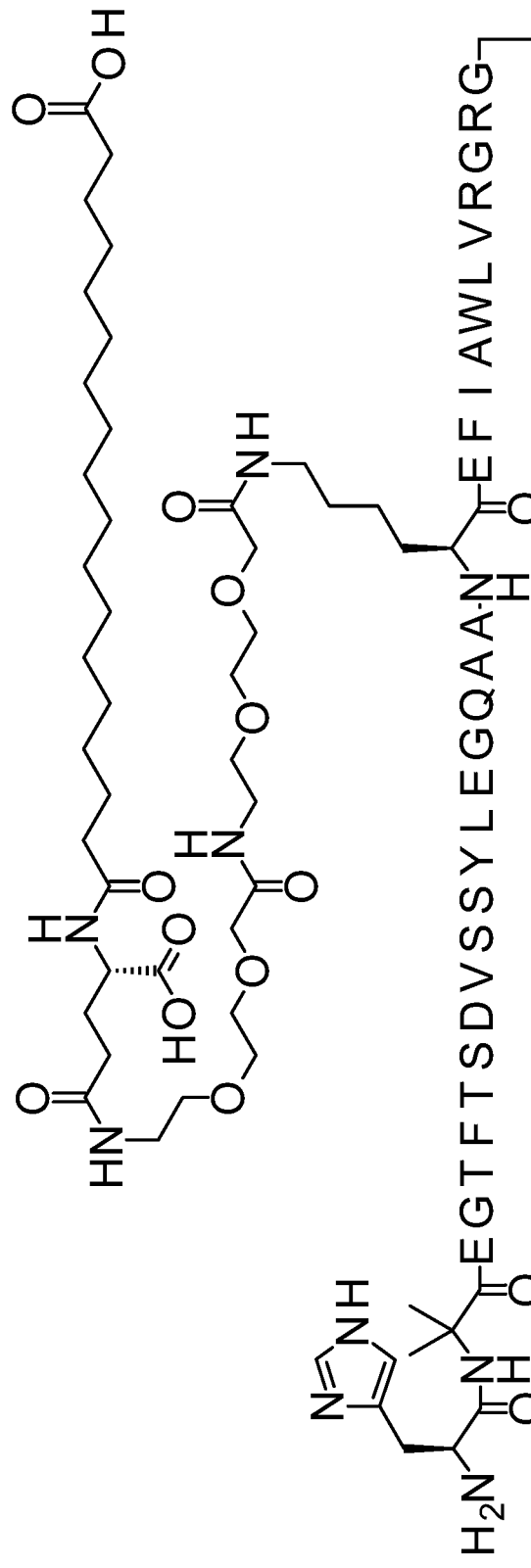
Figure 9:
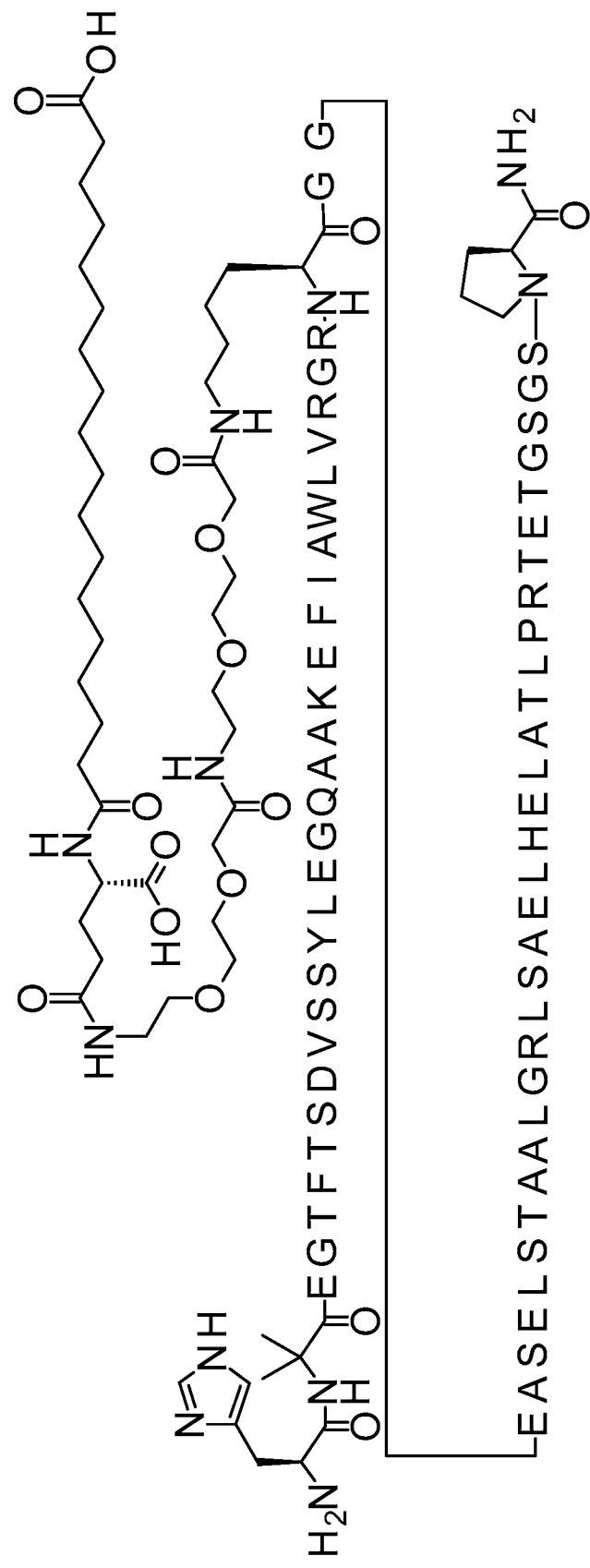
Figure 10:
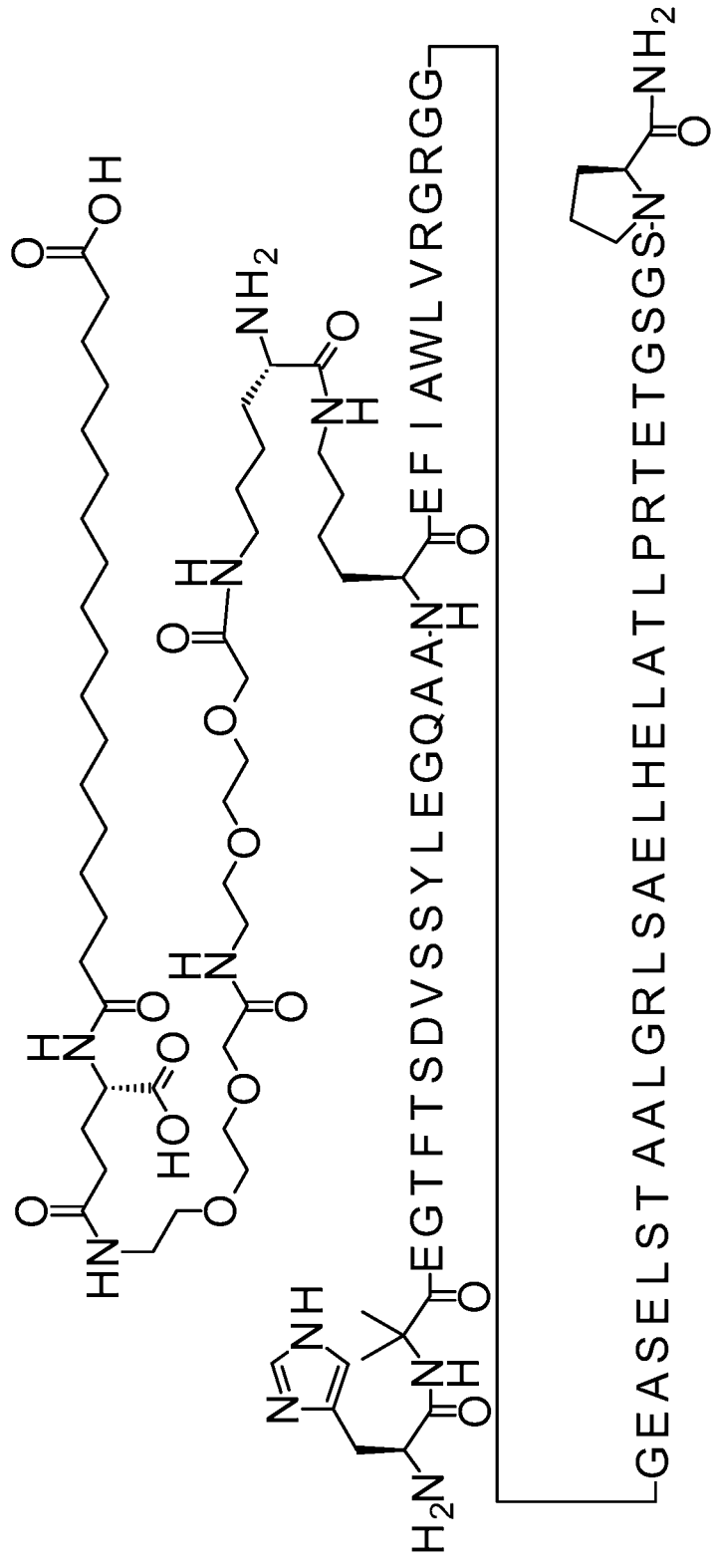
Figure 11:
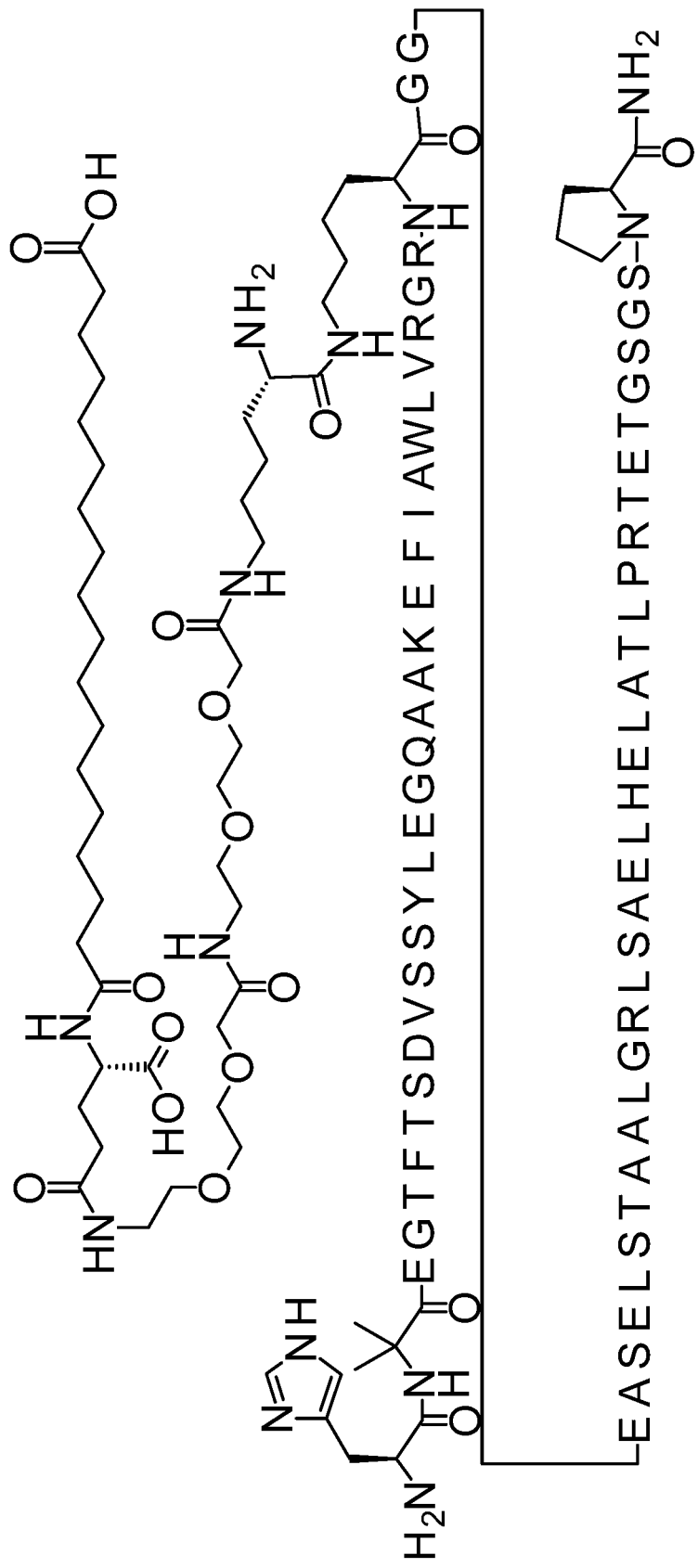
Figure 12:
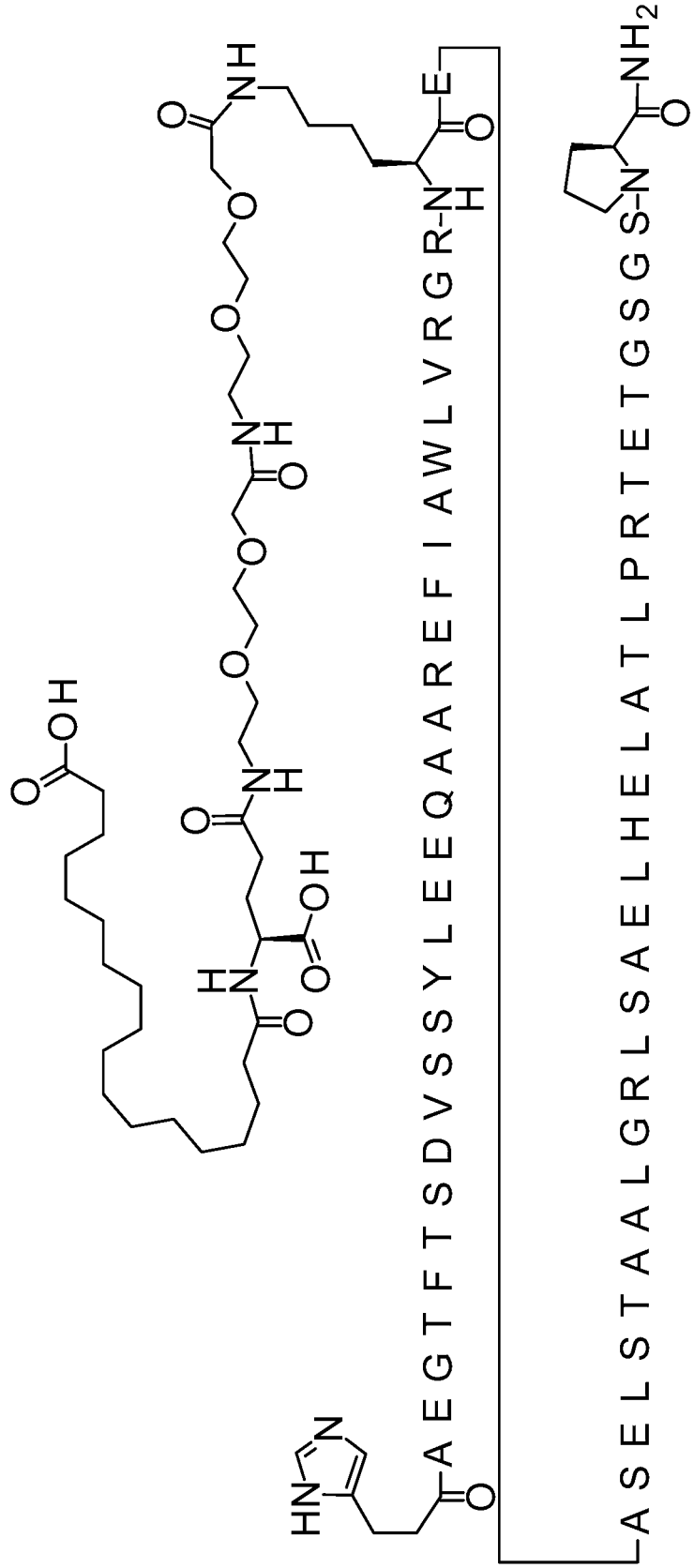
Figure 13:
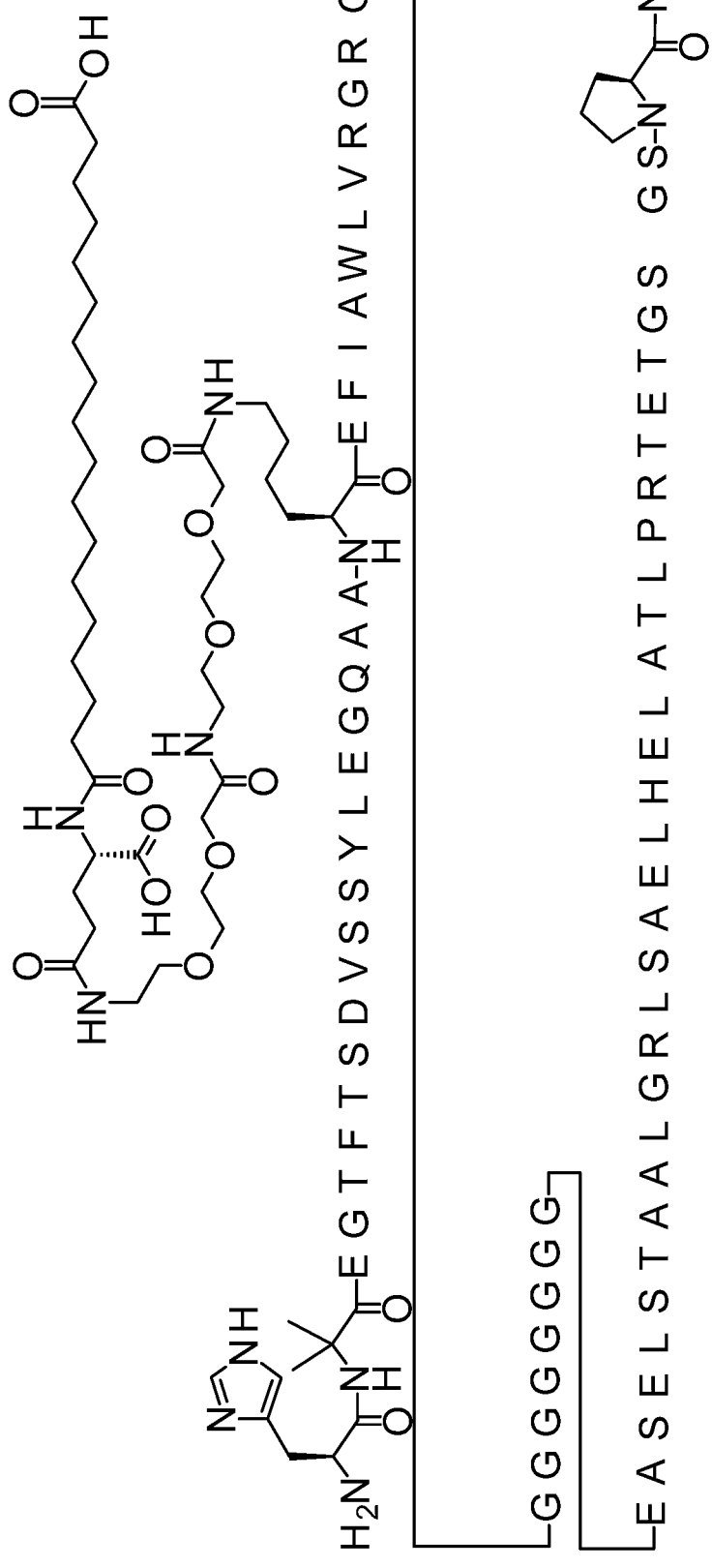
Figure 14:
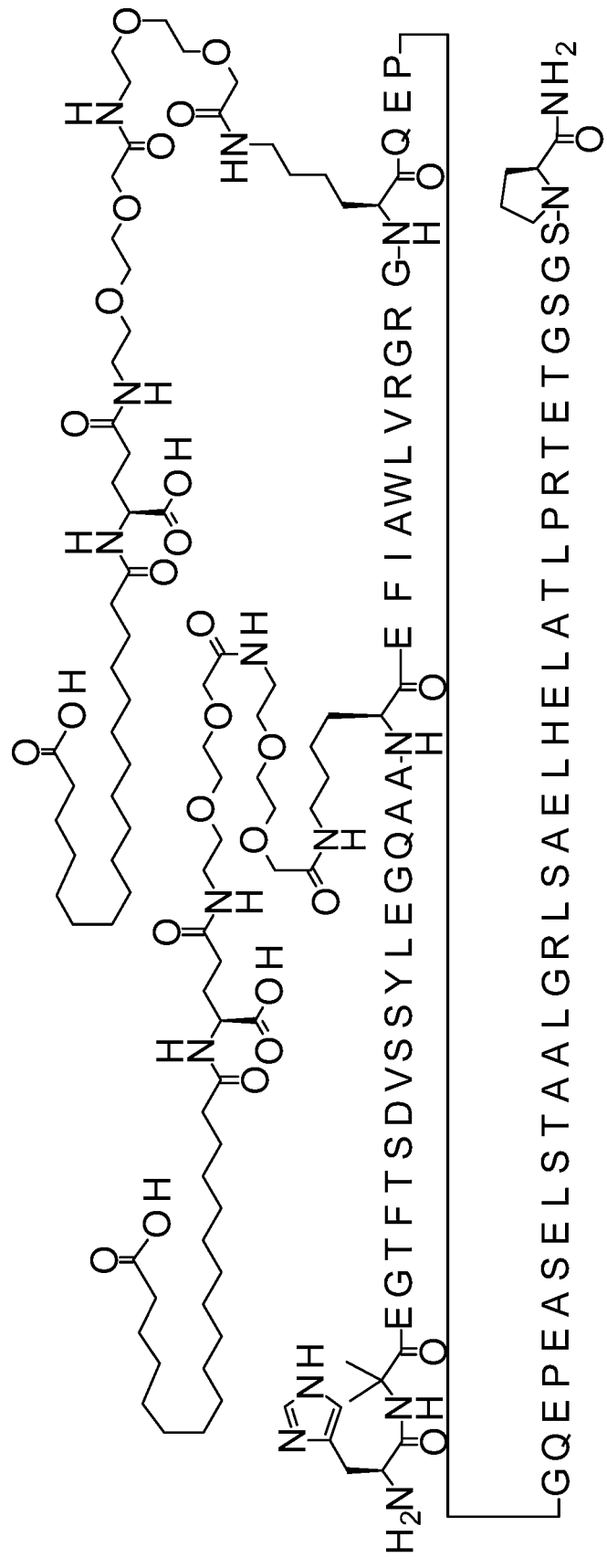
Figure 15:
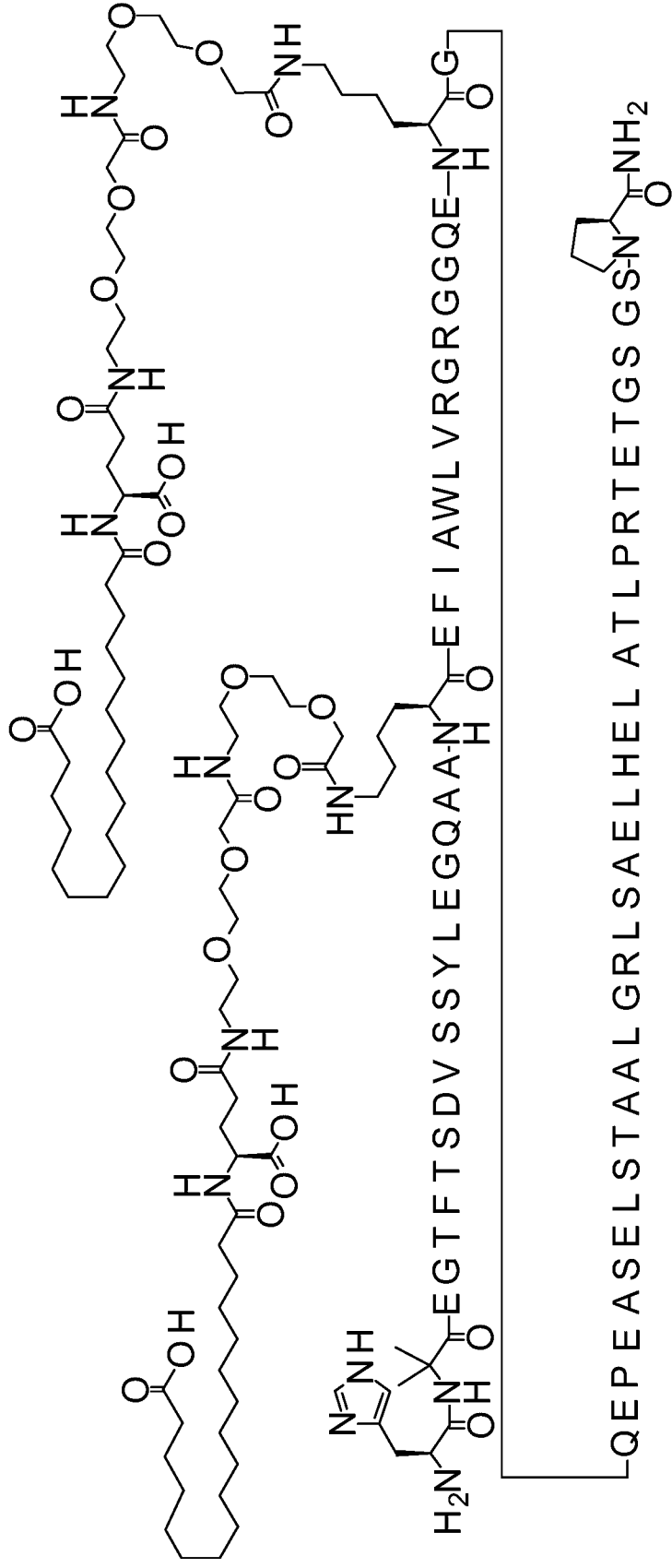
Figure 16:
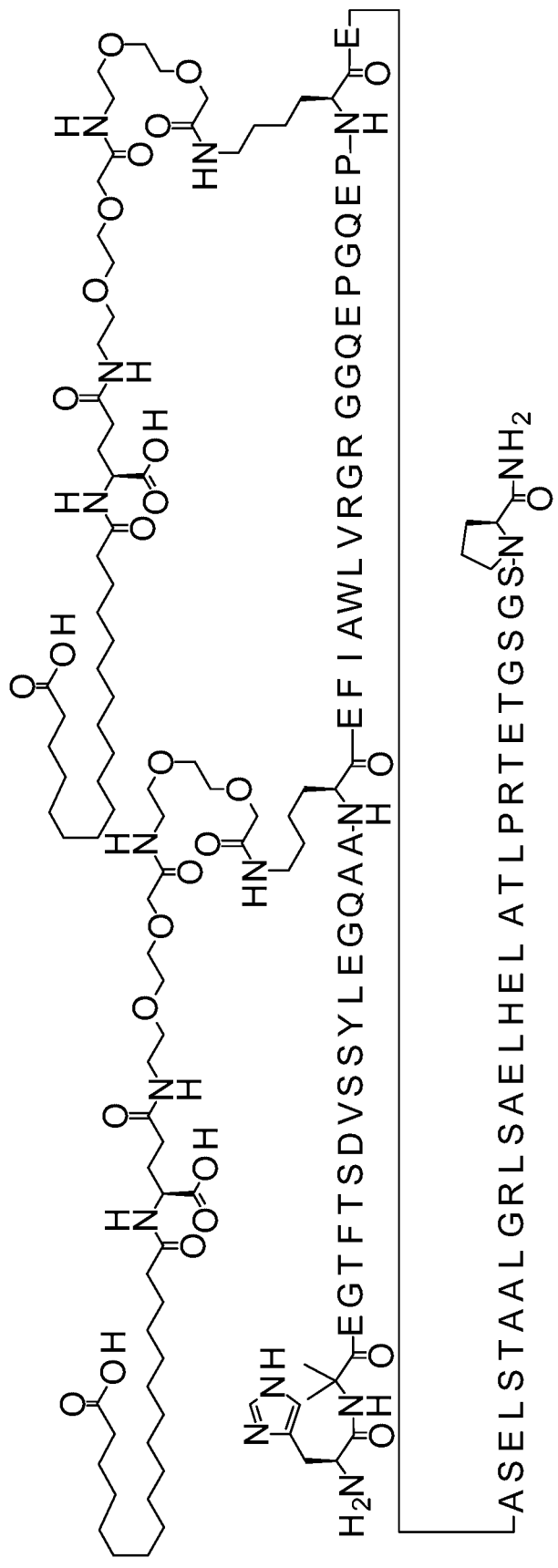
Figure 17:
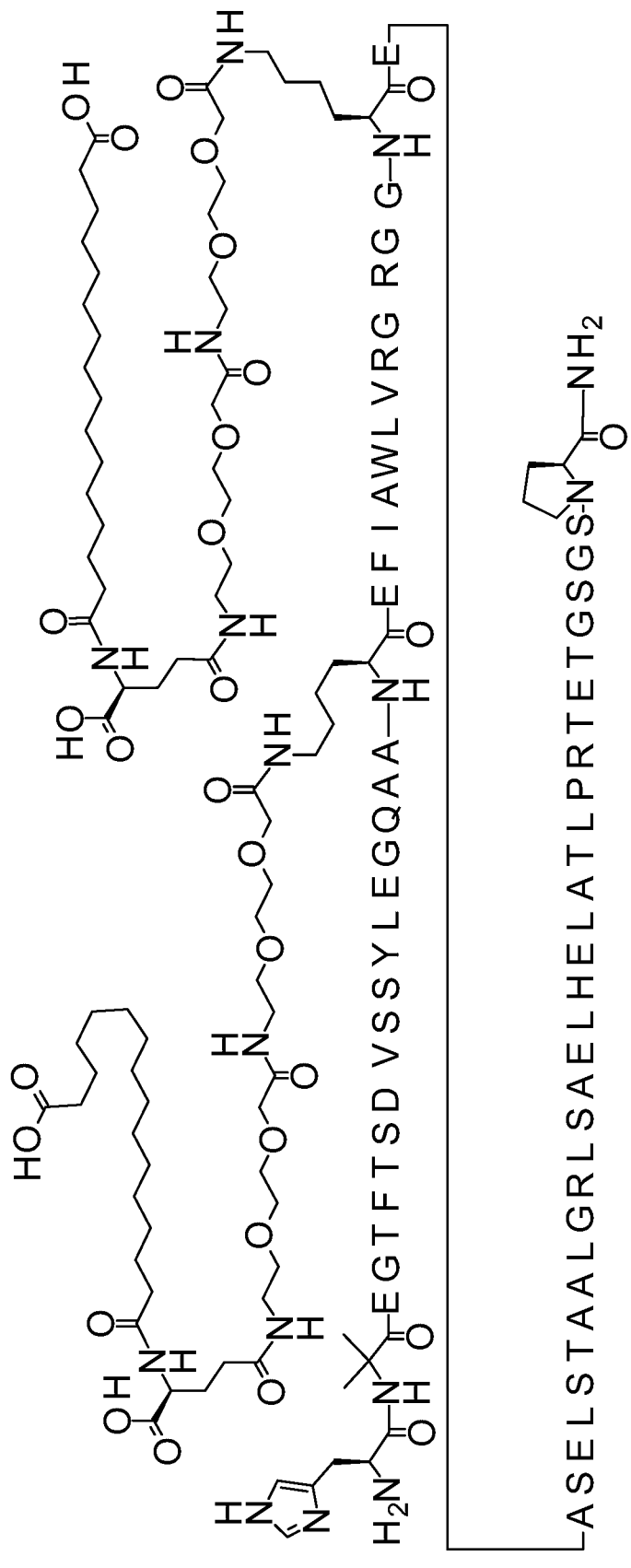
Figure 18:
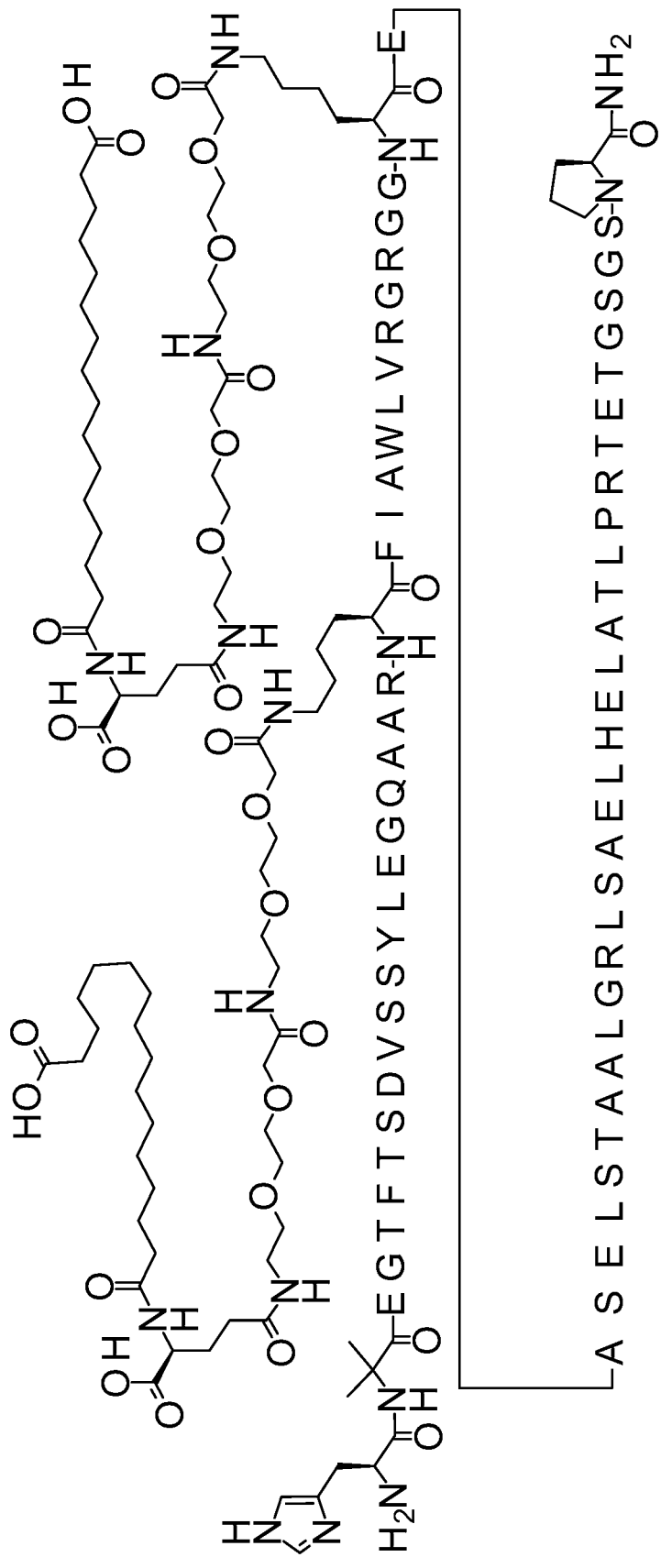
Figure 19:
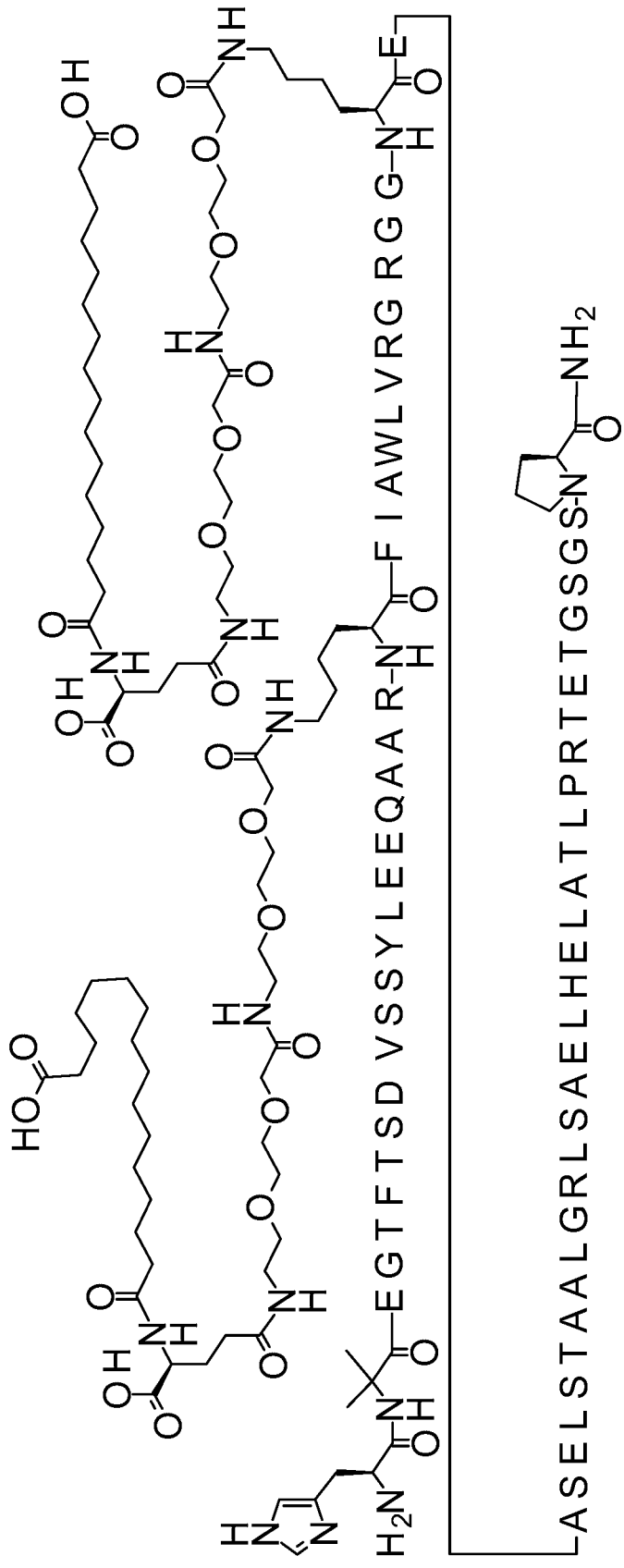
Figure 20:
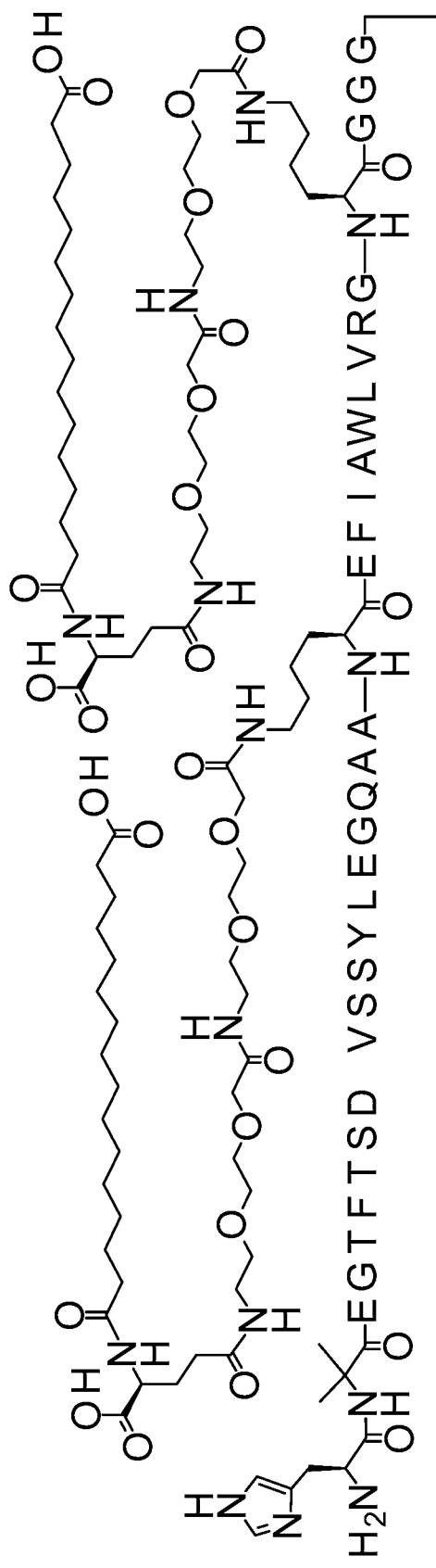
Figure 21:
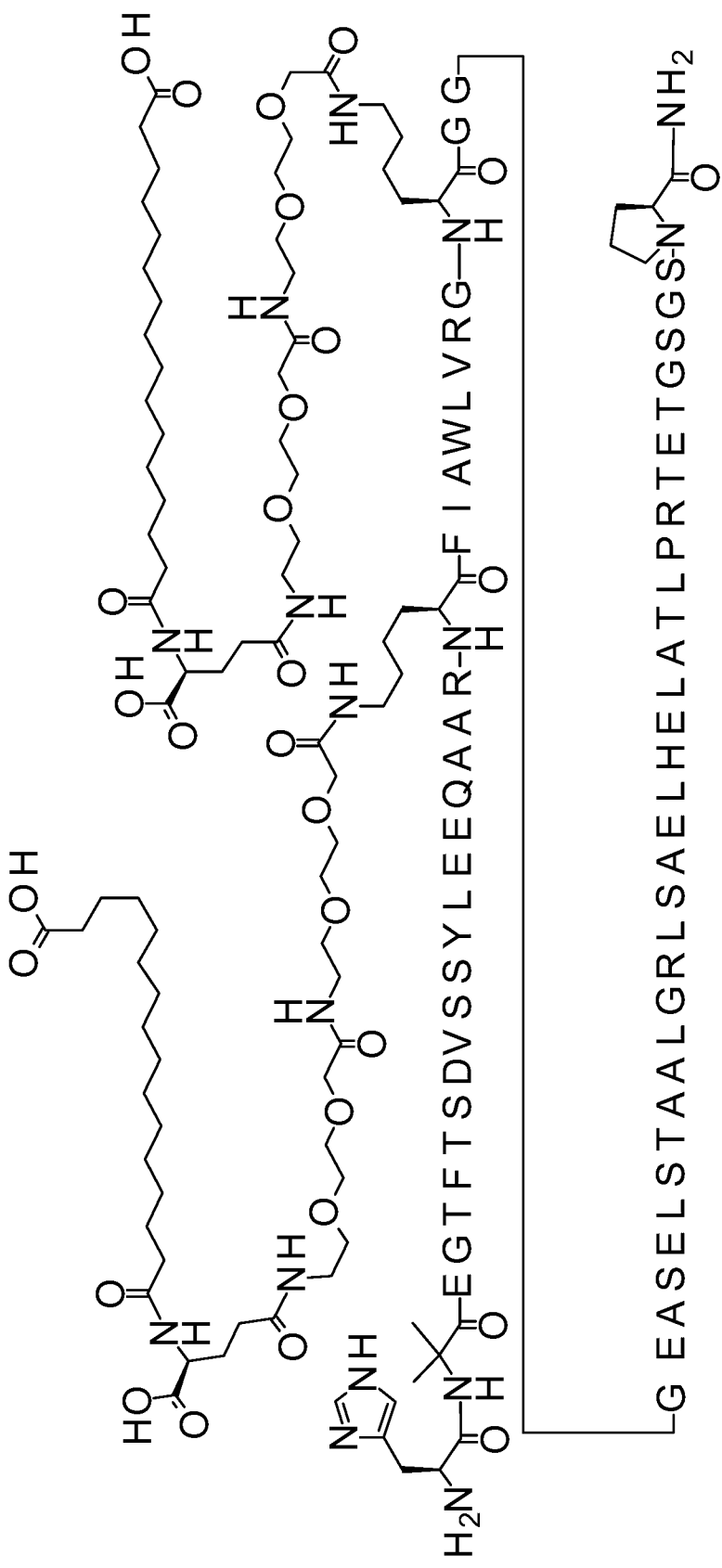
Figure 22:
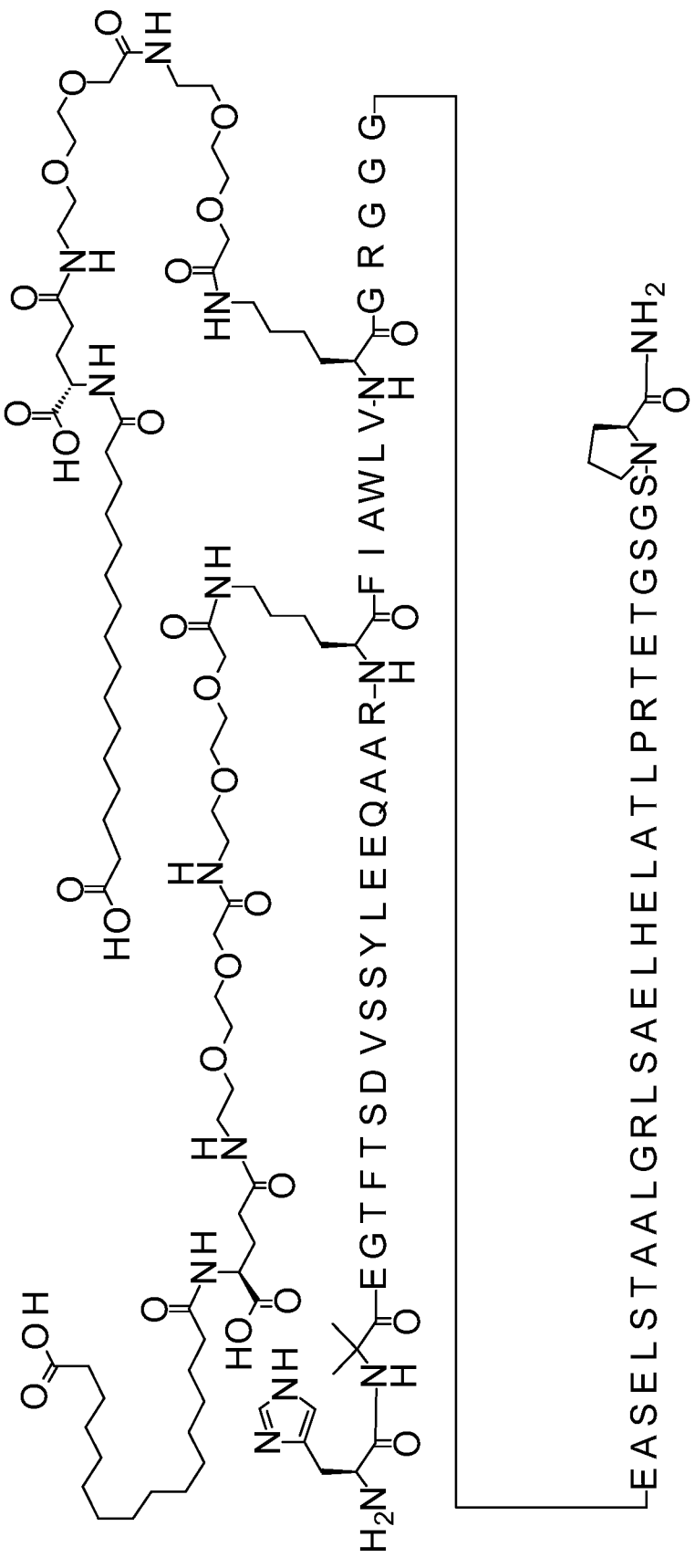
Figure 23:
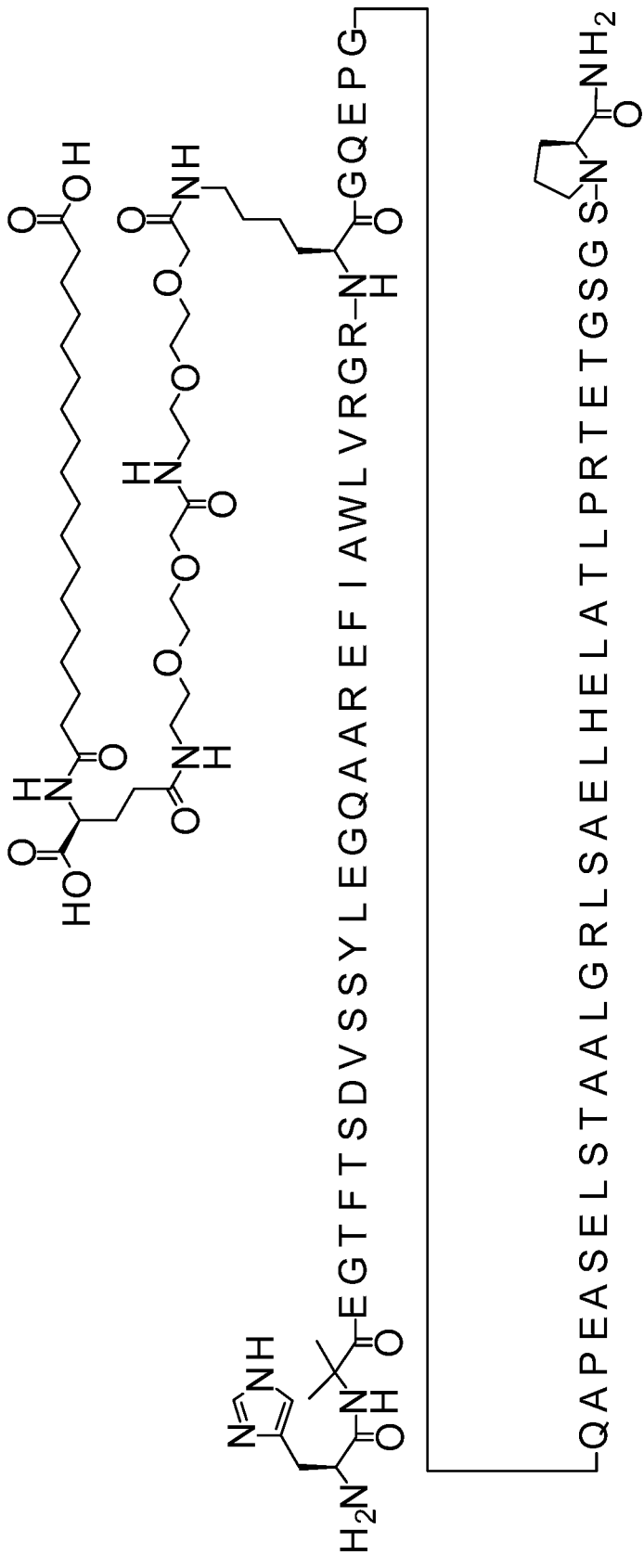
Figure 24:
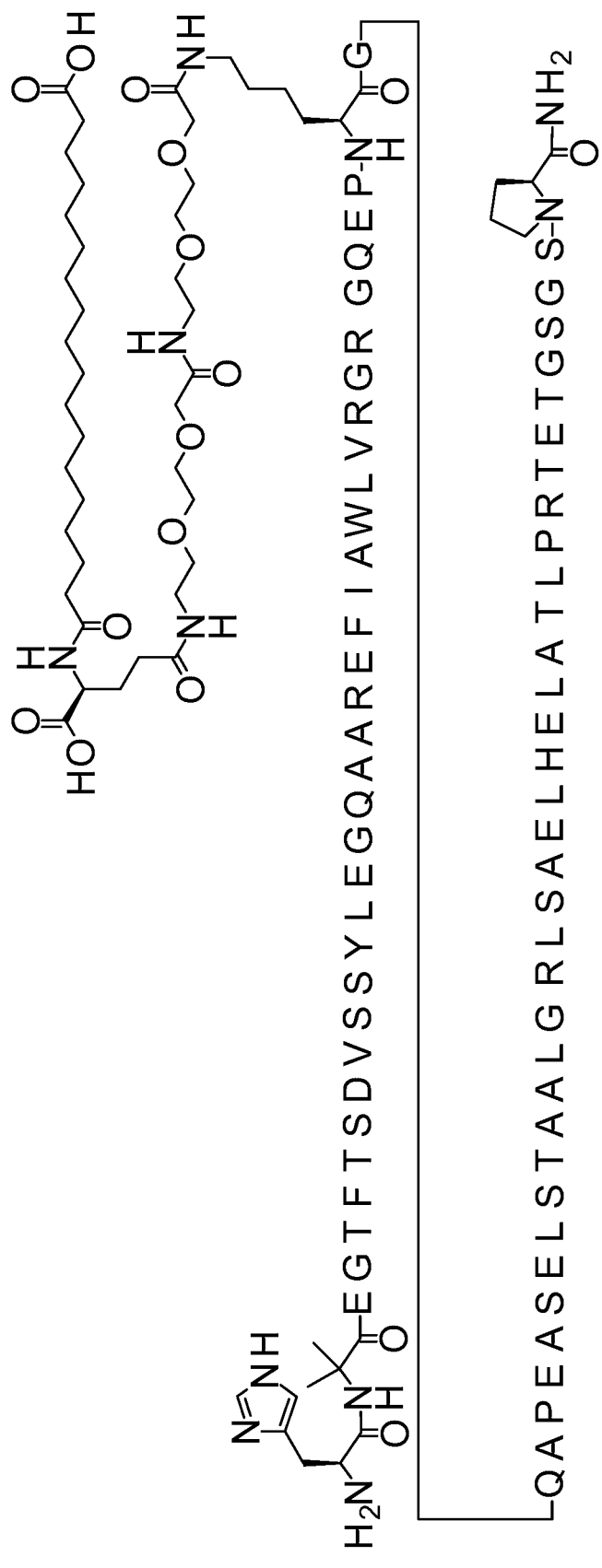
Figure 26:
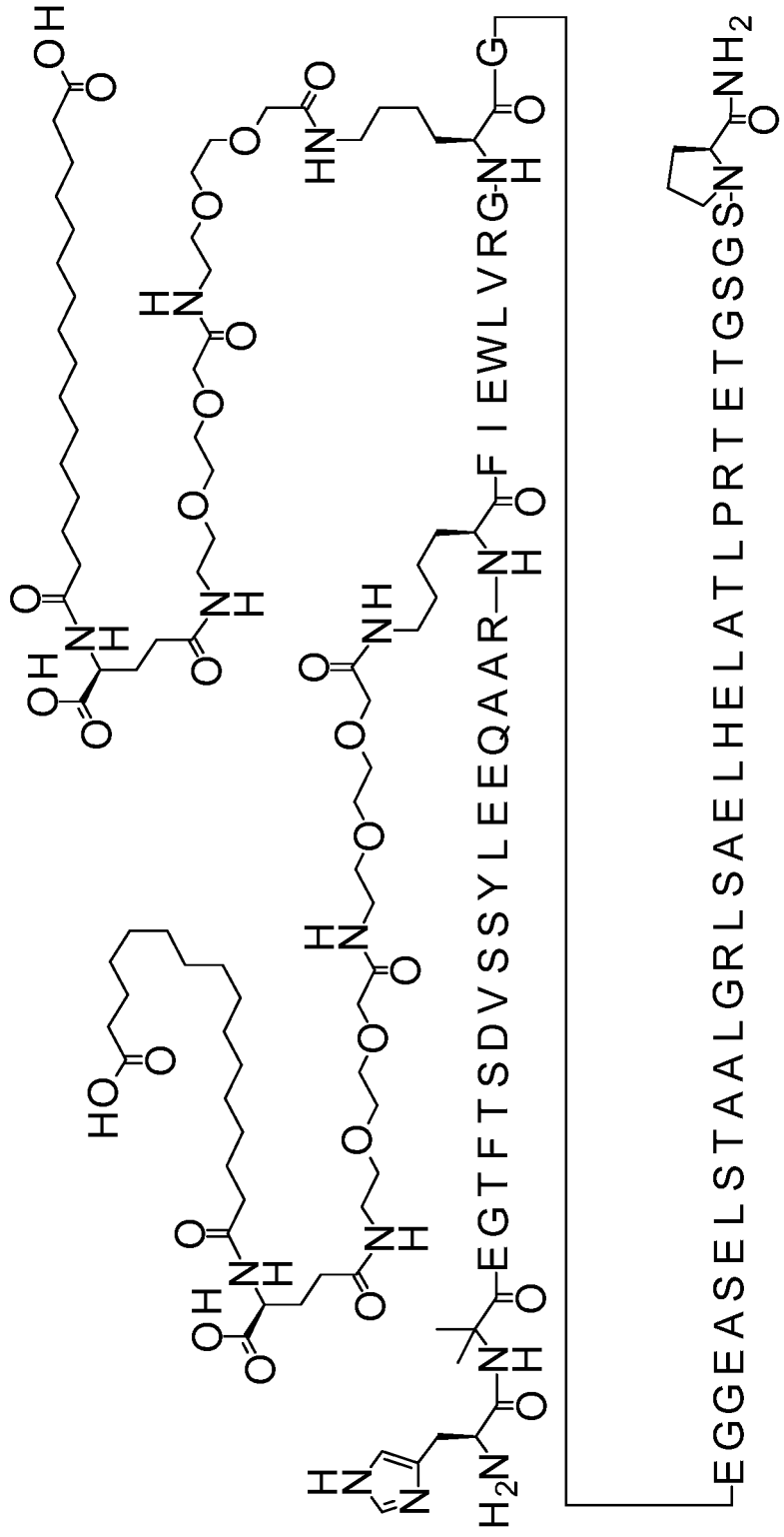
Figure 27:
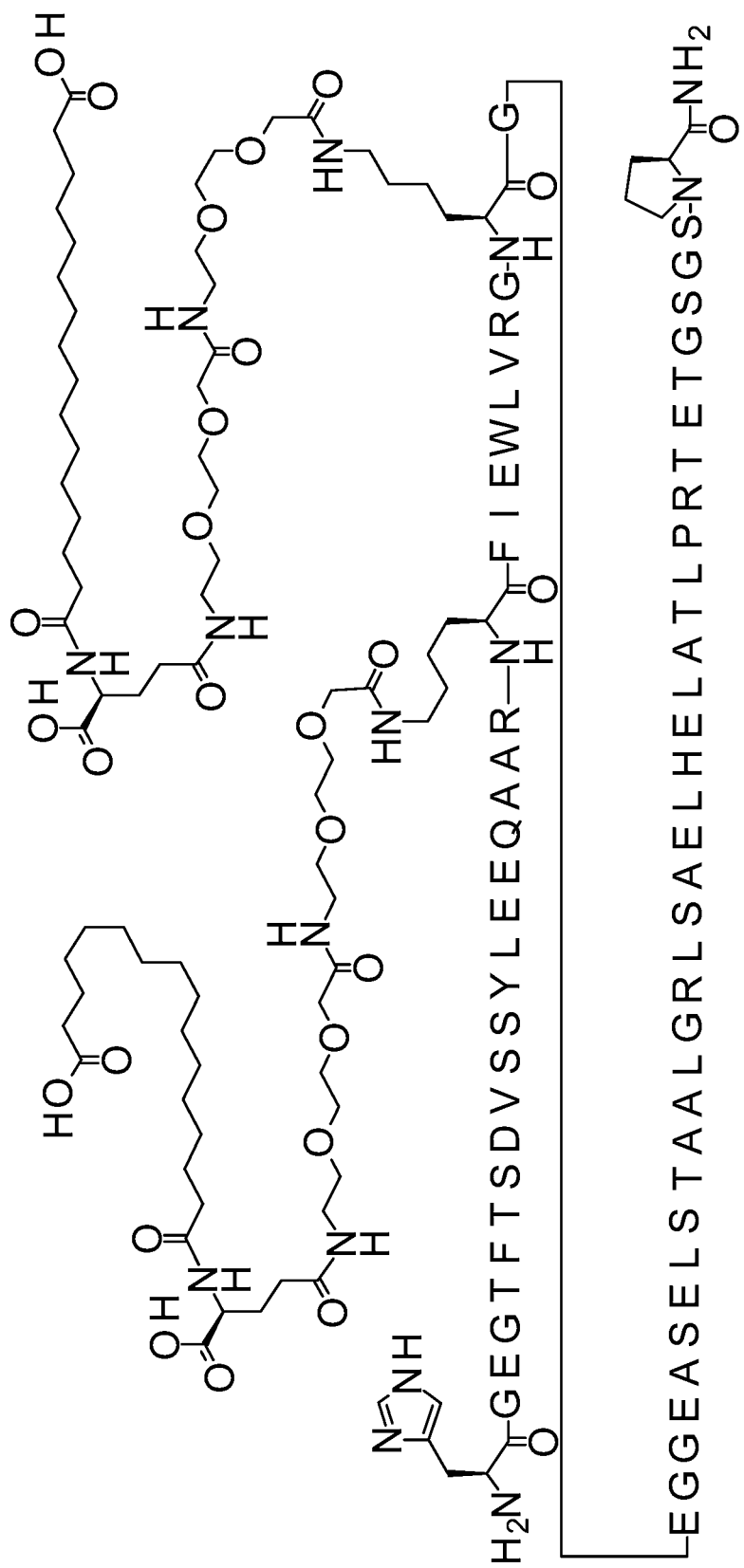
Figure 28:
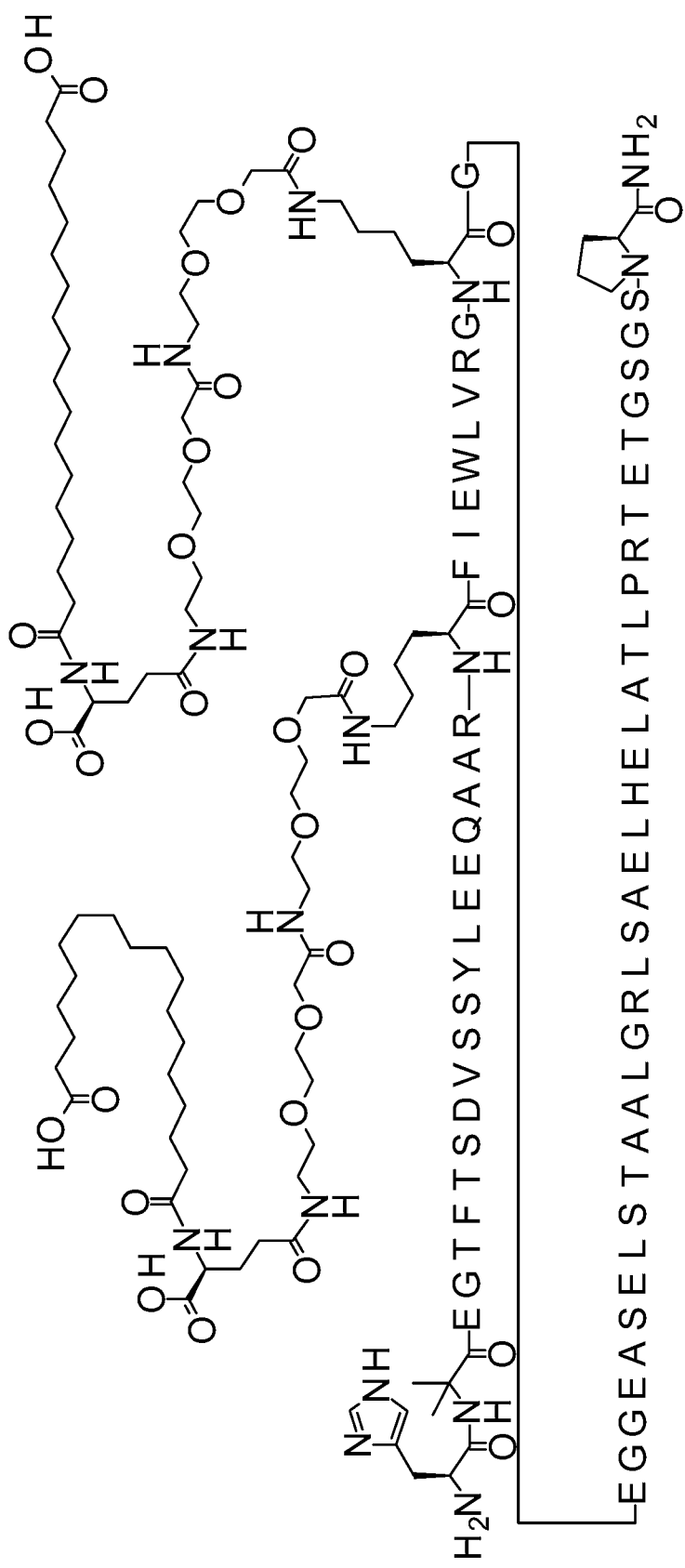
Figure 29:
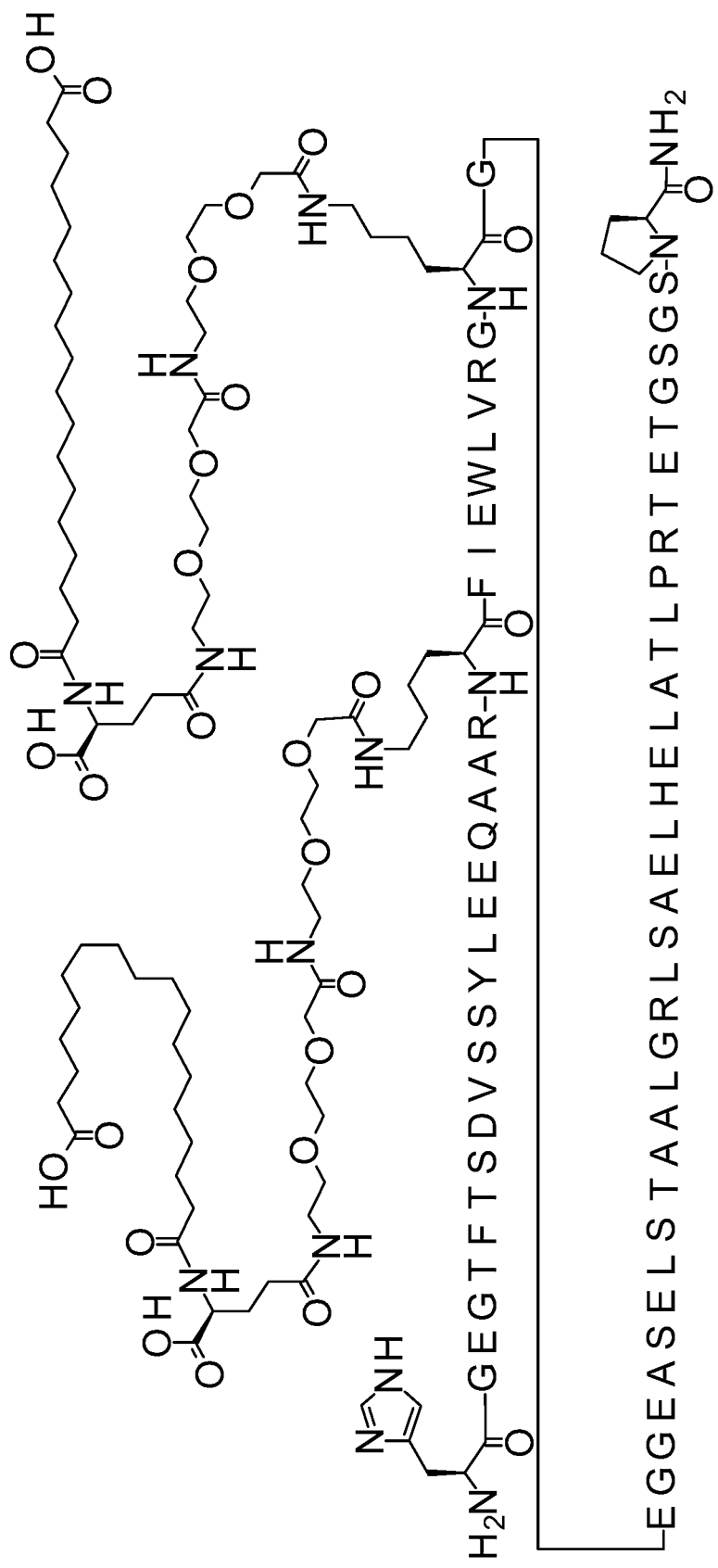
Figure 30:
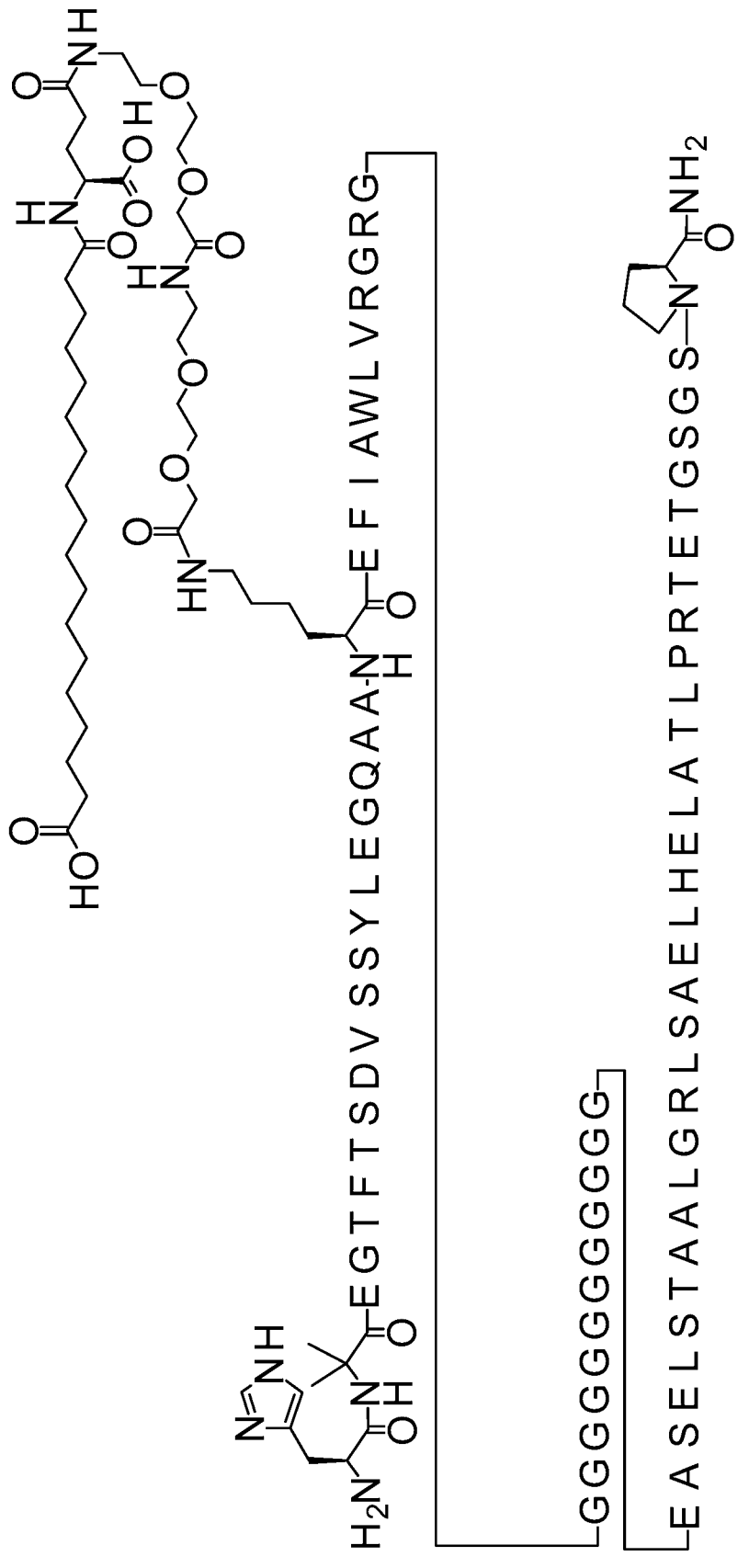
Figure 31:
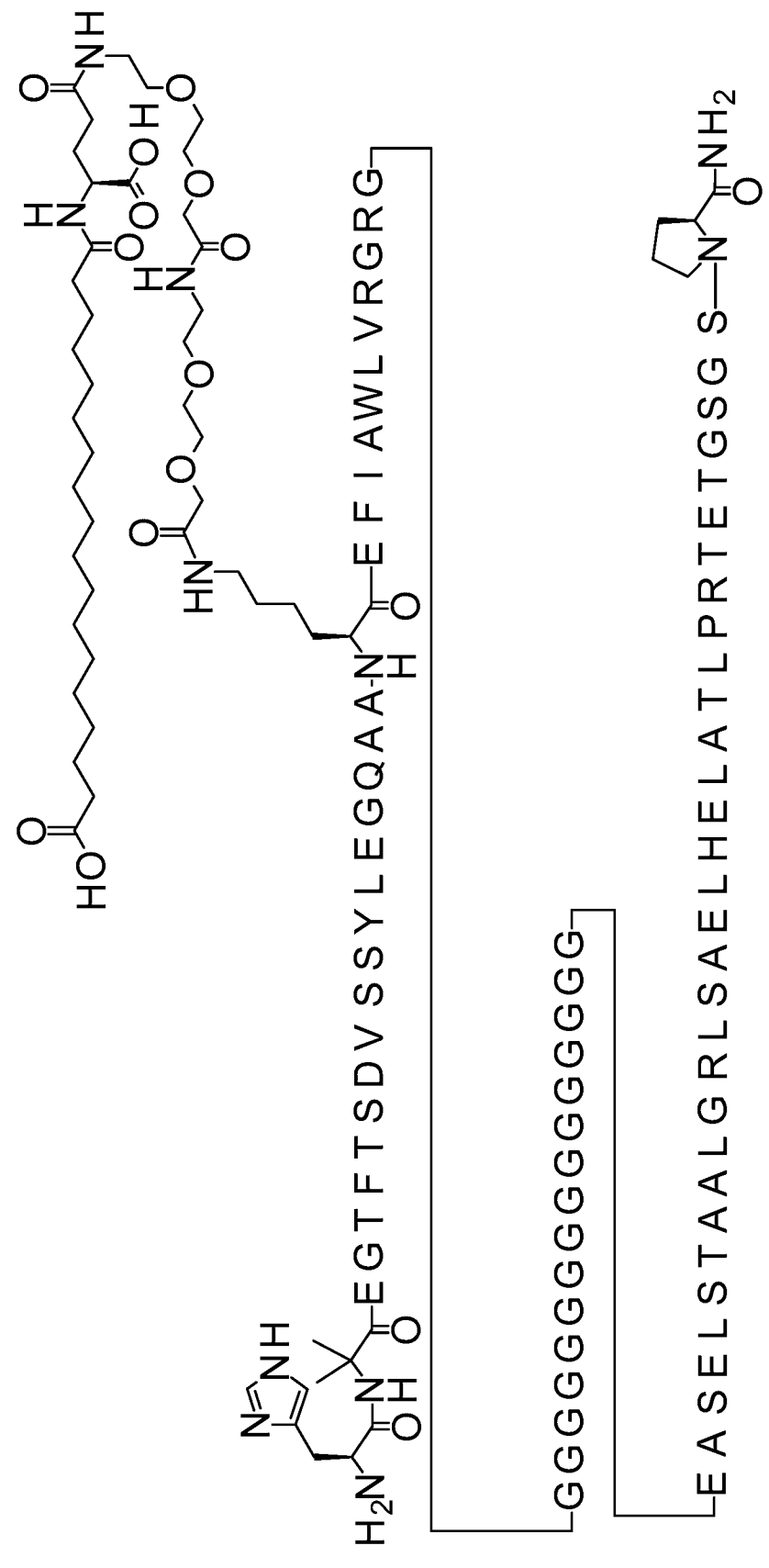
Figure 32:
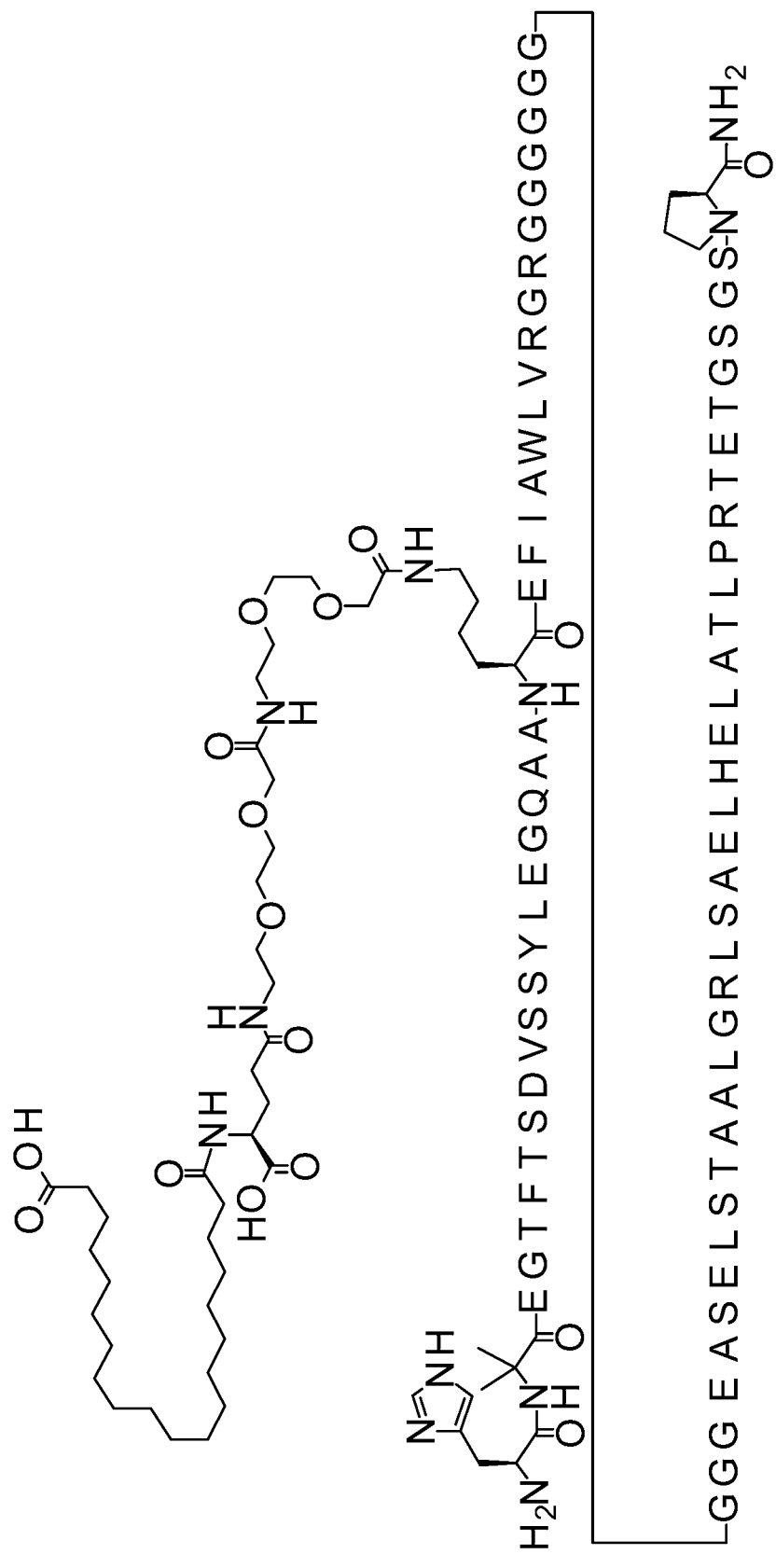
Figure 34:
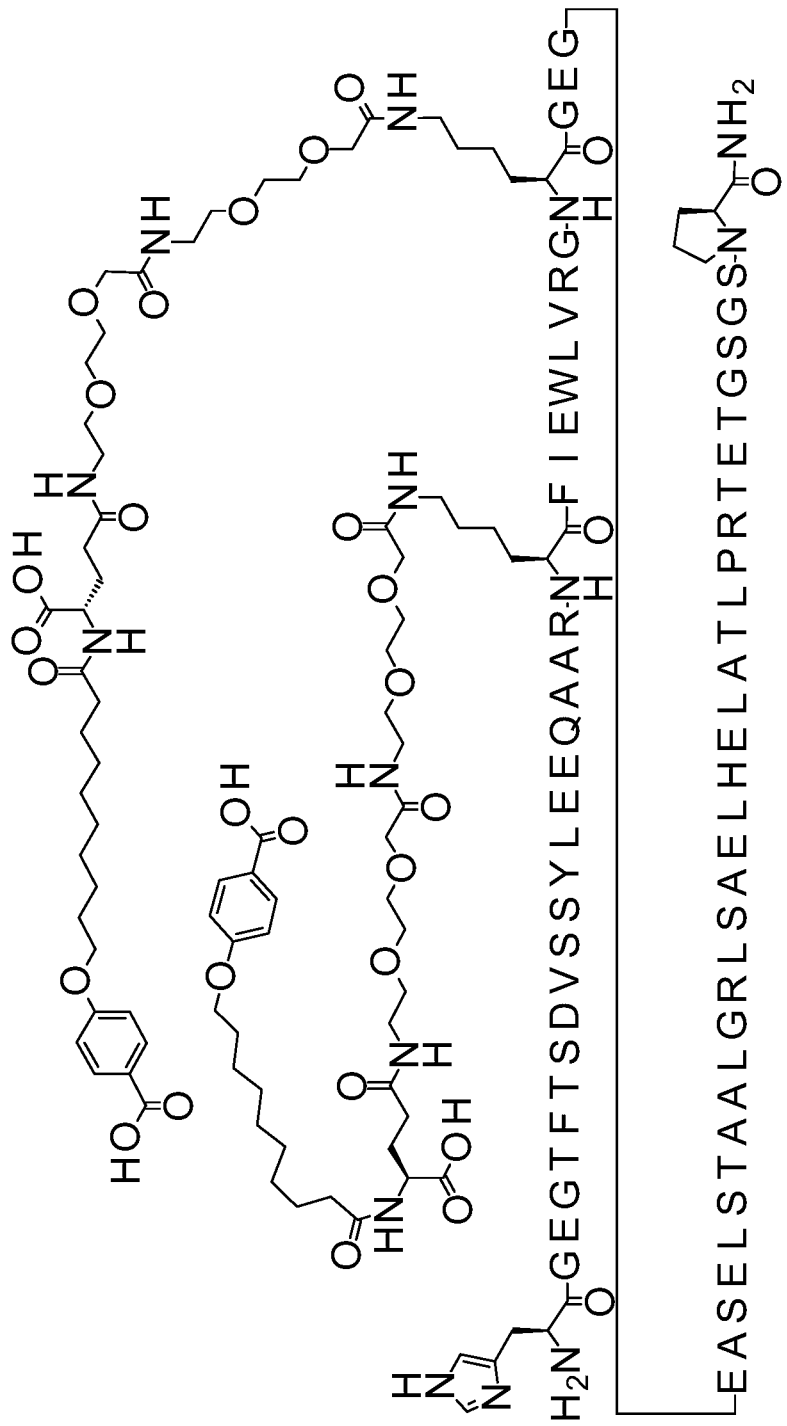
Figure 35:
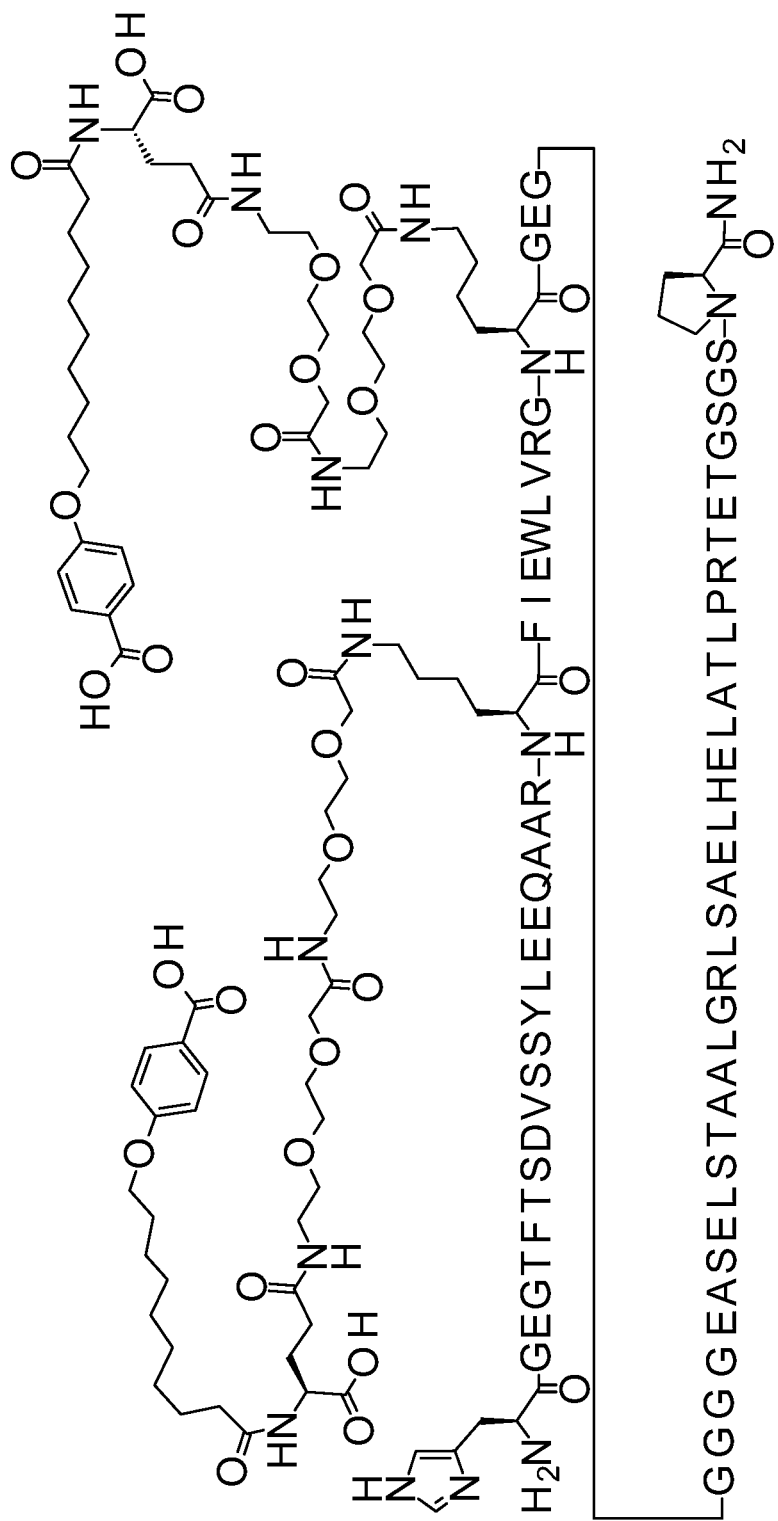
Figure 36:
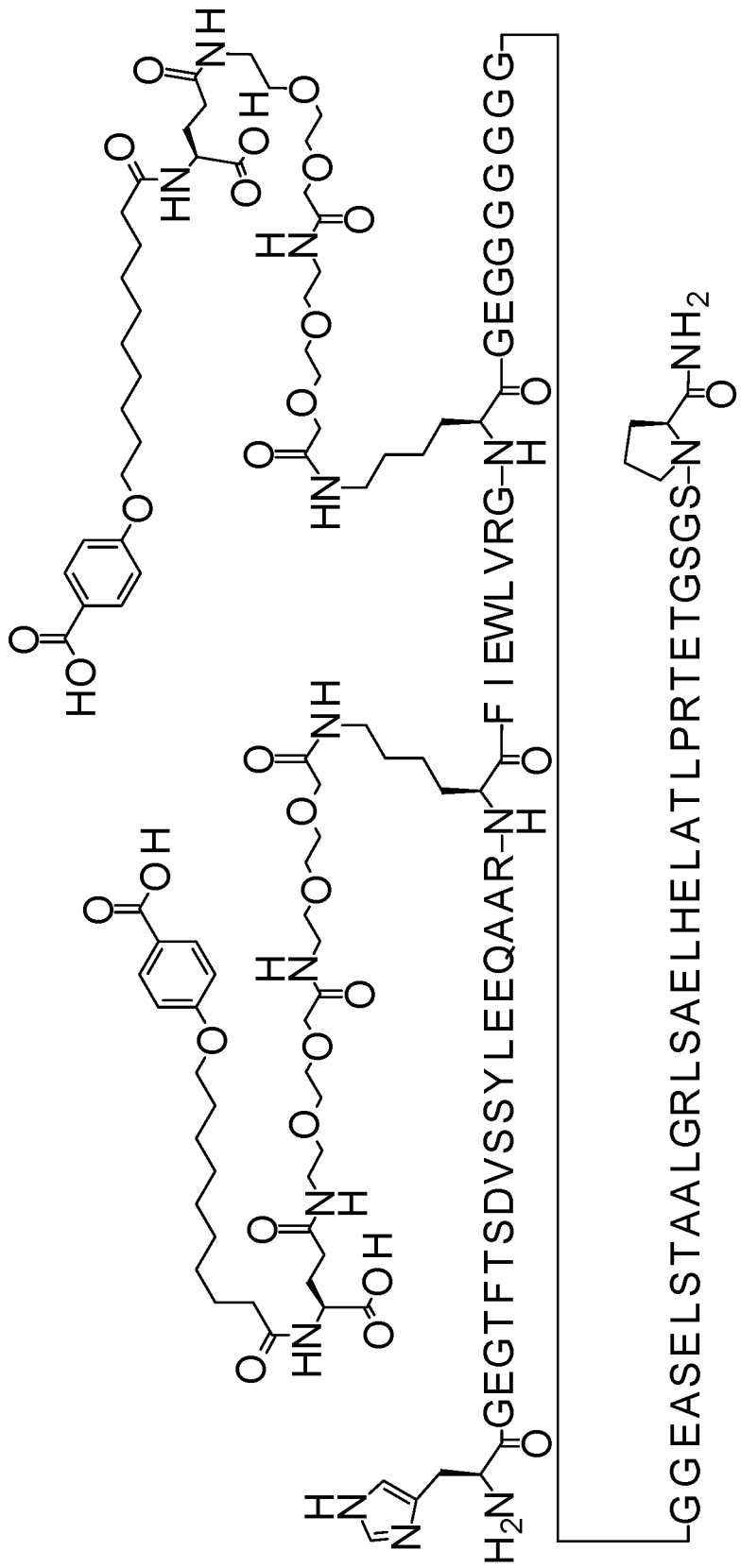
Figure 37:
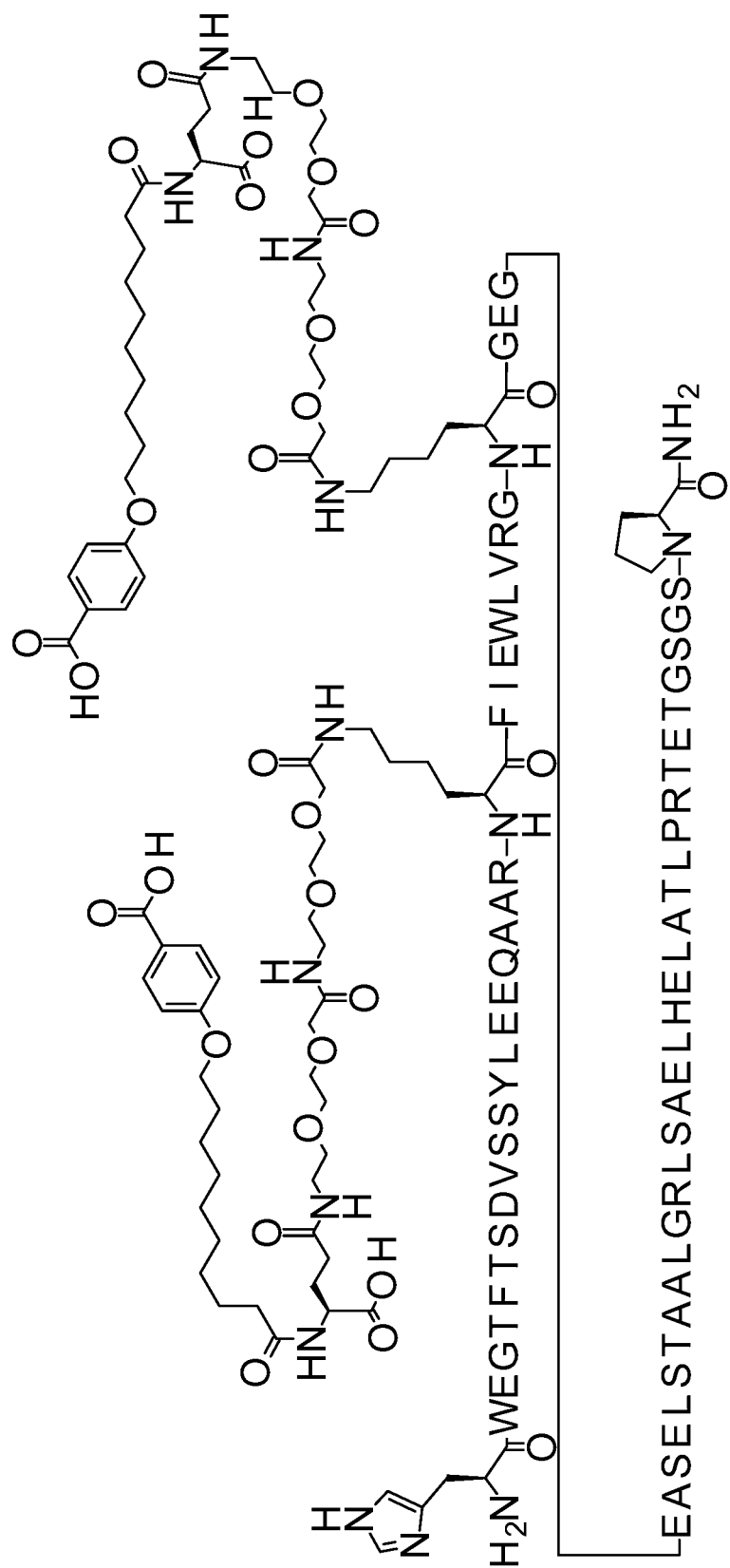
Figure 38:
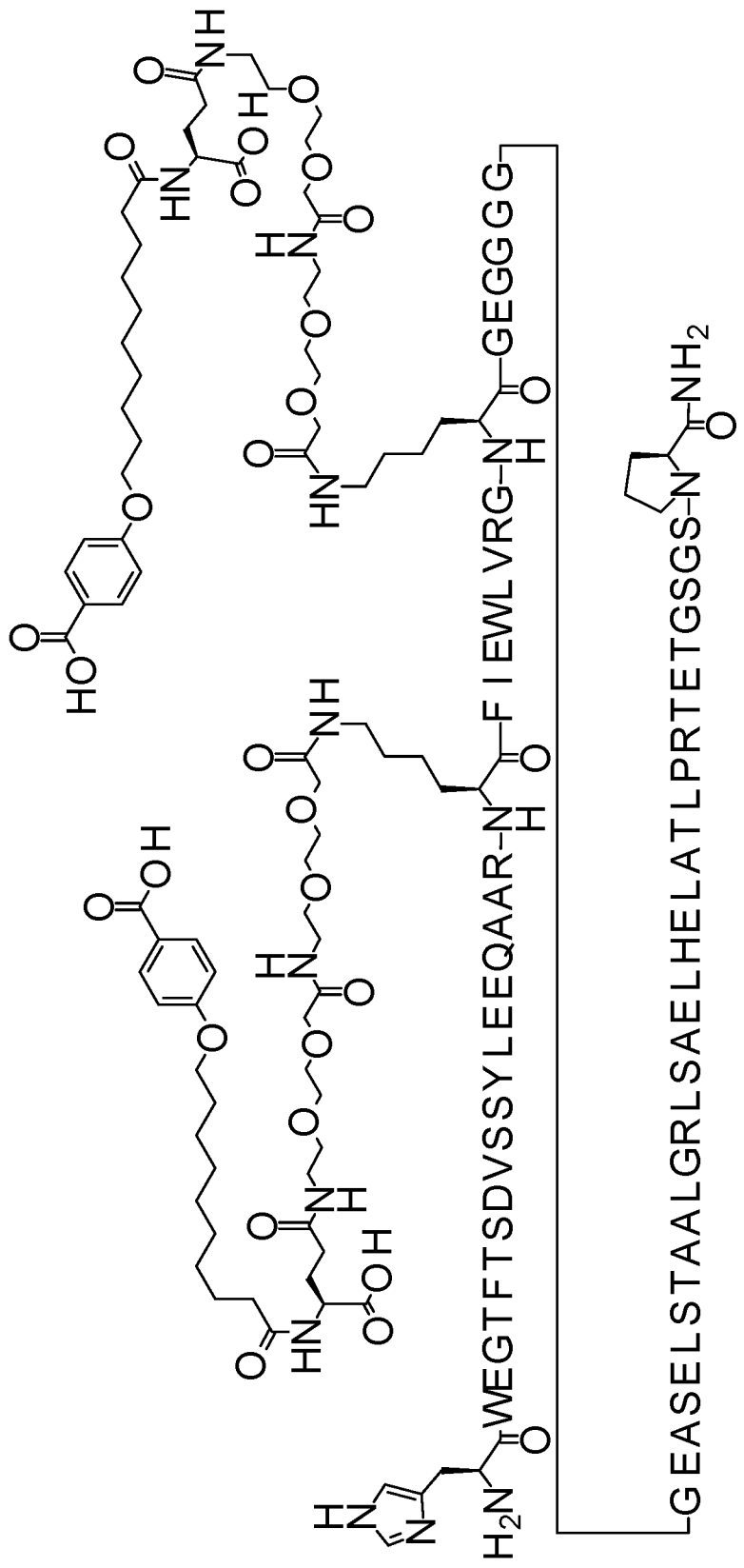
Figure 39:
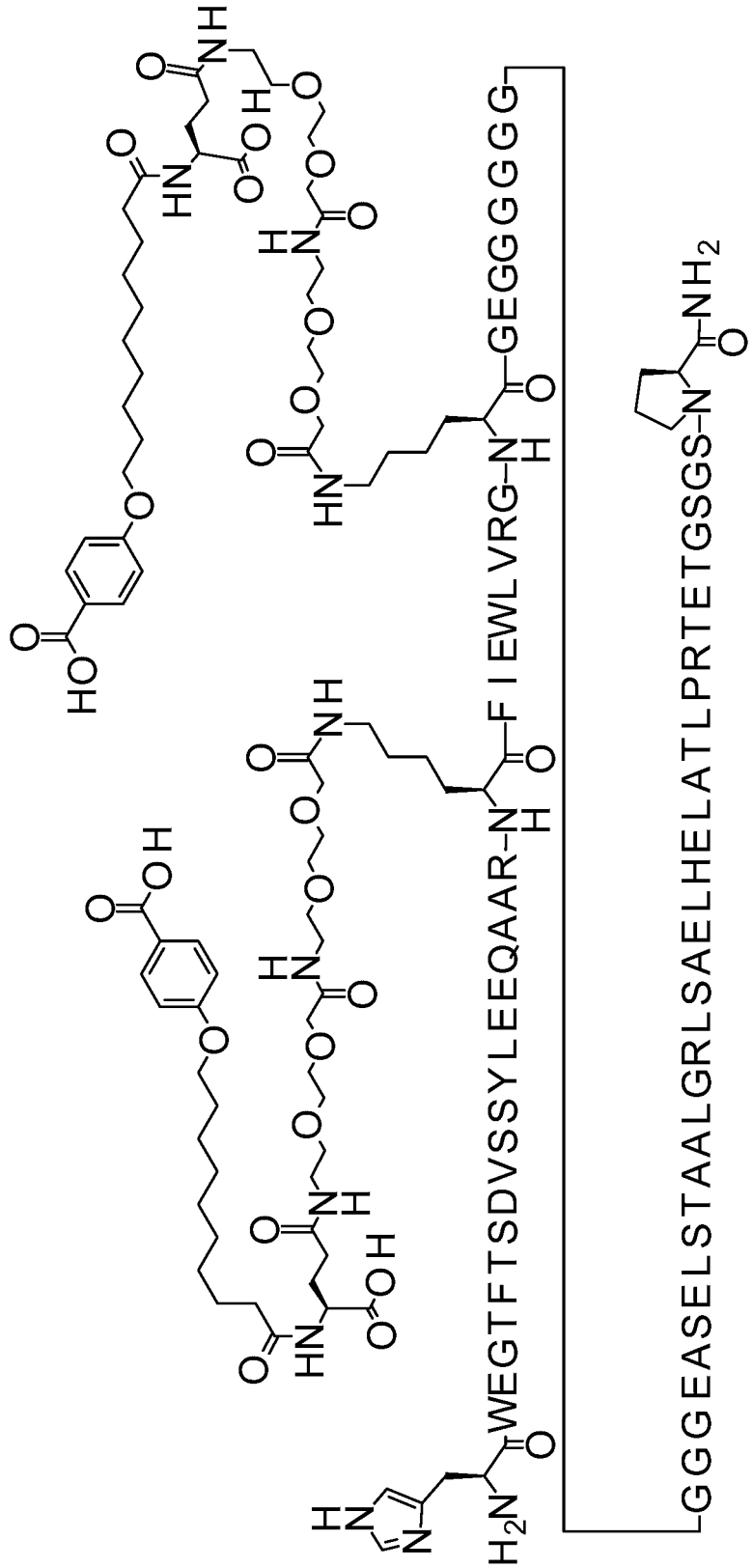
Figure 40:
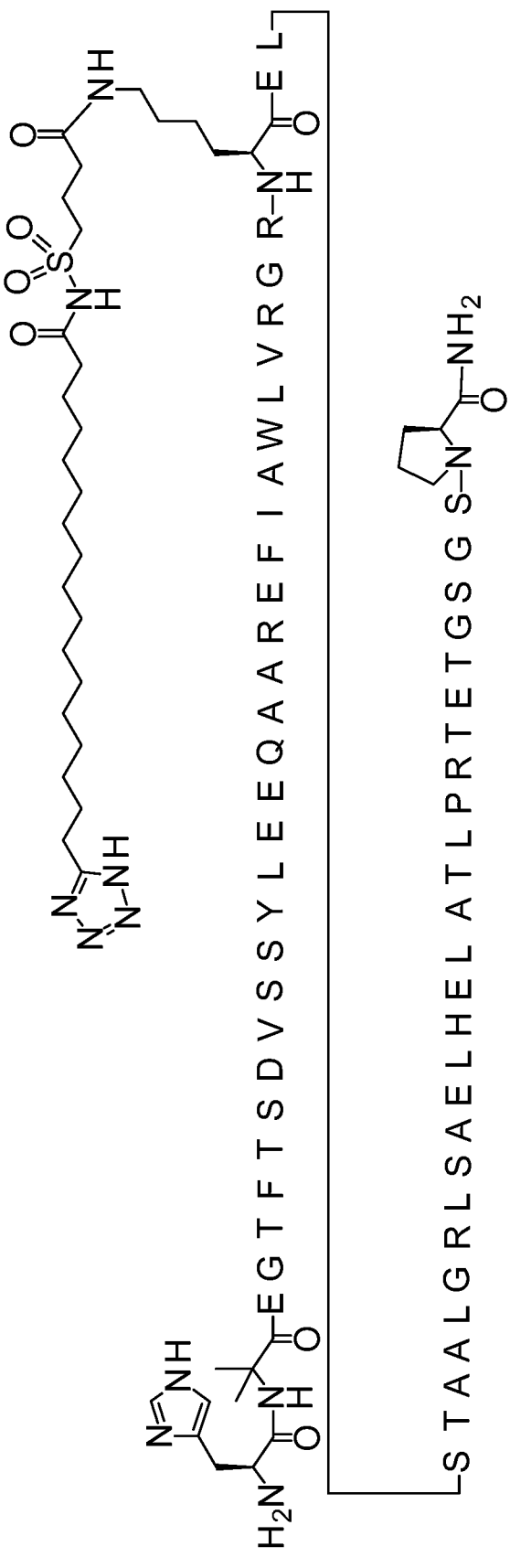
Figure 41:
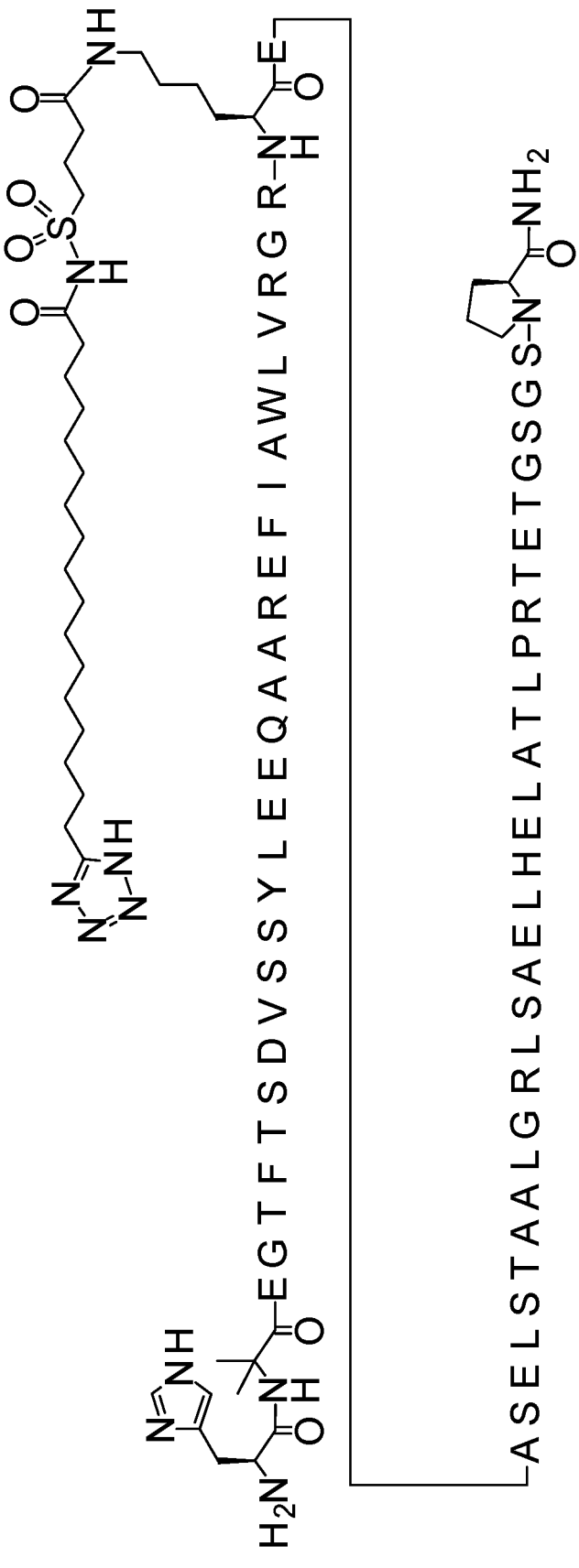
Figure 42:
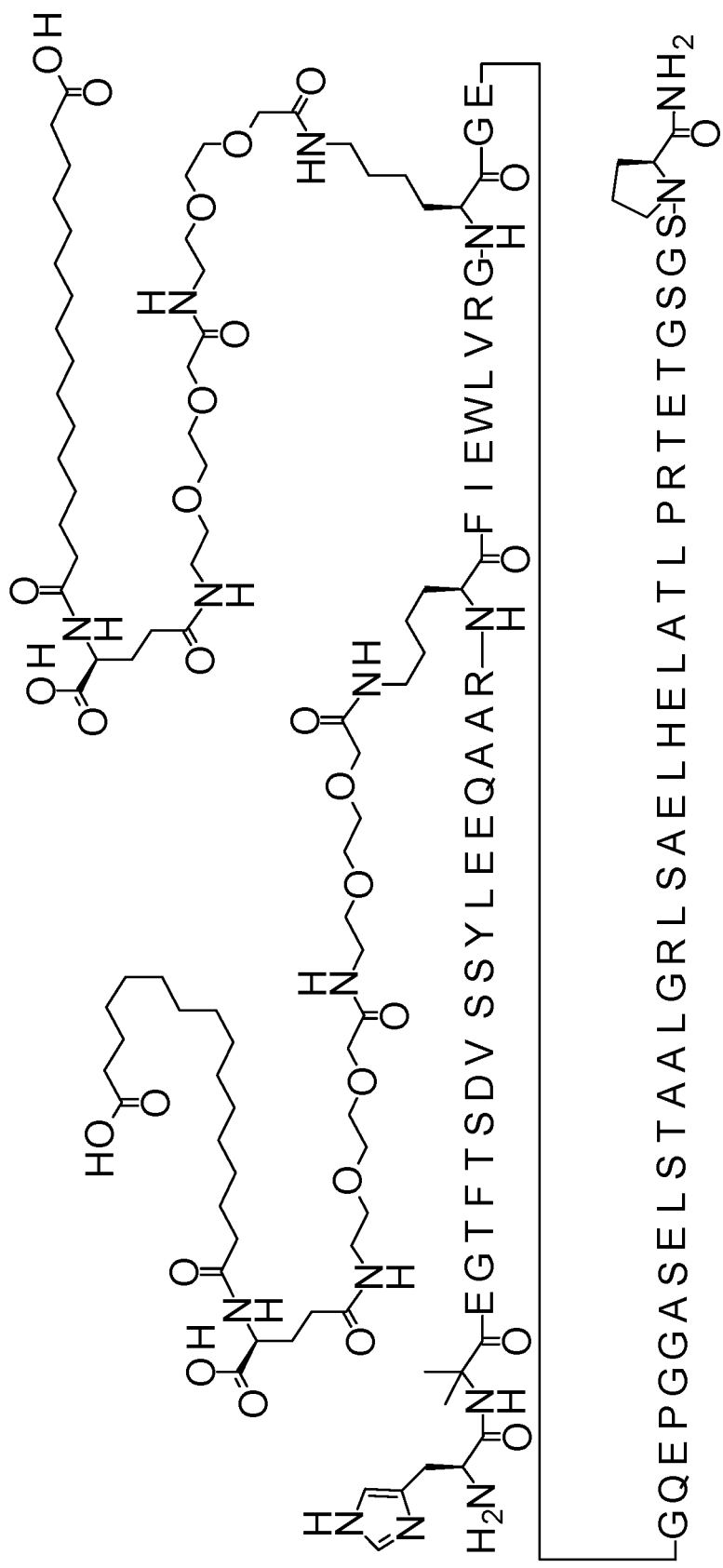
Figure 43:
Figure 44:
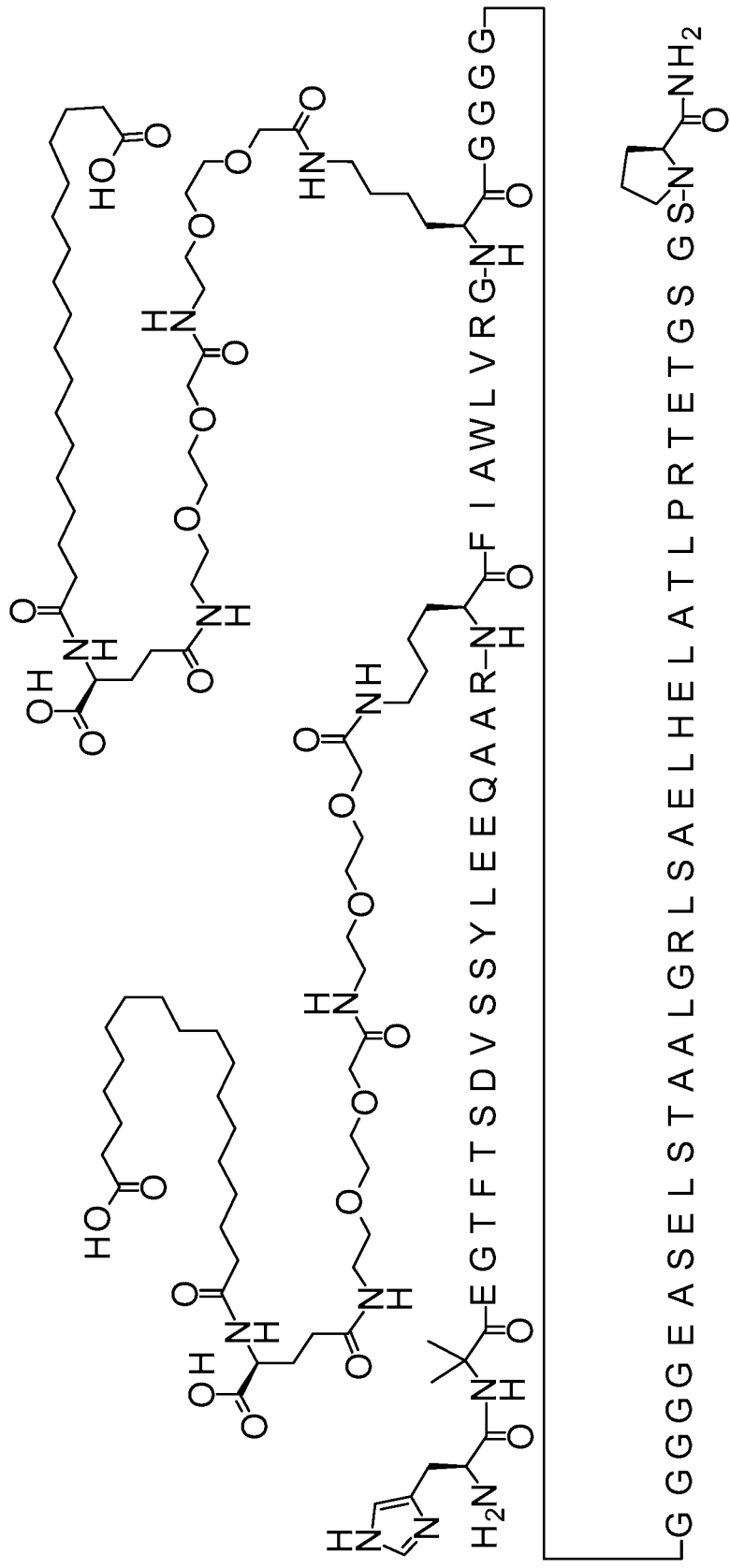
Figure 45:
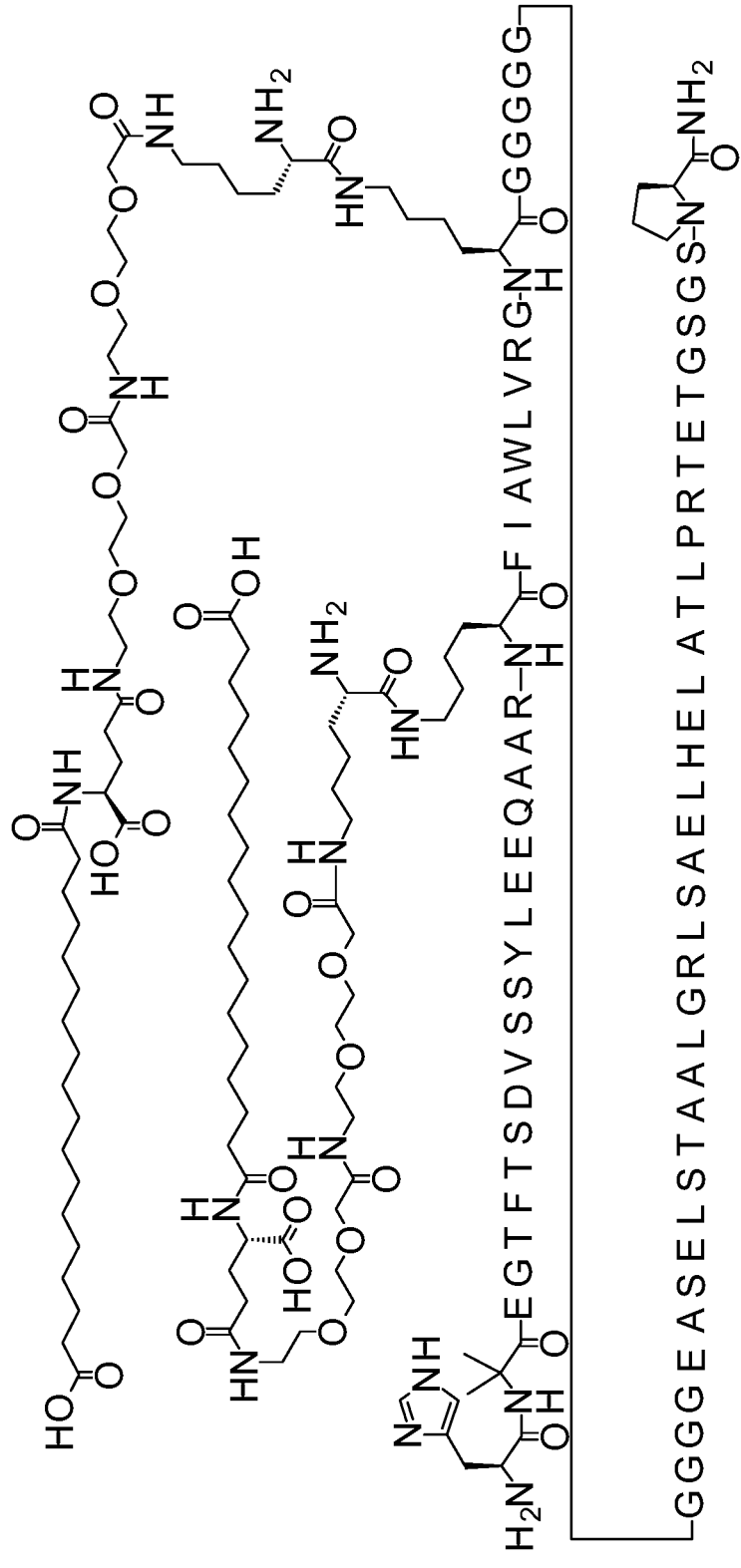
Figure 46:
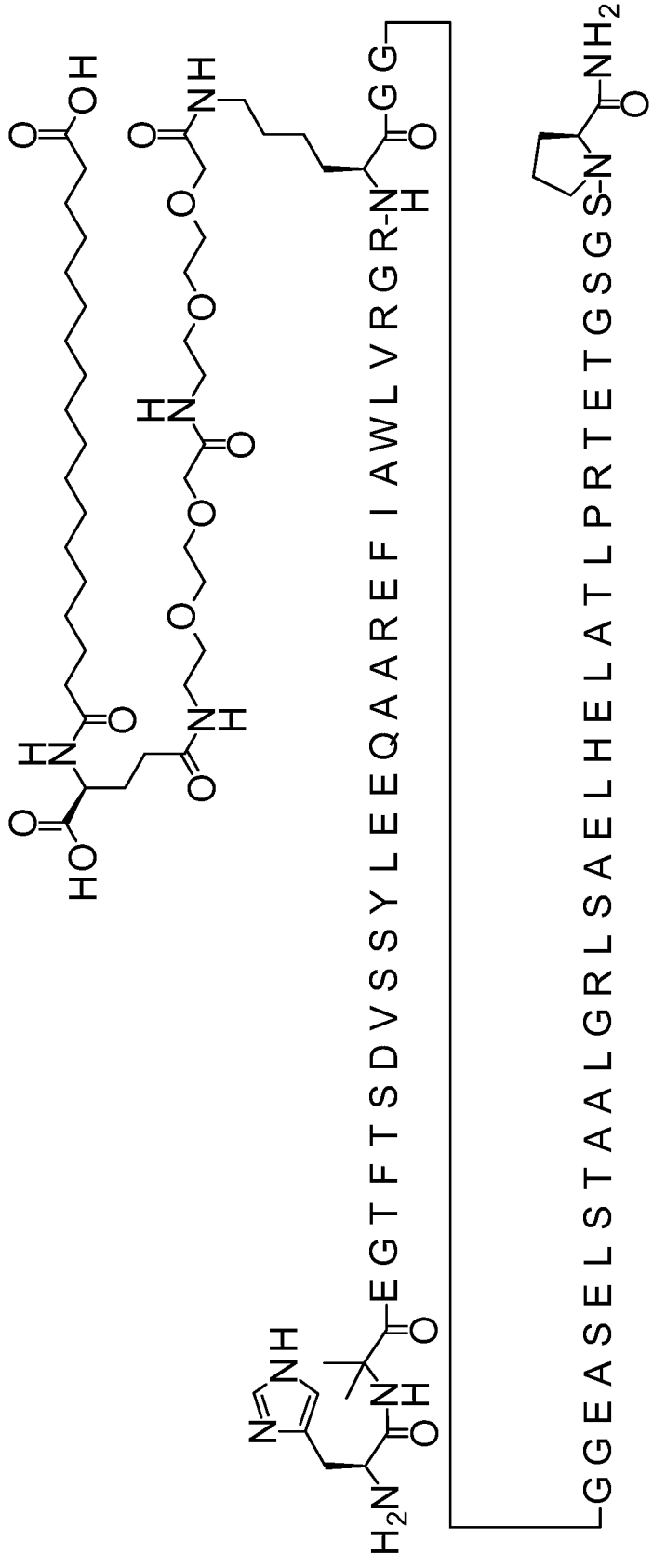
Figure 47:
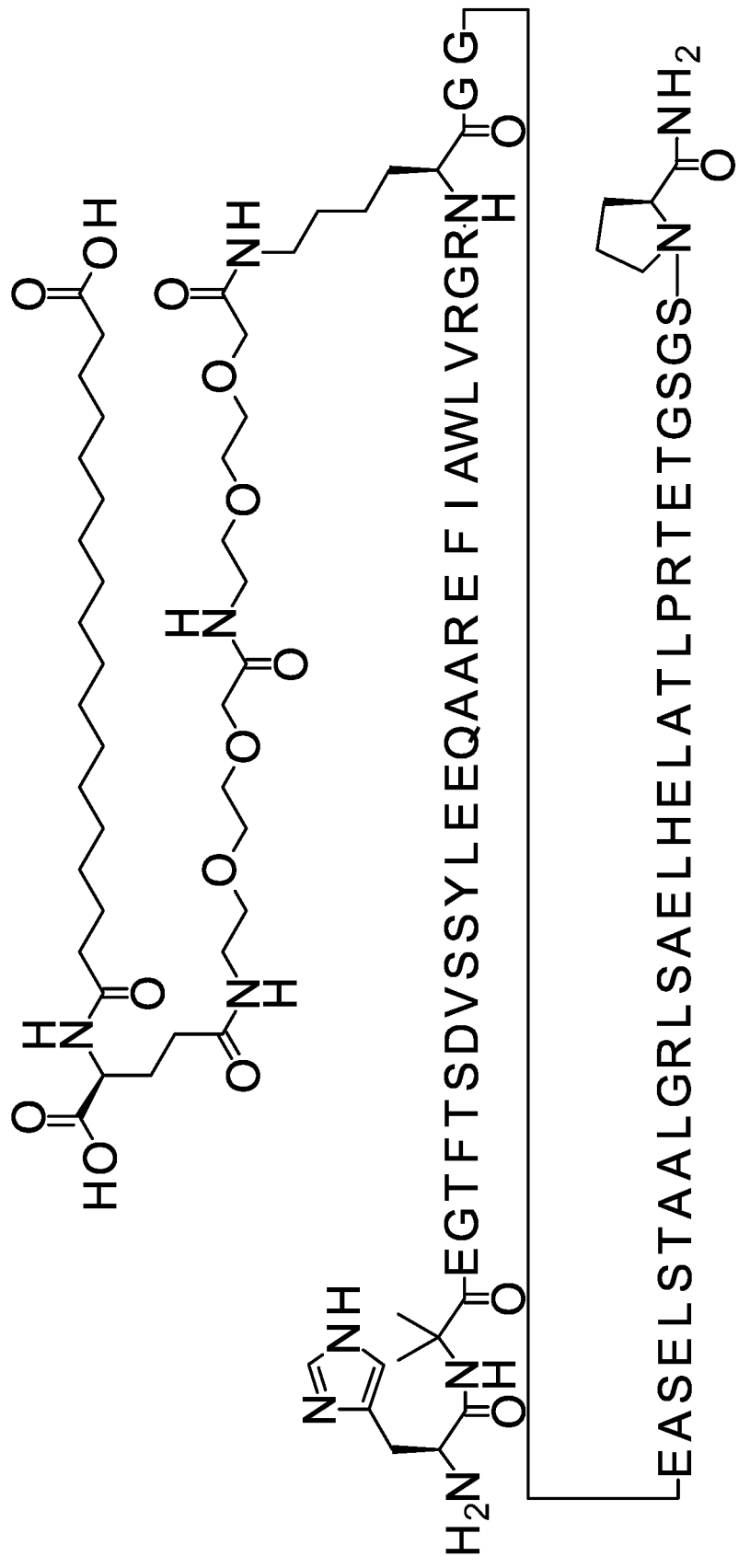
Figure 48:
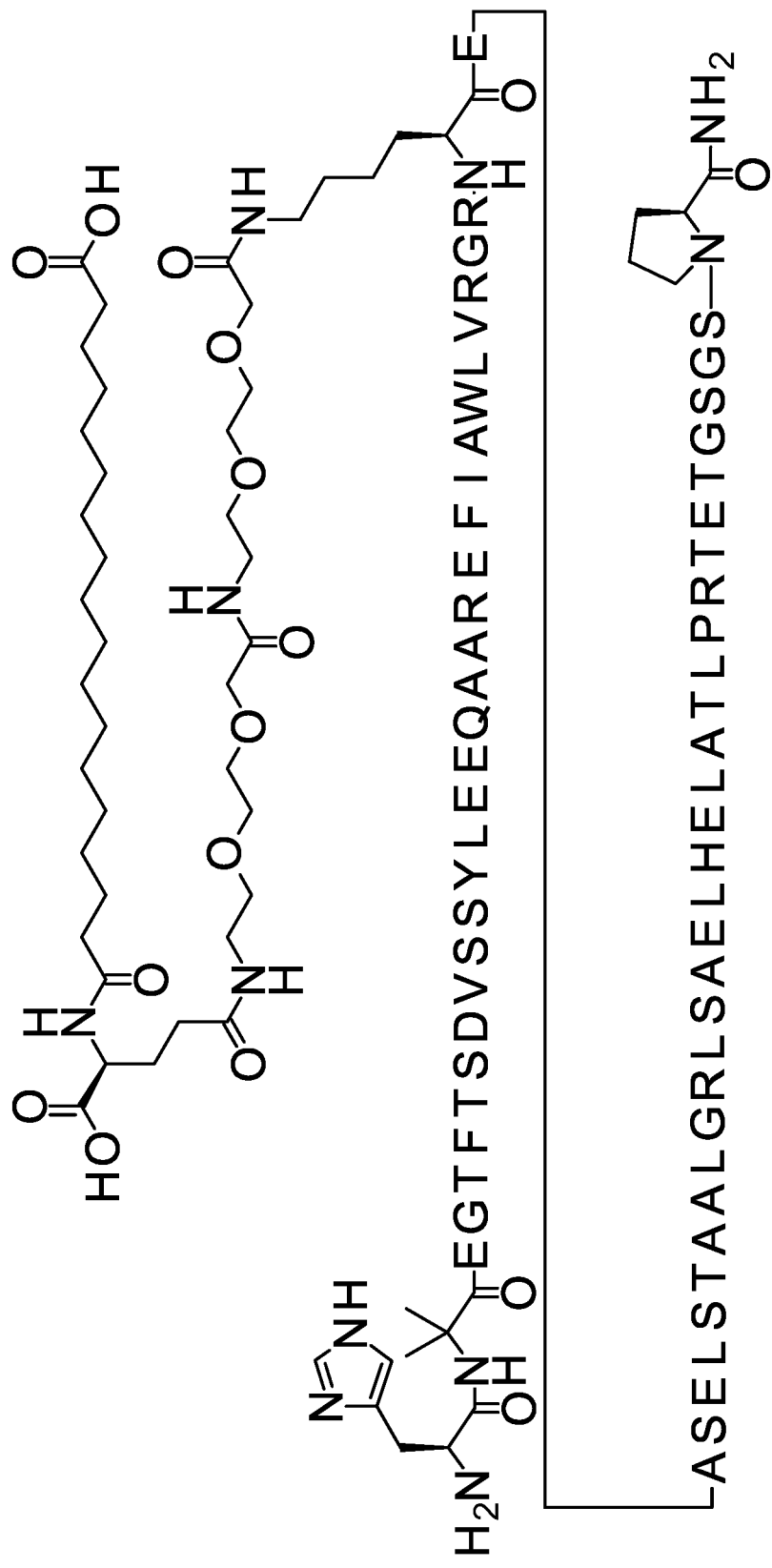
Figure 49:
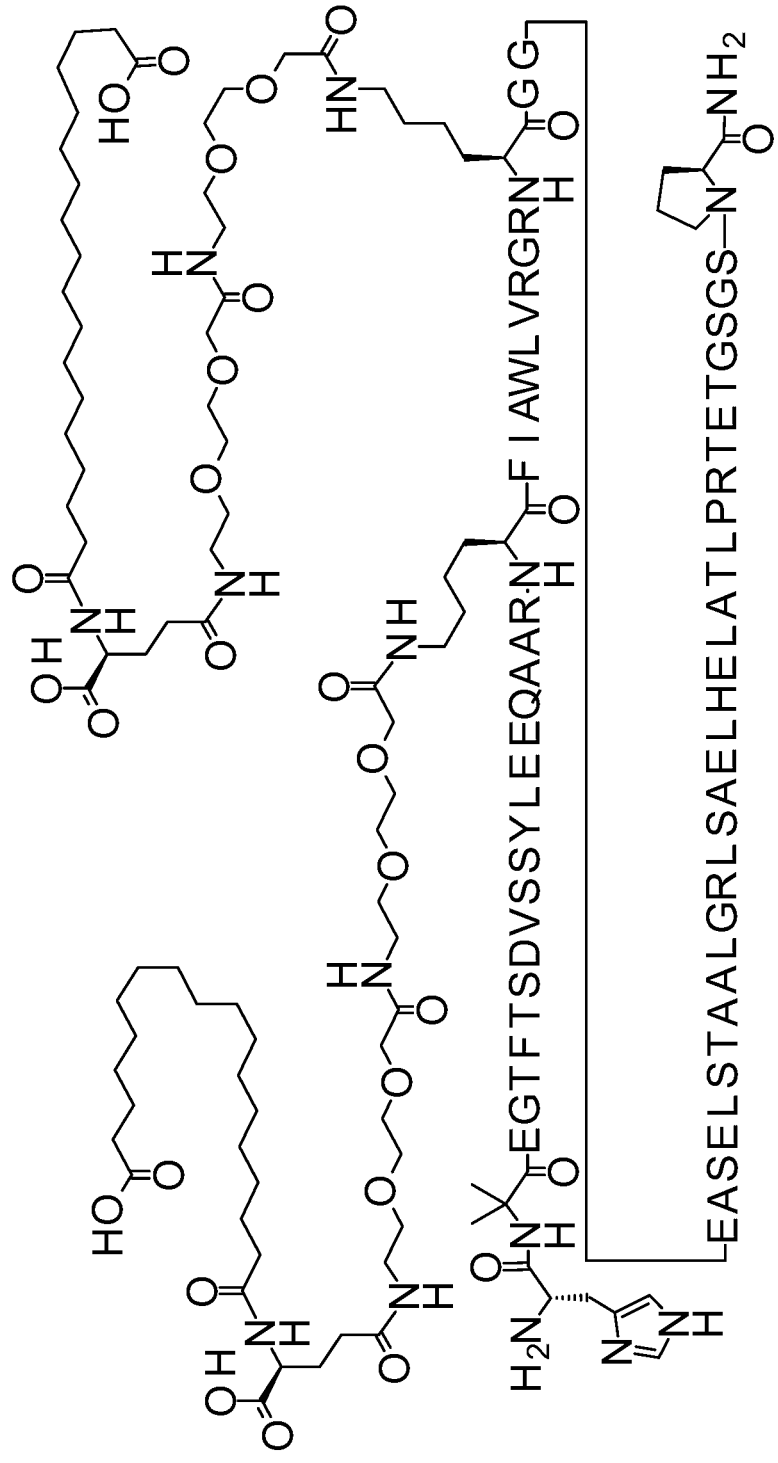
Figure 50:
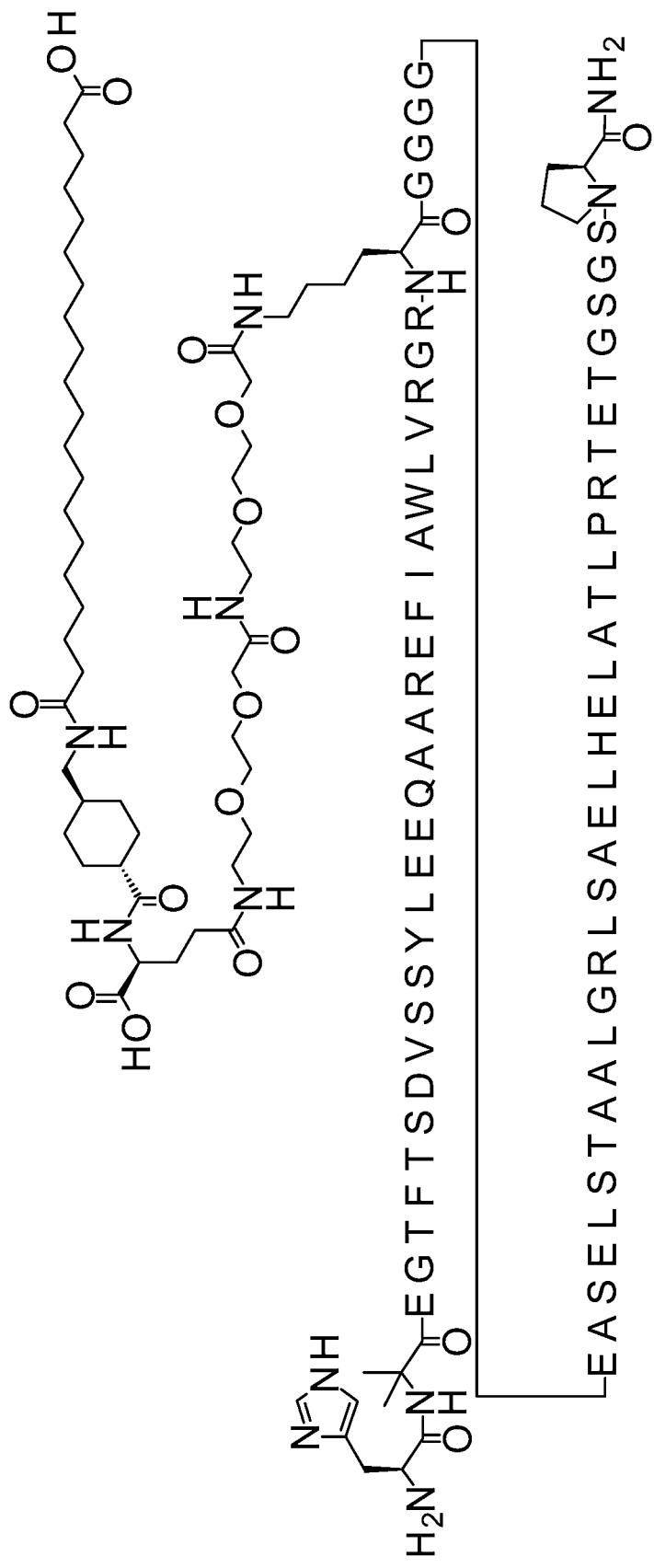
Figure 51:
Figure 52:
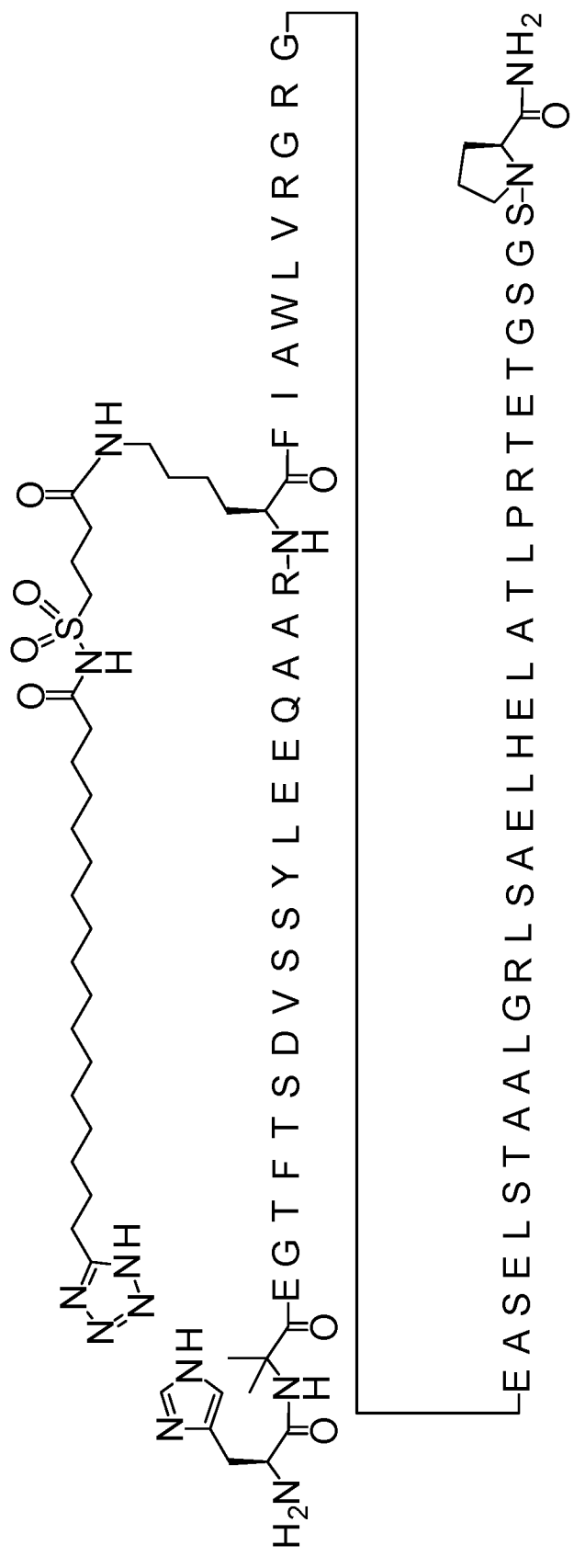
Figure 53:
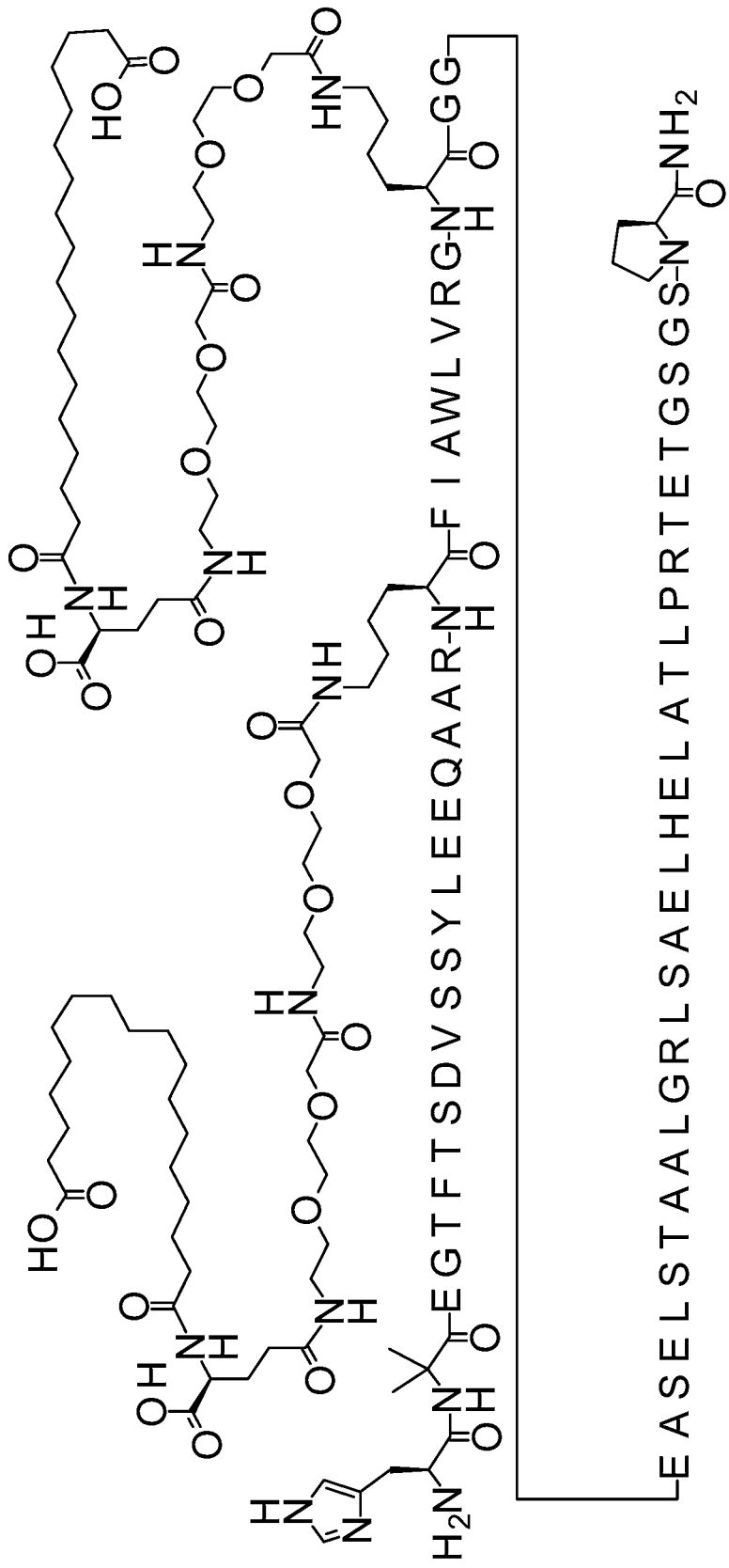
Figure 54:
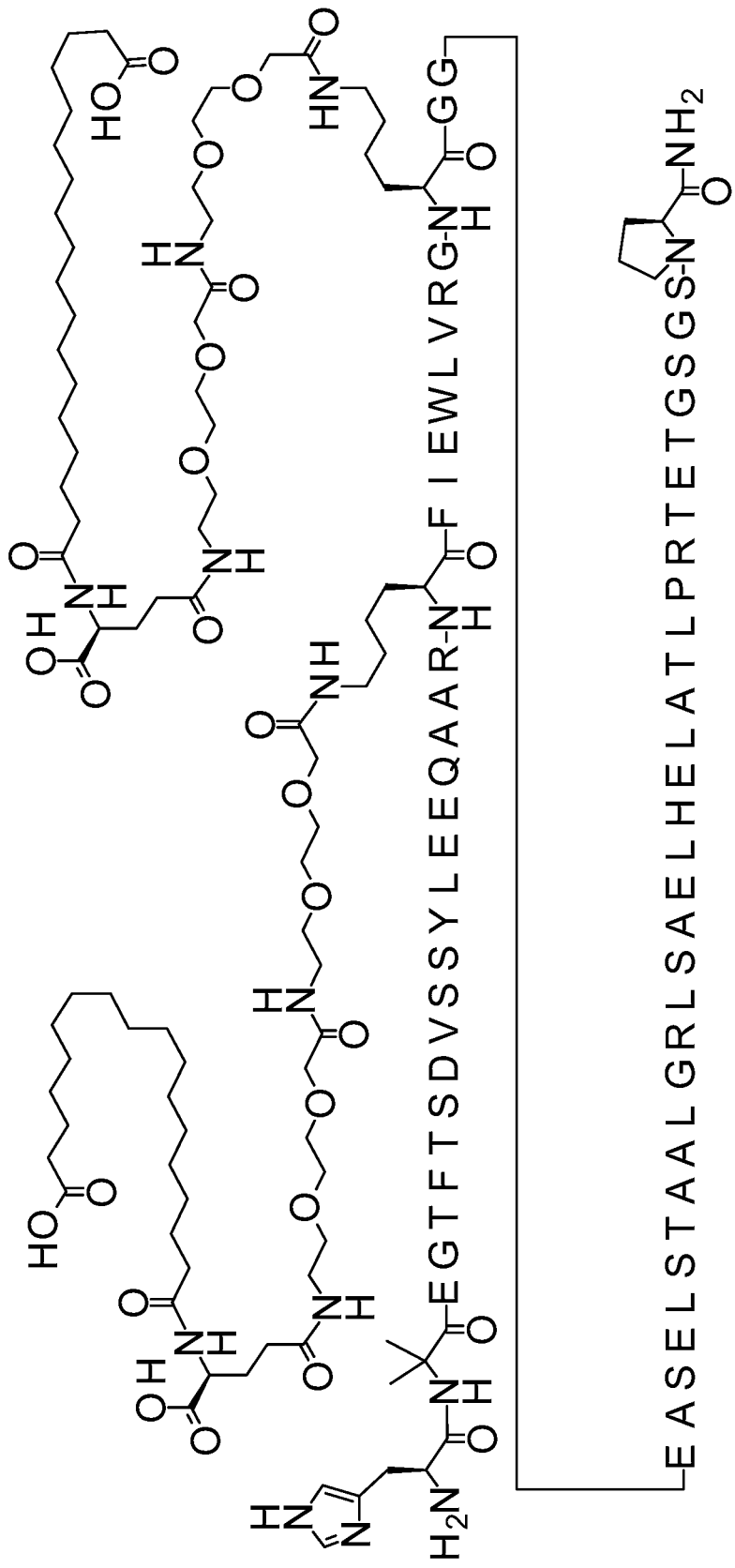
Figure 55:
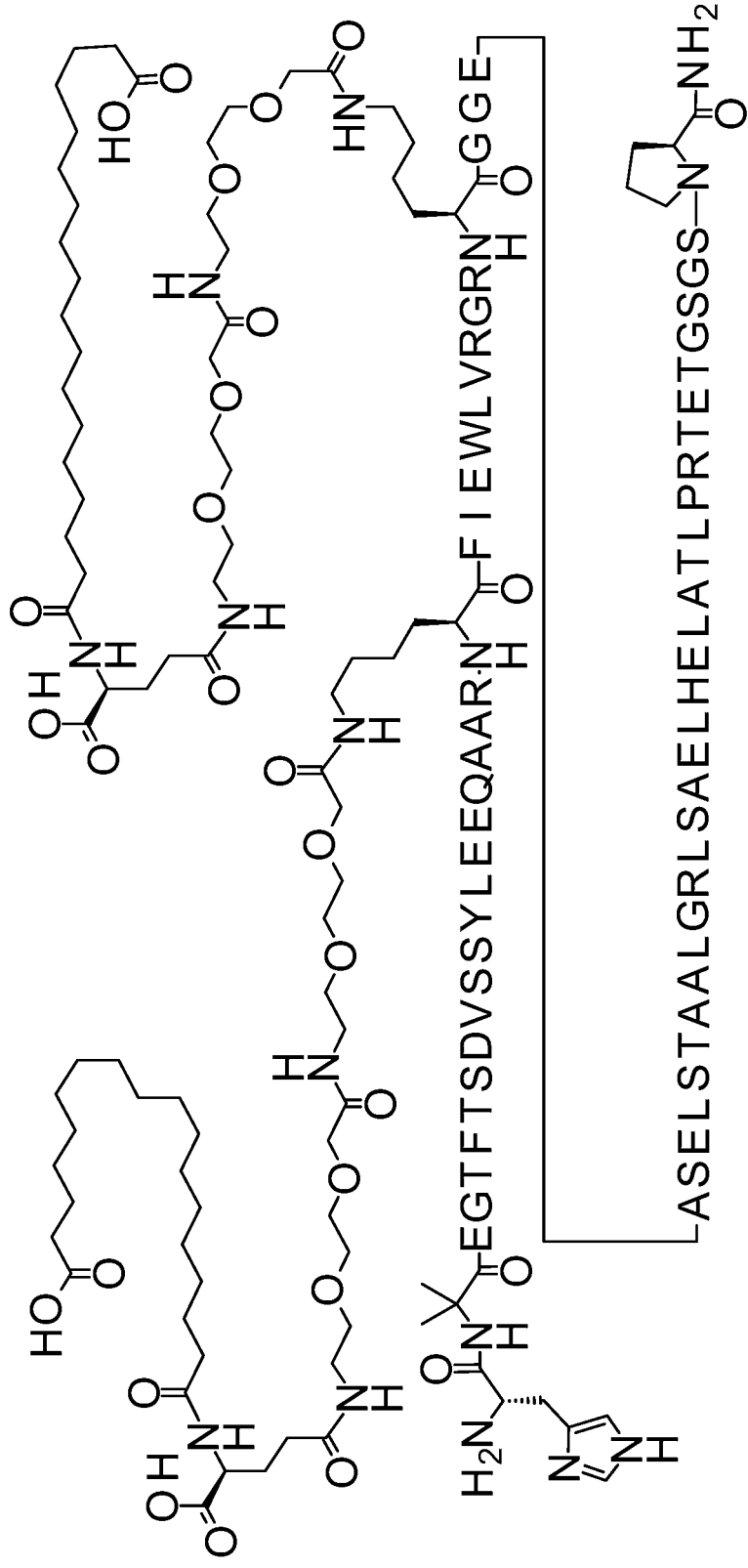
Figure 56:
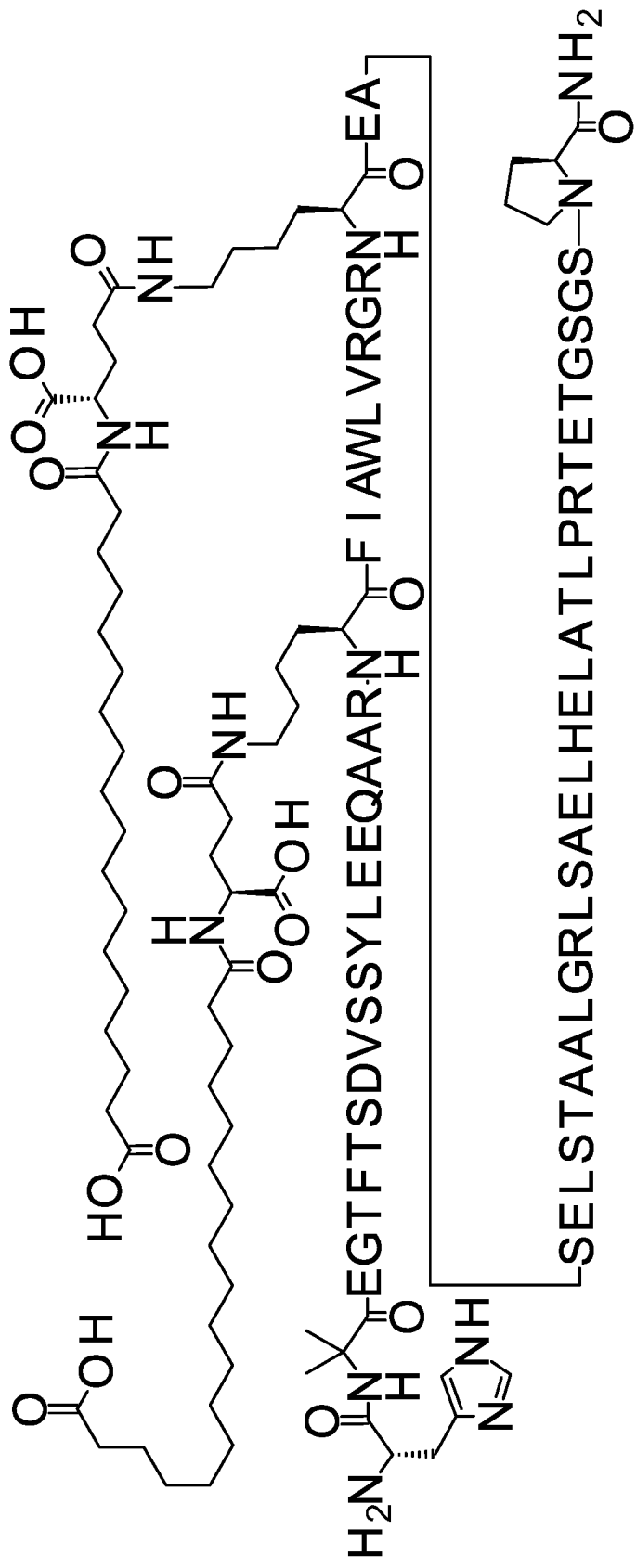
Figure 57:
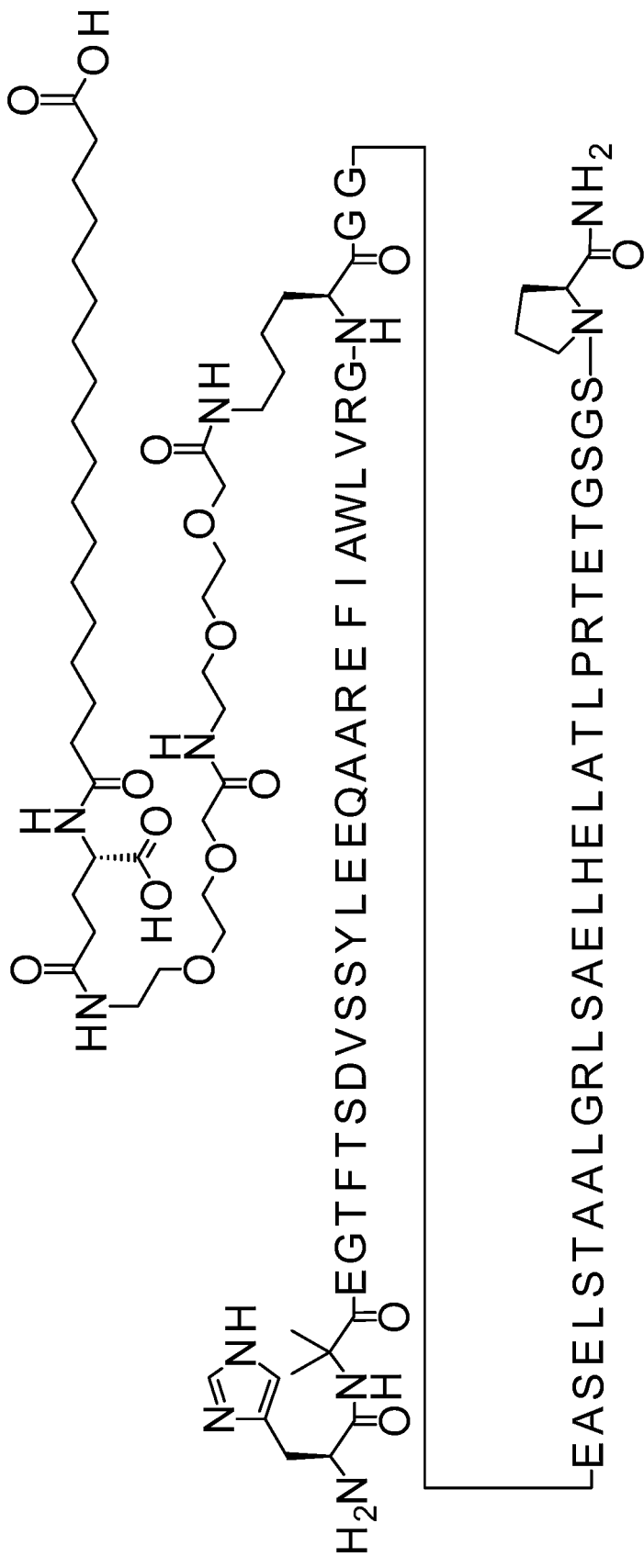
Figure 58:
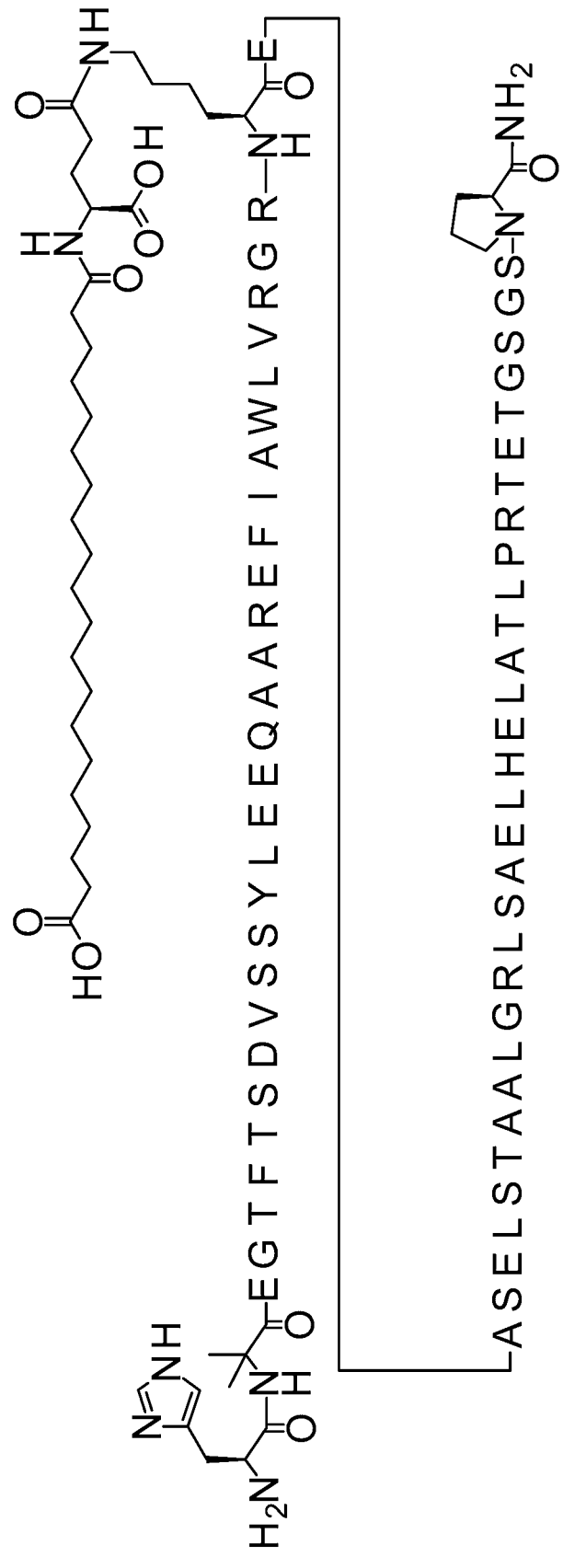
Figure 59:
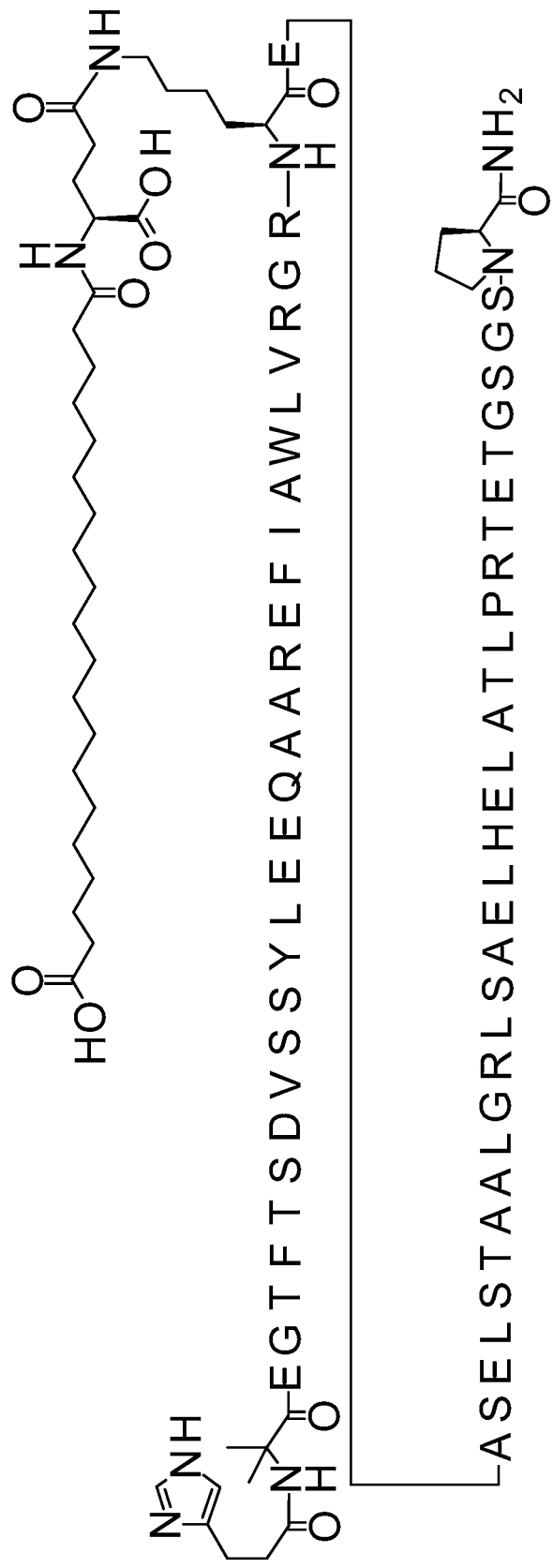
Figure 60:
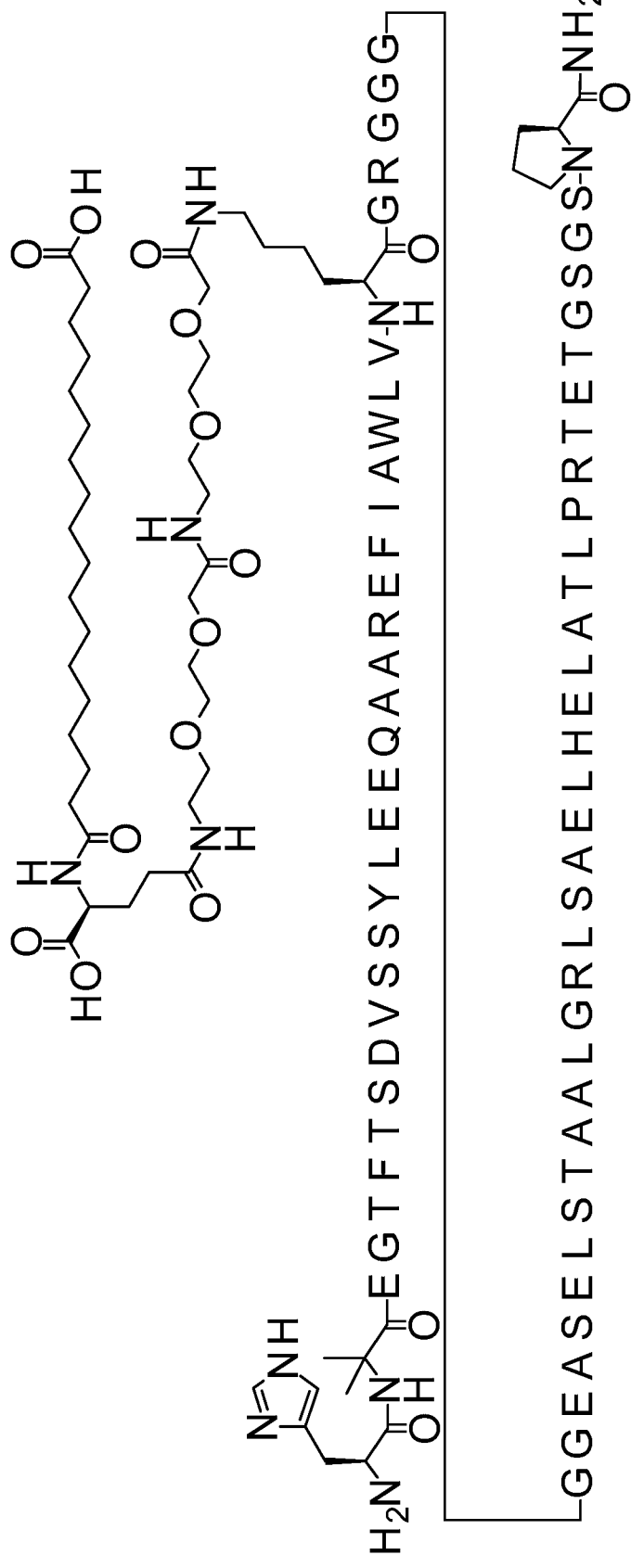
Figure 61:
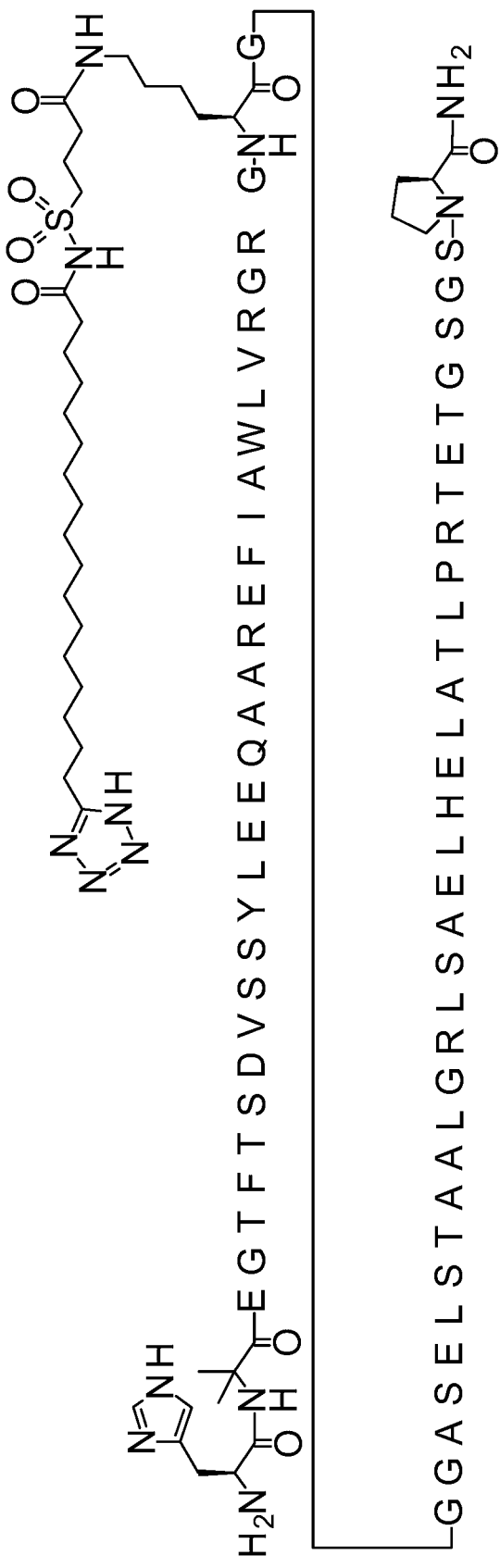
Figure 62:
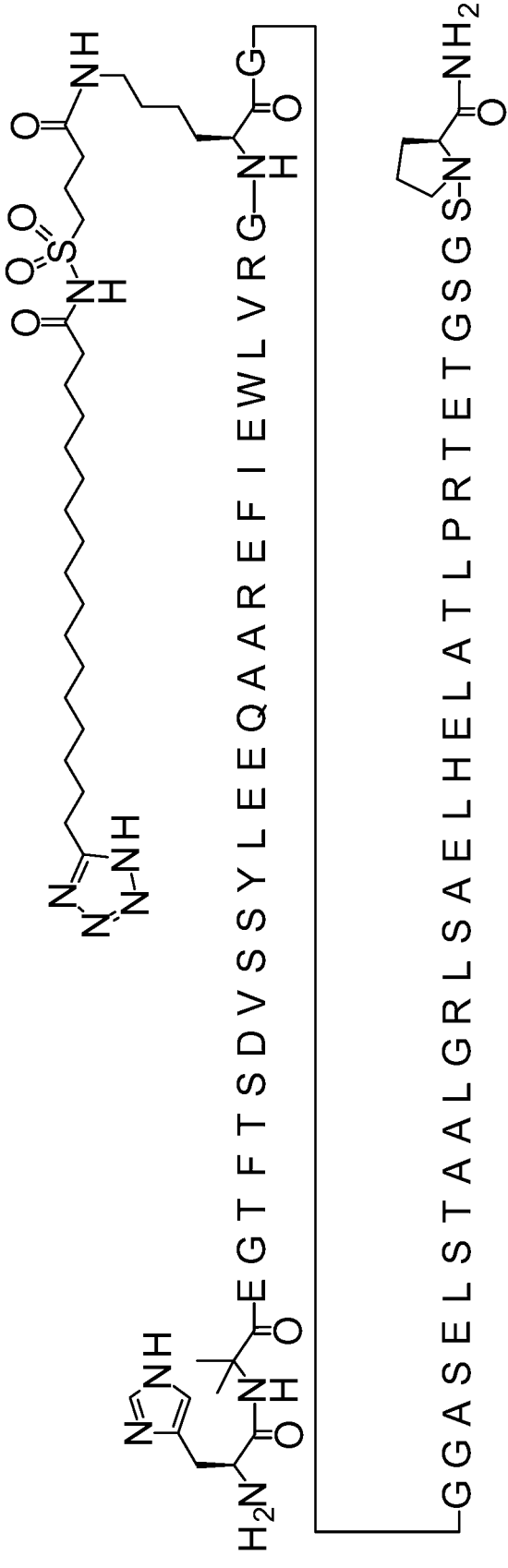
Figure 63:
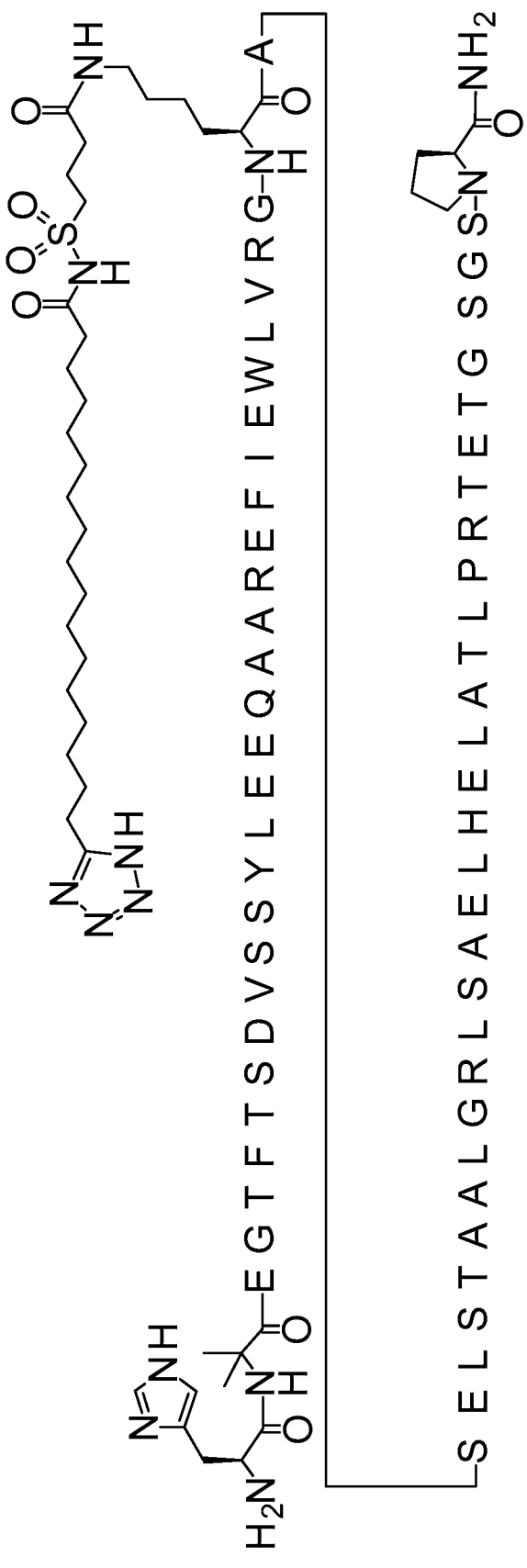
Figure 64:
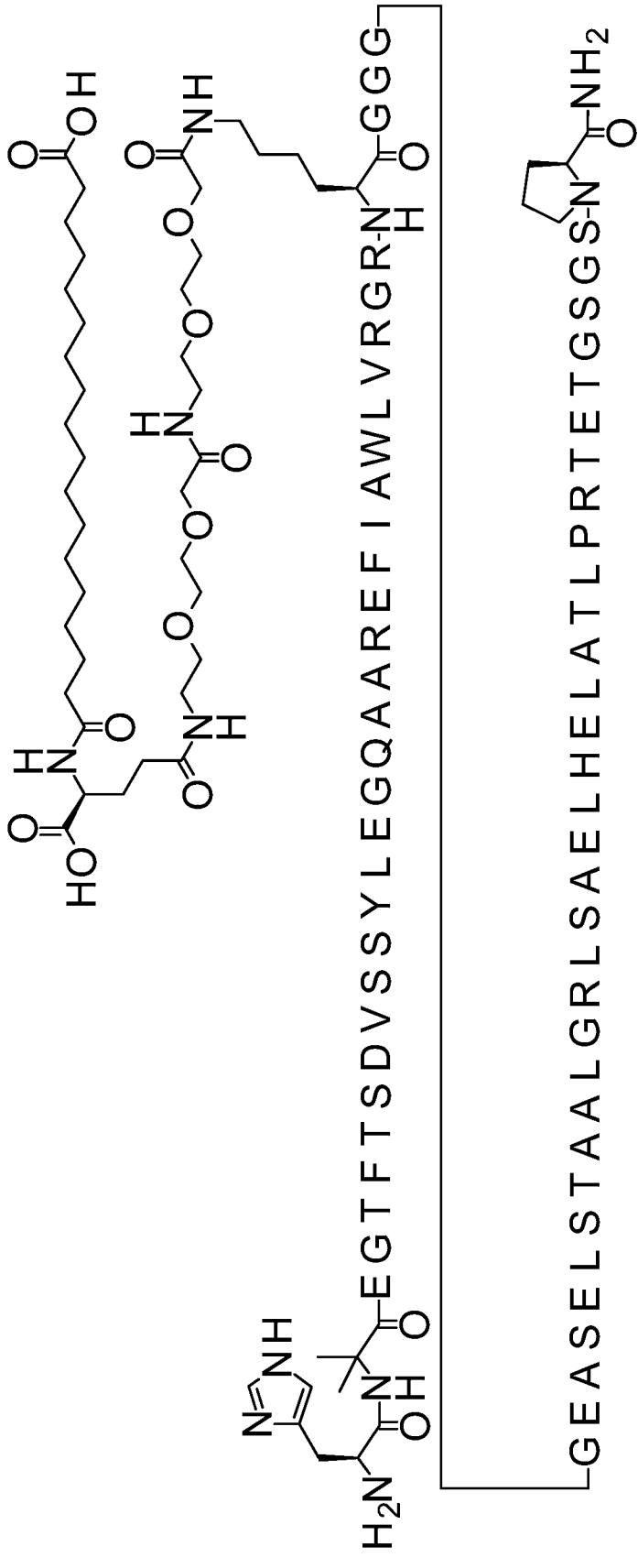
Figure 65:
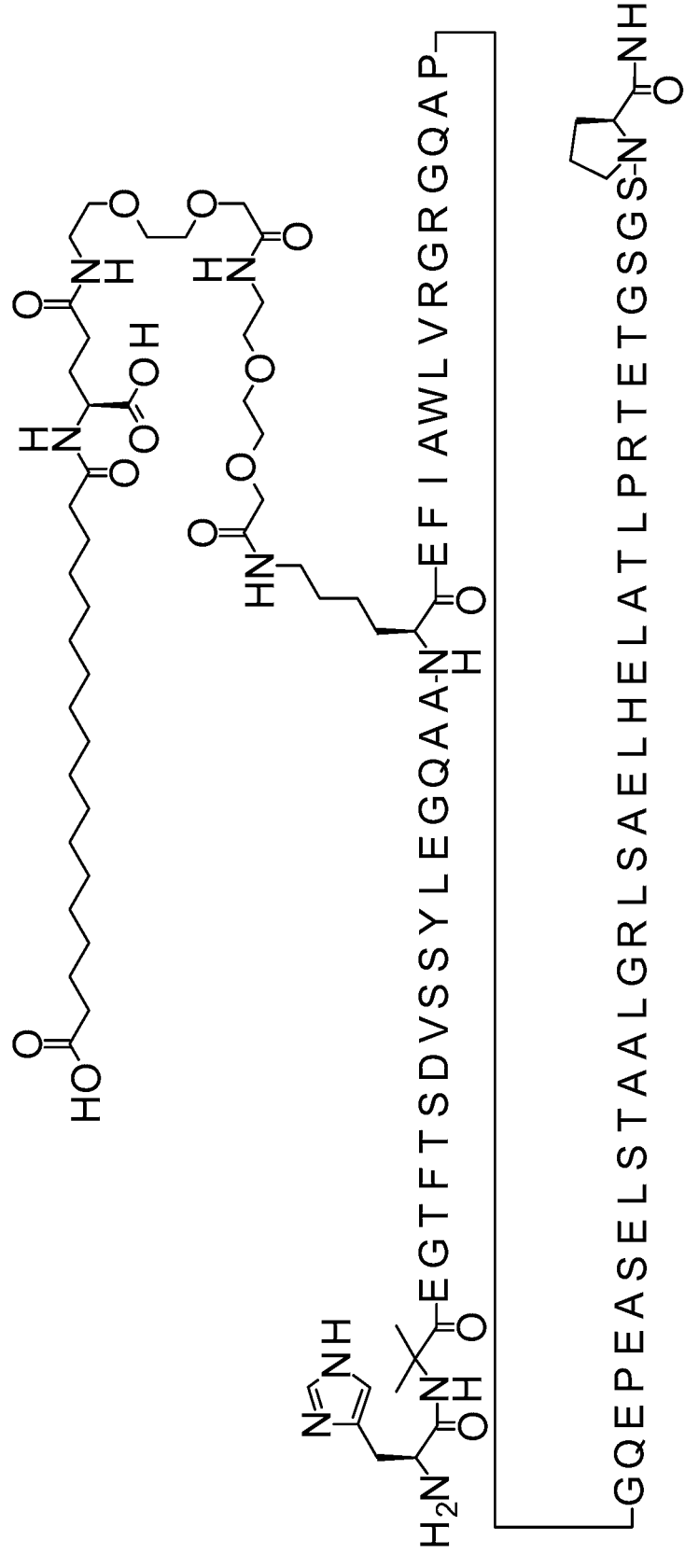
Figure 66:
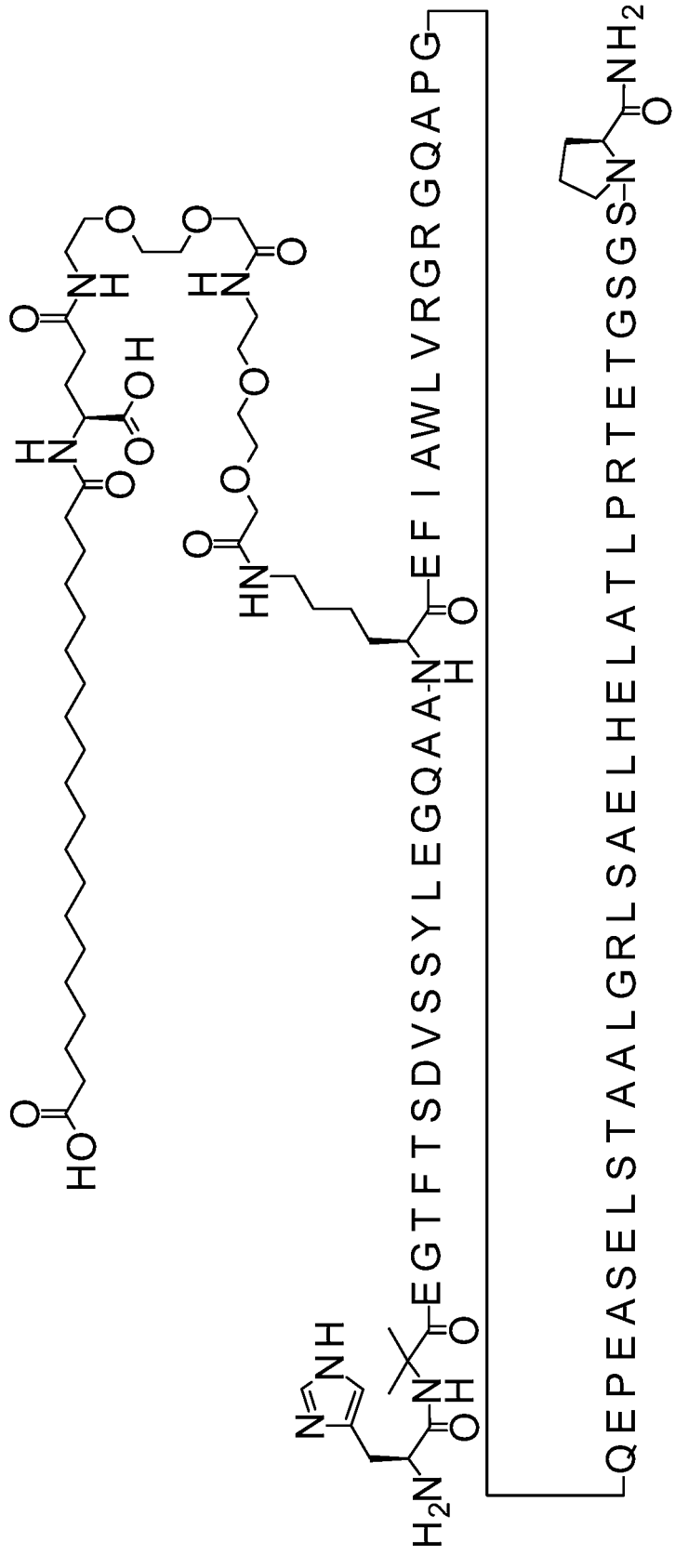
Figure 67:
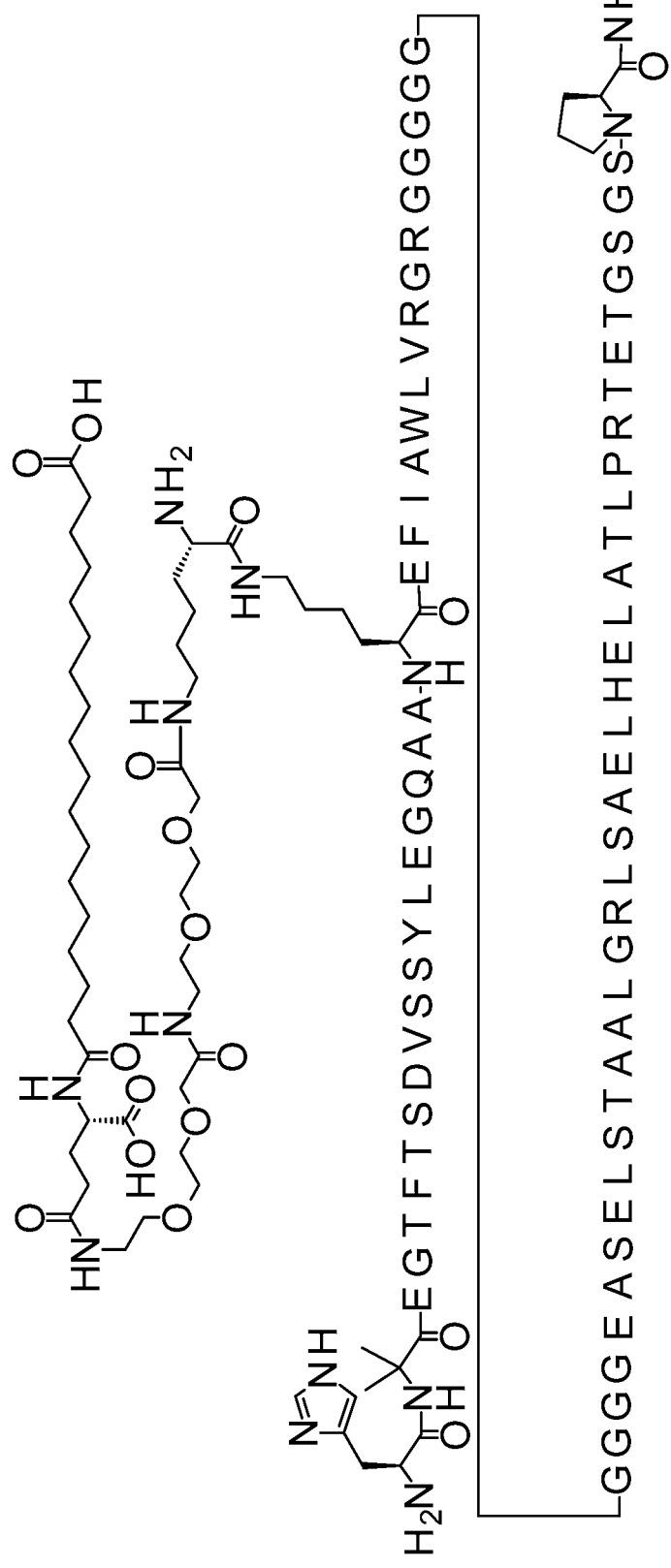
Figure 68:
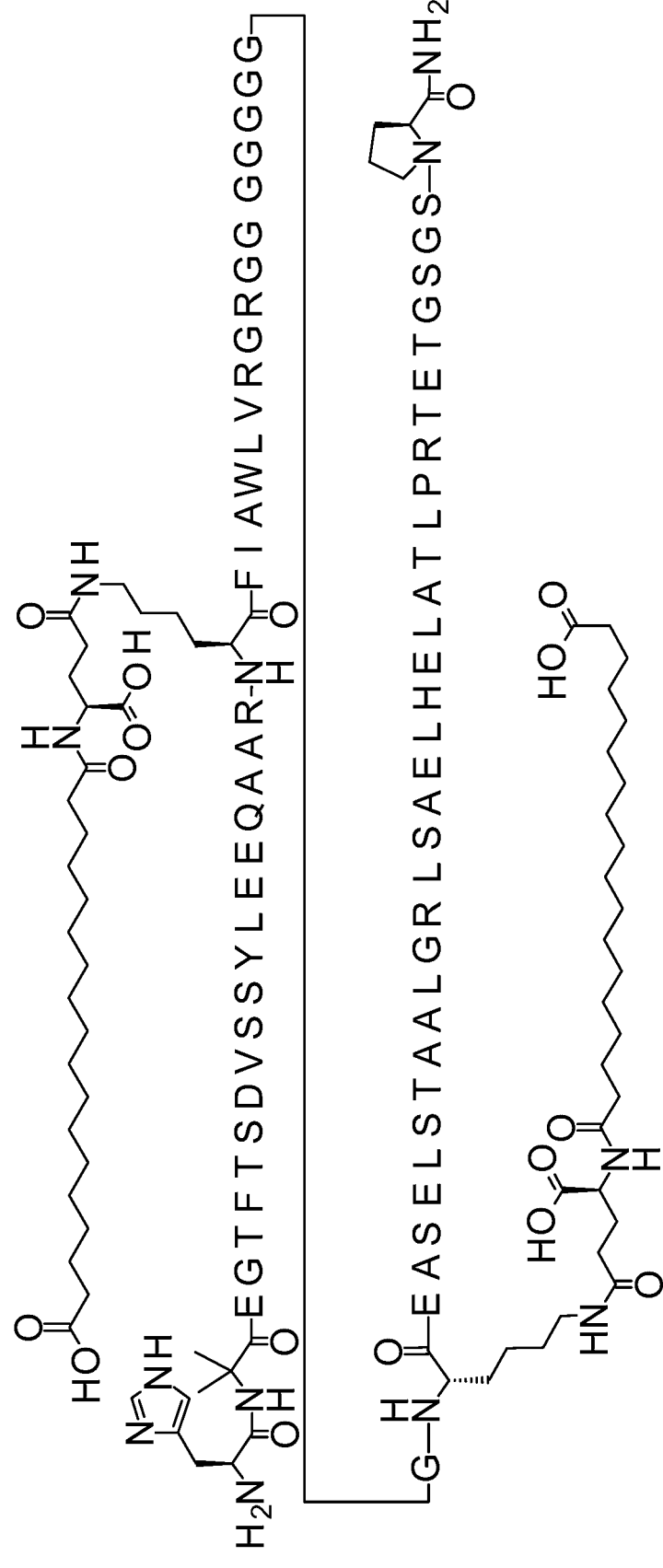
Figure 69:
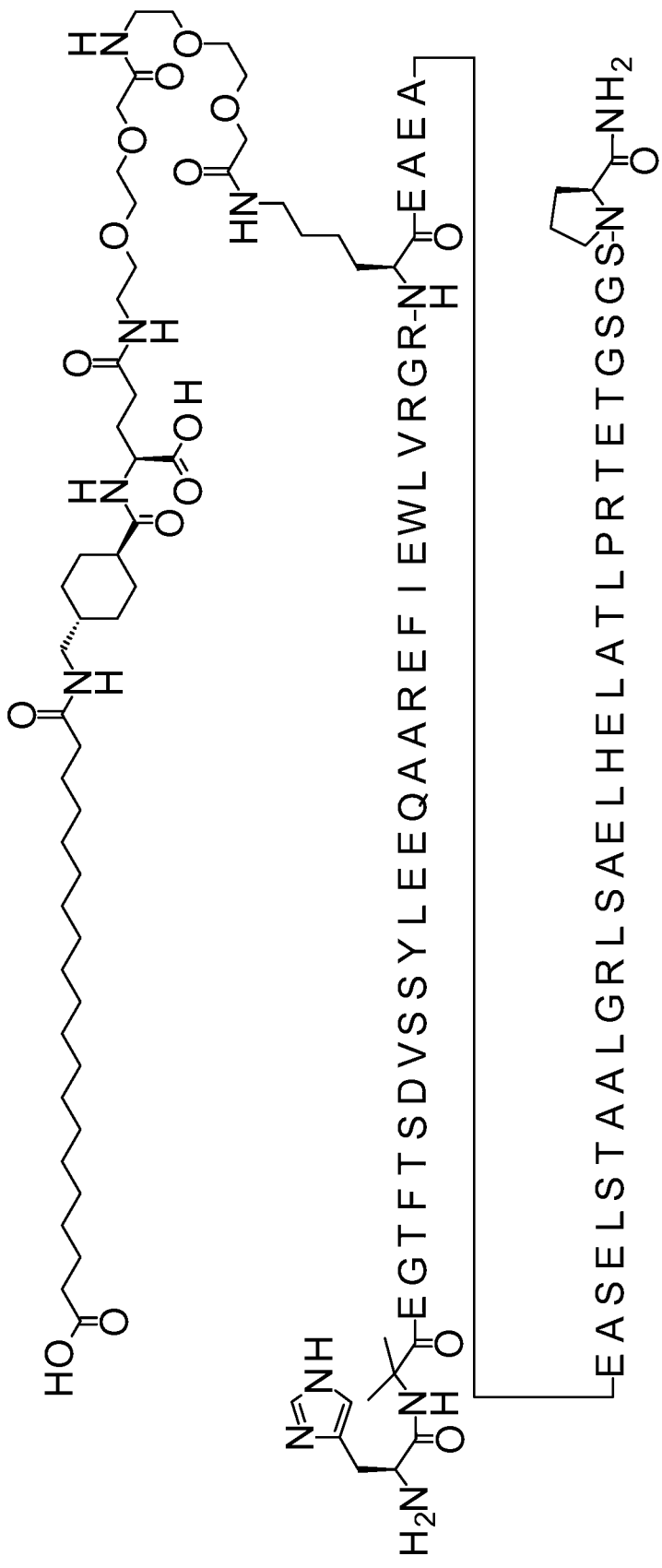
Figure 70:
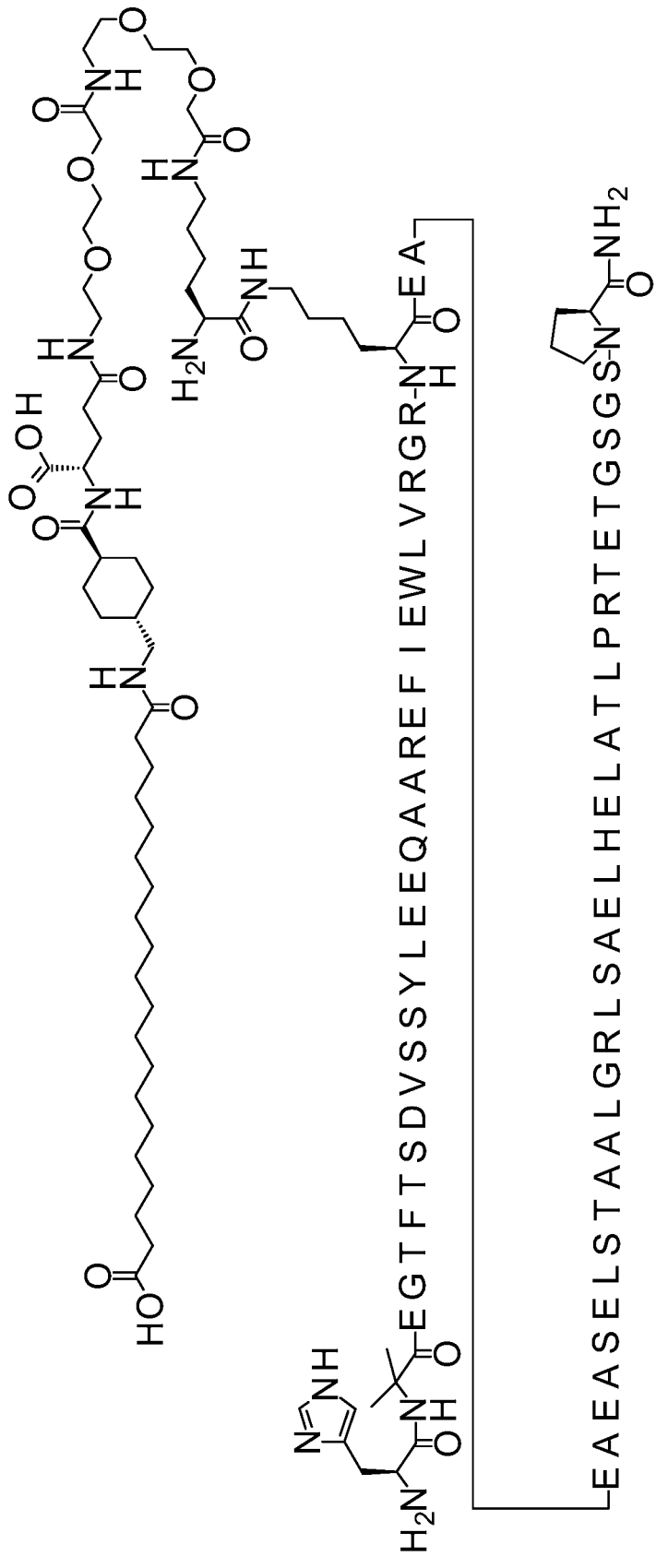
Figure 71:
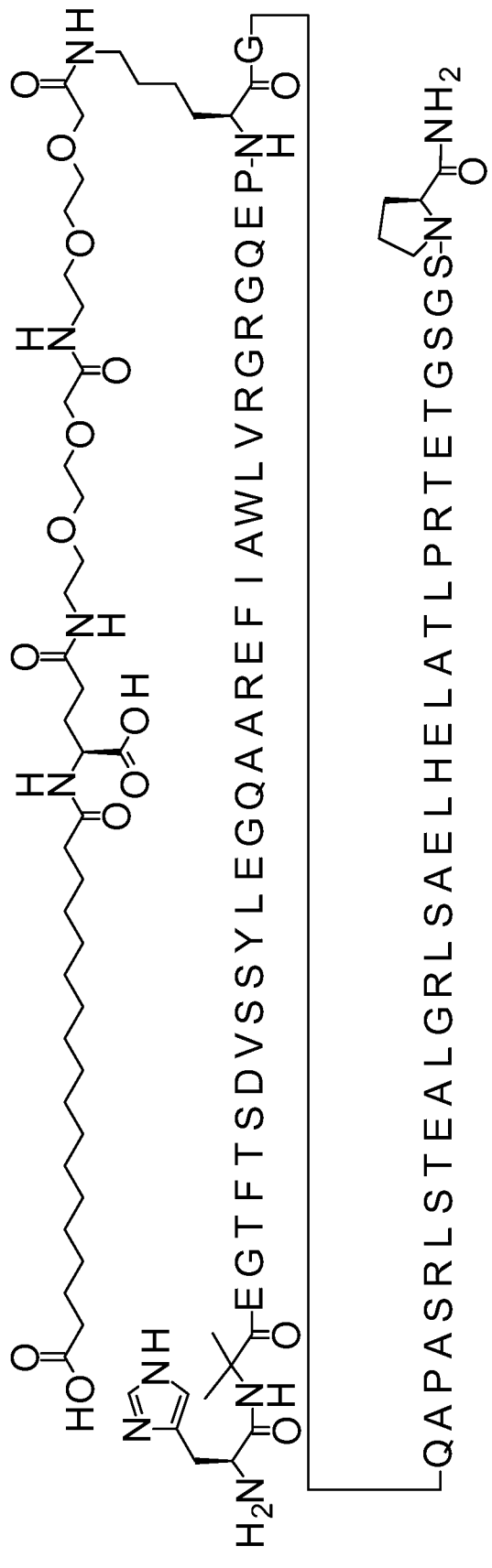
Figure 72:
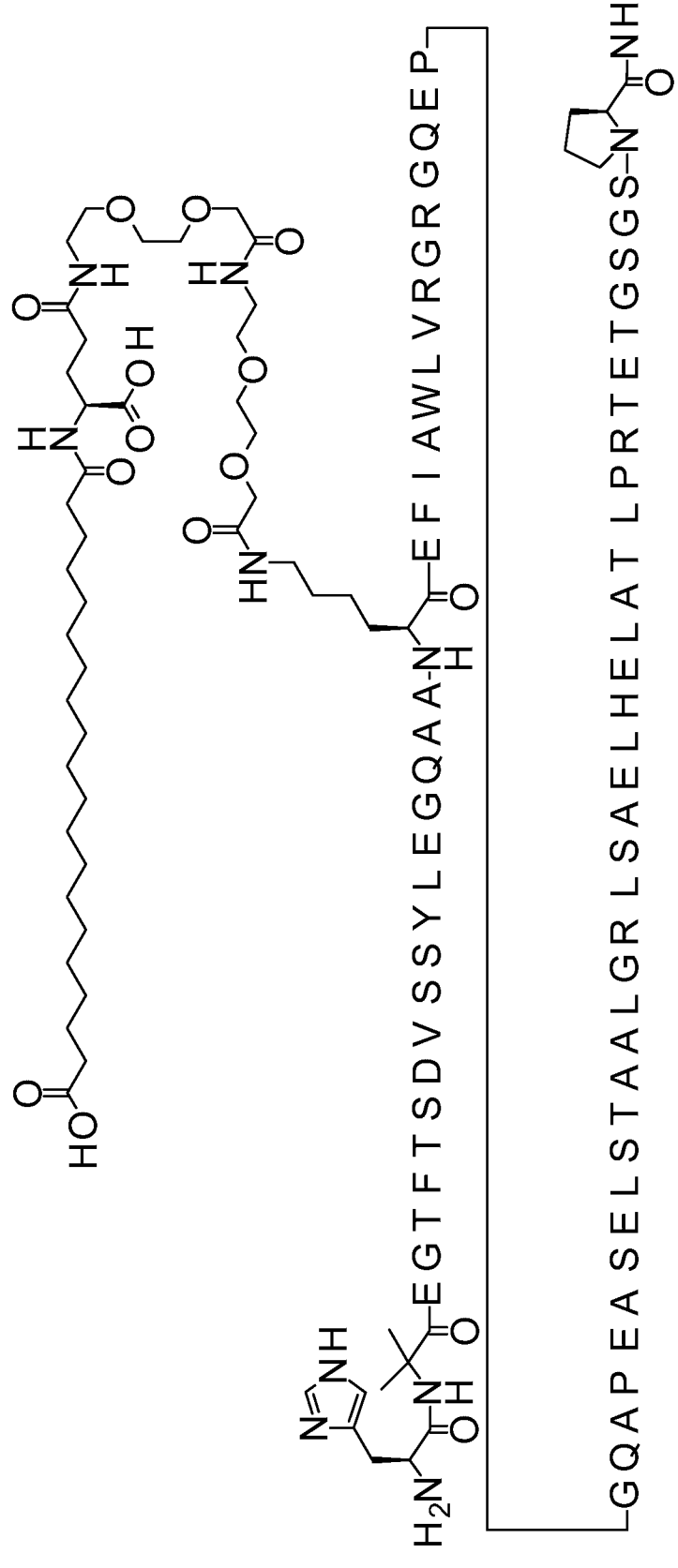
Figure 74:
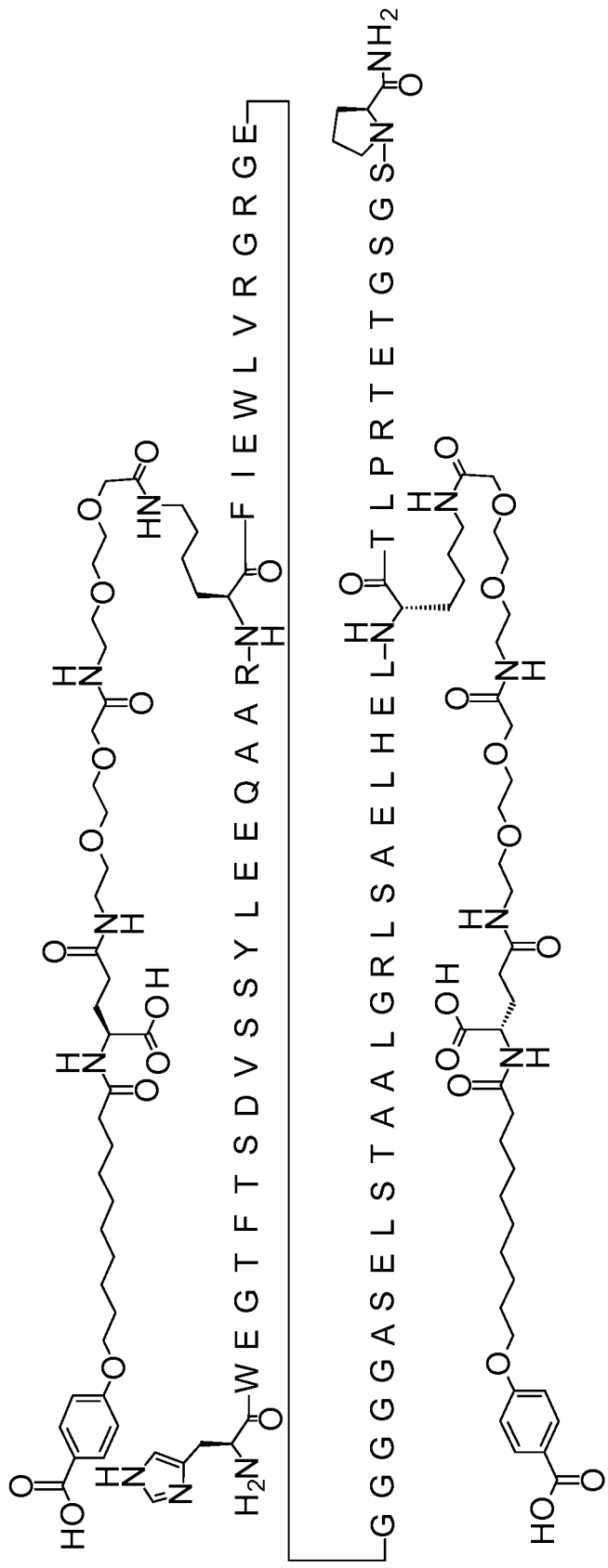
Figure 76:
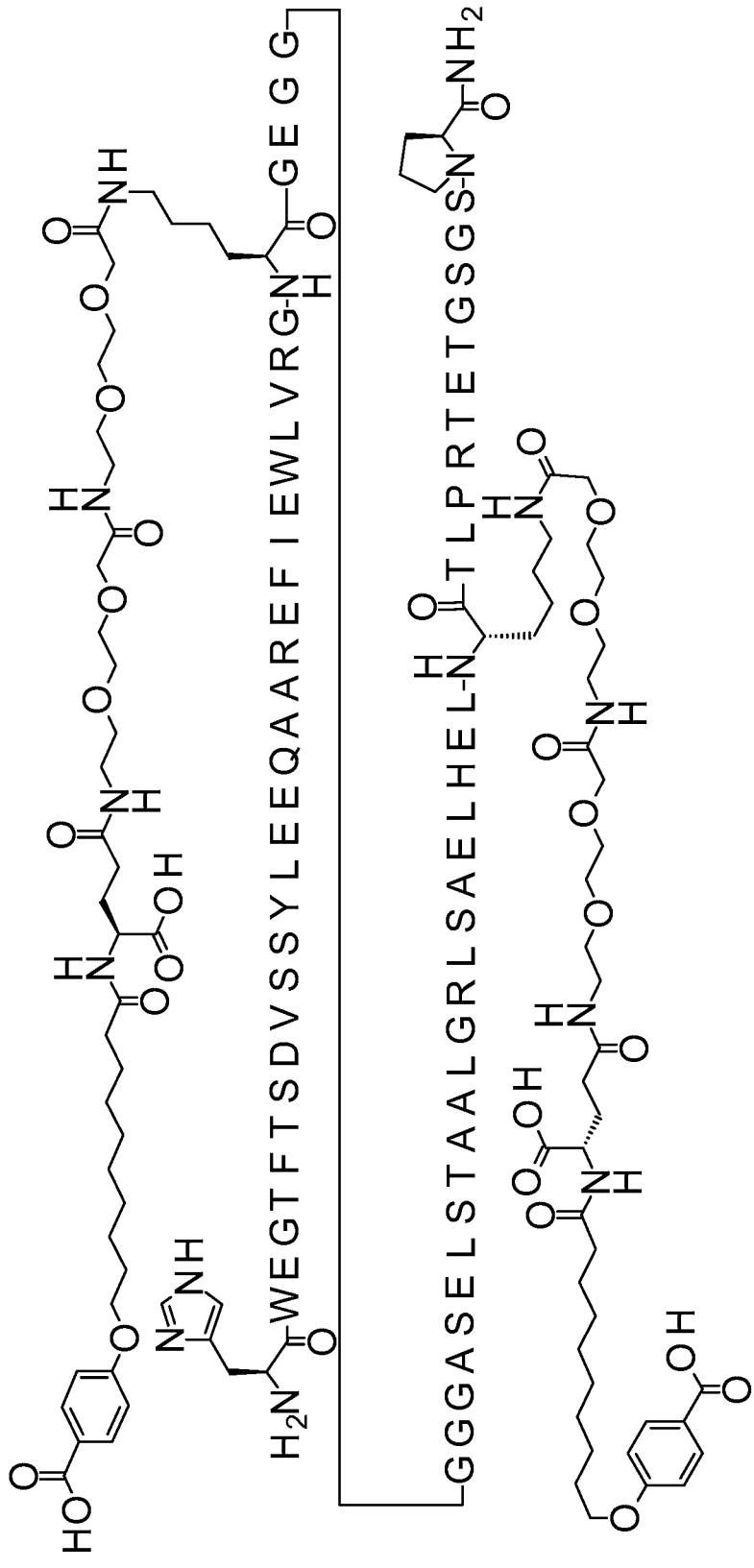
Figure 77:
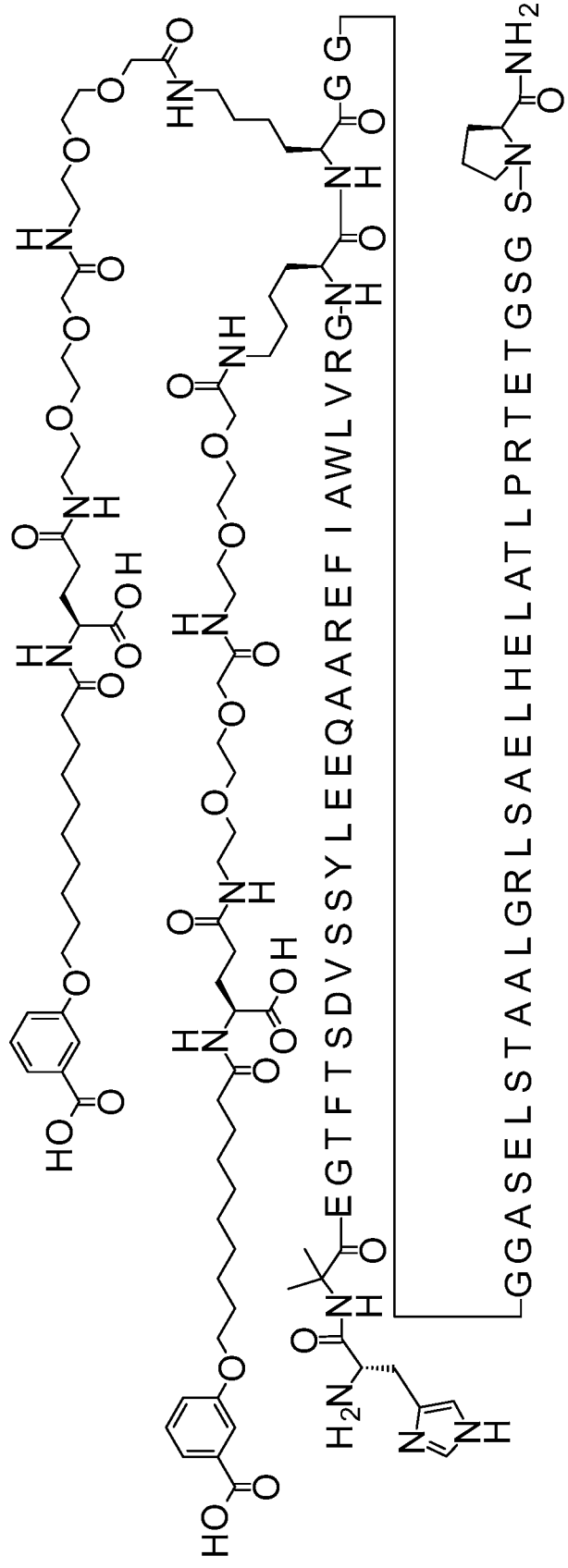
Figure 78:
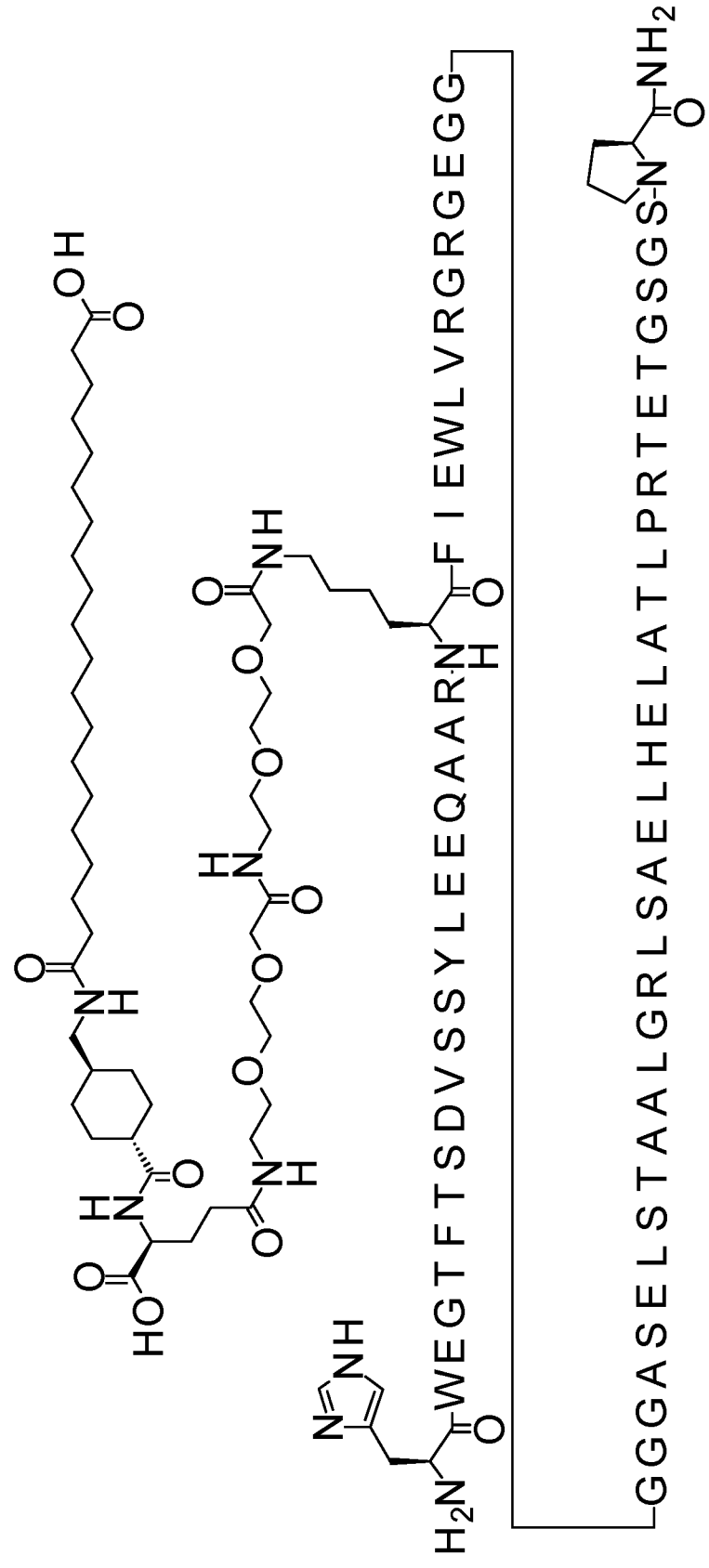
Figure 80:
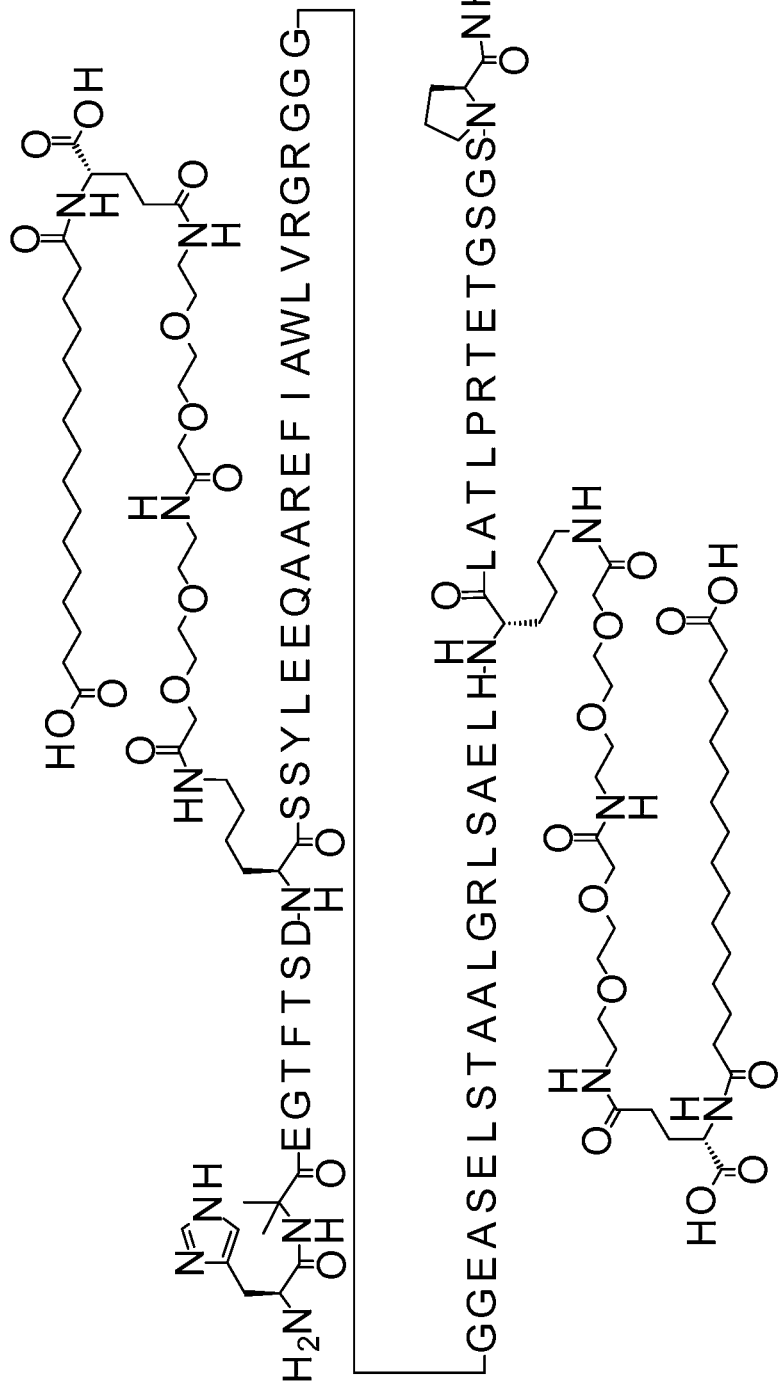
Figure 81:
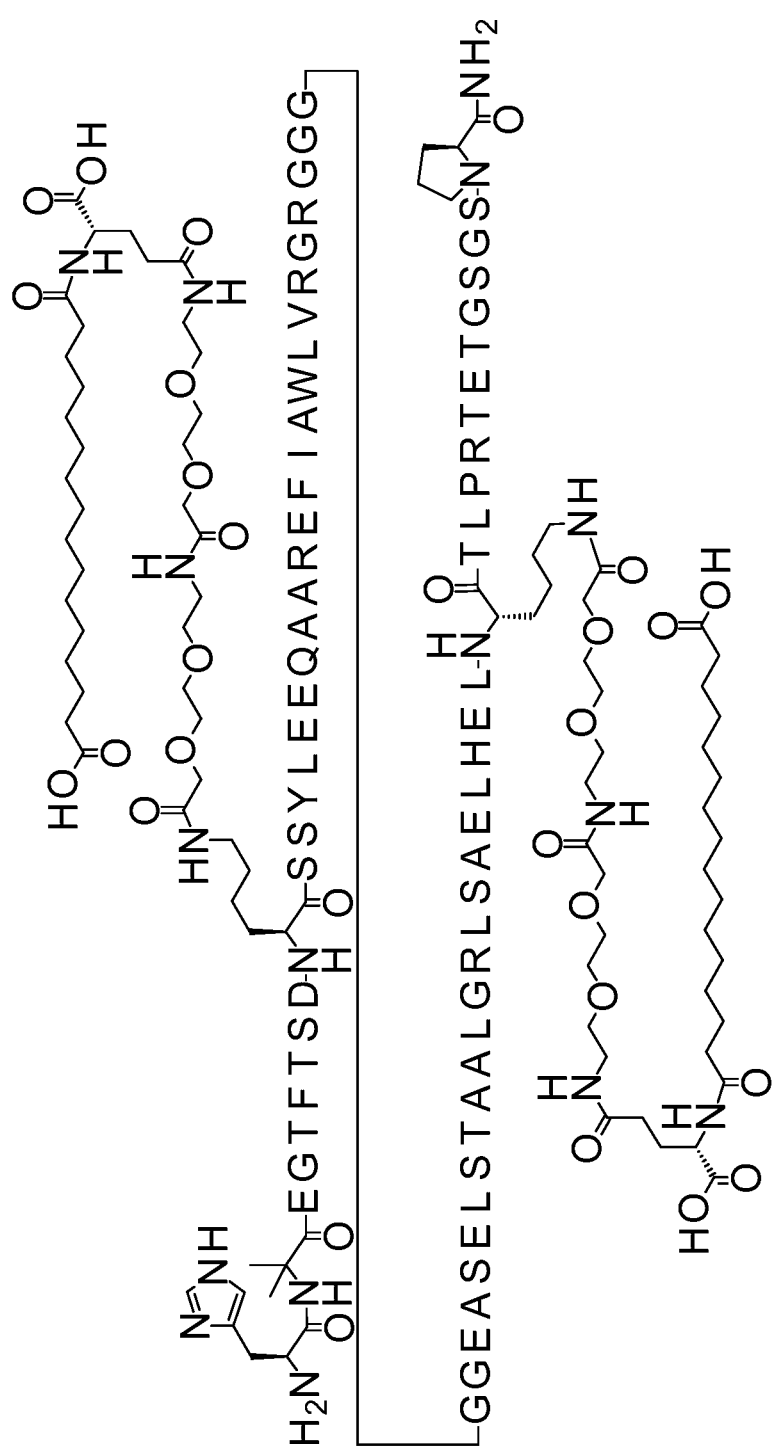
Figure 82:
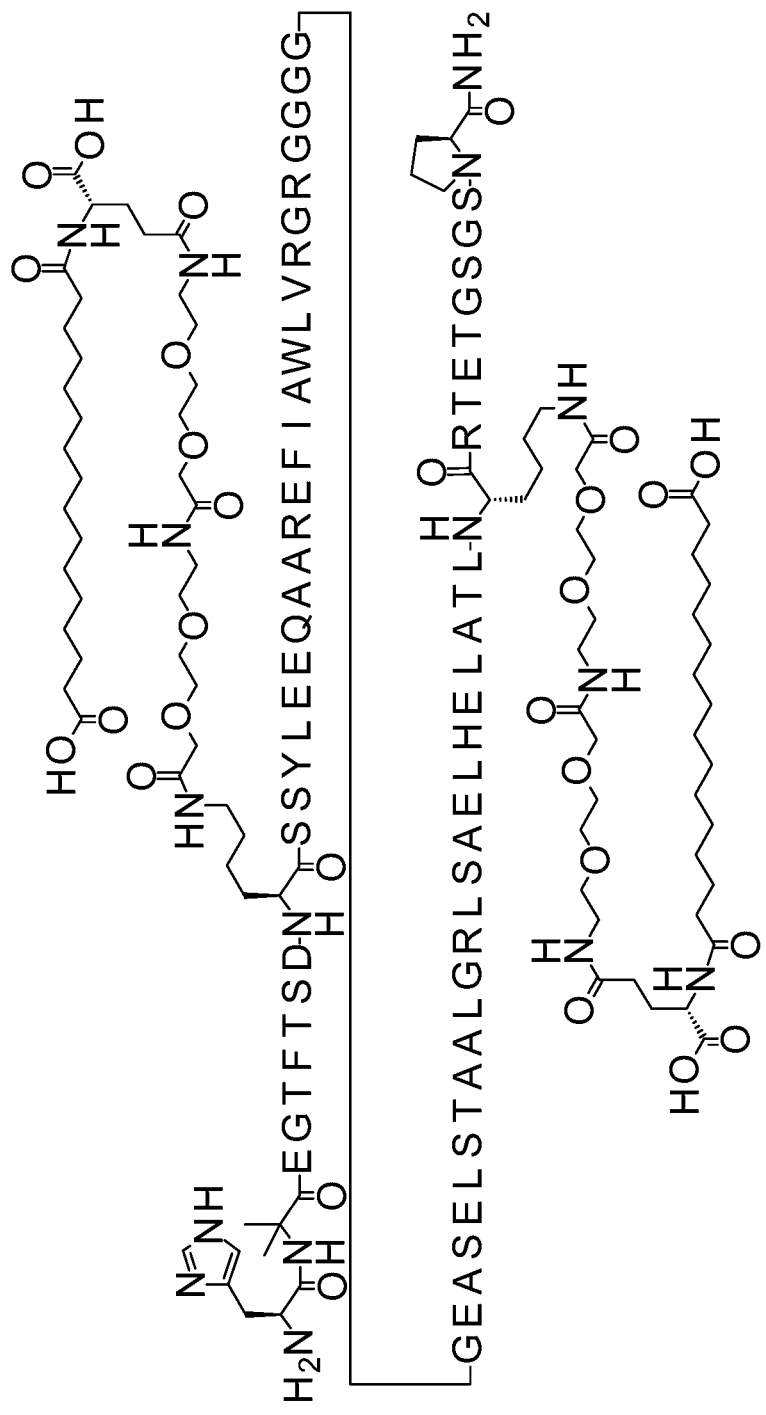
Figure 83:
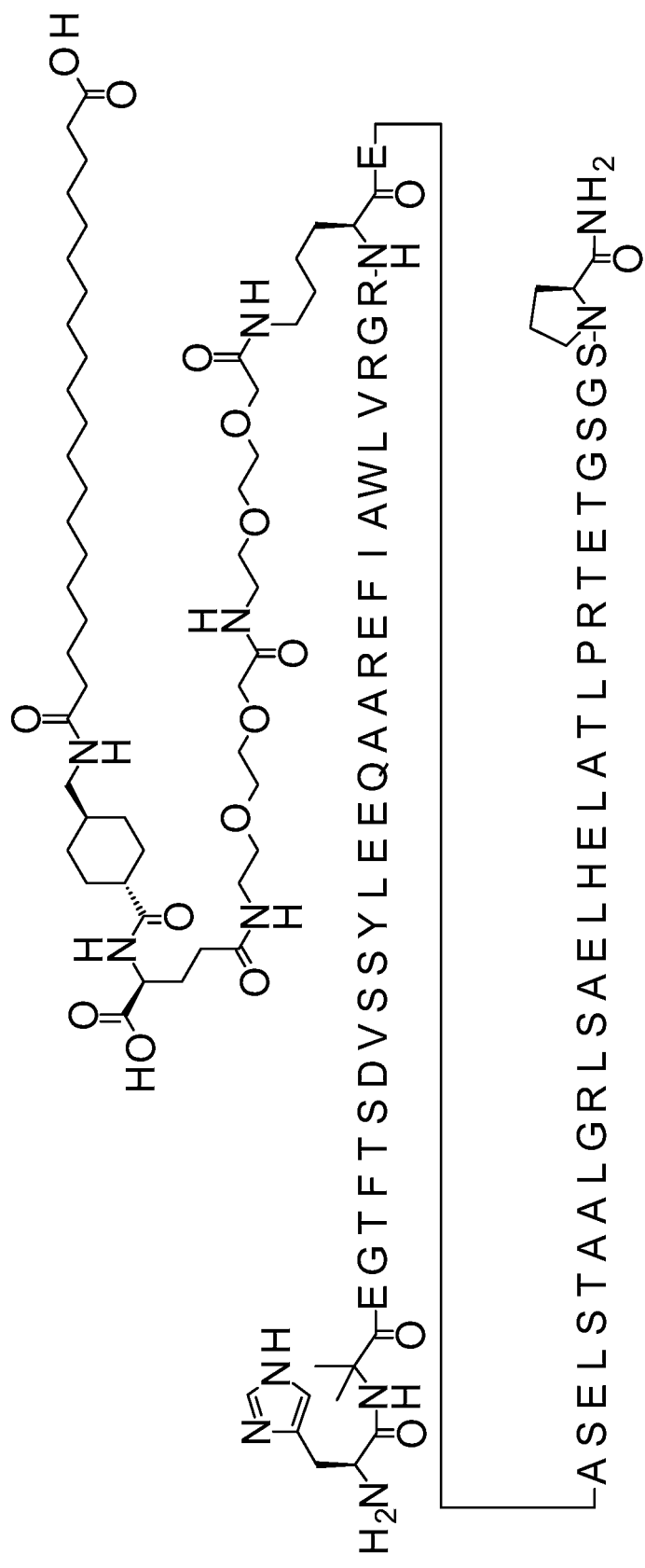
Figure 84:
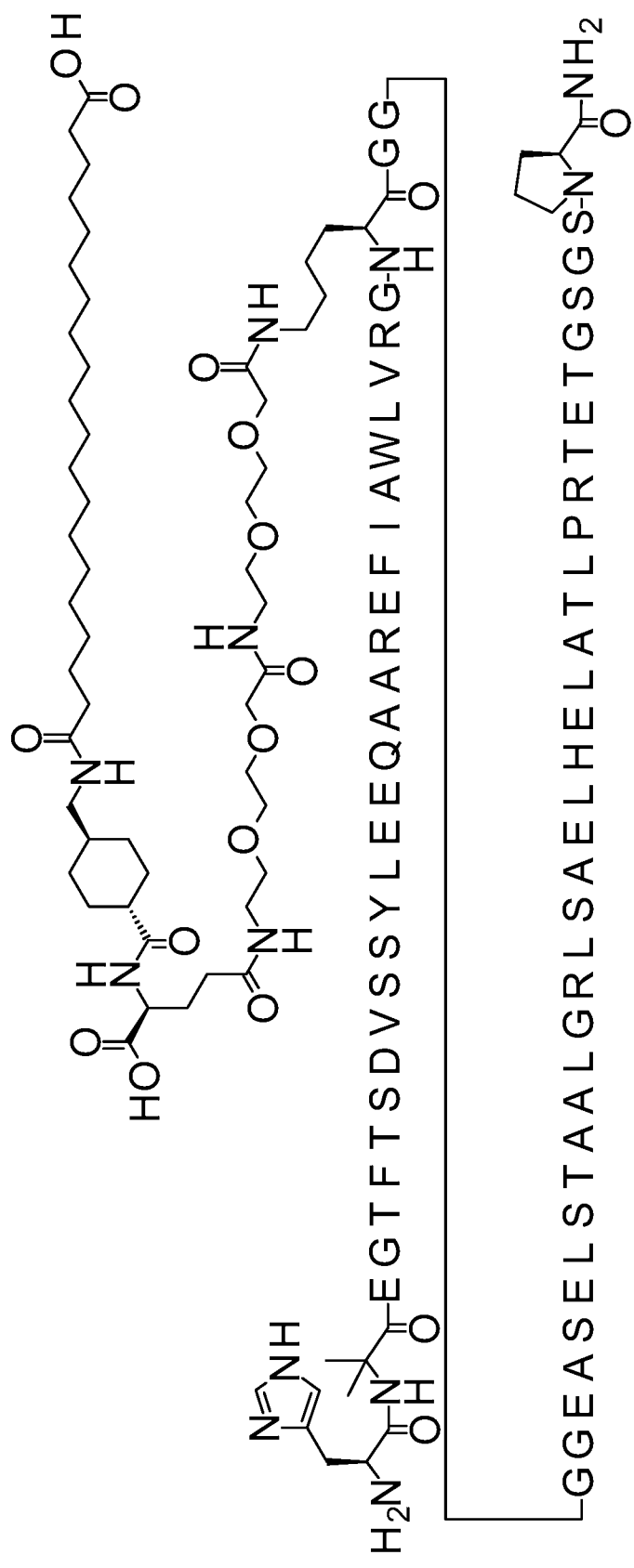
Figure 85:
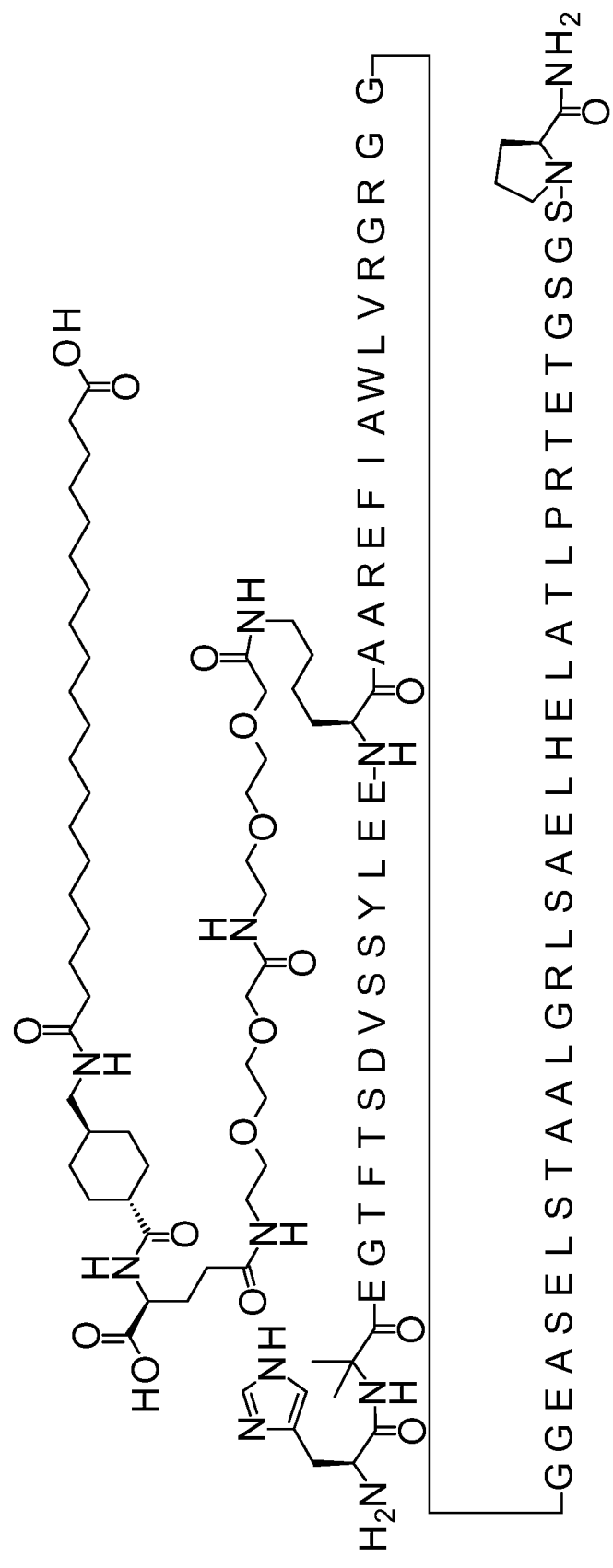
Figure 86:
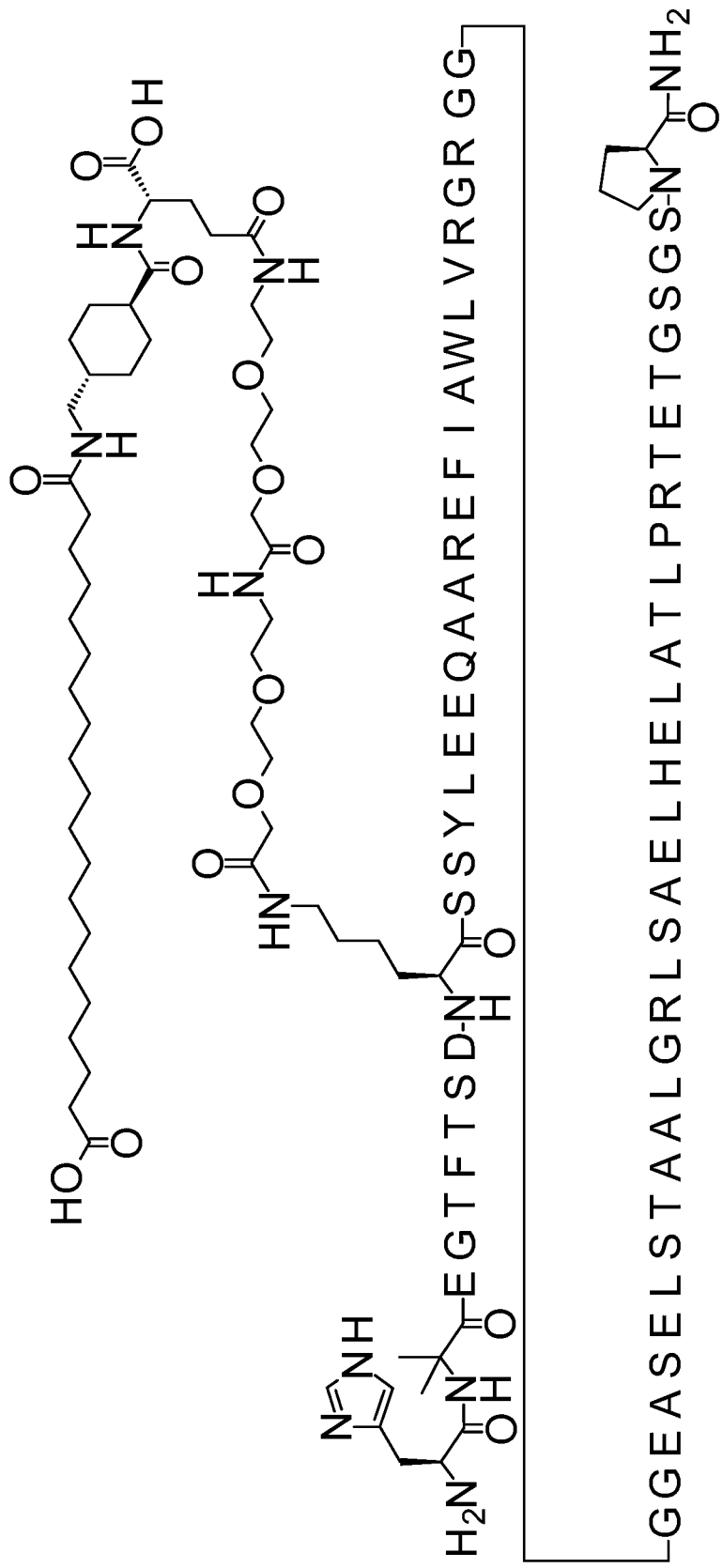
Figure 87:
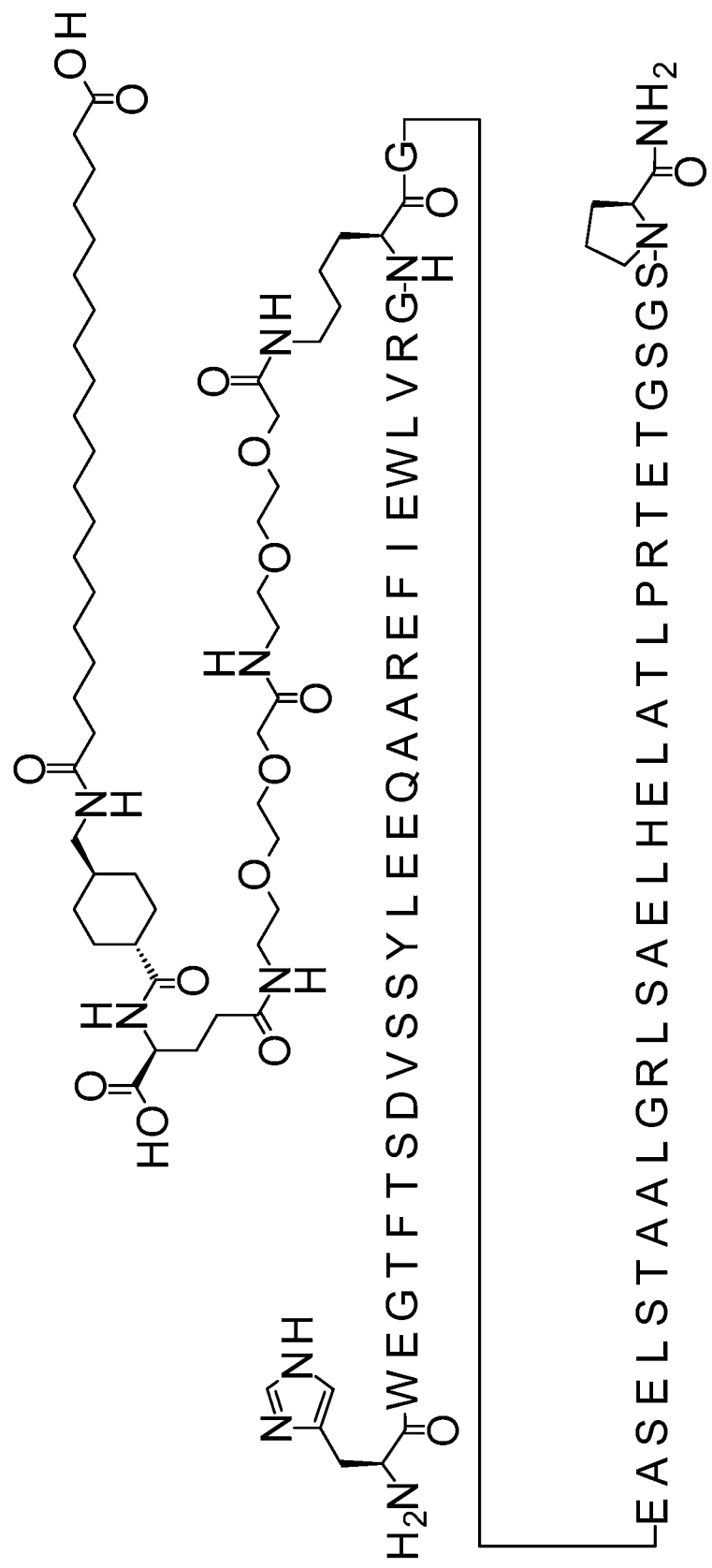
Figure 88:
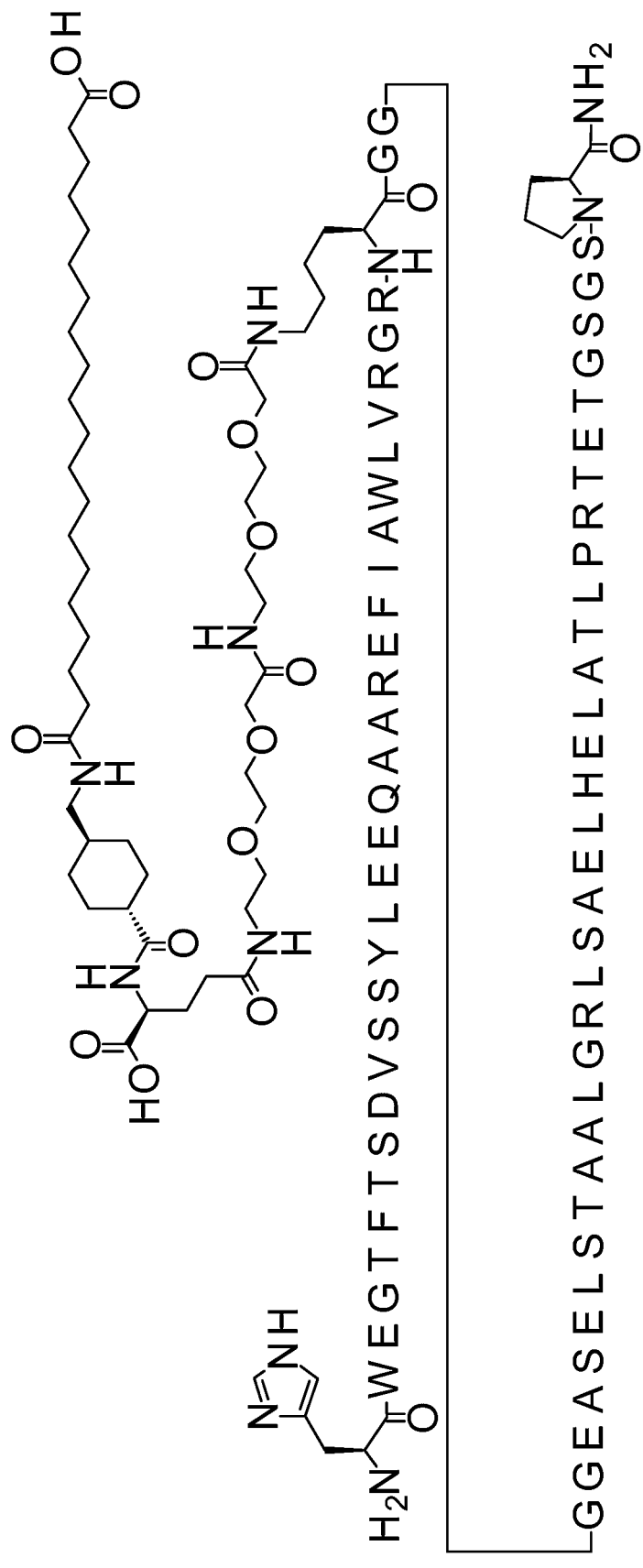
Figure 89:
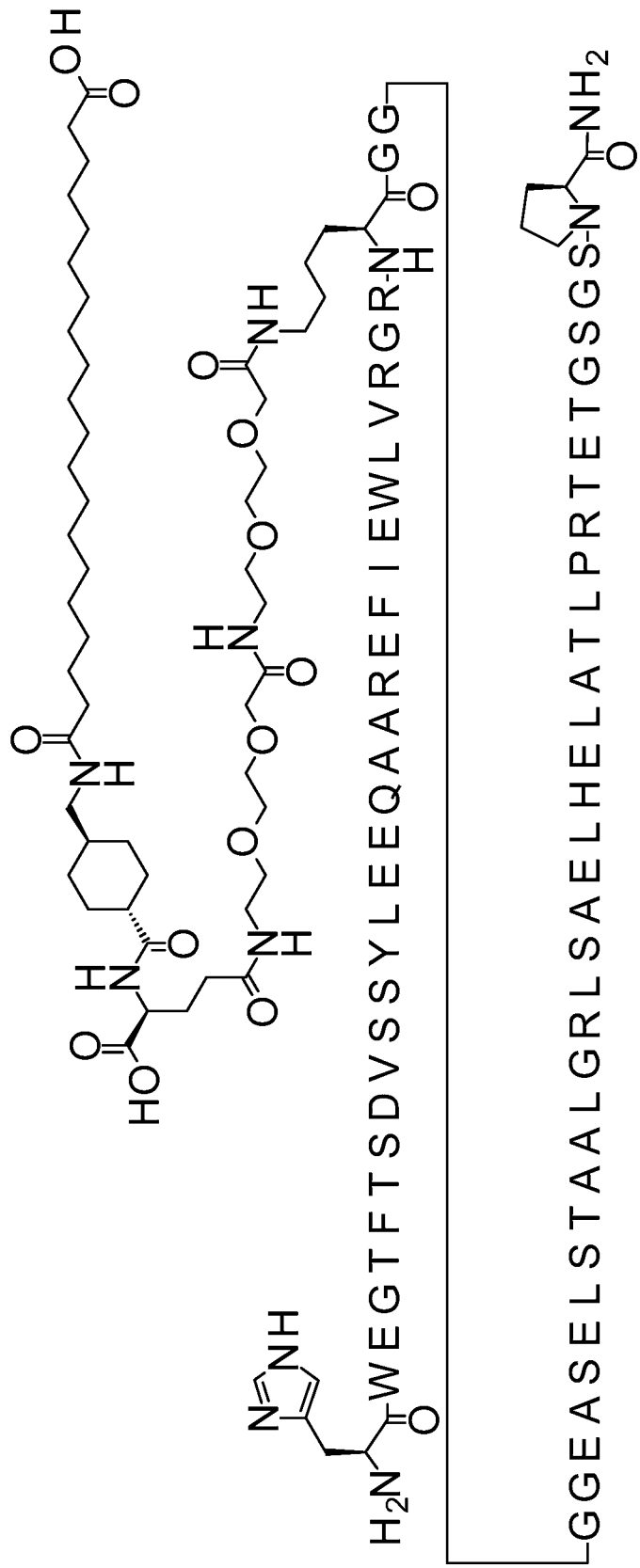
Figure 90:
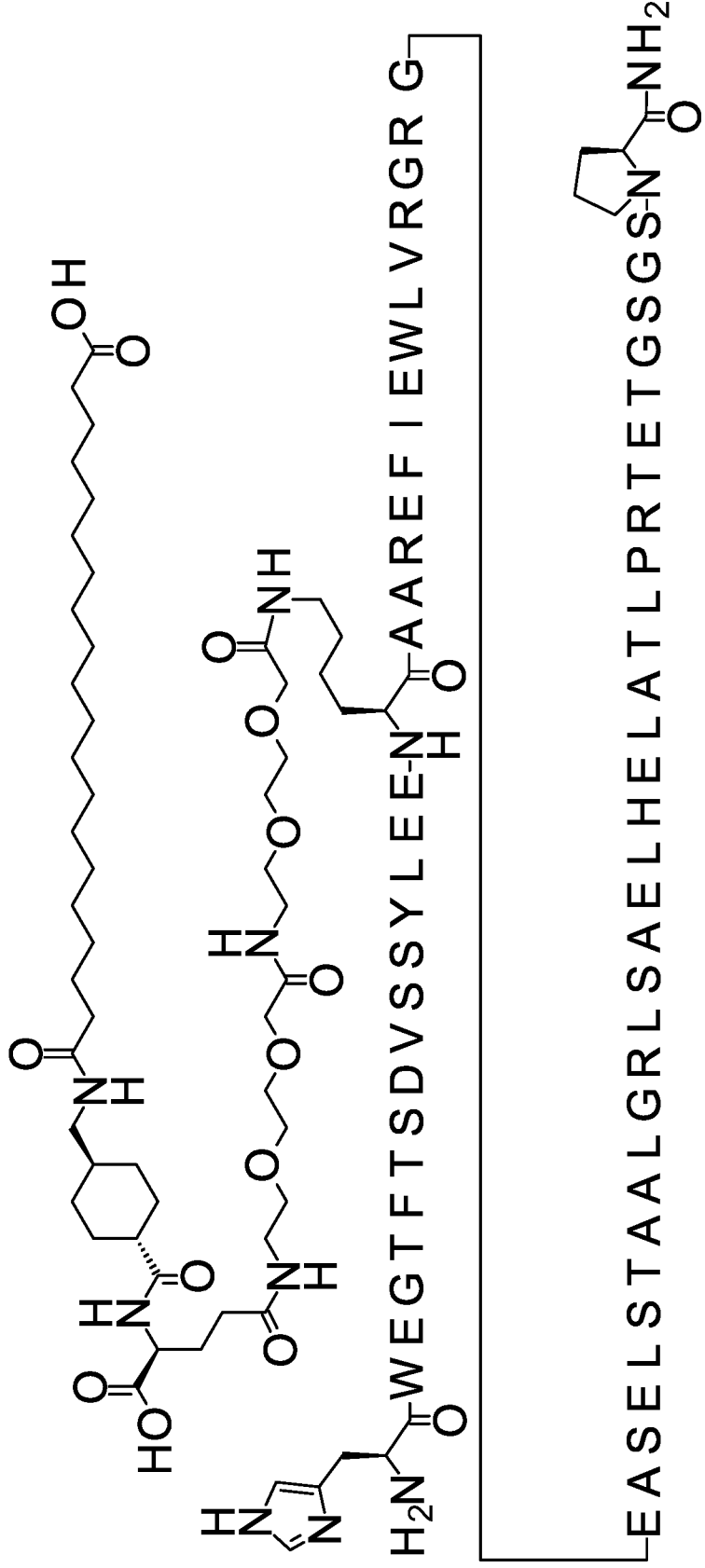
Figure 91:
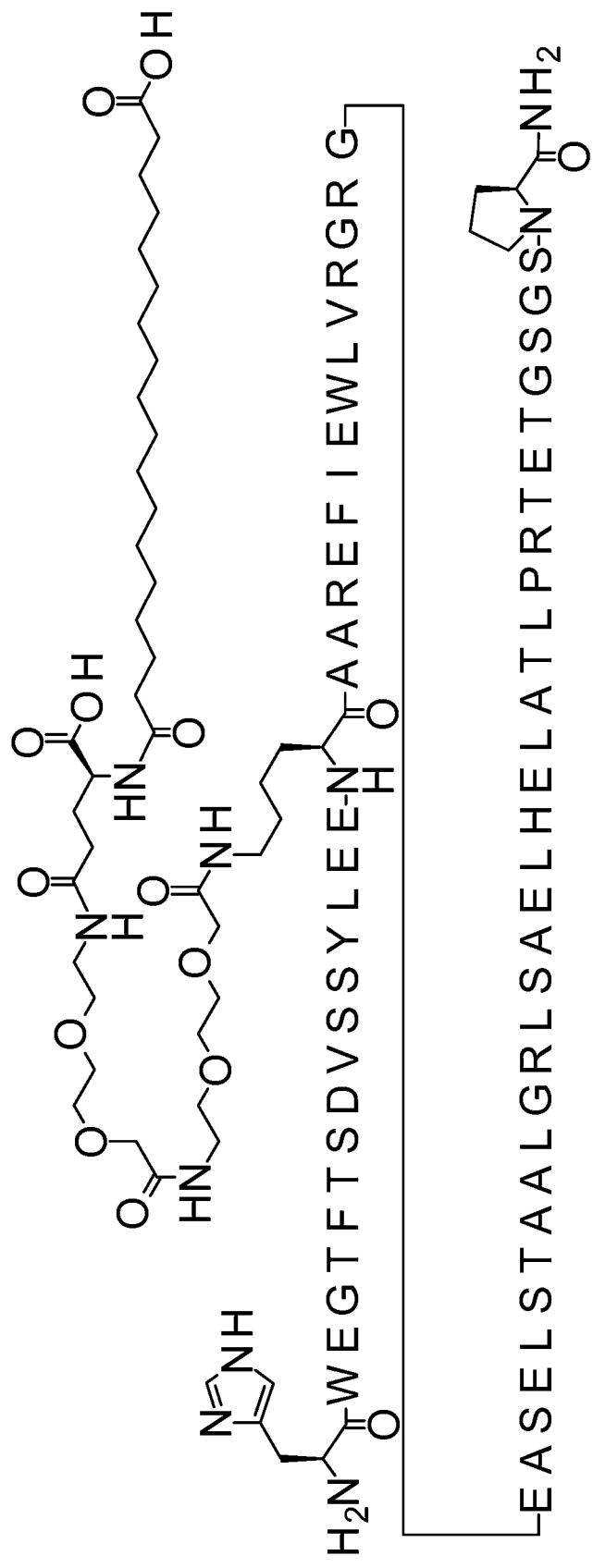
Figure 92:
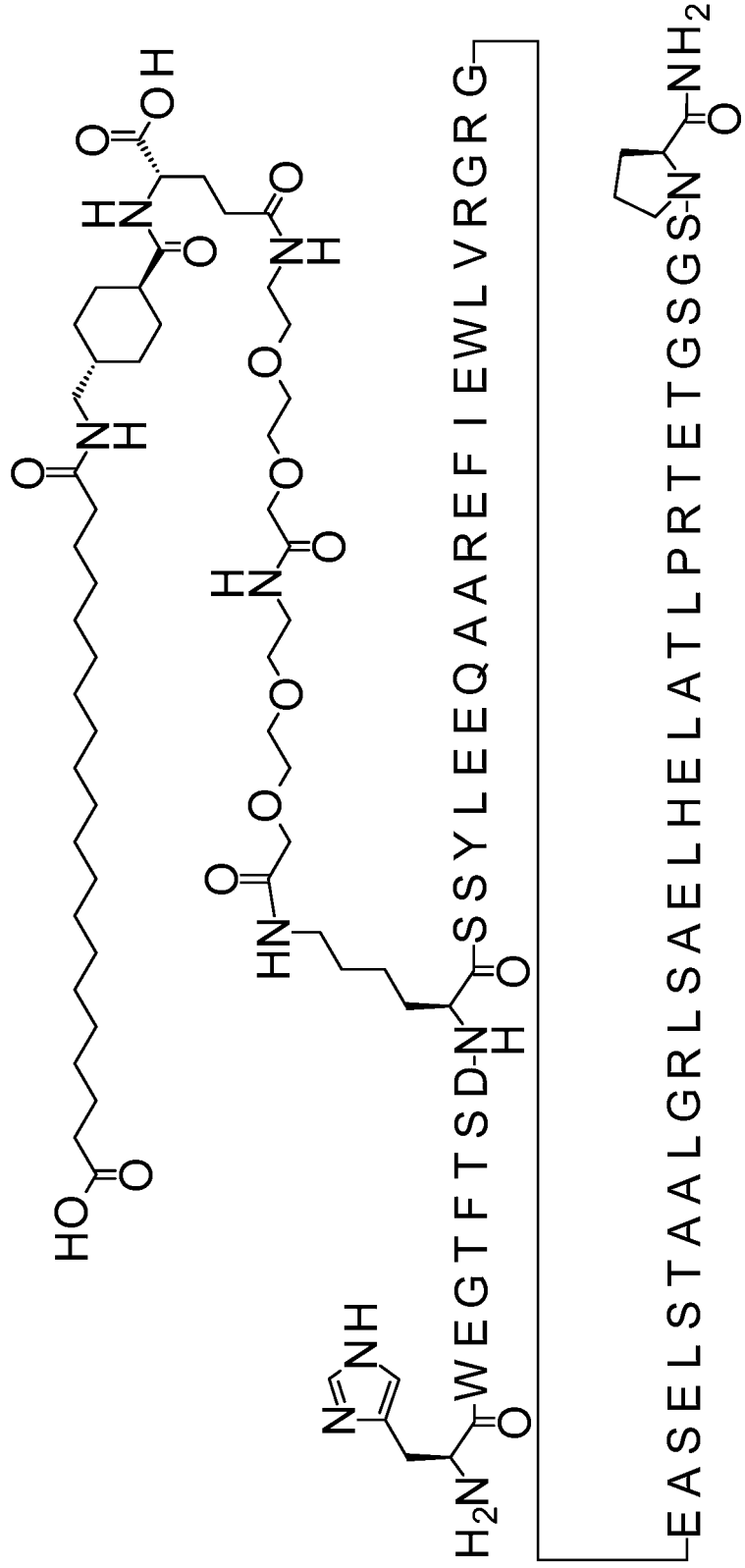
Figure 94:
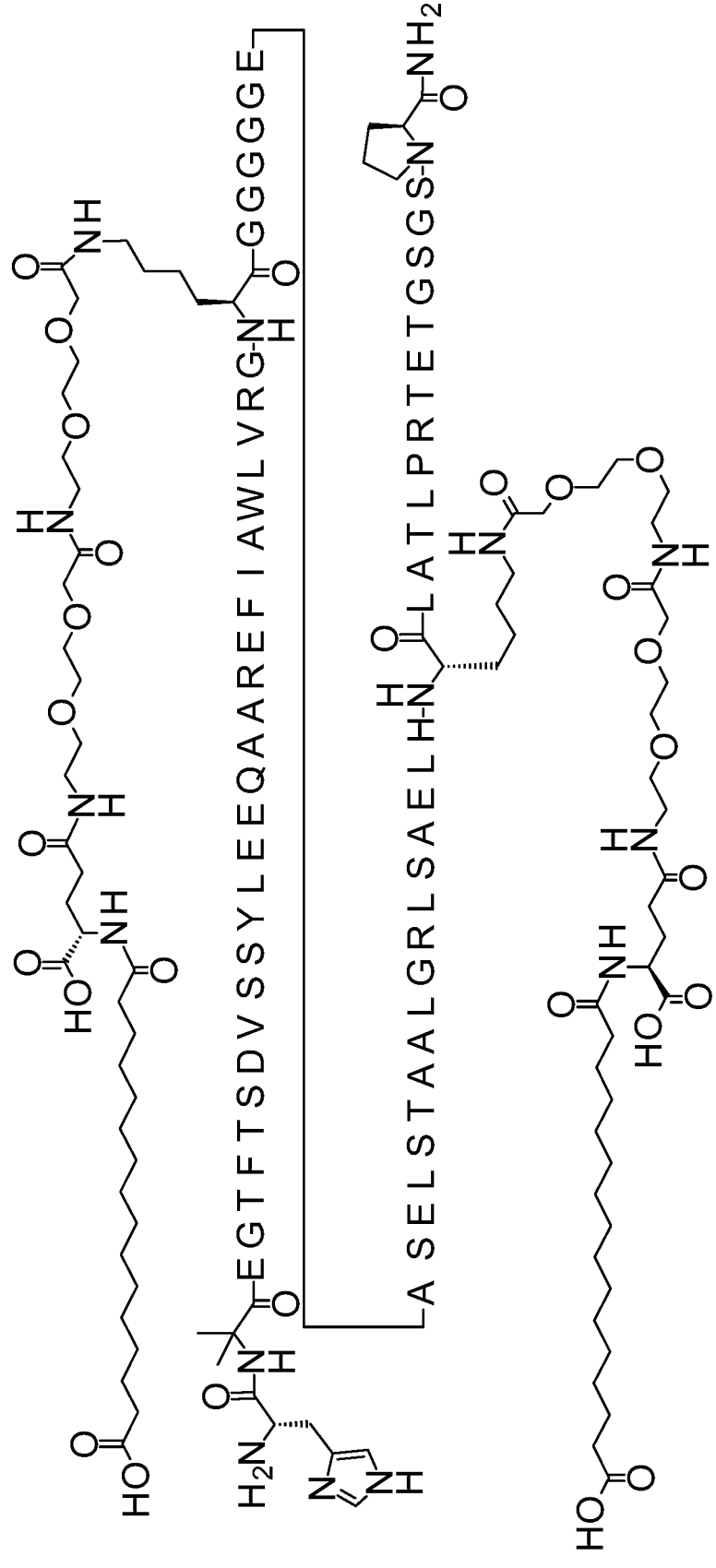

FIG. 1 depicts compound 0007.
FIG. 2 depicts compound 0009.
FIG. 3 depicts compound 0010.
FIG. 4 depicts compound 0019.
FIG. 5 depicts compound 0026.
FIG. 6 depicts compound 0035.
FIG. 7 depicts compound 0039.
FIG. 8 depicts compound 0040.
FIG. 9 depicts compound 0042.
FIG. 10 depicts compound 0044.
FIG. 11 depicts compound 0045.
FIG. 12 depicts compound 0051.
FIG. 13 depicts compound 0052.
FIG. 14 depicts compound 0056.
FIG. 15 depicts compound 0057.
FIG. 16 depicts compound 0071.
FIG. 17 depicts compound 0072.
FIG. 18 depicts compound 0073.
FIG. 19 depicts compound 0074.
FIG. 20 depicts compound 0075.
FIG. 21 depicts compound 0076.
FIG. 22 depicts compound 0077.
FIG. 23 depicts compound 0083.
FIG. 24 depicts compound 0084.
FIG. 25 depicts compound 0085.
FIG. 26 depicts compound 0086.
FIG. 27 depicts compound 0087.
FIG. 28 depicts compound 0089.
FIG. 29 depicts compound 0090.
FIG. 30 depicts compound 0092.
FIG. 31 depicts compound 0093.
FIG. 32 depicts compound 0094.
FIG. 33 depicts compound 0095.
FIG. 34 depicts compound 0096.
FIG. 35 depicts compound 0097.
FIG. 36 depicts compound 0098.
FIG. 37 depicts compound 0099.
FIG. 38 depicts compound 0100.
FIG. 39 depicts compound 0101.
FIG. 40 depicts compound 0102.
FIG. 41 depicts compound 0103.
FIG. 42 depicts compound 0105.
FIG. 43 depicts compound 0106.
FIG. 44 depicts compound 0109.
FIG. 45 depicts compound 0110.
FIG. 46 depicts compound 0111.
FIG. 47 depicts compound 0114.
FIG. 48 depicts compound 0115.
FIG. 49 depicts compound 0116.
FIG. 50 depicts compound 0120.
FIG. 51 depicts compound 0124.
FIG. 52 depicts compound 0125.
FIG. 53 depicts compound 0127.
FIG. 54 depicts compound 0128.
FIG. 55 depicts compound 0129.
FIG. 56 depicts compound 0131.
FIG. 57 depicts compound 0132.
FIG. 58 depicts compound 0141.
FIG. 59 depicts compound 0142.
FIG. 60 depicts compound 0144.
FIG. 61 depicts compound 0145.
FIG. 62 depicts compound 0146.
FIG. 63 depicts compound 0147.
FIG. 64 depicts compound 0151.
FIG. 65 depicts compound 0156.
FIG. 66 depicts compound 0157.
FIG. 67 depicts compound 0159.
FIG. 68 depicts compound 0160.
FIG. 69 depicts compound 0179.
FIG. 70 depicts compound 0180.
FIG. 71 depicts compound 0191.
FIG. 72 depicts compound 0202.
FIG. 73 depicts compound 0231.
FIG. 74 depicts compound 0232.
FIG. 75 depicts compound 0233.
FIG. 76 depicts compound 0234.
FIG. 77 depicts compound 0235.
FIG. 78 depicts compound 0254.
FIG. 79 depicts compound 0255.
FIG. 80 depicts compound 0259.
FIG. 81 depicts compound 0260.
FIG. 82 depicts compound 0261.
FIG. 83 depicts compound 0263.
FIG. 84 depicts compound 0264.
FIG. 85 depicts compound 0265.
FIG. 86 depicts compound 0266.
FIG. 87 depicts compound 0267.
FIG. 88 depicts compound 0268.
FIG. 89 depicts compound 0269.
FIG. 90 depicts compound 0270.
FIG. 91 depicts compound 0271.
FIG. 92 depicts compound 0272.
FIG. 93 depicts compound 0273.
FIG. 94 depicts compound 0280.

Figure 95:
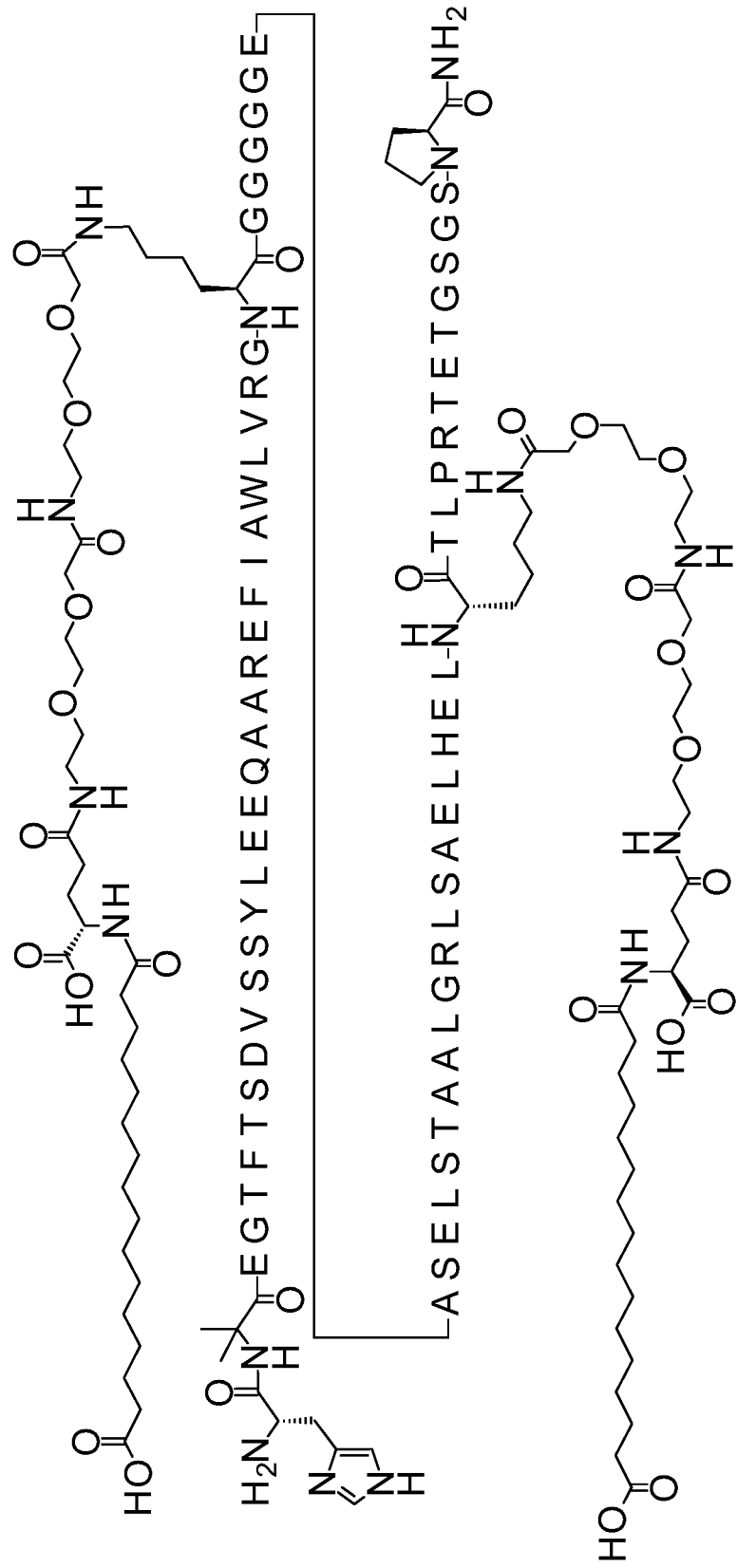
Figure 96:
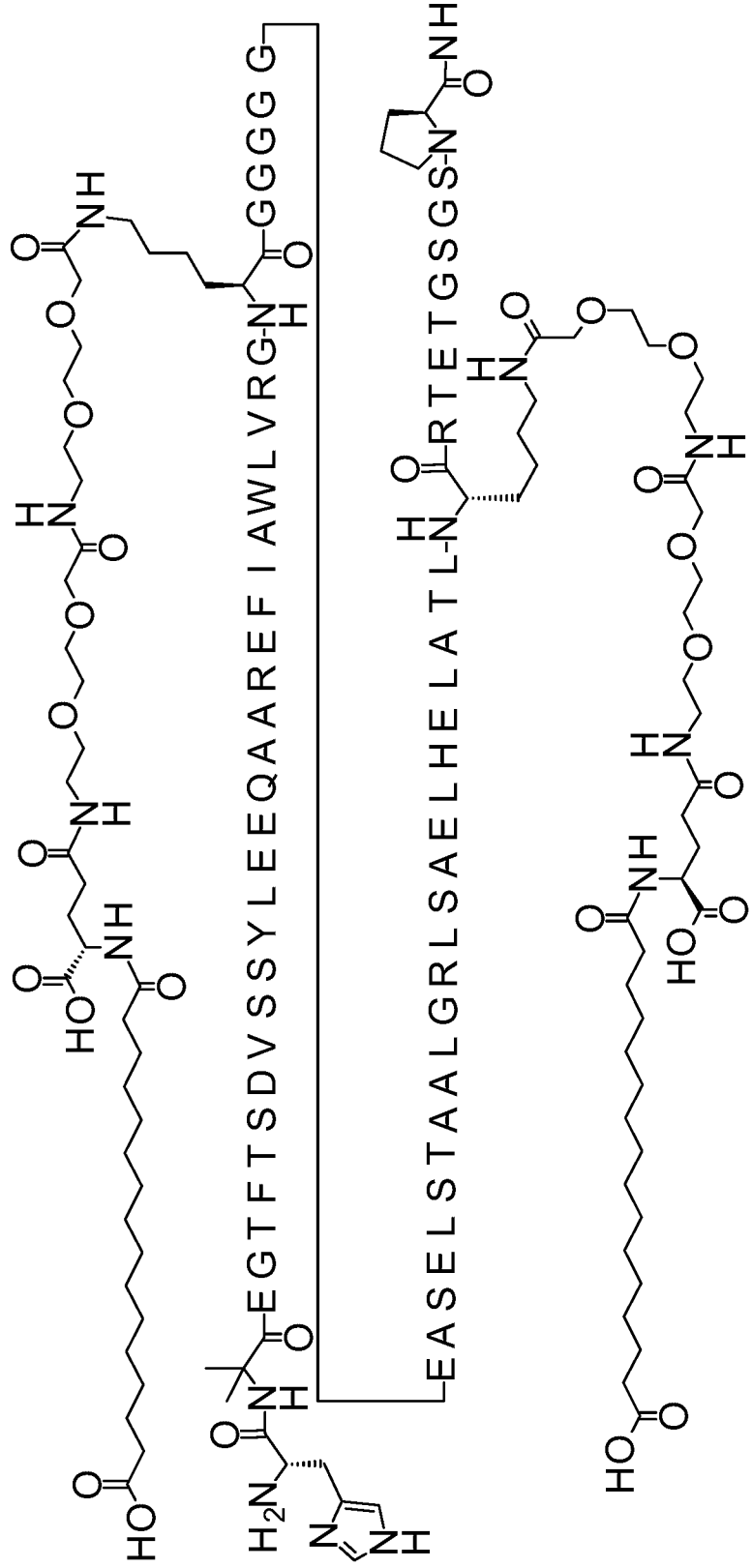
Figure 97:
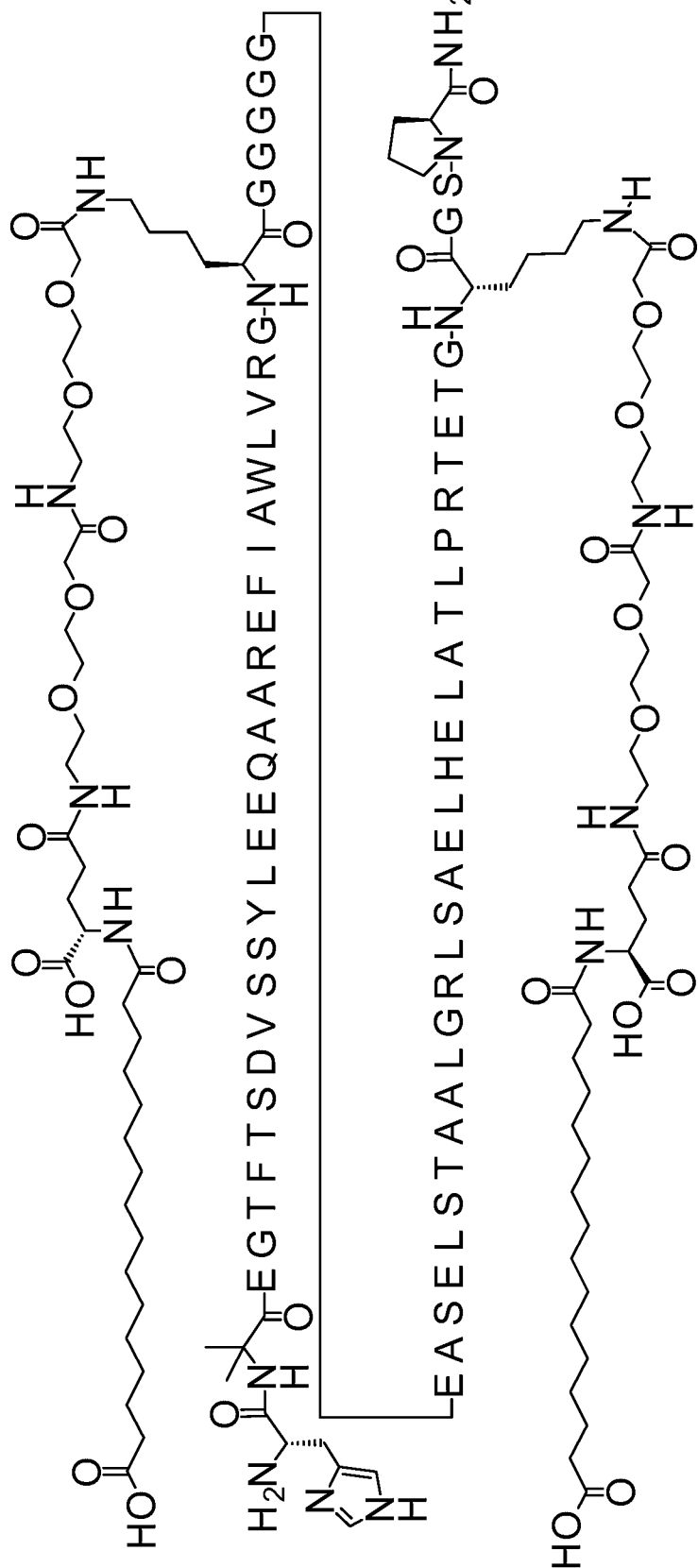
Figure 99:
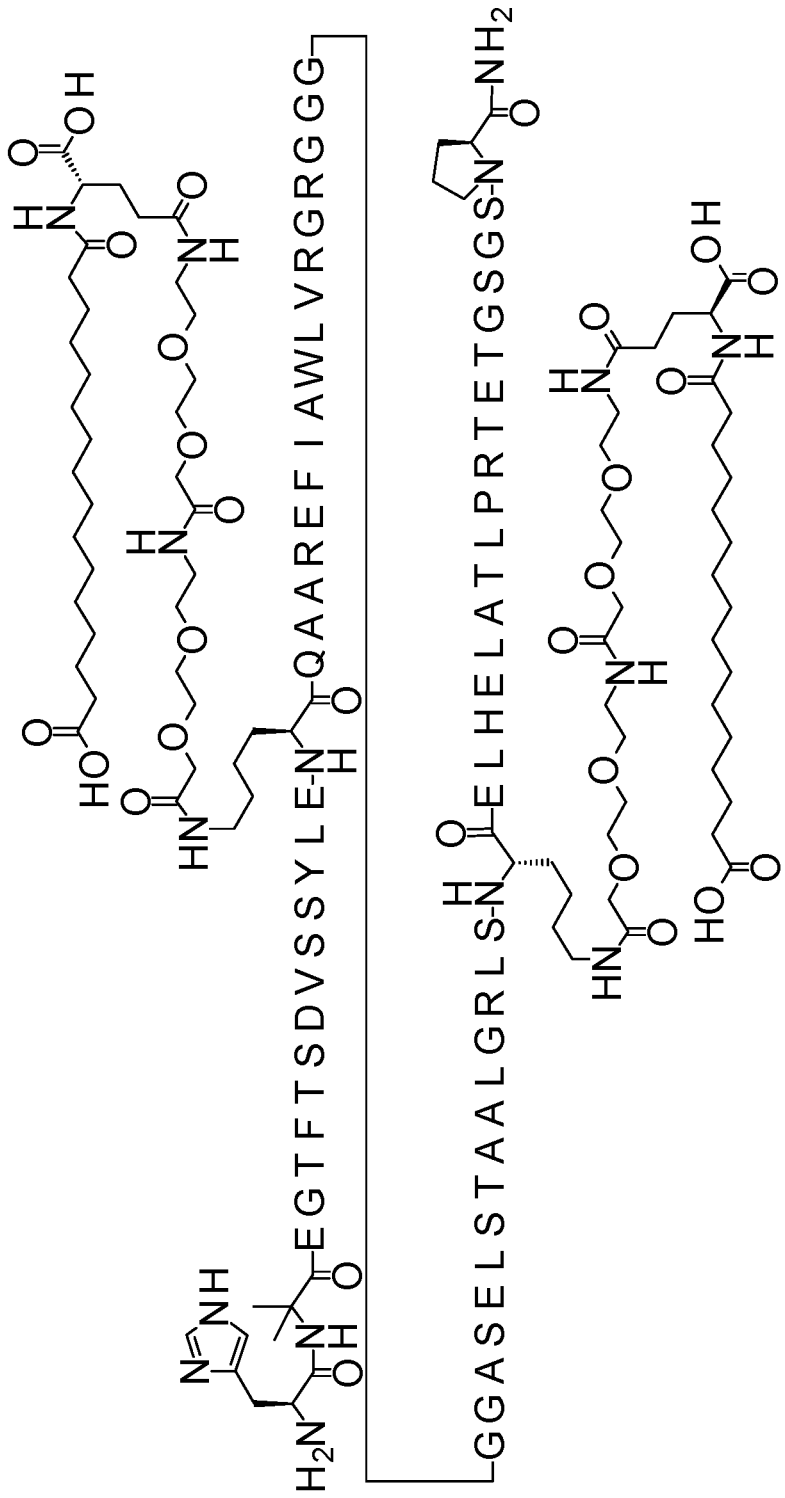
Figure 100:
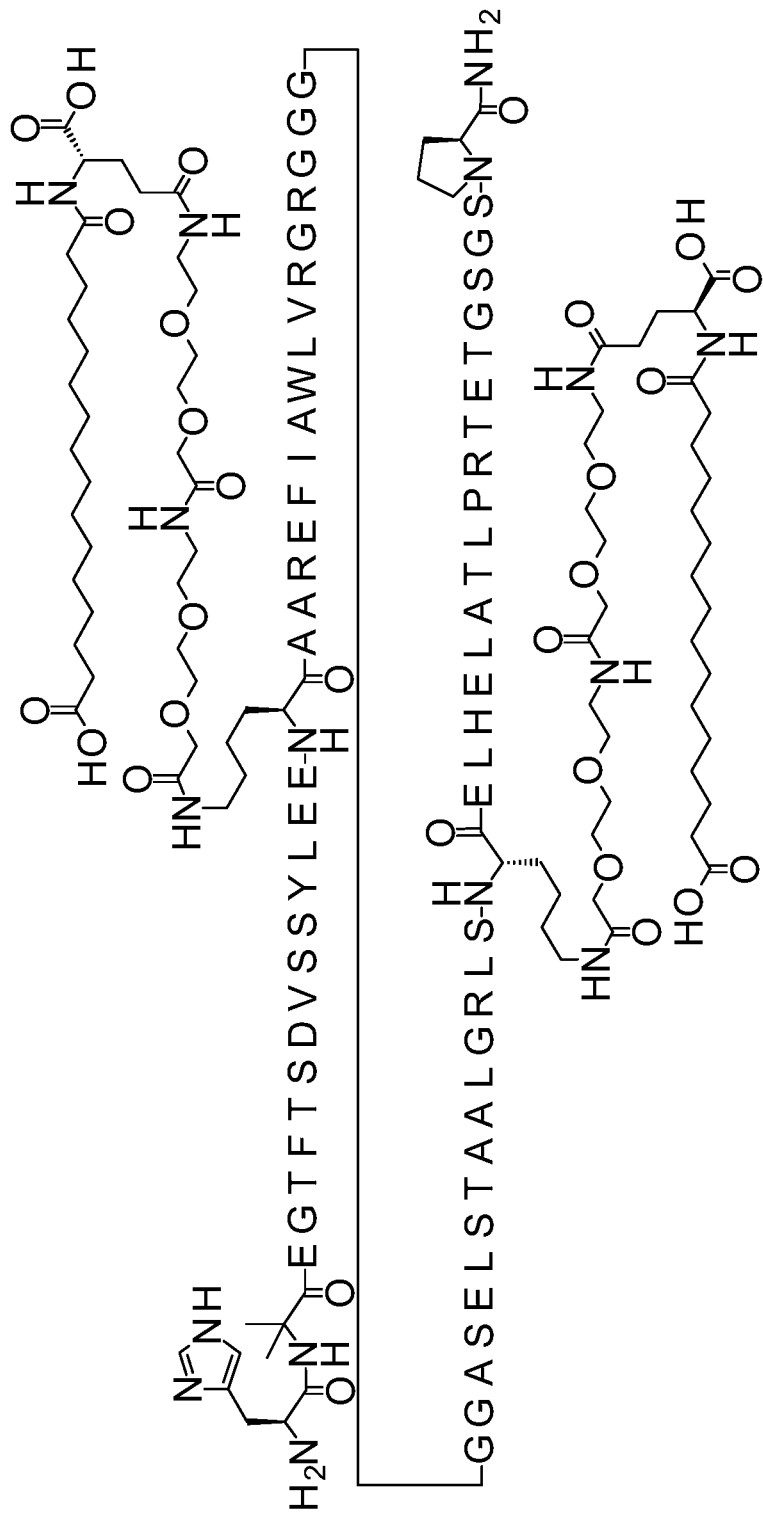
Figure 102:
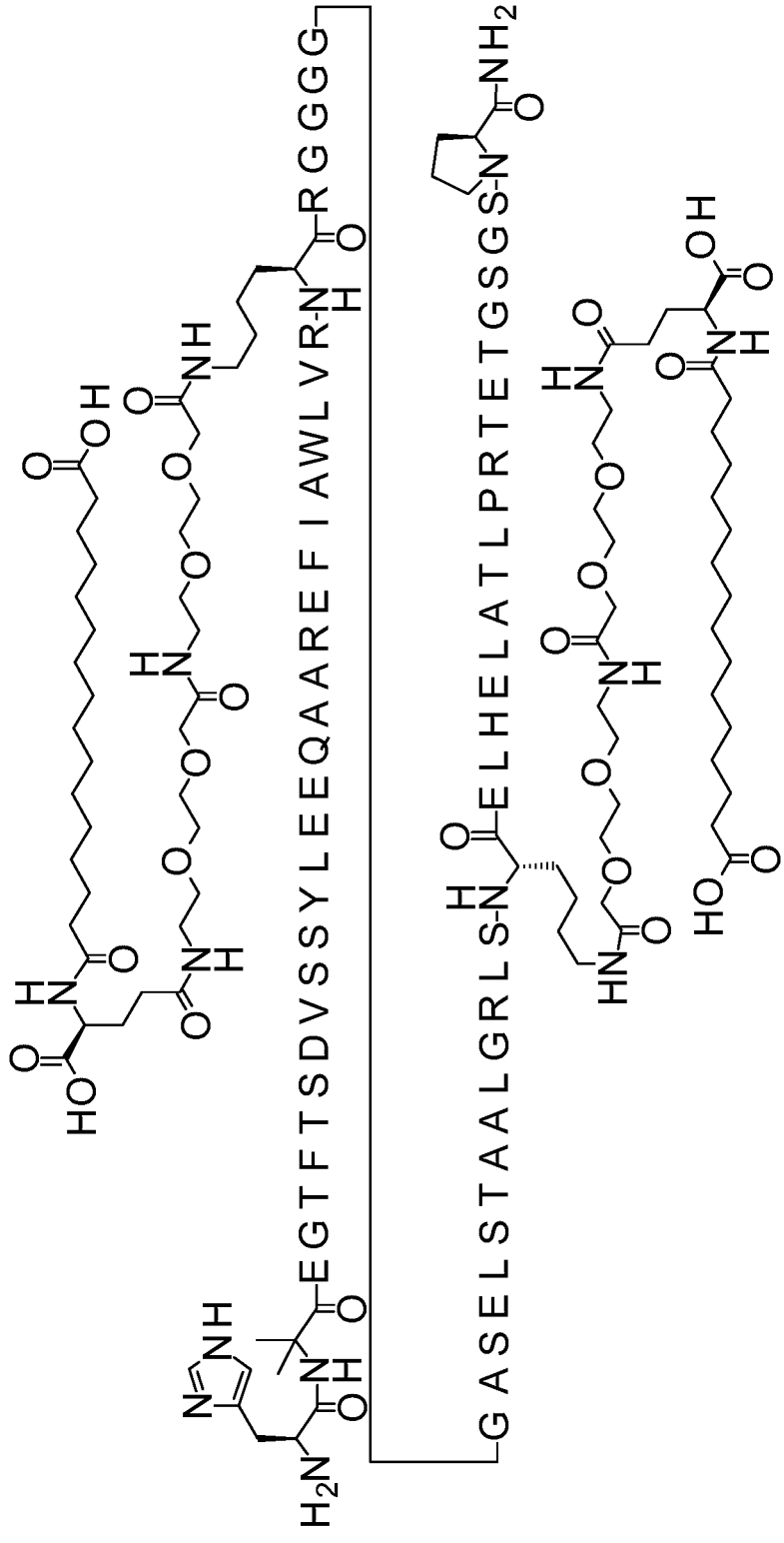
Figure 105:
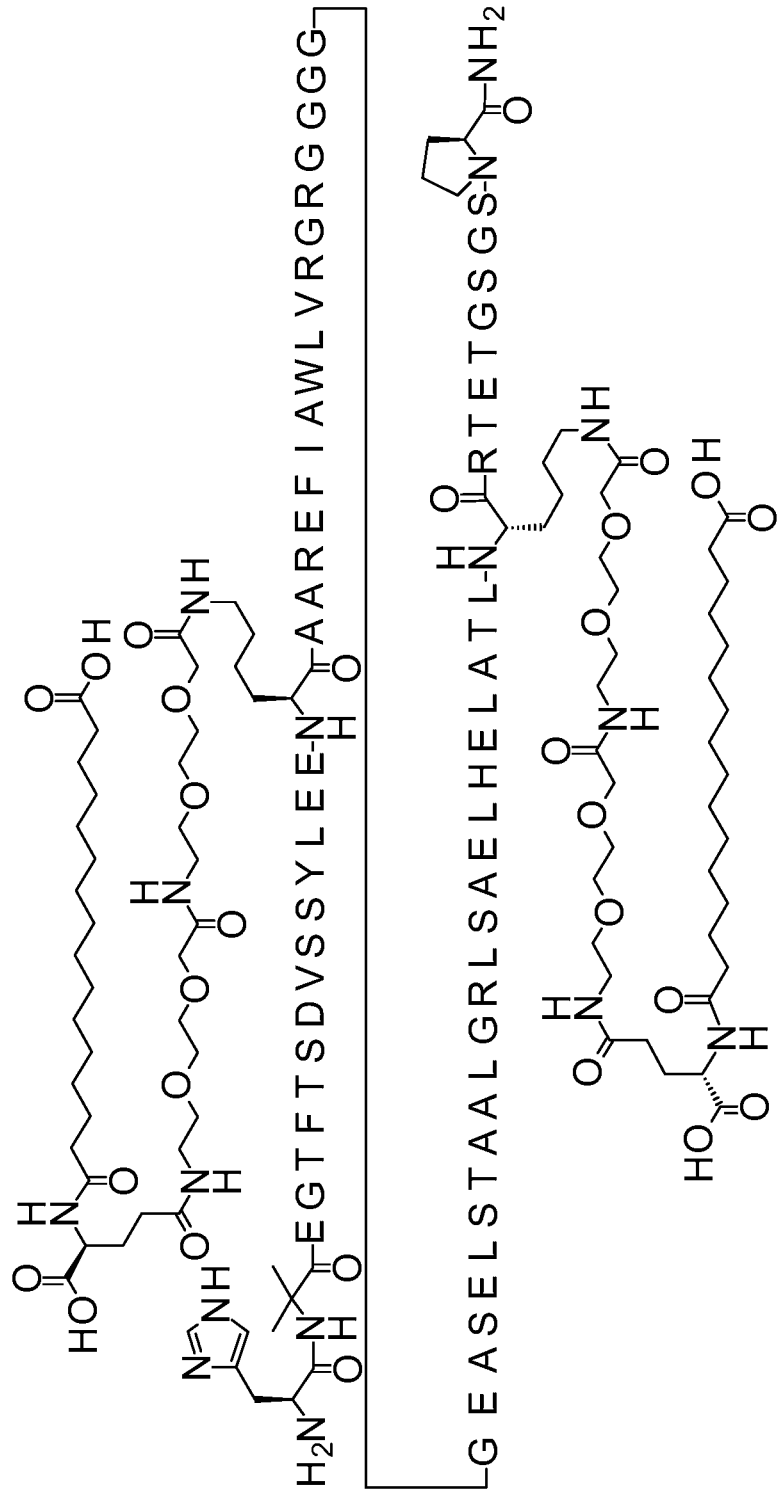
Figure 106:
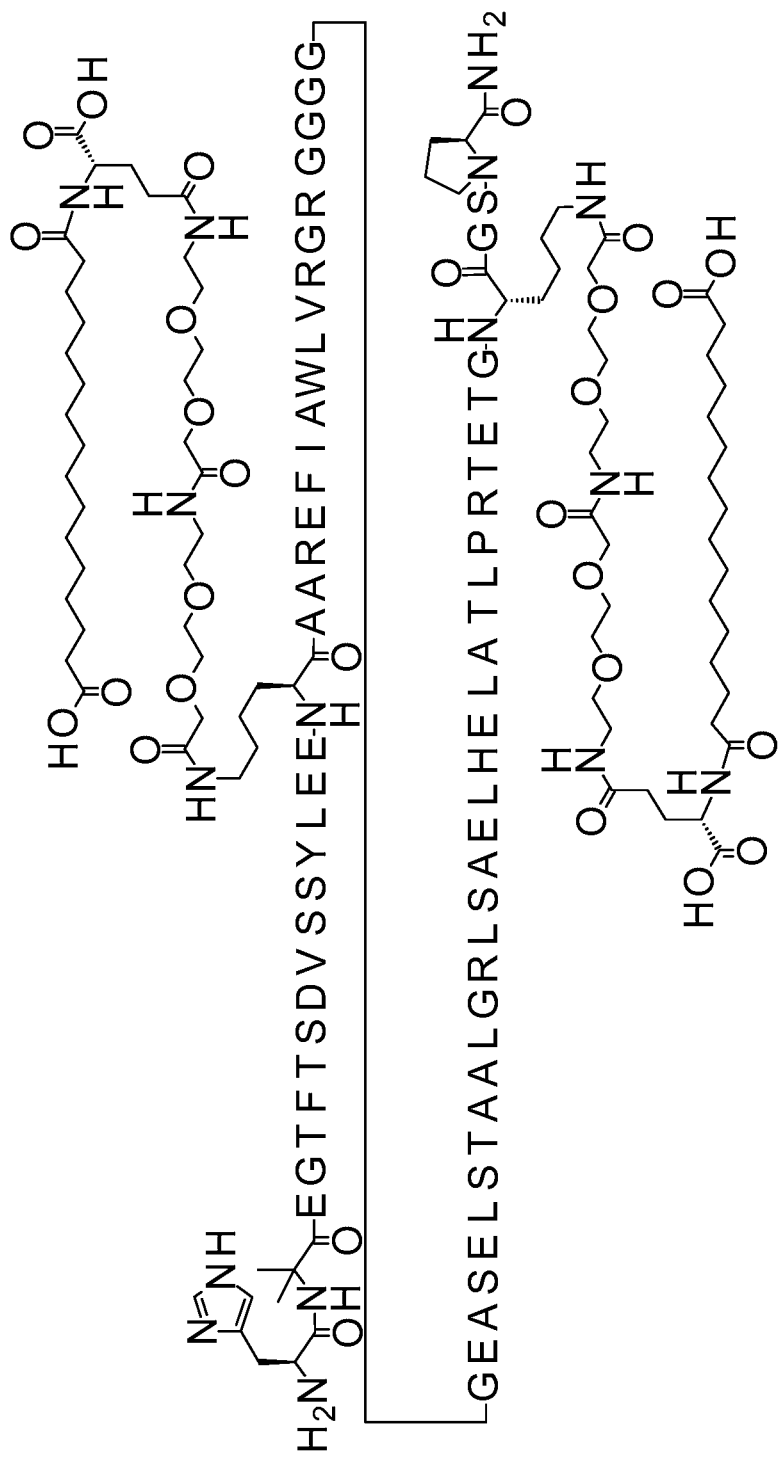
Figure 107:
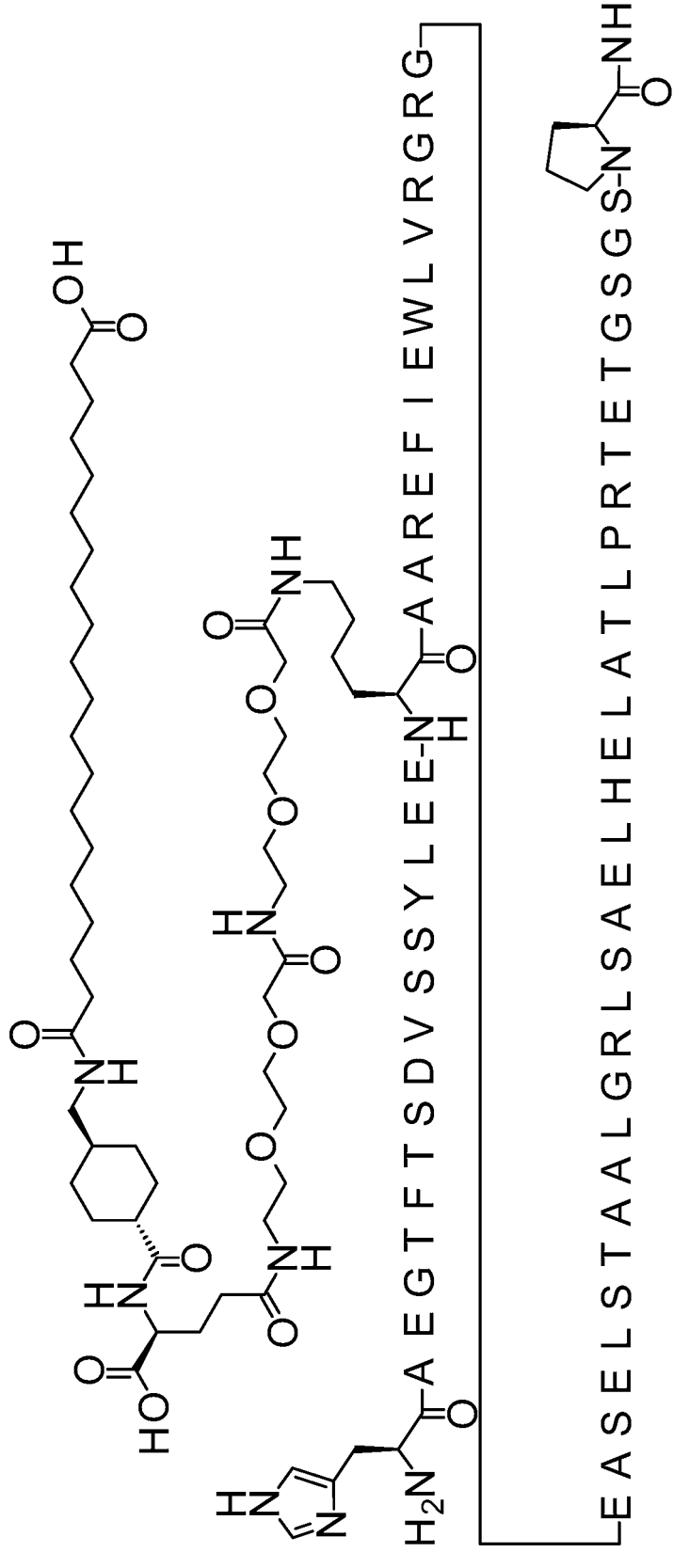
Figure 108:
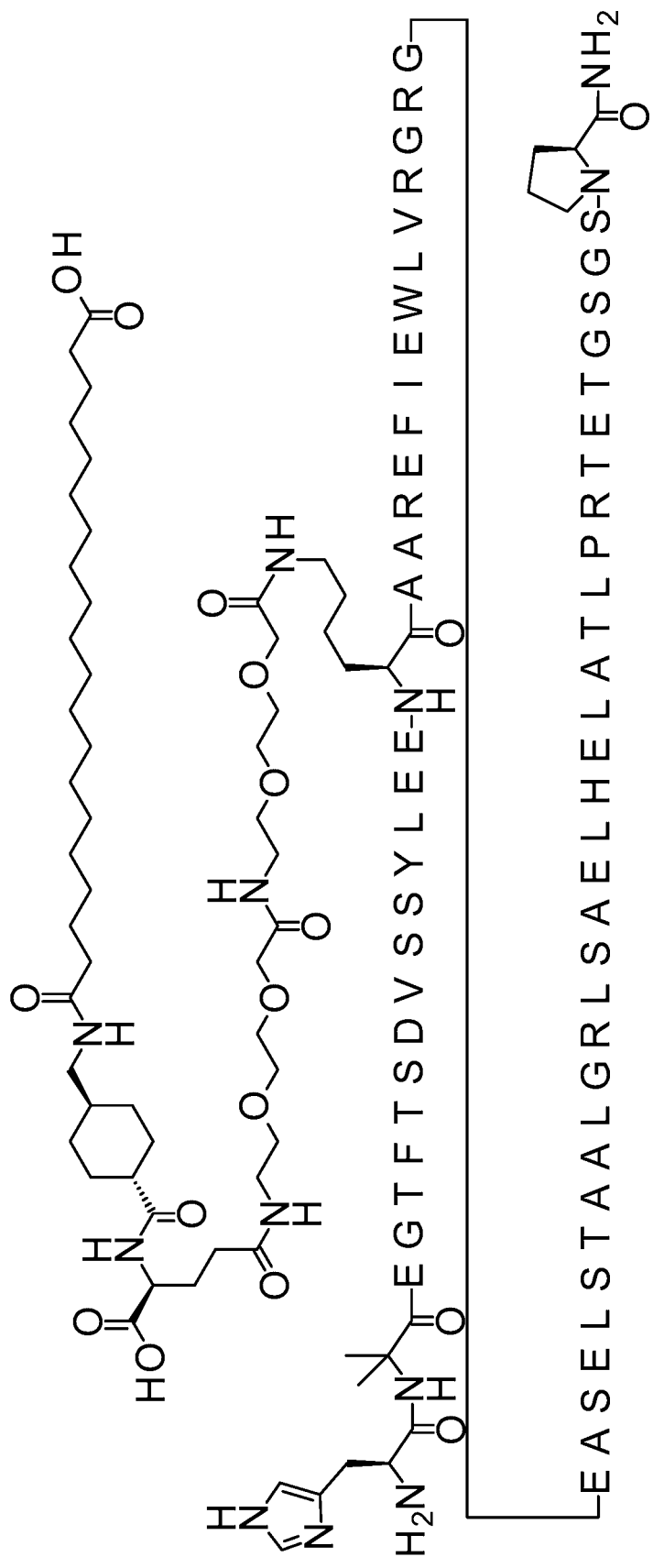
Figure 109:
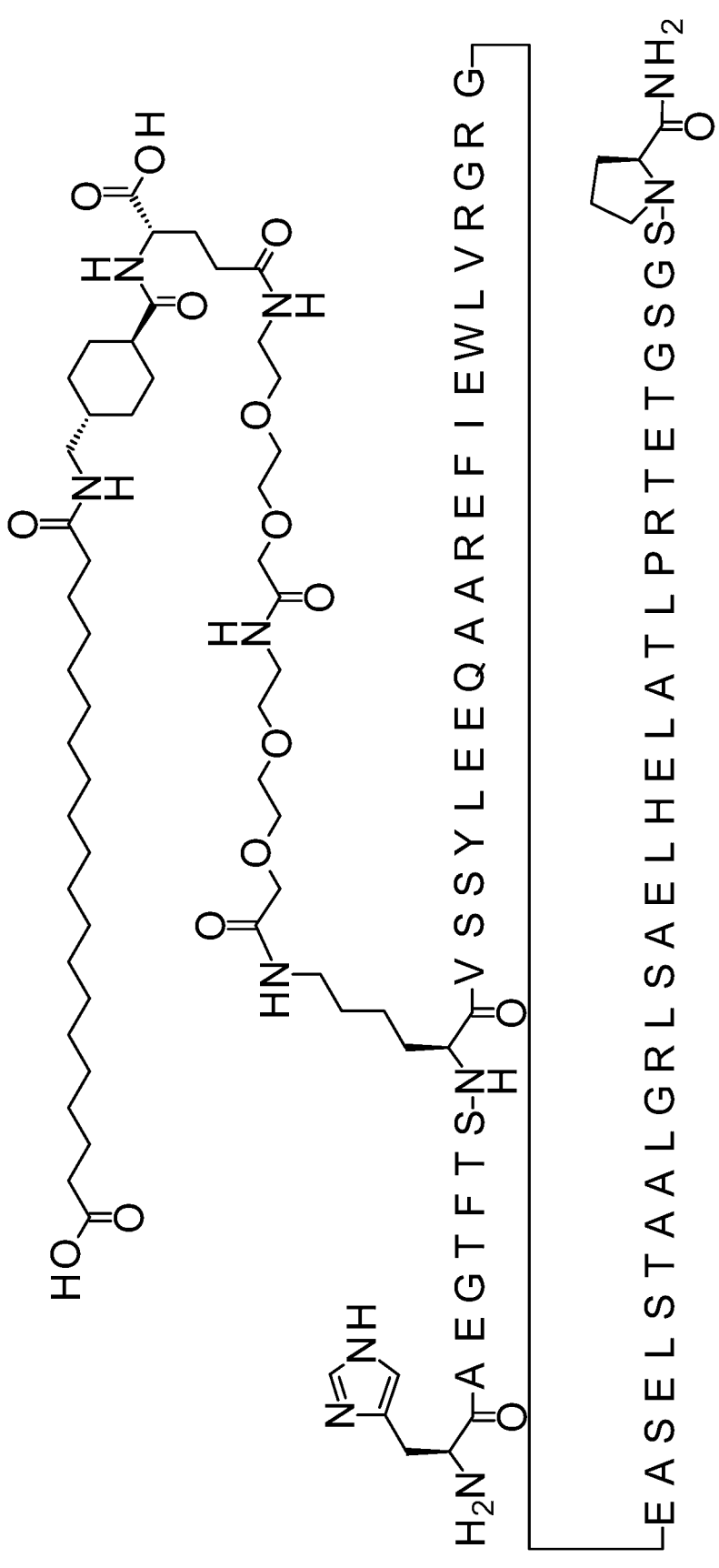
Figure 110:
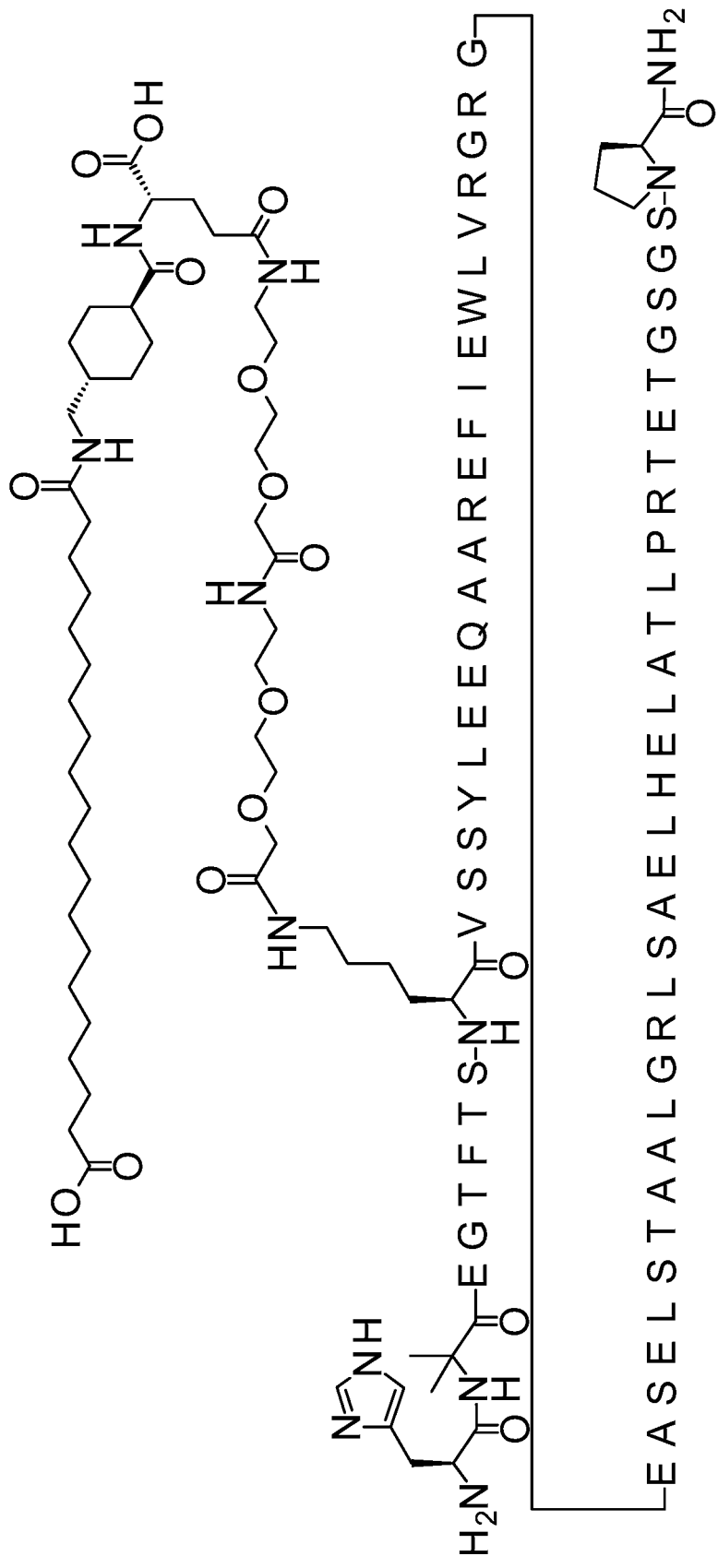
Figure 111:
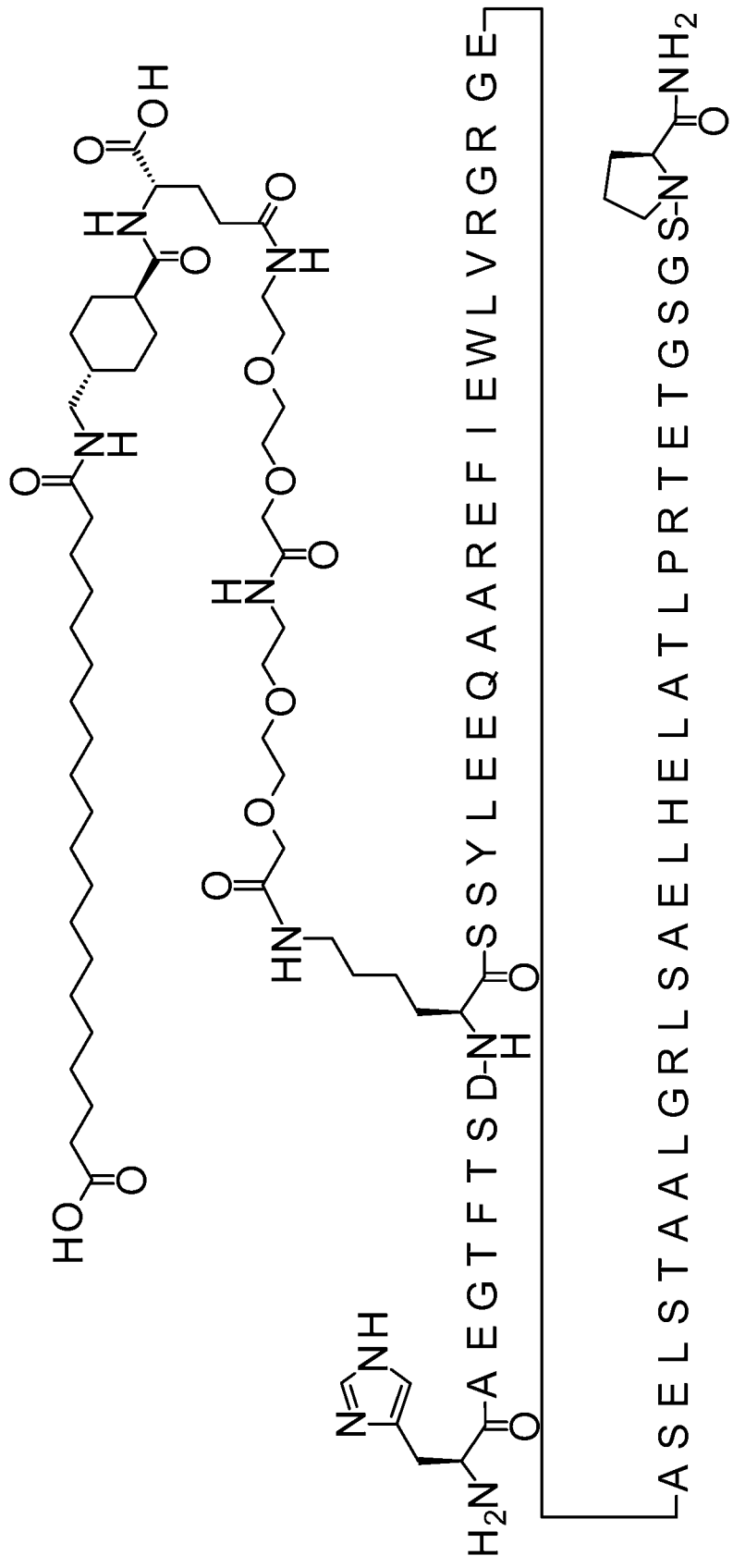
Figure 112:
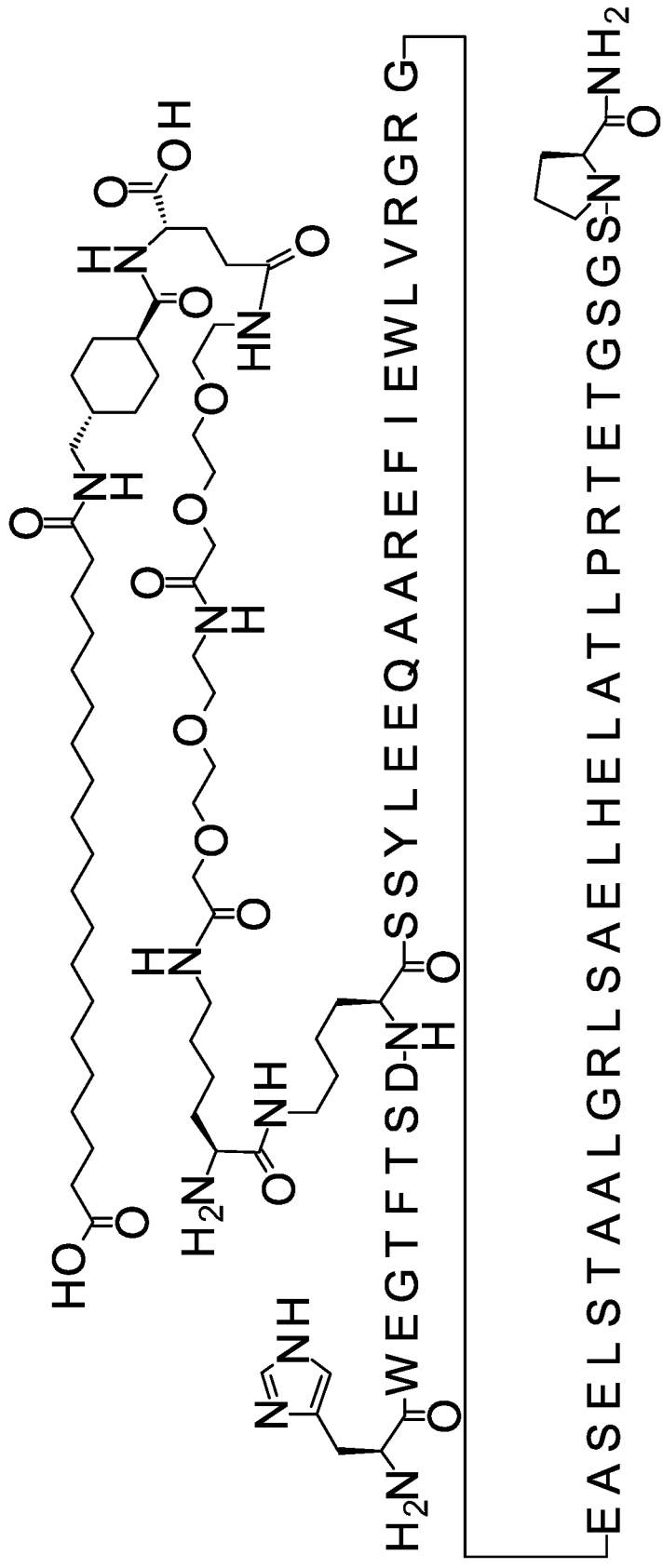
Figure 113:
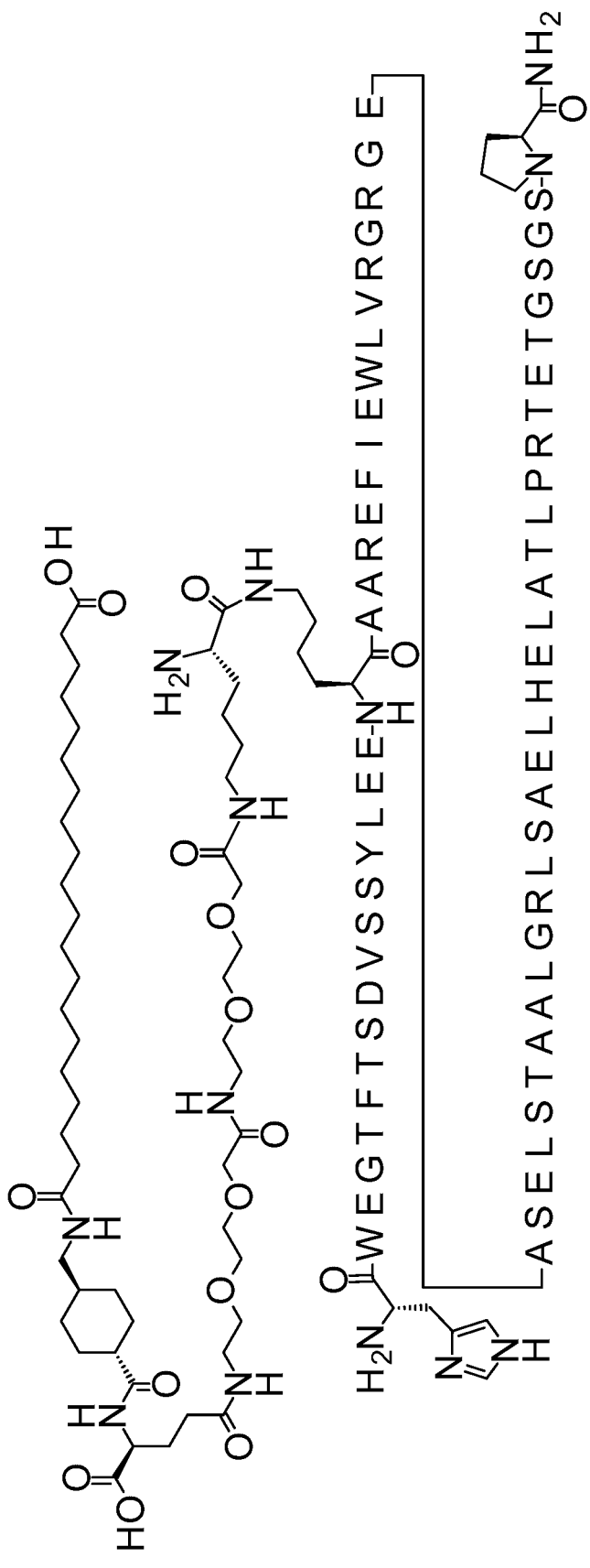
Figure 114:
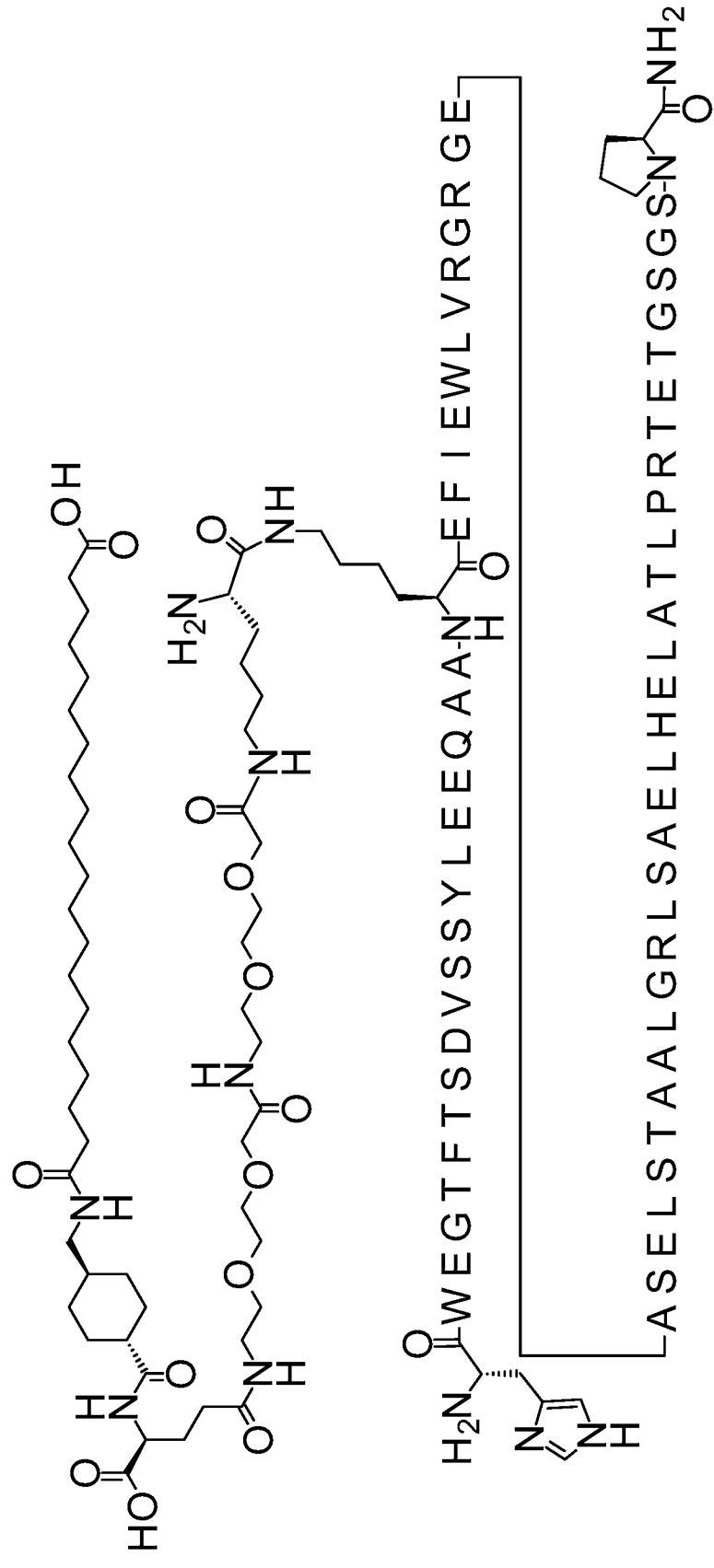
Figure 115:
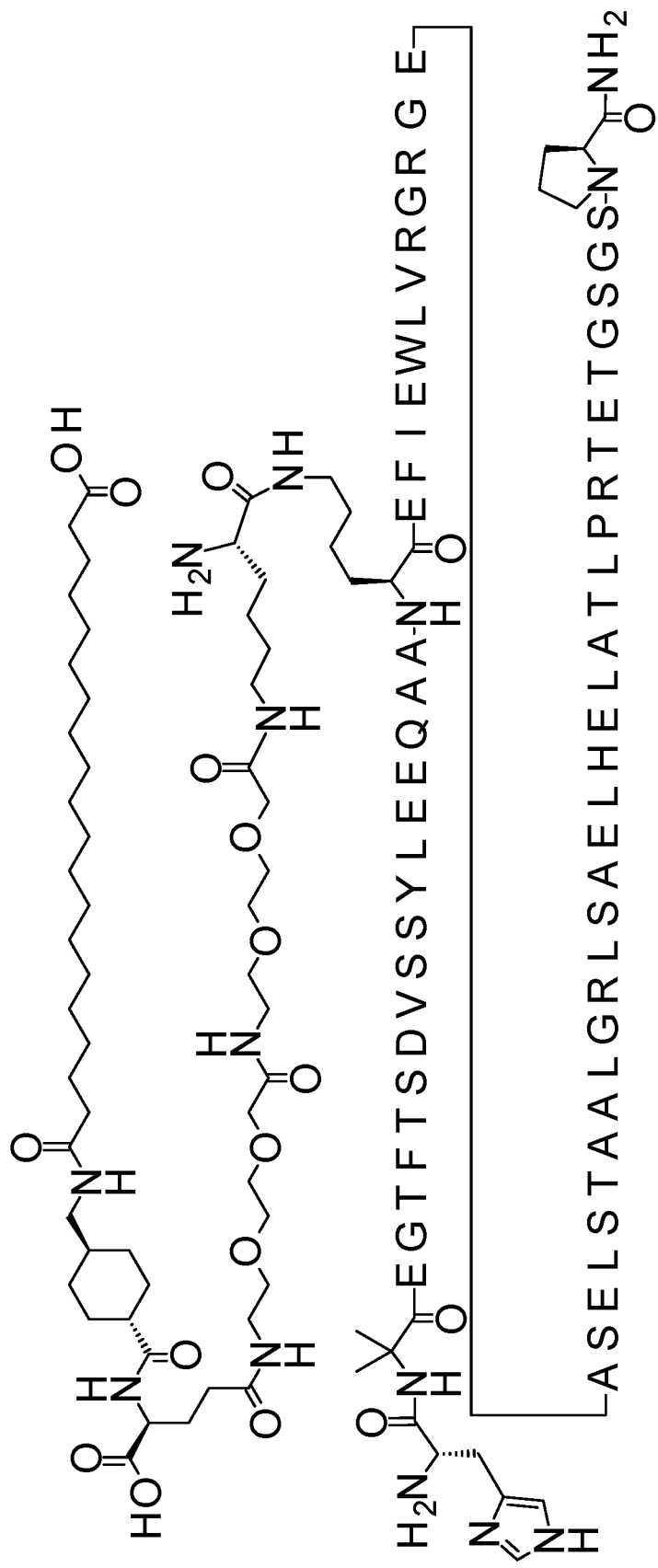
Figure 116:
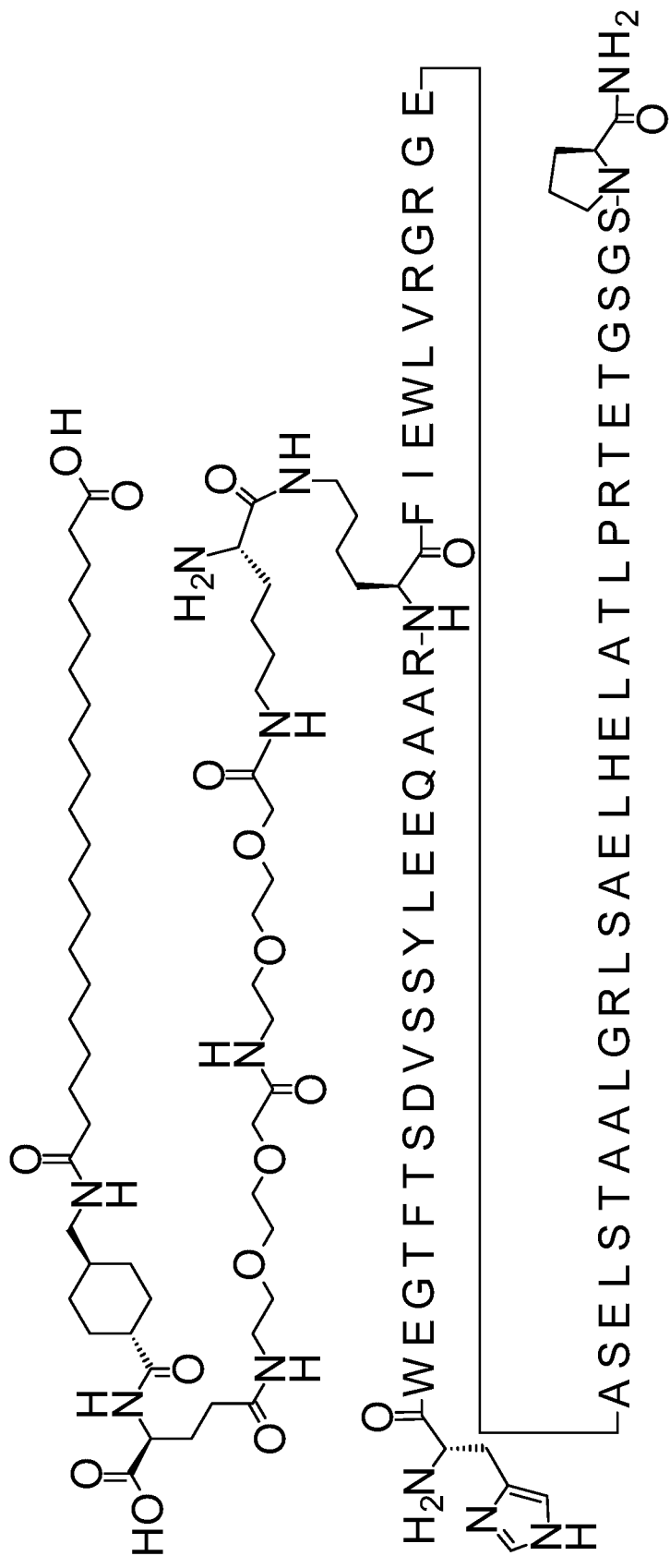
Figure 117:
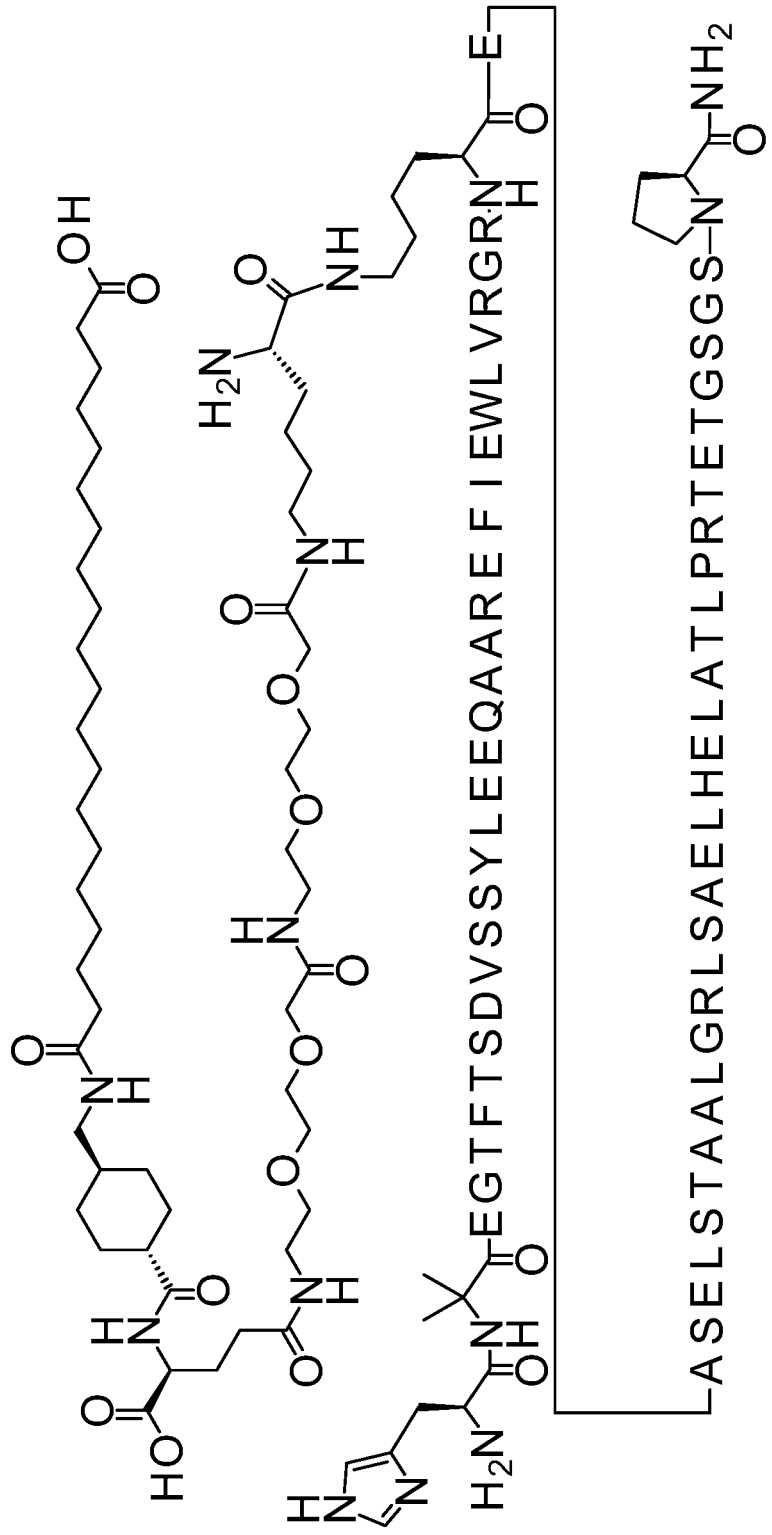
Figure 118:
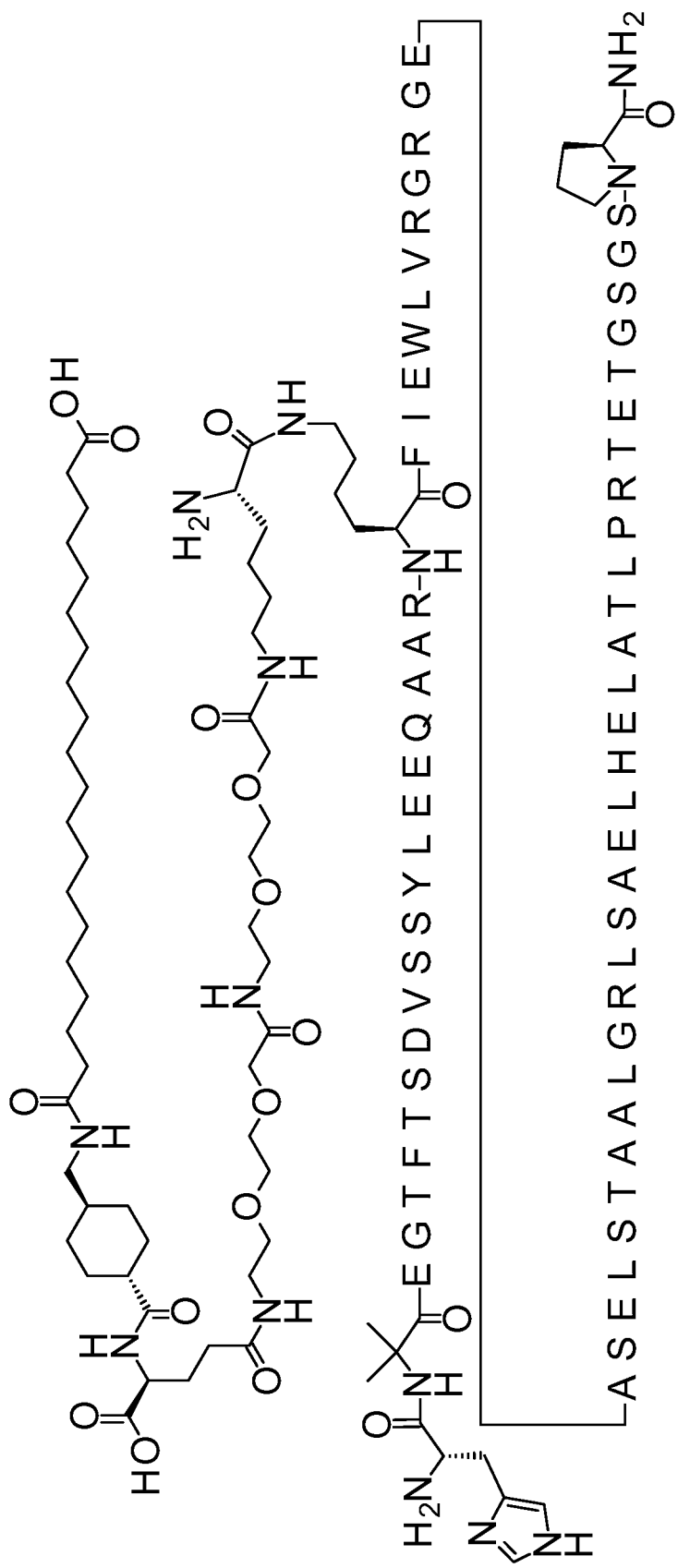
Figure 119:
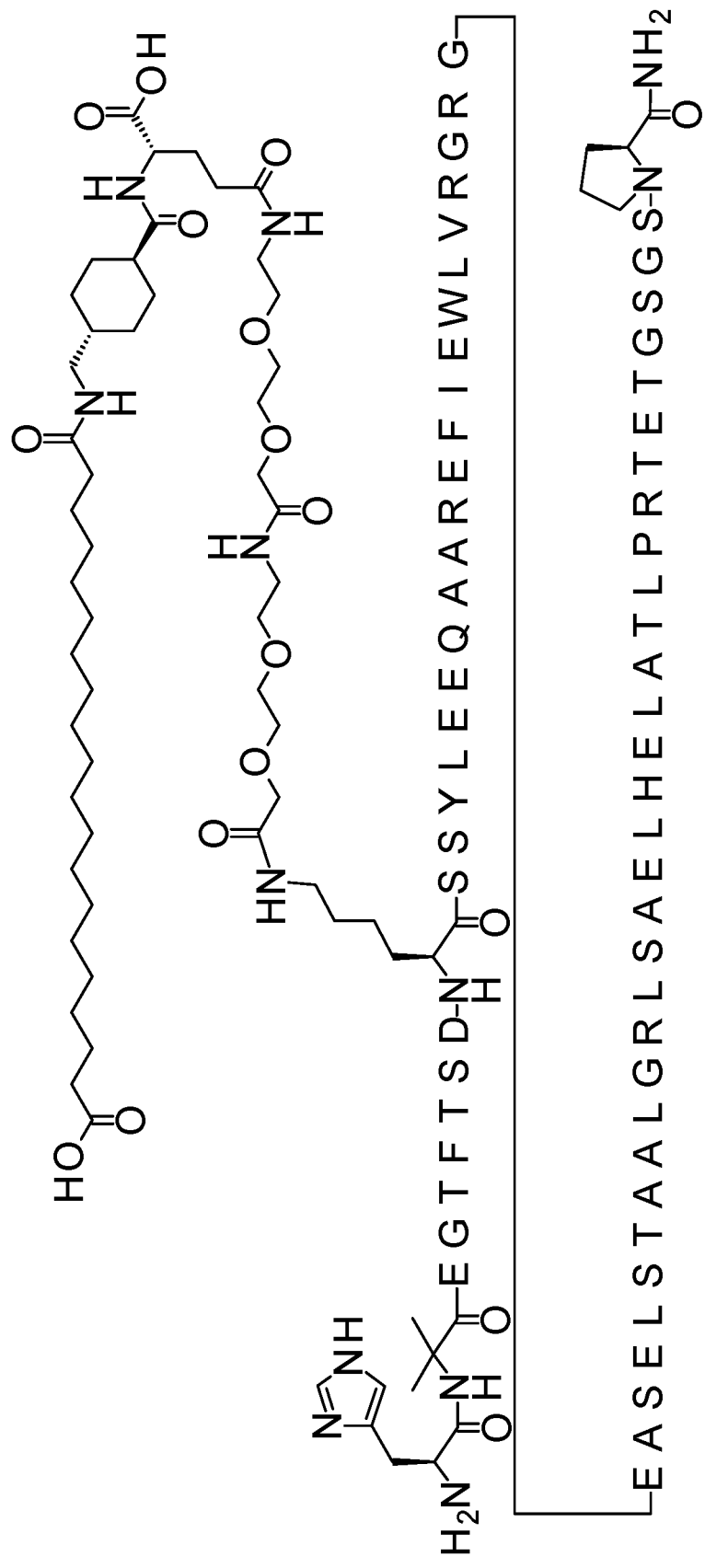
Figure 120:
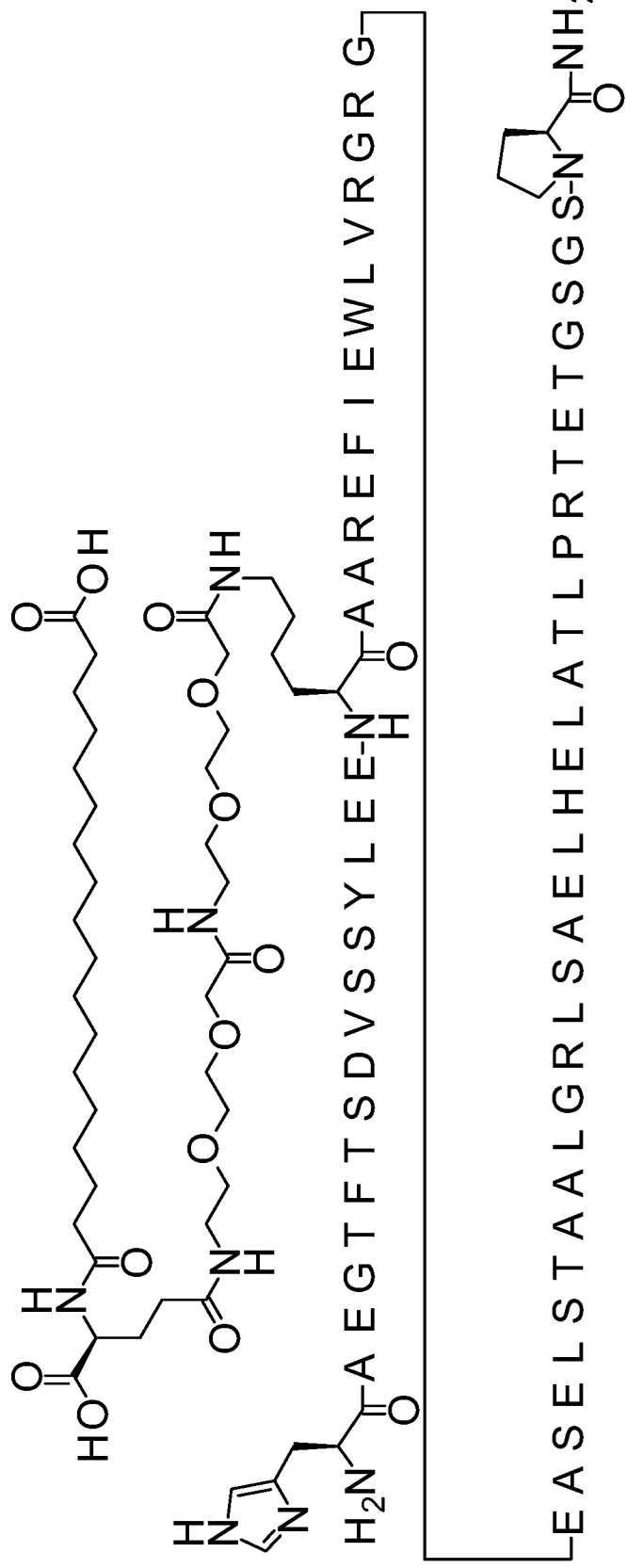
Figure 121:
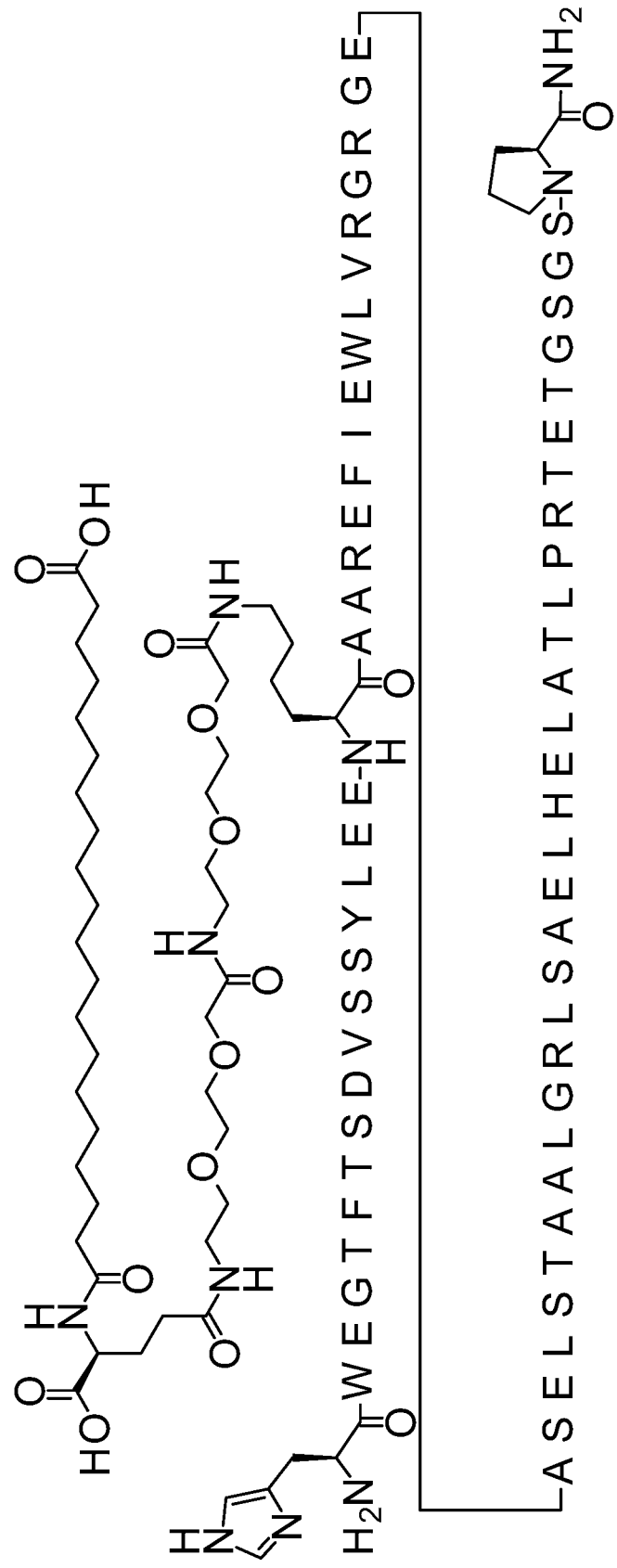
Figure 122:
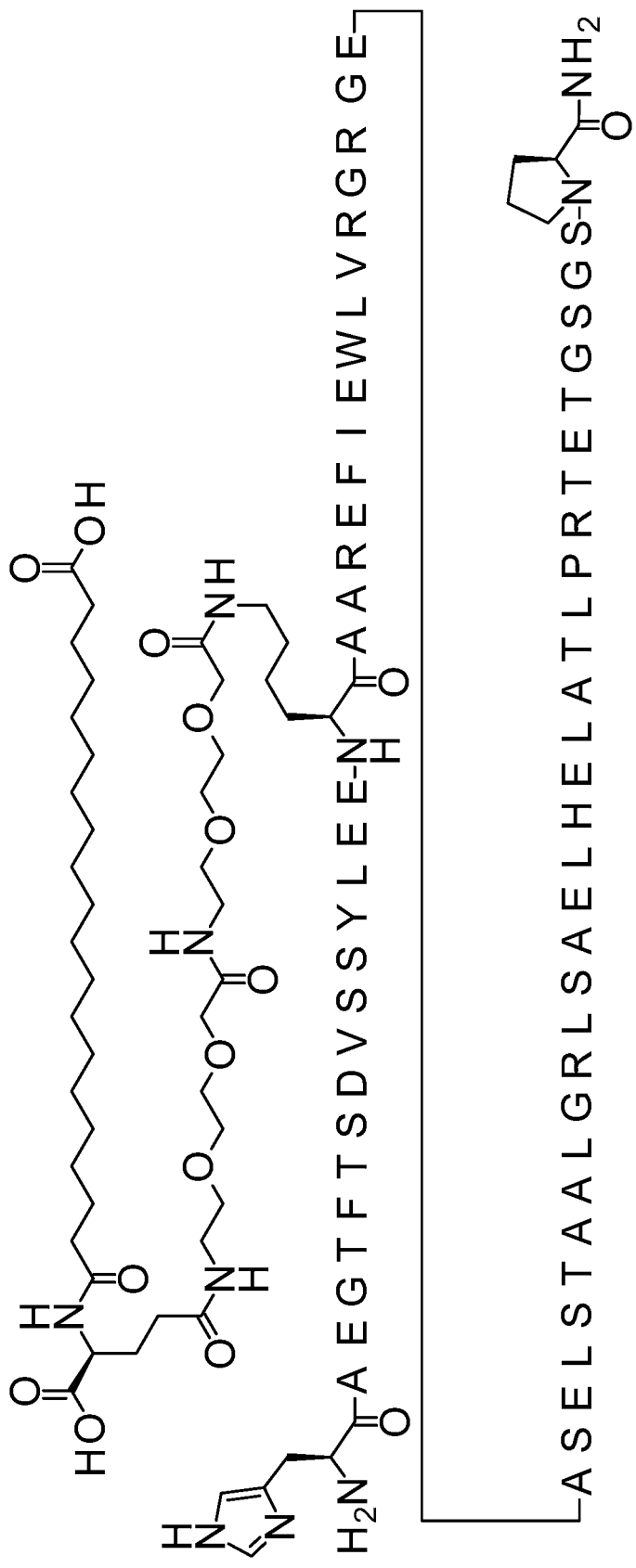
Figure 123:
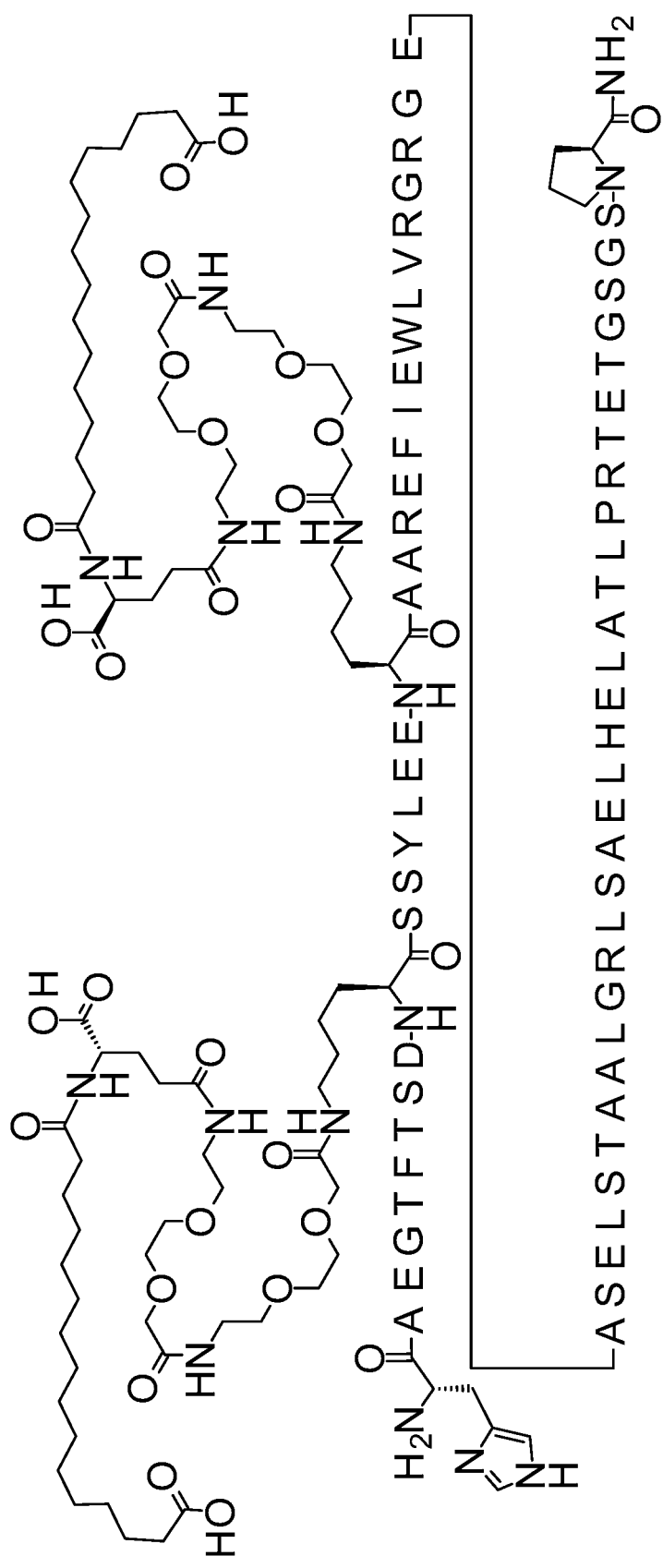
Figure 124:
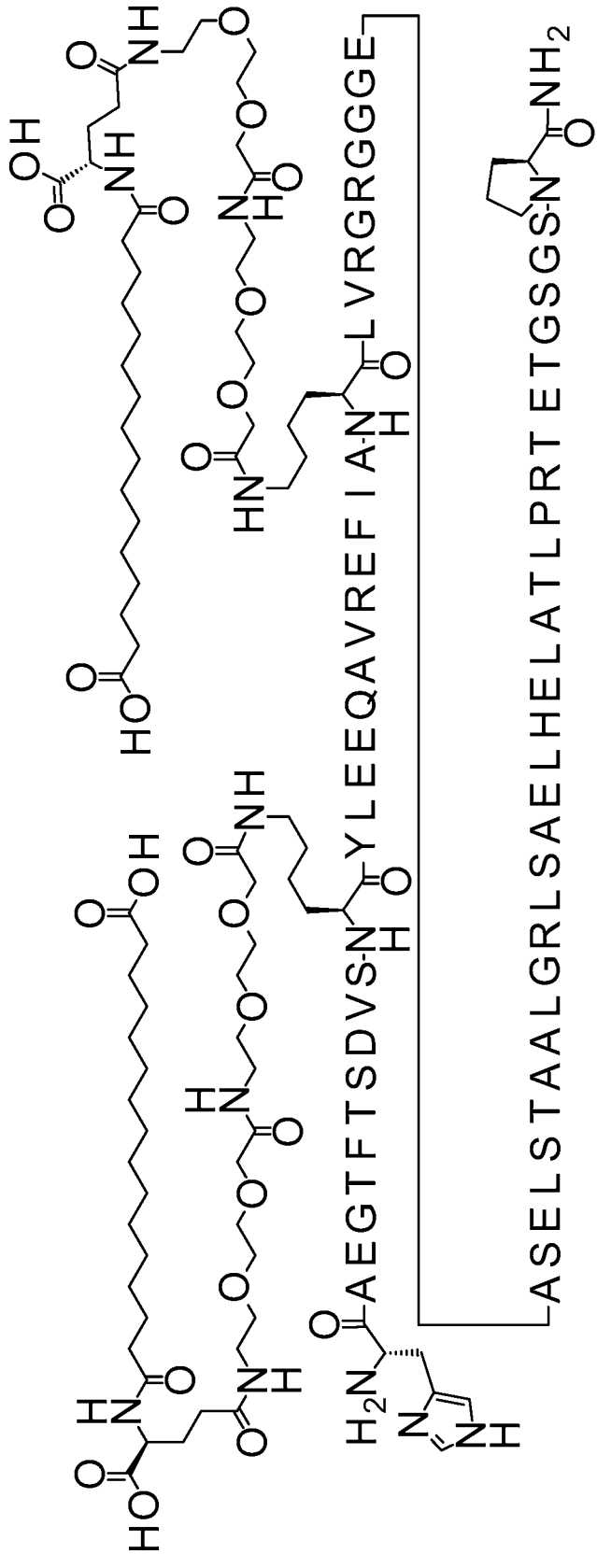
Figure 125:
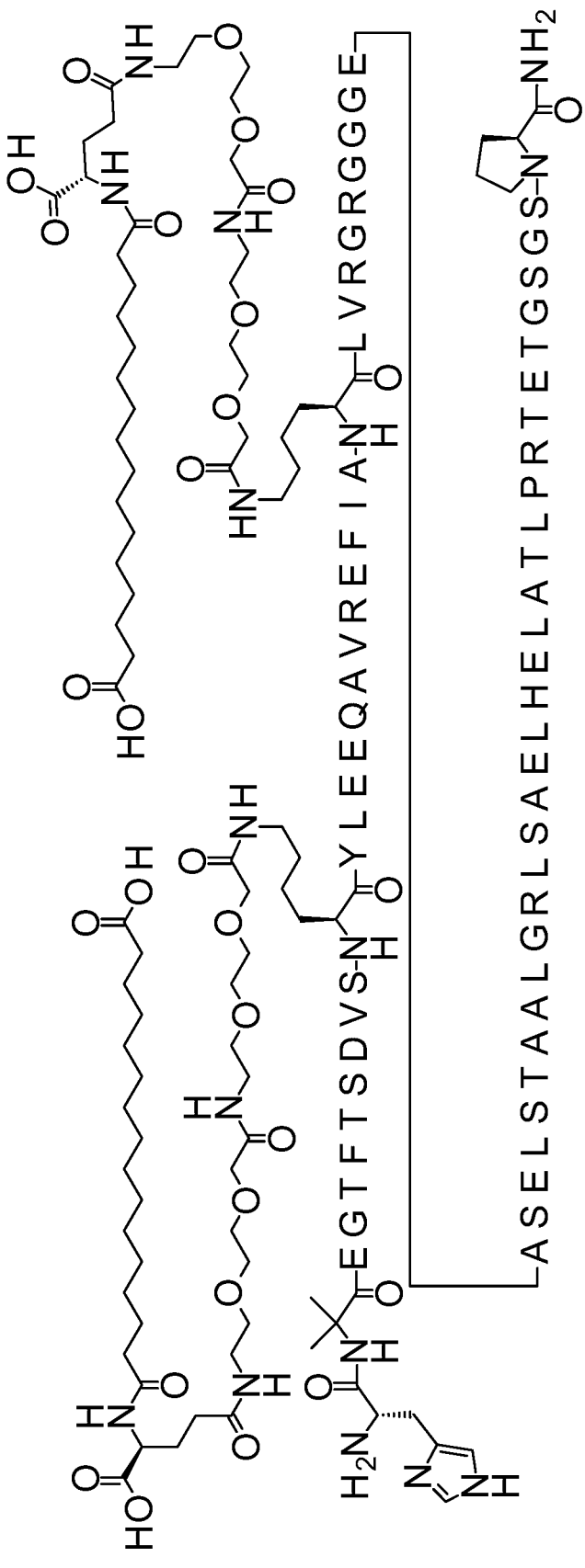
Figure 126:
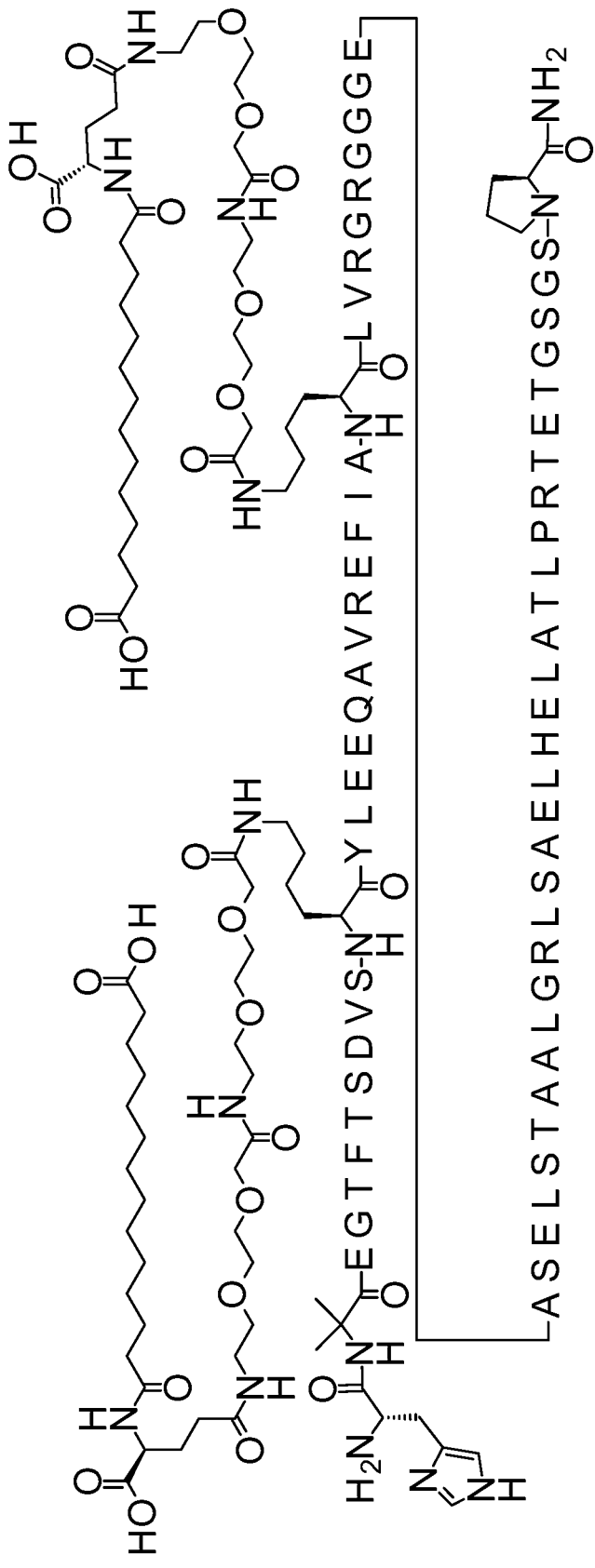
Figure 127:
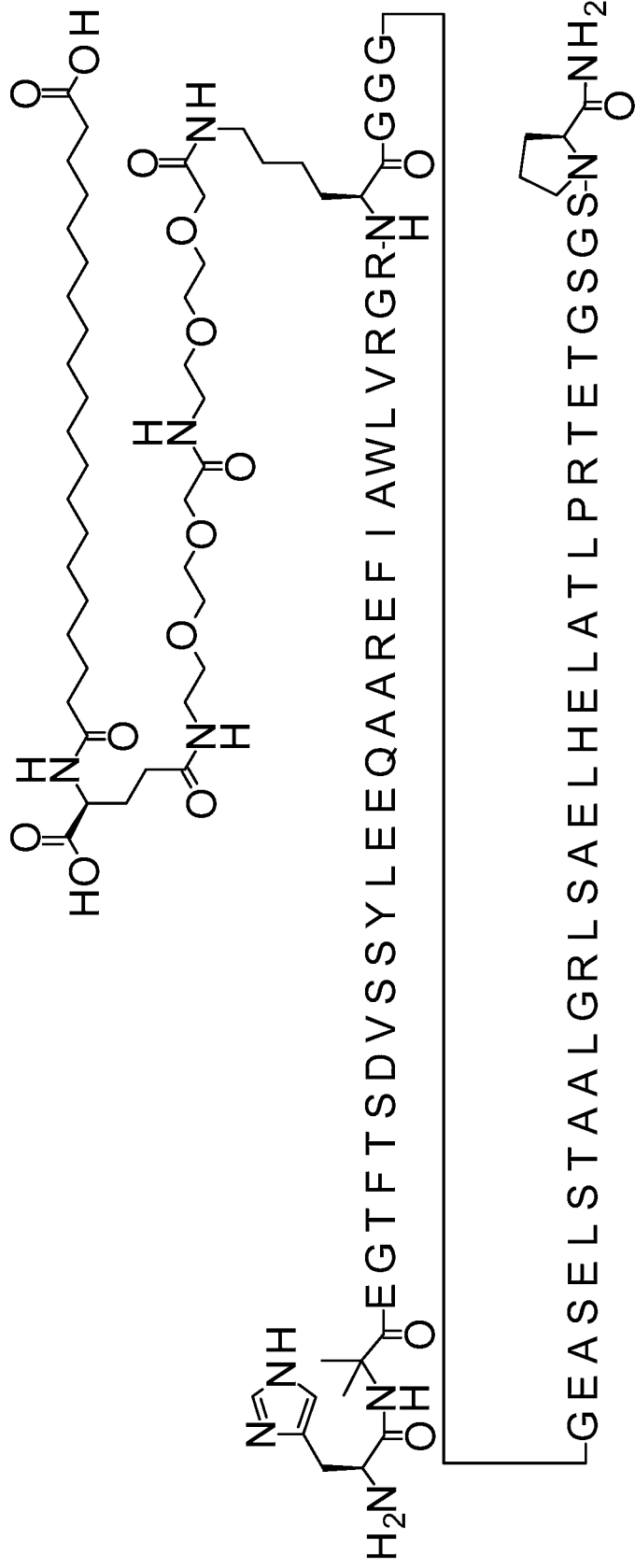
Figure 128:
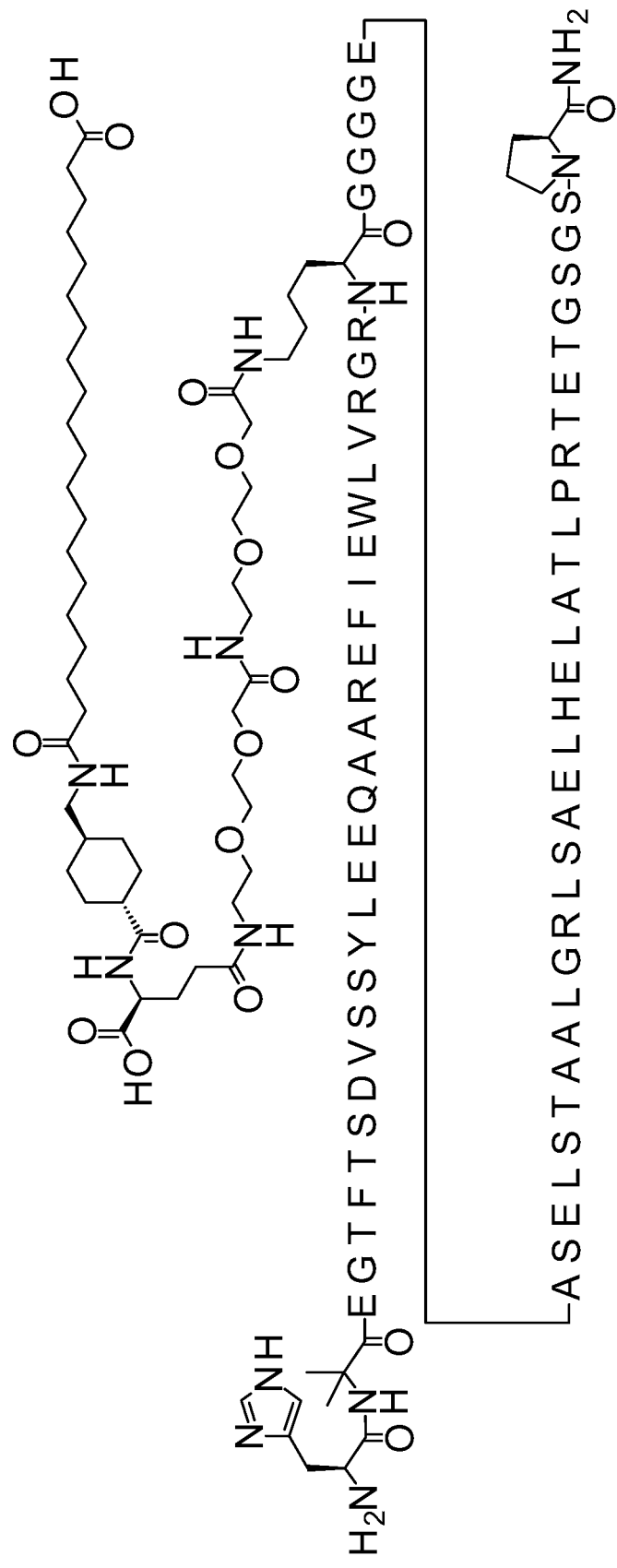
Figure 129:
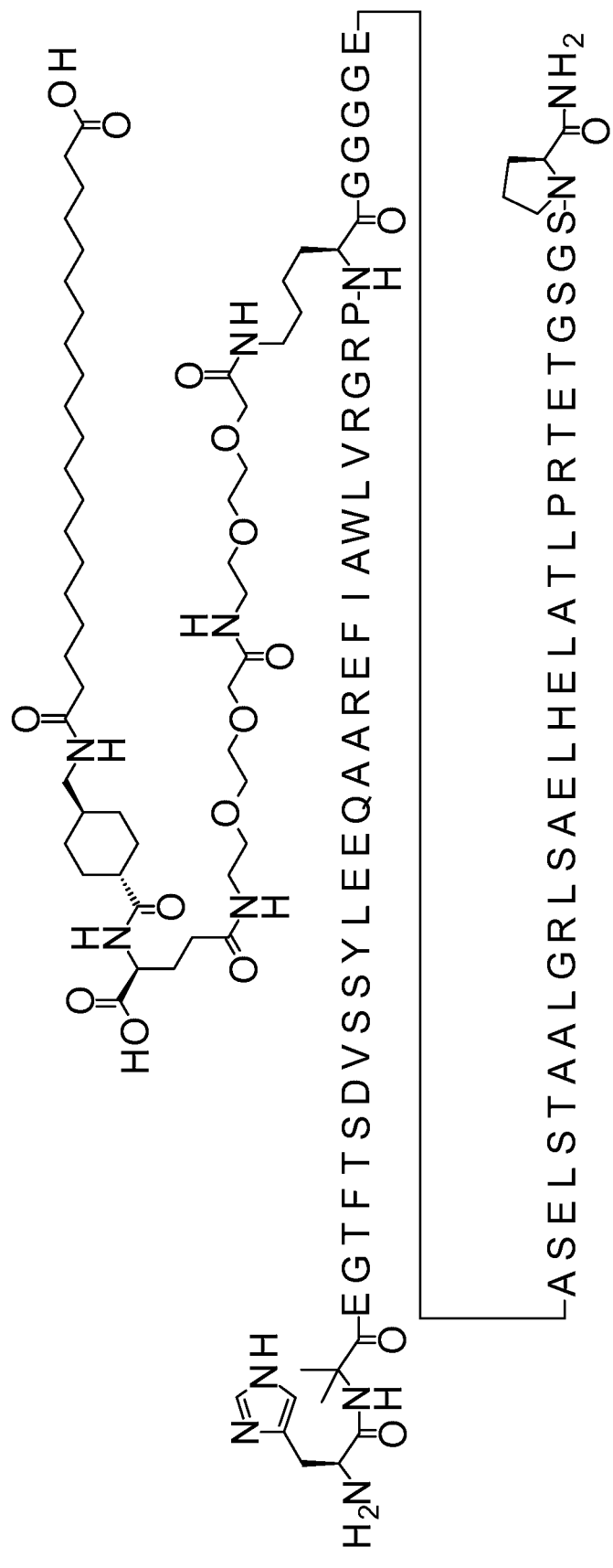
Figure 130:
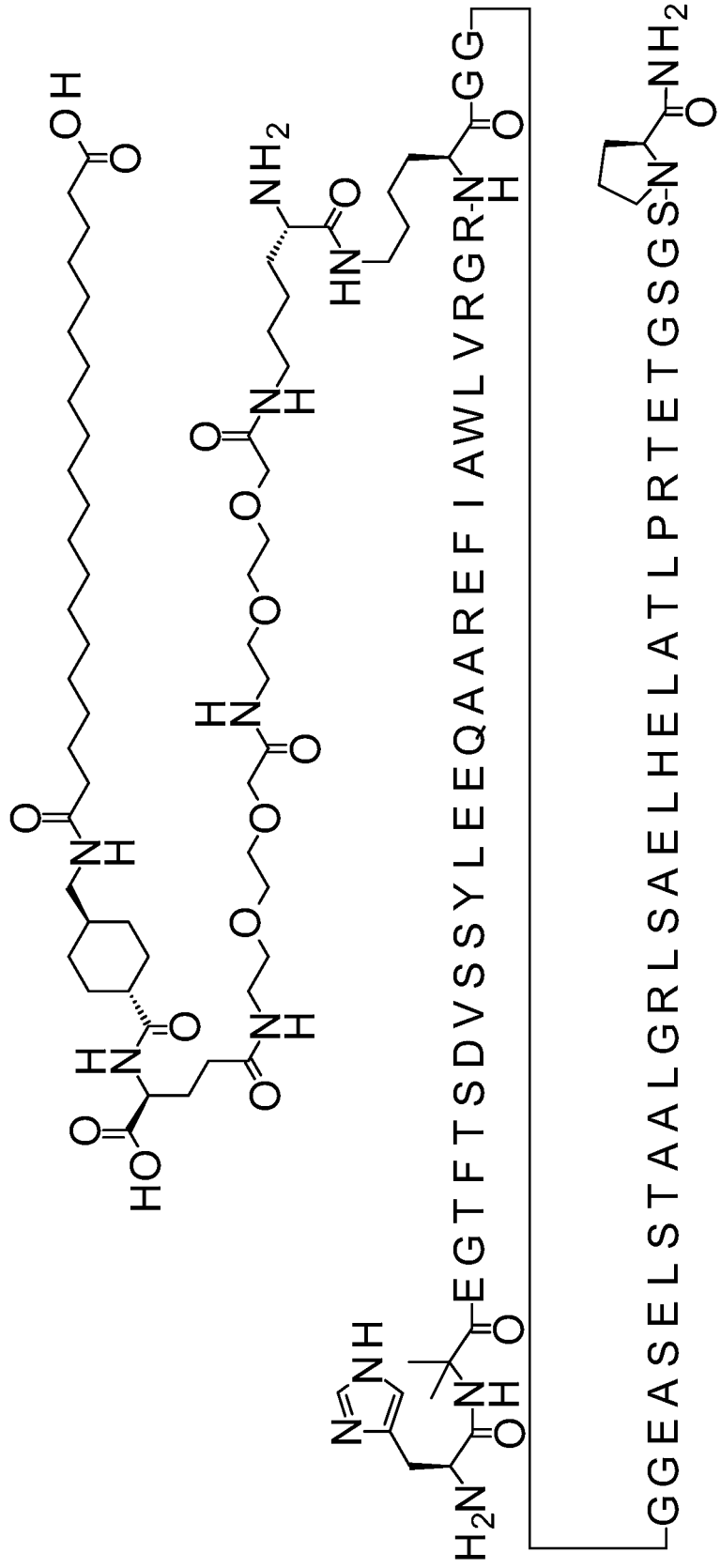
Figure 131:
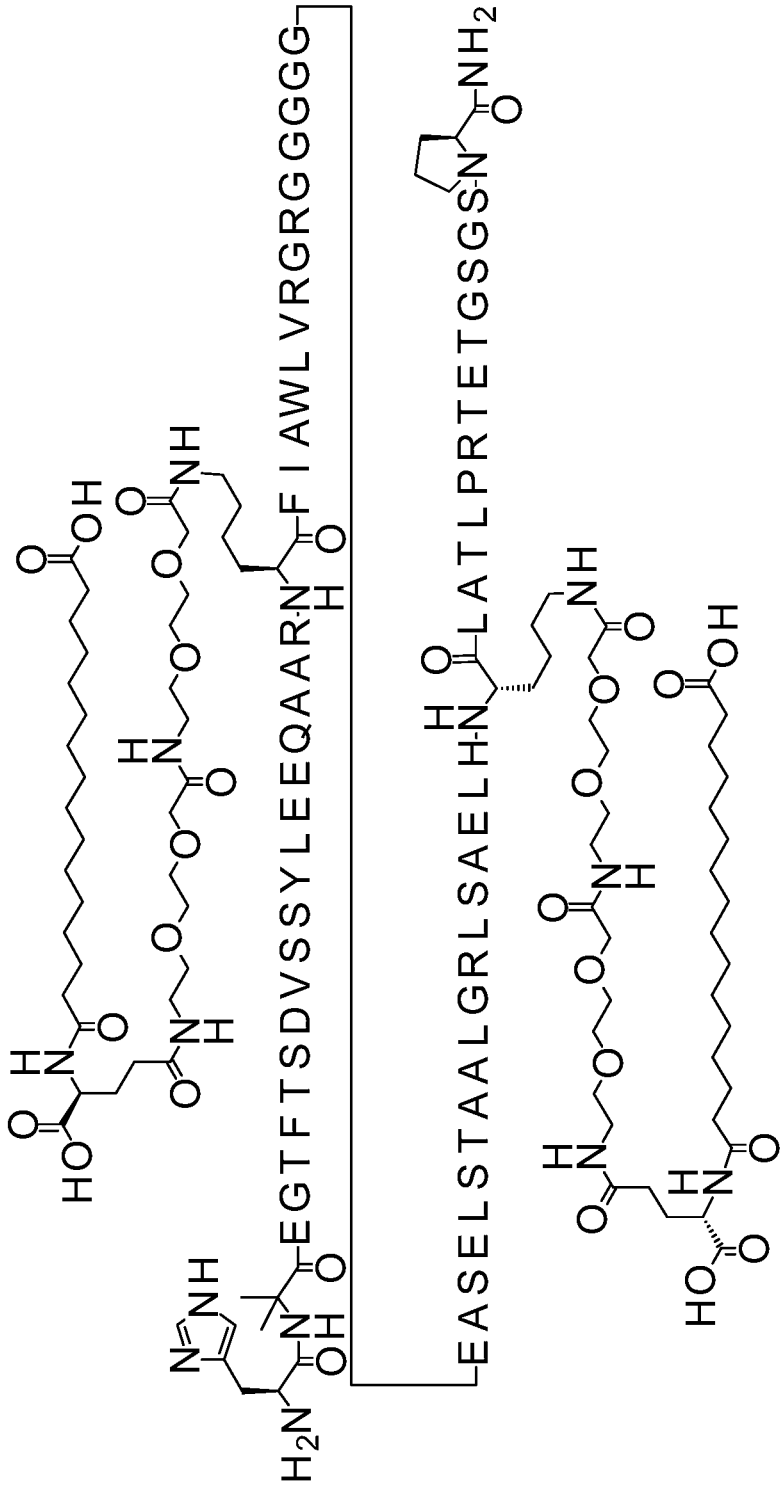
Figure 132:
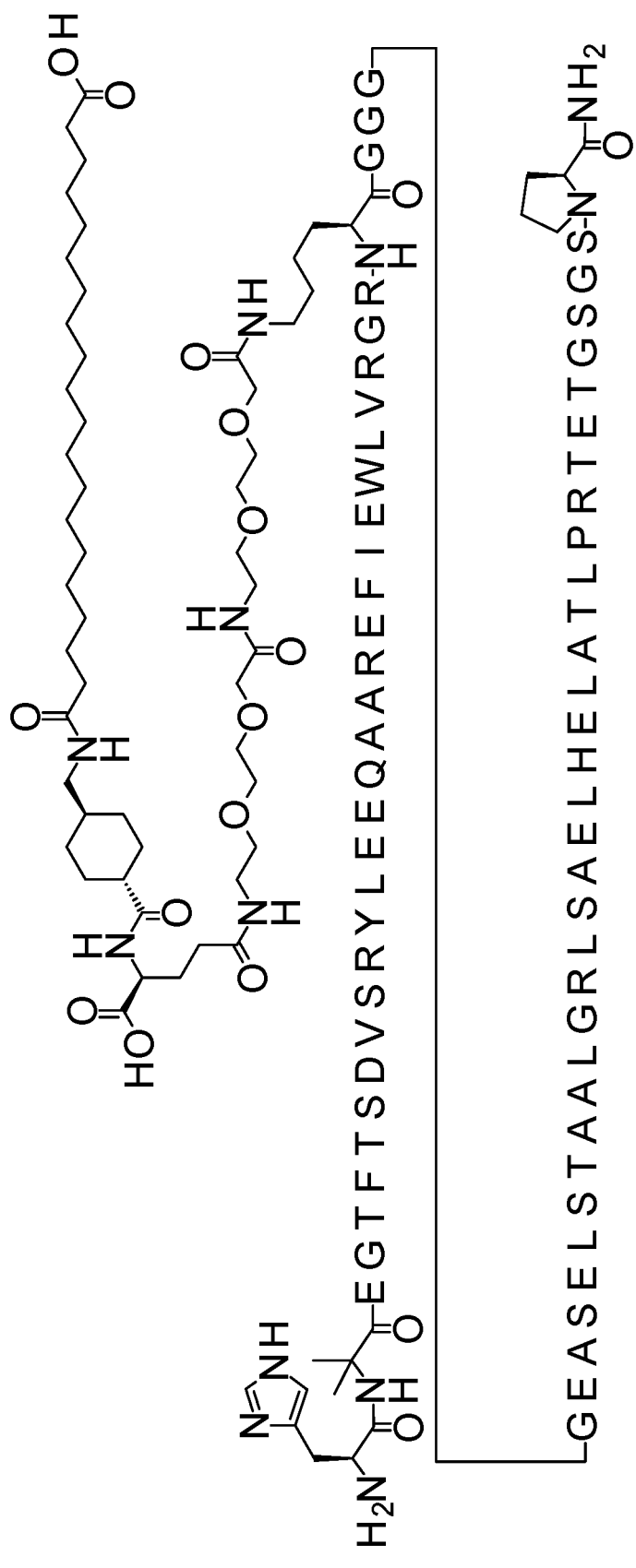
Figure 133:
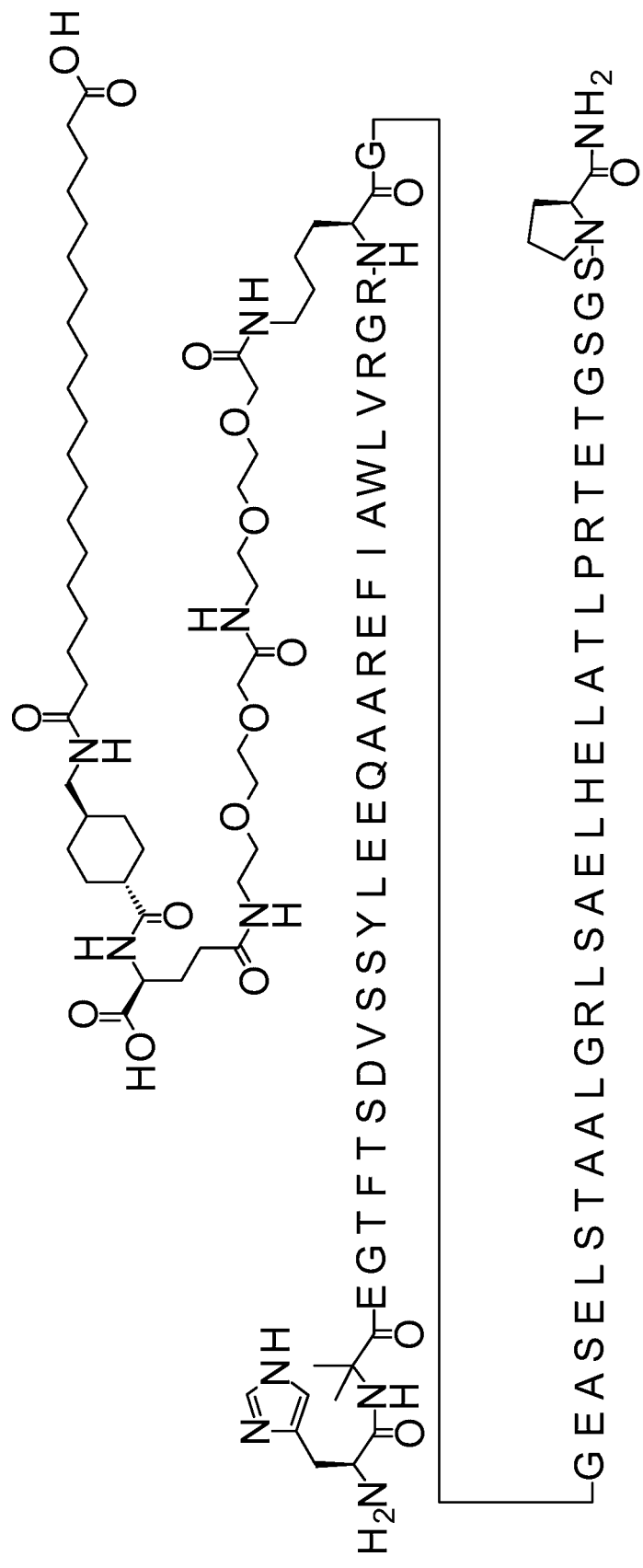
Figure 134:
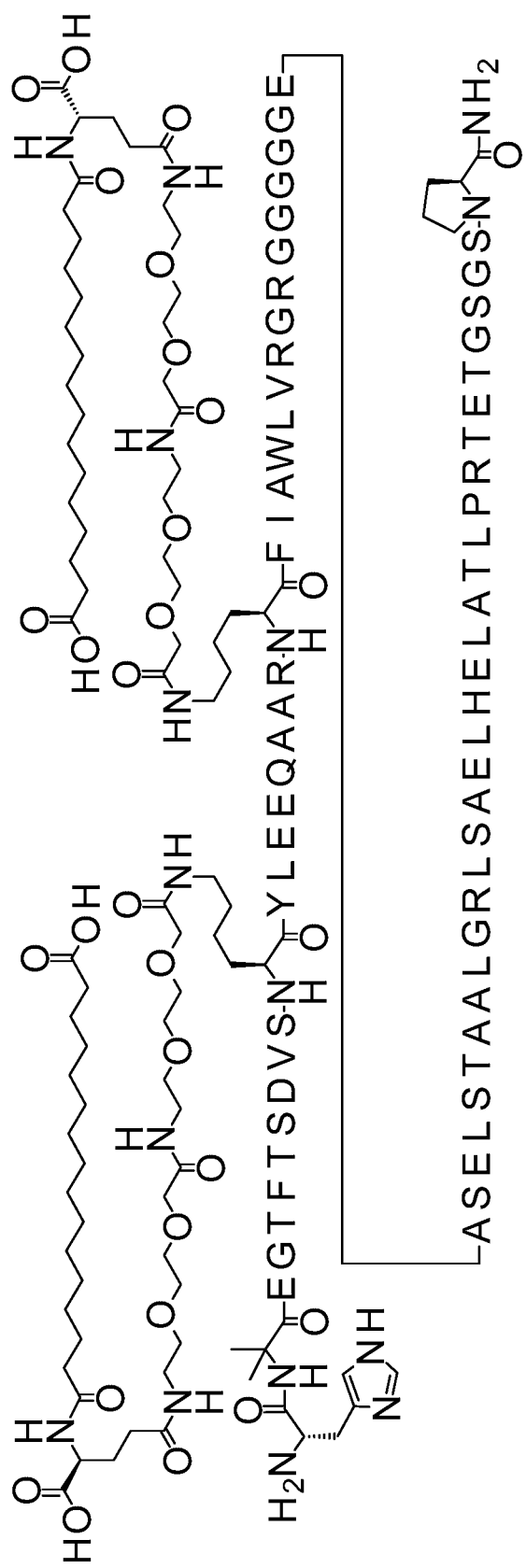
Figure 135:
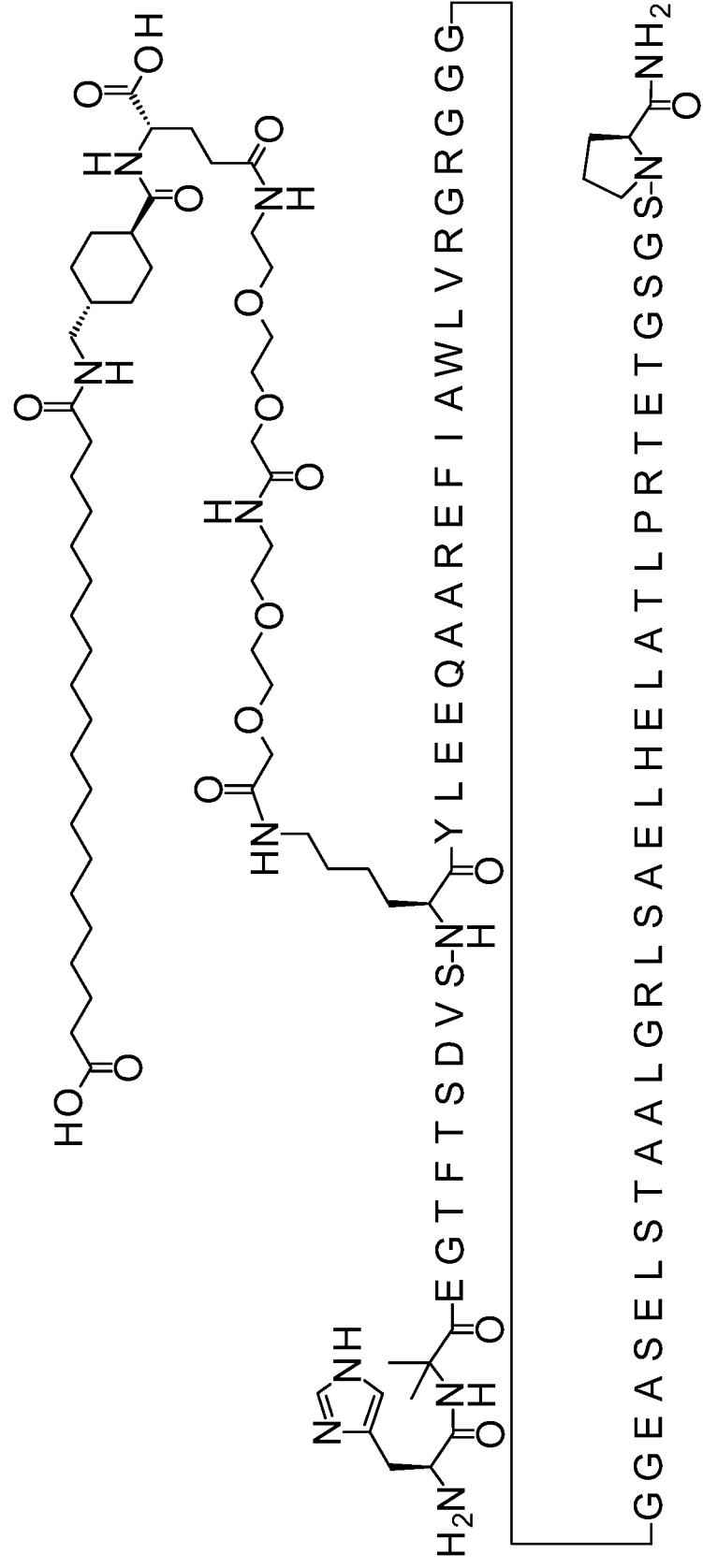
Figure 136:
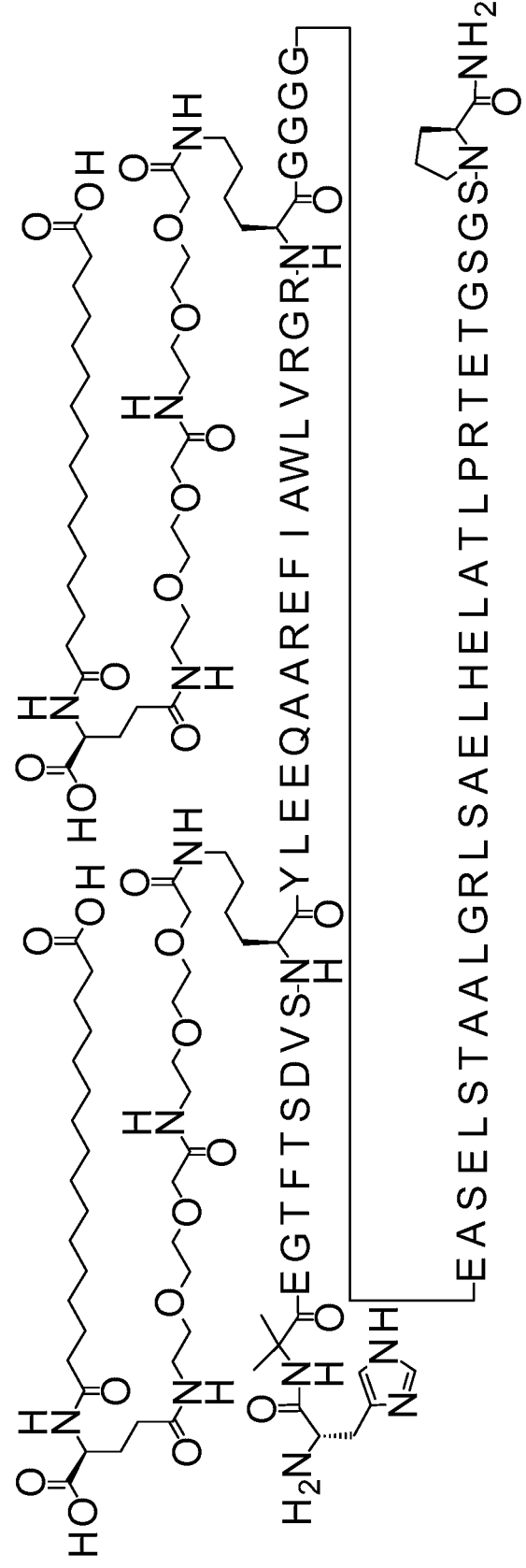
Figure 137:
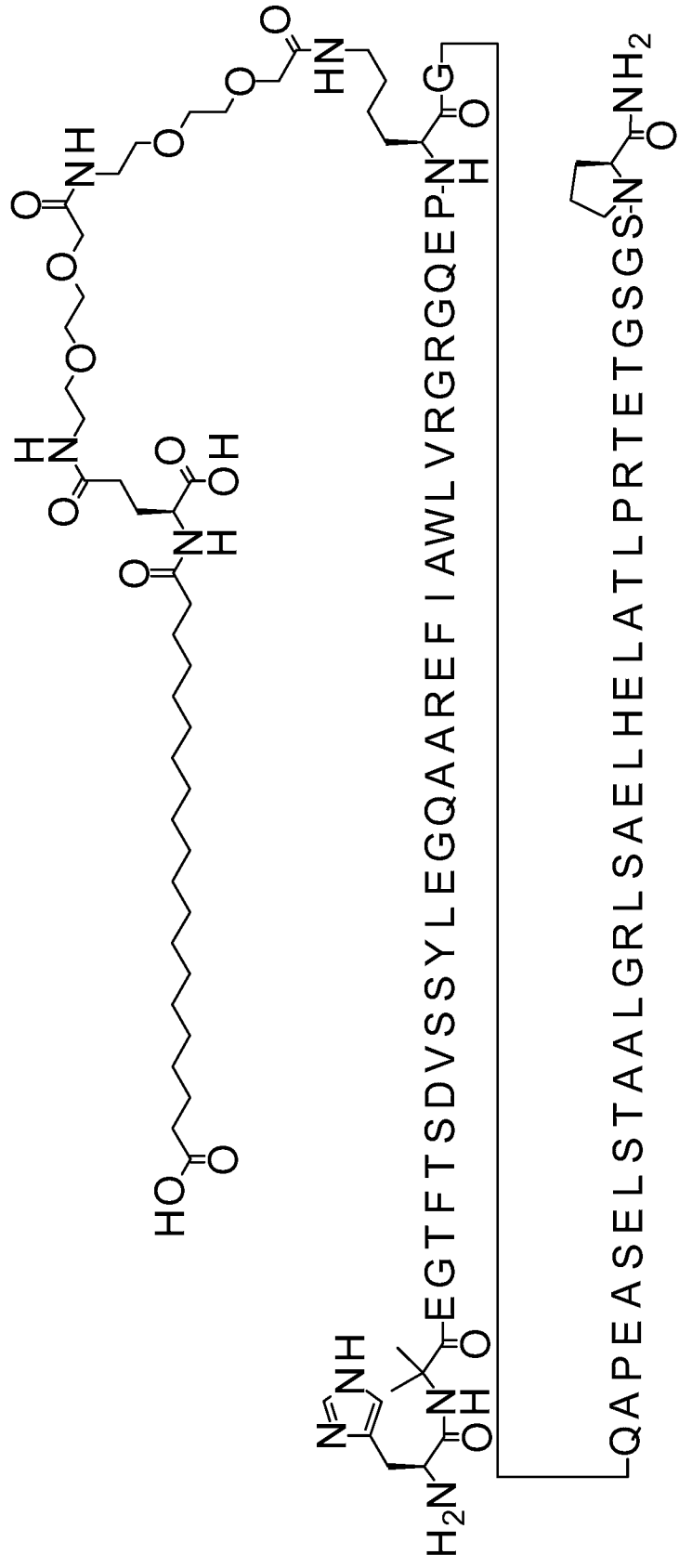
Figure 138:
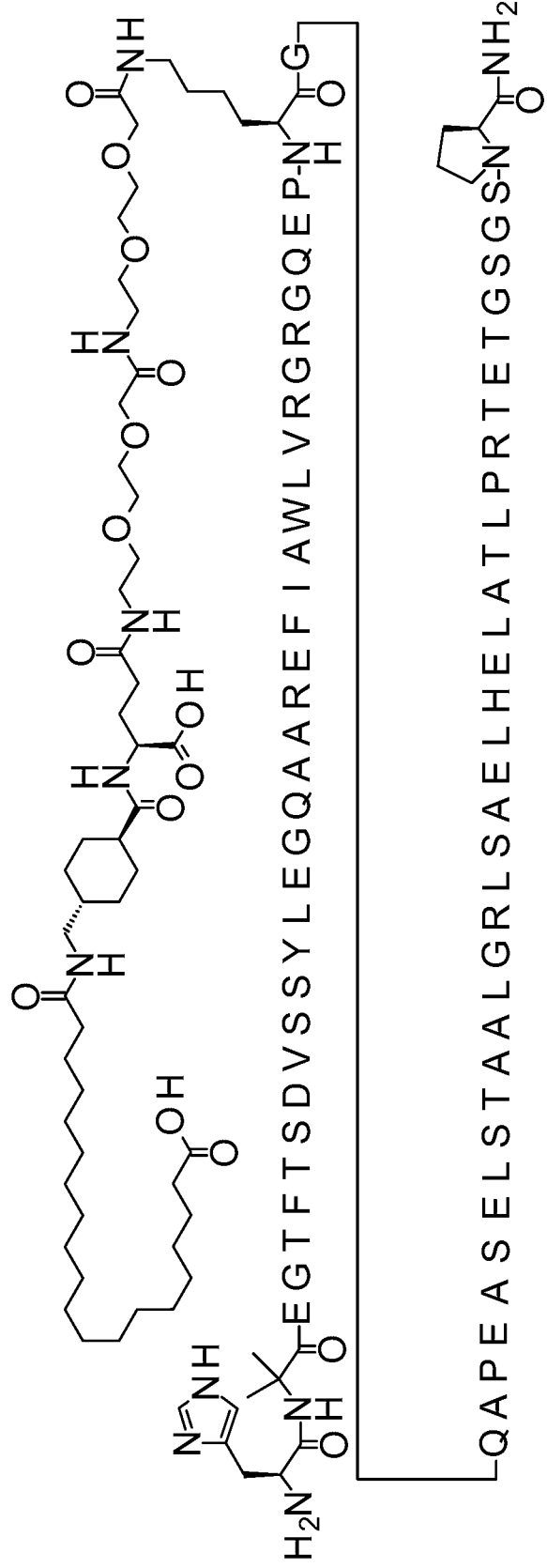
Figure 139:
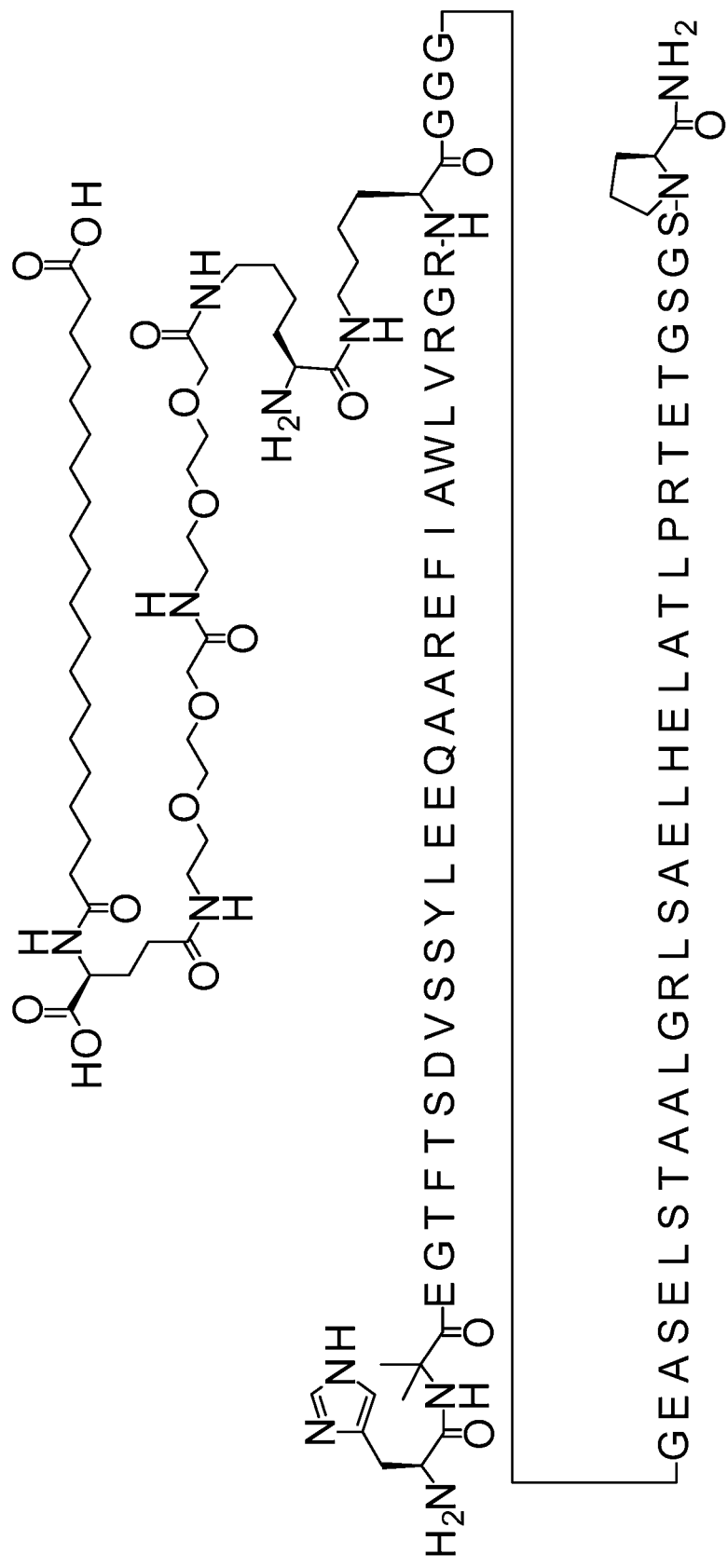
Figure 140:
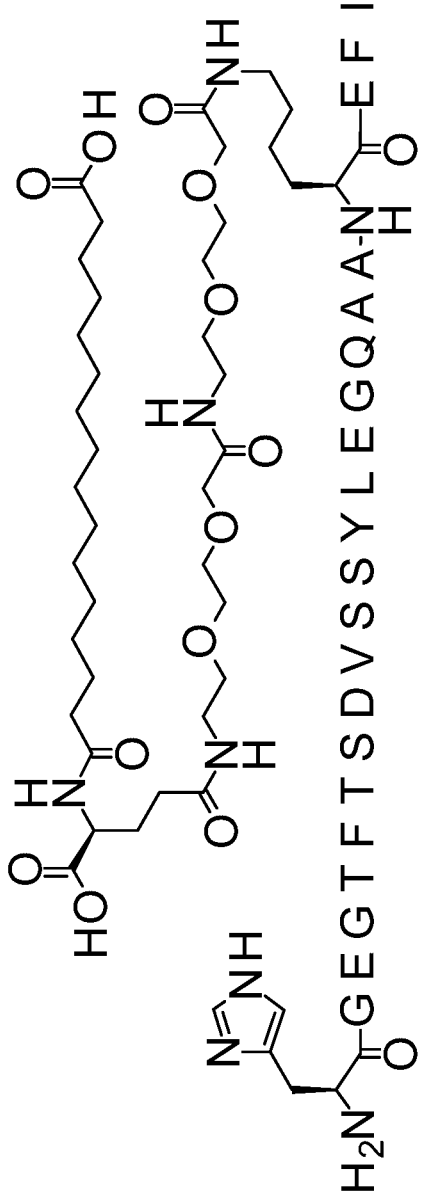
Figure 141:
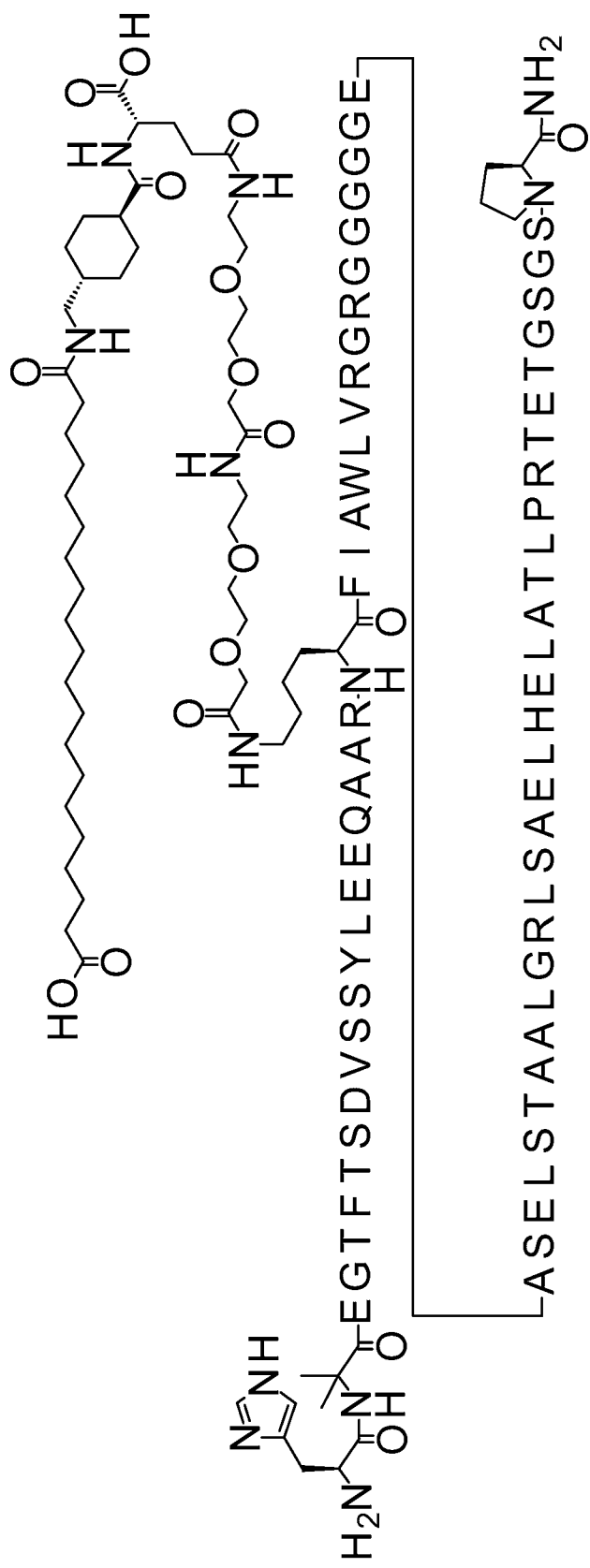
Figure 142:
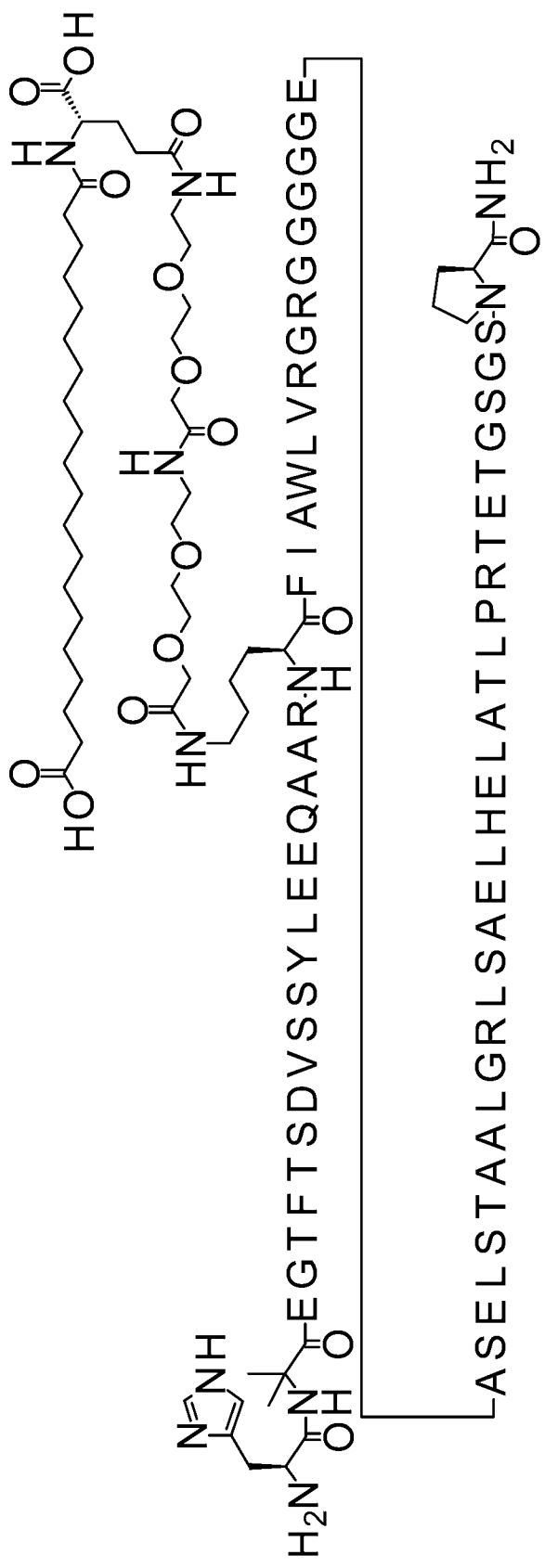
Figure 143:
Figure 144:
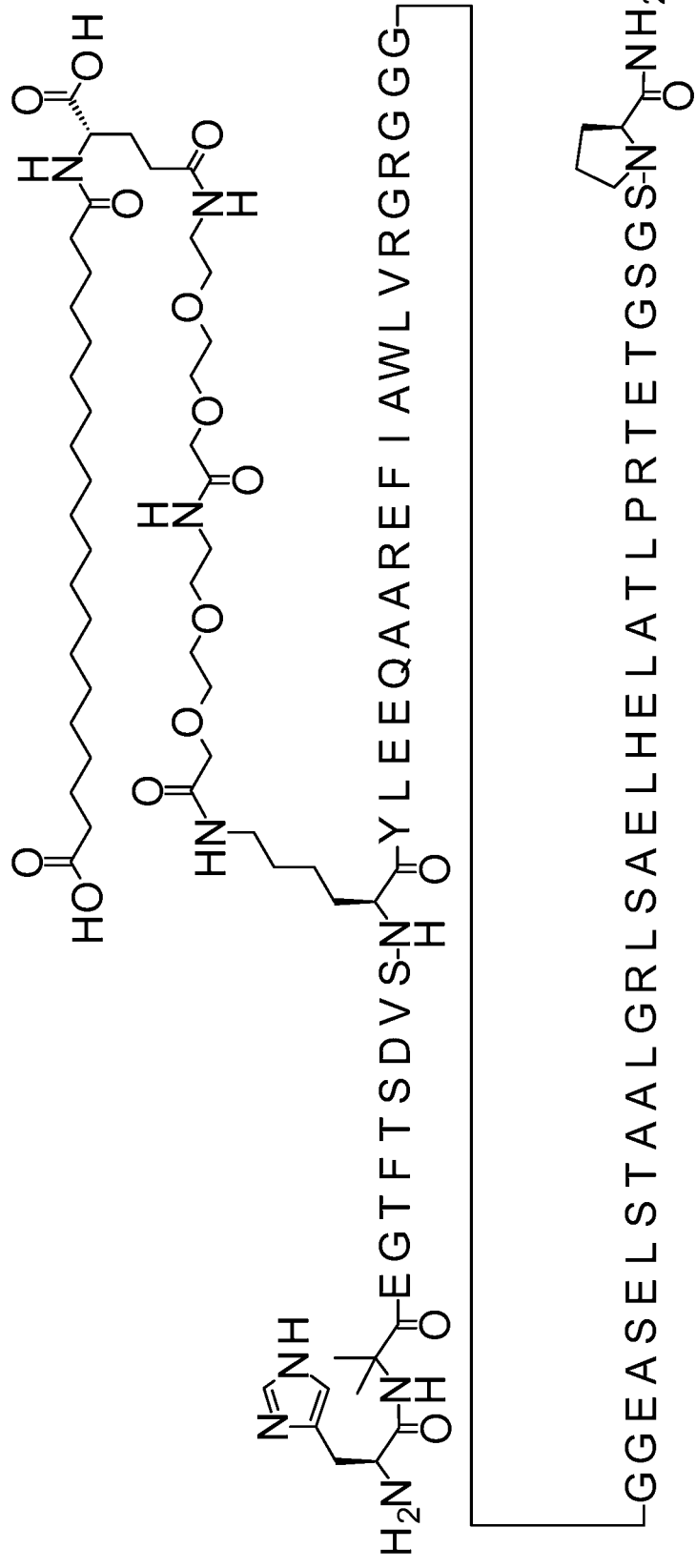
Figure 145:
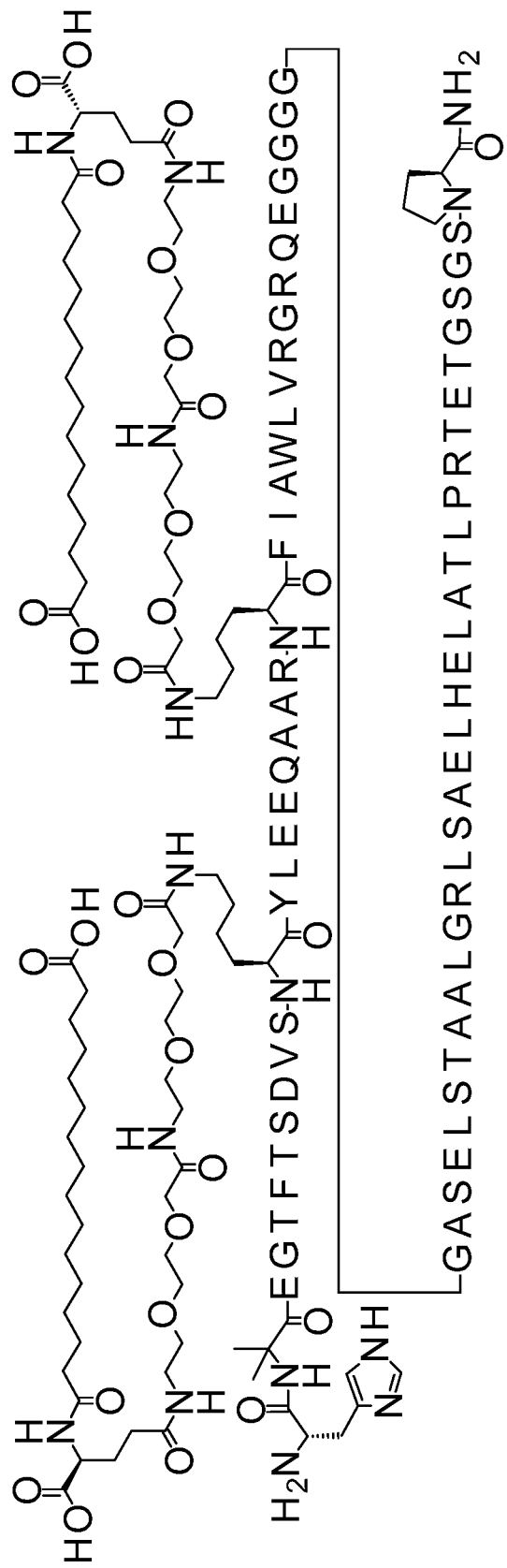
Figure 146:
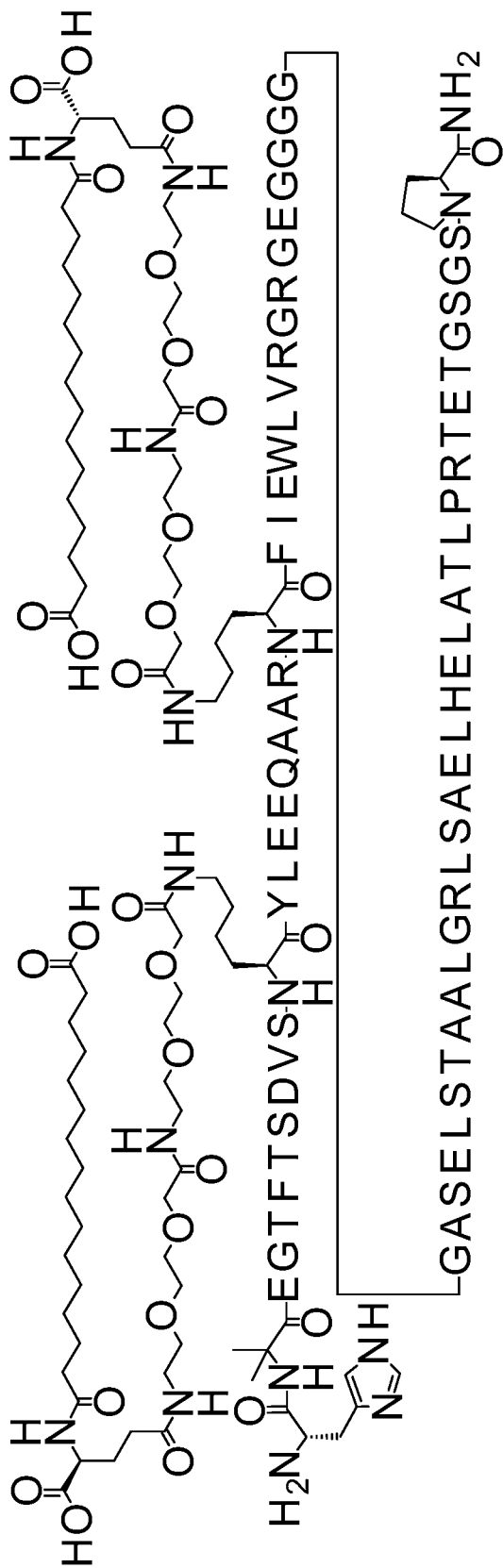
Figure 147:
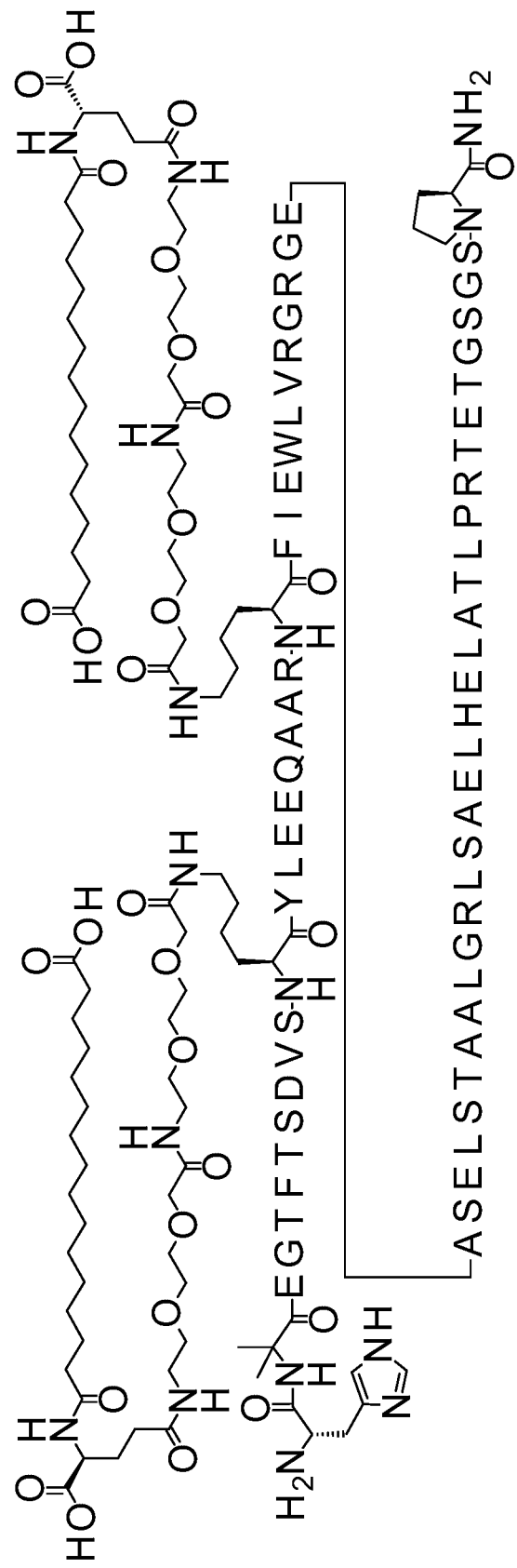
Figure 148:
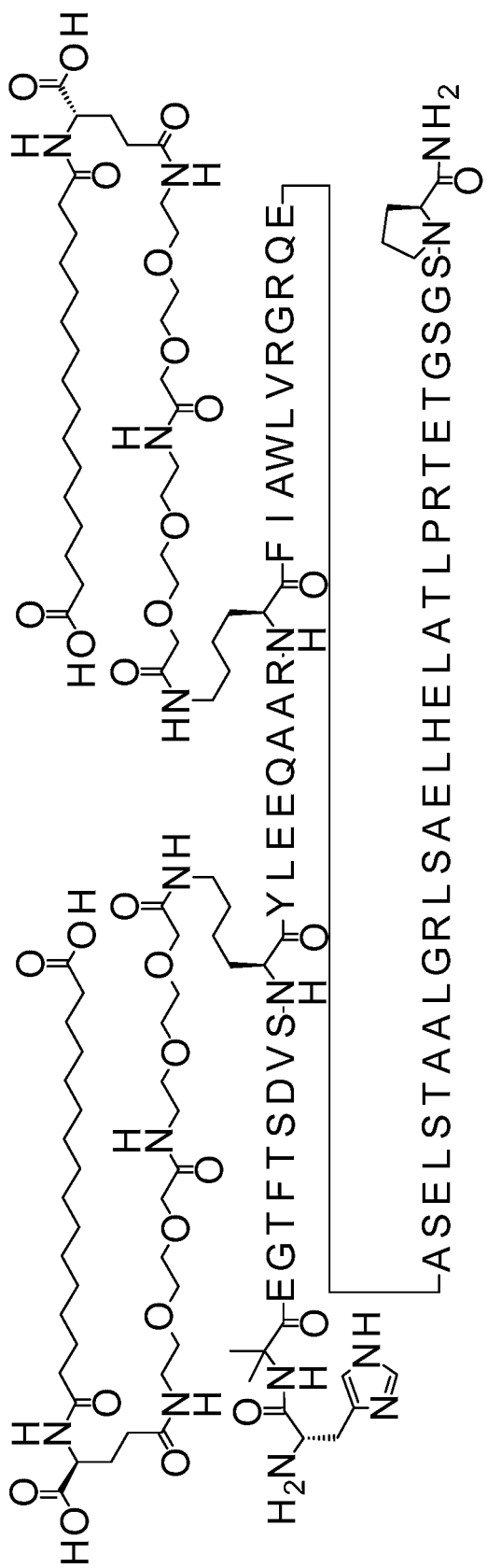
Figure 149:
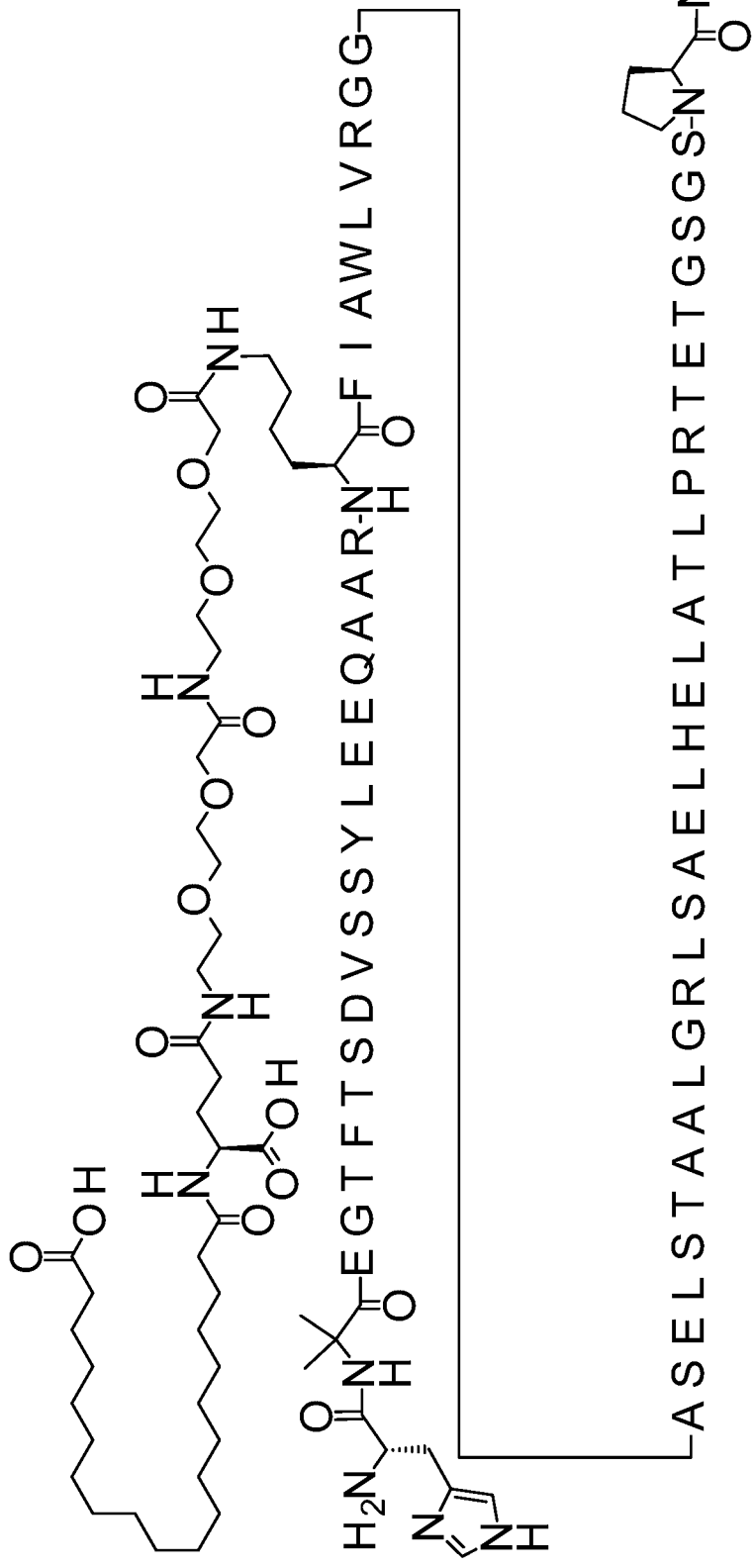
Figure 150:
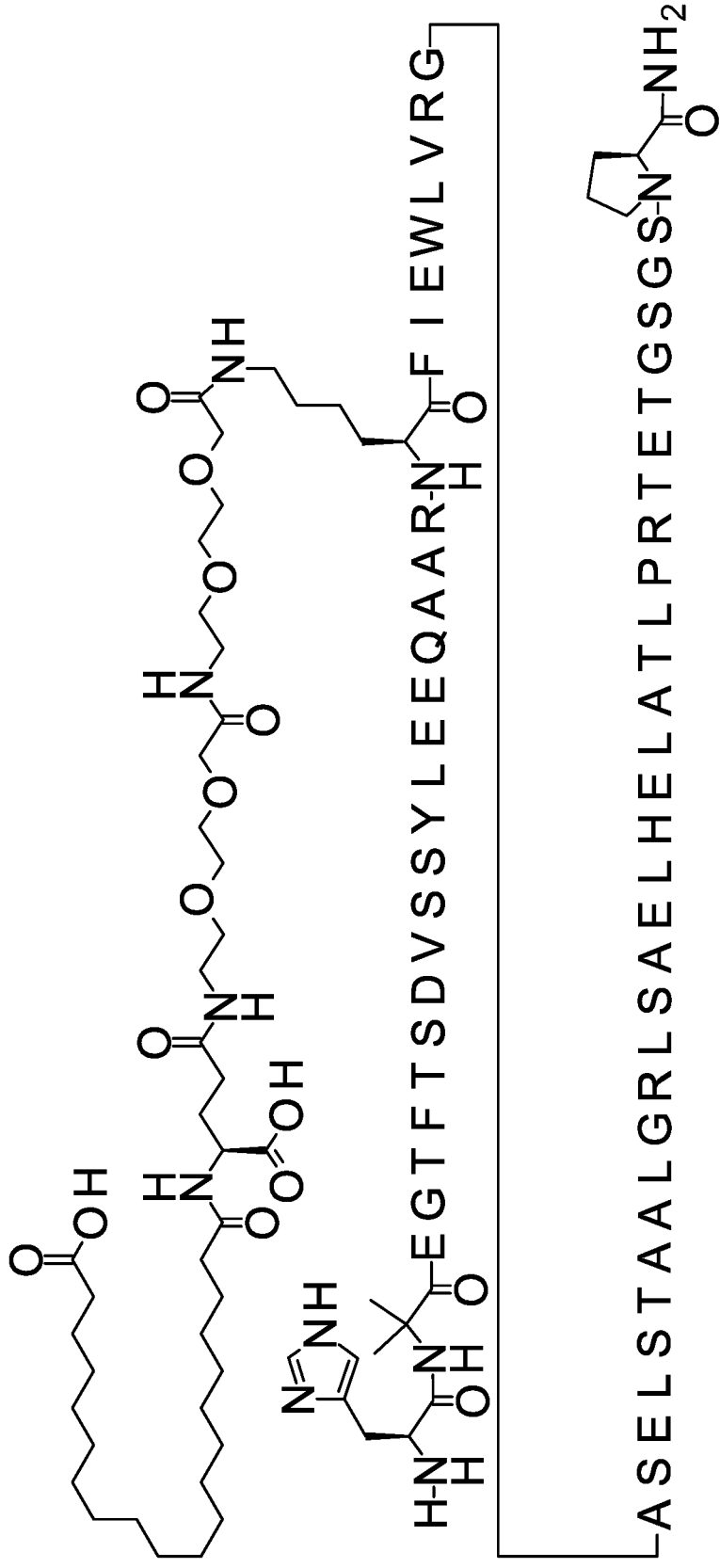
Figure 151:
Figure 152:
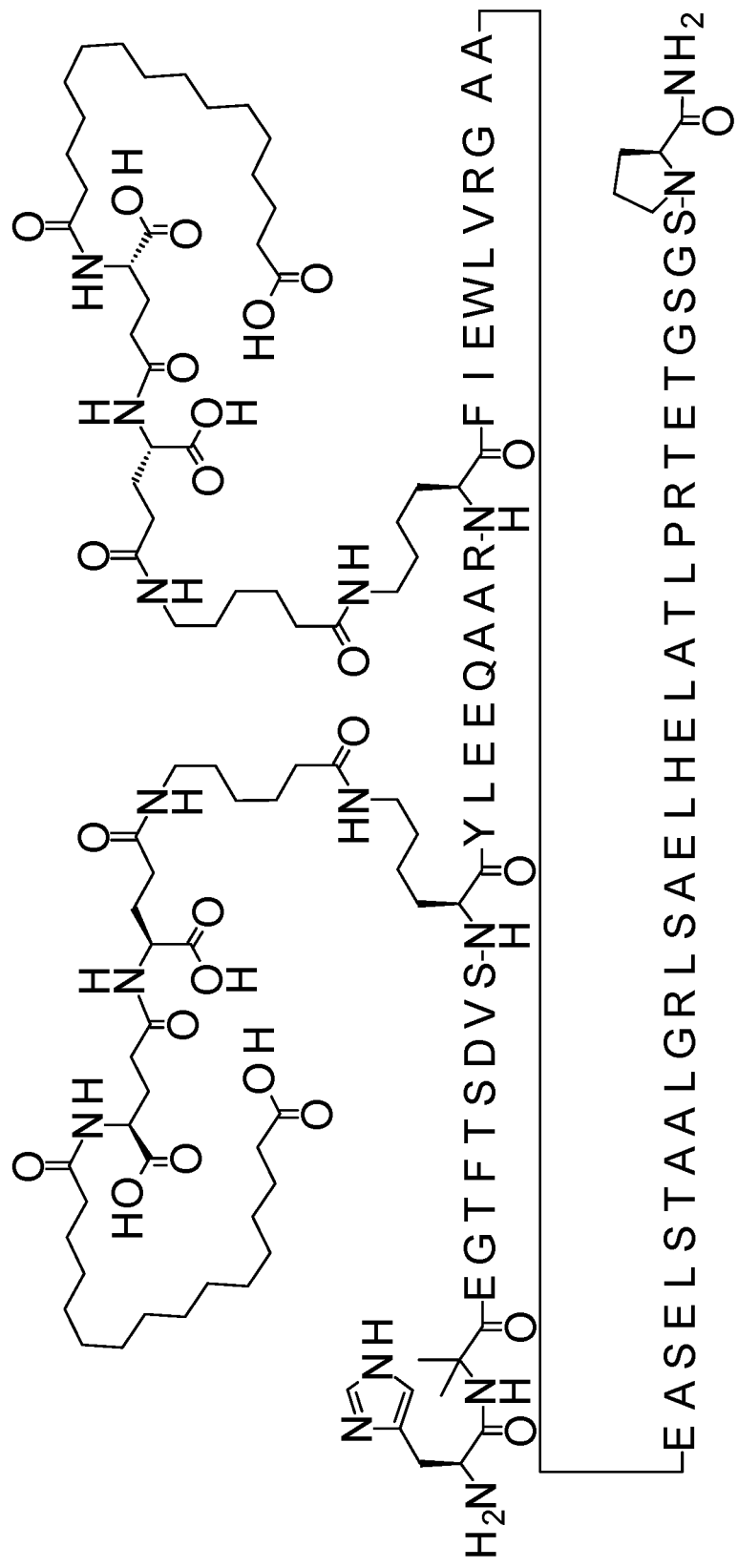
Figure 153:
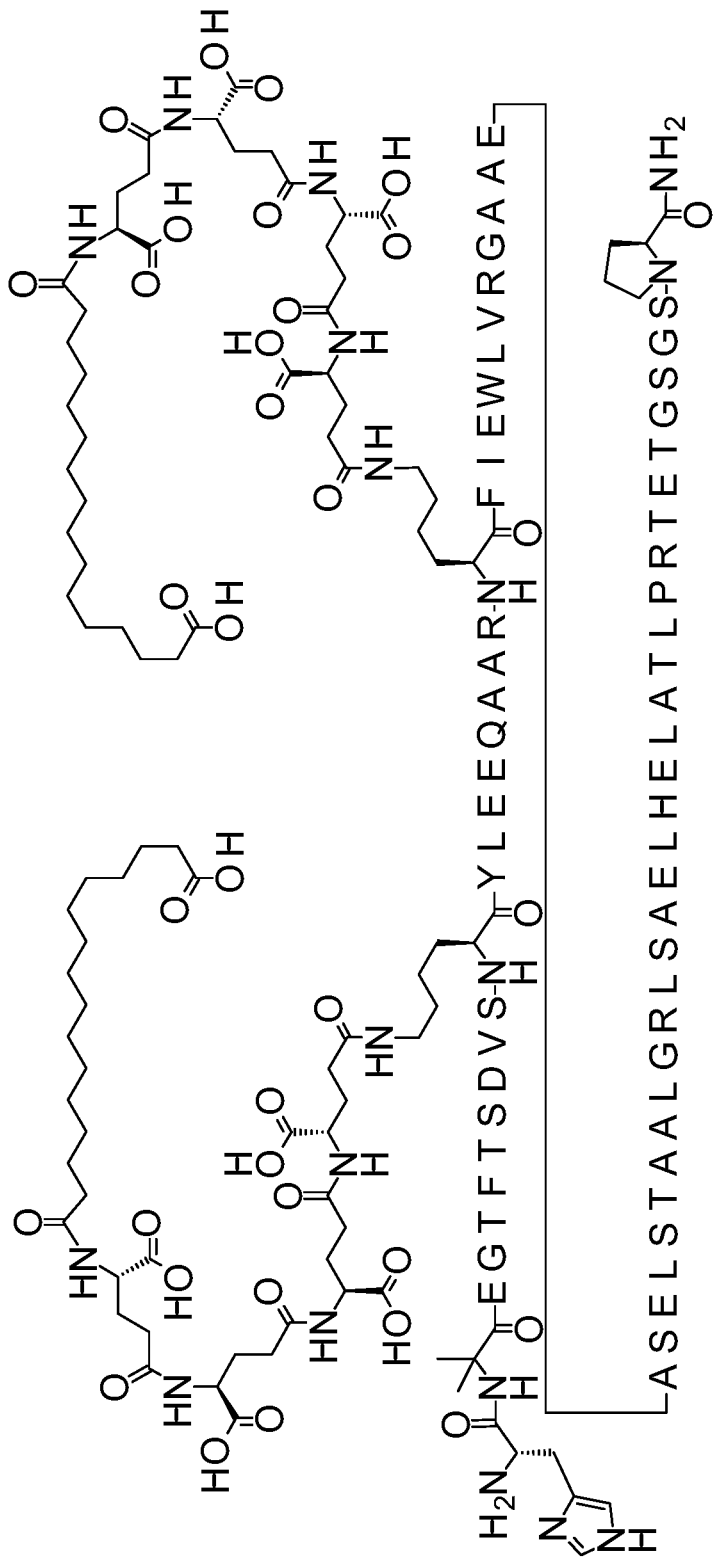
Figure 154:
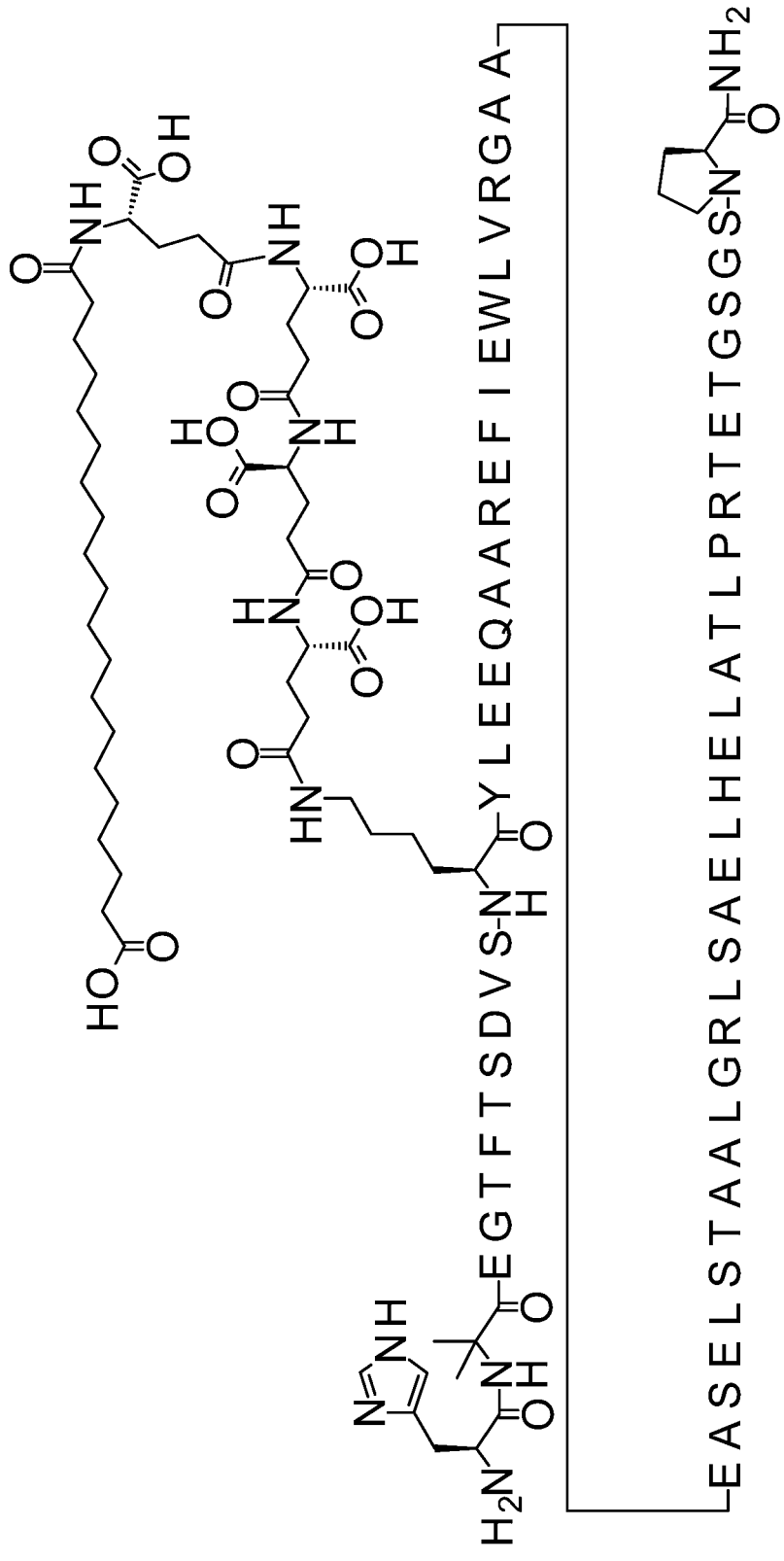
Figure 155:
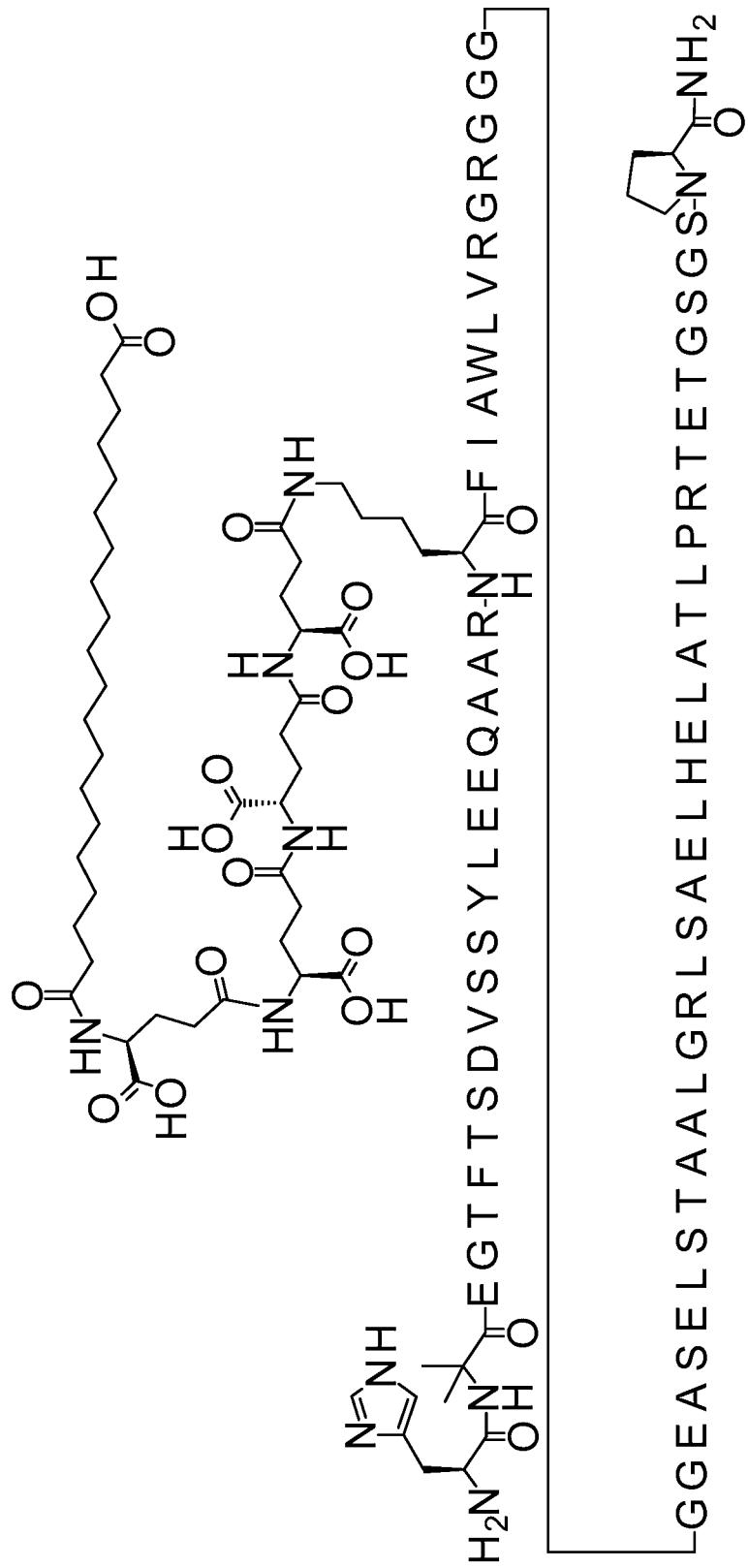
Figure 156:
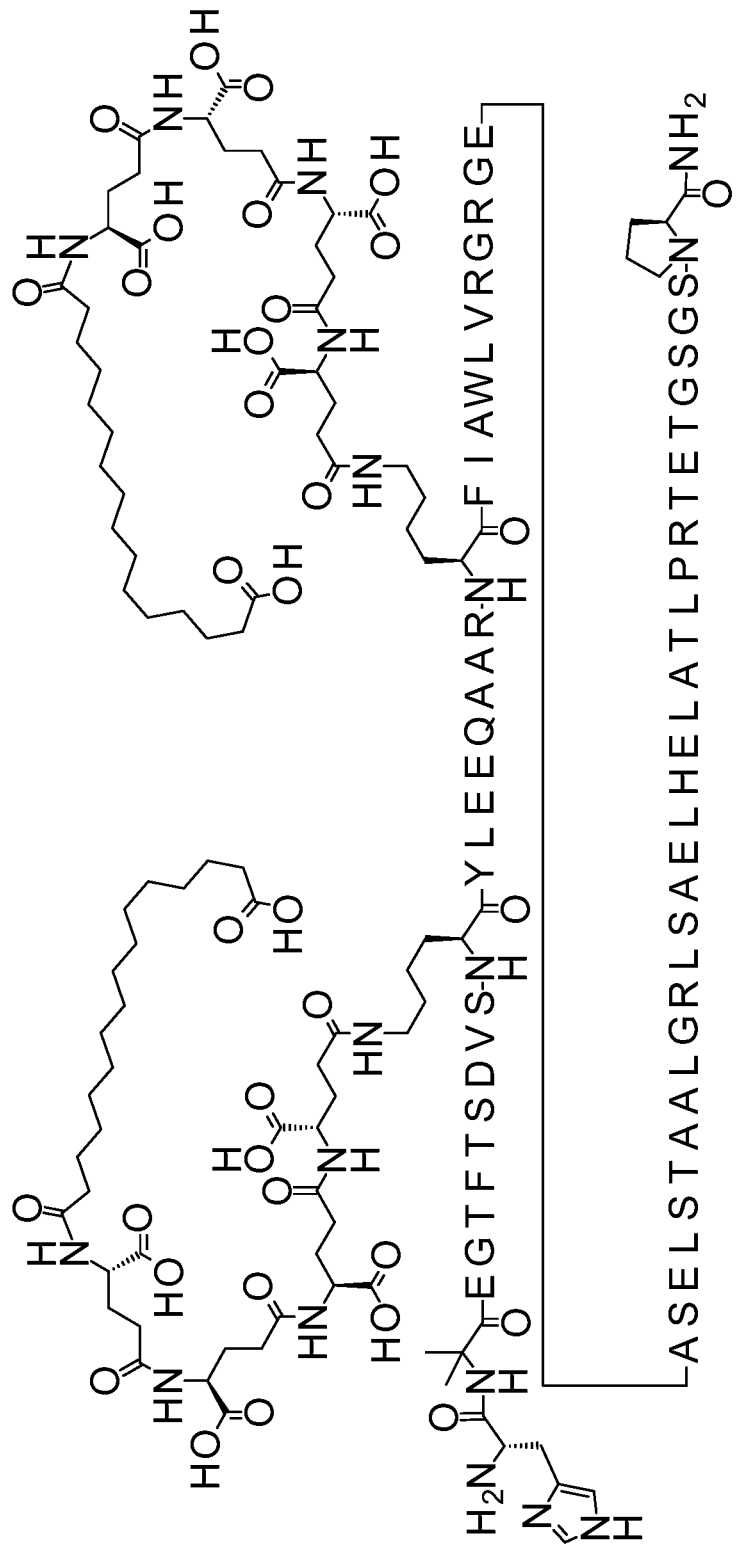
Figure 158:
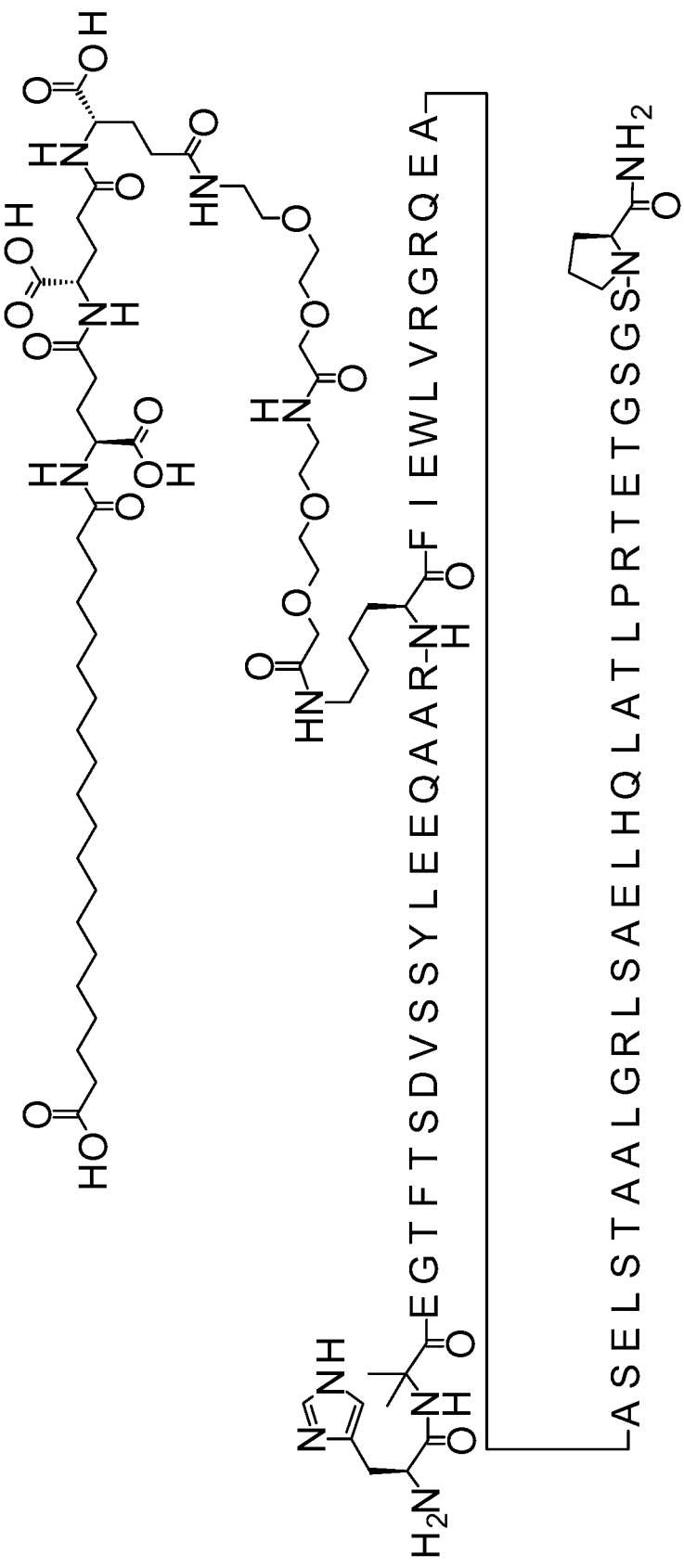
Figure 159:
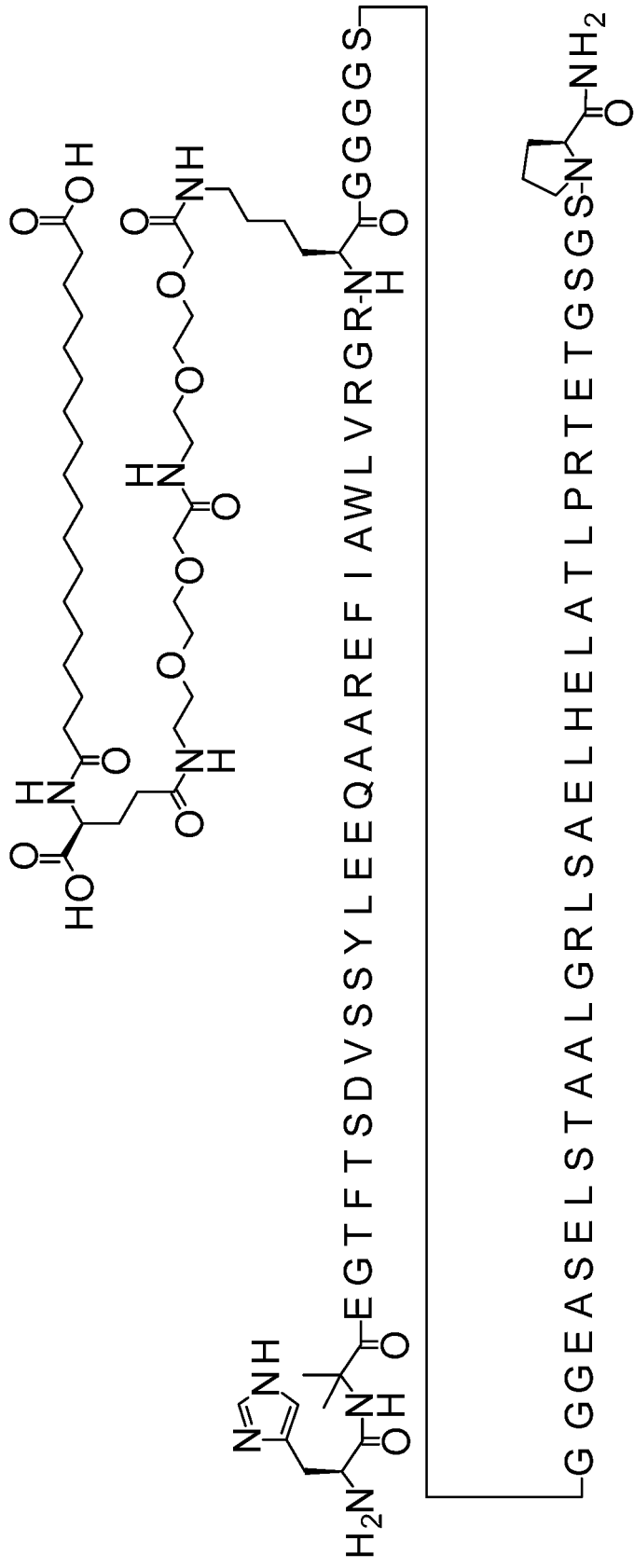
Figure 160:
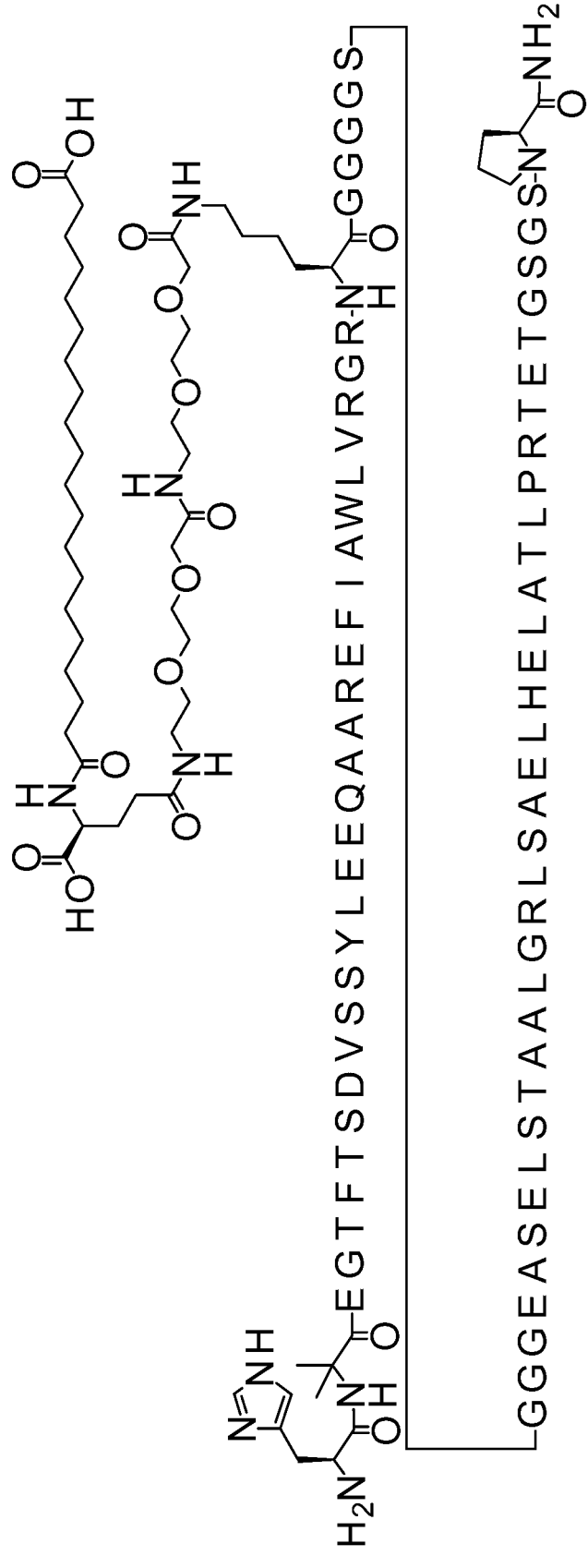
Figure 161:
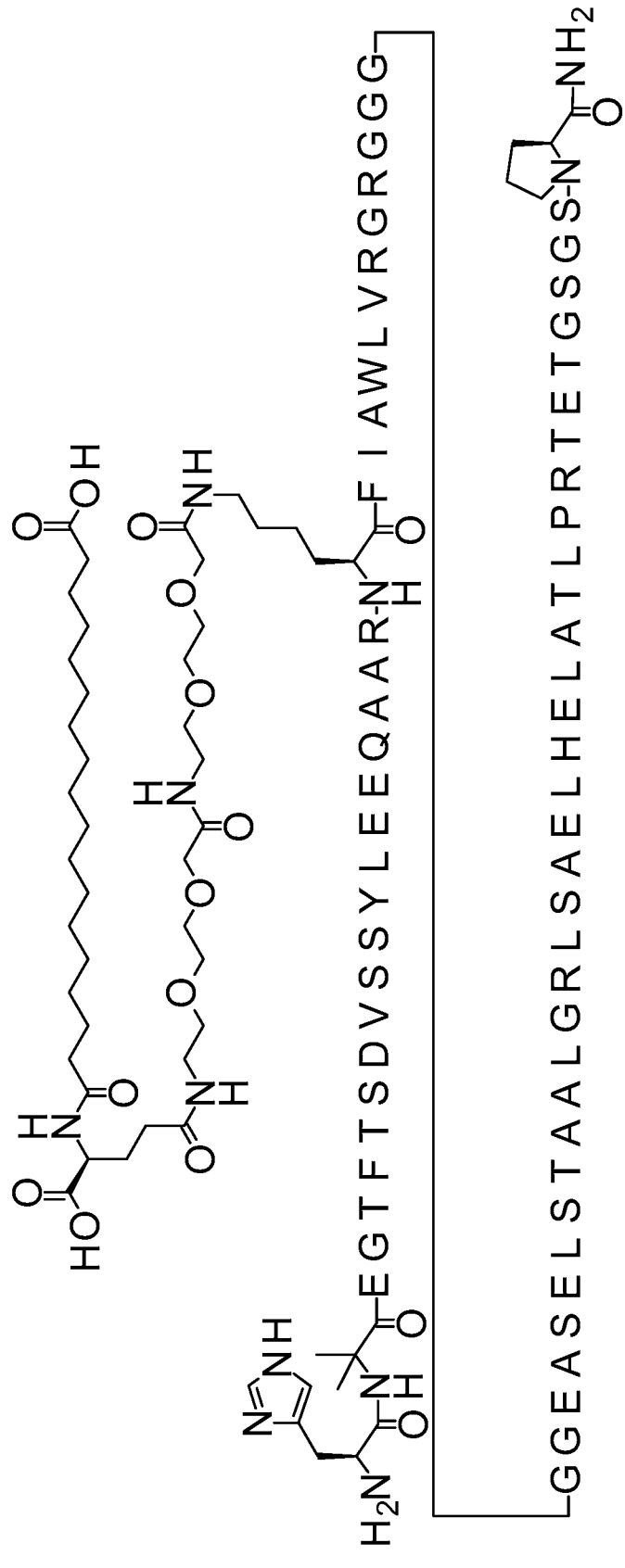
Figure 162:
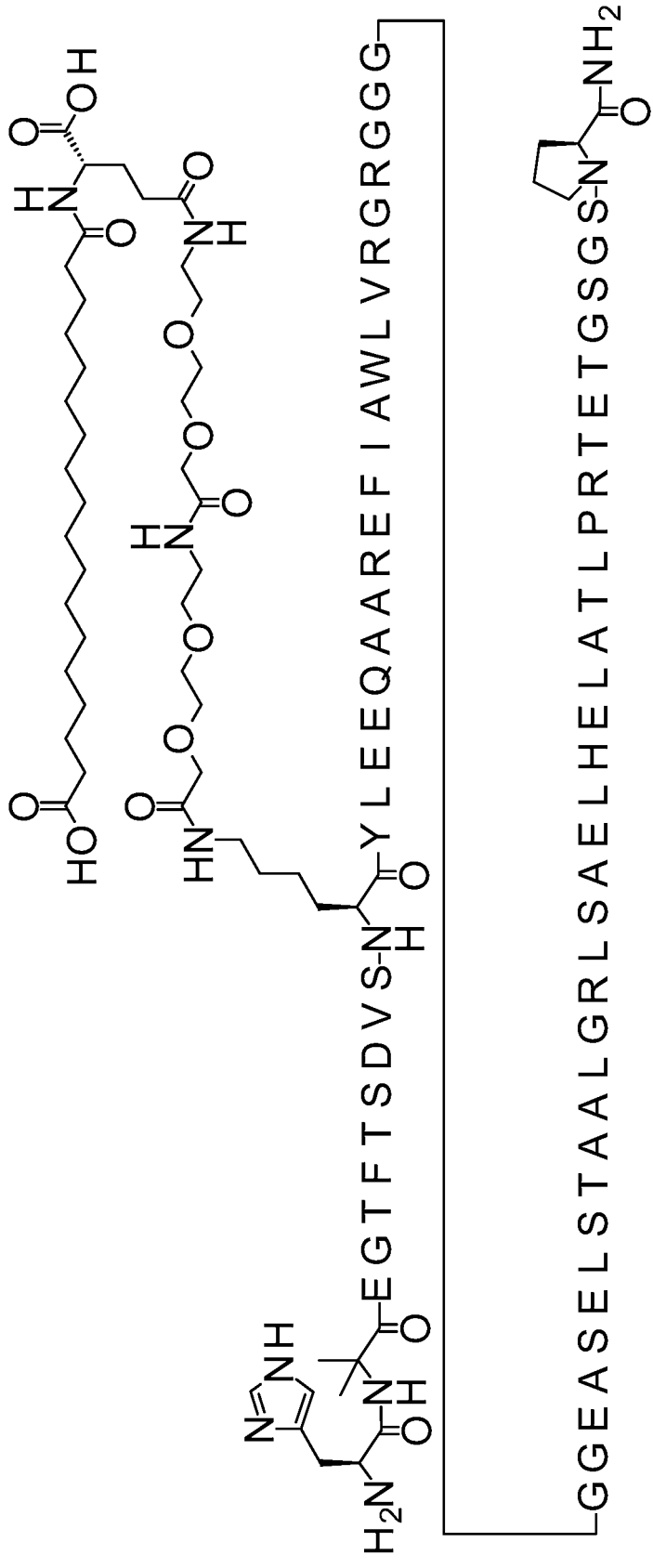
Figure 163:
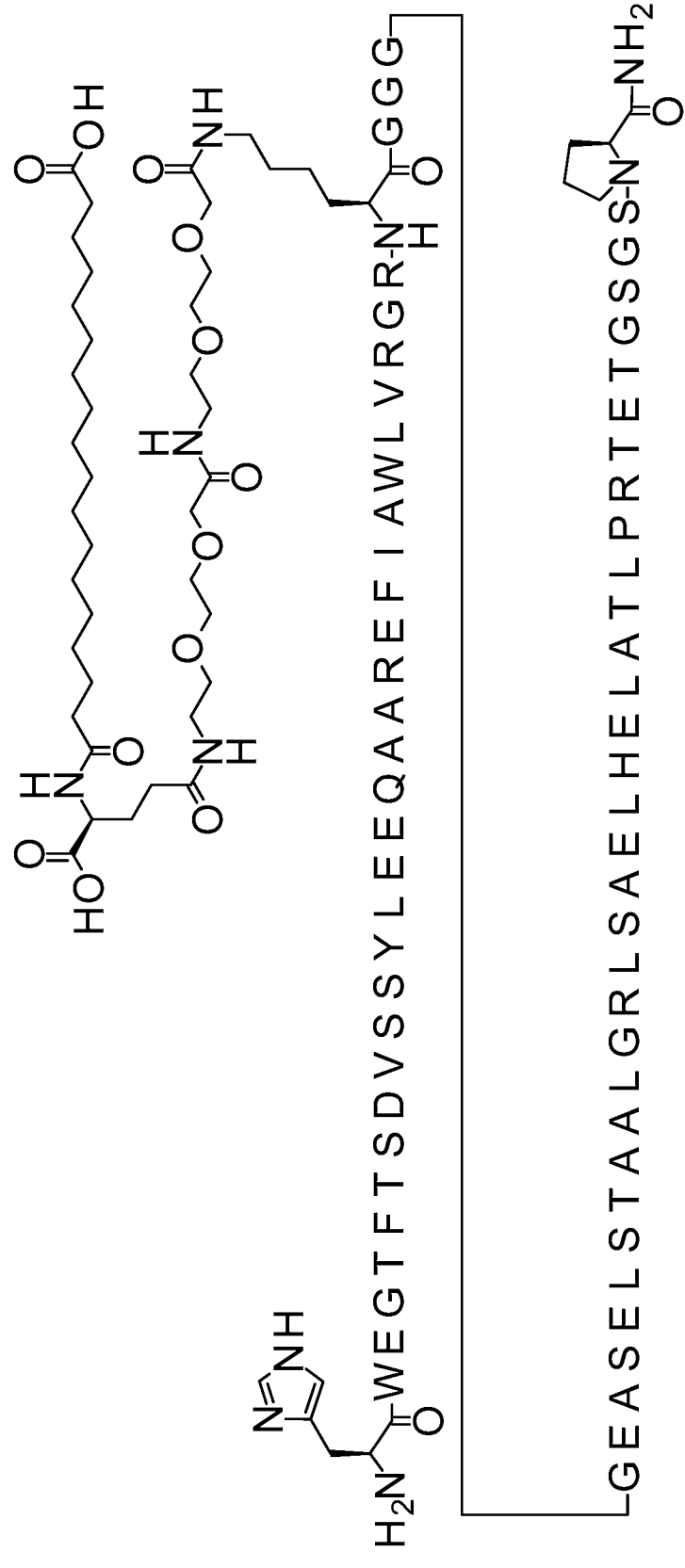
Figure 164:
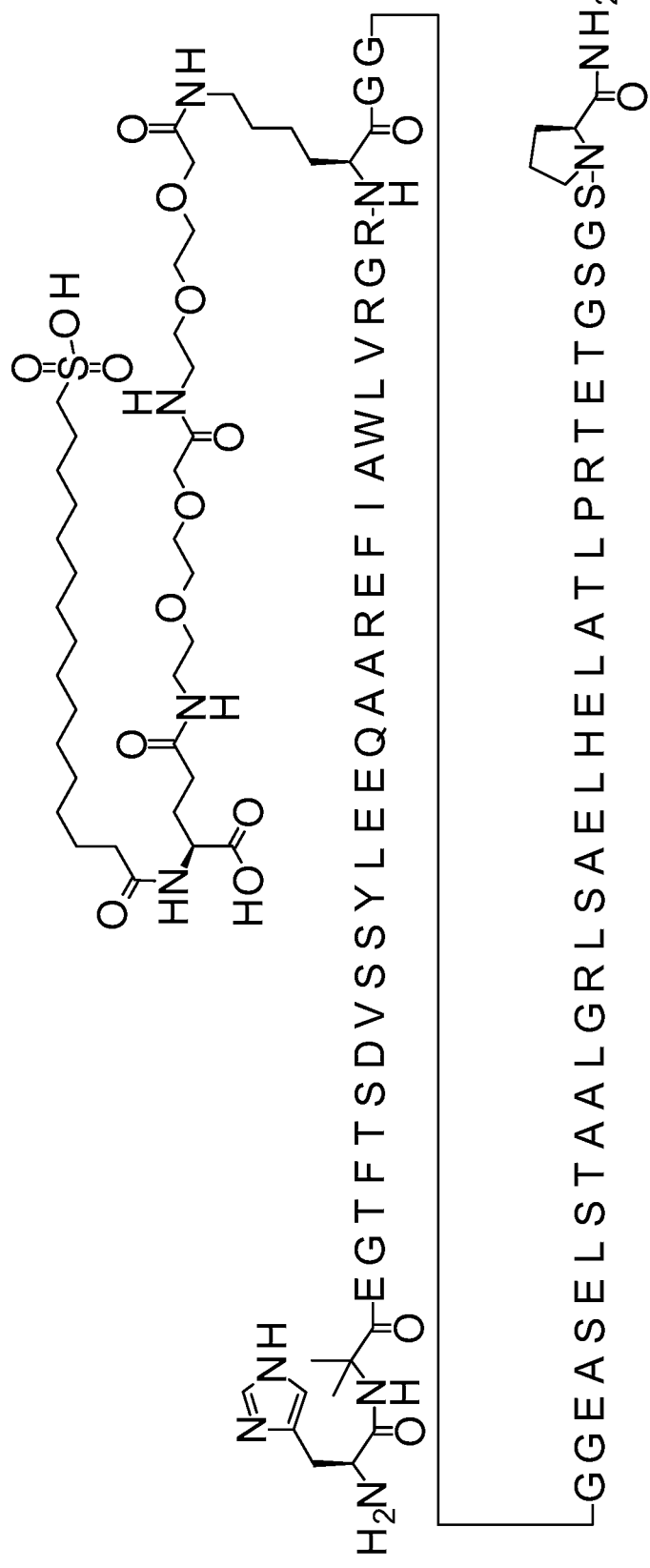
Figure 165:
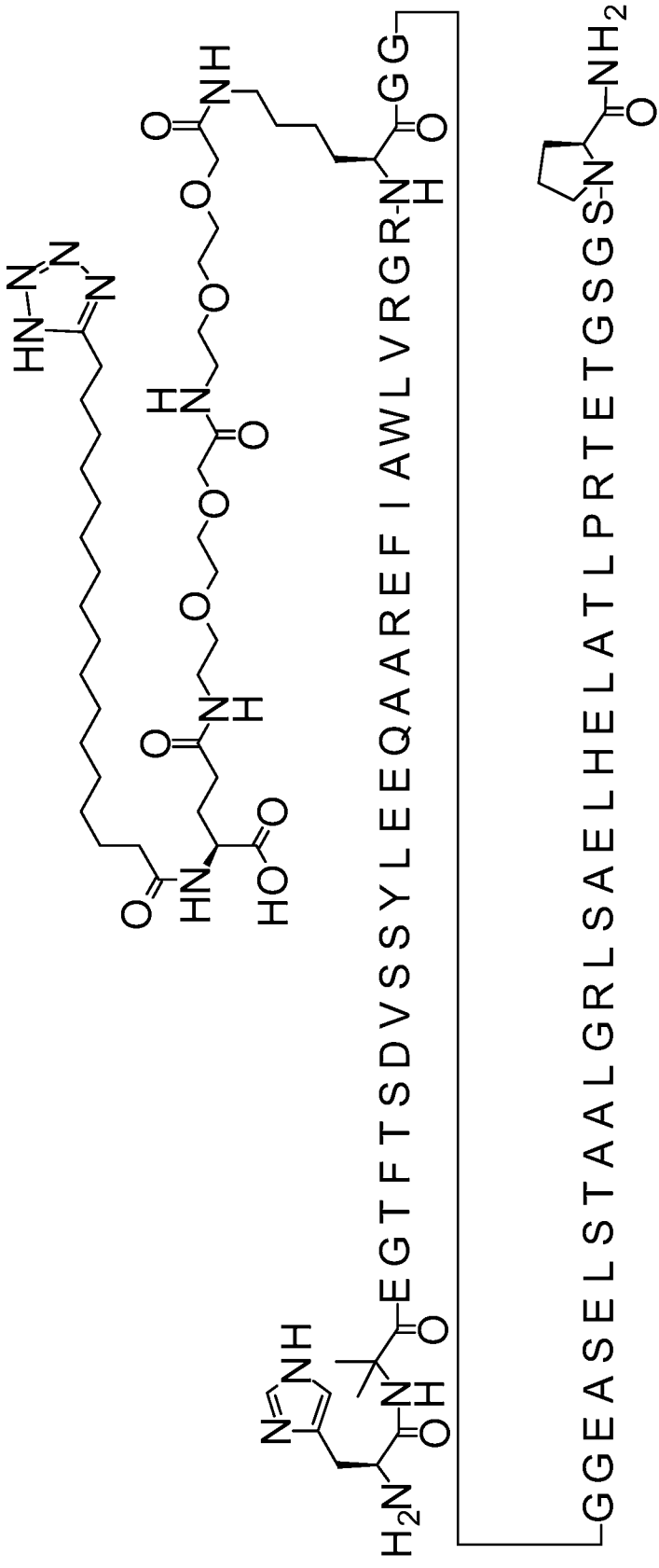
Figure 166:
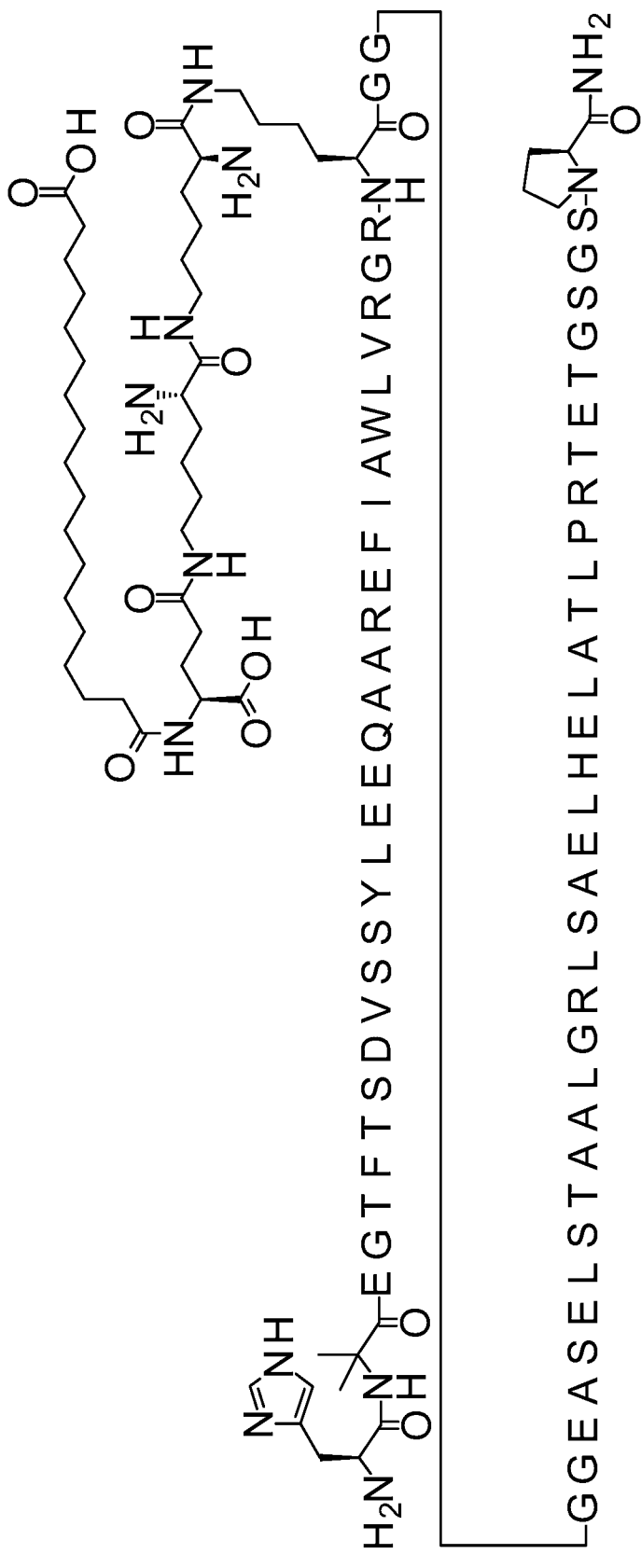
Figure 167:
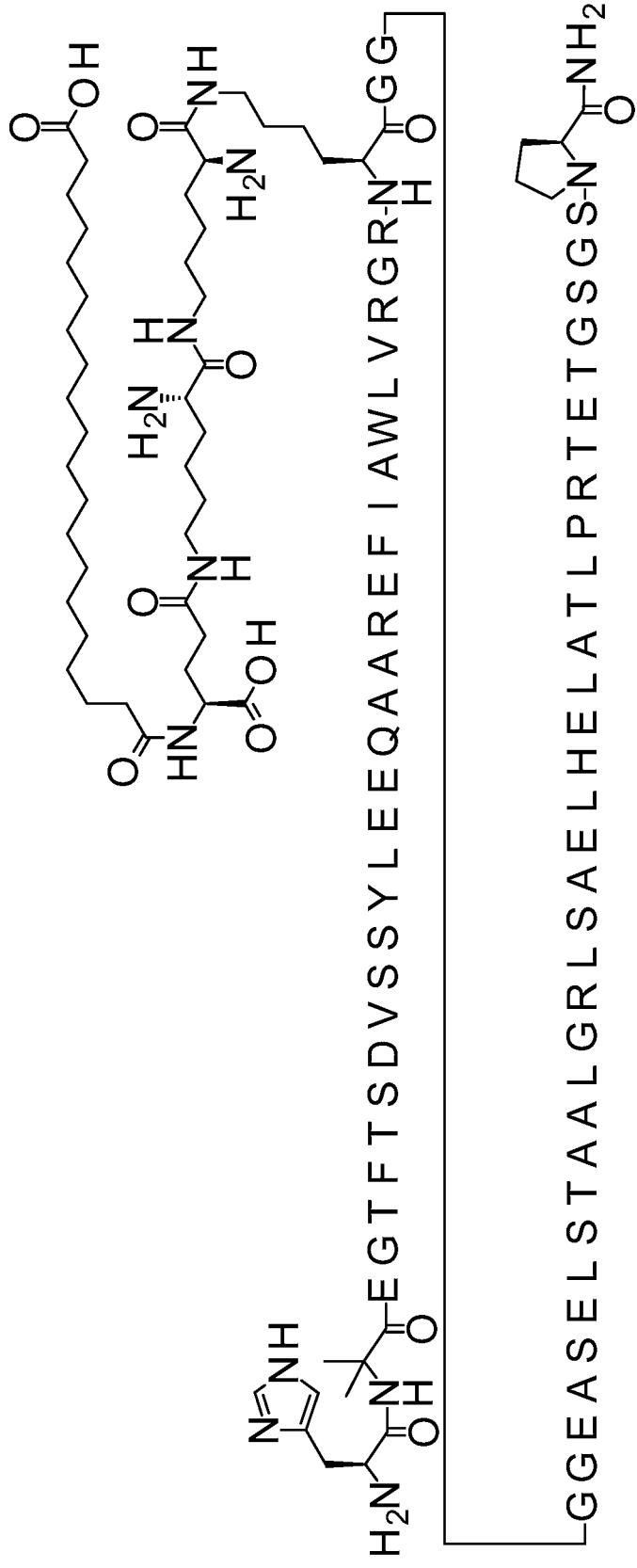
Figure 168:
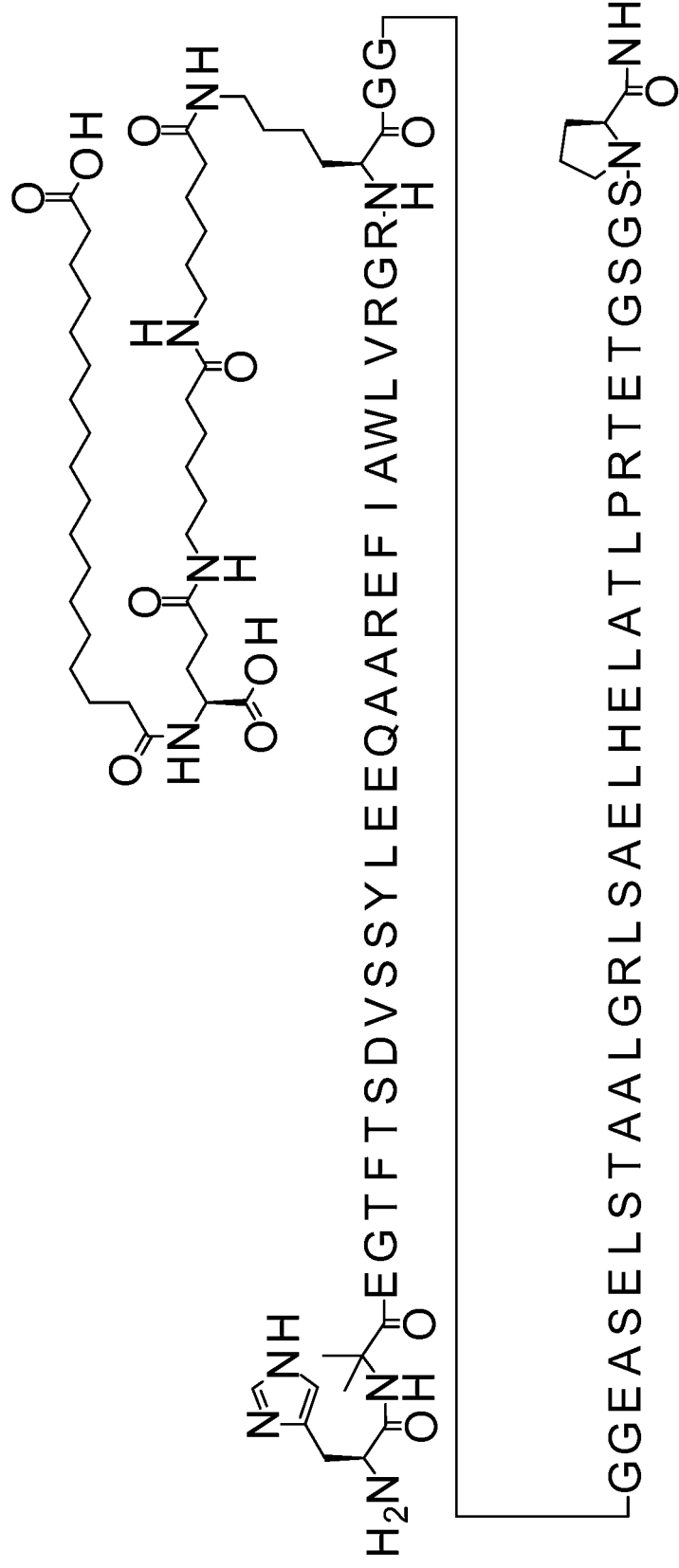
Figure 169:
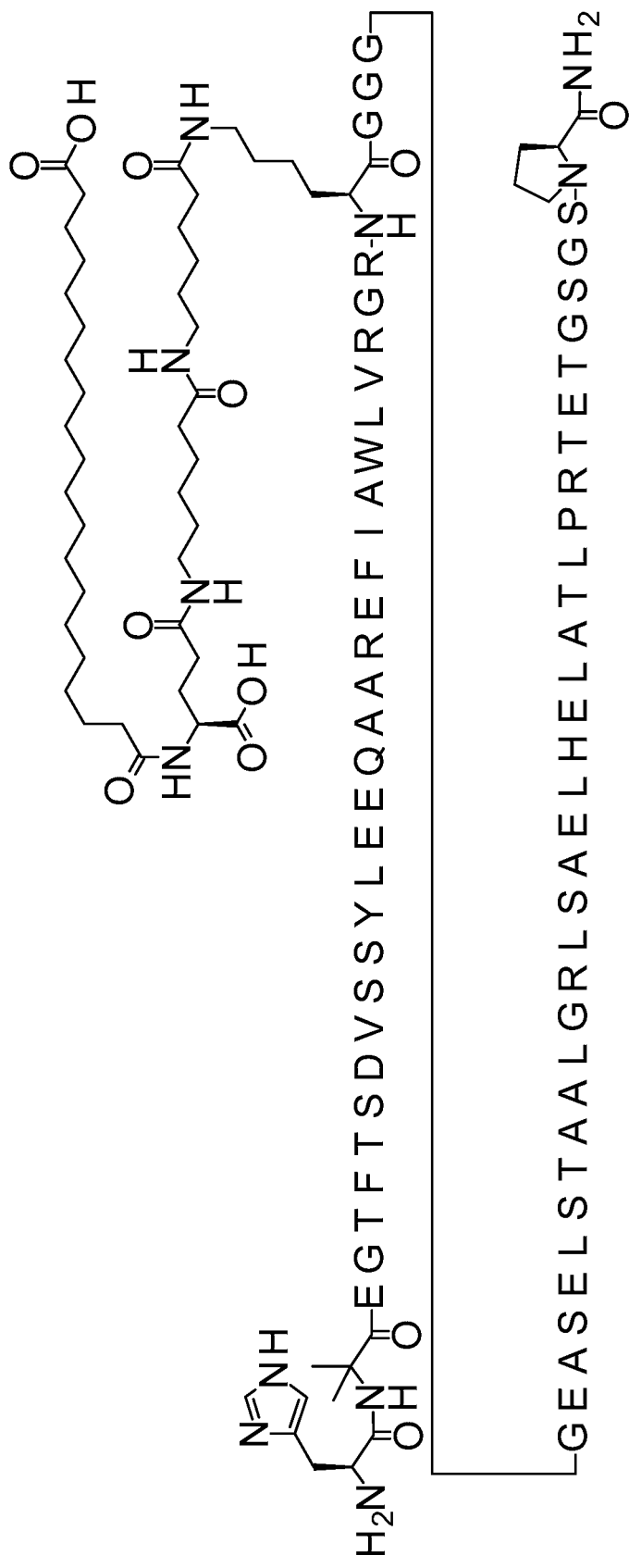
Figure 170:
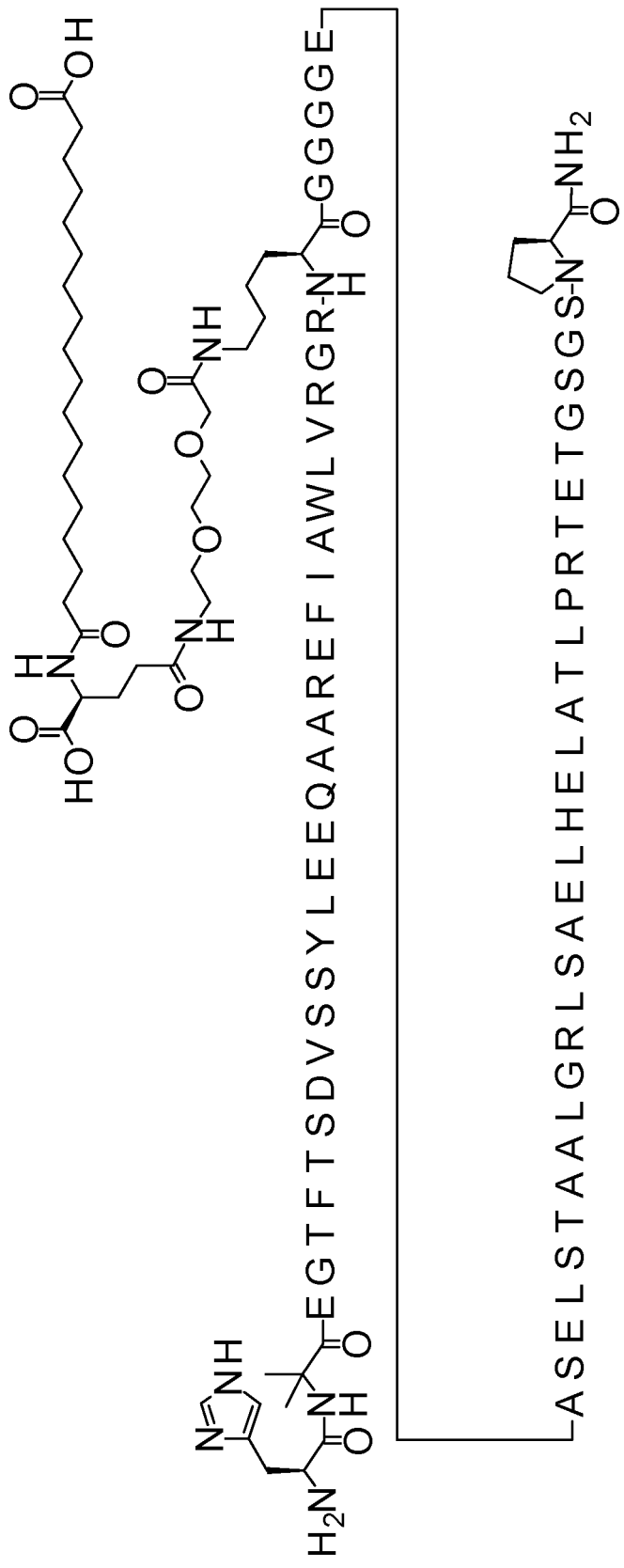
Figure 171:
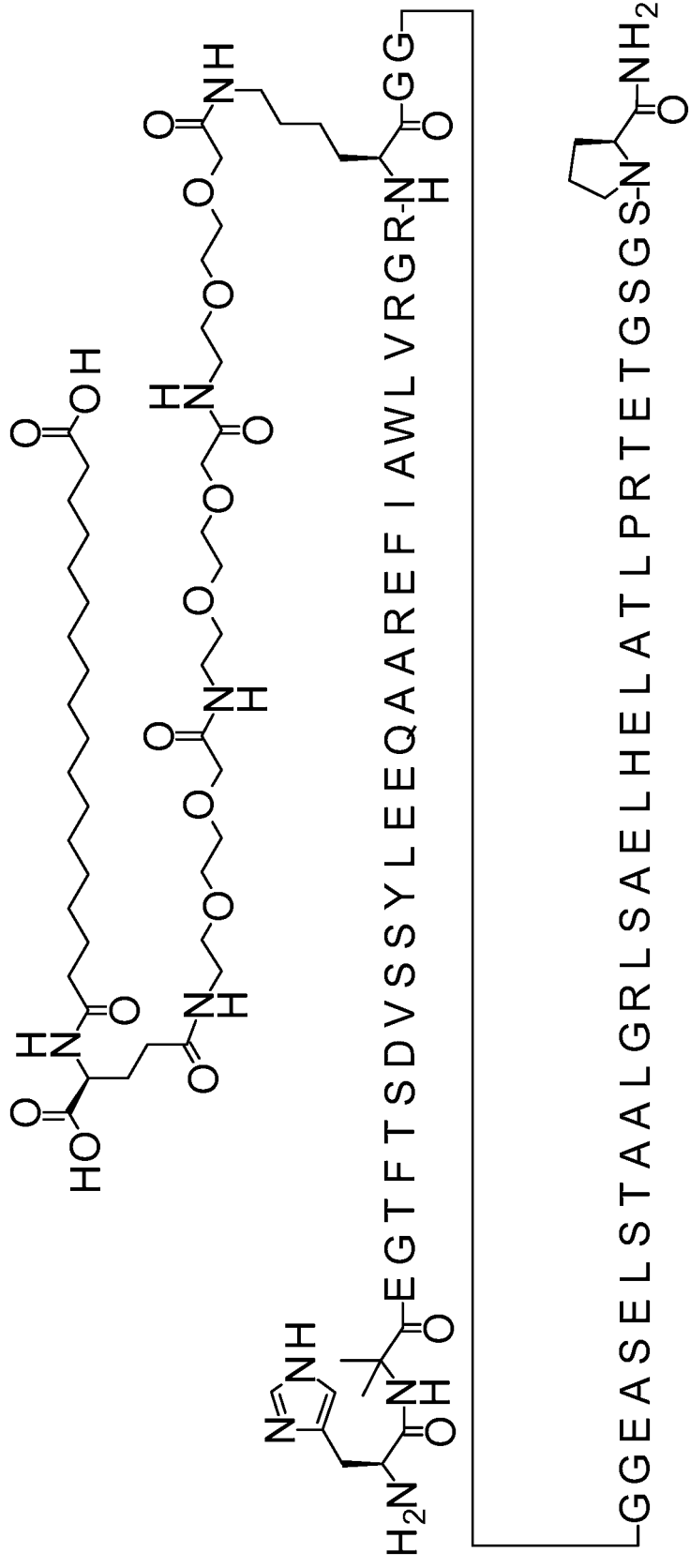
Figure 172:
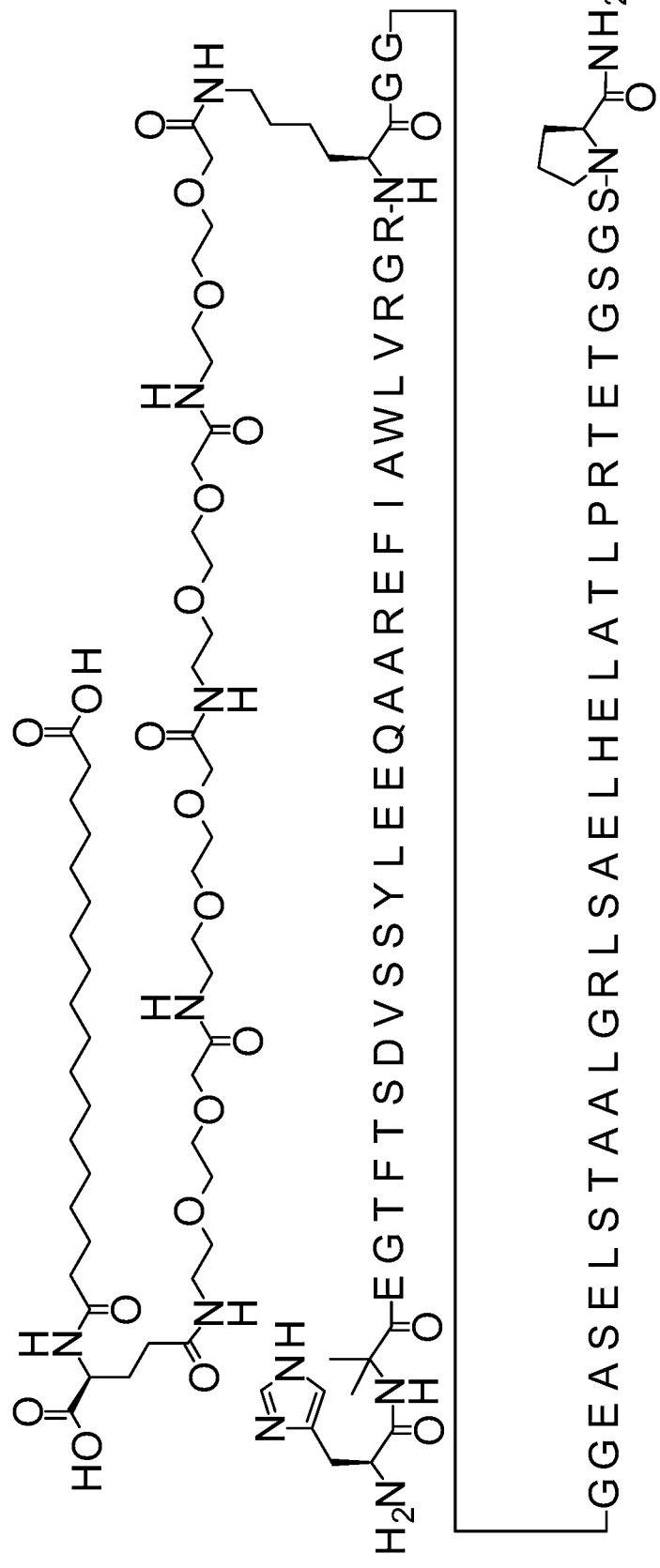
Figure 174:
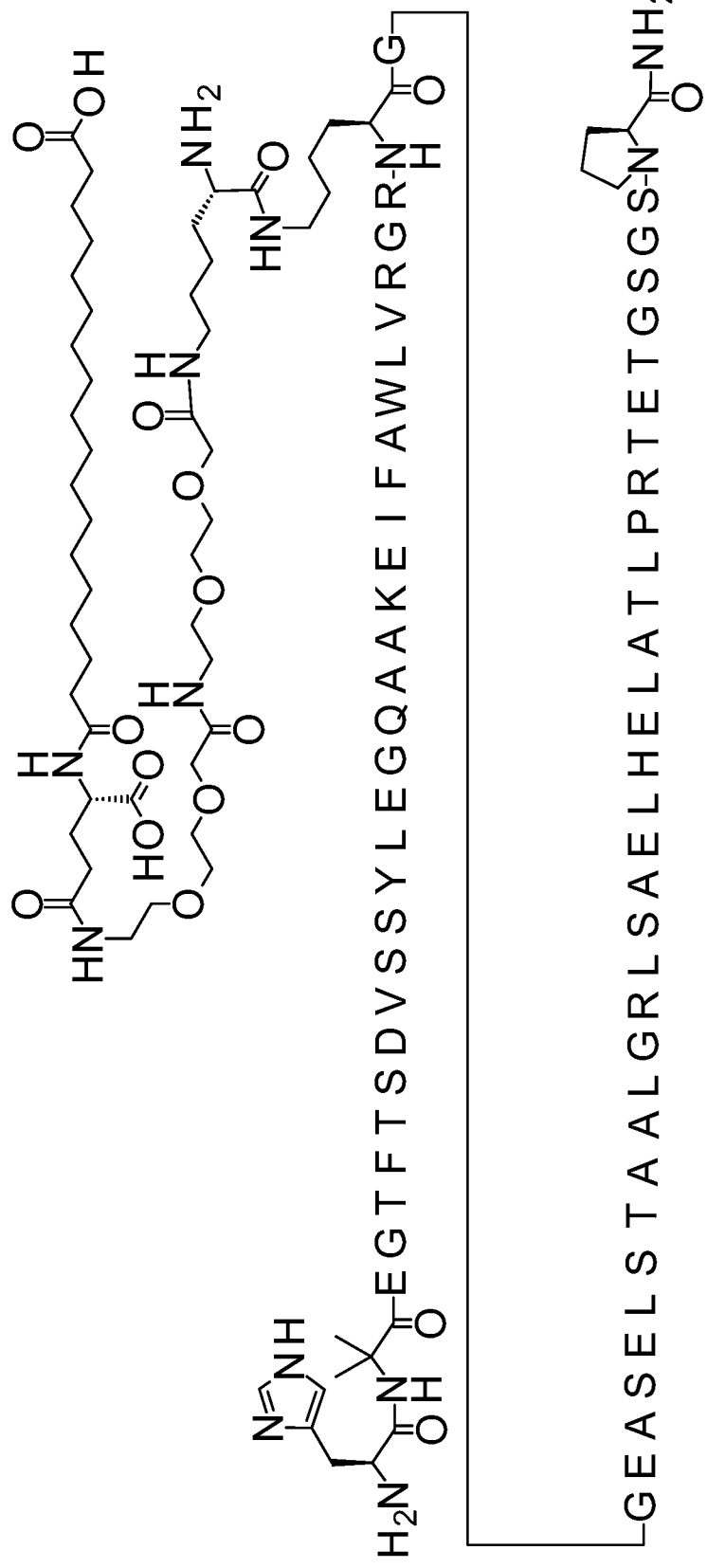
Figure 175:
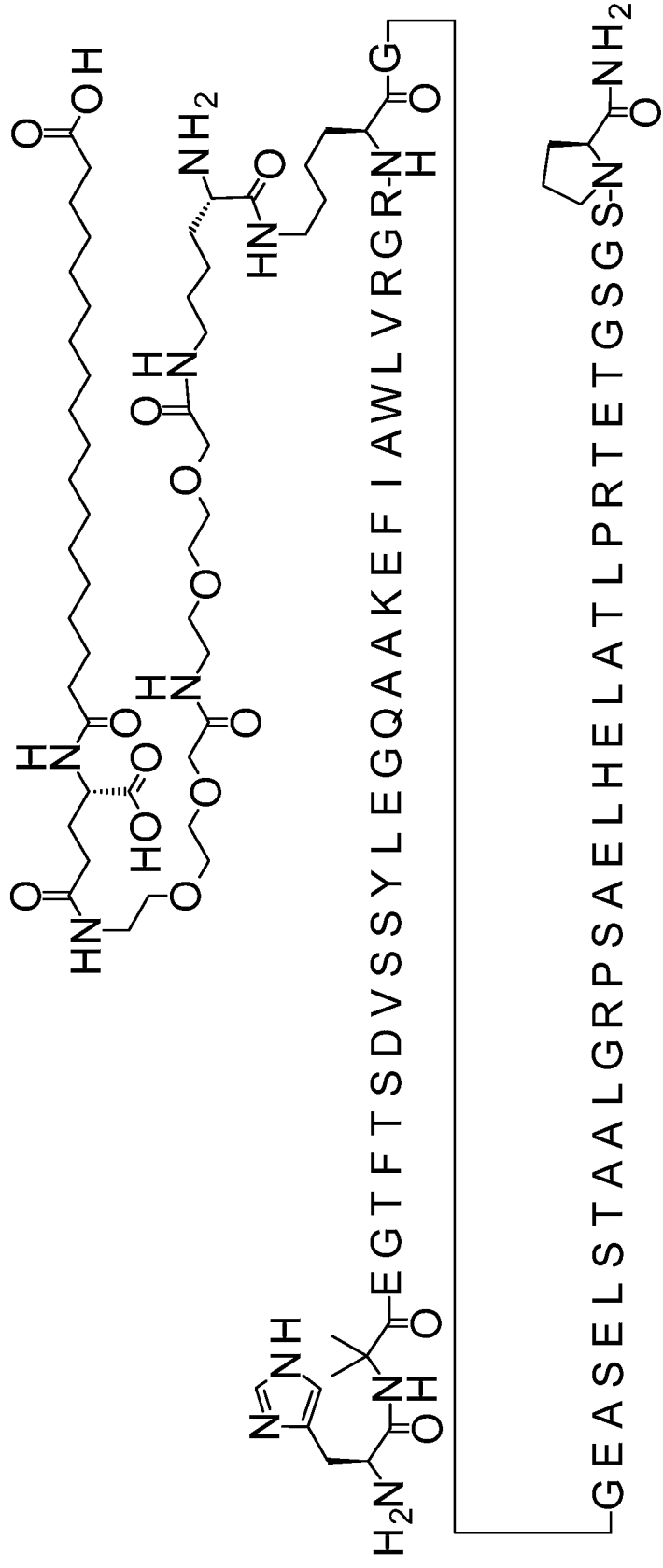
Figure 177:
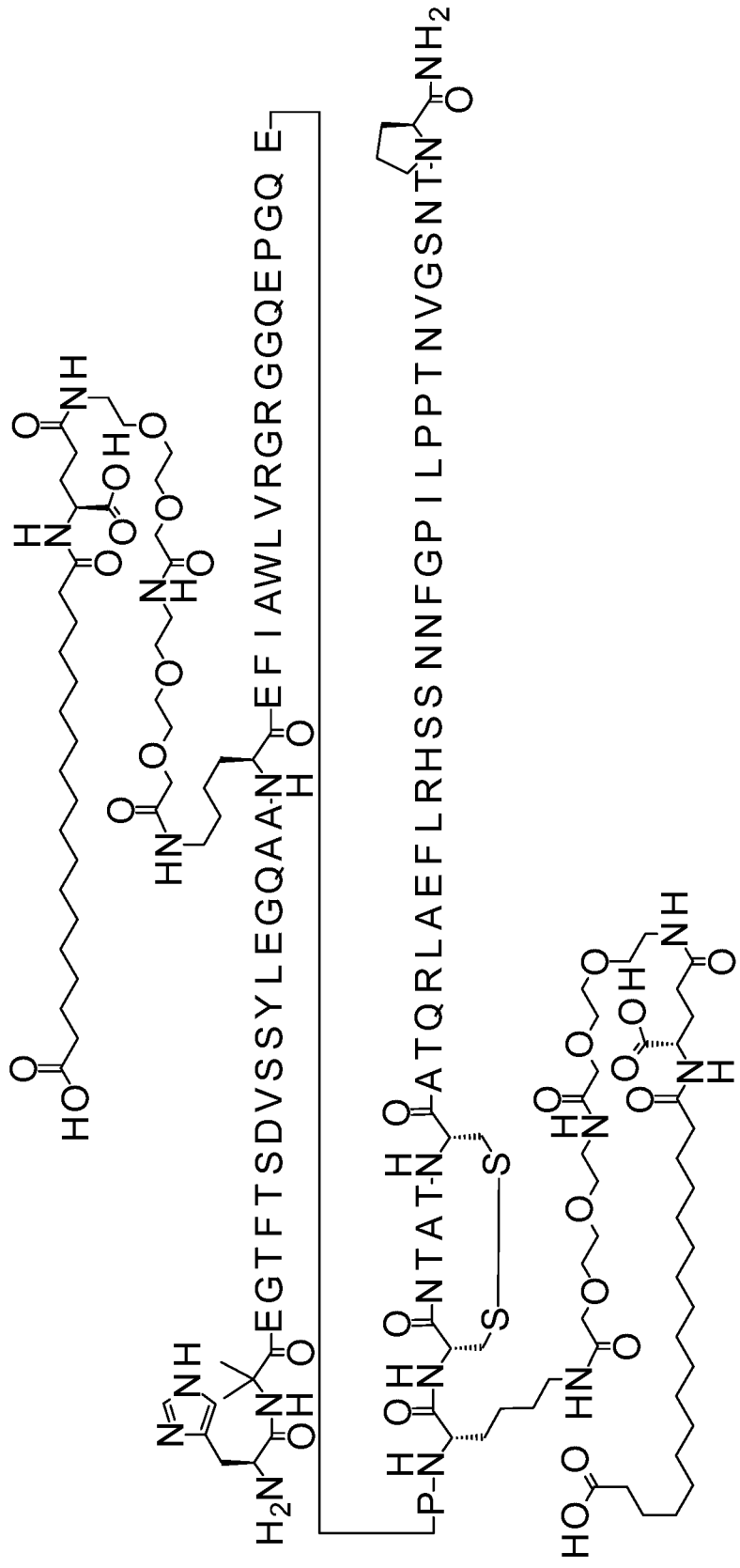
Figure 178:
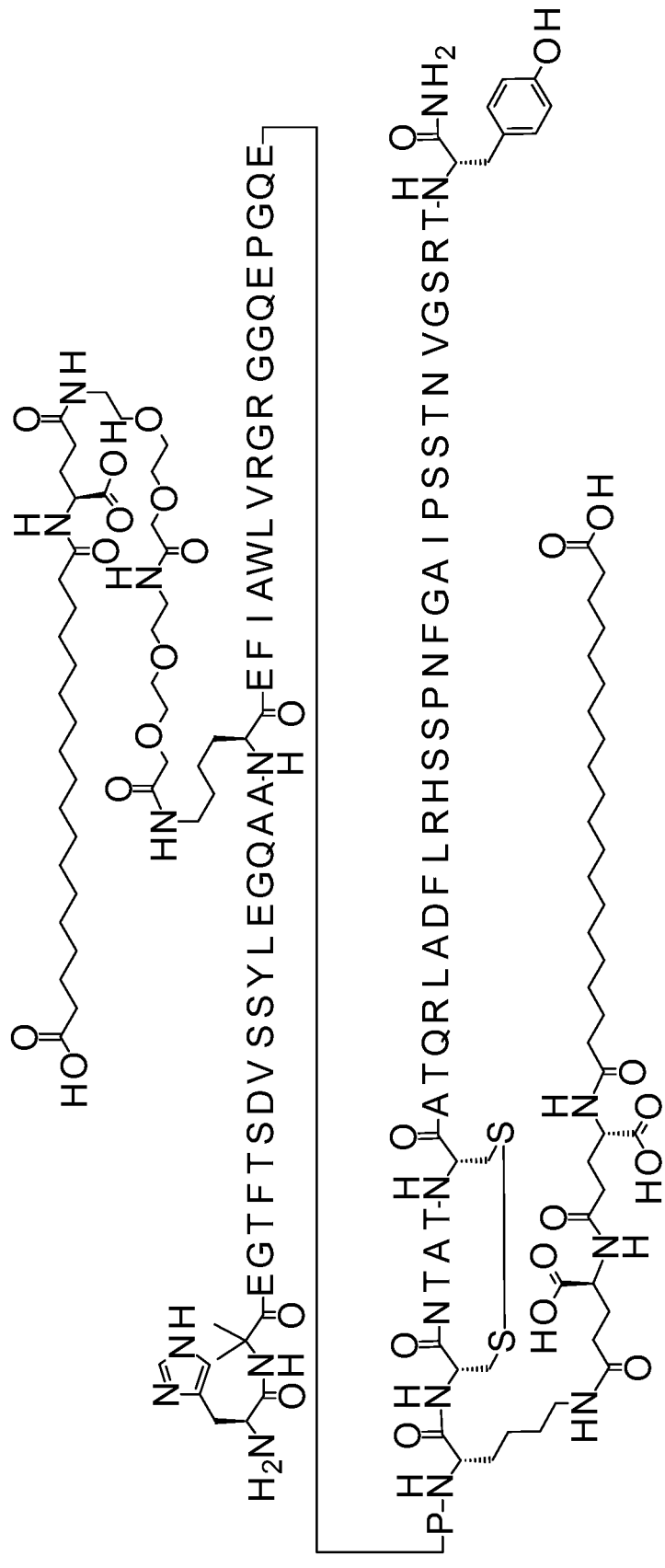
Figure 179:
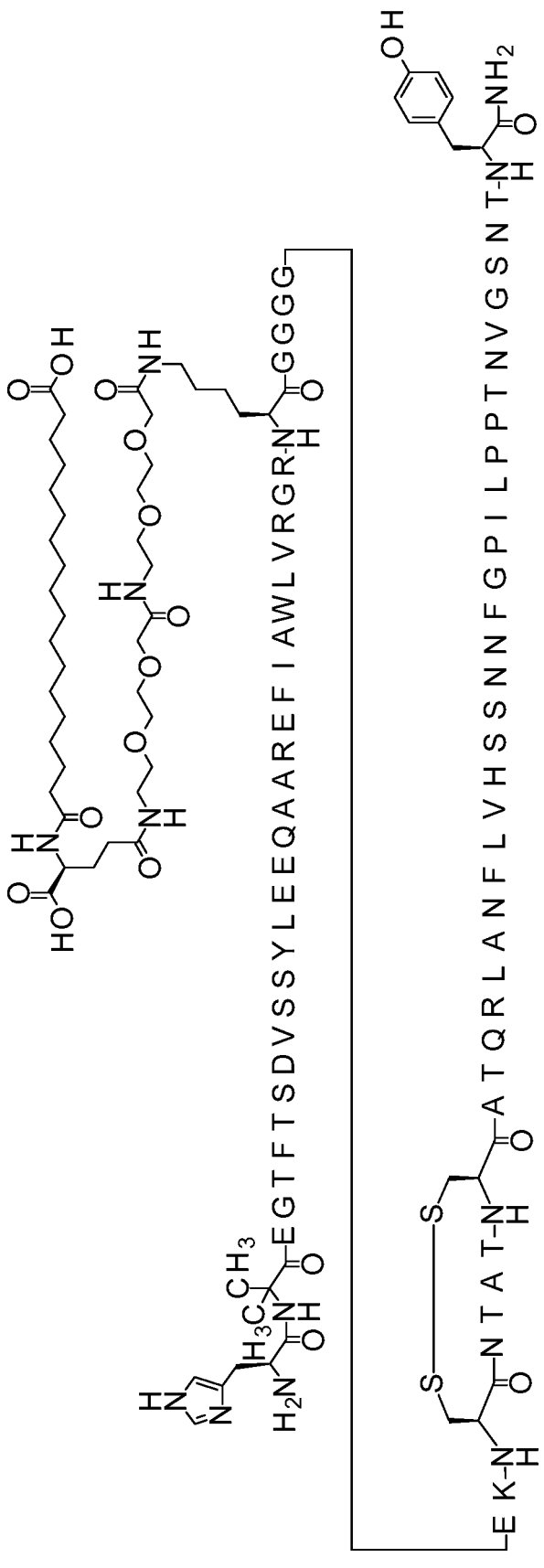
Figure 181:
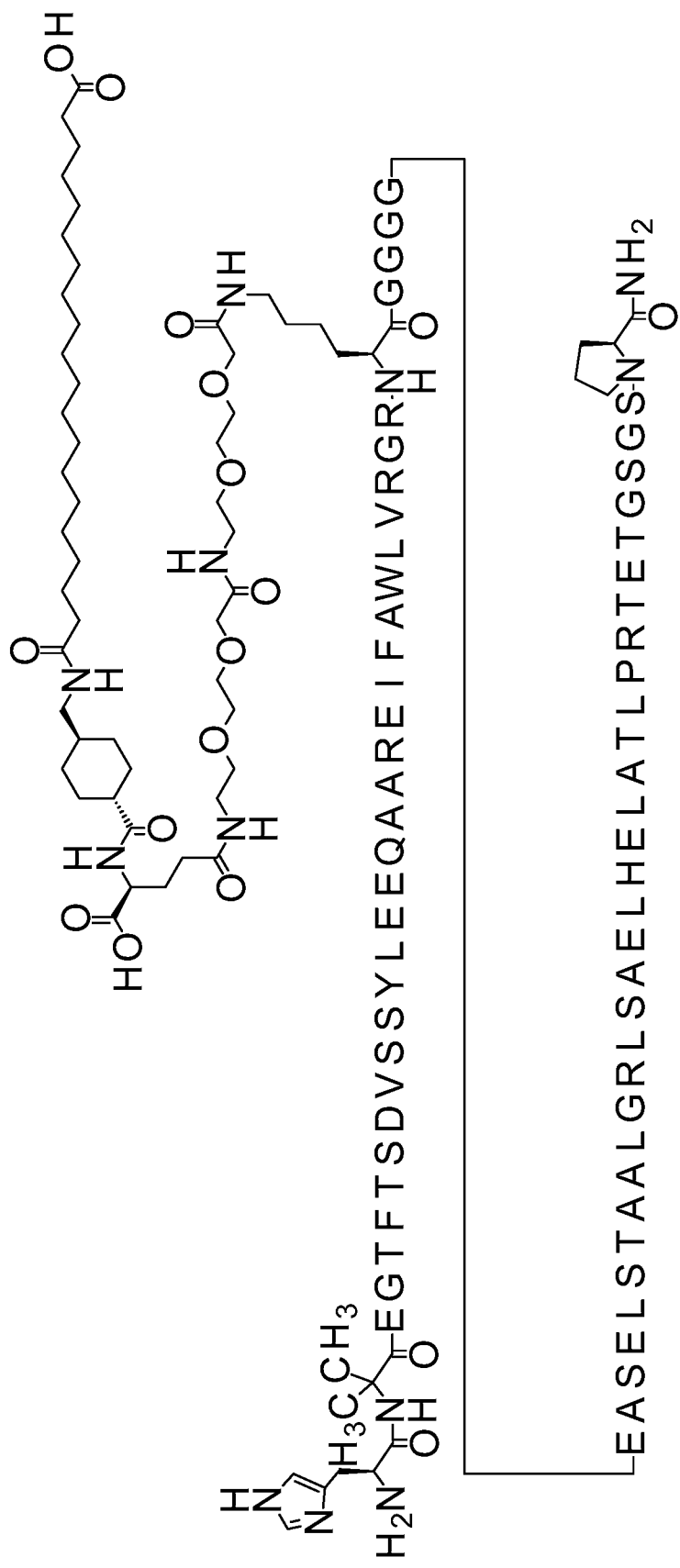
Figure 182:
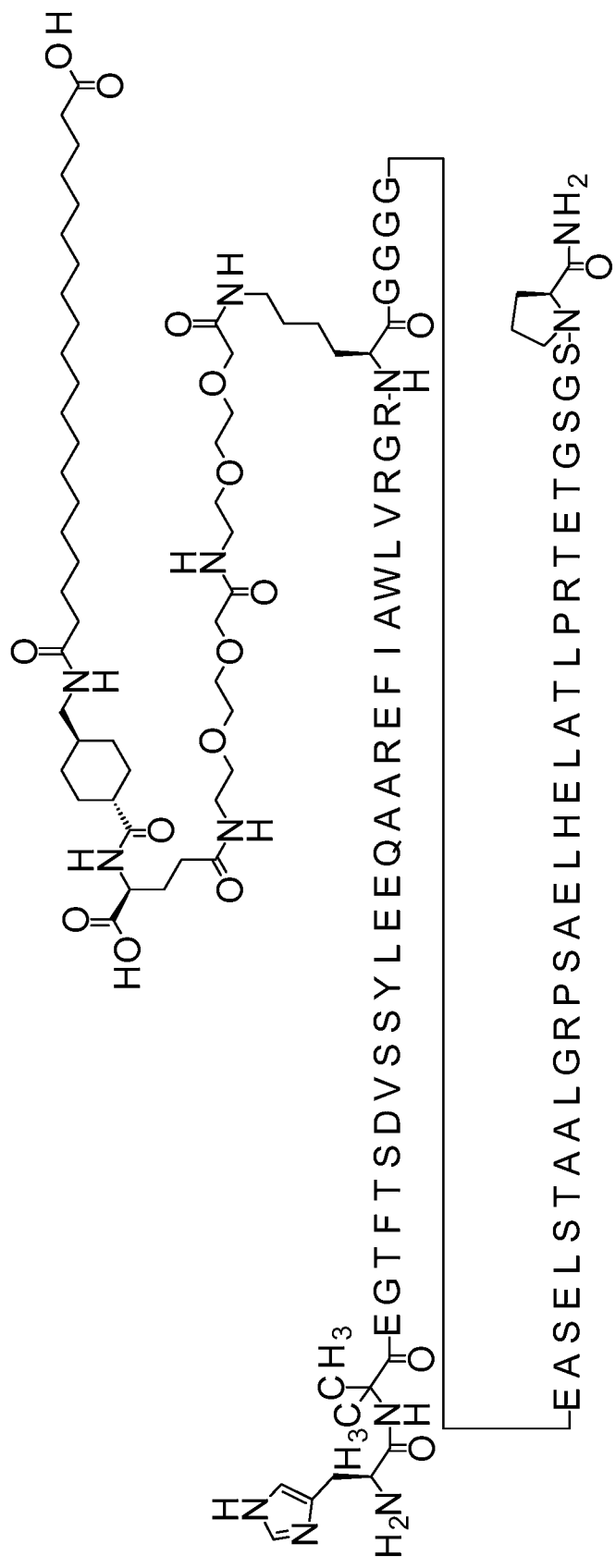
Figure 183:

FIG. 95 depicts compound 0281.
FIG. 96 depicts compound 0284.
FIG. 97 depicts compound 0285.
FIG. 98 depicts compound 0292.
FIG. 99 depicts compound 0294.
FIG. 100 depicts compound 0295.
FIG. 101 depicts compound 0296.
FIG. 102 depicts compound 0297.
FIG. 103 depicts compound 0299.
FIG. 104 depicts compound 0396.
FIG. 105 depicts compound 0397.
FIG. 106 depicts compound 0411.
FIG. 107 depicts compound 0414.
FIG. 108 depicts compound 0415.
FIG. 109 depicts compound 0416.
FIG. 110 depicts compound 0417.
FIG. 111 depicts compound 0431.
FIG. 112 depicts compound 0433.
FIG. 113 depicts compound 0434.
FIG. 114 depicts compound 0435.
FIG. 115 depicts compound 0436.
FIG. 116 depicts compound 0437.
FIG. 117 depicts compound 0438.
FIG. 118 depicts compound 0439.
FIG. 119 depicts compound 0440.
FIG. 120 depicts compound 0472.
FIG. 121 depicts compound 0473.
FIG. 122 depicts compound 0474.
FIG. 123 depicts compound 0475.
FIG. 124 depicts compound 0482.
FIG. 125 depicts compound 0483.
FIG. 126 depicts compound 0484.
FIG. 127 depicts compound 0502.
FIG. 128 depicts compound 0503.
FIG. 129 depicts compound 0504.
FIG. 130 depicts compound 0506.
FIG. 131 depicts compound 0509.
FIG. 132 depicts compound 0511.
FIG. 133 depicts compound 0512.
FIG. 134 depicts compound 0516.
FIG. 135 depicts compound 0518.
FIG. 136 depicts compound 0528.
FIG. 137 depicts compound 0529.
FIG. 138 depicts compound 0539.
FIG. 139 depicts compound 0552.
FIG. 140 depicts compound 0560.
FIG. 141 depicts compound 0561.
FIG. 142 depicts compound 0562.
FIG. 143 depicts compound 0564.
FIG. 144 depicts compound 0565.
FIG. 145 depicts compound 0575.
FIG. 146 depicts compound 0576.
FIG. 147 depicts compound 0577.
FIG. 148 depicts compound 0578.
FIG. 149 depicts compound 0580.
FIG. 150 depicts compound 0581.
FIG. 151 depicts compound 0629.
FIG. 152 depicts compound 0630.
FIG. 153 depicts compound 0631.
FIG. 154 depicts compound 0632.
FIG. 155 depicts compound 0633.
FIG. 156 depicts compound 0634.
FIG. 157 depicts compound 0635.
FIG. 158 depicts compound 0636.
FIG. 159 depicts compound 0637.
FIG. 160 depicts compound 0638.
FIG. 161 depicts compound 0639.
FIG. 162 depicts compound 0640.
FIG. 163 depicts compound 0648.
FIG. 164 depicts compound 0654.
FIG. 165 depicts compound 0655.
FIG. 166 depicts compound 0656.
FIG. 167 depicts compound 0657.
FIG. 168 depicts compound 0658.
FIG. 169 depicts compound 0659.
FIG. 170 depicts compound 0660.
FIG. 171 depicts compound 0661.
FIG. 172 depicts compound 0662.
FIG. 173 depicts compound 0663.
FIGS. 174-182 depict the manufactured comparator compounds that are further described in Example 1.
FIG. 174 depicts comparator compound 0164.
FIG. 175 depicts comparator compound 0185.
FIG. 176 depicts comparator compound 0015.
FIG. 177 depicts comparator compound 0016.
FIG. 178 depicts comparator compound 0668.
FIG. 179 depicts comparator compound 0671.
FIG. 180 depicts comparator compound 0672.
FIG. 181 depicts comparator compound 0167.
FIG. 182 depicts comparator compound 0192.
FIG. 183 depicts amylin receptor agonist 1806.

DESCRIPTION

The current invention relates to a compound comprising an amylin receptor agonist and a GLP-1 receptor agonist. The compound disclosed herein is capable of activating or "agonising" both the GLP-1 receptor and the amylin receptor system: it is a "GLP-1 receptor-amylin receptor co-agonist". The compound may further comprise one, two or three protraction moieties.

The compound disclosed herein may be a potent GLP-1 receptor agonist.

The compound disclosed herein may be a potent amylin receptor agonist.

The compound disclosed herein may provide a similar level of activation of both receptor systems; that is, it may be "balanced". Relatively "balanced" receptor activation is advantageous because the relative ratio of the compound's GLP-1 and amylin receptor agonist portions is locked to the molecule; it is not possible to titrate the two receptor agonists, relative to one another. Ultimately, where a molecule is "balanced", it may be dosed such that both hormone systems are activated without side-effects outweighing benefits.

A compound that is highly potent on one receptor and much less potent on the other would be "unbalanced". For example, a compound that were highly potent on the GLP-1 receptor (for example, having an $EC_{50}$ value of <50 pM) and considerably less potent on the amylin receptor system (for example, having an $EC_{50}$ value of >200 pM) would be "unbalanced"; that is, it would be likely to behave as a GLP-1 receptor agonist only. Such a compound would be unable to achieve optimal efficacy from both hormone systems because side-effects arising from activation of the GLP-1 receptor would prevent administration of a dose sufficiently high to achieve activation of the amylin hormone system as well. The opposite situation might occur if the compound were highly potent on the amylin receptor (for example, having an $EC_{50}$ value of <50 pM) and considerably less potent on the GLP-1 receptor (for example, having an $EC_{50}$ value of >200 pM).

Furthermore, the compounds disclosed herein have a long half-life compared to their native ligands. The compound disclosed herein may possess a long biological half-life, relative to dosing interval, thus reducing the variability in steady state exposure.

The compound disclosed herein may be orally bioavailable, hence suitable for oral administration of subjects in need thereof.

Both the polypeptide backbone and the protraction moiety have been engineered and refined in order to achieve a compound having all of the above properties.

Receptor Agonist

A "receptor agonist" or "agonist" is a ligand, such as a compound, that binds to and activates a biological receptor to produce a biological response. A full agonist may be defined as being one that elicits a response of the same magnitude as the natural ligand (see e.g. "Principles of Biochemistry", A L Lehninger, D L Nelson, M M Cox, Second Edition, Worth Publishers, 1993, page 763). Receptors can be activated by either endogenous agonists, such as endogenous hormones, or exogenous agonists, such as pharmaceutical drugs.

Co-Agonist

In the context of the current invention, a "co-agonist" is a compound comprising two different ligands, each of which binds to a given biological receptor to produce a biological response that is characteristic of the natural ligand. The co-agonists disclosed herein are herein referred to as "GLP-1-amylin co-agonists" or "GLP-1 receptor-amylin receptor co-agonists".

GLP-1 Receptor-Amylin Receptor Co-Agonist

The compound disclosed herein is a "GLP-1 receptor-amylin receptor co-agonist" or "GLP-1-amylin receptor co-agonist". The GLP-1 receptor-amylin receptor co-agonist comprises a GLP-1 receptor agonist, an optional peptide linker and an amylin receptor agonist. The GLP-1 receptor agonist component binds to and activates the GLP-1 receptor and the amylin receptor agonist component binds to and activates at least the human amylin 3 receptor (AMYR3).

The molecular format may be a single chain polypeptide backbone comprising one, two or three lysine (Lys, K) residues. The molecular format may be a single chain polypeptide backbone comprising one, two or three cysteine (Cys, C) residues. The molecular format may be a single chain polypeptide backbone comprising one, two or three lysine (Lys, K) and/or cysteine (Cys, C) residues. The GLP-1 receptor-amylin receptor co-agonist may further comprise 1-3 protraction moieties. A protraction moiety may be covalently bound to said lysine (Lys, K) or cysteine (Cys, C) residue(s).

The amide moiety at the C-terminus of the amylin receptor agonist must be free in order for the amylin receptor agonist to retain maximal bioactivity. Hence, the C-terminal residue of the GLP-1 receptor agonist is covalently linked to the N-terminal residue of either the optional peptide linker or the amylin receptor agonist and the N-terminal residue of the amylin receptor agonist is covalently linked to the C-terminal of either the optional peptide linker or the GLP-1 receptor agonist. When present, the peptide linker comprises 1-30 naturally occurring amino acids.

The polypeptide backbone of the GLP-1 receptor-amylin receptor co-agonist may comprise 1, 2 or 3 lysine residues. The polypeptide backbone of the GLP-1 receptor-amylin receptor co-agonist may comprise 1 or 2 lysine residues. The polypeptide backbone of the GLP-1 receptor-amylin receptor co-agonist may comprise 1 lysine residue.

The polypeptide backbone of the GLP-1 receptor-amylin receptor co-agonist may comprise 1, 2 or 3 cysteine residues. The polypeptide backbone of the GLP-1 receptor-amylin receptor co-agonist may comprise 1 or 2 cysteine residues. The polypeptide backbone of the GLP-1 receptor-amylin receptor co-agonist may comprise 1 cysteine residue.

The polypeptide backbone of the GLP-1 receptor-amylin receptor co-agonist may herein be referred to as "R1" and described by Formula I:
Z1-Z2-Z3,
wherein Z1 is a GLP-1 receptor agonist peptide, Z2 is an optional peptide linker and Z3 is an amylin receptor agonist peptide.

Z1 may comprise a maximum of 9 amino acid modifications, relative to wild type GLP-1 (7-37) (SEQ ID NO: 1). The C-terminus of Z1 is attached either to Z2, when Z2 is present, or to Z3, when Z2 is absent.

Z2 is an optional peptide linker. When present, its N-terminus is attached to the C-terminus of Z1 and its C-terminus is attached to the N-terminus of Z3.

Z3 may comprise a maximum of 7 amino acid modifications, relative to SEQ ID NO: 79. The C-terminus of Z3 is modified with an amide group. The N-terminus of Z3 is attached to the C-terminus of Z2, when Z2 is present, or to the C-terminus of Z1, when Z2 is absent.

Z1-Z2-Z3 comprises one, two or three lysine and/or cysteine residues. Each lysine and/or cysteine residue may be covalently bound to a protraction moiety, which may be referred to herein as "R2-R3", wherein "R2" is an optional linker and "R3" is a protractor.

The GLP-1 receptor-amylin receptor co-agonist may exhibit a variety of properties rendering it useful as a medicament, as described herein.

The GLP-1 receptor-amylin receptor co-agonist may be potent on the GLP-1 receptor and on the amylin receptor. The in vitro potency of the GLP-1 receptor-amylin receptor co-agonist on the GLP-1 receptor and on the amylin-3 receptor may be measured as described in Assays 1 and 2, respectively. The potency of the compound may be described by means of its $EC_{50}$ values. $EC_{50}$ represents the concentration of compound upon which 50% of its maximal effect is observed. The lower the $EC_{50}$ value, the more potent the compound.

When tested as described in Assay 1, the GLP-1 receptor-amylin receptor co-agonist disclosed herein may have an $EC_{50}$ value of less than 300 pM, such as less than 200 pM, such as less than 150 pM, preferably less than 100 pM, such as less than 75 pM, even more preferably less than 50 pM, such as less than 40 pM, such as less than 30 pM, such as less than 20 pM, such as less than 10 pM.

When tested as described in Assay 2, the GLP-1 receptor-amylin receptor co-agonist disclosed herein may have an $EC_{50}$ value of less than 300 pM, such as less than 200 pM, such as less than 150 pM, preferably less than 100 pM, such as less than 75 pM, preferably less than 50 pM, such as less than 40 pM, such as less than 30 pM, such as less than 20 pM, such as less than 10 pM.

The in vivo pharmacology, including half-life, of the GLP-1 receptor-amylin receptor co-agonist described herein may be assessed as described in Examples 4 and 5.

The half-life of the GLP-1 receptor-amylin receptor co-agonist in animal subjects may be as long as 125 hours, or longer. The half-life of the GLP-1 receptor-amylin receptor co-agonist in animal subjects may be at least 4 hours. The half-life of the GLP-1 receptor-amylin receptor co-agonist may be more than 5, 10, 15, 20, 25, 30, 35, 40, 45, 50, 55, 60, 65, 70, 75, 80, 85, 90, 95, 100, 105, 110, 115, 120 hours. The half-life of the GLP-1 receptor-amylin receptor co-agonist may be 15-60 hours, such as 20-55 hours, such as 25-50 hours.

The GLP-1 receptor-amylin receptor co-agonist may be orally bioavailable; that is, present in the bloodstream following per oral administration.

The GLP-1 receptor-amylin receptor co-agonist disclosed herein may reduce food intake in a subject. Administration of the GLP-1 receptor-amylin receptor co-agonist disclosed herein may result in an acute reduction in the intake of food. The in vivo effect of the GLP-1 receptor-amylin receptor co-agonist on food intake in rats may be assessed as described in Example 5. Administration of the GLP-1 receptor-amylin receptor co-agonist disclosed herein may result in a food intake in rats, relative to vehicle, which is 0-90%, such as 0-80%, such as 0-70%, such as 0-60%, preferably 0-50%, even more preferably 0-40%, within 0-24 hours after a single subcutaneous injection of 10 nmol/kg of said co-agonist, wherein a food intake of 0% relative to vehicle means that the rat does not eat. Administration of the GLP-1 receptor-amylin receptor co-agonist disclosed herein may result in a food intake in rats, relative to vehicle, which is 0-90%, such as 0-80%, such as 0-70%, such as 0-60%, preferably 0-50%, even more preferably 0-40%, within 24-48 hours after a single subcutaneous injection of 10 nmol/kg of said co-agonist, wherein a food intake of 0% relative to vehicle means that the rat does not eat.

GLP-1

The term "GLP-1" or "native GLP-1" herein refers to human Glucagon-Like Peptide-1 (GLP-1(7-37)), shown in the sequence listing as SEQ ID NO: 1. In the sequence listing, the amino acid residues are consecutively numbered 1-31. Therefore, the first amino acid in wild type human GLP-1(7-37)—that is, the N-terminal histidine—is number "1" in SEQ ID NO: 1.

GLP-1 Receptor Agonist

The compounds disclosed herein comprise a GLP-1 receptor agonist. A "GLP-1 receptor agonist" may be defined as a ligand which is capable of binding to the GLP-1 receptor and producing a biological response similar to that of the natural ligand, glucagon-like peptide 1 (GLP-1). A "full" GLP-1 receptor agonist may be defined as a GLP-1 receptor agonist which is capable of eliciting a biological response of the same magnitude as GLP-1.

Semaglutide, disclosed in WO2006/097537, Example 4, is an example of an exogenous GLP-1 receptor agonist.

The GLP-1 receptor agonist must have a free N-terminus. Therefore, the compounds disclosed herein comprise a GLP-1 receptor agonist which is attached to either the optional peptide or the amylin receptor agonist at its C-terminus.

The GLP-1 receptor agonist comprises polypeptide "Z1".

The compound disclosed herein may comprise a GLP-1 receptor agonist which is a polypeptide variant of GLP-1 (7-37) (SEQ ID NO: 1). The GLP-1 receptor agonist may be a derivative of a polypeptide variant of GLP-1(7-37).

The GLP-1 receptor agonist may comprise a polypeptide comprising 0, 1, 2 or 3 lysine residues and a maximum of 9 amino acid modifications, relative to human GLP-1 (SEQ ID NO: 1). The GLP-1 receptor agonist may comprise a polypeptide comprising 1 or 2 lysine residues and a maximum of 9 amino acid modifications relative to human GLP-1 (SEQ ID NO: 1). The GLP-1 receptor agonist may comprise a polypeptide comprising 1 lysine residue and a maximum of 9 amino acid modifications, relative to human GLP-1 (SEQ ID NO: 1).

The GLP-1 receptor agonist may comprise a polypeptide comprising 0, 1, 2 or 3 lysine residues and a maximum of 8 amino acid modifications, relative to human GLP-1 (SEQ ID NO: 1). The GLP-1 receptor agonist may comprise a polypeptide comprising 1 or 2 lysine residues and a maximum of 8 amino acid modifications relative to human GLP-1 (SEQ ID NO: 1). The GLP-1 receptor agonist may comprise a polypeptide comprising 1 lysine residue and a maximum of 8 amino acid modifications, relative to human GLP-1 (SEQ ID NO: 1).

The GLP-1 receptor agonist may comprise a polypeptide comprising 0, 1, 2 or 3 lysine residues and a maximum of 7 amino acid modifications, relative to human GLP-1 (SEQ ID NO: 1). The GLP-1 receptor agonist may comprise a polypeptide comprising 1 or 2 lysine residues and a maximum of 7 amino acid modifications relative to human GLP-1 (SEQ ID NO: 1). The GLP-1 receptor agonist may comprise a polypeptide comprising 1 lysine residue and a maximum of 7 amino acid modifications, relative to human GLP-1 (SEQ ID NO: 1).

The GLP-1 receptor agonist may comprise a polypeptide comprising 0, 1, 2 or 3 lysine residues and a maximum of 6 amino acid modifications, relative to human GLP-1 (SEQ ID NO: 1). The GLP-1 receptor agonist may comprise a polypeptide comprising 1 or 2 lysine residues and a maximum of 6 amino acid modifications relative to human GLP-1 (SEQ ID NO: 1). The GLP-1 receptor agonist may comprise a polypeptide comprising 1 lysine residue and a maximum of 6 amino acid modifications, relative to human GLP-1 (SEQ ID NO: 1).

The GLP-1 receptor agonist may comprise a polypeptide comprising 0, 1, 2 or 3 lysine residues and a maximum of 5 amino acid modifications, relative to human GLP-1 (SEQ ID NO: 1). The GLP-1 receptor agonist may comprise a polypeptide comprising 1 or 2 lysine residues and a maximum of 5 amino acid modifications relative to human GLP-1 (SEQ ID NO: 1). The GLP-1 receptor agonist may comprise a polypeptide comprising 1 lysine residue and a maximum of 5 amino acid modifications, relative to human GLP-1 (SEQ ID NO: 1).

The GLP-1 receptor agonist may comprise a polypeptide comprising 0, 1, 2 or 3 lysine residues and a maximum of 4 amino acid modifications, relative to human GLP-1 (SEQ ID NO: 1). The GLP-1 receptor agonist may comprise a polypeptide comprising 1 or 2 lysine residues and a maximum of 4 amino acid modifications relative to human GLP-1 (SEQ ID NO: 1). The GLP-1 receptor agonist may comprise a polypeptide comprising 1 lysine residue and a maximum of 4 amino acid modifications, relative to human GLP-1 (SEQ ID NO: 1).

The GLP-1 receptor agonist may comprise a polypeptide comprising 0, 1, 2 or 3 lysine residues and a maximum of 3 amino acid modifications, relative to human GLP-1 (SEQ ID NO: 1). The GLP-1 receptor agonist may comprise a polypeptide comprising 1 or 2 lysine residues and a maximum of 3 amino acid modifications relative to human GLP-1 (SEQ ID NO: 1). The GLP-1 receptor agonist may comprise a polypeptide comprising 1 lysine residue and a maximum of 3 amino acid modifications, relative to human GLP-1 (SEQ ID NO: 1).

The GLP-1 receptor agonist may comprise a polypeptide comprising 0, 1, 2 or 3 lysine residues and a maximum of 2 amino acid modifications, relative to human GLP-1 (SEQ ID NO: 1). The GLP-1 receptor agonist may comprise a polypeptide comprising 1 or 2 lysine residues and a maximum of 2 amino acid modifications relative to human GLP-1 (SEQ ID NO: 1). The GLP-1 receptor agonist may comprise a polypeptide comprising 1 lysine residue and a maximum of 2 amino acid modifications, relative to human GLP-1 (SEQ ID NO: 1).

The GLP-1 receptor agonist may comprise a polypeptide comprising 0, 1, 2 or 3 cysteine residues and a maximum of 9 amino acid modifications, relative to human GLP-1 (SEQ ID NO: 1). The GLP-1 receptor agonist may comprise a polypeptide comprising 1 or 2 cysteine residues and a maximum of 9 amino acid modifications relative to wild type human GLP-1 (SEQ ID NO: 1). The GLP-1 receptor agonist may comprise a polypeptide comprising 1 cysteine residue and a maximum of 9 amino acid modifications, relative to human GLP-1 (SEQ ID NO: 1).

The GLP-1 receptor agonist may comprise a polypeptide comprising 0, 1, 2 or 3 cysteine residues and a maximum of 8 amino acid modifications, relative to human GLP-1 (SEQ ID NO: 1). The GLP-1 receptor agonist may comprise a polypeptide comprising 1 or 2 cysteine residues and a maximum of 8 amino acid modifications relative to human GLP-1 (SEQ ID NO: 1). The GLP-1 receptor agonist may comprise a polypeptide comprising 1 cysteine residue and a maximum of 8 amino acid modifications, relative to human GLP-1 (SEQ ID NO: 1).

The GLP-1 receptor agonist may comprise a polypeptide comprising 0, 1, 2 or 3 cysteine residues and a maximum of 7 amino acid modifications, relative to human GLP-1 (SEQ ID NO: 1). The GLP-1 receptor agonist may comprise a polypeptide comprising 1 or 2 cysteine residues and a maximum of 7 amino acid modifications relative to human GLP-1 (SEQ ID NO: 1). The GLP-1 receptor agonist may comprise a polypeptide comprising 1 cysteine residue and a maximum of 7 amino acid modifications, relative to human GLP-1 (SEQ ID NO: 1).

The GLP-1 receptor agonist may comprise a polypeptide comprising 0, 1, 2 or 3 cysteine residues and a maximum of 6 amino acid modifications, relative to human GLP-1 (SEQ ID NO: 1). The GLP-1 receptor agonist may comprise a polypeptide comprising 1 or 2 cysteine residues and a maximum of 6 amino acid modifications relative to human GLP-1 (SEQ ID NO: 1). The GLP-1 receptor agonist may comprise a polypeptide comprising 1 cysteine residue and a maximum of 6 amino acid modifications, relative to human GLP-1 (SEQ ID NO: 1).

The GLP-1 receptor agonist may comprise a polypeptide comprising 0, 1, 2 or 3 cysteine residues and a maximum of 5 amino acid modifications, relative to human GLP-1 (SEQ ID NO: 1). The GLP-1 receptor agonist may comprise a polypeptide comprising 1 or 2 cysteine residues and a maximum of 5 amino acid modifications relative to human GLP-1 (SEQ ID NO: 1). The GLP-1 receptor agonist may comprise a polypeptide comprising 1 cysteine residue and a maximum of 5 amino acid modifications, relative to human GLP-1 (SEQ ID NO: 1).

The GLP-1 receptor agonist may comprise a polypeptide comprising 0, 1, 2 or 3 cysteine residues and a maximum of 4 amino acid modifications, relative to human GLP-1 (SEQ ID NO: 1). The GLP-1 receptor agonist may comprise a polypeptide comprising 1 or 2 cysteine residues and a maximum of 4 amino acid modifications relative to human GLP-1 (SEQ ID NO: 1). The GLP-1 receptor agonist may comprise a polypeptide comprising 1 cysteine residue and a maximum of 4 amino acid modifications, relative to human GLP-1 (SEQ ID NO: 1).

The GLP-1 receptor agonist may comprise a polypeptide comprising 0, 1, 2 or 3 cysteine residues and a maximum of 3 amino acid modifications, relative to human GLP-1 (SEQ ID NO: 1). The GLP-1 receptor agonist may comprise a polypeptide comprising 1 or 2 cysteine residues and a maximum of 3 amino acid modifications relative to human GLP-1 (SEQ ID NO: 1). The GLP-1 receptor agonist may comprise a polypeptide comprising 1 cysteine residue and a maximum of 3 amino acid modifications, relative to human GLP-1 (SEQ ID NO: 1).

The GLP-1 receptor agonist may comprise a polypeptide comprising 0, 1, 2 or 3 cysteine residues and a maximum of 2 amino acid modifications, relative to human GLP-1 (SEQ ID NO: 1). The GLP-1 receptor agonist may comprise a polypeptide comprising 1 or 2 cysteine residues and a maximum of 2 amino acid modifications relative to human GLP-1 (SEQ ID NO: 1). The GLP-1 receptor agonist may comprise a polypeptide comprising 1 cysteine residue and a maximum of 2 amino acid modifications, relative to human GLP-1 (SEQ ID NO: 1).

The GLP-1 receptor agonist may comprise a phenylalanine residue (Phe, F), tryptophan (Trp, W) or tyrosine (Tyr, Y) residue at position 28 relative to the amino acid sequence and numbering of human GLP-1(7-37). Relative to SEQ ID NO: 1, the numbering is shifted by −6, as shown in Formula II, SEQ ID NO: 238 and SEQ ID NO: 255. Hence, the GLP-1 receptor agonist may comprise a phenylalanine residue (Phe, F), tryptophan (Trp, W) or tyrosine (Tyr, Y) residue at position 22, relative to SEQ ID NO: 1, SEQ ID NO: 238 or SEQ ID NO: 255. The GLP-1 receptor agonist may not comprise an isoleucine (Iie, 1) at position 22, relative to SEQ ID NO: 1, SEQ ID NO: 238 or SEQ ID NO: 255.

The GLP-1 receptor agonist may comprise an isoleucine (Iie, 1) leucine (Leu, L) or valine (Val, V) residue at position 29, relative to the amino acid sequence and numbering of human GLP-1(7-37). Relative to SEQ ID NO: 1, the numbering is shifted by −6, as shown in Formula II and SEQ ID NO: 238. Hence, the GLP-1 receptor agonist may comprise an isoleucine (Iie, 1) leucine (Leu, L) or valine (Val, V) residue at position 23, relative to SEQ ID NO: 1, SEQ ID NO: 238 or SEQ ID NO: 255.

The GLP-1 receptor agonist may comprise an Imp (imidazopropionyl or deamino histidine) of formula Chem. 1 at position 7, relative to the amino acid sequence and numbering of human GLP-1(7-37). Relative to SEQ ID NO: 1, the numbering is shifted by −6, as shown in Formula II and SEQ ID NO: 238.

Chem. 1

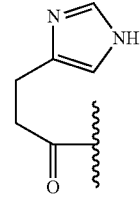

The GLP-1 receptor agonist may comprise an Aib (alpha (α)-aminoisobutyryl, α-aminoisobutyric acid or α-methylalanine) of formula Chem. 2 at position 8, relative to the relative to the amino acid sequence and numbering of human GLP-1(7-37). Relative to SEQ ID NO: 1, the numbering is shifted by −6, as shown in Formula II and SEQ ID NO: 238.

Chem 2

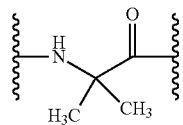

The GLP-1 receptor agonist may comprise a lysine (Lys, K) residue at any one of positions 9, 10, 12, 16, 17, 20, 21, 24, 25, 28, 29, 30 or 31, relative to SEQ ID NO: 238 or SEQ ID NO: 255.

The GLP-1 receptor agonist disclosed herein may have Formula II, depicted in the sequence listing (SEQ ID NO: 238) as follows:

Xaa1-Xaa2-Glu-Gly-Thr-Phe-Thr-Ser-Xaa9-Xaa10-Ser-Xaa12-Tyr-Leu-Glu-Xaa16-Xaa17-Ala-Xaa19-Xaa20-Xaa21-Xaa22-Xaa23-Xaa24-Xaa25-Leu-Val-Xaa28-Xaa29-Xaa30-Xaa31, wherein
Xaa1 is His (H) or Imp,
Xaa2 is Aib, Ala (A), Gly (G) or Trp (W),
Xaa9 is Cys (C), Asp (D) or Lys (K),
Xaa10 is Cys (C), Lys (K) or Val (V),
Xaa12 is Cys (C), Lys (K), Arg (R) or Ser (S),
Xaa16 is Cys (C), Glu (E), Gly (G) or Lys (K),
Xaa17 is Cys (C), Gin (Q) or Lys (K),
Xaa19 is Ala (A) or Val (V),
Xaa20 is Cys (C), Lys (K) or Arg (R),
Xaa21 is Cys (C), Glu (E) or Lys (K),
Xaa22 is Phe (F), Trp (W) or Tyr (Y),
Xaa23 is lie (I), Leu (L) or Val (V),
Xaa24 is Ala (A), Cys (C), Glu (E) or Lys (K),
Xaa25 is Cys (C), Lys (K) or Trp (W),
Xaa28 is Cys (C), Lys (K) or Arg (R),
Xaa29 is Cys (C), Lys (K) or Gly (G),
Xaa30 is Cys (C), Ala (A), Gly (G), Lys (K), Arg (R) or absent,
Xaa31 is Ala (A), Cys (C), Lys (K), Gly (G), Gln (Q) or absent.

The skilled person often refers to the amino acid modifications of a GLP-1 receptor agonist by reference to the standard human, wild-type GLP-1(7-37) nomenclature. In the literature, the first amino acid in GLP-1(7-37) is referred to as being number 7, and subsequent amino acid residues are numbered accordingly, ending with a glycine at number 37.

Therefore, the skilled person might number the residues in Formula II as follows, Xaa1 of Formula II corresponding to Xaa7 in GLP-1(7-37), and so on:

Xaa7-Xaa8-Glu-Gly-Thr-Phe-Thr-Ser-Xaa15-Xaa16-Ser-Xaa18-Tyr-Leu-Glu-Xaa22-Xaa23-Ala-Xaa25-Xaa26-Xaa27-Xaa28-Xaa29-Xaa30-Xaa31-Leu-Val-Xaa34-Xaa35-Xaa36-Xaa37, wherein:
Xaa7 is His (H) or Imp,
Xaa8 is Aib, Ala (A), Gly (G), Trp (W),
Xaa15 is Cys (C), Asp (D) or Lys (K),
Xaa16 is Cys (C), Lys (K) or Val (V),
Xaa18 is Cys (C), Lys (K), Arg (R) or Ser (S),
Xaa22 is Cys (C), Glu (E), Gly (G) or Lys (K),
Xaa23 is Cys (C), Gln (Q) or Lys (K),
Xaa25 is Ala (A) or Val (V),
Xaa26 is Cys (C), Lys (K) or Arg (R),
Xaa27 is Cys (C), Glu (E) or Lys (K),
Xaa28 is Phe (F), Trp (W) or Tyr (Y),
Xaa29 is Ile (I), Leu (L) or Val (V),
Xaa30 is Ala (A), Cys (C), Glu (E) or Leu (L),
Xaa31 is Cys (C), Lys (K) or Trp (W),
Xaa34 is Cys (C), Lys (K) or Arg (R)
Xaa35 is Cys (C), Lys (K) or Gly (G),
Xaa36 is Cys (C), Ala (A), Gly (G), Lys (K), Arg (R) or absent,
Xaa37 is Ala (A), Cys (C), Lys (K), Gly (G), Gln (Q) or absent.

The GLP-1 receptor agonist disclosed herein may have Formula II, depicted in the sequence listing (SEQ ID NO: 255) as follows:

Xaa1-Xaa2-Glu-Gly-Thr-Phe-Thr-Ser-Xaa9-Xaa10-Ser-Xaa12-Tyr-Leu-Glu-Xaa16-Xaa17-Ala-Xaa19-Xaa20-Xaa21-Xaa22-Xaa23-Xaa24-Xaa25-Leu-Val-Xaa28-Xaa29-Xaa30-Xaa31, wherein
Xaa1 is His (H) or Imp,
Xaa2 is Aib, Ala (A), Gly (G) or Trp (W),
Xaa9 is Asp (D) or Lys (K),
Xaa10 is Lys (K) or Val (V),
Xaa12 is Lys (K), Arg (R) or Ser (S),
Xaa16 is Glu (E), Gly (G) or Lys (K),
Xaa17 is Gln (Q) or Lys (K),
Xaa19 is Ala (A) or Val (V),
Xaa20 is Lys (K) or Arg (R),
Xaa21 is Glu (E) or Lys (K),
Xaa22 is Phe (F),
Xaa23 is lie (I),
Xaa24 is Ala (A), Glu (E) or Lys (K),
Xaa25 is Lys (K) or Trp (W),
Xaa28 is Lys (K) or Arg (R),
Xaa29 is Lys (K) or Gly (G),
Xaa30 is Ala (A), Gly (G), Lys (K), Arg (R) or absent,
Xaa31 is Ala (A), Lys (K), Gly (G), Gln (Q) or absent.

The GLP-1 receptor agonist peptide (Z1) may be described by reference to sequences in the sequence listing. The GLP-1 receptor co-agonist disclosed herein may comprise a GLP-1 receptor agonist peptide (Z1) which is selected from any one of those depicted in SEQ ID NOs 2-78.

The GLP-1 receptor agonists disclosed herein agonise, or activate, the GLP-1 receptor. This term refers to the ability to bind to the GLP-1 receptor and initiate a signal transduction pathway resulting in insulinotropic action or other physiological effects as is known in the art. The GLP-receptor agonists disclosed herein may be tested for GLP-1 receptor activation as described in Examples 2 (in vitro), 4 and 5 (in vivo).

The more potent the compound, the lower its $EC_{50}$ value. A compound is considered a highly potent GLP-1 receptor agonist when its $EC_{50}$ value is below approximately 50 pM. A compound is considered to have medium potency when its $EC_{50}$ value is 50-250 pM. A compound is considered to have a poorer potency when its $EC_{50}$ value value is 250-1000 pM. A compound is considered inactive when its $EC_{50}$ value is above 1000 pM.

The GLP-1 receptor agonist may have an $EC_{50}$ in a human GLP-1 receptor functional assay (see Assay 1) of about 300 pM or less. The GLP-1 receptor agonist may have an $EC_{50}$ in a human GLP-1 receptor functional assay of about 200 pM or less. The GLP-1 receptor agonist may have an $EC_{50}$ in a human GLP-1 receptor functional assay of about 150 pM or less. The GLP-1 receptor agonist may have an $EC_{50}$ in a human GLP-1 receptor functional assay of about 100 pM or less. The GLP-1 receptor agonist may have an $EC_{50}$ in a human GLP-1 receptor functional assay of about 90 pM or less. The GLP-1 receptor agonist may have an $EC_{50}$ in a human GLP-1 receptor functional assay of about 80 pM or less. The GLP-1 receptor agonist may have an $EC_{50}$ in a human GLP-1 receptor functional assay of about 70 pM or less. The GLP-1 receptor agonist may have an $EC_{50}$ in a human GLP-1 receptor functional assay of about 60 pM or less. Preferably, the GLP-1 receptor agonist has an $EC_{50}$ in a human GLP-1 receptor functional assay of about 50 pM or less. The GLP-1 receptor agonist may have an $EC_{50}$ in a human GLP-1 receptor functional assay of about 40 pM or less. The GLP-1 receptor agonist may have an $EC_{50}$ in a human GLP-1 receptor functional assay of about 30 pM or less. The GLP-1 receptor agonist may have an $EC_{50}$ in a human GLP-1 receptor functional assay of about 25 pM or less. The GLP-1 receptor agonist may have an $EC_{50}$ in a human GLP-1 receptor functional assay of about 20 pM or less. The GLP-1 receptor agonist may have an $EC_{50}$ in a human GLP-1 receptor functional assay of about 19 pM or less. The GLP-1 receptor agonist may have an $EC_{50}$ in a human GLP-1 receptor functional assay of about 18 pM or less. The GLP-1 receptor agonist may have an $EC_{50}$ in a human GLP-1 receptor functional assay of about 17 pM or less. The GLP-1 receptor agonist may have an $EC_{50}$ in a human GLP-1 receptor functional assay of about 16 pM or less. The GLP-1 receptor agonist may have an $EC_{50}$ in a human GLP-1 receptor functional assay of about 15 pM or less. The GLP-1 receptor agonist may have an $EC_{50}$ in a human GLP-1 receptor functional assay of about 14 pM or less. The GLP-1 receptor agonist may have an $EC_{50}$ in a human GLP-1 receptor functional assay of about 13 pM or less. The GLP-1 receptor agonist may have an $EC_{50}$ in a human GLP-1 receptor functional assay of about 12 pM or less. The GLP-1 receptor agonist may have an $EC_{50}$ in a human GLP-1 receptor functional assay of about 11 pM or less. The GLP-1 receptor agonist may have an $EC_{50}$ in a human GLP-1 receptor functional assay of about 10 pM or less. The GLP-1 receptor agonist may have an $EC_{50}$ in a human GLP-1 receptor functional assay of about 5 pM or less.

The GLP-1 receptor agonist may have a similar potency as semaglutide.

Amylin

The term "amylin" herein refers to a polypeptide having the same amino acid sequence as an endogenous amylin, such as human amylin.

Amylin Receptor

An amylin receptor agonist may activate or agonise the calcitonin receptor (CTR) and/or the amylin receptors (AMYRs). Amylin receptors consist of heterodimers of two components: the calcitonin receptor (CTR) and one of three receptor activity-modifying proteins (RAMP1-3), resulting in three possible complexes, AMYR1-3. Unless otherwise specified herein, "amylin receptor" at least refers to amylin receptor 3 (AMYR3). Nonetheless, some cross-reactivity can be expected.

Amylin Receptor Agonists

The compounds disclosed herein comprise an amylin receptor agonist. An "amylin receptor agonist" may be defined as a chemical entity which is capable of binding to the amylin receptor and is capable of activating it. In the context of the current invention, an "amylin receptor agonist" is capable of binding to and activating at least the AMYR3 complex. The amylin receptor agonist may also be capable of agonising the calcitonin receptor and AMYR1-2.

Examples of endogenous amylin receptor agonists are human amylin and human calcitonin. Examples of exogenous amylin receptor agonists are pramlintide and cagrilintide (disclosed in WO2012/168432).

The amylin receptor agonist disclosed herein comprises peptide "Z3". The amylin receptor agonist disclosed herein comprises a C-terminal amide, which is essential for bioactivity.

The amylin receptor agonist may comprise a polypeptide comprising 0, 1, 2 or 3 lysine residues and a maximum of 7 amino acid modifications, relative to SEQ ID NO: 79. The amylin receptor agonist may comprise a polypeptide comprising 1 or 2 lysine residues and a maximum of 7 amino acid modifications, relative to SEQ ID NO: 79. The amylin receptor agonist may comprise a polypeptide comprising 1 lysine residue and a maximum of 7 amino acid modifications, relative to SEQ ID NO: 79.

The amylin receptor agonist may comprise a polypeptide comprising 0, 1, 2 or 3 lysine residues and a maximum of 6 amino acid modifications, relative to SEQ ID NO: 79. The amylin receptor agonist may comprise a polypeptide comprising 1 or 2 lysine residues and a maximum of 6 amino acid modifications, relative to SEQ ID NO: 79. The amylin receptor agonist may comprise a polypeptide comprising 1 lysine residue and a maximum of 6 amino acid modifications, relative to SEQ ID NO: 79.

The amylin receptor agonist may comprise a polypeptide comprising 0, 1, 2 or 3 lysine residues and a maximum of 5 amino acid modifications, relative to SEQ ID NO: 79. The amylin receptor agonist may comprise a polypeptide comprising 1 or 2 lysine residues and a maximum of 5 amino acid modifications, relative to SEQ ID NO: 79. The amylin receptor agonist may comprise a polypeptide comprising 1 lysine residue and a maximum of 5 amino acid modifications, relative to SEQ ID NO: 79.

The amylin receptor agonist may comprise a polypeptide comprising 0, 1, 2 or 3 lysine residues and a maximum of 4 amino acid modifications, relative to SEQ ID NO: 79. The amylin receptor agonist may comprise a polypeptide comprising 1 or 2 lysine residues and a maximum of 4 amino acid modifications, relative to SEQ ID NO: 79. The amylin receptor agonist may comprise a polypeptide comprising 1 lysine residue and a maximum of 4 amino acid modifications, relative to SEQ ID NO: 79.

The amylin receptor agonist may comprise a polypeptide comprising 0, 1, 2 or 3 lysine residues and a maximum of 3 amino acid modifications, relative to SEQ ID NO: 79. The amylin receptor agonist may comprise a polypeptide comprising 1 or 2 lysine residues and a maximum of 3 amino acid modifications, relative to SEQ ID NO: 79. The amylin receptor agonist may comprise a polypeptide comprising 1 lysine residue and a maximum of 3 amino acid modifications, relative to SEQ ID NO: 79.

The amylin receptor agonist may comprise a polypeptide comprising 0, 1, 2 or 3 lysine residues and a maximum of 2 amino acid modifications, relative to SEQ ID NO: 79. The amylin receptor agonist may comprise a polypeptide comprising 1 or 2 lysine residues and a maximum of 2 amino acid modifications, relative to SEQ ID NO: 79. The amylin receptor agonist may comprise a polypeptide comprising 1 lysine residue and a maximum of 2 amino acid modifications, relative to SEQ ID NO: 79.

The amylin receptor agonist may comprise a polypeptide comprising 0, 1, 2 or 3 lysine residues and 1 amino acid modification, relative to SEQ ID NO: 79. The amylin receptor agonist may comprise a polypeptide comprising 1 or 2 lysine residues and 1 amino acid modification, relative to SEQ ID NO: 79. The amylin receptor agonist may comprise a polypeptide comprising 1 lysine residue and 1 modification, relative to SEQ ID NO: 79.

The amylin receptor agonist may comprise a polypeptide comprising 0, 1, 2 or 3 cysteine residues and a maximum of 7 amino acid modifications, relative to SEQ ID NO: 79. The amylin receptor agonist may comprise a polypeptide comprising 1 or 2 cysteine residues and a maximum of 7 amino acid modifications, relative to SEQ ID NO: 79. The amylin receptor agonist may comprise a polypeptide comprising 1 cysteine residue and a maximum of 7 amino acid modifications, relative to SEQ ID NO: 79.

The amylin receptor agonist may comprise a polypeptide comprising 0, 1, 2 or 3 cysteine residues and a maximum of 6 amino acid modifications, relative to SEQ ID NO: 79. The amylin receptor agonist may comprise a polypeptide comprising 1 or 2 cysteine residues and a maximum of 6 amino acid modifications, relative to SEQ ID NO: 79. The amylin receptor agonist may comprise a polypeptide comprising 1 cysteine residue and a maximum of 6 amino acid modifications, relative to SEQ ID NO: 79.

The amylin receptor agonist may comprise a polypeptide comprising 0, 1, 2 or 3 cysteine residues and a maximum of 5 amino acid modifications, relative to SEQ ID NO: 79. The amylin receptor agonist may comprise a polypeptide comprising 1 or 2 cysteine residues and a maximum of 5 amino acid modifications, relative to SEQ ID NO: 79. The amylin receptor agonist may comprise a polypeptide comprising 1 cysteine residue and a maximum of 5 amino acid modifications, relative to SEQ ID NO: 79.

The amylin receptor agonist may comprise a polypeptide comprising 0, 1, 2 or 3 cysteine residues and a maximum of 4 amino acid modifications, relative to SEQ ID NO: 79. The amylin receptor agonist may comprise a polypeptide comprising 1 or 2 cysteine residues and a maximum of 4 amino acid modifications, relative to SEQ ID NO: 79. The amylin receptor agonist may comprise a polypeptide comprising 1 cysteine residue and a maximum of 4 amino acid modifications, relative to SEQ ID NO: 79.

The amylin receptor agonist may comprise a polypeptide comprising 0, 1, 2 or 3 cysteine residues and a maximum of 3 amino acid modifications, relative to SEQ ID NO: 79. The amylin receptor agonist may comprise a polypeptide comprising 1 or 2 cysteine residues and a maximum of 3 amino acid modifications, relative to SEQ ID NO: 79. The amylin receptor agonist may comprise a polypeptide comprising 1 cysteine residue and a maximum of 3 amino acid modifications, relative to SEQ ID NO: 79.

The amylin receptor agonist may comprise a polypeptide comprising 0, 1, 2 or 3 cysteine residues and a maximum of 2 amino acid modifications, relative to SEQ ID NO: 79. The amylin receptor agonist may comprise a polypeptide comprising 1 or 2 cysteine residues and a maximum of 2 amino acid modifications, relative to SEQ ID NO: 79. The amylin receptor agonist may comprise a polypeptide comprising 1 cysteine residue and a maximum of 2 amino acid modifications, relative to SEQ ID NO: 79.

The amylin receptor agonist may comprise a polypeptide comprising 0, 1, 2 or 3 cysteine residues and 1 amino acid modification, relative to SEQ ID NO: 79. The amylin receptor agonist may comprise a polypeptide comprising 1 or 2 cysteine residues and 1 amino acid modification, relative to SEQ ID NO: 79. The amylin receptor agonist may comprise a polypeptide comprising 1 cysteine residue and 1 modification, relative to SEQ ID NO: 79.

The amylin receptor agonist may not comprise a proline at position 12, relative to SEQ ID NO: 240 or SEQ ID NO: 256.

The amylin receptor agonist may comprise a lysine (Lys, K) residue at any one of positions 1, 2, 3, 7, 14, 18, 20, 23 or 29 relative to SEQ ID NO: 240 or SEQ ID NO: 256.

The GLP-1 receptor-amylin receptor co-agonist disclosed herein may comprise an amylin receptor agonist according to Formula III (SEQ ID NO: 240):
Xaa1-Xaa2-Xaa3-Leu-Ser-Thr-Xaa7-Ala-Leu-Gly-Arg-Leu-Ser-Xaa14-Glu-Leu-His-Xaa18-Leu-Xaa20-Thr-Leu-Xaa23-Arg-Thr-Glu-Thr-Gly-Xaa29-Gly-Ser-Xaa32, wherein
Xaa1 is Ala (A), Cys (C), Lys (K) or absent,
Xaa2 is Cys (C), Lys (K) or Ser (S),
Xaa3 is Cys (C), Glu (E), Lys (K) or Arg (R),
Xaa7 is Ala (A), Cys (C), Glu (E) or Lys (K),
Xaa14 is Ala (A), Cys (C) or Lys (K),
Xaa18 is Cys (C), Glu (E), Lys (K) or Gln (Q),
Xaa20 is Ala (A), Cys (C) or Lys (K),
Xaa23 is Cys (C), Lys (K) or Pro (P),
Xaa29 is Cys (C), Ser (S) or Lys (K) and
Xaa32 is Pro (P) or Tyr (Y).

The GLP-1 receptor-amylin receptor co-agonist disclosed herein may comprise an amylin receptor agonist according to Formula III:
Xaa1-Xaa2-Xaa3-Leu-Ser Thr-Xaa7-Ala-Leu-Gly-Arg-Leu-Ser-Xaa14-Glu-Leu-His-Xaa18-Leu-Xaa20-Thr-Leu-Xaa23-Arg-Thr-Glu-Thr-Gly-Xaa29-Gly-Ser-Xaa32, wherein
Xaa1 is Ala (A), Lys (K) or absent,
Xaa2 is Lys (K) or Ser (S),
Xaa3 is Glu (E), Lys (K) or Arg (R),
Xaa7 is Ala (A), Glu (E) or Lys (K),
Xaa14 is Ala (A) or Lys (K),
Xaa18 is Glu (E), Lys (K) or Gln (Q),
Xaa20 is Ala (A) or Lys (K),
Xaa23 is Lys (K) or Pro (P),
Xaa29 is Ser (S) or Lys (K) and
Xaa32 is Pro (P) or Tyr (Y).

The amylin receptor agonist may comprise a polypeptide (Z3) represented by any one of SEQ ID NOs: 79-88. Hence, the polypeptide backbone of the amylin receptor agonist described herein (73) may be described by reference to sequences in the sequence listing.

The amylin receptor agonists disclosed herein agonise, or activate, the amylin receptors. The amylin agonists disclosed herein may be tested for amylin activity as described in Examples 2 (in vitro), 4 and 5 (in vivo).

The more potent the compound, the lower its $EC_{50}$ value. A compound is considered a highly potent amylin-receptor agonist when its $EC_{50}$ value is below 50 pM. A compound is considered to have medium potency when its $EC_{50}$ value is 50-250 pM. A compound is considered to have a poorer potency when its $EC_{50}$ value is 250-1000 pM. A compound is considered impotent when its $EC_{50}$ value is above 1000 pM.

The amylin receptor agonist may have an $EC_{50}$ in a human amylin receptor functional assay (see Assay 2) of about 300 pM or less. The amylin receptor agonist may have an $EC_{50}$ in a human amylin receptor functional assay of about 250 pM or less. The amylin receptor agonist may have an $EC_{50}$ in a human amylin receptor functional assay of about 200 pM or less. The amylin receptor agonist may have an $EC_{50}$ in a human amylin receptor functional assay of about 150 pM or less. The amylin receptor agonist may have an $EC_{50}$ in a human amylin receptor functional assay of about 100 pM or less. The amylin receptor agonist may have an $EC_{50}$ in a human amylin receptor functional assay of about 90 pM or less. The amylin receptor agonist may have an $EC_{50}$ in a human amylin receptor functional assay of about 80 pM or less. The amylin receptor agonist may have an $EC_{50}$ in a human amylin receptor functional assay of about 70 pM or less. The amylin receptor agonist may have an $EC_{50}$ in a human amylin receptor functional assay of about 60 pM or less. Preferably, the amylin receptor agonist has an $EC_{50}$ in a human amylin receptor functional assay of about 50 pM or less. The amylin receptor agonist may have an $EC_{50}$ in a human amylin receptor functional assay of about 40 pM or less. The amylin receptor agonist may have an $EC_{50}$ in a human amylin receptor functional assay of about 30 pM or less. The amylin receptor agonist may have an $EC_{50}$ in a human amylin receptor functional assay of about 25 pM or less. The amylin receptor agonist may have an $EC_{50}$ in a human amylin receptor functional assay of about 20 pM or less. The amylin receptor agonist may have an $EC_{50}$ in a human amylin receptor functional assay of about 19 pM or less. The amylin receptor agonist may have an $EC_{50}$ in a human amylin receptor functional assay of about 18 pM or less. The amylin receptor agonist may have an $EC_{50}$ in a human amylin receptor functional assay of about 17 pM or less. The amylin receptor agonist may have an $EC_{50}$ in a human amylin receptor functional assay of about 16 pM or less. The amylin receptor agonist may have an $EC_{50}$ in a human amylin receptor functional assay of about 15 pM or less. The amylin receptor agonist may have an $EC_{50}$ in a human amylin receptor functional assay of about 14 pM or less. The amylin receptor agonist may have an $EC_{50}$ in a human amylin receptor functional assay of about 13 pM or less. The amylin receptor agonist may have an $EC_{50}$ in a human amylin receptor functional assay of about 12 pM or less. The amylin receptor agonist may have an $EC_{50}$ in a human amylin receptor functional assay of about 11 pM or less. The amylin receptor agonist may have an $EC_{50}$ in a human amylin receptor functional assay of about 10 pM or less. The amylin receptor agonist may have an $EC_{50}$ in a human amylin receptor functional assay of about 5 pM or less.

The amylin receptor agonist disclosed herein may have a similar potency as that of cagrilintide, pramlintide or amylin receptor agonist 1806.

Peptide Linkers

The GLP-1 receptor-amylin receptor co-agonist polypeptide backbone disclosed herein, R1, may comprise an optional peptide linker, Z2, which may be represented by Formula IV (SEQ ID NO: 239):

Xaa1-Xaa2-Xaa3-Xaa4-Xaa5-Xaa6-Xaa7-Xaa8-Xaa9-

Xaa10-Xaa11-Xaa12-Xaa13-Xaa14-Xaa15-Xaa16-Xaa17-

Xaa18-Xaa19-Xaa20-Xaa21-Xaa22-Xaa23-Xaa24-Xaa25-

Xaa26-Xaa27-Xaa28-Xaa29-Xaa30 wherein Xaa1-30 is absent or is independently selected from any 7 naturally occurring, or canonical, amino acid residue(s).

Hence, the optional peptide linker may comprise 1-30 canonical amino acid residues. The optional peptide linker may comprise 1-25 canonical amino acid residues. The optional peptide linker may comprise 1-20 canonical amino acid residues, such as 1-15, 1-10 or 1-5 canonical amino acid residues.

In the context of the optional peptide linker, Xaa may be selected from any non-aromatic amino acid residue. Xaa may be a charged amino acid. Xaa may be a polar amino acid. Xaa may be a hydrophobic amino acid.

Xaa may be selected from the group consisting of alanine (Ala, A), cysteine (Cys, C), glutamic acid (E), glycine (G), isoleucine (Ile, I), lysine (Lys, K), glutamine (Q), serine (S) and/or proline (Pro, P).

Xaa may be selected from the group consisting of alanine (A), glutamic acid (E), glycine (G), isoleucine (I), lysine (K), glutamine (Q), serine (S) and/or proline (P).

The optional peptide linker (Z2) may be any one of the peptide linkers represented by SEQ ID NOs 89-116. The optional peptide linker (Z2) may be any one of the peptide linkers listed in Table 1. The optional peptide linker may be GGGGE.

TABLE 1

Optional peptide linkers (Z2)

| SEQ ID | Peptide linker |
|---|---|
| — | E |
| — | GE |
| — | GG |
| — | EA |
| — | EGE |
| — | GGE |
| — | GKE |
| 89 | EGGE |
| 90 | GGGE |
| 91 | GGGG |
| 92 | KGGG |
| 93 | EAEAE |
| 94 | GGGGE |
| 95 | EGEGEE |
| 96 | EGGGGG |
| 97 | KGGGGE |
| 98 | EGEGEKE |
| 99 | EGGGGGE |
| 100 | EGQEPGG |
| 101 | QEPGQAPE |
| 102 | QAPGQEPE |
| 103 | QEPKGQAP |
| 104 | GGGGGGGK |
| 105 | GGGGSGGGE |
| 106 | GQEPGQEPE |
| 107 | KQEPGQEPE |
| 108 | GQEKGQEPE |
| 109 | QEPGQAPKE |
| 110 | QEPKGQAPE |
| 111 | GGGGGGGGE |
| 112 | GQEPGQEPKE |
| 113 | KGQEPGQAPE |

TABLE 1-continued

Optional peptide linkers (Z2)

| SEQ ID | Peptide linker |
|---|---|
| 114 | EGGGGGGGGGE |
| 115 | GGGGGGGGGGGE |
| 116 | GGGGGGGGGGGGGGGE |

Polypeptide

The term "polypeptide" or "peptide", as used herein, refers to a compound consisting of a series of amino acid residues that are interconnected by amide (or peptide) bonds.

The polypeptide backbone, of the GLP-1 receptor-amylin receptor co-agonist (R1) disclosed herein, typically comprises 60-85 amino acid residues linked together by peptide bonds. R1 comprises a peptide, Z1-Z2-Z3, which is a GLP-1 receptor agonist (Z1), an optional peptide linker (Z2) and a peptide which is an amylin receptor agonist (Z3).

Amino Acids

Amino acids are molecules containing an amine group and a carboxylic acid group, and, optionally, one or more additional groups, often referred to as a side chain.

The term "amino acid" includes canonical amino acids (which are genetically encoded), and unnatural amino acids.

Non-limiting examples of unnatural amino acids are Aib (α-aminoisobutyric acid), deamino histidine (alternative name 3-(imidazol-4-yl)propanoic acid, abbreviated Imp (imidazopropionyl) and the D-isomers of the canonical amino acids.

All amino acid residues within the polypeptide for which the optical isomer is not stated is herein to be understood to mean the L-isomer, unless otherwise specified.

The GLP-1 receptor agonist peptide (Z1) disclosed herein may have a maximum of 9 amino acid modifications, relative to human GLP-1 (SEQ ID NO: 1). The amylin receptor agonist peptide (Z3) disclosed herein may have a maximum of 7 amino acid modifications, relative to SEQ ID NO: 79. Herein, "amino acid modification" refers to the substitution, addition or deletion of an amino acid at a given position in the reference sequence.

Protraction Moiety

The GLP-1 receptor-amylin receptor co-agonist disclosed herein may further comprise one, two or three "protraction moieties". A protraction moiety may be represented by the general formula "R2-R3", in which R2 is an optional linker and R3 is a protractor. Each protraction moiety attaches to a lysine or a cysteine residue in the polypeptide backbone (R1) of the compound.

A protraction moiety may consist of one protractor.

A protraction moiety may comprise one linker and one protractor.

A protraction moiety may comprise one linker and two protractors.

When the linker (R2) is present, the protraction moiety attaches to the polypeptide backbone (R1) via R2. When the linker (R2) is absent, R3 attaches to the polypeptide backbone.

The protraction moiety (R2-R3) may attach to a lysine residue in the GLP-1 receptor agonist portion of the polypeptide backbone (the "Z1" in Z1-Z2-Z3). The protraction moiety may attach to a lysine residue in the optional peptide linker portion of the polypeptide backbone (the "22" in Z1-Z2-Z3). The protraction moiety may attach to a lysine residue in the amylin receptor agonist portion of the polypeptide backbone (the "Z3" in Z1-Z2-Z3). Where the protraction moiety attaches to a lysine residue via an amide linkage, the GLP-1 receptor-amylin receptor co-agonist is considered to be "acylated".

The GLP-1 receptor-amylin receptor co-agonist disclosed herein may comprise a single lysine residue, to which a single protraction moiety is attached.

The GLP-1 receptor-amylin receptor co-agonist disclosed herein may comprise two lysine residues and two protraction moieties. The compound disclosed herein may comprise two lysine residues and two identical protraction moieties.

The GLP-1 receptor-amylin receptor co-agonist disclosed herein may comprise three lysine residues and three protraction moieties. The compound disclosed herein may comprise three lysine residues and three identical protraction moieties.

The protraction moiety may attach to a cysteine residue in the GLP-1 receptor agonist portion of the polypeptide backbone (the "Z1" in Z1-Z2-Z3). The protraction moiety may attach to a cysteine residue in the optional peptide linker portion of the polypeptide backbone (the "Z2" in Z1-Z2-Z3). The protraction moiety may attach to a cysteine residue in the amylin receptor agonist portion of the polypeptide backbone (the "Z3" in Z1-Z2-Z3). Where the protraction moiety attaches to a cysteine residue via a thioether linkage, the GLP-1 receptor-amylin receptor co-agonist is considered to be "alkylated".

The GLP-1 receptor-amylin receptor co-agonist disclosed herein may comprise a single cysteine residue, to which a single protraction moiety is attached.

The GLP-1 receptor-amylin receptor co-agonist disclosed herein may comprise two cysteine residues and two protraction moieties. The GLP-1 receptor-amylin receptor co-agonist disclosed herein may comprise two cysteine residues and two identical protraction moieties.

The compound disclosed herein may comprise three cysteine residues and three protraction moieties. The compound disclosed herein may comprise three cysteine residues and three identical protraction moieties.

Where the GLP-1 receptor-amylin receptor co-agonist comprises two or three protraction moieties, the protracting moieties are similar, preferably substantially identical, or, most preferably, identical.

In the context of chemical moieties such as the protraction moieties disclosed herein, similarity and/or identity may be determined using any suitable computer program and/or algorithm known in the art.

The skilled person may refer to compounds comprising a protraction moiety as being "derivatives". For example, an "amylin derivative" is understood to be an amylin receptor agonist comprising a protraction moiety.

Herein, the term "protraction moiety" refers to a half-life extending, synthetic moiety comprising a "protractor" (R3) and an optional "side-chain linker" or "linker" (R2). R2 may join R3 to the side chain of a lysine or cysteine residue in R1, the polypeptide backbone of the GLP-1 receptor-amylin receptor co-agonist.

The protraction moiety may be capable of non-covalently binding to albumin, thereby promoting the circulation of the GLP-1 receptor-amylin receptor co-agonist in the blood stream and prolonging its half-life. Thus, the skilled person may also refer to the protraction moiety as being an "albumin binding moiety".

The protractor (R3) may comprise an acyl group. The acyl group may be branched or unbranched. The acyl group may be saturated or unsaturated. The protractor (R3) may comprise a fatty acyl group. The acyl group may be branched or unbranched. The acyl group may be saturated or unsaturated.

The protractor (R3) may comprise a distal carboxylic acid group.

The protractor (R3) may comprise a fatty acid group.

The protractor ("R3") may comprise a fatty acid group and an amide group.

The protractor (R3) may comprise a distal carboxylic acid group and an amide group.

The protractor (R3) may comprise an alkyl group.

The protractor (R3) may comprise an aryl group.

The protractor (R3) may comprise a tetrazole group.

The protractor (R3) may comprise a sulfonic acid group.

The protractor (R3) may comprise a phenoxy group.

The protractor (R3) may comprise a benzoic acid group.

The protractor (R3) may comprise a group defined by:

Chem. 3: HOOC—$(CH_2)_n$—CO—* wherein n is an integer in the range of 8-30, which may also be referred to as a C(n+2) diacid or as Chem. 3b:

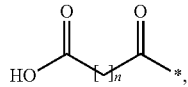

wherein n is an integer in the range of 8-30.

The protractor (R3) may comprise 8-30 carbon atoms. The protractor may comprise 8, 9, 10, 11, 12, 13, 14, 15, 16, 17, 18, 19, 20, 21, 22, 23, 24, 25, 26, 27, 28, 29 or 30 carbon atoms.

The protractor (R3) may comprise 6-30 consecutive —$CH_2$— groups. The protractor (R3) may comprise a carbon chain comprising at least 6, 7, 8, 9, 10, 11, 12, 13, 14, 15, 16, 17, 18, 19, 20, 21, 22, 23, 24, 25, 26, 27, 28, 29 or 30 consecutive —$CH_2$— groups.

The protractor (R3) may comprise 12-26 carbon atoms. The "protractor", or "side chain", may comprise 12, 13, 14, 15, 16, 17, 18, 19, 20, 21, 22, 23, 24, 25 or 26 carbon atoms.

The protractor (R3) may comprise 10-26 consecutive —$CH_2$— groups. The protractor (R3) may comprise a carbon chain comprising 10, 11, 12, 13, 14, 15, 16, 17, 18, 19, 20, 21, 22, 23, 24, 25 or 26 consecutive —$CH_2$— groups.

The protractor (R3) may comprise 16-22 carbon atoms. The compound may comprise a single protraction moiety which comprises a side chain comprising 16, 17, 18, 19, 20, 21 or 22 carbon atoms.

The protractor (R3) may comprise 14-20 consecutive —$CH_2$— groups. The protractor (R3) may comprise a carbon chain comprising 14, 15, 16, 17, 18, 19 or 20 consecutive —$CH_2$— groups.

The protractor (R3) may comprise 16-22 consecutive carbon atoms and 14-20 consecutive —$CH_2$— groups.

The protractor (R3) may comprise 16 consecutive carbon atoms and 14 consecutive —$CH_2$— groups.

The protractor (R3) may comprise 18 consecutive carbon atoms and 16 consecutive —$CH_2$— groups.

The protractor (R3) may comprise 20 consecutive carbon atoms and 18 consecutive —$CH_2$— groups.

The protractor (R3) may comprise 22 consecutive carbon atoms and 20 consecutive —$CH_2$— groups.

The GLP-1 receptor-amylin receptor co-agonist may comprise two protraction moieties, each of which comprises 14, 15, 16, 17, 18, 19 or 20 carbon atoms. The GLP-1 receptor-amylin receptor co-agonist may comprise two protraction moieties, wherein each protractor (R3) comprises 12, 13, 14, 15, 16, 17 or 18 consecutive —$CH_2$— groups.

The GLP-1 receptor-amylin receptor co-agonist may comprise two C14 diacids, two C16 diacids or two C18 diacids.

The GLP-1 receptor-amylin receptor co-agonist may comprise three protraction moieties, each of which comprises a protractor comprising 12, 13, 14, 15, 16, 17, 18, 19 or 20 carbon atoms. The GLP-1 receptor-amylin receptor co-agonist may comprise three protraction moieties, wherein the protractor (R3) comprises 10, 11, 12 13, 14, 15, 16, 17 or 18 consecutive —$CH_2$— groups.

The protraction moiety (R2-R3) may be covalently attached to a lysine residue in the polypeptide backbone (R1). The protraction moiety may be attached via an amide bond formed between a carboxylic acid group in the protraction moiety and the epsilon amino group of the lysine residue.

The protraction moiety (R2-R3) may be covalently attached to a cysteine residue in the polypeptide backbone (R1). The protraction moiety may be attached via a thioether bond formed between the protraction moiety and the sulphur atom of the cysteine residue in the polypeptide.

As mentioned above, the compound disclosed herein may comprise one, two or three lysine or cysteine residues and thence one, two or three protraction moieties (R2-R3), wherein each protraction moiety is attached to a side chain of a single lysine or cysteine residue.

The protraction moiety may be attached to the polypeptide backbone described herein (R1) via a lysine (K) residue at any one of positions 9, 10, 12, 16, 17, 20, 21, 24, 25, 28, 29, 30 or 31 of the GLP-1 receptor agonist portion of the polypeptide backbone (Z1), relative to SEQ ID NO: 238 or SEQ ID NO: 255.

The protraction moiety may be attached to the polypeptide backbone (R1) via a lysine (K) residue in the optional linker (Z2).

The protraction moiety may be attached to the polypeptide backbone (R1) via a lysine (K) residue at any one of positions 1, 2, 3, 7, 10, 14, 18, 20, 23 or 29 of the amylin receptor agonist portion of the polypeptide backbone (Z3), relative to SEQ ID NO: 240 or SEQ ID NO: 256.

The protraction moiety may be attached to the polypeptide backbone (R1) via a cysteine (C) residue at any one of positions 9, 10, 12, 16, 17, 20, 21, 24, 25, 28, 29, 30 or 31 of the GLP-1 receptor agonist portion of the polypeptide backbone (Z1), relative to SEQ ID NO: 238.

The protraction moiety may be attached to the polypeptide backbone (R1) via a cysteine (C) residue in the optional linker portion of the polypeptide backbone (Z2).

The protraction moiety may be attached to the polypeptide described herein via a cysteine (C) residue in the amylin receptor agonist portion of the polypeptide backbone (Z3). The cysteine residue may be at any one of positions 1, 2, 3, 7, 10, 14, 18, 20, 23 or 29, relative to SEQ ID NO: 240.

The GLP-1 receptor-amylin receptor co-agonist disclosed herein may comprise a protractor (R3) which is selected from any one of those depicted in Table 2. In Table 2, R2 represents the optional linker which connects the depicted protractor (R3) to the polypeptide backbone (R1). R1 is not shown in the table.

TABLE 2

Protractors (R3)

| Protractor number | Structure | In compounds |
|---|---|---|
| 1 | 3-(9-carboxynonyloxy) benzoic acid | 0235 (2x) |
| 2 | 4-(9-carboxynonyloxy) benzoic acid | 0096 (2x), 0097 (2x), 0098 (2x), 0099 (2x), 0100 (2x), 0101 (2x), 0231 (2x), 0232 (2x), 0233 (2x), 0234 (2x), |
| 3 | 4-(10-carboxydecyloxy) benzoic acid | 0255 (2x) |
| 4 | C14 diacid | 0039 (2x), 0484 (2x), 0635 (3x) |
| 5 | C16 diacid | 0560, 0564 (2x), 0630 (2x), 0631 (2x), 0634 (2x), 0072 (2x), 0073 (2x), 0074 (2x), 0075 (2x), 0076 (2x), 0077 (2x), 0086 (2x), 0087 (2x), 0105 (2x), 0259 (2x), 0260 (2x), 0261 (2x), 0280 (2x), 0281 (2x), 0284 (2x), 0285 (2x), 0292 (2x), 0294 (2x), 0295 (2x), 0296 (2x), 0297 (2x), 0299 (2x), 0396 (2x), 0397 (2x), 0411 (2x), 0475 (2x), 0482 (2x), 0483 (2x), 0509 (2x), |

TABLE 2-continued
| Protractors (R3) | | |
|---|---|---|
| Protractor number | Structure | In compounds |
| | | 0516 (2x), 0528 (2x), 0575 (2x), 0576 (2x), 0577 (2x), 0578 (2x), 0629 (2x) |
| 6 | 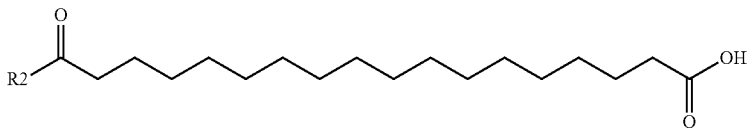<br>C18 diacid | 0658, 0656, 0007, 0009, 0010, 0019, 0026, 0040, 0042, 0051, 0052, 0083, 0084, 0085, 0092, 0093, 0111, 0114, 0115, 0132, 0144, 0151, 0156, 0191, 0271, 0273, 0472, 0637, 0639, 0640, 0648, 0044, 0045, 0159, 0661, 0662, 0660, 0131 (2x), 0160 (2x), 0056 (2x), 0057 (2x), 0071 (2x), 0089 (2x), 0090 (2x), 0106 (2x), 0109 (2x), 0116 (2x), 0127 (2x), 0128 (2x), 0129 (2x), 0110 (2x) |
| 7 | 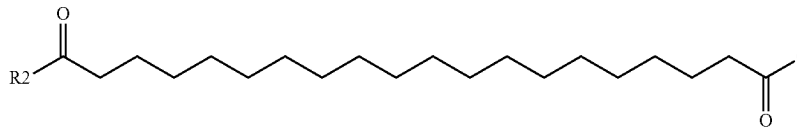<br>C20 diacid | 0636, 0632, 0633, 0141, 0142, 0659, 0657, 0094, 0157, 0202, 0473, 0474, 0502, 0529, 0562, 0565, 0580, 0581, 0638, 0552, 0663, 0035, 0095, 0120, 0254, 0263, 0264, 0265, 0266, 0267, 0268, 0269, 0270, 0272, 0414, 0415, 0416, 0417, 0431, 0440, 0503, 0504, 0511, 0512, 0518, 0539, 0561, 0433, 0434, 0435, 0436, 0437, 0438, 0439, 0506, 0179, 0180 |

TABLE 2-continued

Protractors (R3)

| Protractor number | Structure | In compounds |
|---|---|---|
| 8 | 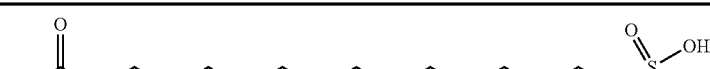 C16-sulfonic acid | 0654 |
| 9 | 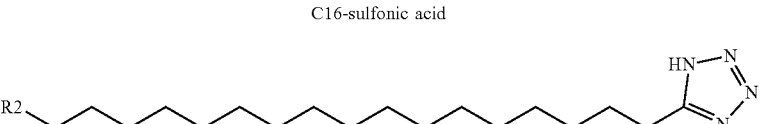 C17-tetrazole | 0102, 0103, 0124, 0125, 0145, 0146, 0147, 0655 |

As mentioned above, the protraction moiety ("R2-R3") may comprise an optional side-chain linker, "R2".

The optional side-chain linker (R2) may comprise Ado, Aeep or Aeeep, sulfonamide, Trx, ε-Lys, Ahx, Glu, γGlu, Gly, Ser, Ala, Thr and/or a bond.

The optional side-chain linker may comprise at least a moiety which may be represented by the following chemical formula:

$$*-NH-(CH_2)_2-(O-(CH_2)]_k-O-(CH_2)_n-CO-* \quad \text{Chem 4a}$$

Chem. 4b wherein k is an integer in the range of 1-5, and n is an integer in the range of 1-5. When k=1 and n=1, the linker element may be designated Ado, or a 8-amino-3,6-dioxaoctanoyl, which may be represented by the following chemical formula:

$$*-NH-(CH_2)_2-O-(CH_2)_2-O-CH_2-CO-* \quad \text{Chem. 5a}$$

or

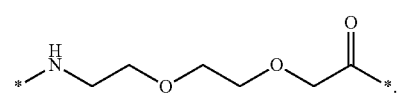

Chem. 5b

When k=1 and n=2, the linker element may be designated Aeep, which may be represented by the following chemical formula:

$$*-NH-(CH_2)_2-O-(CH_2)_2-O-(CH_2)_2-CO-*, \quad \text{Chem. 6}$$

or

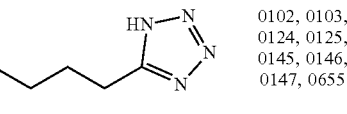

Chem. 6b

When k=2 and n=2, the linker element may be designated Aeeep, which may be represented by the following chemical formula:

$$*-NH-(CH_2)_2-O-(CH_2)_2-O-(CH_2)_2-O-(CH_2)_2-CO-*, \quad \text{Chem. 7a}$$

or

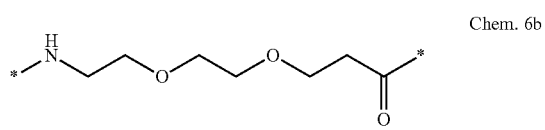 [SMILES: *NCCOCCOCCC(*)=O]

Chem. 7b

The optional side-chain linker may comprise a sulfonamide-C4 moiety. A sulfonamide-C4 group is a sulfonamide group attached to a 4-butanoyl group and having the following chemical formula:

$$*NH-S(O)_2-CH_2-CH_2-CH_2-CO-* \quad \text{Chem 9a}$$

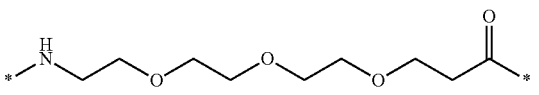

Chem 9b

The optional side-chain linker may comprise Trx. Trx is also referred to as Tranexamic acid, trans-4-(aminomethyl) cyclohexanecarboxylic acid and has the following chemical formula:

$$*-NH-CH_2-(C6H10)-CO-* \quad \text{or} \quad \text{Chem. 10a}$$

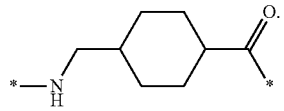

Chem. 10b

The optional side-chain linker may comprise epsilon-lysine (ε-Lys).

The optional side-chain linker may comprise lysine (Lys).

The optional side-chain linker may comprise Ahx. Ahx is also referred to as Aminocaproic acid, 6-aminohexanoic acid and is defined by

*—NH—(CH2)5-CO—*  or    Chem 11a

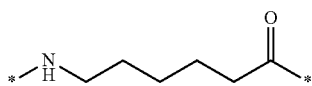

Chem 11b

The optional side-chain linker may comprise a Glu di-radical, such as Chem. 12:

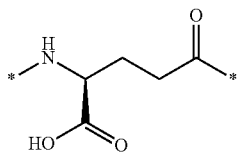 [SMILES: *N[C@@H](CCC(*)=O)C(=O)O]

wherein the Glu di-radical may be included p times, where p is an integer in the range of 1-3.

Chem. 12 may also be referred to as gamma-Glu, or briefly γGlu, due to the fact that it is the gamma carboxy group of the amino acid glutamic acid which is here used for connection to another linker element, or to the epsilon-amino group of lysine. As explained above, the other linker element may, for example, be another Glu residue, or an Ado molecule. The amino group of Glu in turn forms an amide bond with the carboxy group of the protracting moiety, or with the carboxy group of, e.g., an Ado molecule, if present, or with the gamma-carboxy group of, e.g., another Glu, if present.

The GLP-1 receptor-amylin receptor co-agonist disclosed herein may comprise a side-chain linker (R2) which is selected from any one of those depicted in Table 3. In Table 3, "R1" represents the polypeptide backbone (Z1-Z2-Z3), R2 (depicted) represents the side-chain linker and "R3" represents the protractor.)

TABLE 3

Optional linkers ("R2")

| Linker number | Structure | In compounds |
|---|---|---|
| 1 | 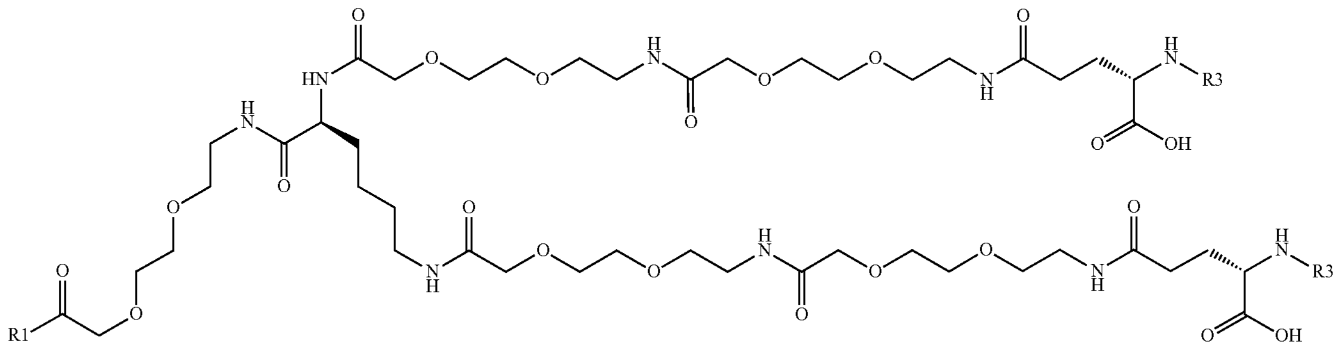 | 0564 |
| 2 | 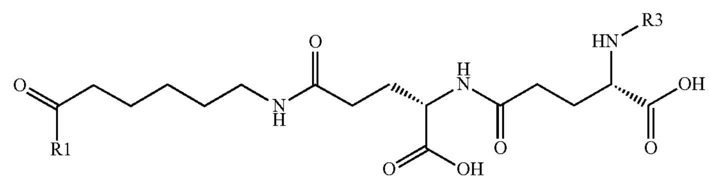 | 0630 (2x) |
| 3 | 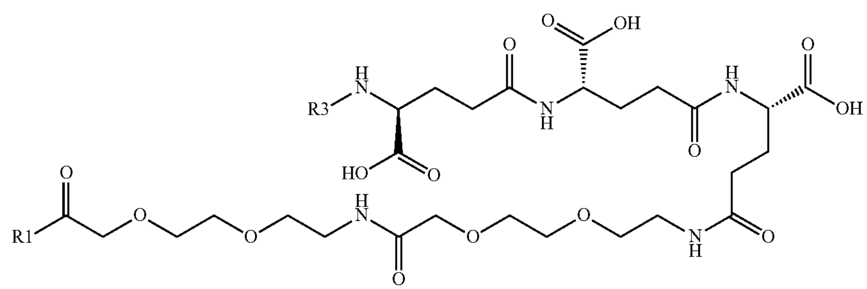 | 0636 |

TABLE 3-continued

Optional linkers ("R2")

| Linker number | Structure | In compounds |
|---|---|---|
| 4 | [structure: tri-glutamate linker with R1 acyl and R3 amine] | 0621 (2x), 0632, 0633, 0634 (2x) |
| 5 | [structure: glutamate with R1 acyl and R3 amine] | 0141, 0142, 0131 (2x), 0160 (2x) |
| 6 | [structure: glutamate-aminohexanoyl with R1 and R3] | 658, 659 |
| 7 | [structure: lysine-like linker with R1 and R3] | 656, 657 |
| 8 | [structure: glutamate-PEG linker with R1 and R3] | 0560, 0007, 0009, 0010, 0019, 0026, 0040, 0042, 0051, 0052, 0083, 0084, 0085, 0092, 0093, 0111, 0114, 0115, 0132, 0144, 0151, 0156, 0191, 0271, 0273, 0472, 0637, 0639, 0640, 0648, |

TABLE 3-continued

Optional linkers ("R2")

| Linker number | Structure | In compounds |
|---|---|---|
| | | 0094, 0457, 0202, 0473, 0474, 0502, 0529, 0562, 0565, 0580, 0581, 0638, 0654, 0655, 0635 (3x), 0235 (2x), 0096 (2x), 0097 (2x), 0098 (2x), 0099 (2x), 0100 (2x), 0101 (2x), 0231 (2x), 0232 (2x), 0233 (2x), 0234 (2x), 0255 (2x), 0039 (2x), 0484 (2x), 0072 (2x), 0073 (2x), 0074 (2x), 0075 (2x), 0076 (2x), 0077 (2x), 0086 (2x), 0087 (2x), 0105 (2x), 0259 (2x), 0260 (2x), 0261 (2x), 0280 (2x), 0281 (2x), 0284 (2x), 0285 (2x), 0292 (2x), 0294 (2x), 0295 (2x), 0296 (2x), 0297 (2x), 0299 (2x), 0396 (2x), 0397 (2x), 0411 (2x), 0475 (2x), |

TABLE 3-continued
Optional linkers ("R2")
| Linker number | Structure | In compounds |
|---|---|---|
| 9 | 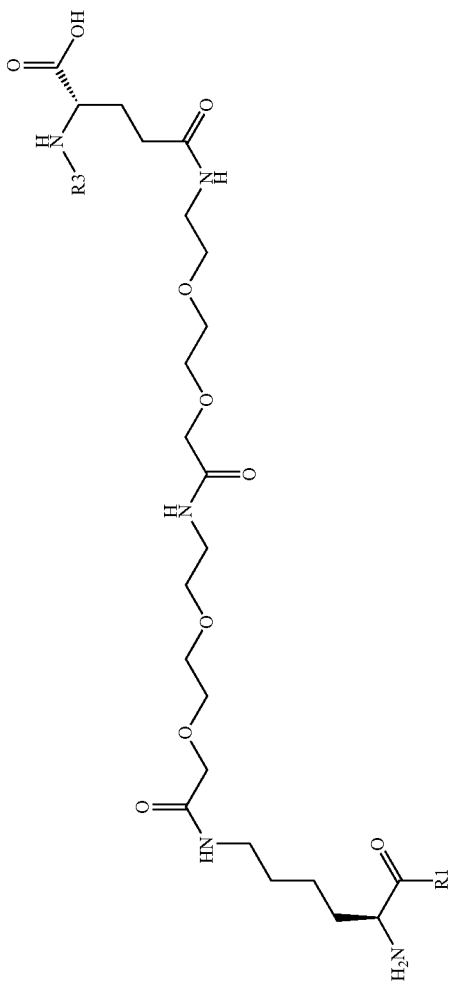 | 0482 (2x), 0483 (2x), 0509 (2x), 0516 (2x), 0528 (2x), 0575 (2x), 0576 (2x), 0577 (2x), 0578 (2x), 0629 (2x), 0056 (2x), 0057 (2x), 0071 (2x), 0089 (2x), 0090 (2x), 0106 (2x), 0109 (2x), 0116 (2x), 0127 (2x), 0128 (2x), 0129 (2x), 0044, 0045, 0159, 0552, 0110 (2x) |

TABLE 3-continued

Optional linkers ("R2")

| Linker number | Structure | In compounds |
|---|---|---|
| 10 | 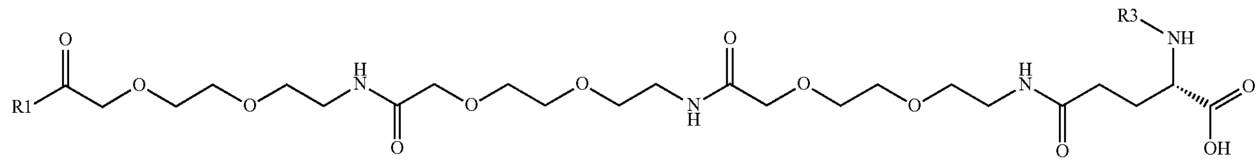 | 0661 |
| 11 | 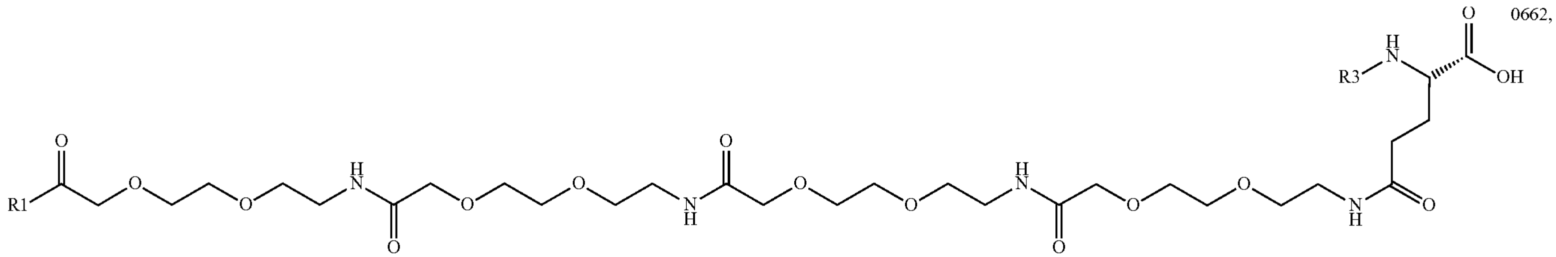 | 0662, 0663 |
| 12 | 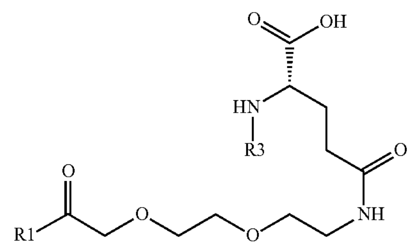 | 0660 |
| 13 | 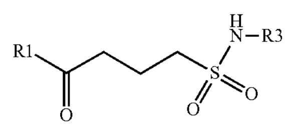 | 0102, 0103, 0124, 0125, 0145, 0146, 0147 |

TABLE 3-continued
Optional linkers ("R2")
| Linker number | Structure | In compounds |
|---|---|---|
| 14 | 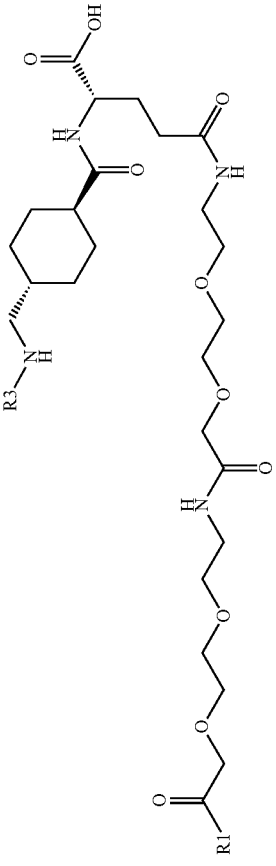 | 0035, 0095, 0120, 0254, 0263, 0264, 0265, 0266, 0267, 0268, 0269, 0270, 0272, 0414, 0415, 0416, 0417, 0431, 0440, 0503, 0504, 0511, 0512, 0518, 0539, 0561, 0179 |
| 15 | 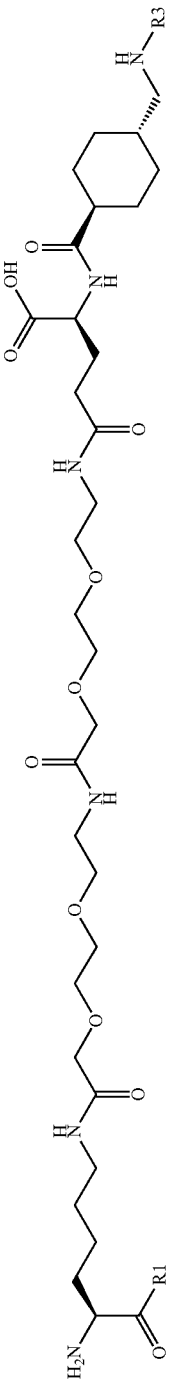 | 0433, 0434, 0435, 0436, 0437, 0438, 0439, 0506, 0180 |

The co-agonists may exist in different stereoisomeric forms having the same molecular formula and sequence of bonded atoms but differing only in the three-dimensional orientation of their atoms in space. The stereoisomerism of the exemplified co-agonists is indicated in the experimental section, in the names as well as the structures, using standard nomenclature. Unless otherwise stated the invention relates to all stereoisomeric forms of the embodied derivative.

Methods of Production

The compounds disclosed herein may, for instance, be produced by classical peptide synthesis, e.g. solid phase peptide synthesis using t-Boc or Fmoc chemistry, or other well established techniques, see e.g. Greene and Wuts, "Protective Groups in Organic Synthesis", John Wiley & Sons, 1999; Florencio Zaragoza Dorwald, "Organic Synthesis on Solid Phase", Wiley-VCH Verlag GmbH, 2000; and "Fmoc Solid Phase Peptide Synthesis", Edited by W. C. Chan and P. D. White, Oxford University Press, 2000.

Alternatively, the compounds may be produced by recombinant methods, e.g. by culturing a host cell containing a DNA sequence encoding the peptide sequence and capable of expressing the peptide, in a suitable nutrient medium under conditions permitting the expression of the peptide. Non-limiting examples of host cells suitable for expression of these peptides are *Escherichia coli, Saccharomyces cerevisiae* and mammalian BHK or CHO cell lines.

The co-agonists that include non-natural amino acids and/or covalently attached substituents may be produced as described in the experimental part.

Specific examples of methods of preparing a number of the disclosed compounds are included in the examples.

A further aspect of the invention relates to a method for preparing the peptides described herein.

A further aspect of the invention relates to a method for preparing the receptor co-agonists described herein.

In one embodiment, the method for preparing a compound as described herein comprises a step of solid phase peptide synthesis. The substituent may be built sequentially as part of the solid phase peptide synthesis or produced separately and attached via the lysine residue after peptide synthesis.

In one embodiment, the compounds are produced by a two-step process whereby two peptide fragments are ligated after attachment of the substituent to one of the peptide fragments.

Pharmaceutical Compositions

Also disclosed herein is a pharmaceutical composition comprising the GLP-1 receptor-amylin receptor co-agonist disclosed herein. Pharmaceutical compositions comprising the GLP-1 receptor-amylin receptor co-agonist, or a pharmaceutically acceptable salt thereof, and one or more pharmaceutically acceptable excipients, may be prepared using methods known to the person skilled in the art.

The term "pharmaceutically acceptable excipient" refers to any ingredient in the pharmaceutical composition which is not the active pharmaceutical ingredient. The excipient may be functional or inert and may serve one or more purposes. For example, the excipient may enhance absorption of the active substance. The excipient might be, amongst others, a buffer, an antimicrobial preservative, an isotonicity agent, a carrier, a vehicle, a filler, a binder, a lubricant, a glidant, a disintegrant, a flow control agent, a crystallization inhibitor, a solubilizer, a stabilizer, a colouring agent, a flavoring agent, a surfactant, an emulsifier. The amount of each excipient used may vary within ranges conventional in the art.

The pharmaceutical composition may be suitable for oral administration. Techniques and excipients which may be used to formulate orally administered pharmaceutical compositions are described in *Handbook of Pharmaceutical Excipients* (e.g. 8$^{th}$ edition, Sheskey et al., Eds., American Pharmaceuticals Association and Pharmaceutical Press, publications department of the Royal Pharmaceutical Society of Great Britain (2017) and later editions); and *Remington: The Science and Practice of Pharmacy* (e.g. 22nd edition, Remington and Allen, Eds., Pharmaceutical Press (2013), and later editions).

The pharmaceutical formulation may be a solid pharmaceutical formulation (e.g. a compressed tablet or capsule) containing the active pharmaceutical ingredient, for example as a freeze-dried or spray-dried composition, and may be used as is, dissolved prior to use, or combined with excipients in the formulation.

The pharmaceutical composition may be a solid formulation containing the compound disclosed herein, a salt of N-[8-(2-hydroxybenzoyl)amino]caprylate and one or more further excipients, as is described in the art. For example, the solid formulation may be as described in WO 2012/080471, WO2013/139694, WO 2013/189988, WO 2019/149880, WO2019/215063 or WO2021/219710.

Alternatively, the pharmaceutical composition may be a liquid formulation, such as an aqueous formulation. Such liquid composition may be suitable for oral administration or for parenteral administration. Liquid compositions that are suitable for injection can be prepared using conventional techniques of the pharmaceutical industry which involve dissolving and mixing the ingredients as appropriate to give the desired end product. Thus, according to one procedure, the compound described herein is dissolved in a suitable buffer at a suitable pH. The composition may be sterilized, for example, by sterile filtration. Techniques and excipients which may be used to prepare liquid formulations are described in *Handbook of Pharmaceutical Excipients* (e.g. 8$^{th}$ edition, Sheskey et al., Eds., American Pharmaceuticals Association and Pharmaceutical Press, publications department of the Royal Pharmaceutical Society of Great Britain (2017) and later editions); and *Remington: The Science and Practice of Pharmacy* (e.g. 22nd edition, Remington and Allen, Eds., Pharmaceutical Press (2013), and later editions).

Pharmaceutical Indications

The GLP-1 receptor-amylin receptor co-agonist disclosed herein may be used as a medicament.

The GLP-1 receptor-amylin receptor co-agonist disclosed herein may be used for the following medical treatments:
  (i) prevention and/or treatment of all forms of diabetes, such as hyperglycaemia, type 2 diabetes, impaired glucose tolerance, type 1 diabetes, non-insulin dependent diabetes, MODY (maturity onset diabetes of the young), gestational diabetes, and/or for reduction of HbA1c;
  (ii) delaying or preventing diabetic disease progression, such as progression in type 2 diabetes, delaying the progression of impaired glucose tolerance (IGT) to insulin requiring type 2 diabetes, and/or delaying the progression of non-insulin requiring type 2 diabetes to insulin requiring type 2 diabetes;
  (iii) prevention and/or treatment of eating disorders, such as obesity, e.g. by decreasing food intake, reducing body weight, suppressing appetite, inducing satiety; treating or preventing binge eating disorder, food cravings, bulimia nervosa and/or obesity induced by administration of an antipsychotic or a steroid; reduction of gastric motility; and/or delaying gastric emptying;
(iv) weight maintenance after successful weight loss (either drug induced or by diet and exercise)—i.e. prevention of weight gain after successful weight loss;
(v) prevention and/or treatment of cardiovascular diseases, such as delaying or reducing development of a major adverse cardiovascular event (MACE) selected from the group consisting of cardiovascular death, non-fatal myocardial infarction, non-fatal stroke, revascularisation, hospitalisation for unstable angina pectoris, and hospitalisation for heart failure.
(vi) prevention and/or treatment of non-alcoholic steatohepatitis (NASH);
(vii) prevention and/or treatment of cognitive impairment, such as that caused by Alzheimer's disease.

In some embodiments the indication is (i). In some embodiments the indication is (ii). In a still further particular aspect the indication is (iii). In some embodiments the indication is (iv). In some embodiments the indication is (v). In some embodiments the indication is (vi). In some embodiments the indication is (vii). In some embodiments the indication is type 2 diabetes and/or obesity.

The term "treatment", as used herein, refers to the medical therapy of any human or other vertebrate subject in need thereof. Said subject is expected to have undergone physical examination by a medical practitioner, or a veterinary medical practitioner, who has given a tentative or definitive diagnosis which would indicate that the use of said specific treatment is beneficial to the health of said human or other vertebrate. The timing and purpose of said treatment may vary from one individual to another, according to the status quo of the subject's health. Thus, said treatment may be prophylactic (preventative), palliative, symptomatic and/or curative.

In some embodiments the indication is (i) and (iii). In some embodiments the indication is (ii) and (iii).

In some embodiments the subject suffering from obesity is human, such as an adult human or a paediatric human (including infants, children, and adolescents).

Body mass index (BMI) is a measure of body fat based on height and weight. The formula for calculation is BMI=weight in kilograms/height in meters$^2$. A human subject suffering from obesity may have a BMI of ≥30; this subject may also be referred to as being obese. In some embodiments the human subject suffering from obesity may have a BMI of ≥35 or a BMI in the range of ≥30 to <40. In some embodiments the obesity is severe obesity or morbid obesity, wherein the human subject may have a BMI of ≥40.

In some embodiments the invention relates to a method for treatment or prevention of overweight, optionally in the presence of at least one weight-related comorbidity. In some embodiments the invention relates to use of the formulation for treatment or prevention of overweight, optionally in the presence of at least one weight-related comorbidity. In some embodiments the subject suffering from overweight is human, such as an adult human or a paediatric human (including infants, children, and adolescents). In some embodiments a human subject suffering from overweight may have a BMI of ≥25, such as a BMI of ≥27, such as a BMI of ≥30, such as a BMI of ≥35 or a BMI of ≥40. In some embodiments a human subject suffering from overweight has a BMI in the range of 25 to <30 or in the range of 27 to <30. In some embodiments the weight-related comorbidity is selected from the group consisting of hypertension, diabetes (such as type 2 diabetes), dyslipidaemia, high cholesterol and obstructive sleep apnoea.

The term "reduction of body weight" may include treatment or prevention of obesity and/or overweight.

Administration of the compound disclosed herein may be as an adjunct to a reduced-calorie diet and increased physical activity for chronic weight management in adult or paediatric patients with an initial body mass index (BMI) of 30 kg/m$^2$ or greater (obesity) or 27 kg/m$^2$ or greater (overweight) in the presence of at least one weight-related comorbidity (e.g. hypertension, type 2 diabetes mellitus, or dyslipidemia).

Dosing Frequency

The GLP-1 receptor-amylin receptor co-agonist disclosed herein may be administered approximately once daily, such as once every 12-36 hours, such as once every 18-30 hours, such as approximately once every 24 hours.

The GLP-1 amylin receptor co-agonist disclosed herein may be administered approximately once every other day, such as once every 36-60 hours, such as once every 42-54 hours, such as approximately once every 48 hours.

The GLP-1 amylin receptor co-agonist disclosed herein may be administered approximately twice daily, such as once every 6-18 hours, such as once every 9-15 hours, such as approximately once every 12 hours.

Following is a non-limiting list of embodiments of the present invention.

EMBODIMENTS

1. A GLP-1 receptor-amylin receptor co-agonist comprising a polypeptide (R1) according to Formula I:
Z1-Z2-Z3,
comprising 1-3 lysine (Lys, K) residues and, optionally, no disulfide bridge; wherein:
Z1 is a GLP-1 receptor agonist peptide comprising a maximum of 9 amino acid modifications, relative to SEQ ID NO: 1 (human GLP-1(7-37));
Z2 is an optional peptide linker;
Z3 is an amylin receptor agonist peptide comprising a C-terminal amide and a maximum of 7 amino acid modifications, relative to SEQ ID NO: 79.

2. A GLP-1 receptor-amylin receptor co-agonist comprising a polypeptide (R1) according to Formula I:
Z1-Z2-Z3,
comprising 1-3 lysine (Lys, K) and/or cysteine (Cys, C) residues and no disulfide bridge;
wherein:
Z1 is a GLP-1 receptor agonist peptide comprising a maximum of 9 amino acid modifications, relative to SEQ ID NO: 1 (human GLP-1(7-37);
Z2 is an optional peptide linker;
Z3 is an amylin receptor agonist peptide comprising a C-terminal amide and a maximum of 7 amino acid modifications, relative to SEQ ID NO: 79.

3. The GLP-1 receptor-amylin receptor co-agonist according to any one of the preceding embodiments, further comprising 1-3 protraction moieties (R2-R3), attached to the polypeptide (R1) via said 1-3 lysine residues.

4. The GLP-1 receptor-amylin receptor co-agonist according to the preceding embodiment, comprising 1-3 lysine residues.

5. The GLP-1 receptor-amylin receptor co-agonist according to any one of the preceding embodiments, comprising 1-2 lysine residues.

6. The GLP-1 receptor-amylin receptor co-agonist according to any one of the preceding embodiments, comprising 1 lysine residue.

7. The GLP-1 receptor-amylin receptor co-agonist according to any one of the preceding embodiments, comprising 1-3 cysteine residues.
8. The GLP-1 receptor-amylin receptor co-agonist according to any one of the preceding embodiments, comprising 1-2 cysteine residues.
9. The GLP-1 receptor-amylin receptor co-agonist according to any one of the preceding embodiments, comprising 1 cysteine residue.
10. The GLP-1 receptor-amylin receptor co-agonist according to any one of the preceding embodiments, wherein the GLP-1 receptor agonist peptide (Z1) comprises 0-3 lysine (Lys, K) residues at any one, or combination of, positions 9, 10, 12, 16, 17, 20, 21, 24, 25, 28, 29, 30 and/or 31, relative to SEQ ID NO: 238 or SEQ ID NO: 255.
11. The GLP-1 receptor-amylin receptor co-agonist according to any one of the preceding embodiments, wherein the GLP-1 receptor agonist peptide (Z1) comprises 2 lysine (Lys, K) residues at positions:
12 and either 21, 30 or 31, or
21 and either 30 or 31,
relative to SEQ ID NO: 238 or SEQ ID NO: 255.
12. The GLP-1 receptor-amylin receptor co-agonist according to any one of the preceding embodiments, wherein the GLP-1 receptor agonist peptide (Z1) comprises 2 lysine (Lys, K) residues at positions:
12 and either 21 or 31, or
21 and 31, relative to SEQ ID NO: 238 or SEQ ID NO: 255.
13. The GLP-1 receptor-amylin receptor co-agonist according to any one of the preceding embodiments, wherein the GLP-1 receptor agonist peptide (Z1) comprises 1 lysine residue (Lys, K) at any one of positions 12, 17, 20, 21, 28, 30 or 31.
14. The GLP-1 receptor-amylin receptor co-agonist according to any one of the preceding embodiments, wherein the GLP-1 receptor agonist peptide (Z1) comprises 1 lysine residue (Lys, K) at position 31.
15. The GLP-1 receptor-amylin receptor co-agonist according to any one of the preceding embodiments, wherein the peptide linker (Z2) comprises 0-3 lysine (K) residues.
16. The GLP-1 receptor-amylin receptor co-agonist according to any one of the preceding embodiments, wherein the peptide linker (Z2) comprises 1-2 lysine (Lys, K) residues.
17. The GLP-1 receptor-amylin receptor co-agonist according to any one of the preceding embodiments, wherein the peptide linker (Z2) comprises 1 lysine (Lys, K) residue.
18. The GLP-1 receptor-amylin receptor co-agonist according to any one of the preceding embodiments, wherein the peptide linker (Z2) comprises 0-3 cysteine (Cys, C) residues.
19. The GLP-1 receptor-amylin receptor co-agonist according to any one of the preceding embodiments, wherein the peptide linker (Z2) comprises 1-2 cysteine (Cys, C) residues.
20. The GLP-1 receptor-amylin receptor co-agonist according to any one of the preceding embodiments, wherein the peptide linker (Z2) comprises 1 cysteine (Cys, C) residue.
21. The GLP-1 receptor-amylin receptor agonist according to any one of the preceding claims, wherein the amylin receptor agonist peptide (Z3) comprises 0-3 lysine (Lys, K) residues.
22. The GLP-1 receptor-amylin receptor agonist according to any one of the preceding claims, wherein the amylin receptor agonist peptide (Z3) comprises 0-3 cysteine (Cys, C) residues.
23. The GLP-1 receptor-amylin receptor co-agonist according to any one of the preceding claims, wherein the amylin receptor agonist peptide (Z3) comprises 1-3 lysine (Lys, K) residues at any one of positions 1, 2, 3, 7, 14, 18, 20, 23 and/or 29, relative to SEQ ID NO: 240 or SEQ ID NO: 256.
24. The GLP-1 receptor-amylin receptor co-agonist according to any one of the preceding claims, wherein the amylin receptor agonist peptide (Z3) comprises 1 lysine (Lys, K) residue at any one of positions 14, 18, 20, 23, 29; relative to SEQ ID NO: 240 or SEQ ID NO: 256.
25. The GLP-1 receptor-amylin receptor co-agonist according to any one of the preceding claims, wherein the amylin receptor agonist peptide (Z3) comprises 1 lysine (Lys, K) residue at position 18, relative to SEQ ID NO: 240 or SEQ ID NO: 256.
26. The GLP-1 receptor-amylin receptor co-agonist according to any one of the preceding embodiments, comprising a GLP-1 receptor agonist (Z1) according to Formula II (SEQ ID NO 238):
Xaa1-Xaa2-Glu-Gly-Thr-Phe-Thr-Ser-Xaa9-Xaa10-Ser-Xaa12-Tyr-Leu-Glu-Xaa16-Xaa17-Ala-Xaa19-Xaa20-Xaa21-Xaa22-Xaa23-Xaa24-Xaa25-Leu-Val-Xaa28-Xaa29-Xaa30-Xaa31,
and wherein
Xaa1 is His (H) or Imp,
Xaa2 is Aib, Ala (A), Gly (G) or Trp (W),
Xaa9 is Cys (C), Asp (D) or Lys (K),
Xaa10 is Cys (C), Lys (K) or Val (V),
Xaa12 is Cys (C), Lys (K), Arg (R) or Ser (S),
Xaa16 is Cys (C), Glu (E), Gly (G) or Lys (K),
Xaa17 is Cys (C), Gln (Q) or Lys (K),
Xaa19 is Ala (A) or Val (V),
Xaa20 is Cys (C), Lys (K) or Arg (R),
Xaa21 is Cys (C), Glu (E) or Lys (K),
Xaa22 is Phe (F), Trp (W) or Tyr (Y),
Xaa23 is Ile (I), Leu (L) or Val (V),
Xaa24 is Ala (A), Cys (C), Glu (E) or Lys (K),
Xaa25 is Cys (C), Lys (K) or Trp (W),
Xaa28 is Cys (C), Lys (K) or Arg (R),
Xaa29 is Cys (C), Lys (K) or Gly (G),
Xaa30 is Ala (A), Cys (C), Gly (G), Lys (K), Arg (R) or absent,
Xaa31 is Ala (A), Cys (C), Lys (K), Gly (G), Gln (Q) or absent.
27. The GLP-1 receptor-amylin receptor co-agonist according to any one of the preceding embodiments, comprising a GLP-1 receptor agonist (Z1) according to Formula II (SEQ ID NO: 255):
Xaa1-Xaa2-Glu-Gly-Thr-Phe-Thr-Ser-Xaa9-Xaa10-Ser-Xaa12-Tyr-Leu-Glu-Xaa16-Xaa17-Ala-Xaa19-Xaa20-Xaa21-Xaa22-Xaa23-Xaa24-Xaa25-Leu-Val-Xaa28-Xaa29-Xaa30-Xaa31,
and wherein
Xaa1 is His (H) or Imp,
Xaa2 is Aib, Ala (A), Gly (G) or Trp (W),
Xaa9 is Asp (D) or Lys (K),
Xaa10 is Lys (K) or Val (V),
Xaa12 is Lys (K), Arg (R) or Ser (S),
Xaa16 is Glu (E), Gly (G) or Lys (K),
Xaa17 is Gln (Q) or Lys (K),
Xaa19 is Ala (A) or Val (V), Xaa20 is Lys (K) or Arg (R),
Xaa21 is Glu (E) or Lys (K),
Xaa22 is Phe (F), Trp (W) or Tyr (Y),
Xaa23 is Ile (I), Leu (L) or Val (V),
Xaa24 is Ala (A), Glu (E) or Lys (K),
Xaa25 is Lys (K) or Trp (W),
Xaa28 is Lys (K) or Arg (R),
Xaa29 is Lys (K) or Gly (G),
Xaa30 is Ala (A), Gly (G), Lys (K), Arg (R) or absent,
Xaa31 is Ala (A), Lys (K), Gly (G), Gln (Q) or absent.

28. The GLP-1 receptor-amylin receptor co-agonist according to any one of the preceding embodiments, wherein the GLP-1 receptor agonist peptide (Z1) does not comprise an isoleucine (Ile, I) at position 22, relative to SEQ ID NO: 238 or SEQ ID NO: 255.

29. The GLP-1 receptor-amylin receptor co-agonist according to any one of the preceding embodiments, wherein the GLP-1 receptor agonist peptide (Z1) comprises a phenylalanine (Phe, F), a tryptophan (W) or a tyrosine (Tyr, Y) at position 22, relative to SEQ ID NO: 238 or SEQ ID NO: 255.

30. The GLP-1 receptor-amylin receptor co-agonist according to any one of the preceding embodiments, wherein the GLP-1 receptor agonist peptide (Z1) comprises a phenylalanine (Phe, F) at position 22, relative to SEQ ID NO: 238 or SEQ ID NO: 255.

31. The GLP-1 receptor-amylin receptor co-agonist according to any one of the preceding embodiments, wherein the GLP-1 receptor agonist peptide (Z1) comprises an isoleucine (Ile, 1), a leucine (Leu, L) or a valine (Val, V) at position 23, relative to SEQ ID NO: 238 or SEQ ID NO: 255.

32. The GLP-1 receptor-amylin receptor co-agonist according to any one of the preceding embodiments, wherein the GLP-1 receptor agonist peptide (Z1) comprises an isoleucine (Ile, 1) at position 23, relative to SEQ ID NO: 238 or SEQ ID NO: 255.

33. The GLP-1 receptor-amylin receptor co-agonist according to any one of the preceding embodiments, comprising a GLP-1 receptor agonist (Z1) according to Formula II (SEQ ID NO: 255):
Xaa1-Xaa2-Glu-Gly-Thr-Phe-Thr-Ser-Xaa9-Xaa10-Ser-Xaa12-Tyr-Leu-Glu-Xaa16-Xaa17-Ala-Xaa19-Xaa20-Xaa21-Phe-Ile-Xaa24-Xaa25-Leu-Val-Xaa28-Xaa29-Xaa30-Xaa31,
wherein
Xaa1 is His (H) or Imp,
Xaa2 is Aib, Ala (A), Gly (G) or Trp (W),
Xaa9 is Asp (D) or Lys (K),
Xaa10 is Lys (K) or Val (V),
Xaa12 is Lys (K), Arg (R) or Ser (S),
Xaa16 is Glu (E), Gly (G) or Lys (K),
Xaa17 is Gln (Q) or Lys (K)
Xaa19 is Ala (A) or Val (V),
Xaa20 is Lys (K) or Arg (R),
Xaa21 is Glu (E) or Lys (K),
Xaa24 is Ala (A), Glu (E) or Lys (K),
Xaa25 is Lys (K) or Trp (W),
Xaa28 is Lys (K) or Arg (R)
Xaa29 is Lys (K) or Gly (G),
Xaa30 is Ala (A), Gly (G), Lys (K), Arg (R) or absent,
Xaa31 is Ala (A), Lys (K), Gly (G), Gln (Q) or absent.

34. The GLP-1 receptor-amylin receptor co-agonist according to any one of the preceding embodiments, wherein Z1 is
Xaa1-Xaa2-Glu-Gly-Thr-Phe-Thr-Ser-Xaa9-Xaa10-S-Xaa12-Tyr-Leu-Glu-Xaa16-Xaa17-Ala-Xaa19-Xaa20-Xaa21-Phe-Ile-Xaa24-Xaa25-Leu-Val-Xaa28-Xaa29-Xaa30-Xaa31,
and wherein
Xaa1 is His (H) or Imp,
Xaa2 is Aib, Ala (A), Gly (G) or Trp (W),
Xaa9 is Cys (C) or Asp (D),
Xaa10 is Cys (C) or Val (V),
Xaa12 is Cys (C), Arg (R) or Ser (S),
Xaa16 is Cys (C), Glu (E) or Gly (G)
Xaa17 is Cys (C) or Gln (Q),
Xaa19 is Ala (A) or Val (V),
Xaa20 is Cys (C) or Arg (R),
Xaa21 is Cys (C) or Glu (E),
Xaa24 is Ala (A), Cys (C) or Glu (E)
Xaa25 is Cys (C) or Trp (W),
Xaa28 is Cys (C) or Arg (R),
Xaa29 is Cys (C) or Gly (G),
Xaa30 is Cys (C), Ala (A), Gly (G), Arg (R) or absent,
Xaa31 is Ala (A), Cys (C), Gly (G), Gln (Q) or absent.

35. The GLP-1 receptor-amylin receptor co-agonist according to any one of the preceding embodiments, wherein the amylin receptor agonist peptide (Z3) does not comprise a proline (Pro, P) at position 12, relative to SEQ ID NO: 240 or SEQ ID NO: 256.

36. The GLP-1 receptor-amylin receptor co-agonist according to any one of the preceding embodiments, wherein the amylin receptor agonist peptide (Z3) comprises a leucine (Leu, L) at position 12, relative to SEQ ID NO: 240 or SEQ ID NO: 256.

37. The GLP-1 receptor-amylin receptor co-agonist according to any one of the preceding embodiments, wherein the amylin receptor agonist peptide (Z3) comprises a leucine at position 12 (Leu12), relative to SEQ ID NO: 240 or SEQ ID NO: 256.

38. The GLP-1 receptor-amylin receptor co-agonist according to any one of the preceding embodiments, wherein optional linker Z2 is absent or comprises 1-30, 1-25 or 1-20 naturally occurring amino acid residues (SEQ ID NO 239).

39. The GLP-1 receptor-amylin receptor co-agonist according to any one of the preceding embodiments, wherein optional linker Z2 comprises 0-20 amino acid residues selected from the group consisting of Ala (A), Glu (E), Gly (G), Lys (K), Pro (P) and Gln (Q).

40. The GLP-1 receptor-amylin receptor co-agonist according to any one of the preceding embodiments, wherein optional linker Z2 is any one of those listed in Table 1.

41. The GLP-1 receptor-amylin receptor co-agonist according to any one of the preceding embodiments, comprising an amylin receptor agonist peptide (Z3) according to Formula III (SEQ ID NO 240):
Xaa1-Xaa2-Xaa3-Leu-Ser Thr-Xaa7-Ala-Leu-Gly-Arg-Leu-Ser-Xaa14-Glu-Leu-His-Xaa18-Leu-Xaa20-Thr-Leu-Xaa23-Arg-Thr-Glu-Thr-Gly-Xaa29-Gly-Ser-Xaa32,
wherein
Xaa1 is Ala (A), Cys (C), Lys (K) or is absent,
Xaa2 is Cys (C), Lys (K) or Ser (S),
Xaa3 is Cys (C), Glu (E), Lys (K) or Arg (R),
Xaa7 is Ala (A), Cys (C), Glu (E) or Lys (K),
Xaa14 is Ala (A), Cys (C) or Lys (K),
Xaa18 is Cys (C), Glu (E), Lys (K) or Gln (Q),
Xaa20 is Ala (A), Cys (C) or Lys (K),
Xaa23 is Cys (C), Lys (K) or Pro (P),
Xaa29 is Cys (C), Ser (S) or Lys (K) and
Xaa32 is Pro (P) or Tyr (Y).

42. The GLP-1 receptor-amylin receptor co-agonist according to any one of the preceding embodiments, comprising an amylin receptor agonist (Z3) according to Formula III (SEQ ID NO 256):

$Xaa_1$-$Xaa_2$-$Xaa_3$-Leu-Ser-Thr-$Xaa_7$-Ala-Leu-Gly-Arg-Leu-Ser-$Xaa_{14}$-Glu-Leu-His-$Xaa_{18}$-Leu-$Xaa_{20}$-Thr-Leu-$Xaa_{23}$-Arg-Thr-Glu-Thr-Gly-$Xaa_{29}$-Gly-Ser-$Xaa_{32}$, wherein
Xaa1 is Ala (A) or Lys (K) or is absent,
Xaa2 is Lys (K) or Ser (S),
Xaa3 is Glu (E), Lys (K) or Arg (R),
Xaa7 is Ala (A), Glu (E) or Lys (K),
Xaa14 is Ala (A) or Lys (K),
Xaa18 is Glu (E), Lys (K) or Gln (Q),
Xaa20 is Ala (A) or Lys (K),
Xaa23 is Lys (K) or Pro (P),
Xaa29 is Ser (S) or Lys (K) and
Xaa32 is Pro (P) or Tyr (Y).

43. The GLP-1 receptor-amylin receptor co-agonist according to any one of the preceding embodiments, wherein the GLP-1 receptor agonist peptide (Z1) comprises 2, 3, 4, 5, 6, 7, 8 or 9 amino acid modifications relative to human GLP-1(7-37).

44. The GLP-1 receptor-amylin receptor co-agonist according to any one of the preceding embodiments, wherein the GLP-1 receptor agonist peptide (Z1) comprises 1 or 2 substitutions of a naturally occurring amino acid residue with 1 or 2 unnatural amino acids.

45. The GLP-1 receptor-amylin receptor co-agonist according to any one of the preceding embodiments, wherein the GLP-1 receptor agonist peptide (Z1) comprises an imidazole propionyl (Imp) at position 7, relative to human GLP-1(7-37), or at position 1, relative to SEQ ID NO: 238 or SEQ ID NO: 255.

46. The GLP-1 receptor-amylin receptor co-agonist according to any one of the preceding embodiments, wherein the GLP-1 receptor agonist (Z1) comprises an alpha-aminoisobutyryl (Aib) at position 8, relative to human GLP-1(7-37), or at position 2, relative to SEQ ID NO: 238 or SEQ ID NO: 255.

47. The GLP-1 receptor-amylin receptor co-agonist according to any one of the preceding embodiments, wherein the GLP-1 receptor agonist peptide (Z1) comprises an alanine (Ala, A) at any one of positions 8, 25, 30 or 37, relative to human GLP-1(7-37), or at any one of positions 2, 19, 24 or 31, relative to SEQ ID NO: 238 or SEQ ID NO: 255.

48. The GLP-1 receptor-amylin receptor co-agonist according to any one of the preceding embodiments, wherein the GLP-1 receptor agonist (Z1) comprises an arginine residue (Arg, R) at any one of positions 26 or 34, relative to human GLP-1(7-37), or at any one of positions 18 or 26, relative to SEQ ID NO: 238 or SEQ ID NO: 255.

49. The GLP-1 receptor-amylin receptor co-agonist according to any one of the preceding embodiments, wherein the GLP-1 receptor agonist (Z1) comprises an aspartic acid residue (Asp, D) at position 15, relative to human GLP-1(7-37), or at position 9, relative to SEQ ID NO: 238 or SEQ ID NO: 255.

50. The GLP-1 receptor-amylin receptor co-agonist according to any one of the preceding embodiments, wherein the GLP-1 receptor agonist (Z1) comprises a glutamic acid residue (Glu, E) at any one of positions 22, 27 or 30, relative to human GLP-1(7-37), or at any one of positions 16, 21 or 24, relative to SEQ ID NO: 238 or SEQ ID NO: 255.

51. The GLP-1 receptor-amylin receptor co-agonist according to any one of the preceding embodiments, wherein the GLP-1 receptor agonist (Z1) comprises a glycine residue (Gly, G) at any one of positions 8 or 36, relative to human GLP-1(7-37), or at any one of positions 2 or 30, relative to SEQ ID NO: 238 or SEQ ID NO: 255.

52. The GLP-1 receptor-amylin receptor co-agonist according to any one of the preceding embodiments, wherein the GLP-1 receptor agonist (Z1) comprises a histidine residue (His, H) at position 7, relative to human GLP-1(7-37), or at position 1, relative to SEQ ID NO: 238 or SEQ ID NO: 255.

53. The GLP-1 receptor-amylin receptor co-agonist according to any one of the preceding embodiments, wherein the GLP-1 receptor agonist (Z1) comprises a serine residue (Ser, S) at position 18, relative to human GLP-1(7-37), or at positions 12, relative to SEQ ID NO: 238 or SEQ ID NO: 255.

54. The GLP-1 receptor-amylin receptor co-agonist according to any one of the preceding embodiments, wherein the GLP-1 receptor agonist (Z1) comprises a tryptophan residue (Trp, W) at any one of positions 8 or 31, relative to human GLP-1(7-37), or at any one of positions 2 or 25, relative to SEQ ID NO: 238 or SEQ ID NO: 255.

55. The GLP-1 receptor-amylin receptor co-agonist according to any one of the preceding embodiments, wherein the GLP-1 receptor agonist (Z1) comprises a valine residue (Val, V) at any one of positions 16 or 25, relative to human GLP-1(7-37), or at any one of positions 10 or 19, relative to SEQ ID NO: 238 or SEQ ID NO: 255.

56. The GLP-1 receptor-amylin receptor co-agonist according to any one of the preceding embodiments, wherein the amylin receptor agonist peptide (Z3) comprises 0, 1, 2, 3 or 4 amino acid modifications, relative to SEQ ID NO: 79.

57. The GLP-1 receptor-amylin receptor co-agonist according to any one of the preceding embodiments, wherein the amylin receptor agonist peptide (Z3) comprises 0, 1, 2 or 3 amino acid modifications, relative to SEQ ID NO: 79.

58. The GLP-1 receptor-amylin receptor co-agonist according to any one of the preceding embodiments, wherein the amylin receptor agonist peptide (Z3) comprises 0, 1 or 2 amino acid modifications, relative to SEQ ID NO: 79.

59. The GLP-1 receptor-amylin receptor co-agonist according to any one of the preceding embodiments, wherein the amylin receptor agonist peptide (Z3) comprises 0 or 1 amino acid modifications, relative to SEQ ID NO: 79.

60. The GLP-1 receptor-amylin receptor co-agonist according to any one of the preceding embodiments, wherein the amylin receptor agonist peptide (Z3) comprises a lysine (Lys, K) residue at any one of positions 1, 2, 3, 7, 10, 14, 18, 20, 23 or 29 relative to SEQ ID NO: 240 or SEQ ID NO: 256.

61. The GLP-1 receptor-amylin receptor co-agonist according to any one of the preceding embodiments, wherein the amylin receptor agonist peptide (Z3) comprises a lysine (Lys, K) residue at any one of positions 2, 14, 18, 20, 23 or 29 relative to SEQ ID NO: 240 or SEQ ID NO: 256.

62. The GLP-1 receptor-amylin receptor co-agonist according to any one of the preceding embodiments, wherein the amylin receptor agonist peptide (Z3) comprises an arginine (Arg, R) residue at position 3, relative to SEQ ID NO: 240 or SEQ ID NO: 256.

63. The GLP-1 receptor-amylin receptor co-agonist according to any one of the preceding embodiments, wherein the amylin receptor agonist peptide (Z3) comprises a Glu (E) residue at position 7, relative to SEQ ID NO: 240 or SEQ ID NO: 256.

64. The GLP-1 receptor-amylin receptor co-agonist according to any one of the preceding embodiments, wherein the amylin receptor agonist peptide (Z3) comprises a Leu (L) at position 12, relative to SEQ ID NO 79.

65. The GLP-1 receptor-amylin receptor co-agonist according to any one of the preceding embodiments, wherein Z1 is a GLP-1 receptor agonist selected from the group consisting of SEQ ID NOs 2-78.

66. The GLP-1 receptor-amylin receptor co-agonist according to any one of the preceding embodiments, wherein Z2 is any amino acid residue or peptide presented in Table 1.

67. The GLP-1 receptor-amylin receptor co-agonist according to any one of the preceding embodiments, wherein Z3 is an amylin receptor agonist peptide (Z3) selected from the group consisting of SEQ ID NOs 79-88.

68. The GLP-1 receptor-amylin receptor co-agonist according to any one of the preceding embodiments, further comprising a protraction moiety attached to each lysine residue.

69. The GLP-1 receptor-amylin receptor co-agonist according to any one of the preceding embodiments, wherein each lysine residue is acylated.

70. The GLP-1 receptor-amylin receptor co-agonist according to any one of the preceding embodiments, wherein said protraction moiety comprises a C14-C20 diacid.

71. The GLP-1 receptor-amylin receptor co-agonist according to any one of the preceding embodiments, wherein the protraction moiety comprises a C14 diacid, a C16 diacid, a C18 diacid, a C20 diacid, a C18-tetrazole, a C14-sulfonic acid, 4-(9-carboxynonyloxy) benzoic acid, 4-(10-carboxydecyloxy) benzoic acid or 3-(9-carboxynonyloxy) benzoic acid.

72. The GLP-1 receptor-amylin receptor co-agonist according to any one of the preceding embodiments, comprising two C14 diacids, C16 diacids or C18 diacids.

73. The GLP-1 receptor-amylin receptor co-agonist according to any one of the preceding embodiments, comprising three C14 diacids.

74. The GLP-1 receptor-amylin receptor co-agonist according to any one of the preceding embodiments, wherein the lysine is attached to any one of the optional linkers ("R2") presented in Table 3.

75. A GLP-1 receptor-amylin receptor co-agonist comprising a polypeptide selected from any one of SEQ ID NOs 117-236.

76. A GLP-1 receptor-amylin receptor co-agonist selected from any one of those identified in Example 1a.

77. A pharmaceutically acceptable salt of the GLP-1 receptor-amylin receptor co-agonist according to any one of the preceding embodiments.

78. A pharmaceutical formulation comprising a GLP-1 receptor-amylin receptor co-agonist according to any one of the preceding embodiments.

79. The pharmaceutical formulation according to the preceding embodiment, which is for oral administration.

80. The pharmaceutical formulation according to the preceding embodiment, which is a solid pharmaceutical formulation.

81. The solid pharmaceutical formulation according to the preceding embodiment, which is a tablet.

82. The tablet according to the preceding embodiment, comprising sodium N-(8-(2-hydroxybenzoyl)amino) caprylate and magnesium stearate.

83. The tablet according to the preceding embodiment, comprising 75-600 mg sodium N-(8-(2-hydroxybenzoyl)amino)caprylate and 7-8.5 mg magnesium stearate.

84. The pharmaceutical formulation according to any one of embodiments 78-83, which is for dosing approximately once daily, such as once every 12-36 hours, such as once every 18-30 hours, such as approximately once every 24 hours.

85. A GLP-1 receptor-amylin receptor co-agonist according to any one of embodiments 1-77 or the formulation according to any one of embodiments 78-84 for use as a medicament.

86. The GLP-1 receptor-amylin receptor co-agonist according to any one of embodiments 1-77 or the formulation according to any one of embodiments 78-84, for use in the treatment of subjects with an initial body mass index (BMI) of 27 or more, such as 30 or more.

87. The GLP-1 receptor-amylin receptor co-agonist according to any one of embodiments 1-77 or the formulation according to any one of embodiments 78-84, for use in the treatment of subjects with an initial body mass index (BMI) of 27 or more and at least one weight-related co-morbidity.

88. The GLP-1 receptor-amylin receptor co-agonist according to any one of embodiments 1-77 or the formulation according to any one of embodiments 78-84, for use as an adjunct to a reduced-calorie diet and increased physical activity for chronic weight management in adult subjects with an initial body mass index (BMI) of 30 kg/m2 or greater (obesity) or 27 kg/m2 or greater (overweight) in the presence of at least one weight-related co-morbidity.

89. Use according to the preceding embodiments, wherein said co-morbidity is diabetes and/or a cardiovascular disease.

90. The GLP-1 receptor-amylin receptor co-agonist according to any one of embodiments 1-77 or the formulation according to any one of embodiments 78-84, for use in the treatment of subjects with diabetes, such as type II diabetes.

91. The GLP-1 receptor-amylin receptor co-agonist according to any one of embodiments 1-77 or the formulation according to any one of embodiments 78-84, for use in the treatment and/or prevention of cardiovascular disease.

92. The GLP-1 receptor-amylin receptor co-agonist according to any one of embodiments 1-77 or the formulation according to any one of embodiments 78-84, for use in the treatment of NASH.

93. The GLP-1 receptor-amylin receptor co-agonist according to any one of embodiments 1-77 or the formulation according to any one of embodiments 78-84, for use in the treatment and/or prevention of cognitive impairment, such as that caused by Alzheimer's disease.

EXAMPLES

Example 1: Synthesis of GLP-1 Receptor-Amylin Receptor Co-Agonists and Comparator Compounds This example provides the identity, materials for making and methods of synthesis of many compounds according to the current invention.

Also provided are the identity, materials for making and methods of synthesis of the comparator compounds described herein.

Materials and Methods

LIST OF ABBREVIATIONS

The following abbreviations are used in the following, in alphabetical order:
Ac: acetyl
Aib: alpha-aminoisobutyric acid
AUC: Area Under the Curve
Boc: t-butyloxycarbonyl
DCM: dichloromethane
DIC: diisopropylcarbodiimide
DIPEA: N,N-diisopropylethylamine or Hünig's base
DMF: dimethyl formamide
DODT: 3,6-dioxa-1,8-octanedithiol
DTT: dithiothreitol
EDTA: ethylenediaminetetraacetic acid
ELISA: Enzyme Linked Immuno Sorbent Assay
Fmoc: 9-fluorenylmethyloxycarbonyl
HFIP: 1,1,1,3,3,3-hexafluoro-2-propanol or hexafluoroisopropanol
HOBt: 1-hydroxybenzotriazole
HPLC: High Performance Liquid Chromatography
HSA: Human Serum Albumin
Imp: imidazolepropionyl
i.v.: intravenously
LCMS or LC-MS: Liquid Chromatography Mass Spectroscopy
MeCN: acetonitrile
Mtt: 4-methyltrityl
NHS: N-hydroxysuccinimide
NMP: N-methyl pyrrolidone
Oxyma Pure®: cyano-hydroxyimino-acetic acid ethyl ester
PK: pharmacokinetic
QTof: Quantitative Time of Flight
s.c.: subcutaneously
SD: Standard Deviation
SEC-HPLC: Size Exclusion High Performance Liquic Chromatography
SEM: Standard Error of Mean
tBu: t-butyl
TFA: trifluoroacetic acid
TIS: triisopropylsilane
Trt: triphenylmethyl or trityl
Trx: tranexamic acid
UPLC: Ultra Performance Liquid Chromatography General Methods of Preparation This section relates to general methods for solid phase peptide synthesis (SPPS methods, including methods for cleaving the peptide from the resin and removal of the protecting groups and for its purification) Included as well are LCMS methods for detecting and characterising the resulting peptide.

Resins used for the preparation of C-terminal peptide amides were PAL Amide AM resin (loading e.g. 0.6 mmol/g) or H-Rink Amide-ChemMatrix resin (loading e.g. 0.5 mmol/g) or Rink Amide AM polystyrene resin (loading e.g. 0.3-0.7 mmol/g) or Tentagel® rink amide resin (loading e.g. 0.2-0.3 mmol/g) or similar resins suitable for SPPS.

The Fmoc-protected amino acid derivatives used comprised amongst others the standard recommended: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Phe-OH, Fmoc-Pro-OH, Fmoc-Ser(tBu)-OH, Fmoc-Thr(tBu)-OH, Fmoc-Trp(Boc)-OH or Fmoc-Trp-OH, Fmoc-Tyr(tBu)-OH, Fmoc-Val-OH, Fmoc-Lys(Mtt)-OH, Fmoc-Aib-OH, etc. supplied from e.g. AAPPTEC, Anaspec, Bachem, ChemImpex, Iris Biotech, Midwest Biotech, Gyros Protein Technologies or Novabiochem. Other building blocks such as Fmoc-pseudoprolines and similar derivatives were employed in some difficult sequences. Where nothing else is specified the natural L-form of the amino acids are used. The N-terminal amino acid was Boc protected at the alpha amino group, either by using a reagent with the Boc group pre-installed (e.g. Boc-His(Trt)-OH for peptides with His at the N-terminus) or by exchanging the N-terminal Fmoc protective group for the Boc protective group after installation of the amino acid at the peptide N-terminus. Fmoc-Lys(Mtt)-OH and similar derivatives, such as, but not limited to Fmoc-Lys(ivDDE) etc. bearing an orthogonal protecting group at the epsilon amino position, were used in the cases where side chain instalment was relevant. The epsilon amino derivative would be liberated using a suitable orthogonal deprotecting agent, such as HFIP in DCM, and the side chain installed either stepwise with SPPS or by coupling the epsilon amino functionality directly to the activated ester (e.g. NHS ester) sidechain building block.

In case of stepwise side chain attachment using SPPS, the following suitably protected building blocks such as, but not limited to, Fmoc-8-amino-3,6-dioxaoctanoic acid (Fmoc-OEG-OH), Fmoc-tranexamic acid (Fmoc-Trx-OH), Fmoc-Glu-OtBu, octadecanedioic acid mono-tert-butyl ester, nonadecanedioic acid mono-tert-butyl ester, eicosanedioic acid mono-tert-butyl ester, hexadecanedioic acid mono-tert-butyl ester, tetradecanedioic acid mono-tert-butyl ester, or 4-(9-carboxynonyloxy) benzoic acid tert-butyl ester were used. All operations stated below were performed within a 50-450 µmol synthesis scale range.

SPPS of the Peptidyl Backbone:

SPPS was performed using Fmoc based chemistry on a SymphonyX Solid Phase Peptide Synthesizer from Protein Technologies (Tucson, AZ 85714 U.S.A.). Fmoc-deprotection was achieved with 20% piperidine in DMF, containing between 0 and 0.2 M Oxyma. Peptide couplings were performed using DIC/Oxyma Pure®. Amino acid/Oxyma Pure® solutions (0.3 M/0.3 M in DMF at a molar excess of 3-12 fold) were added to the resin followed by the same molar equivalent of DIC (as a 0.6-1.5M solution in DMF) and collidine (1.5M in DMF). The step-wise assembly was done using the following steps: 1) pre-swelling of resin with DMF; 2) Fmoc-deprotection by the use of 20% piperidine in DMF containing between 0 and 0.2M Oxyma Pure® for 1-5 treatments of 5-30 min each; 3) washes with DMF to remove traces of piperidine; 4) coupling of Fmoc-amino acid with 3-12 eq. of Fmoc-amino acid as a 0.3M solution in 0.3M Oxyma Pure® in DMF mixed with an equimolar volume of DIC and collidine for 1-12 hours. In the case of sterically hindered amino acids, this coupling step was repeated once or twice; 5) washes with DMF to remove excess reagents; 6) final wash with DCM at the completion of the assembly which made the resin ready for attachment of a modifying group on lysine side chain.

Alternatively, SPPS was performed using Fmoc based chemistry on a SymphonyX Solid Phase Peptide Synthesizer from Protein Technologies (Tucson, AZ 85714 U.S.A.). Fmoc-deprotection was achieved with 20% piperidine in DMF, containing between 0 and 0.2 M Oxyma. Peptide couplings were performed using DIC/Oxyma Pure®. Amino acid/Oxyma Pure® solutions (0.3 M/0.3 M in DMF at a molar excess of 3-12 fold) were added to the resin followed by the same molar equivalent of DIC (as a 0.6M solution in DMF). The step-wise assembly was done using the following steps: 1) pre-swelling of resin with DMF; 2) Fmoc-deprotection by the use of 20% piperidine in DMF containing between 0 and 0.2M Oxyma Pure® for 1-5 treatments of 5-30 min each; 3) washes with DMF to remove traces of piperidine; 4) coupling of Fmoc-amino acid with 3-12 eq. of Fmoc-amino acid as a 0.3M solution in 0.3M Oxyma Pure® in DMF mixed with an equimolar volume of DIC for 1-12 hours. In the case of sterically hindered amino acids, this coupling step was repeated once or twice; 5) washes with DMF to remove excess reagents; 6) final wash with DCM at the completion of the assembly which made the resin ready for attachment of a modifying group on lysine side chain.

Alternatively, the protected peptidyl resin was synthesized according to the Fmoc strategy on a Prelude solid phase peptide synthesiser (Protein Technologies, Tucson, USA) using the manufacturer supplied machine protocols. Coupling was done by the use of DIC (dicyclohexylcarbodiimide) and Oxyma Pure (ethyl 2-cyano-2-(hydroxyimino)-acetate, Merck, Novabiochem, Switzerland) mediated couplings in DMF. The coupling of the Fmoc-amino acid was done as described above using 4-8 time excess of amino acid relative to resin substitution (4-8 eq). Coupling time ranged from 1 hour up to 6 hours. The Fmoc-Arg(pbf)-OH was coupled using a double coupling procedure (1 hour+1 hour). The step-wise solid phase assembly on the Prelude was done using the following steps: 1) deprotection (removal of Fmoc) by the use of 20-25% piperidine in DMF for 2×4-10 min; step 2) Wash (removal of piperidine) with DMF and DCM, step 3) Coupling of Fmoc-amino acid (0.3M Fmoc-amino acid in 0.3M Oxyma Pure in DMF) 3-10 eq excess for 1-4 hours coupling initiated by adding ⅒ volume of 3M DIC in DMF and ⅒ volume collidine in DMF Mixing was done by occasional bubbling with nitrogen, step 4) Wash (removal of excess amino acid and reagents by the use of DMF and DCM). The last step included washing with DCM which made the resin ready for attachment of a modifying group on lysine side chain.

Attachment of Side Chains to Resin Bound Protected Peptide Backbone:

The N-epsilon-lysine Mtt protection group was removed by washing the resin with a suitable orthogonally deprotection mixture such as, but not limited to, 20-30% HFIP in DCM, containing 0-5% TIS in multiple cycles (e.g. 1×5 min and 2×20 min) before washing with piperidine, DMF and DCM.

Acylation was performed either manually, or on a solid phase peptide synthesizer, such as, but not limited to the SymphonyX Solid Phase Peptide Synthesizer from Protein Technologies (Tucson, AZ 85714 U.S.A.) as described in this method's section "SPPS of the peptidyl backbone" using stepwise addition of building blocks such as, but not limited to, Fmoc-8-amino-3,6-dioxaoctanoic acid (Fmoc-OEG-OH), Fmoc-Glu-OtBu, Fmoc-tranexamic acid (Fmoc-Trx-OH). Introduction of the fatty acid moiety was achieved using a suitable building block, such as, but not limited to, octadecanedioic acid mono-tert-butyl ester, eicosanedioic acid mono-tert-butyl ester, hexadecanedioic acid mono-tert-butyl ester, tetradecanedioic acid mono-tert-butyl ester, 4-(9-carboxynonyloxy) benzoic acid tert-butyl ester.

Alternatively the side chain moiety could be installed in 1 step, directly after removal of the Mtt group, as described in the first part of this section, by using the a suitable side chain building block equipped with an activated ester, e.g. NHS.

Cleavage of Resin Bound Peptide and Purification

After synthesis the resin was washed with DCM, and the peptidyl resin subject to treatment with TFA mixtures in presence of 1-20 volume % scavenger agents such as, but not limited to, water, TIS, DTT and DODT. The cleavage reactions would typically be carried out at room temperature and a duration of 1-3 hours. Alternatively, the cleavage could be carried out at elevated temperatures (e.g. 50 degrees Celsius), for shorter times (15-60 minutes). The cleavage reaction was followed by precipitation of the crude peptide using cold (e.g. 5 degrees Celsius) diethyl ether. The precipitate was washed with diethylether and dissolved in a suitable mixture of water and MeCN. Optionally, suitable water-miscible co-solvents such as acetic acid were used.

The crude peptide solution was purified by reversed-phase preparative HPLC (Waters Deltaprep 4000) on a column containing C18-silica gel. Elution was performed with an increasing gradient of MeCN in water containing 0.1% TFA. Relevant fractions were analysed by analytical UPLC. Fractions containing the pure target peptide were pooled and freeze dried.

Alternatively, or when further purification was necessary, the crude peptide or lyophilized peptide TFA salt isolated as described above was dissolved in a neutral (e.g. pH 7-8) aqueous buffer based on common buffer salts such as, but not limited to, sodium hydrogen phosphate or ammonium bicarbonate and purified with reversed-phase preparative HPLC (Waters Deltaprep 4000) on a column containing C18-silica gel. Elution was performed with an increasing gradient of MeCN in aqueous buffer (such as, but not limited to, sodium phosphate (5-100 mM, pH 7-8, or 2-40 g/l ammonium bicarbonate). Relevant fractions were analysed by analytical UPLC. Fractions containing the pure target peptide were pooled and acidified with TFA until pH 2 and diluted with water until the total concentration of MeCN was <20%. Optionally, the resulting mixture was degassed by filtration using vacuum. The solution was then purified by reversed-phase preparative HPLC (Waters Deltaprep 4000) on a column containing C18-silica gel. Elution was performed with an increasing gradient of MeCN in water containing 0.1% TFA. Relevant fractions were analysed by analytical UPLC. Fractions containing the pure target peptide were pooled and freeze dried LCMS Characterization Methods:
LCMS34:

LCMS34 was performed on a set up consisting of Waters Acquity UPLC H Class system and Waters Xevo G2-XS QTof. Eluents: A: 0.1% formic acid in MQ water; B: 0.1% formic acid in MeCN.

The analysis was performed at RT (column temp 40° C.) by injecting an appropriate volume of the sample onto the column which was eluted with a gradient of A and B. The UPLC conditions, detector settings, and mass spectrometer settings were: Column: Waters Acquity BEH, C-18, 1.7 μm, 2.1 mm×50 mm. Gradient: Linear 5%-95% B during 4.0 min at 0.4 ml/min. Detection: MS resolution mode, ionisation method: ES. Scan: 50-4000 amu.

LCMS36:

LCMS36 was performed on a set up consisting of Waters Acquity UPLC H Class system and Waters Xevo G2-XS QTof. Eluents: A: 0.1% formic acid in MQ water; B: 0.1% formic acid in MeCN.

The analysis was performed at RT (column temp 60 C) by injecting an appropriate volume of the sample onto the column which was eluted with a gradient of A and B. The UPLC conditions, detector settings, and mass spectrometer settings were: Column: Phenomenex Aeris, C-4, 3.6 μm widepore, 2.1 mm×50 mm. Gradient: stepwise over 8 minutes; 5%-25% B during 1.0 min, 25%-65% B, during 6 minutes, 65-95% B during 0.5 minutes, 95% B isocratic for 0.5 minutes, at 0.4 ml/min. Detection: MS resolution mode, ionisation method: ES. Scan: 50-4000 amu.

LCMS_ZQ:

LCMS_ZQ was performed on a LCMS instrument consisting of Waters Acquity UPLC system coupled with Waters Acquity TUV detector and Waters Micromass ZQ 2000 detector. Eluents: A—0.05% TFA in MQ-water, B—0.05% TFA in acetonitrile.

The analysis was performed at RT (column temperature 40° C.) by injecting appropriate volume (0.2-10 μl) of the sample onto the column which was eluted with a gradient of A and B. Column: Waters Acquity UPLC BEH, C-18, 1.7 μm, 2.1 mm×50 mm. Gradient run time: Linear 5-95% B over 4.5 min, then 95% B for 0.5 min, 95-5% B for 0.5 min, 5% B for 0.5 min at a flow rate of 0.45 ml/min. Detection: Ionization method: Electron spray positive, Scanning range: 200-2048 (m/z), Capillary voltage: 3.0 kV, Cone Voltage: 20 V, Scan time: 0.9 s, Interscan delay: 0.1 s, Detection method: quadrupole.

LCMS01:

LCMS_01 was performed on a setup consisting of Waters Acquity UPLC system and LCT Premier XE mass spectrometer from Micromass. Eluents: A: 0.1% Formic acid in MQ water; B: 0.1% Formic acid in MeCN. The analysis was performed at RT (column temp 40 C) by injecting an appropriate volume of the sample onto the column which was eluted with a gradient of A and B. The UPLC conditions, detector settings and mass spectrometer settings were: Column: Waters Acquity UPLC BEH, C-18, 1.7 μm, 2.1 mm×50 mm. Gradient: Linear 5%-95% B during 4.0 min at 0.4 ml/min. Detection: 214 nm (analogue output from TUV (Tunable UV detector)) MS ionisation mode: API-ES. Scan: 500-2000 atomic mass units (amu).

Manufactured Compounds

Example 1a: Compounds According to the Invention

Compound 0007

H-Aib-EGTFTSDVSSYLEGOAA-K([2-[2-[2-[[2-[2-[2-[[(4S)-4-carboxy-4-(17-carboxyheptadecanoylamino)butanoyl]amino]ethoxy]ethoxyacetyl]amino]ethoxy]ethoxy]acetyl])-EFIAWLVRGRGGGEASELSTAALGRLSAELHEL-ATLPRTETGSGSP-amide

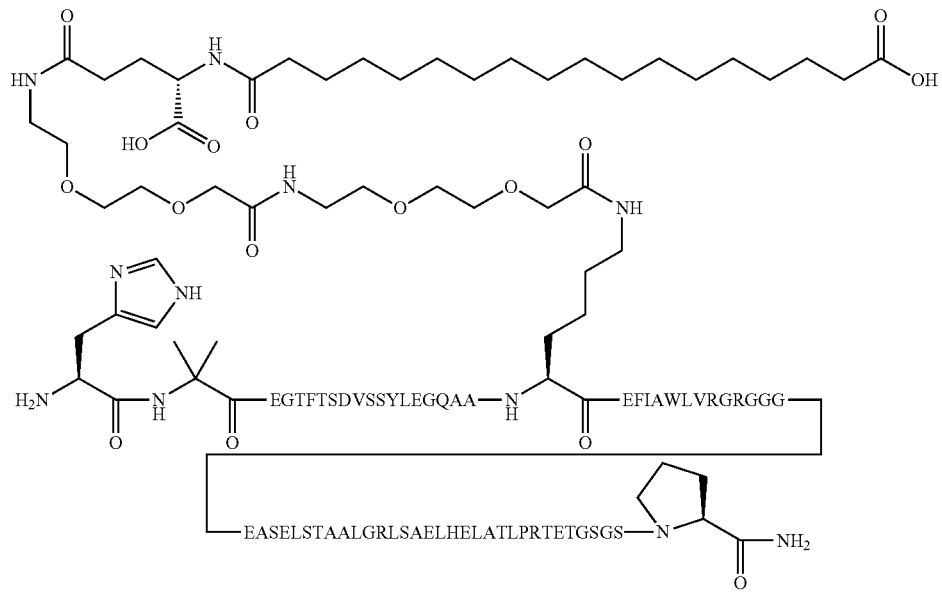

$C_{332}H_{531}N_{89}O_{112}$

Molecular weight (average) calculated: 7561.3 g/mol mono isotopic mass: 7556.9 g/mol LCMS34: found $(M+5H)^{5+}$1513.3 (most abundant)

The amino acid sequence of HXEGTFTSDVS-SYLEGQAAKEFIAWLVRGRGGGEASELSTAALGRL-SAELHELATLPRTETGSGSP has SEQ ID NO: 117

Compound 0009

H-Aib-EGTFTSDVSSYLEGQAAREFIAWLVRG-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-GEGEGEEASELSTAALGRLSAELHELATLPRTETGSGSP-amide

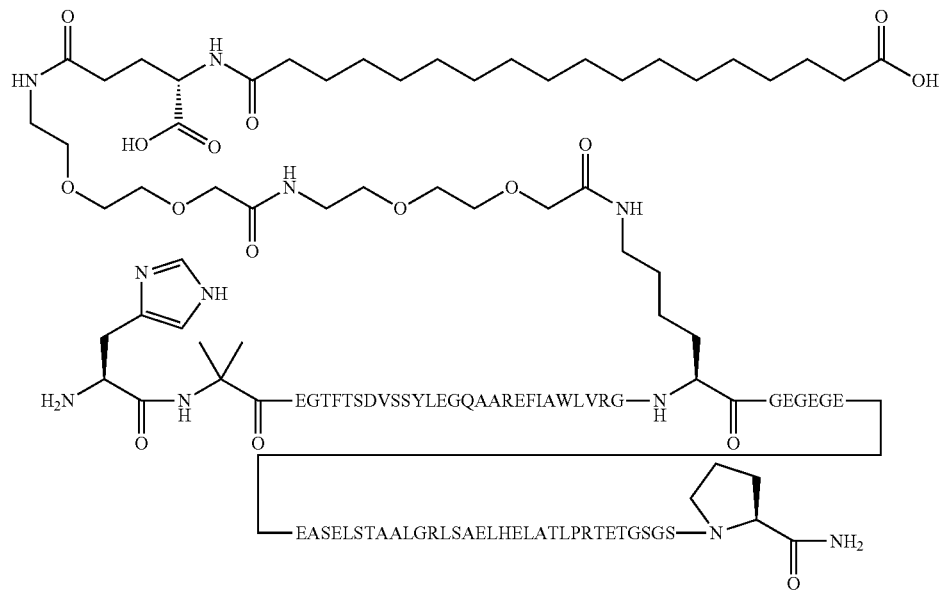

$C_{347}H_{552}N_{92}O_{121}$

Molecular weight (average) calculated: 7948.6 g/mol mono isotopic mass: 7944.0 g/mol LCMS34: found $(M+5H)^{5+}$ 1591 (most abundant)

The amino acid sequence of HXEGTFTSDVSSYLEGQAAREFIAWLVRGKGEGEGEEASELSTAALGRLSAELHELATLPRTETGSGSP has SEQ ID NO: 118

Compound 0010

H-Aib-EGTFTSDVSSYLEGQAAREFIAWLVRGRGEGEGE-K([2-[2-[2-[[2-[2-[2-[[(4S)-4-carboxy-4-(17-carboxyheptadecanoylamino)butanoyl]amino]ethoxy]ethoxy]acetyl]amino)ethoxy]ethoxy]acetyl])-EASELSTAALGRLSAELHELATLPRTETGSGSP-amide

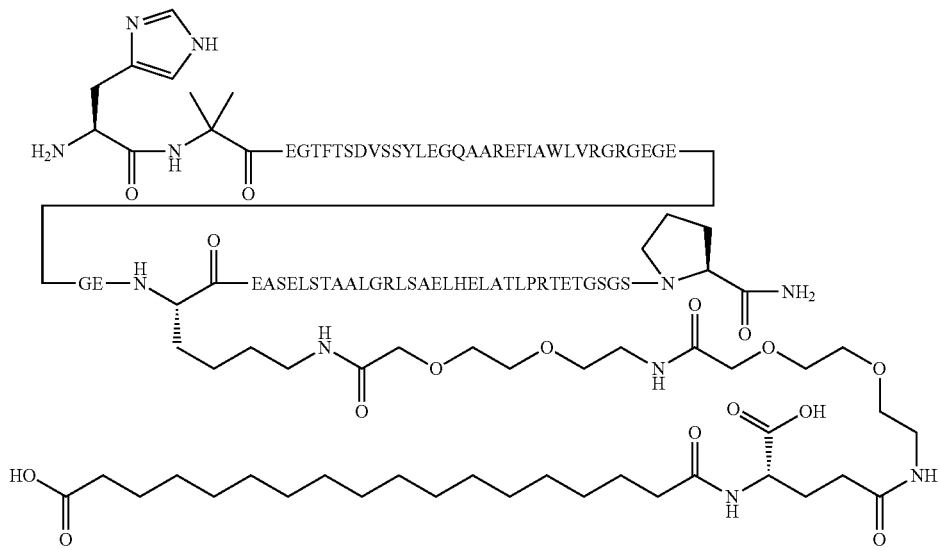

$C_{353}H_{564}N_{96}O_{122}$
Molecular weight (average) calculated: 8104.8 g/mol
mono isotopic mass: 8100.1 g/mol
LCMS34: found $(M+5H)^{5+}$ 1622 (most abundant)
The amino acid sequence of HXEGTFTSDVS-SYLEGQAAREFIAWLVRGRGEGEGEKEASELSTAAL-GRLSAELHELATLPRTETGSGSP has SEQ ID NO: 119
Compound 0019
H-Aib-EGTFTSDVSSYLEGQAA-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-EFIAWLVRGRGGQEPGOEPEASELSTAALGRLS-AELHELATLPRTETGSGSP-amide $C_{362}H_{575}N_{97}O_{124}$
Molecular weight (average) calculated: 8270.0144 g/mol
mono isotopic mass: 8265.1670 g/mol
LCMS36: found $(M+5H)^{5+}$1654.85 (most abundant)
The amino acid sequence of HXEGTFTSDVS-SYLEGQAAKEFIAWLVRGRGGQEPGOEPEASEL-STAALGRLSAELHELATLPRTETGSGSP has SEQ ID NO: 120
Compound 0026
H-Aib-EGTFTSDVSSYLEGQAA-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-EFIAWLVRGRGOEPGQAPEASELSTA-ALGRLSAELHELATLPRTETGSGSP-amide

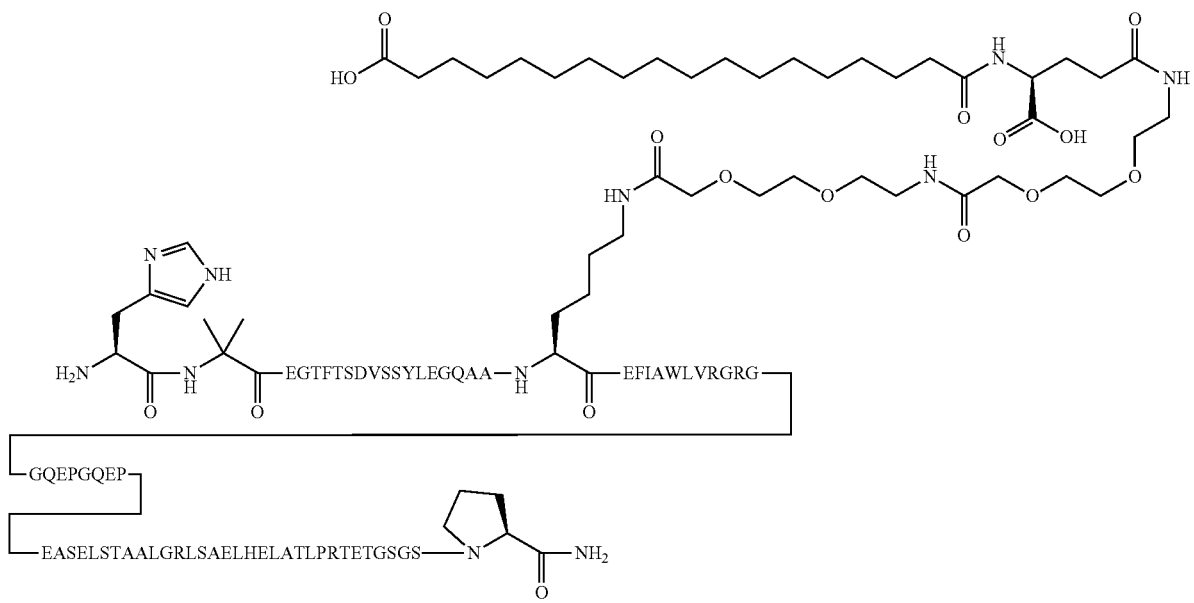

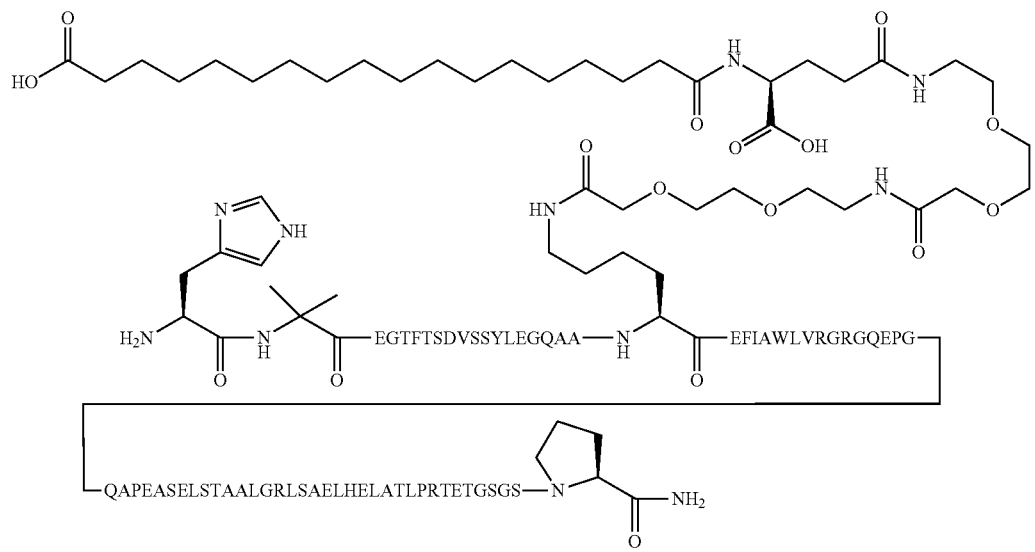

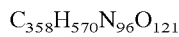

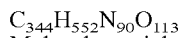

$C_{358}H_{570}N_{96}O_{121}$
Molecular weight (average) calculated: 8154.9270 g/mol
mono isotopic mass: 8150.1400 g/mol
LCMS34: found (M+5H)$^{5+}$1631.04 (most abundant)
The amino acid sequence of HXEGTFTSDVS-SYLEGQAAKEFIAWLVRGRGQEPGQAPEASEL-STAALGRLSAELHELATLPRTETGSGSP has SEQ ID NO: 121
Compound 0035
Imp-AEGTFTSDVSSYLEEQAAREFIAWLVRGR-K([2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl])-EASELSTAALGRLSAELHELATLPRTETGSGSP-amide $C_{344}H_{552}N_{90}O_{113}$
Molecular weight (average) calculated: 7756.5989 g/mol
mono isotopic mass: 7752.0214 g/mol
LCMS01: found (M+5H)$^{5+}$ 1552 (most abundant)
The amino acid sequence of XAEGTFTSDVSSYLE-EQAAREFIAWLVRGRKEASELSTAALGRLSAEL-HELATLPRTETGSGSP has SEQ ID NO: 122
Compound 0039
HGEGTFTSDVSSYLEEQAAR-K([2-[2-[2-[[2-[2-[2-[(4S)-4-carboxy-4-(13-carboxytridecanoylamino)butanoyl]amino]ethoxy]ethoxy]acetyl]amino]ethoxy]ethoxy]acetyl])-FIEWLVRG-K([2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl])-GEASELSTAALGRLSAELHELATLPRTETGSGSP-amide

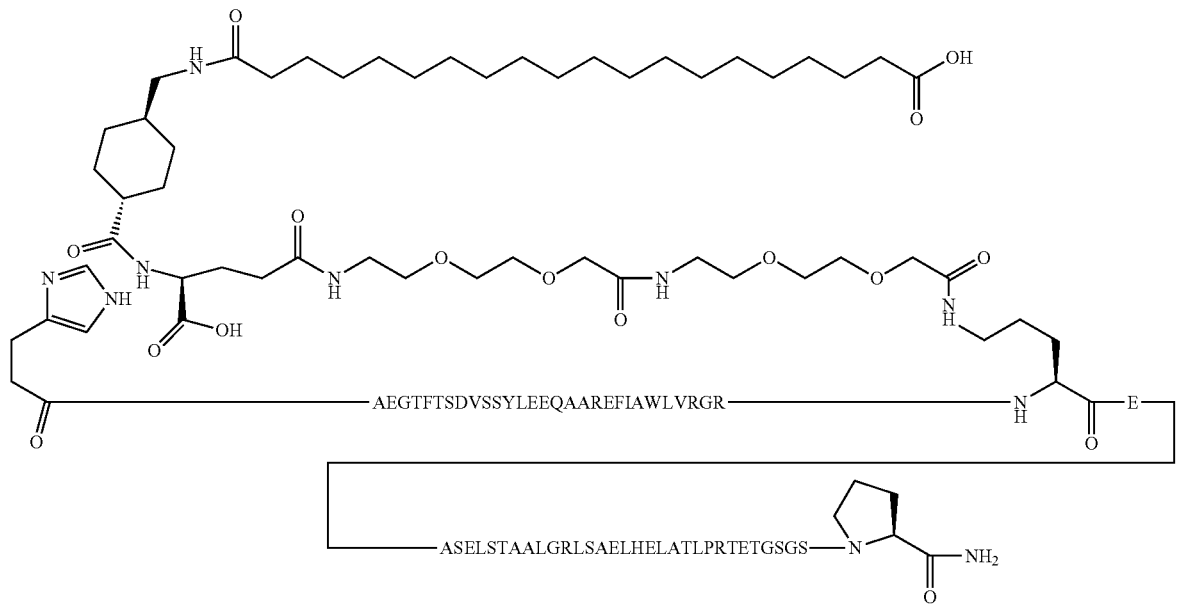

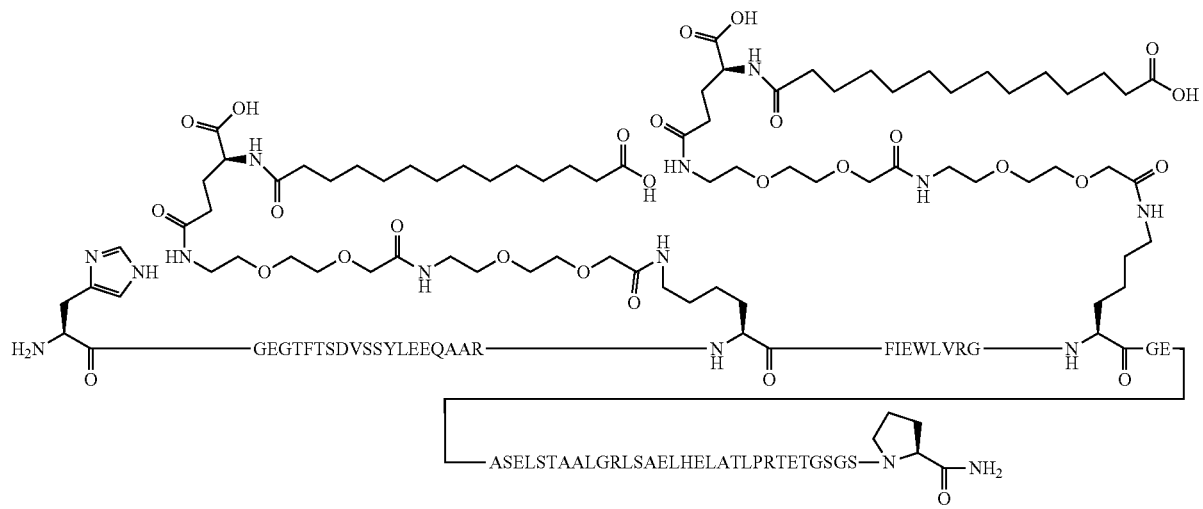

$C_{359}H_{577}N_{91}O_{124}$
Molecular weight (average) calculated: 8151.9580 g/mol
mono isotopic mass: 8147.1642 g/mol
LCMS01: found (M+5H)$^{5+}$1631.6 (most abundant)
The amino acid sequence of HGEGTFTSDVS-SYLEEGAARKFIEWLVRGKGEASELSTAALGRL-SAELHELATLPRTETGSGSP has SEQ ID NO: 123
Compound 0040
H-Aib-EGTFTSDVSSYLEGQAA-K([2-[2-[2-[2-[2-[2-[[(4S)-4-carboxy-4-(17-carboxyheptadecanoylamino)butanoyl]aminoethoxy]ethoxy]acetyl]amino]ethoxy]ethoxyacetyl])-EFIAWLVRGRGGGGEASELSTAALGRLSAELHELATLPRTETGSGSP-amide $C_{334}H_{534}N_{90}O_{113}$
Molecular weight (average) calculated: 7618.3490 g/mol
mono isotopic mass: 7613.8806 g/mol
LCMS34: found (M+5H)$^{5+}$1524.92 (most abundant)
The amino acid sequence of HXEGTFTSDVS-SYLEGQAAKEFIAWLVRGRGGGGEASELSTAALGRL-SAELHELATLPRTETGSGSP has SEQ ID NO: 124
Compound 0042
H-Aib-EGTFTSDVSSYLEGQAAKEFIAWLVRGR-K([2-[2-[2-[2-[2-[2-[[(4S)-4-carboxy-4-(17-carboxyheptadecanoylamino)butanoyl]amino]ethoxy]ethoxy]acetyl]amino]ethoxy]ethoxy]acetyl])-GGEASELSTAALGRLSAELHELATLPRTETGSGSP-amide

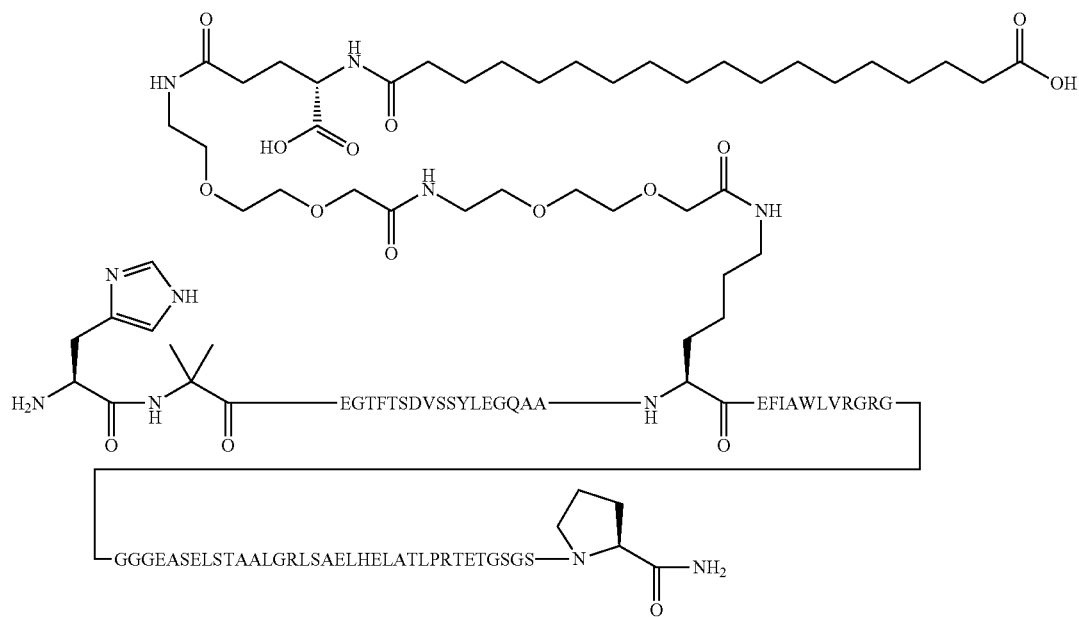

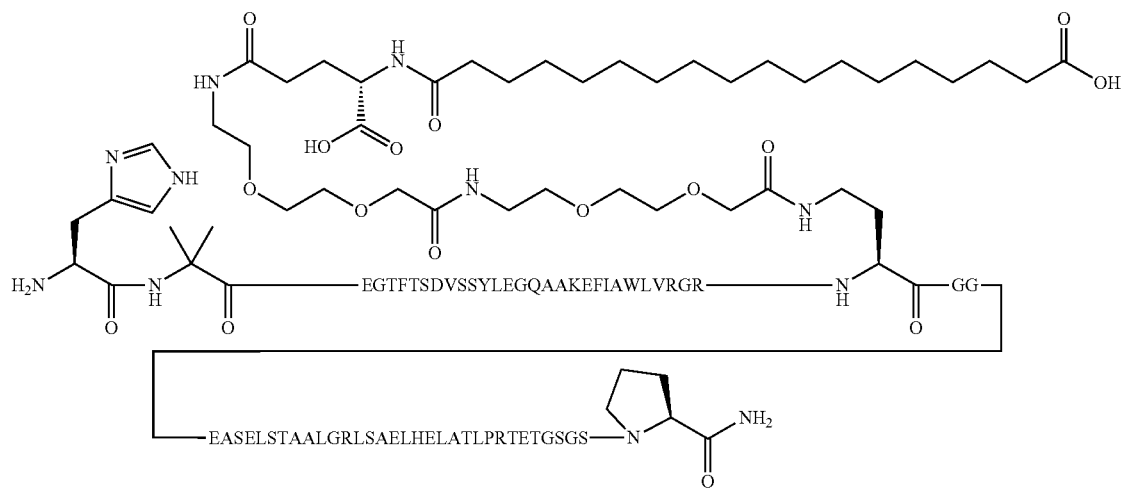

$C_{336}H_{540}N_{90}O_{112}$
Molecular weight (average) calculated: 7632.4186 g/mol
mono isotopic mass: 7627.9326 g/mol
LCMS34: found (M+5H)$^{5+}$ 1527.76 (most abundant)
The amino acid sequence of HXEGTFTSDVSSVLEGO-MAKEFIAWLVRGRKGGEASELSTAALGRLSAEL-HELATLPRTETGSGSP has SEQ ID NO: 125
Compound 0044
H-Aib-EGTFTSDVSSYLEGOAA-K([(2S)-2-amino-6-[[2-[2-[2-[[2-[2-[2-[(4S)-4-carboxy-4-(17-carboxyheptadecanoylamino)butanoy]amino]ethoxy]ethoxy]acetyl]amino]ethoxy]ethoxy]acetyl]amino]hexanoyl])-EFIAWLVRGRGGGEASELSTAALGRLSAELHEL-ATLPRTETGSGSP-amide $C_{338}H_{543}N_{91}O_{113}$
Molecular weight (average) calculated: 7689.4699 g/mol
mono isotopic mass: 7684.9541 g/mol
LCMS34: found (M+5H)$^{5+}$1538.8 (most abundant)
The amino acid sequence of HXEGTFTSDVS-SYLEGQAAKEFIAWLVRGRGGGEASELSTAALGRL-SAELHELATLPRTETGSGSP has SEQ ID NO: 117
Compound 0045
H-Aib-EGTFTSDVSSYLEGQAAKEFIAWLVRGR-K([(2S)-2-amino-6-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]hexanoyl])-GGEASELSTAALGRLSAELHELATLPRTETGSGSP-amide

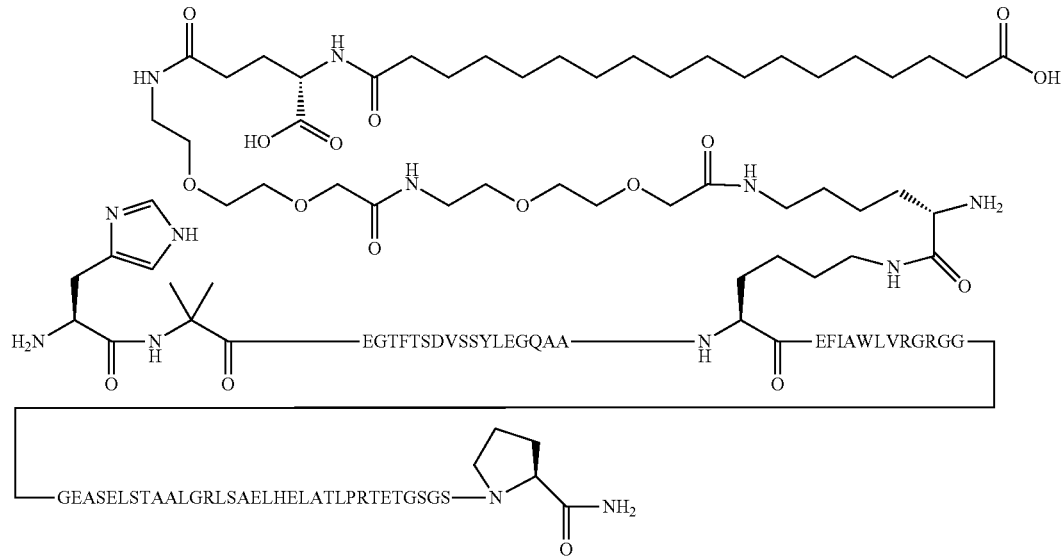

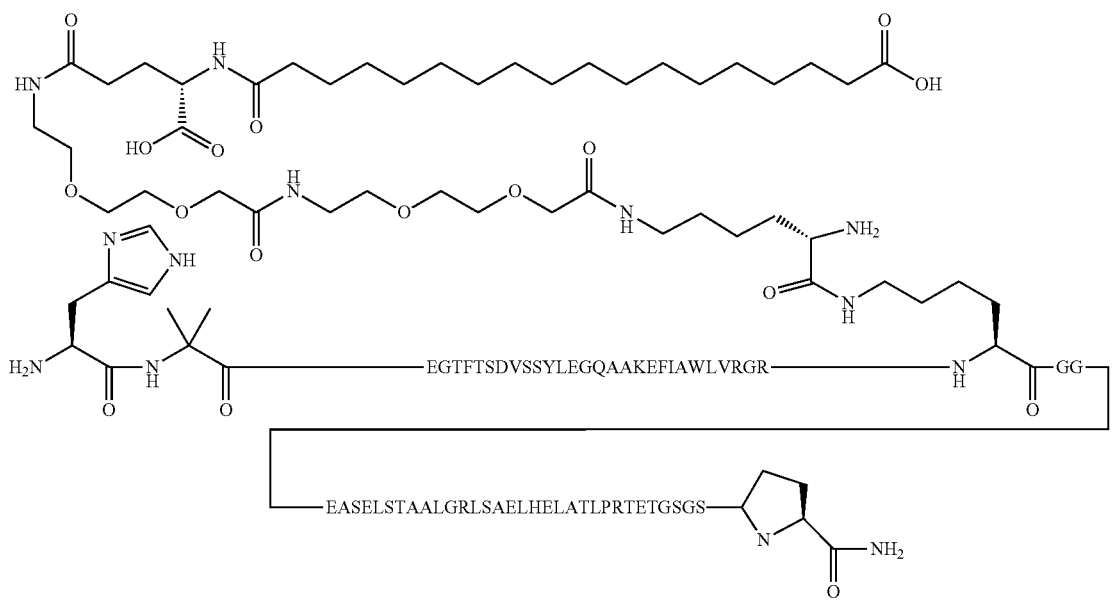

$C_{342}H_{552}N_{92}O_{113}$
Molecular weight (average) calculated: 7760.5909 g/mol
mono isotopic mass: 7756.0276 g/mol
LCMS34: found $(M+5H)^{5+}$1553.22 (most abundant)
The amino acid sequence of HXEGTFTSDVS-SYLEGQAAKEFIAWLVRGRKGGEASELSTAALGRL-SAELHELATLPRTETGSGSP has SEQ ID NO: 125
Compound 0051
Imp-AEGTFTSDVSSYLEEQAAREFIAWLVRGR-K([2-[2-[2-[[2-[2-[2-[(4S)-4-carboxy-4-(17-carboxyheptade-canoylamino)butanoyl]amino]ethoxy]ethoxy]acetyl]amino]ethoxy]ethoxy]acetyl])-EASELSTAALGRLSAELHELATLPRTETGSGSP-amide $C_{344}H_{552}N_{90}O_{113}$
Molecular weight (average) calculated 7589.3508 g/mol
mono isotopic mass: 7584.8904 g/mol
LCMS01: found $(M+5H)^{5+}$1519.1 (most abundant)
The amino acid sequence of XAEGTFTSDVSSYLE-EQAAREFIAWLVRGRKEASELSTAALGRLSAEL-HELATLPRTETGSGSP has SEQ ID NO: 122
Compound 0052
H-Aib-EGTFTSDVSSYLEGQAA-K([2-[2-[2-[[2-[2-[2-[[(4S)-4-carboxy-4-(17-carboxyheptadecanoylamino)bu-tanoyl]amino]ethoxy]ethoxy]acetyl]amino]ethoxy]ethoxy]acetyl])-EFIAWLVRGRGGGGGGGGGEASELSTAALGRLS-AELHELATLPRTETGSGSP-amide

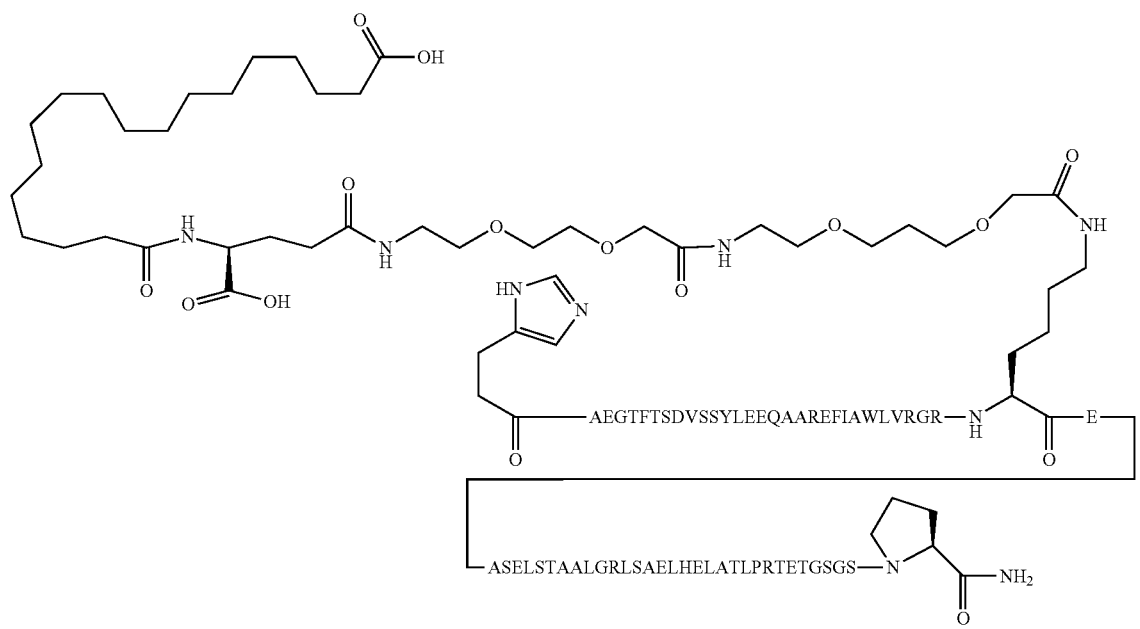

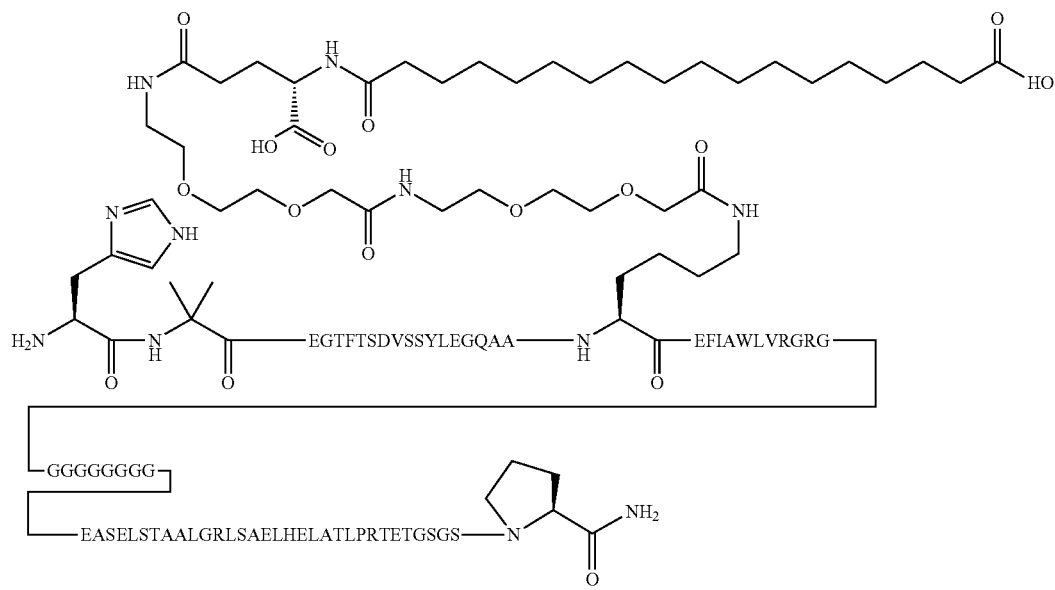

$C_{344}H_{549}N_{95}O_{118}$

Molecular weight (average) calculated: 7903.6056 g/mol mono isotopic mass: 7898.9879 g/mol LCMS34: found (M+5H)$^{5+}$1581.7 (most abundant)

The amino acid sequence of HXEGTFTSDVSSYLE-GQAAKEFIAWLVRGRGGGGGGGGEASELSTAAL-GRLSAELHELATLPRTETGSGSP has SEQ ID NO: 126

Compound 0056

H-Aib-EGTFTSDVSSYLEGQAA-K([2-[2-[2-[[2-[2-[2-[[(4S)-4-carboxy-4-(17-carboxyheptadecanoylamino)bu-tanoyl]amino]ethoxy]ethoxy]acetyl]amino]ethoxy]ethoxy]acetyl])-EFIAWLVRGRG-K([2-[2-[2-[[2-[2-[2-[[(4S)-4-carboxy-4-(17-carboxyheptadec anoylamino)butanoyl]amino]ethoxy]ethoxy]acetyl]amino]ethoxy]ethoxy]acetyl])-QEPGOEPEASELSTAALGRLSAELHELATLPRTE-TGSGSP-amide $C_{401}H_{645}N_{101}O_{136}$ Molecular weight (average) calculated: 9057.0071 g/mol mono isotopic mass: 9051.6660 g/mol LCMS34: found (M+5H)$^{5+}$1812.4 (most abundant)

The amino acid sequence of HXEGTFTSDVS-SYLEGQAAKEFIAWLVRGRGKQEPGQEPEASEL-STAALGRLSAELHELATLPRTETGSGSP has SEQ ID NO: 127

Compound 0057

H-Aib-EGTFTSDVSSYLEGQAA-K([2-[2-[2-[[2-[2-[2-[[(4S)-4-carboxy-4-(17-carboxyheptadecanoylamino)bu-tanoyl]amino]ethoxy]ethoxy]acetyl]amino]ethoxy]ethoxy]acetyl])-EFIAWLVRGRGGQE-K([2-[2-[2-[[2-[2-[2-[[(4S)-4-carboxy-4-(17-carboxyheptadecanoylamino)butanoyl]

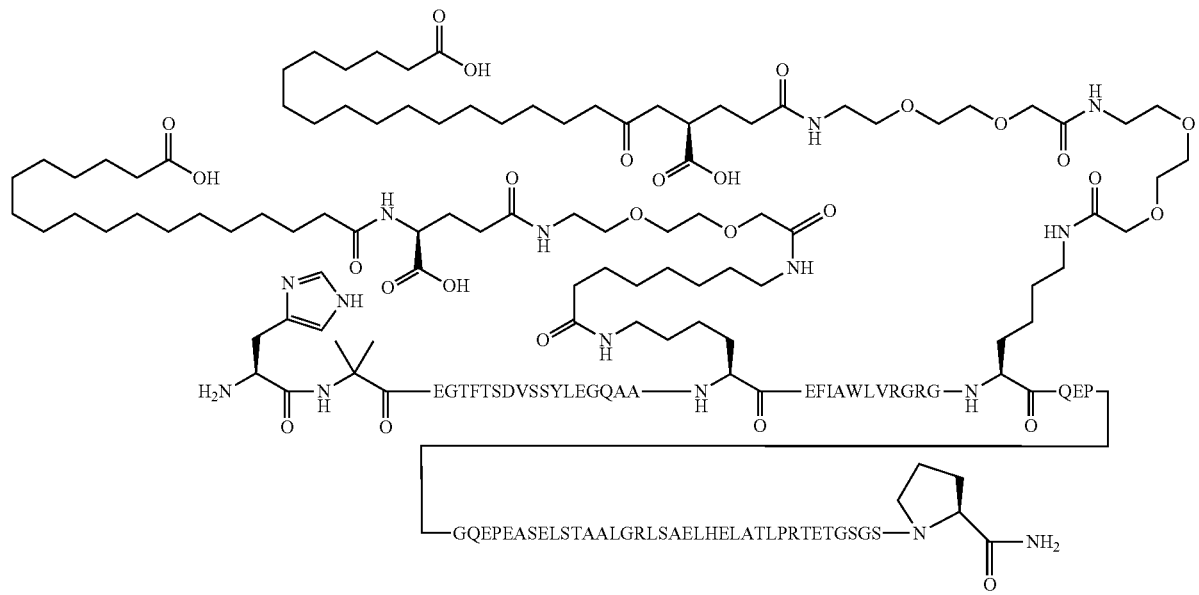

amino]ethoxy]ethoxy]acetyl]amino]ethoxy]ethoxy]acetyl])-GQEPEASELSTAALGRLSAELHELATLPRTETGSGSP-amide

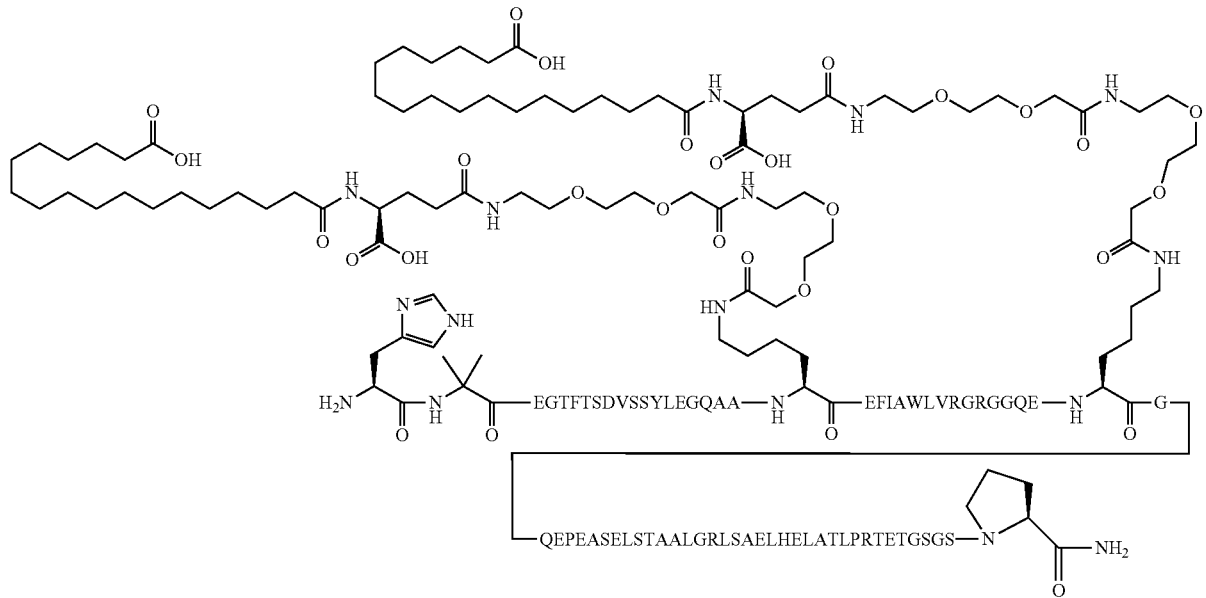

$C_{396}H_{541}N_{101}O_{136}$
Molecular weight (average) calculated: 9016.9432 g/mol
mono isotopic mass: 9011.6347 g/mol
LCMS34: found $(M+5H)^{5+}$1804.1 (most abundant)
The amino acid sequence of HXEGTFTSDVSSYLE-GQAAKEFIAWLVRGRGGQEKGQEPEASELSTAAL-GRLSAELHELATLPRTETGSGSP has SEQ ID NO: 128
Compound 0071
H-Aib-EGTFTSDVSSYLEGQAA-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-EFIAWLVRGRGGQEPGQEP-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl)-EASELSTAALGRLSAELHELATLPRTETGSGSP-amide

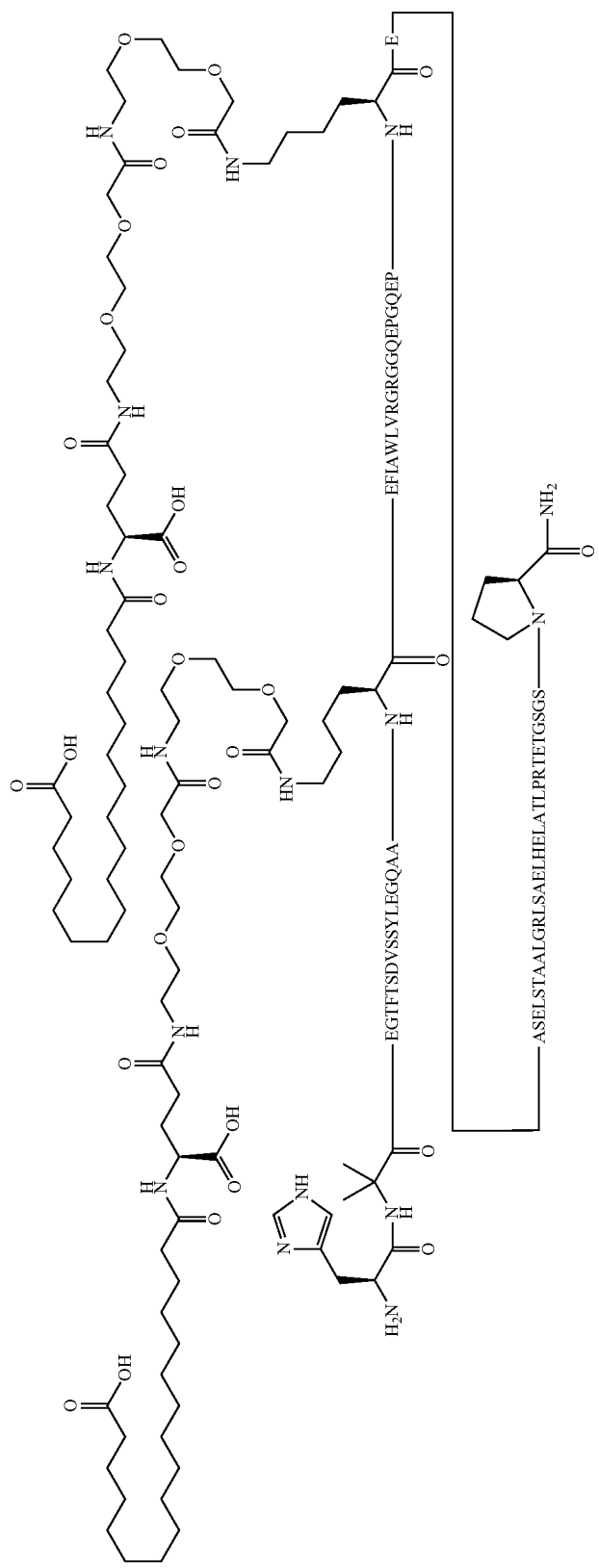

83

$C_{403}H_{648}N_{102}O_{137}$
Molecular weight (average) calculated: 9114.0584 g/mol
mono isotopic mass: 9108.6874 g/mol
LCMS34: found $(M+5H)^{5+}$1823.7 (most abundant)
The amino acid sequence of HXEGTFTSDVSSYLEGQAAKEFIAWLVRGRGGQEPGQEPKEASELSTAALGRLSAELHELATLPRTETGSGSP has SEQ ID NO: 129

84

Compound 0072
H-Aib-EGTFTSDVSSYLEGQAA-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-EFIAWLVRGRGG-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-EASELSTAALGRLSAELHELATLPRTETGSGSP-amide

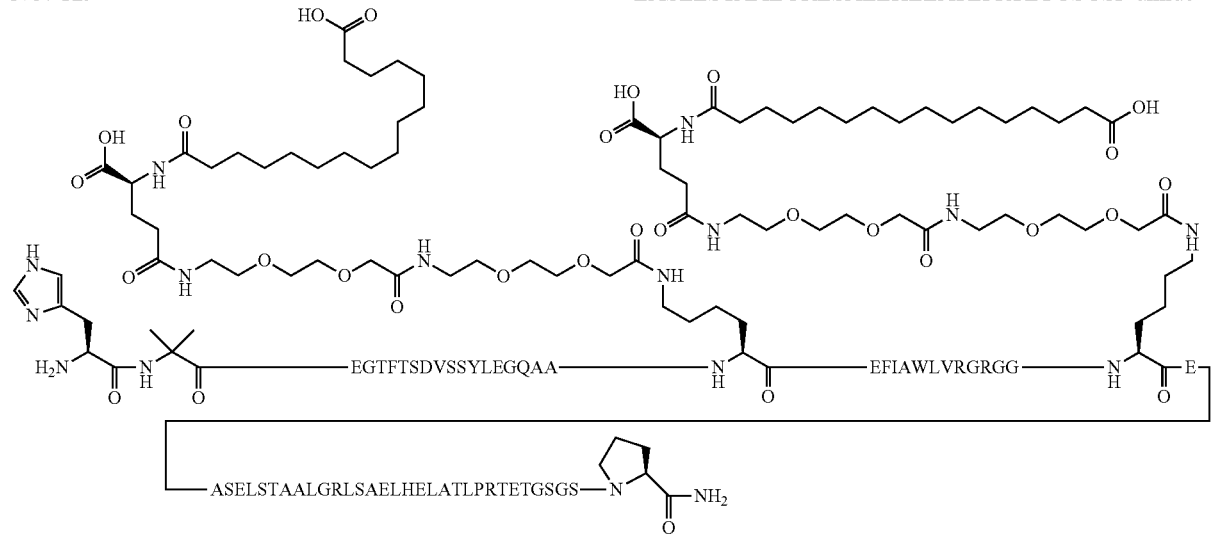

$C_{367}H_{593}N_{93}O_{124}$
Molecular weight (average) calculated: 8292.1840 g/mol
mono isotopic mass: 8287.2955 g/mol
LCMS34: found $(M+5H)^{5+}$1659.27 (most abundant)
The amino acid sequence of HXEGTFTSDVSSYLEGQAAKEFIAWLVRGRGGKEASELSTAALGRLSAELHELATLPRTETGSGSP has SEQ ID NO: 130
Compound 0073
H-Aib-EGTFTSDVSSYLEGQAAR-K([2-[2-[2-[[2-[2-[2-g[(4S)-4-carboxy-4-(15-carboxypentadecanoylamino)butanoyl]amino]ethoxy]ethoxy]acetyl]amino]ethoxy)ethoxy]acetyl])-FIAWLVRGRGG-K([2-[2-[2-[[2-[2-[2-[[(4S)-4-carboxy-4-(15-carboxypentadecanoylamino)butanoyl]amino]ethoxy]ethoxy)acetyl]amino)ethoxy]ethoxy]acetyl])-EASELSTAALGRLSAELHELATLPRTETGSGSP-amide

$C_{368}H_{598}N_{96}O_{122}$
Molecular weight (average) calculated: 8319.2557 g/mol
mono isotopic mass: 8314.3540 g/mol
LCMS34: found $(M+5H)^{5+}$1664.69 (most abundant)
The amino acid sequence of HXEGTFTSDVS-SYLEGQAARKFIAWLVRGRGGKEASELSTAALGRL-SAELHELATLPRTETGSGSP has SEQ ID NO: 131

Compound 0074

H-Aib-EGTFTSDVSSYLEEQAAR-K([2-[2-[2-[[2-[2-[2-[[(4S)-4-carboxy-4-(15-carboxypentadecanoylamino)bu-tanoyl]amino]ethoxy]ethoxy]acetyl]amino]ethoxy]ethoxy]acetyl])-FIAWLVRGRGG-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-EASELSTAALGRLSAELHELATLPRTETGSGSP-amide

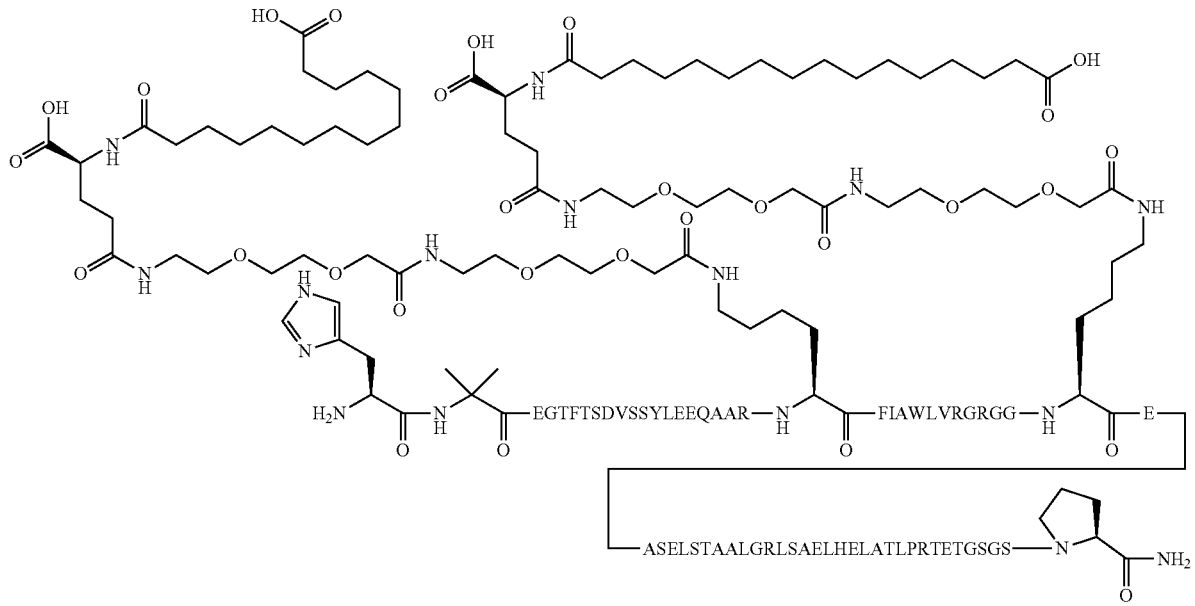

$C_{371}H_{602}N_{96}O_{124}$
Molecular weight (average) calculated: 8391.3184 g/mol
mono isotopic mass: 8386.3752 g/mol
LCMS34: found $(M+5H)^{5+}$1679.1 (most abundant)
The amino acid sequence of HXEGTFTSDVSSYLE-EQAARKFIAWLVRGRGGKEASELSTAALGRLSAEL-HELATLPRTETGSGSP has SEQ ID NO: 132

Compound 0075

H-Aib-EGTFTSDVSSYLEGQAA-K([2-[2-[2-[[2-[2-[2-[[(4S)-4-carboxy-4-(15-carboxypentadecanoylamino)bu-tanoyl]amino]ethoxy]ethoxy]acetyl]amino]ethoxy]ethoxy]acetyl)-EFIAWLVRG-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl)-GGGEASELSTAALGRLSAELHELATLPRTETGSGSP-amide

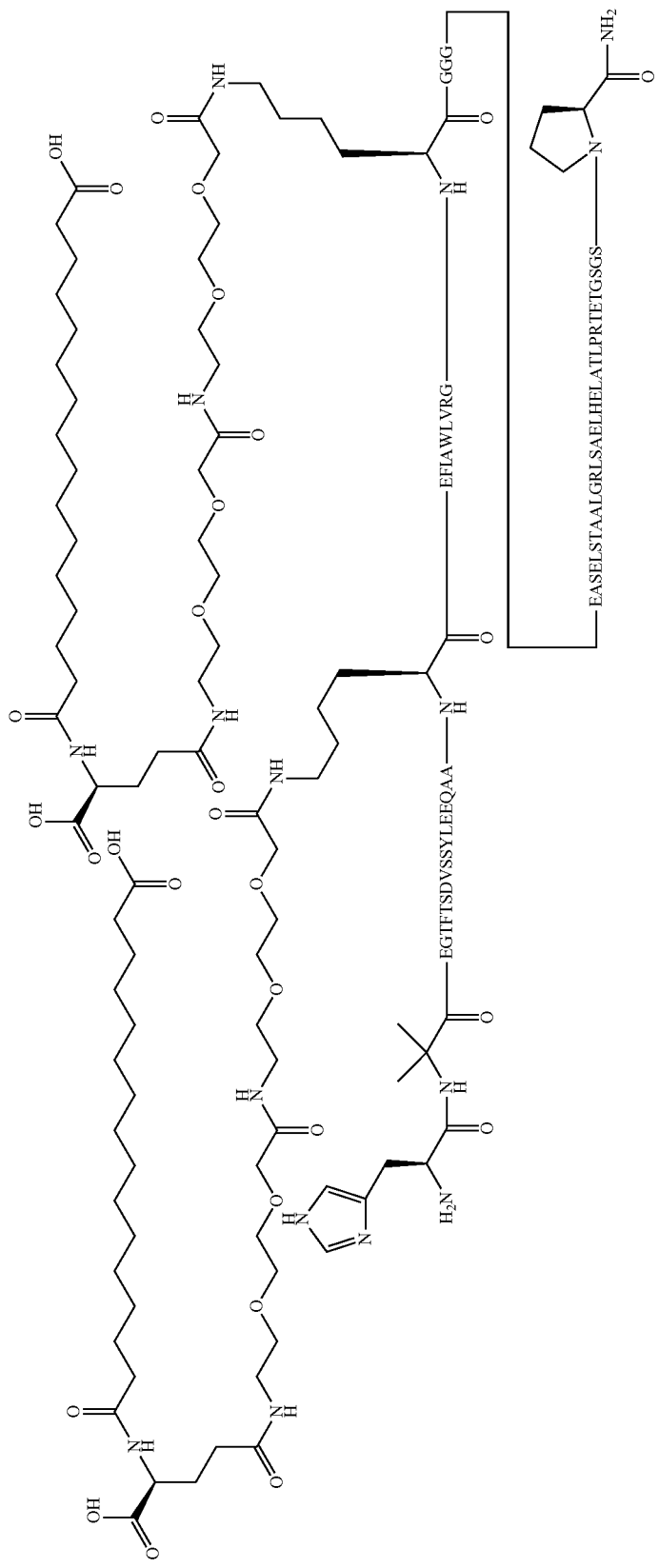

$C_{363}H_{584}N_{90}O_{124}$
Molecular weight (average) calculated: 8193.0497 g/mol
mono isotopic mass: 8188.2159 g/mol
LCMS34: found $(M+5H)^{5+}$1639.45 (most abundant)
The amino acid sequence of HXEGTFTSDVS-SYLEGQAAKEFIAWLVRGKGGGEASELSTAALGRL-SAELHELATLPRTETGSGSP has SEQ ID NO: 133

Compound 0076

H-Aib-EGTFTSDVSSYLEEQAAR-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-FIAWLVRG-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-GGGEASELSTAALGRLSAELHELATLPRTETGSGSP-amide

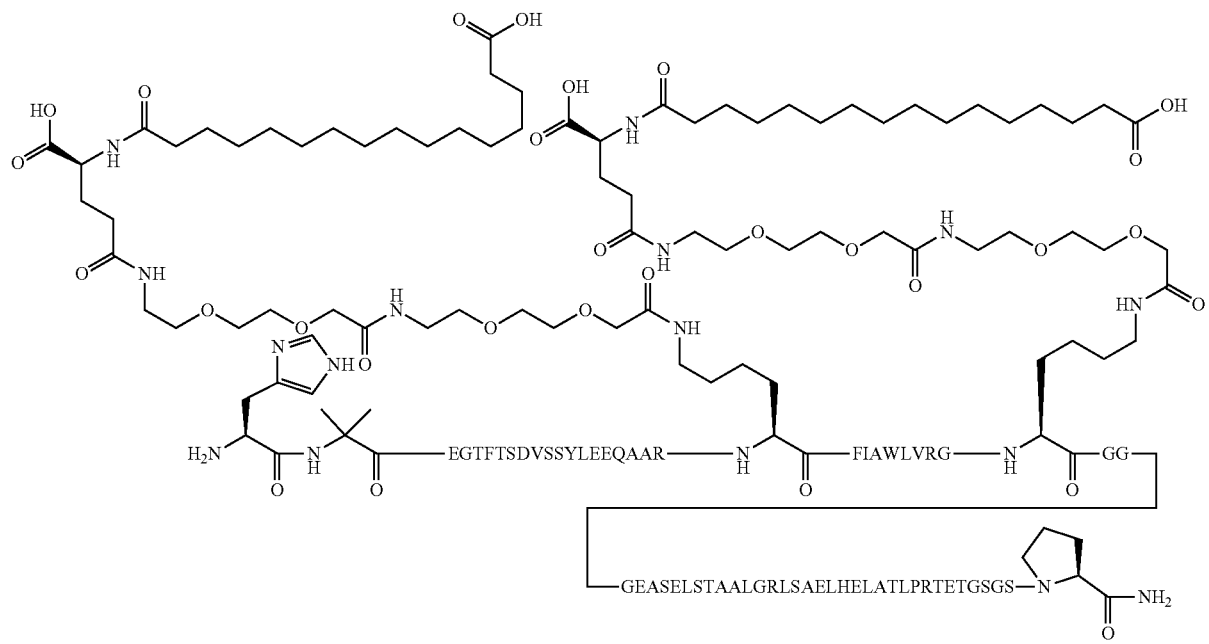

$C_{367}H_{593}N_{93}O_{124}$
Molecular weight (average) calculated: 8292.1840 g/mol
mono isotopic mass: 8287.2955 g/mol
LCMS34: found $(M+5H)^{5+}$1659.48 (most abundant)
The amino acid sequence of HXEGTFTSDVSSYLE-EQAARKFIAWLVRGKGGGEASELSTAALGRLSAEL-HELATLPRTETGSGSP has SEQ ID NO: 134

Compound 0077

H-Aib-EGTFTSDVSSYLEEQAAR-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-FIAWLV-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-GRGGGEASELSTAALGRLSAELHELATLPRTETGSGSP-amide

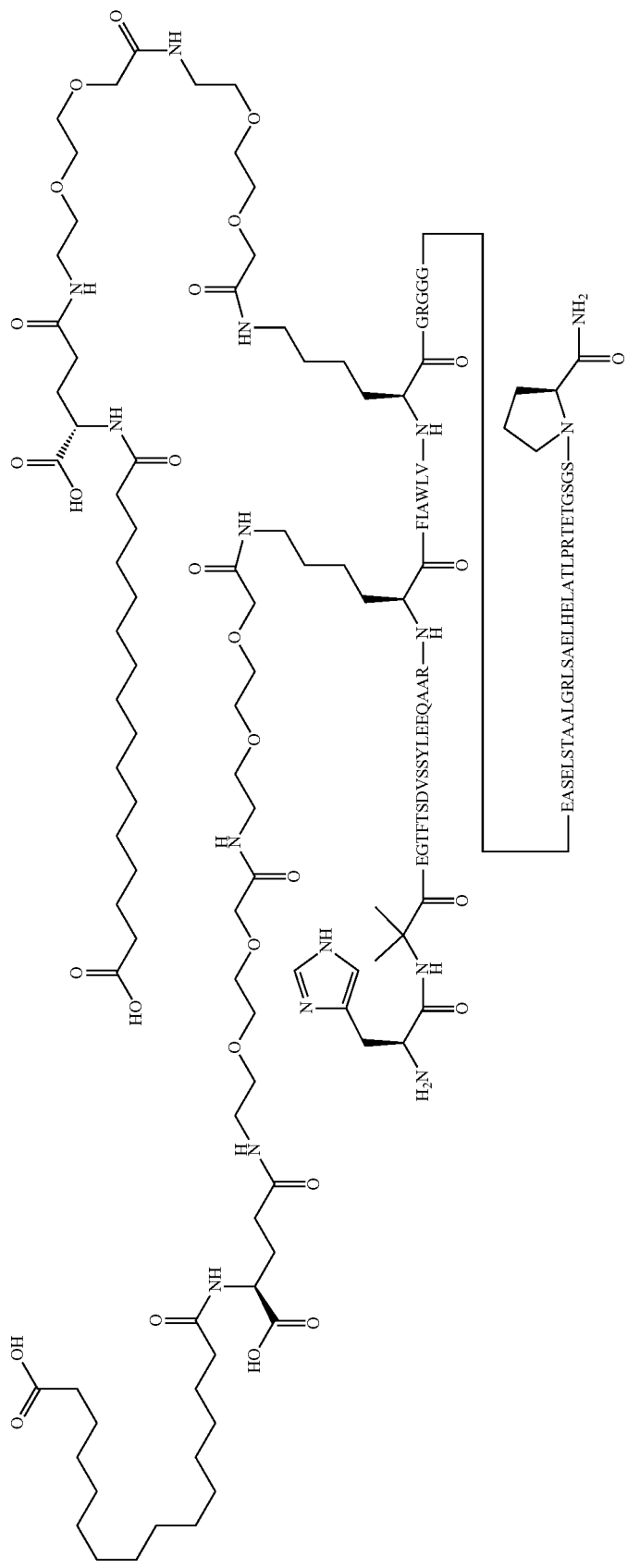

$C_{367}H_{593}N_{93}O_{124}$
Molecular weight (average) calculated: 8292.1840 g/mol
mono isotopic mass: 8287.2955 g/mol
LCMS34: found $(M+5H)^{5+}$1659.48 (most abundant)
The amino acid sequence of HXEGTFTSDVSSYLE-EQAARKFIAWLVKGRGGGEASELSTAALGRLSAEL-HELATLPRTETGSGSP has SEQ ID NO: 135

Compound 0083

H-Aib-EGTFTSDVSSYLEGQAAREFIAWLVRGR-K([2-[2-[2-f[2-[2-[2-[[(4S)-4-carboxy-4(17-carboxyheptade-canoylamino)butanoyl]amino]ethoxy]ethoxy]acetyl]amino]ethoxy]ethoxy]acetyl])-GOEPGQAPEASELSTAALGRLSAELHELATLPRT-ETGSGSP-amide

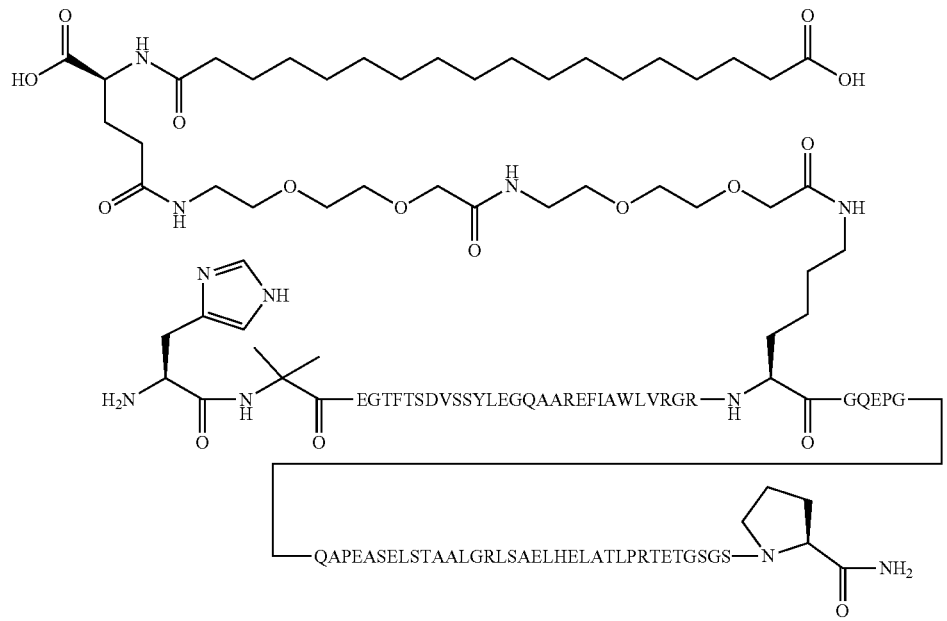

$C_{364}H_{582}N_{100}O_{122}$
Molecular weight (average) calculated: 8311.1127 g/mol
mono isotopic mass: 8306.2411 g/mol
LCMS34: found $(M+5H)^{5+}$1662.34 (mono isotopic)

The amino acid sequence of HXEGTFTSDVSSYLE-GOAAREFIAWLVRGRKGOEPGOAPEASELSTAAL-GRLSAELHELATLPRTETGSGSP has SEQ ID NO: 136

Compound 0084

H-Aib-EGTFTSDVSSYLEGQAAREFIAWLVR-GRGQEP-K([2-[2-[2-[[2-[2-[2-[[(4S)-4-carboxy-4-(17-car-boxyheptadecanoylamino)butanoyl]amino]ethoxy]ethoxy]acetylamino)ethoxy]ethoxy]acetyl])-GQAPEASELSTAALGRLSAELHELATLPRTETGSGSP-amide

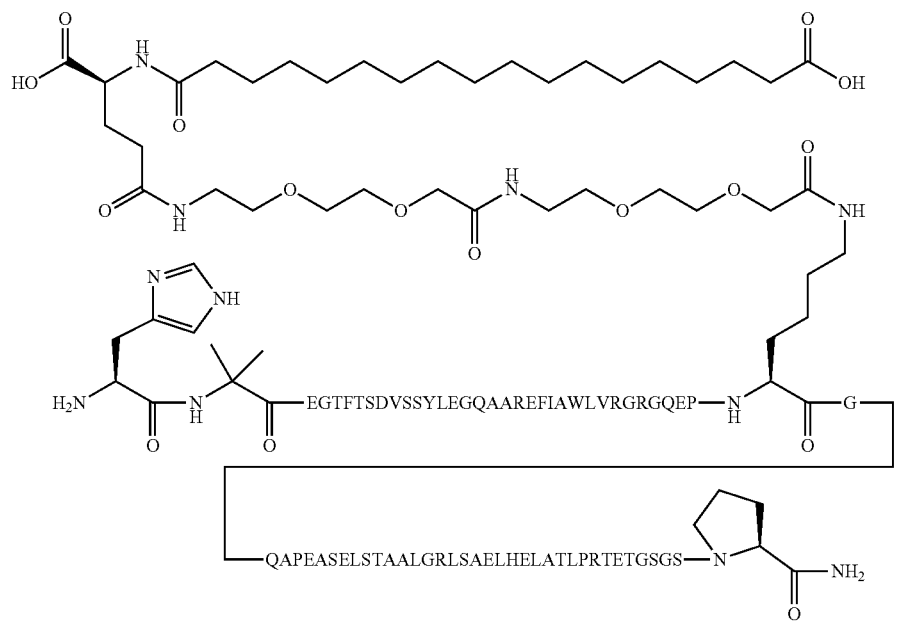

$C_{364}H_{582}N_{100}O_{122}$
Molecular weight (average) calculated: 8311.1127 g/mol
mono isotopic mass: 8306.2411 g/mol
LCMS34: found $(M+5H)^{5+}$ 1663 (most abundant)
The amino acid sequence of HXEGTFTSDVS-SYLEGQAAREFIAWLVRGRGQEPKGQAPEASEL-STAALGRLSAELHELATLPRTETGSGSP has SEQ ID NO: 137

Compound 0085

H-Aib-EGTFTSDVSSYLEGQAAREFIAWLVR-GRGQEPGQAP-K([2-[2-[2-[2-[2-[2-[[(4S)-4-carboxy-4-(17-carboxyheptadecanoylamino)butanoyl]amino]ethoxy]ethoxy]acetyl]amino]ethoxy]ethoxy]acetyl])-EASELSTAALGRLSAELHELATLPRTETGSGSP-amide

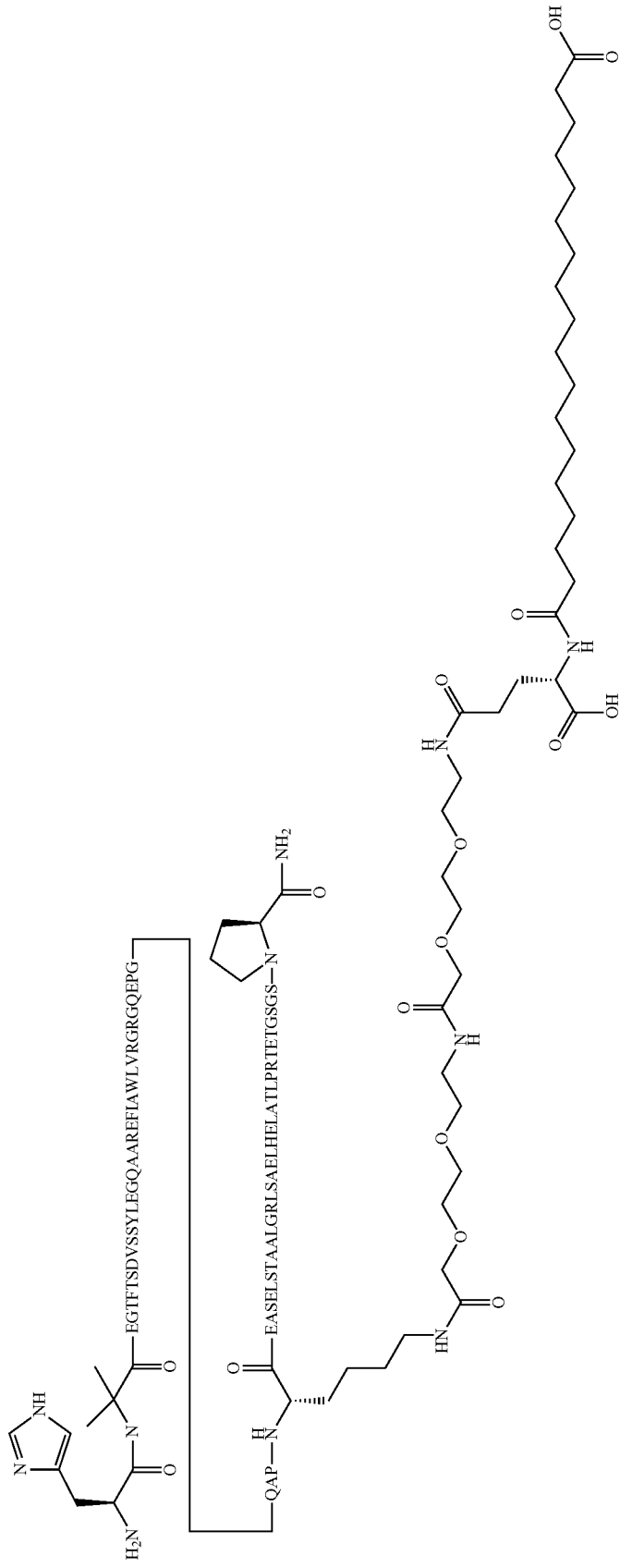

$C_{364}H_{582}N_{100}O_{122}$
Molecular weight (average) calculated: 8311.1127 g/mol
mono isotopic mass: 8306.2411 g/mol
LCMS34: found $(M+5H)^{5+}$1662.24 (mono isotopic)
The amino acid sequence of HXEGTFTSDVS-SYLEGQAAREFIAWLVRGRGOEPGQAPKEASEL-STAALGRLSAELHELATLPRTETGSGSP has SEQ ID NO: 138

Compound 0086

H-Aib-EGTFTSDVSSYLEEQAAR-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-FIEWLVRG-K([2-[2-[2-[[2-[2-[2-[[4S)-4-carboxy-4-(15-carboxypentadecanoylamino)butanoyl]amino]ethoxy]ethoxy]acetyl]amino]ethoxy]ethoxy]acetyl])-GEGGEASELSTAALGRLSAELHELATLPRTETGSGSP-amide

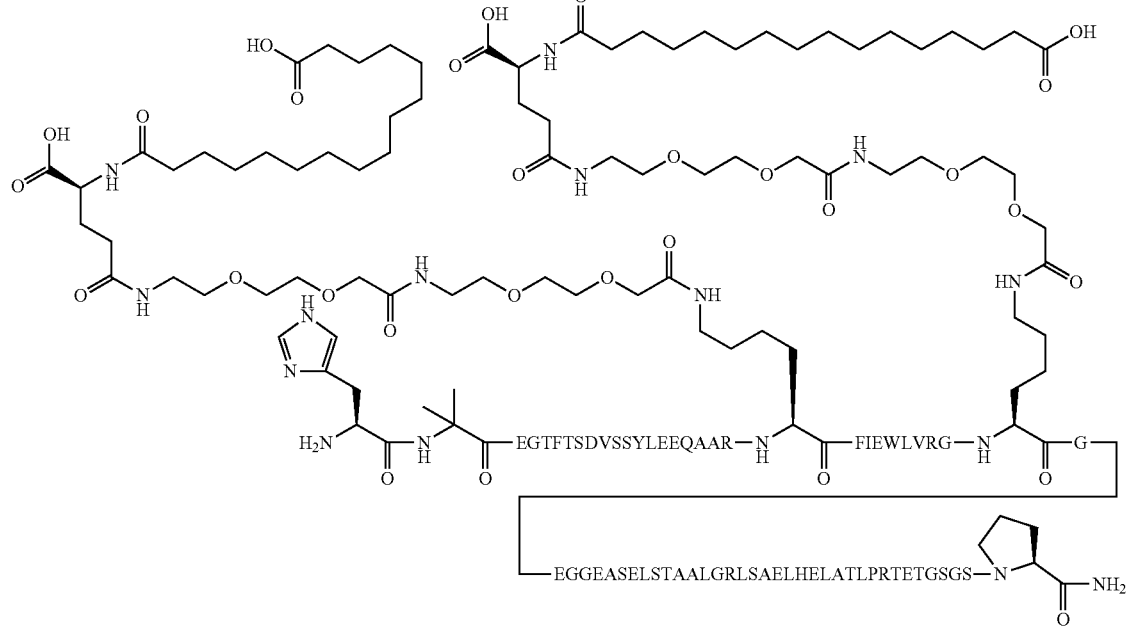

$C_{374}H_{602}N_{94}O_{129}$
Molecular weight (average) calculated: 8479.3341 g/mol
mono isotopic mass: 8474.3436 g/mol
LCMS34: found $(M+5H)^{5+}$1696.69 (most abundant)
The amino acid sequence of HXEGTFTSDVSSYLE-EQAARKFIEWLVRGKGEGGEASELSTAALGRLSAEL-HELATLPRTETGSGSP has SEQ ID NO: 139

Compound 0087

HGEGTFTSDVSSYLEEQAAR-K([2-[2-[2-[[2-[2-[2-[(4S)-4-carboxy-4-(15-carboxypentadecanoylamino)butanoyl]amino]ethoxy]ethoxy]acetyl]amino]ethoxy]ethoxy]acetyl])-FIEWLVRG-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-GEGGEASELSTAALGRLSAELHELATLPRTETGSGSP-amide

101

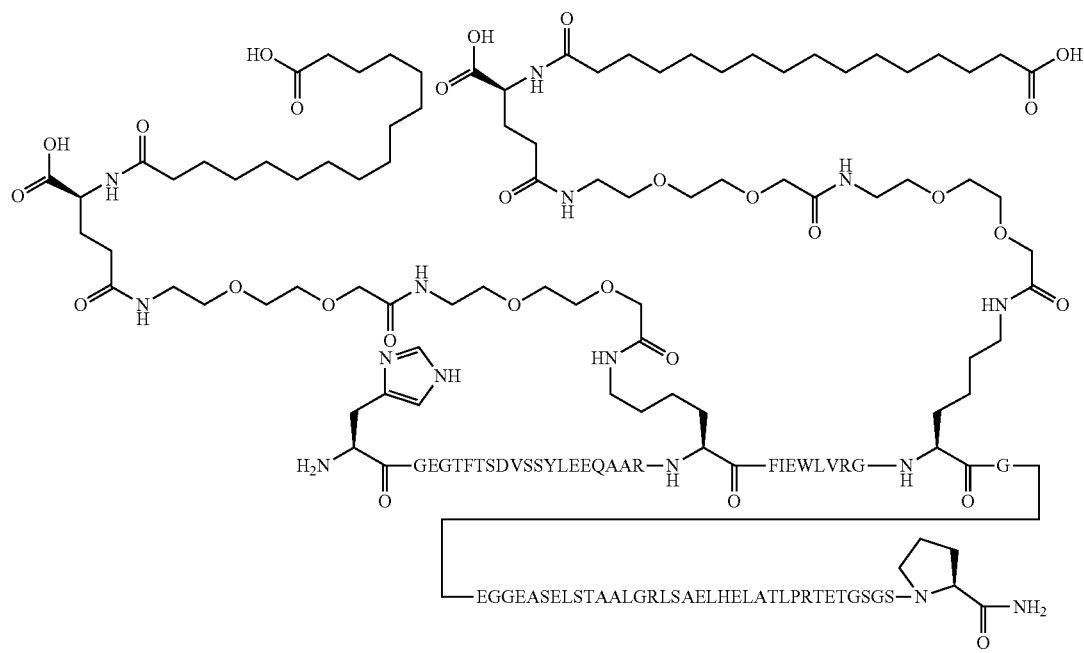

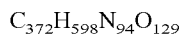

Molecular weight (average) calculated: 8451.2809 g/mol
mono isotopic mass: 8446.3123 g/mol
LCMS34: found (M+5H)$^{5+}$1691.08 (most abundant)

The amino acid sequence of HGEGTFTSDVSSYLEEQAARKFIEWLVRGKGEGGEASELSTAALGRLSAELHELATLPRTETGSGSP has SEQ ID NO: 140

102

Compound 0089
H-Aib-EGTFTSDVSSYLEEQAAR-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-FIEWLVRG-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-GEGGEASELSTAALGRLSAELHELATLPRTETGSGSP-amide

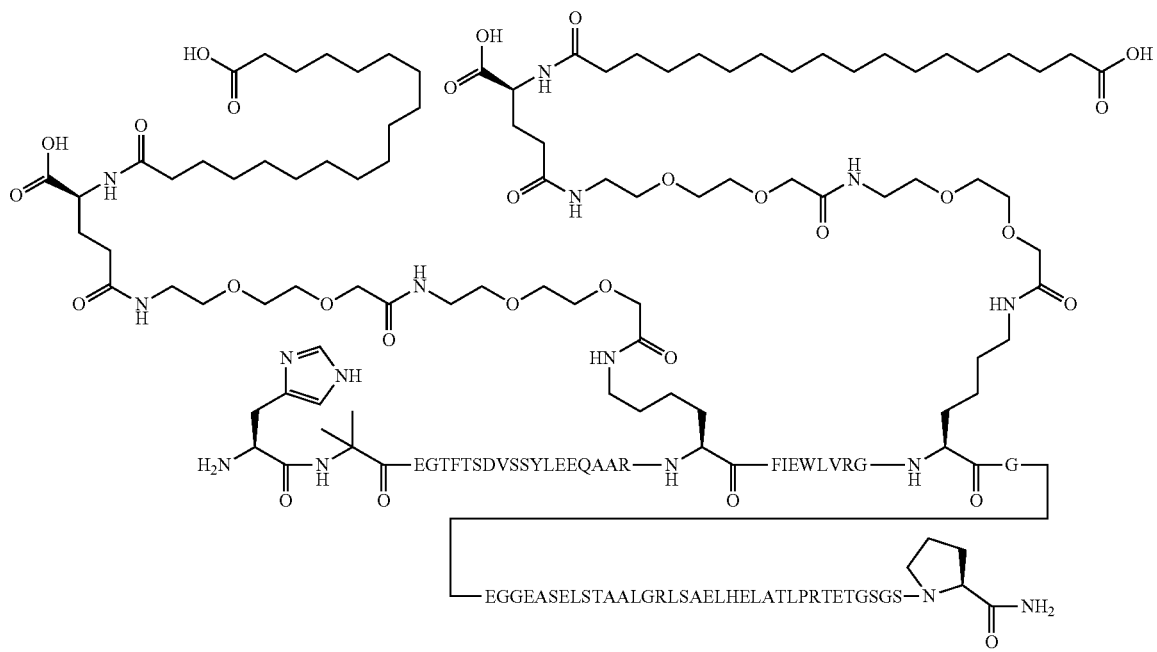

$C_{378}H_{610}N_{94}O_{129}$

Molecular weight (average) calculated: 8535.4404 g/mol mono isotopic mass: 8530.4062 g/mol LCMS34: found $(M+5H)^{5+}$ 1707.9 (most abundant)

The amino acid sequence of HXEGTFTSDVSSYLE-EQAARKFIEWLVRGKGEGGEASELSTAALGRLSAEL-HELATLPRTETGSGSP has SEQ ID NO: 139

Compound 0090

HGEGTFTSDVSSYLEEQAAR-K([2-[2-[2-[[2-[2-[2-[[(4S)-4-carboxy-4-(17-carboxyheptadecanoylamino)bu-tanoyl]amino]ethoxy]ethoxy]acetyl]amino]ethoxy]ethoxy]acetyl])-FIEWLVRG-K([2-[2-[2-[[2-[2-2[(4S)-4-carboxy-4-(17-carboxyheptadecanoylamino)butanoyl]amino]ethoxy]ethoxy]acetyl]amino]ethoxy]ethoxy]acetyl])-GEGGEASELSTAALGRLSAELHELATLPRTETGSGSP-amide

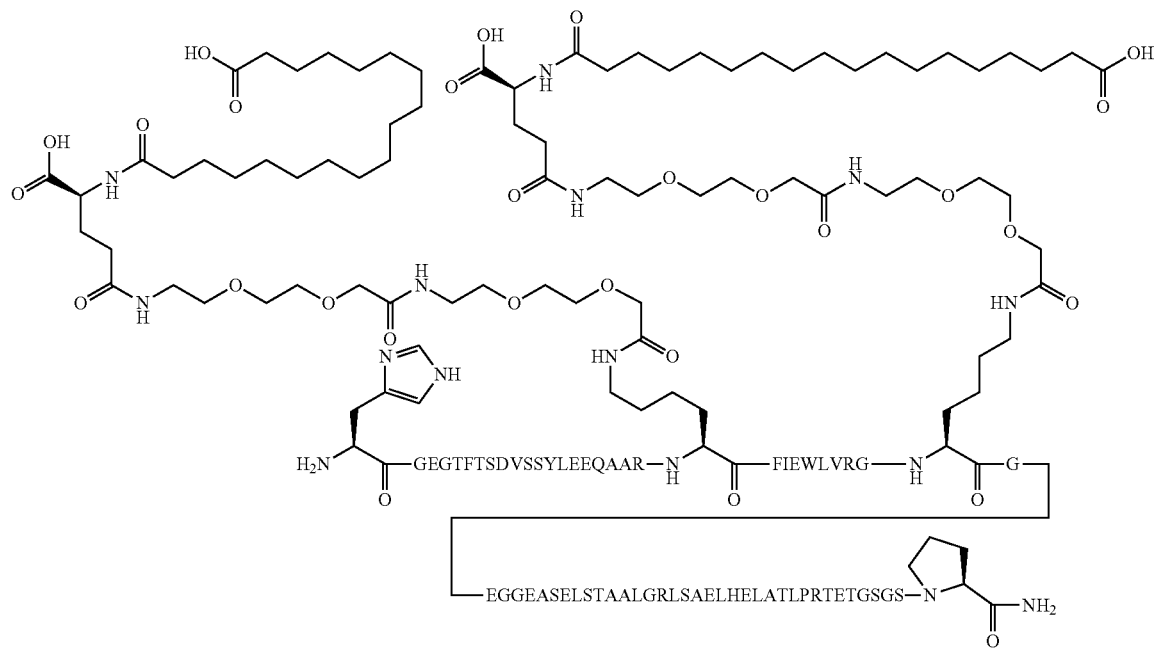

$C_{376}H_{606}N_{94}O_{129}$

Molecular weight (average) calculated: 8507.3872 g/mol mono isotopic mass: 8502.3749 g/mol LCMS34: found $(M+5H)^{5+}$ 1702.49 (most abundant)

The amino acid sequence of HGEGTFTSDVSSYLE-EQAARKFIEWLVRGKGEGGEASELSTAALGRLSAEL-HELATLPRTETGSGSP has SEQ ID NO: 140

Compound 0092

H-Aib-EGTFTSDVSSYLEGQAA-K([2-[2-[2-[[2-[2-[2-[[(4S)-4-carboxy-4-(17-carboxyheptadecanoylamino)bu-tanoyl]amino]ethoxy]ethoxy]acetyl]amino]ethoxy]ethoxy]acetyl])-EFIAWLVRGRGGGGGGGGGGGGGGEASELSTAA-LGRLSAELHELATLPRTETGSGSP-amide

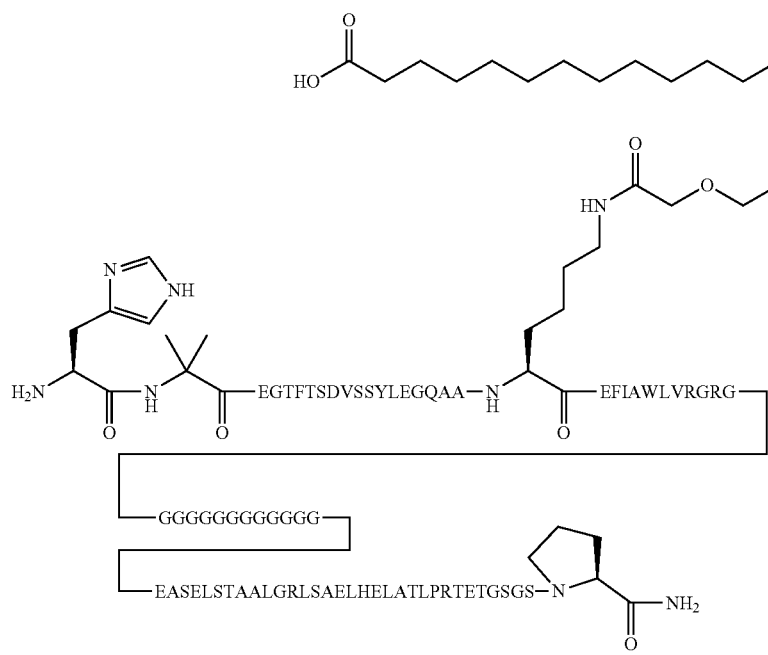

$C_{352}H_{561}N_{99}O_{122}$
Molecular weight (average) calculated: 8131.8108 g/mol
mono isotopic mass: 8127.0737 g/mol
LCMS34: found (M+5H)$^{5+}$1627.5 (most abundant)
The amino acid sequence of HXEGTFTSDVS-SYLEGQAAKEFIAWLVRGRGGGGGGGGGGGGEA-SELSTAALGRLSAELHELATLPRTETGSGSP has SEQ ID NO: 141

Compound 0093

H-Aib-EGTFTSDVSSYLEGQAA-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-EFIAWLVRGRGGGGGGGGGGGGGGGGGEASEL STAALGRLSAELHELATLPRTETGSGSP-amide

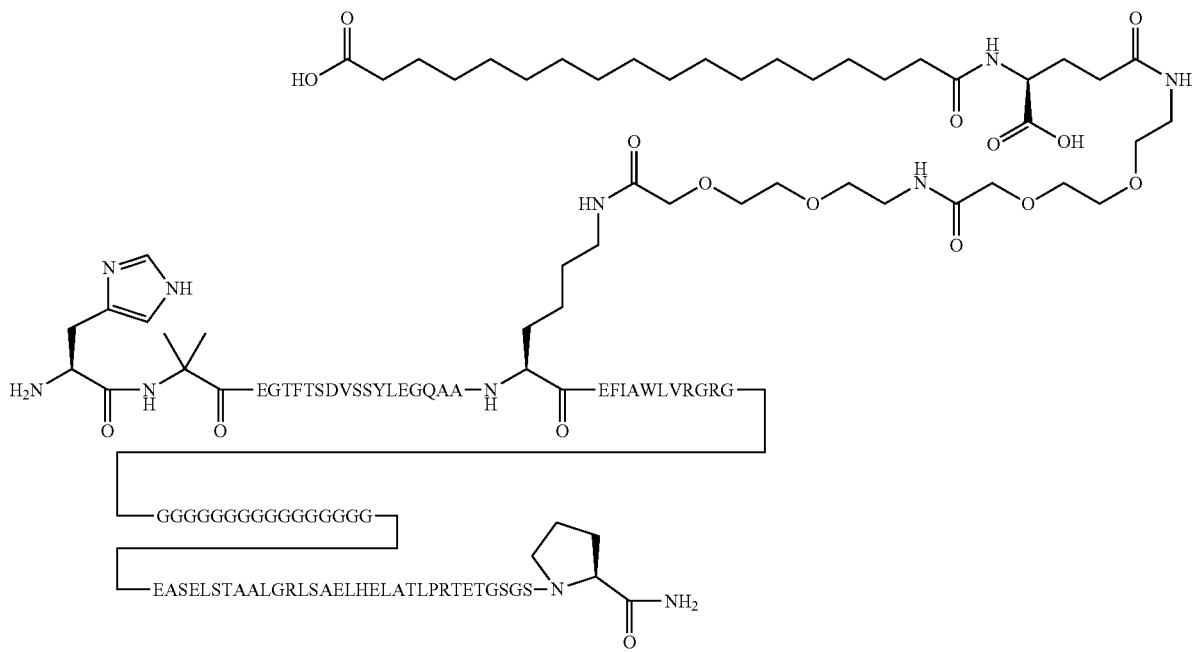

$C_{360}H_{573}N_{103}O_{126}$

Molecular weight (average) calculated: 8360.0161 g/mol mono isotopic mass: 8355.1596 g/mol LCMS34: found $(M+5H)^{5+}$ 1672.8 (most abundant)

The amino acid sequence of HXEGTFTSDVS-SYLEGQAAKEFIAWLVR-GRGGGGGGGGGGGGGGGGGGEASELSTAALGRL-SAELHELATLPRTETGSGSP has SEQ ID NO: 142

Compound 0094

H-Aib-EGTFTSDVSSYLEGQAA-K([2-[2-[2-g[2-[2-[2-[[(4S)-4-carboxy-4-(19-carboxynonadecanoylamino)butanoy]amino]ethoxy]ethoxy]acetyl]amino]ethoxy]ethoxy]acetyl])-EFIAWLVRGRGGGGGGGGGGEASELSTAALGRL-SAELHELATLPRTETGSGSP-amide

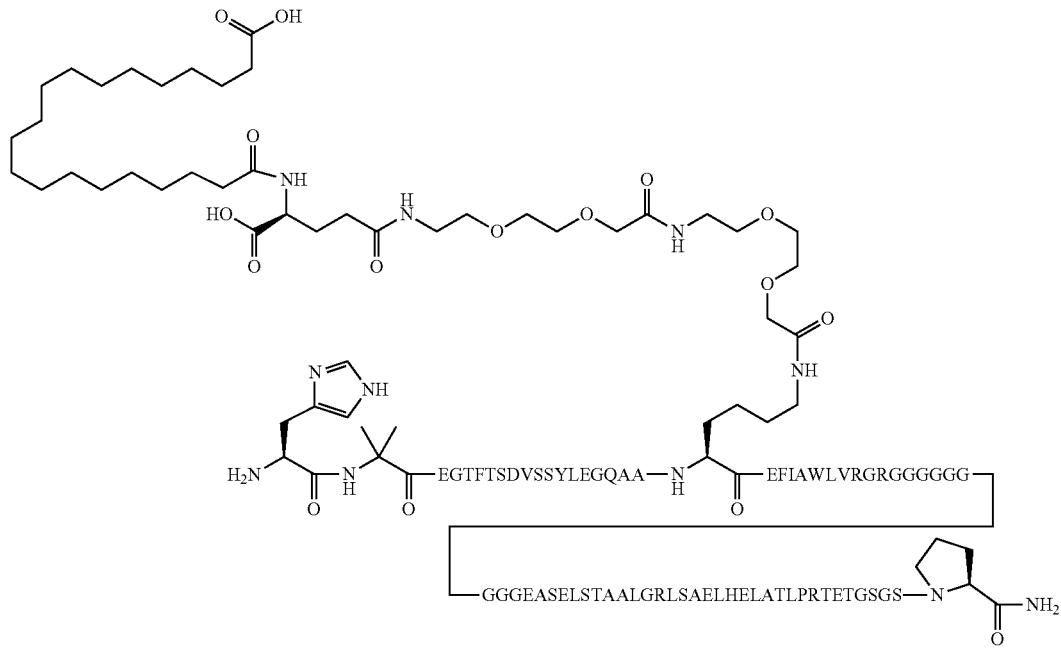

$C_{346}H_{553}N_{95}O_{118}$

Molecular weight (average) calculated: 7931.6587 g/mol mono isotopic mass: 7927.0192 g/mol LCMS34: found $(M+5H)^{5+}$1587.2 (most abundant)

The amino acid sequence of HXEGTFTSDVS-SYLEGQAAKEFIAWLVRGRGGGGGGGGGEASEL-STAALGRLSAELHELATLPRTETGSGSP has SEQ ID NO: 126

Compound 0095

H-Aib-EGTFTSDVSSYLEGQAA-K([2-[2-[2-[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl])-EFIAWLVRGRGGGGGGGGGEASELSTAALGRLS-AELHELATLPRTETGSGSP-amide

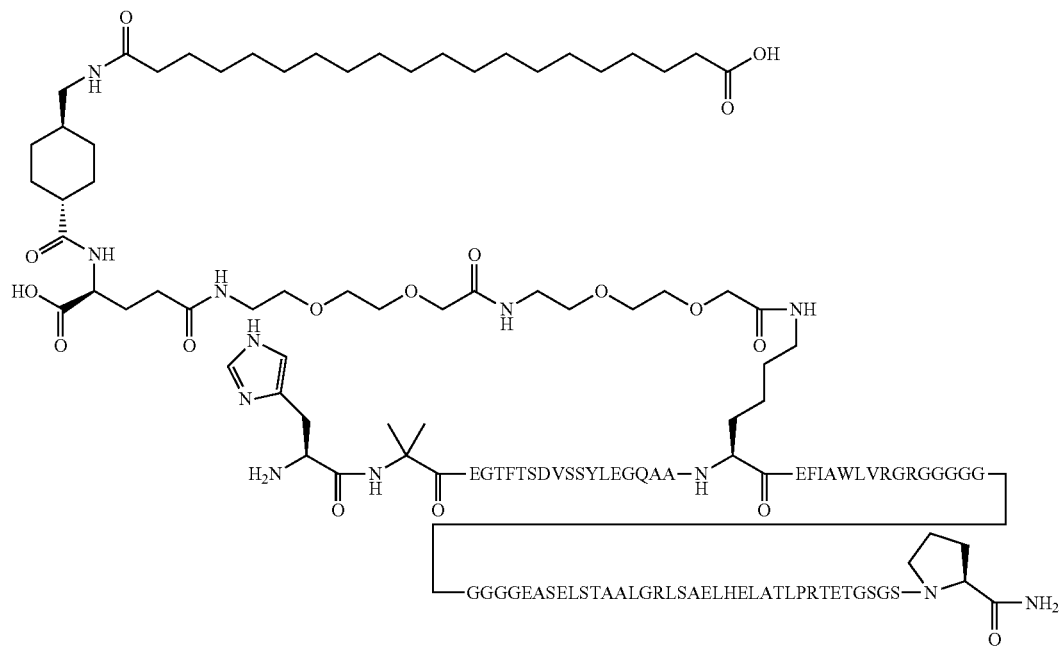

$C_{354}H_{566}N_{96}O_{119}$

Molecular weight (average) calculated: 8070.8536 g/mol mono isotopic mass: 8066.1189 g/mol LCMS34: found $(M+5H)^{5+}$ 1615.0 (most abundant)

The amino acid sequence of HXEGTFTSDVS-SYLEGQAAKEFIAWLVRGRGGGGGGGGEASEL-STAALGRLSAELHELATLPRTETGSGSP has SEQ ID NO: 126

Compound 0096

HGEGTFTSDVSSYLEEQAAR-K([2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl])-FIEWLVRG-K([2-[2-[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl])-GEGEASELSTAALGRLSAELHELATLPRTETGSGSP-amide

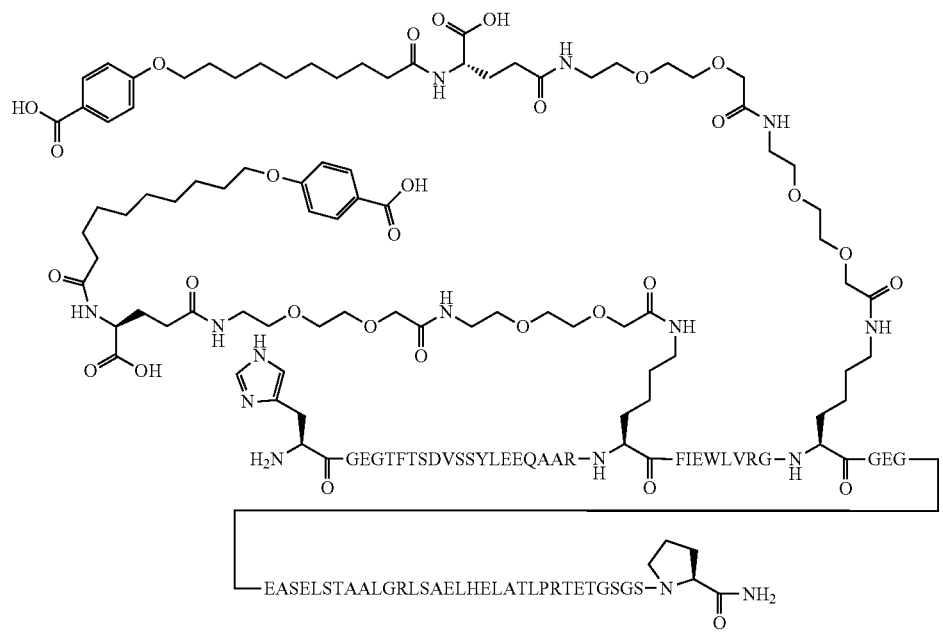

$C_{372}H_{583}N_{93}O_{130}$
Molecular weight (average) calculated: 8438.1545 g/mol
mono isotopic mass: 8433.1868 g/mol
LCMS34: found $(M+5H)^{5+}$ 1688.65 (most abundant)
The amino acid sequence of HGEGTFTSDVSSYLE-EQAARKFIEWLVRGKGEGEASELSTAALGRLSAEL-HELATLPRTETGSGSP has SEQ ID NO: 143

Compound 0097

HGEGTFTSDVSSYLEEQAAR-K([2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl])-FIEWLVRG-K([2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl])-GEGGGGEASELSTAALGRLSAELHELATLPRTE-TGSGSP-amide

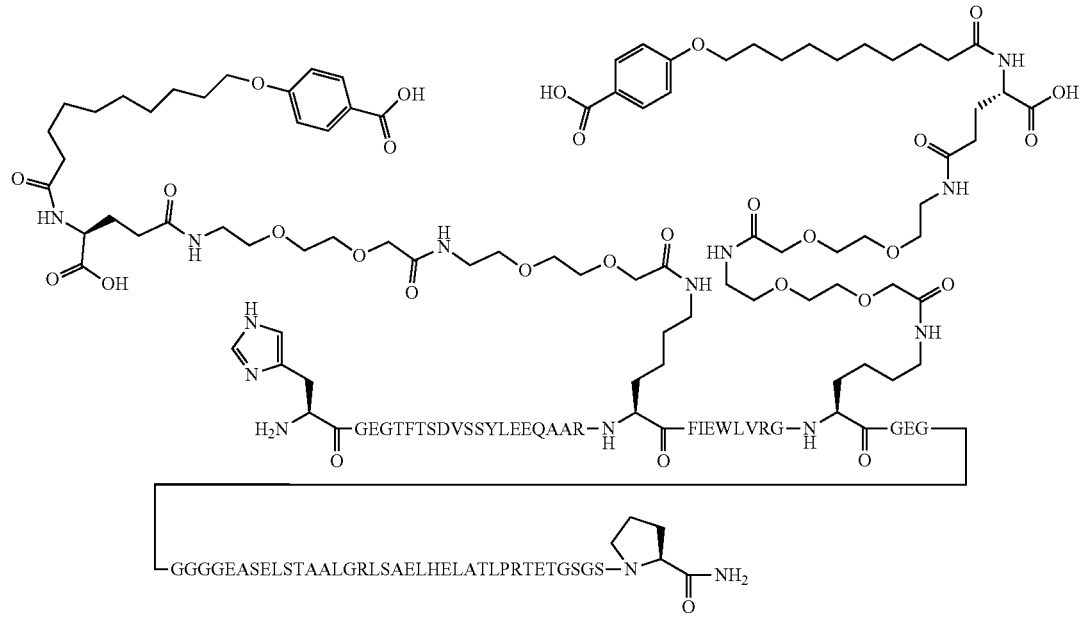

$C_{380}H_{595}N_{97}O_{134}$
Molecular weight (average) calculated: 8666.3598 g/mol
mono isotopic mass: 8661.2726 g/mol
LCMS34: found $(M+5H)^{5+}$ 1734.26 (most abundant)
The amino acid sequence of HGEGTFTSDVSSYLE-EQAARKFIEWLVRGKGEGGGGGEASELSTAALGRL-SAELHELATLPRTETGSGSP has SEQ ID NO: 144

Compound 0098

HGEGTFTSDVSSYLEEQAAR-K([2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl])-FIEWLVRG-K([2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl])-GEGGGGGGGGEASELSTAALGRLSAELHELA-TLPRTETGSGSP-amide

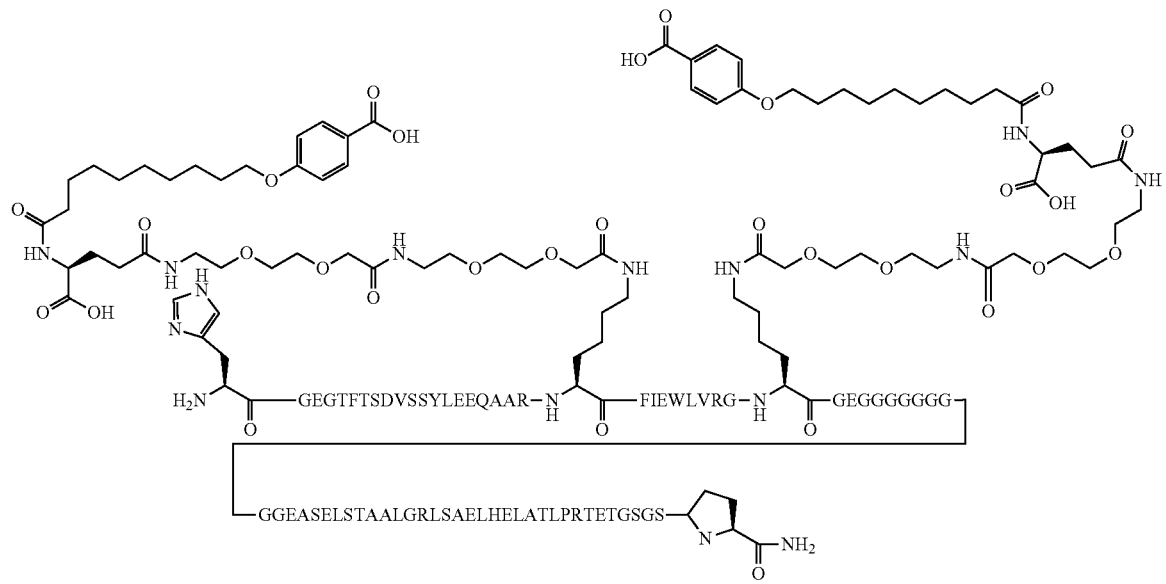

$C_{388}H_{607}N_{101}O_{138}$
Molecular weight (average) calculated: 8894.5651 g/mol
mono isotopic mass: 8889.3585 g/mol LCMS34: found $(M+5H)^{5+}$1779.88 (most abundant)

The amino acid sequence of HGEGTFTSDVSSYLE-EQAARKFIEWLVRGKGEGGGGGGGGGEASEL-STAALGRLSAELHELATLPRTETGSGSP has SEQ ID NO: 145

Compound 0099

HWEGTFTSDVSSYLEEQAAR-K([2-[2-[2-[[2-[2-[2-[[(4S)-4-carboxy-4-[10-(4-carboxyphenoxy)decanoy-lamino]butanoyl]amino]ethoxy]ethoxy]acetyl]amino]ethoxy]ethoxy]acetyl])-FIEWLVRG-K([2-[2-[2-[[2-[2-[2-[[(4S)-4-carboxy-4-[10-(4-carboxyphenoxy)decanoylamino]butanoyl]amino]ethoxy]ethoxy]acetyl] amino]ethoxy]ethoxy]acetyl])-GEGEASELSTAALGRLSAELHELATLPRTETGSGSP-amide

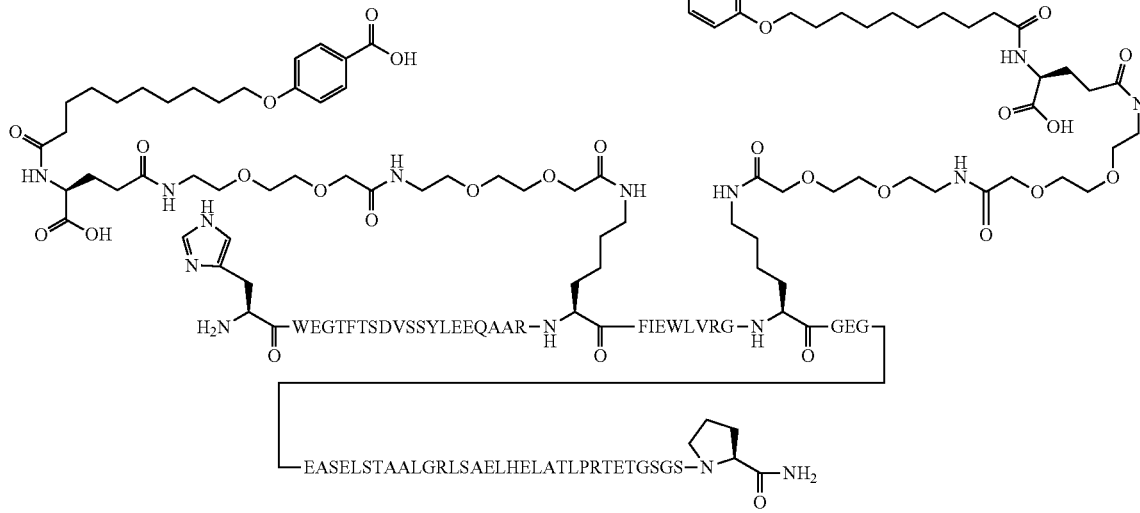

$C_{381}H_{590}N_{94}O_{130}$
Molecular weight (average) calculated: 8567.3131 g/mol
mono isotopic mass: 8562.2446 g/mol
LCMS34: found $(M+5H)^{5+}$1714.46 (most abundant)
The amino acid sequence of HWEGTFTSDVSSYLE-EQAARKFIEWLVRGKGEGEASELSTAALGRLSAEL-HELATLPRTETGSGSP has SEQ ID NO: 146

Compound 0100

HWEGTFTSDVSSYLEEQAAR-K([2-[2-[2-[[2-[2-[2-[[(4S)-4-carboxy-4-[10-(4-carboxyphenoxy)decanoy-lamino]butanoyl]amino]ethoxy]ethoxy]acetyl]amino]ethoxy]ethoxy]acetyl])-FIEWLVRG-K([2-[2-[2-[[2-[2-[2-[[(4S)-4-carboxy-4-[10-(4-carboxyphenoxy)

decanoylamino]butanoyl]ethoxy]ethoxy]acetyl]amino]
ethoxy]ethoxy]acetyl])-
GEGGGGGEASELSTAALGRLSAELHELATLPRTE-
TGSGSP-amide

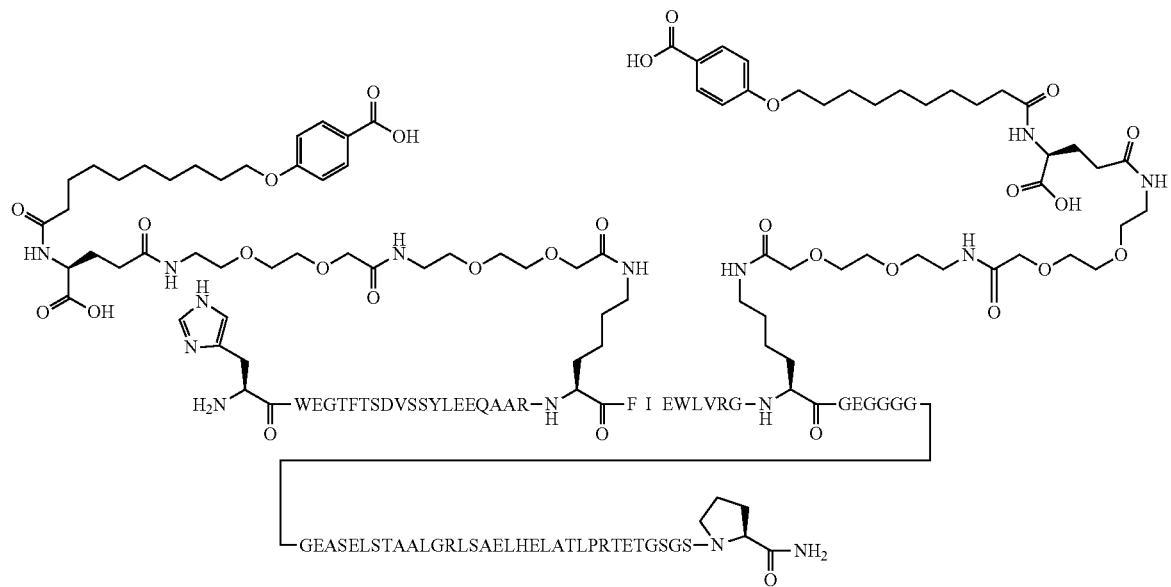

$C_{389}H_{602}N_{98}O_{134}$

Molecular weight (average) calculated: 8795.5184 g/mol mono isotopic mass: 8790.3305 g/mol LCMS34: found $(M+5H)^{5+}$ 1760.08 (most abundant)

The amino acid sequence of HWEGTFTSDVSSYLE-
EQAARKFIEWLVRGKGEGGGGGEASELSTAALGRL-
SAELHELATLPRTETGSGSP has SEQ ID NO: 147

Compound 0101

HWEGTFTSDVSSYLEEQAAR-K([2-[2-[2-[[2-[2-[2-
[[(4S)-4-carboxy-4-[10-(4-carboxyphenoxy)decanoy-
lamino]butanoyl]amino]ethoxy]ethoxy]acetyl]amino]
ethoxy]ethoxy]acetyl])-FIEWLVRG-K([2-[2-[2-[[2-[2-[2-
[[(4S)-4-carboxy-4-[10-(4-carboxyphenoxy)
decanoylamino]butanoyl]aminoethoxy]ethoxy]acetyl]
amino]ethoxy]ethoxy]acetyl])-
GEGGGGGGGGGEASELSTAALGRLSAE-
LHELATLPRTETGSGSP-amide

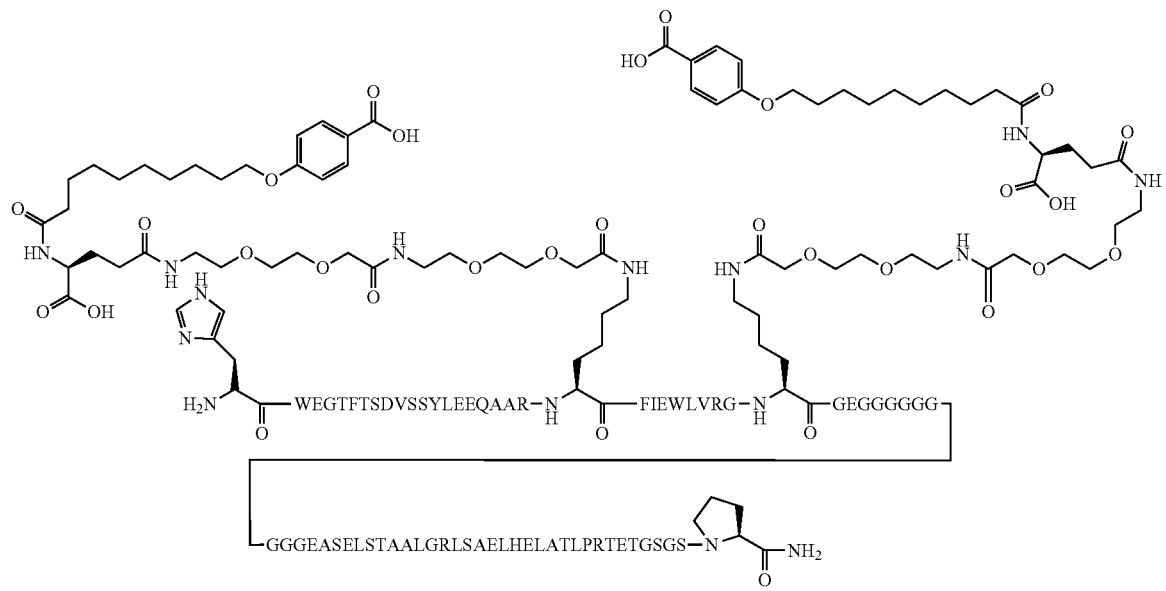

$C_{397}H_{614}N_{102}O_{138}$
Molecular weight (average) calculated: 9023.7237 g/mol
mono isotopic mass: 9018.4163 g/mol
LCMS34: found $(M+5H)^{5+}$ 1805.49 (most abundant)
The amino acid sequence of HWEGTFTSDVSSYLE-EQAARKFIEWLVRGKGEGGGGGGGGEASEL-STAALGRLSAELHELATLPRTETGSGSP has SEQ ID NO: 148

Compound 0102
H-Aib-EGTFTSDVSSYLEEQAAREFIAWLVRGR-K(4-[17-(1H-tetrazol-5-yl)heptadecanoylsulfamoyl]butanoyl)-ELSTAALGRLSAELHELATLPRTETGSGSP-amide

$C_{311}H_{499}N_{89}O_{98}S$
Molecular weight (average) calculated: 7084.8923 g/mol
mono isotopic mass: 7080.6520 g/mol
LCMS01: found $(M+5H)^{5+}$ 1418 (most abundant)
The amino acid sequence of HXEGTFTSDVSSYLE-EQAAREFIAWLVRGRKELSTAALGRLSAELHELATL-PRTETGSGSP has SEQ ID NO: 149

Compound 0103
H-Aib-EGTFTSDVSSYLEEQAAREFIAWLVRGR-K(4-[17-(1H-tetrazol-5-yl)heptadecanoylsulfamoyl]butanoyl)-EASELSTAALGRLSAELHELATL-PRTETGSGSP-amide

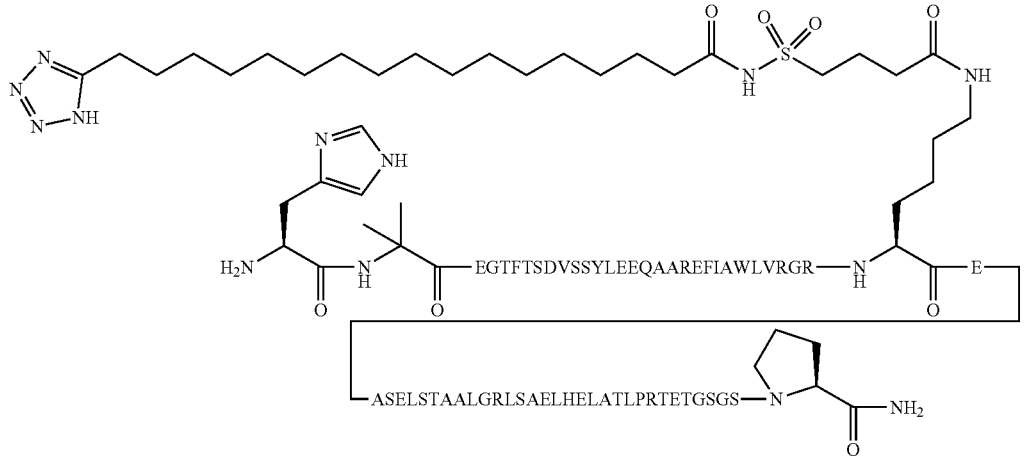

$C_{322}H_{516}N_{92}O_{104}S$
Molecular weight (average) calculated: 7372.1614 g/mol
mono isotopic mass: 7367.7637 g/mol
LCMS01: found (M+5H)$^{5+}$ 1475 (most abundant)
The amino acid sequence of HXEGTFTSDVSSYLEEQAAREFIAWLVRGRKEASELSTAALGRLSAELHELATLPRTETGSGSP has SEQ ID NO: 150

Compound 0105
H-Aib-EGTFTSDVSSYLEEQAAR-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-FIEWLVRG-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-GEGQEPGGASELSTAALGRLSAELHELATLPRTETGSGSP-amide $C_{386}H_{620}N_{98}O_{133}$
Molecular weight (average) calculated: 8761.6298 g/mol
mono isotopic mass: 8756.4764 g/mol
LCMS34: found (M+5H)$^{5+}$ 1753.31 (most abundant)
The amino acid sequence of HXEGTFTSDVSSYLEEQAARKFIEWLVRGKGEGQEPGGASELSTAALGRLSAELHELATLPRTETGSGSP has SEQ ID NO: 151

Compound 0106
H-Aib-EGTFTSDVSSYLEEQAAR-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-FIEWLVRG-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-GEGQEPGGASELSTAALGRLSAELHELATLPRTETGSGSP-amide

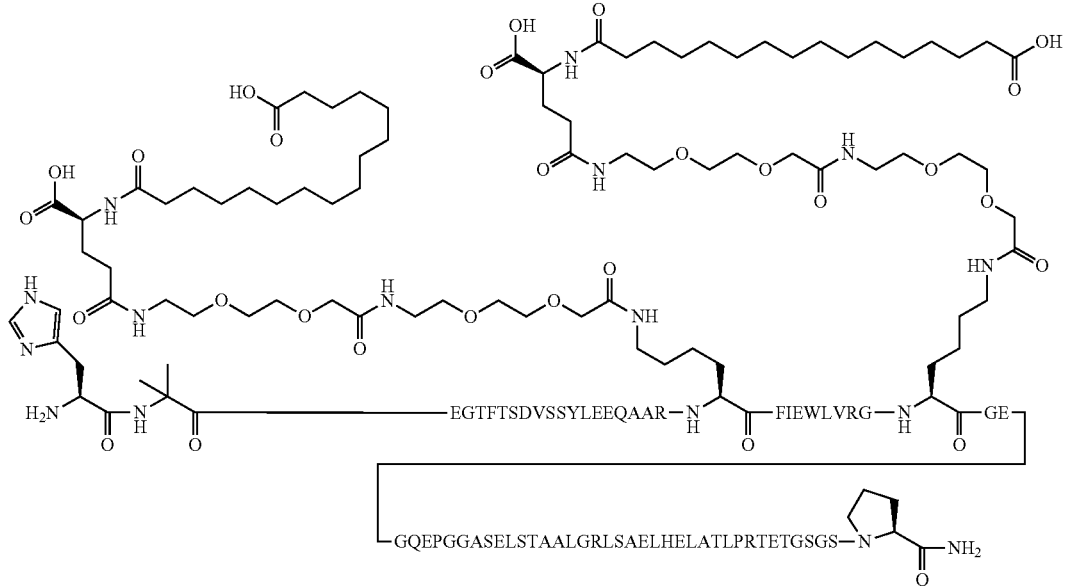

121

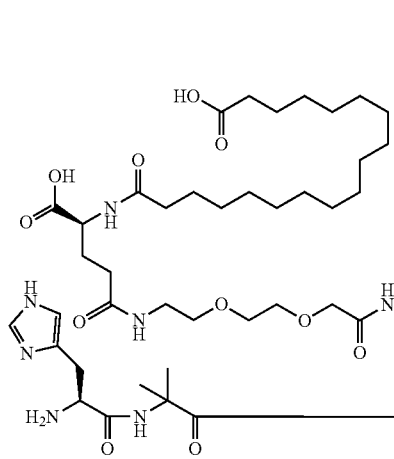

$C_{390}H_{628}N_{98}O_{133}$
Molecular weight (average) calculated: 8817.7361 g/mol
mono isotopic mass: 8812.5390 g/mol
LCMS34: found (M+5H)$^{5+}$1764.33 (most abundant)
The amino acid sequence of HXEGTFTSDVSSYLE-EQAARKFIEWLVRGKGEGOEPGGASELSTAALGRL-SAELHELATLPRTETGSGSP has SEQ ID NO: 151
Compound 0109
H-Aib-EGTFTSDVSSYLEEQAAR-K([2-[2-[2-[[2-[2-[2-[[(4S)-4-carboxy-4-(17-carboxyheptadecanoylamino)bu-tanoyl]amino]ethoxy]ethoxy]acetyl]amino]ethoxy]ethoxy]acetyl])-FIAWLVRG-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-GGGGGGGGGEASELSTAALGRLSAELHELATLPR-TETGSGSP-amide

122

$C_{383}H_{619}N_{99}O_{130}$
Molecular weight (average) calculated: 8690.5983 g/mol
mono isotopic mass: 8685.4869 g/mol
LCMS34: found (M+5H)$^{5+}$1738.9 (most abundant)
The amino acid sequence of HXEGTFTSDVSSYLE-EQAARKFIAWLVRGKGGGGGGGGGEASELSTAAL-GRLSAELHELATLPRTETGSGSP has SEQ ID NO: 152
Compound 0110
H-Aib-EGTFTSDVSSYLEEQAAR-K([(2S)-2-amino-6-[[2-[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl]amino]hexanoyl])-FIAWLVRG-K([(2S)-2-amino-6-[[2-[2-[2-[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]

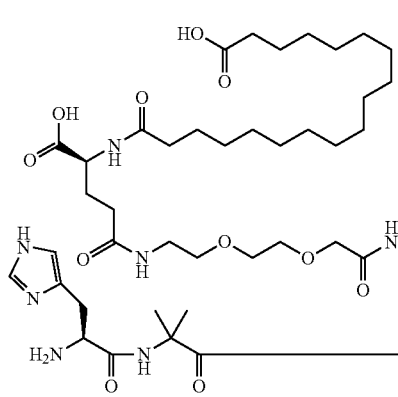

hexanoyl]-
GGGGGGGGGEASELSTAALGRLSAELHELAT-
LPRTETGSGSP-amide

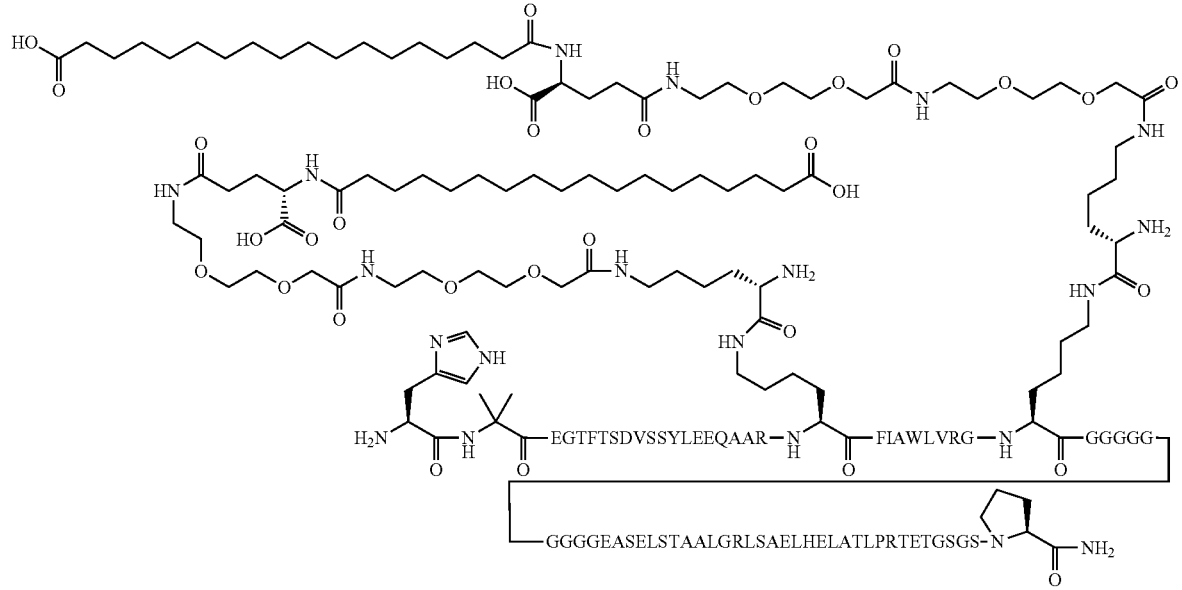

$C_{383}H_{619}N_{99}O_{130}$
Molecular weight (average) calculated: 8946.9428 g/mol
mono isotopic mass: 8941.6768 g/mol
LCMS34: found (M+5H)$^{5+}$ 1790.3 (most abundant)
The amino acid sequence of HXEGTFTSDVSSYLE-
EQAARKFIAWLVRGKGGGGGGGGGEASELSTAAL-
GRLSAELHELATLPRTETGSGSP has SEQ ID NO: 152
Compound 0111
H-Aib-EGTFTSDVSSYLEEOAAREFIAWLVRGR-K
([2-[2-[2-[[2-[2-22-[(4S)-4-carboxy-4-(17-carboxyheptade-
canoylamino)butanoyl]amino]ethoxy]ethoxy]acetyl]amino]
ethoxy]ethoxy]acetyl])-
GGGGEASELSTAALGRLSAELHELATLPRTETGSGSP-
amide $C_{343}H_{550}N_{94}O_{116}$
Molecular weight (average) calculated: 7846.5973 g/mol
mono isotopic mass: 7842.0028 g/mol
LCMS34: found (M+5H)$^{5+}$1570.22 (most abundant)
The amino acid sequence of HXEGTFTSDVSSYLE-
EQAAREFIAWLVRGRKGGGGEASELSTAALGRL-
SAELHELATLPRTETGSGSP has SEQ ID NO: 153
Compound 0114
H-Aib-EGTFTSDVSSYLEEQAAREFIAWLVRGR-K
([2-[2-[2-[[2-[2-[2-[[(4S)-4-carboxy-4-(17-carboxyheptade-
canoylamino)butanoyl]amino]ethoxy]ethoxy]acetyl]amino]
ethoxy]ethoxy]acetyl])-
GGEASELSTAALGRLSAELHELATLPRTETGSGSP-
amide

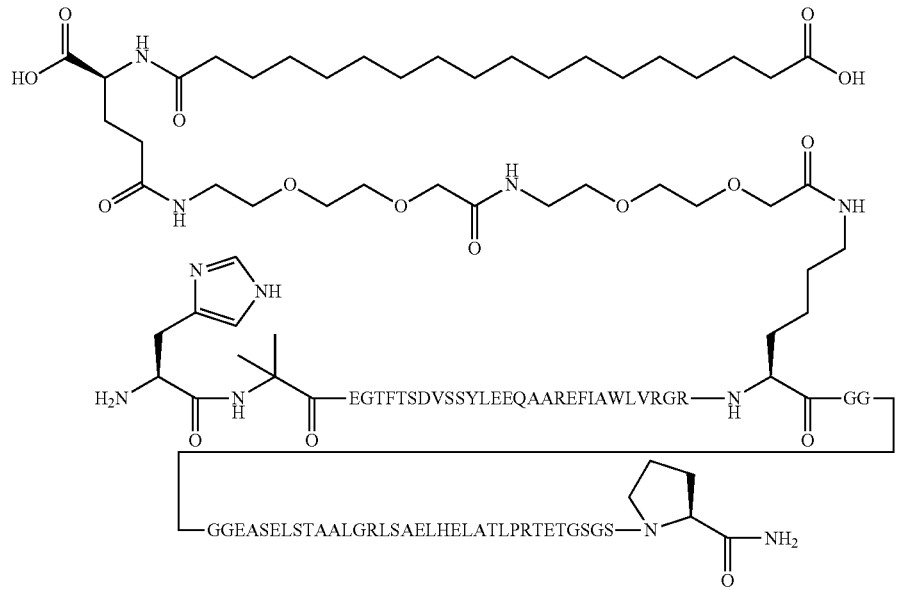

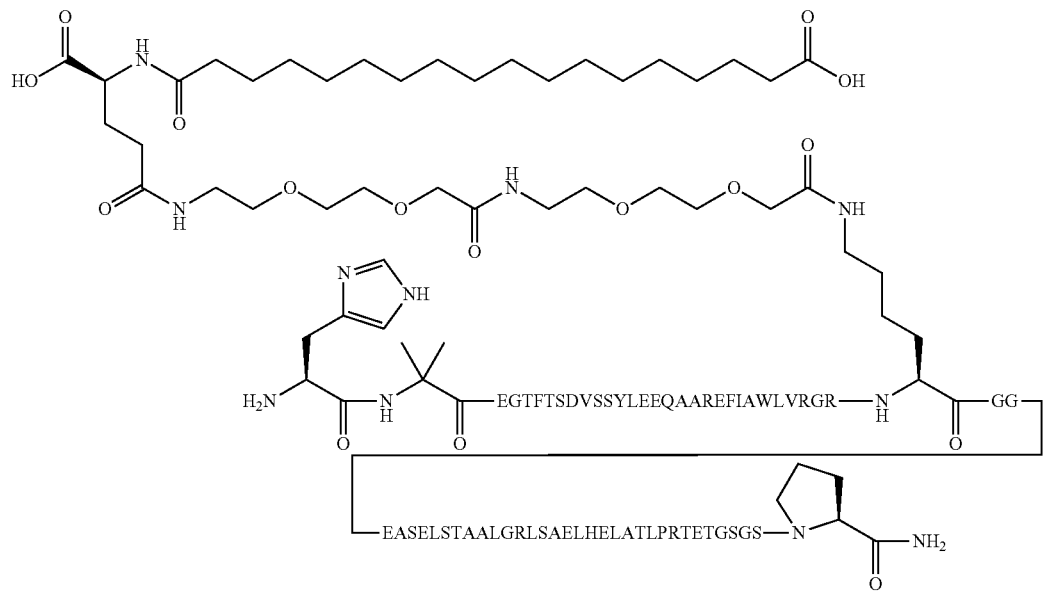

$C_{339}H_{544}N_{92}O_{114}$
Molecular weight (average) calculated: 7732.4947 g/mol
mono isotopic mass: 7727.9599 g/mol
LCMS34: found (M+5H)$^{5+}$1547.4 (most abundant)
The amino acid sequence of HXEGTFTSDVSSYLE-EQAAREFIAWLVRGRKGGEASELSTAALGRLSAEL-HELATLPRTETGSGSP has SEQ ID NO: 154
Compound 0115
H-Aib-EGTFTSDVSSYLEEQAAREFIAWLVRGR-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-EASELSTAALGRLSAELHELATLPRTETGSGSP-amide $C_{335}H_{538}N_{90}O_{112}$
Molecular weight (average) calculated: 7618.3920 g/mol
mono isotopic mass: 7613.9169 g/mol
LCMS34: found (M+5H)$^{5+}$1524.6 (most abundant)
The amino acid sequence of HXEGTFTSDVSSYLE-EQAAREFIAWLVRGRKEASELSTAALGRLSAEL-HELATLPRTETGSGSP has SEQ ID NO: 150
Compound 0116
H-Aib-EGTFTSDVSSYLEEQAAR-K([2-[2-[2-[2-[2-[2-[[(4S)-4-carboxy-4-(17-carboxyheptadecanoylamino)butanoyl]amino]ethoxy]ethoxy]acetyl]amino]ethoxy]ethoxy]acetyl])-FIAWLVRGR-K([2-[2-[2-[[2-[2-[2-[[(4S)-4-carboxy-4-(17-carboxyheptadecanoylamino)butanoyl]

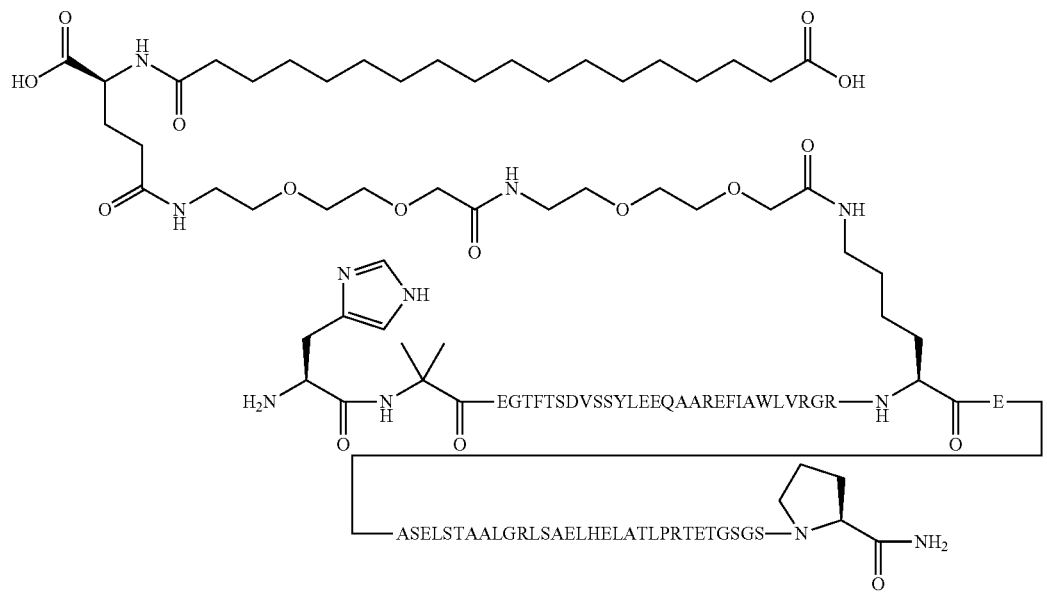

amino]ethoxy]ethoxy]acetyl]amino]ethoxy]ethoxy]acetyl])-GGEASELSTAALGRLSAELHELATLPRTETGSGSP-amide

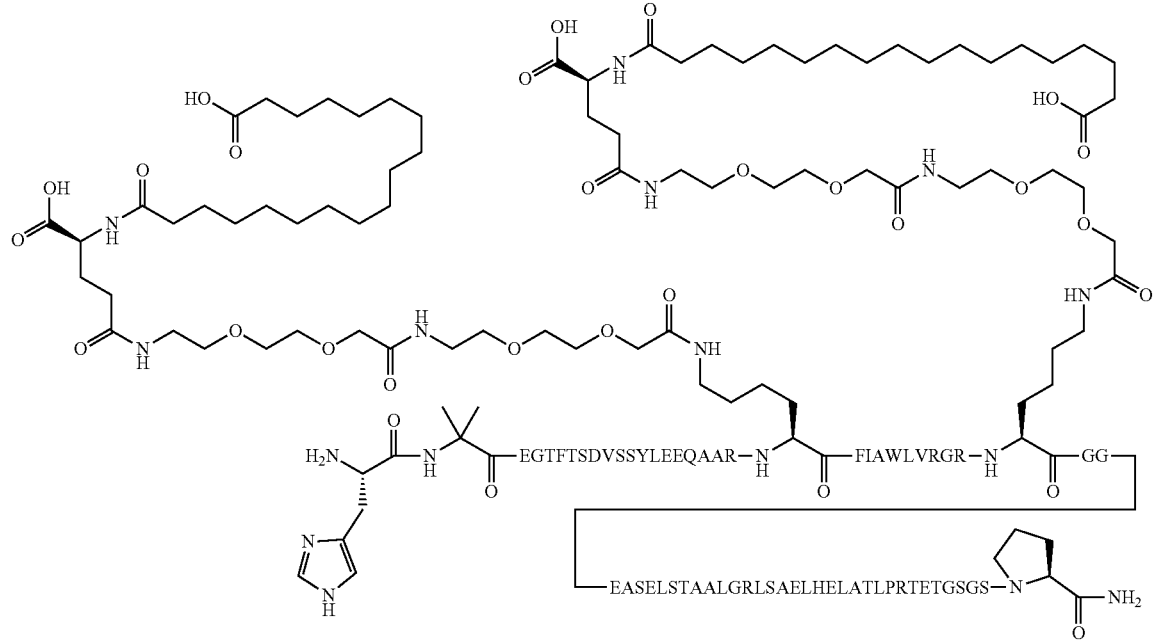

$C_{375}H_{610}N_{96}O_{124}$
Molecular weight (average) calculated: 8447.4247 g/mol
mono isotopic mass: 8442.4378 g/mol
LCMS34: found $(M+5H)^{5+}$ 1690.3 (most abundant)
The amino acid sequence of HXEGTFTSDVSSYLEEQAARKFIAWLVRGRKGGEASELSTAALGRLSAELHELATLPRTETGSGSP has SEQ ID NO: 155

Compound 0120
H-Aib-EGTFTSDVSSYLEEQAAREFIAWLVRGR-K([2-[2-[2-[[2-[2-[2-[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl])-GGGGEASELSTAALGRLSAELHELATLPRTETGSGSP-amide

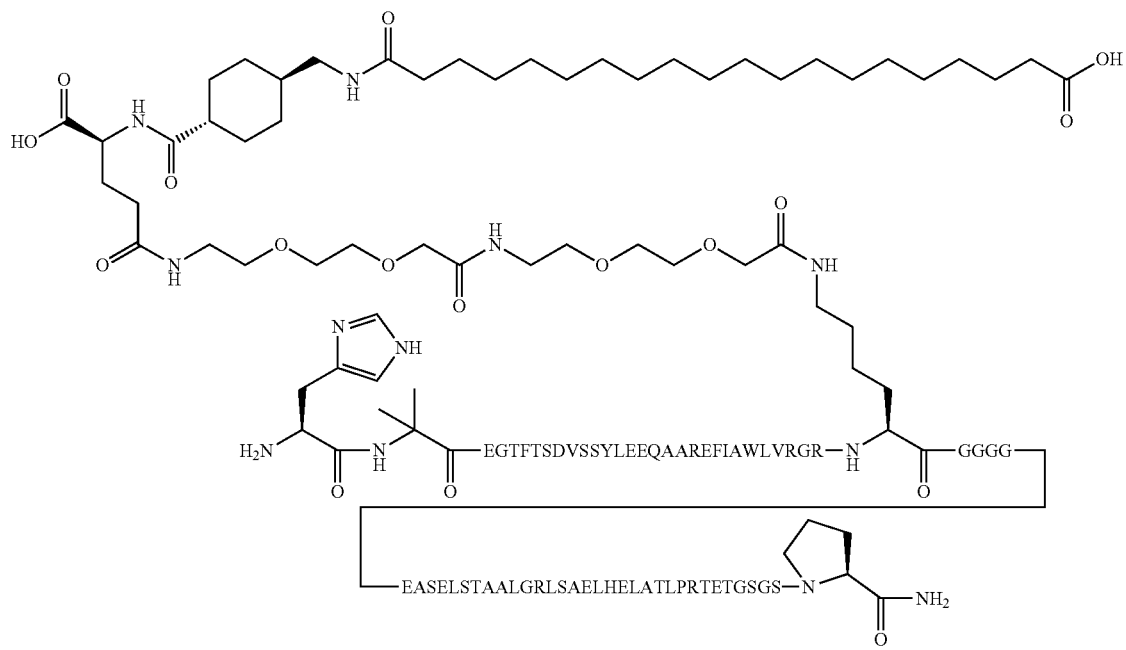

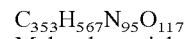

C₃₅₃H₅₆₇N₉₅O₁₁₇
Molecular weight (average) calculated: 8013.8454 g/mol
mono isotopic mass: 8009.1338 g/mol
LCMS34: found (M+5H)⁵⁺ 1603.63 (most abundant)
The amino acid sequence of HXEGTFTSDVSSYLE-EQAAREFIAWLVRGRKGGGGEASELSTAALGRL-SAELHELATLPRTETGSGSP has SEQ ID NO: 153

Compound 0124
Imp-Aib-EGTFTSDVSSYLEEQAAREFIAWLVRGR-K(4-[17-(1H-tetrazol-5-yl)heptadecanoylsulfamoyl]butanoyl)-EASELSTAALGRLSAELHELATL-PRTETGSGSP-amide

C₃₁₉H₅₁₂N₉₂O₁₀₂ S
Molecular weight (average) calculated: 7300.0988 g/mol
mono isotopic mass: 7295.7426 g/mol
LCMS01: found (M+5H)⁵⁺1461 (most abundant)
The amino acid sequence of HXEGTFTSDVSSYLE-EQAARKFIAWLVRGRGEASELSTAALGRLSAEL-HELATLPRTETGSGSP has SEQ ID NO: 157

Compound 0127
H-Aib-EGTFTSDVSSYLEEQAAR-K([2-[2-[2-[[2-[2-(2-[[(4S)-4-carboxy-4-(17-carboxyheptadecanoylamino)butanoyl]amino]ethoxy]ethoxy]acetyl]amino]ethoxy]ethoxy]acetyl])-FIAWLVRG-K([2-[2-[2-[[2-[2-[[-(4S)-4-carboxy-

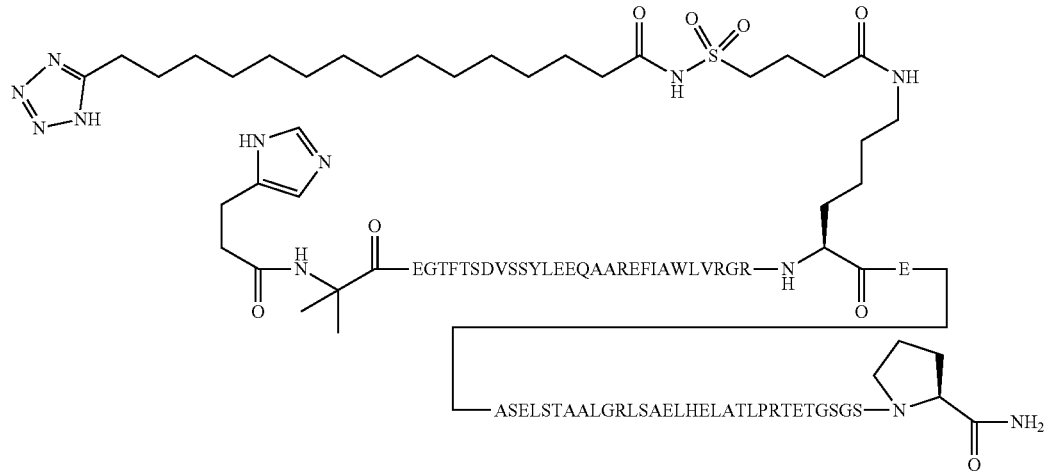

C₃₂₂H₅₁₅N₉₁O₁₀₄ S
Molecular weight (average) calculated: 7357.1468 g/mol
mono isotopic mass: 7352.7528 g/mol
LCMS01: found (M+5H)⁵⁺ 1472 (most abundant)
The amino acid sequence of XXEGTFTSDVSSYLE-EQAAREFIAWLVRGRKEASELSTAALGRLSAEL-HELATLPRTETGSGSP has SEQ ID NO: 156

Compound 0125
H-Aib-EGTFTSDVSSYLEEQAAR-K(4-[17-(1H-tetrazol-5-yl)heptadecanoylsulfamoyl]butanoyl)-FIAWLVRGR-GEASELSTAALGRLSAELHELATLPRTETGSGSP-amide 4-(17-carboxyheptadecanoylamino)butanoyl]amino]ethoxy]ethoxy]acetyl]amino]ethoxy]ethoxy]acetyl])-GGEASELSTAALGRLSAELHELATLPRTETGSGSP-amide

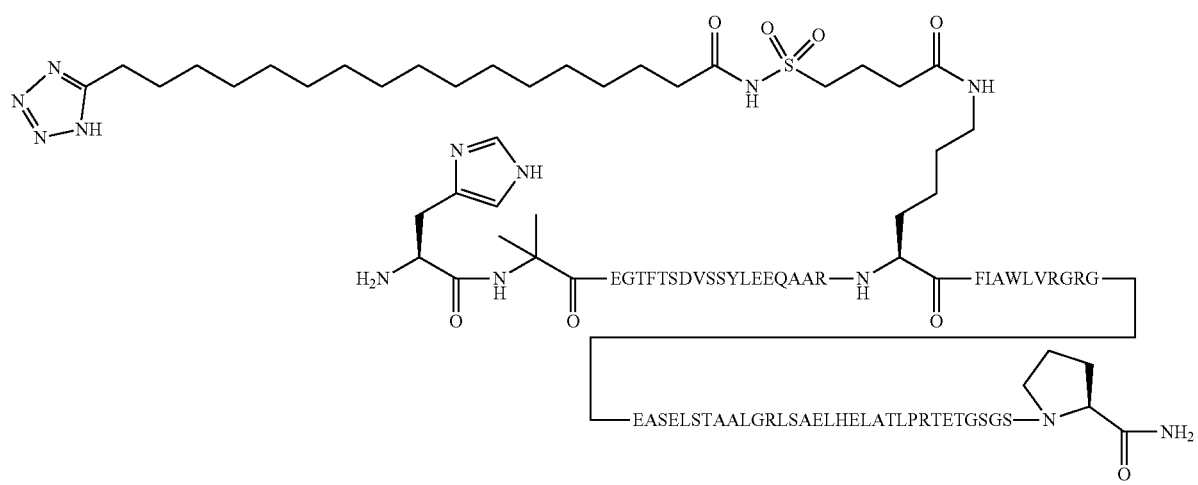

Compound 0120
H-Aib-EGTFTSDVSSYLEEQAAREFIAWLVRGR-K
([2-[2-[2-[[2-[2-[2-[(4S)-4-carboxy-4-[[4-[(19-car

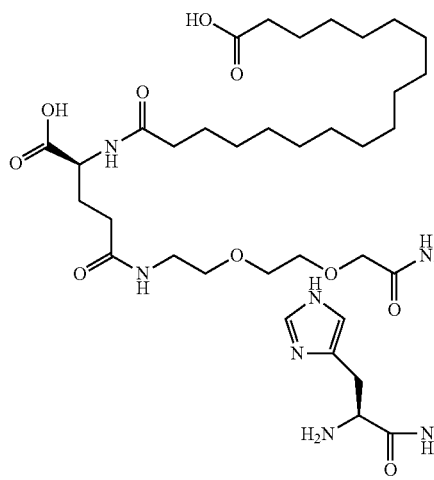
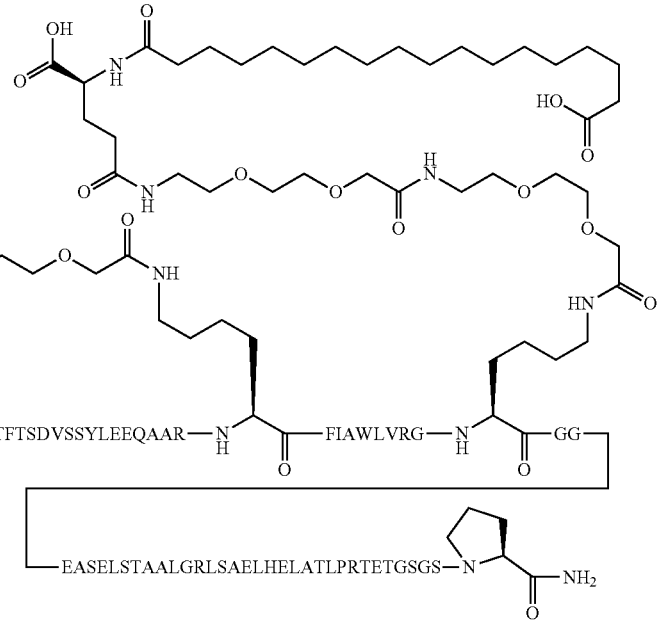

$C_{369}H_{598}N_{92}O_{123}$

Molecular weight (average) calculated: 8291.2390 g/mol mono isotopic mass: 8286.3367 g/mol LCMS34: found $(M+5H)^{5+}$ 1659.1 (most abundant)

The amino acid sequence of HXEGTFTSDVSSYLE-EQAARKFIAWLVRGKGGEASELSTAALGRLSAEL-HELATLPRTETGSGSP has SEQ ID NO: 158

Compound 0128
H-Aib-EGTFTSDVSSYLEEQAAR-K([2-[2-[2-[2-[2-[2-[[(4S)-4-carboxy-4-(17-carboxyheptadecanoylamino)butanoyl]amino]ethoxy]ethoxy]acetyl]amino]ethoxy]ethoxy]acetyl])-FIEWLVRG-K([2-[2-[2-[2-[2-[2-[(4S)-4-carboxy-4-(17-carboxyheptadecanoylamino)butanoyl]amino]ethoxy]ethoxy]acetyl]amino]ethoxy]ethoxy]acetyl])-GGEASELSTAALGRLSAELHELATLPRTETGSGSP-amide

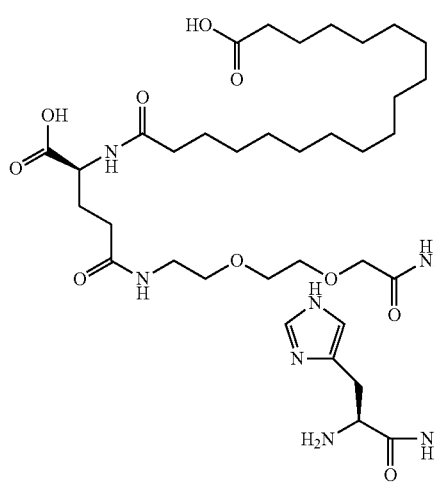
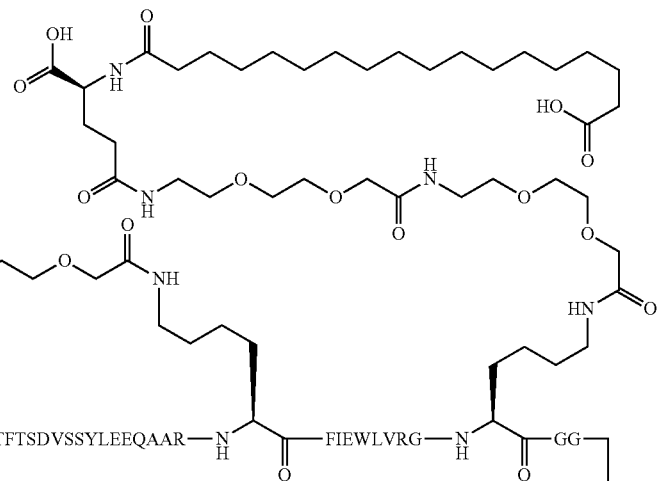
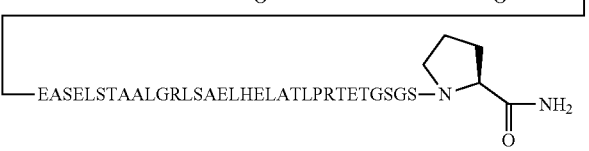

$C_{371}H_{600}N_{92}O_{125}$

Molecular weight (average) calculated: 8349.2751 g/mol mono isotopic mass: 8344.3421 g/mol LCMS34: found $(M+5H)^{5+}$1670.7 (most abundant)

The amino acid sequence of HXEGTFTSDVSSYLE-EQAARKFIEWLVRGKGGEASELSTAALGRLSAEL-HELATLPRTETGSGSP has SEQ ID NO: 159

Compound 0129

H-Aib-EGTFTSDVSSYLEEQAAR-K([2-[2-[2-[[2-[2-[2-[[(4S)-4-carboxy-4-(17-carboxyheptadecanoylamino)bu-tanyl]amino]ethoxy]ethoxy]acetyl]amino]ethoxy]ethoxy]acetyl])-FIEWLVRGR-K([2-[2-[2-[[2-[2-[2-[[(4S)-4-carboxy-4-(17-carboxyheptadecanoano)butanoyl]amino]ethoxy]ethoxy]acetyl]amino]ethoxy]ethoxy]acetyl])-GGEASELSTAALGRLSAELHELATLPRTETGSGSP-amide

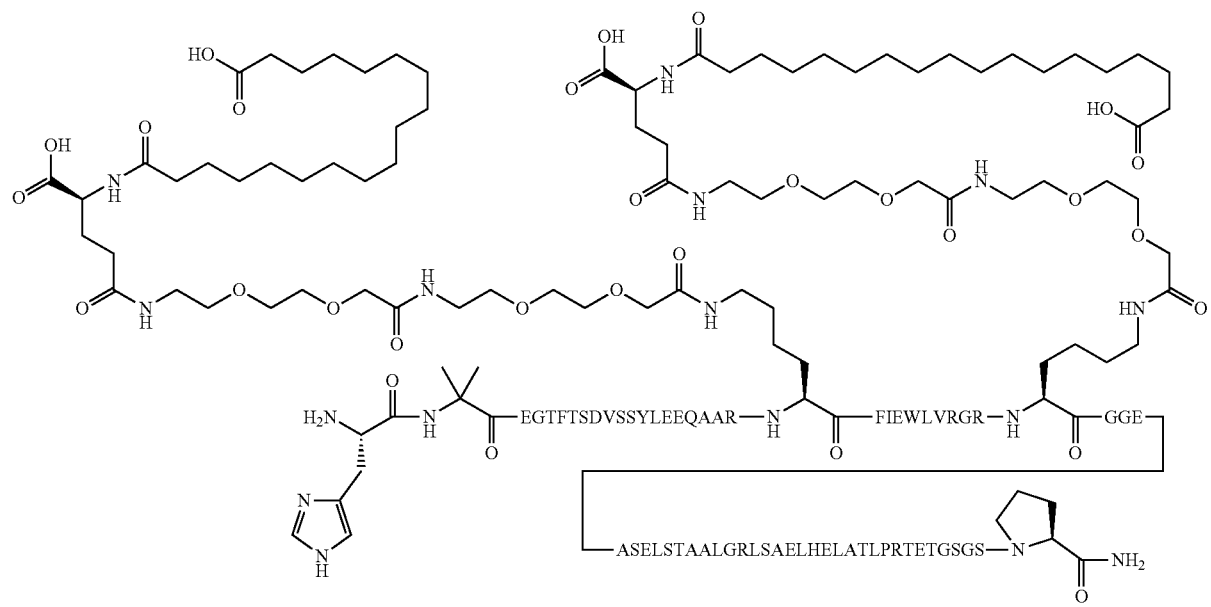

$C_{377}H_{612}N_{96}O_{126}$

Molecular weight (average) calculated: 8505.4608 g/mol mono isotopic mass: 8500.4432 g/mol LCMS_ZQ: found $(M+5H)^{5+}$1702.0 (most abundant)

The amino acid sequence of HXEGTFTSDVSSYLE-EQAARKFIEWLVRGRKGGEASELSTAALGRLSAEL-HELATLPRTETGSGSP has SEQ ID NO: 160

Compound 0131

H-Aib-EGTFTSDVSSYLEEQAAR-K([(4S)-4-carboxy-4-(17-carboxyheptadecanoylamino)butanoyl])-FI-AWLVRGR-K([(4S)-4-carboxy-4-(17-carboxyheptade-canoylamino)butanoyl])-EASELSTAALGRLSAELHELATLPRTETGSGSP-amide

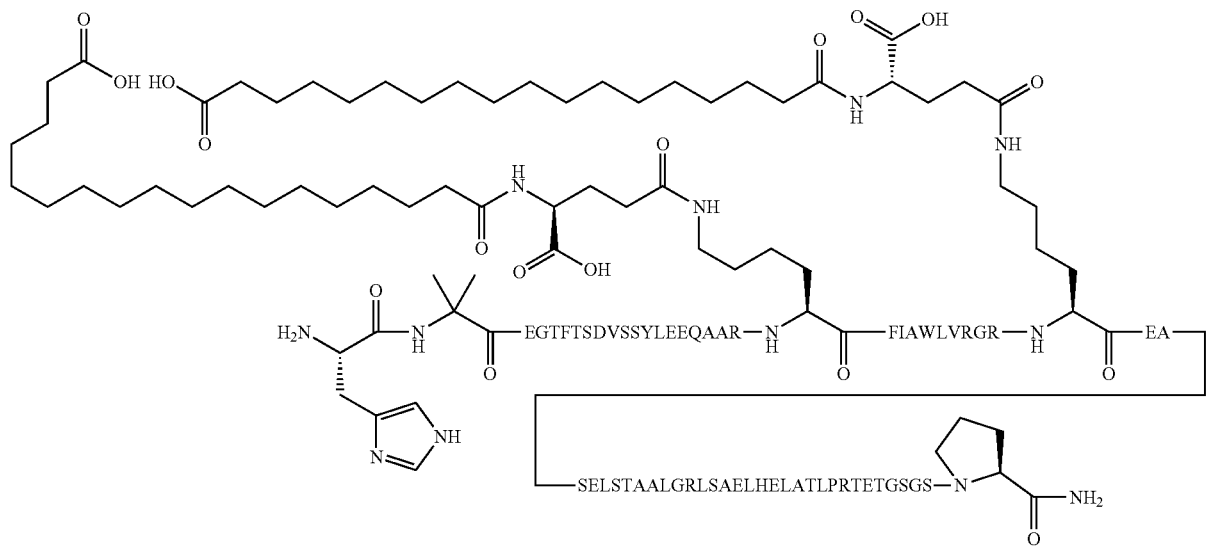

C$_{347}$H$_{560}$N$_{90}$O$_{110}$
Molecular weight (average) calculated: 7752.6963 g/mol
mono isotopic mass: 7748.0993 g/mol
LCMS34: found (M+5H)$^{5+}$1551.6 (most abundant)
The amino acid sequence of HXEGTFTSDVSSYLE-EQAARKFIAWLVRGRKEASELSTAALGRLSAEL-HELATLPRTETGSGSP has SEQ ID NO: 161
Compound 0132
H-Aib-EGTFTSDVSSYLEEQAAREFIAWLVRG-K([2-[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl])-GGEASELSTAALGRLSAELHELATLPRTETGSGSP-amide Molecular weight (average) calculated: 7576.3090 g/mol
mono isotopic mass: 7571.8588 g/mol
LCMS34: found (M+5H)$^{5+}$ 1516.11 (most abundant)
The amino acid sequence of HXEGTFTSDVSSYLE-EQAAREFIAWLVRGKGGEASELSTAALGRLSAEL-HELATLPRTETGSGSP has SEQ ID NO: 162
Compound 0141
H-Aib-EGTFTSDVSSYLEEQAAREFIAWLVRGR-K([(4S)-4-carboxy-4-(19-carboxynonadecanoylamino)butanoyl])-EASELSTAALGRLSAELHELATL-PRTETGSGSP-amide

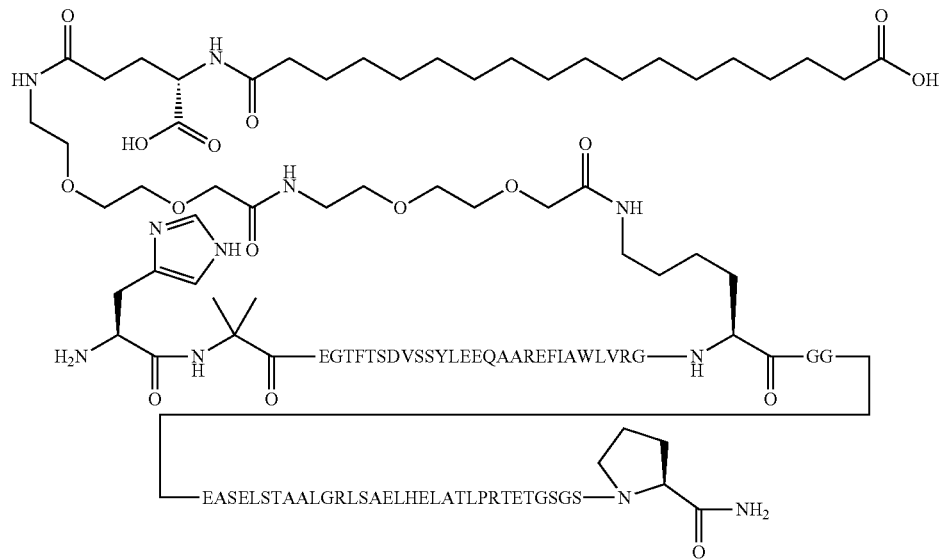

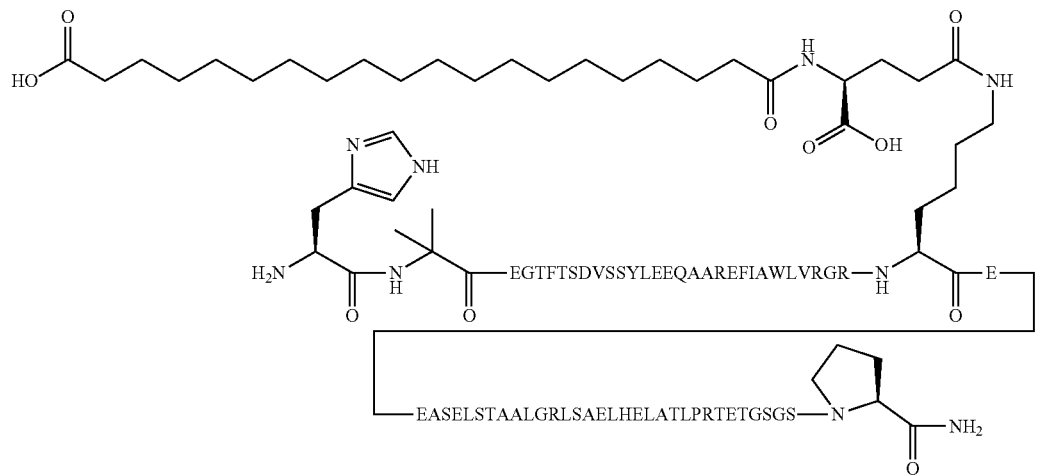

C$_{325}$H$_{520}$N$_{88}$O$_{106}$
Molecular weight (average) calculated: 7356.1323 g/mol
mono isotopic mass: 7351.8005 g/mol
LCMS01: found (M+5H)$^{5+}$ 1472 (most abundant)
The amino acid sequence of HXEGTFTSDVSSYLE-EQAAREFIAWLVRGRKEASELSTAALGRLSAEL-HELATLPRTETGSGSP has SEQ ID NO: 150
Compound 0142
Imp-Aib-EGTFTSDVSSYLEEQAAREFIAWLVRGR-K([(4S)-4-carboxy-4-(19-carboxynonadecanoylamino)butanoyl])-EASELSTAALGRLSAELHELATLPRTETGSGSP-amide C$_{325}$H$_{519}$N$_{87}$O$_{106}$
Molecular weight (average) calculated: 7341.1177 g/mol
mono isotopic mass: 7336.7896 g/mol
LCMS01: found (M+5H)$^{5+}$1469 (most abundant)
The amino acid sequence of XXEGTFTSDVSSYLE-EQAAREFIAWLVRGRKEASELSTAALGRLSAEL-HELATLPRTETGSGSP has SEQ ID NO: 156.
Compound 0144
H-Aib-EGTFTSDVSSYLEEQAAREFIAWLV-K([2-[2-[2-[2-[2-[2-[[(4S)-4-carboxy-4-(17-carboxyheptadecanoylamino)butanoyl]amino]ethoxy]ethoxy]acetyl]amino)

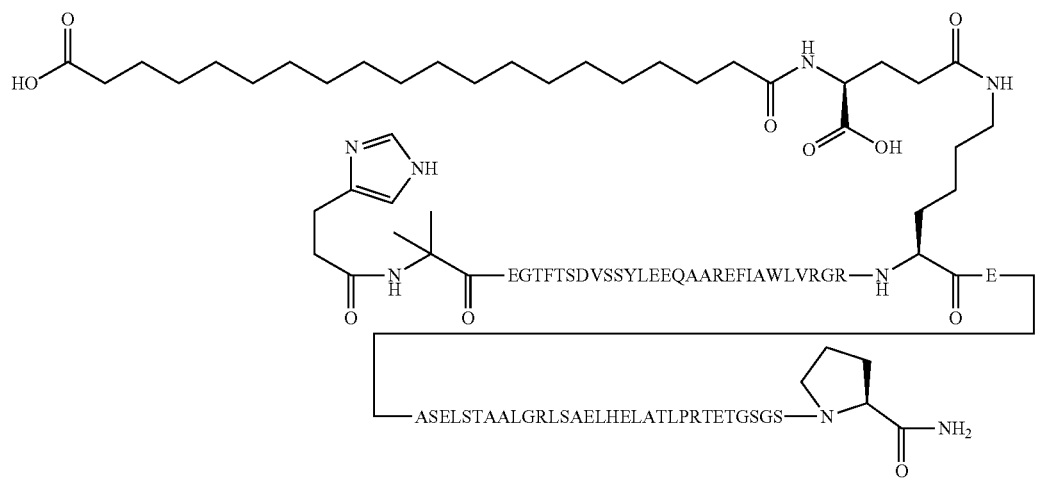

ethoxy]ethoxyacetyl])-GRGGGGGEASELSTAALGRLSAELHELATLPRT-ETGSGSP-amide

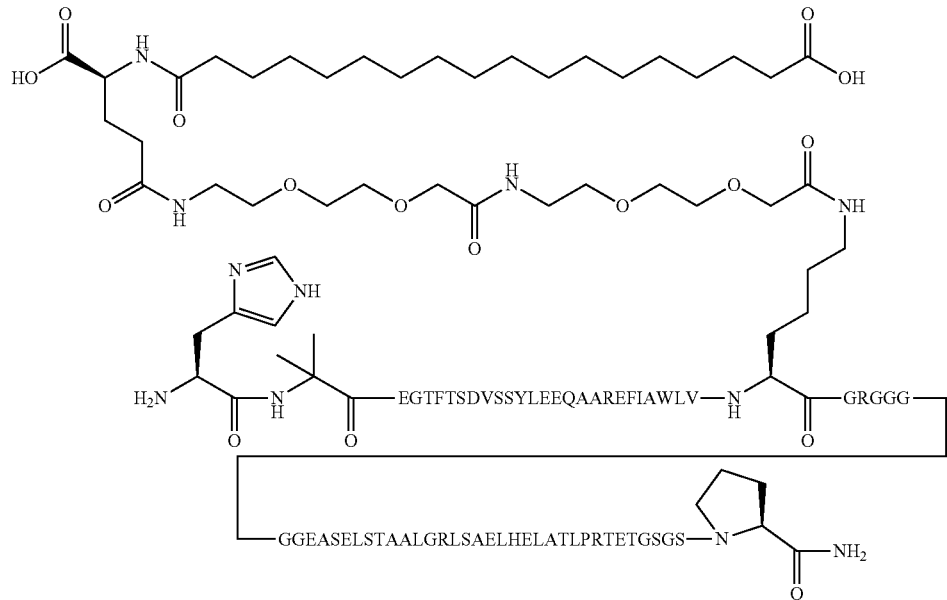

$C_{339}H_{541}N_{91}O_{116}$
Molecular weight (average) calculated: 7747.4629 g/mol
mono isotopic mass: 7742.9232 g/mol
LCMS34: found (M+5H)$^{5+}$1550.39 (most abundant)
The amino acid sequence of HXEGTFTSDVSSYLE-EQAAREFIAWLVKGRGGGGGEASELSTAALGRL-SAELHELATLPRTETGSGSP has SEQ ID NO: 163

Compound 0145
H-Aib-EGTFTSDVSSYLEEQAAREFIAWLVRGRG-K(4-[17-(1H-tetrazol-5-yl)heptadecanoylsulfamoyl]butanoyl)-GGGASELSTAALGRLSAELHELATL-PRTETGSGSP-amide $C_{325}H_{521}N_{95}O_{105}S$
Molecular weight (average) calculated: 7471.2527 g/mol
mono isotopic mass: 7466.8070 g/mol
LCMS01: found (M+5H)$^{5+}$1495 (most abundant)
The amino acid sequence of HXEGTFTSDVSSYLE-EQAAREFIAWLVRGRGKGGGASELSTAALGRLSAEL-HELATLPRTETGSGSP has SEQ ID NO: 164

Compound 0146
H-Aib-EGTFTSDVSSYLEEQAAREFIEWLVRG-K(4-[17-(1H-tetrazol-5-yl)heptadecanoylsulfamoyl]butanoyl)-GGGASELSTAALGRLSAELHELATLPRTETGSGSP-amide

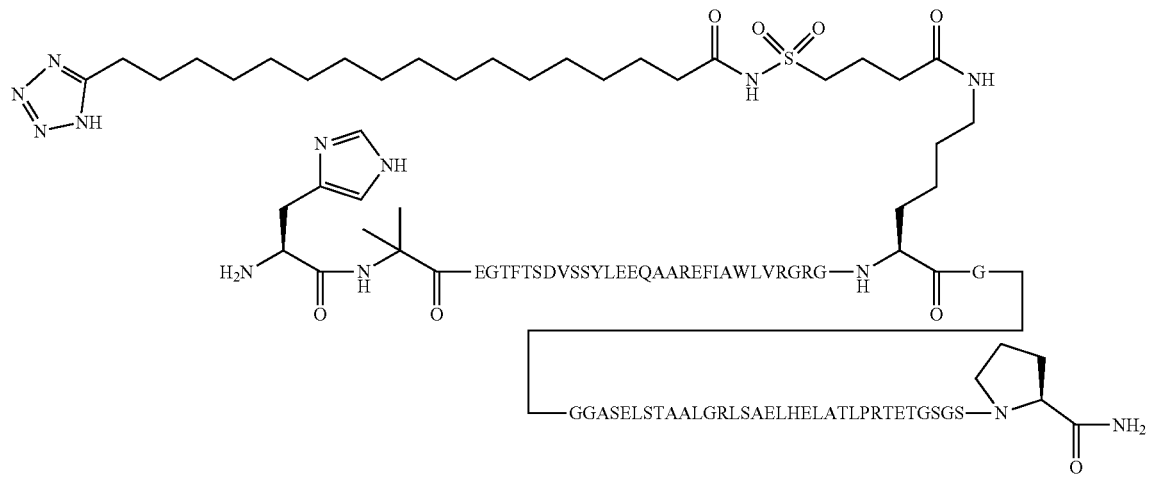

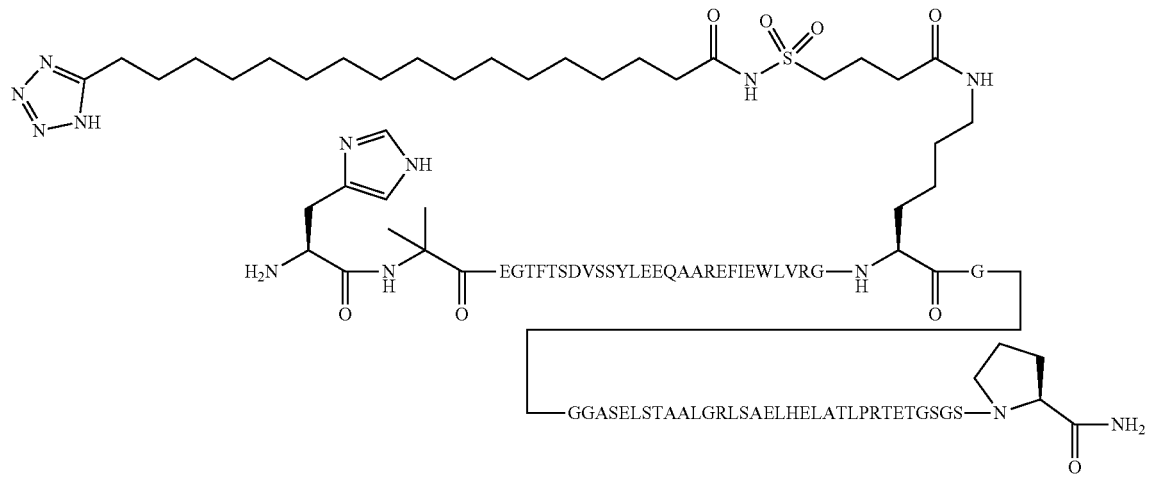

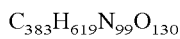

Molecular weight (average) calculated: 7316.0518 g/mol
mono isotopic mass: 7311.6899 g/mol
LCMS01: found $(M+5H)^{5+}$ 1484 (most abundant)
The amino acid sequence of HXEGTFTSDVSSYLE-EQAAREFIEWLVRGKGGGASELSTAALGRLSAEL-HELATLPRTETGSGSP has SEQ ID NO: 165

Compound 0147

H-Aib-EGTFTSDVSSYLEEQAAREFIEWLVRG-K(4-[17-(1H-tetrazol-5-yl)heptadecanoylsulfamoyl]butanoyl)-ASELSTAALGRLSAELHELATLPRTETGSGSP-amide

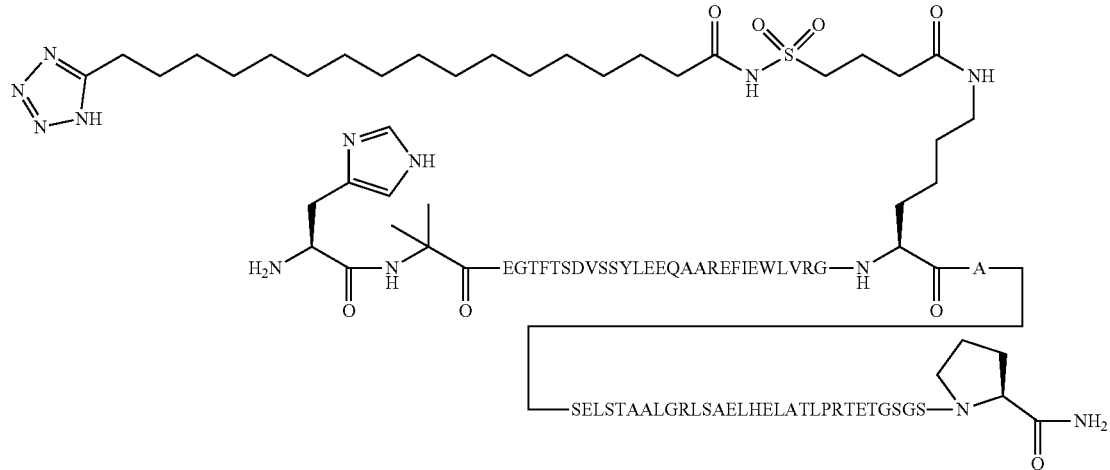

Molecular weight (average) calculated: 7144.8979 g/mol
mono isotopic mass: 7140.6255 g/mol
LCMS01: found $(M+5H)^{5+}$ 1430 (most abundant)
The amino acid sequence of HXEGTFTSDVSSYLE-EQAAREFIEWLVRGKASELSTAALGRLSAEL-HELATLPRTETGSGSP has SEQ ID NO: 166.

Compound 0151

H-Aib-EGTFTSDVSSYLEGQAAREFIAWLVRGR-K([2-[2-[2-[[2-[2-[2-[[(4S)-4-carboxy-4-(17-carboxyheptadecanoylamino)butanoyl]amino]ethoxy]ethoxy]acetyl]amino)ethoxy]ethoxy]acetyl])-GGGGEASELSTAALGRLSAELHELATLPRTETGSGSP-amide

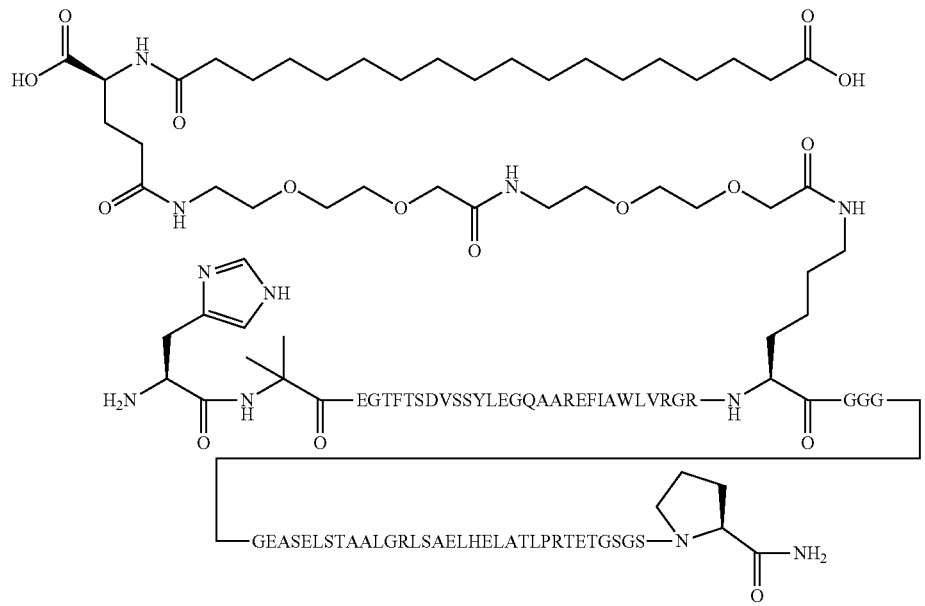

$C_{383}H_{619}N_{99}O_{130}$
Molecular weight (average) calculated: 7774.534 g/mol
mono isotopic mass: 7769.9817 g/mol
LCMS34: found $(M+5H)^{5+}$ 1555.81 (most abundant)
The amino acid sequence of HXEGTFTSDVS-SYLEGQAAREFIAWLVRGRKGGGGEASELSTAAL-GRLSAELHELATLPRTETGSGSP has SEQ ID NO: 167.
Compound 0156
H-Aib-EGTFTSDVSSYLEGQAA-K([2-[2-[2-[[2-[2-[2-[[(4S)-4-carboxy-4-(17-carboxyheptadecanoylamino)bu-tanoyl]amino]ethoxy]ethoxy]acetyl]amino]ethoxy]ethoxy]acetyl])-EFIAWLVRGRGQAPGOEPEASELSTAALGRL-SAELHELATLPRTETGSGSP-amide $C_{358}H_{570}N_{96}O_{121}$
Molecular weight (average) calculated: 8154.9270 g/mol
mono isotopic mass: 8150.1400 g/mol
LCMS34: found $(M+5H)^{5+}$ 1631.04 (mono isotopic)
The amino acid sequence of HXEGTFTSDVSSYLE-GOAAKEFIAWLVRGRGOAPGOEPEASELSTAALGRL-SAELHELATLPRTETGSGSP has SEQ ID NO: 168
Compound 0157
H-Aib-EGTFTSDVSSYLEGOAA-K([2-[2-[2-[[2-[2-[2-[[(4S)-4-carboxy-4-(19-carboxynonadecanoylamino)bu-tanoyl]amino]ethoxy]ethoxy]acetyl]amino]ethoxy]ethoxy]acetyl])-EFIAWLVRGRGOAPGOEPEASE-LSTAALGRLSAELHELATLPRTETGSGSP-amide

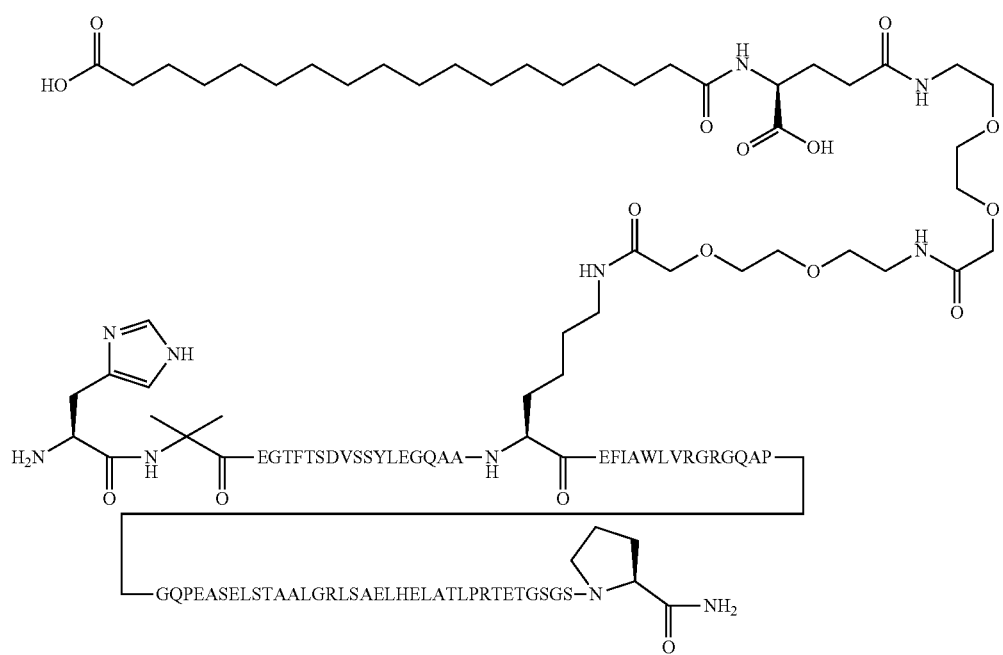

145

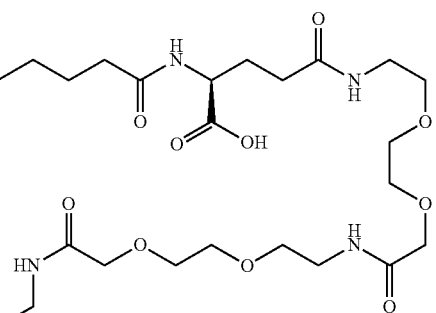
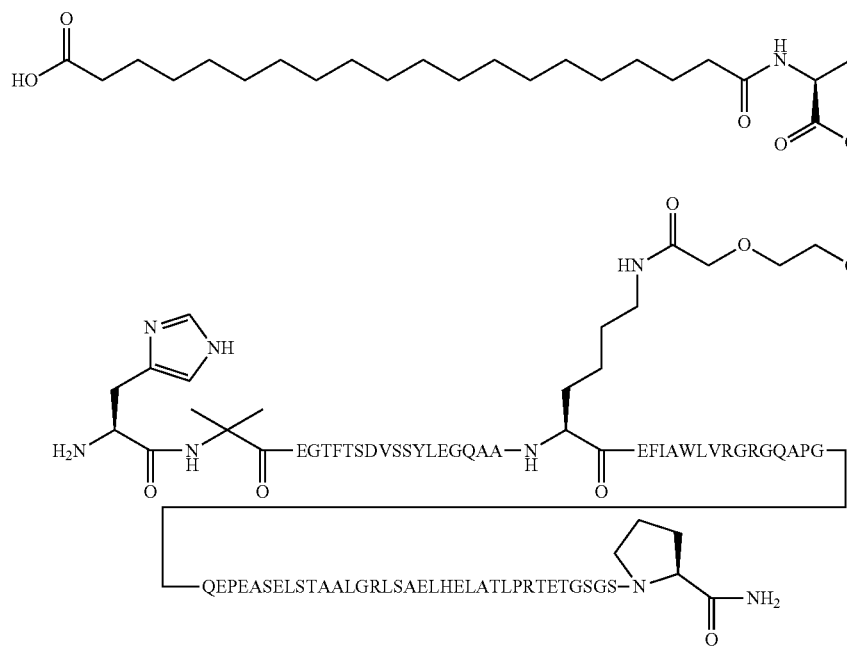

$C_{360}H_{574}N_{96}O_{121}$
Molecular weight (average) calculated: 8182.9802 g/mol
mono isotopic mass: 8178.1713 g/mol
LCMS34: found $(M+5H)^{5+}$ 1636.65 (most abundant)
The amino acid sequence of HXEGTFTSDVS-SYLEGQAAKEFIAWLVRGRGQAPGQEPEASEL-STAALGRLSAELHELATLPRTETGSGSP has SEQ ID NO: 168

146

Compound 0159
H-Aib-EGTFTSDVSSYLEGQAA-K([2S]-2-amino-6-[2-[2-[[2-[2-[2-[[(4S)-4-carboxy-4-(17-carboxyheptade-canoylamino)butanoyl]amino]ethoxy]ethoxy]acetyl]amino]ethoxy]ethoxy]acetyl])-EFIAWLVRGRGGGGGGGGEASELSTAAL-GRLSAELHELATLPRTETGSGSP-amide

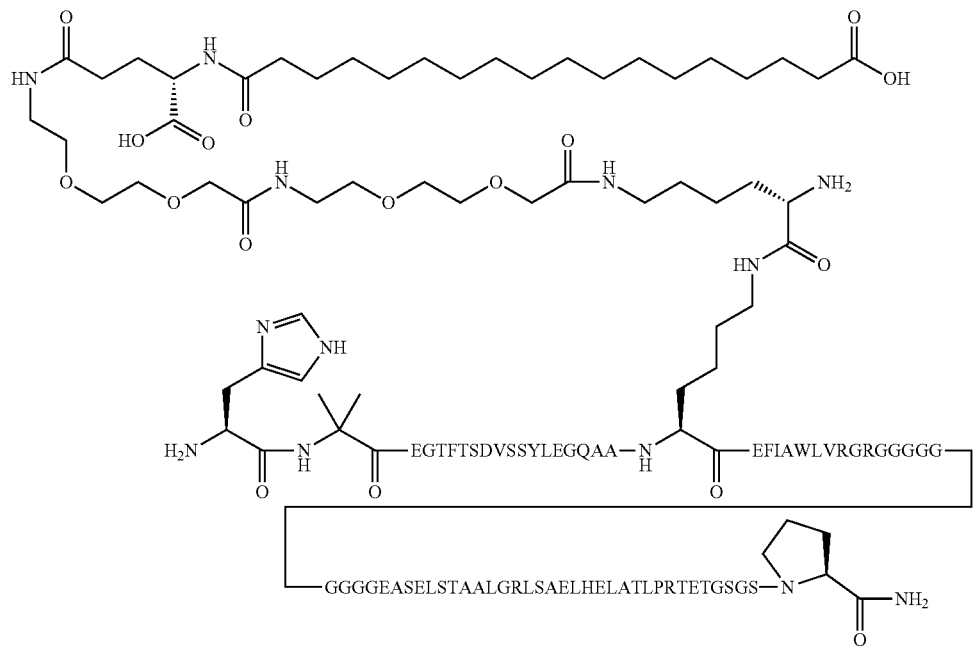

$C_{350}H_{561}N_{97}O_{119}$

Molecular weight (average) calculated: 8031.7778 g/mol mono isotopic mass: 8027.0828 g/mol LCMS34: found $(M+5H)^{5+}$ 1607.2 (most abundant)

The amino acid sequence of HXEGTFTSDVSSYLEGQAAKEFIAWLVRGRGGGGGGGGEASELSTAALGRLSAELHELATLPRTETGSGSP has SEQ ID NO: 126

Compound 0160

H-Aib-EGTFTSDVSSYLEEQAAR-K([(4S)-4-carboxy-4-(17-carboxyheptadecanoylamino)butanoyl])-FIAWLVR-GRGGGGGGGG-K([(4S)-4-carboxy-4-(17-carboxyheptadecanoylamino)butanoyl])-EASELSTAALGRLSAELHELATLPRTETGSGSP-amide

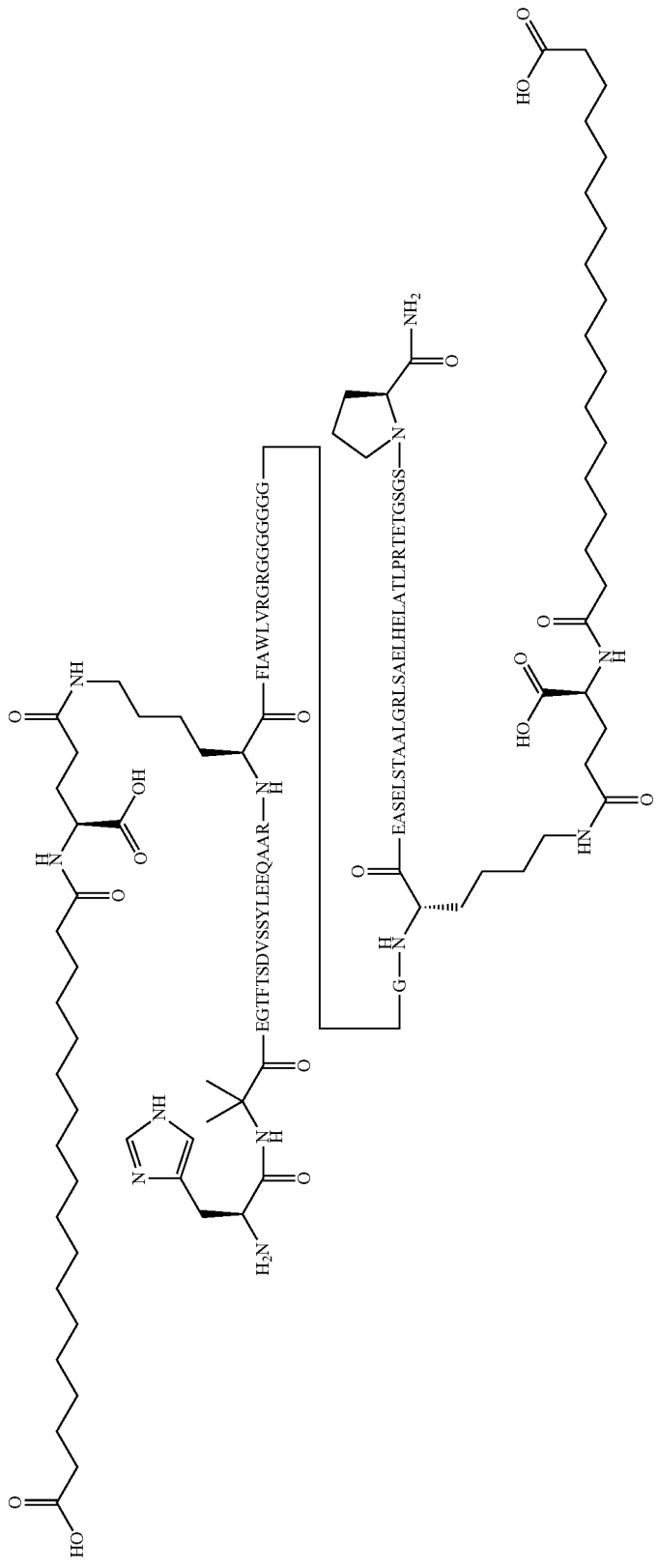

$C_{363}H_{584}N_{98}O_{118}$

Molecular weight (average) calculated: 8209.1069 g/mol mono isotopic mass: 8204.2710 g/mol LCMS34: found $(M+5H)^{5+}$1642.7 (most abundant)

The amino acid sequence of HXEGTFTSDVSSYLE-EQAARKFIAWLVRGRGGGGGGGGKEASELSTAAL-GRLSAELHELATLPRTETGSGSP has SEQ ID NO: 169

Compound 0179

H-Aib-EGTFTSDVSSYLEEQAAREFIEWLVRGR-K([2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl])-EAEAEASELSTAALGRLSAELHELATLPRTETGSGSP-amide

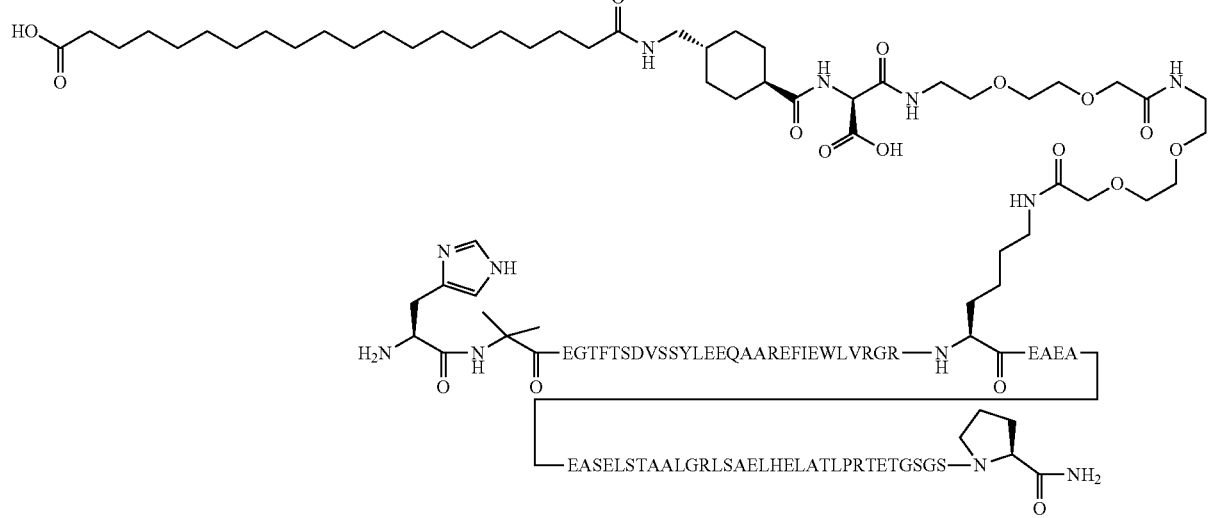

$C_{363}H_{581}N_{95}O_{123}$

Molecular weight (average) calculated: 8244.0599 g/mol

IDC-37 mono isotopic mass: 8239.2129 g/mol

LCMS34: found $(M+5H)^{5+}$1648.86 (mono isotopic)

The amino acid sequence of HXEGTFTSDVSSYLE-EQAAREFIEWLVRGRKEAEAEASELSTAALGRL-SAELHELATLPRTETGSGSP has SEQ ID NO: 170

Compound 0180

H-Aib-EGTFTSDVSSYLEEQAAREFIEWLVRGR-K([(2S)-2-amino-6-[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]hexanoyl])-EAEAEASELSTAALGRLSAELHELATLPRTETGSGSP-amide

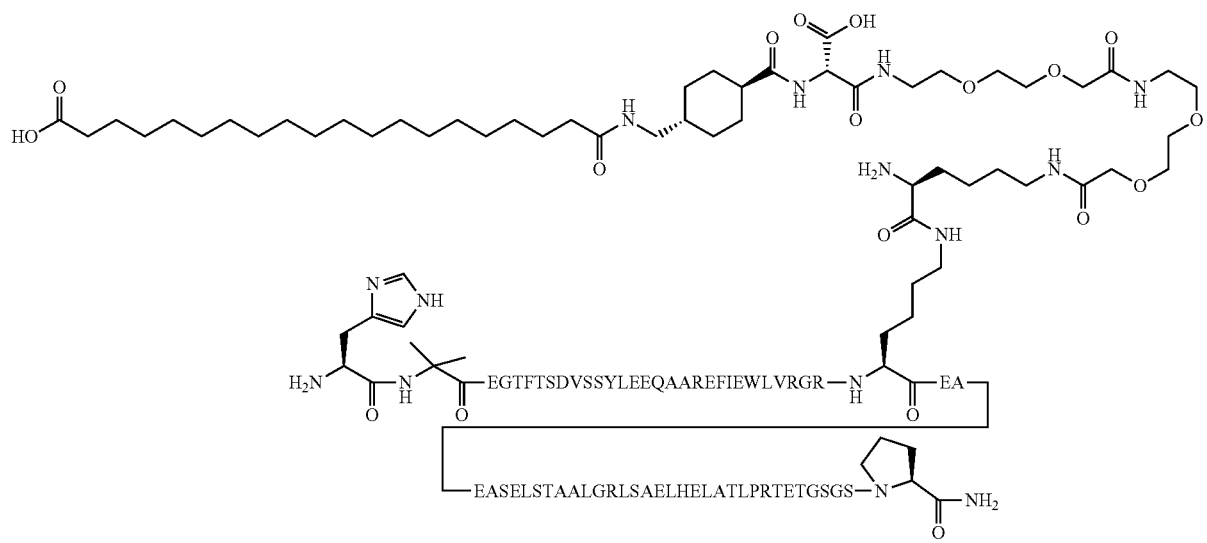

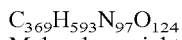

$C_{369}H_{593}N_{97}O_{124}$
Molecular weight (average) calculated: 8372.2322 g/mol
mono isotopic mass: 8367.3078 g/mol
LCMS34: found $(M+5H)^{5+}$ 1674.46 (mono isotopic)
The amino acid sequence of HXEGTFTSDVSSYLE-EQAAREFIEWLVRGRKEAEAEASELSTAALGRL-SAELHELATLPRTETGSGSP has SEQ ID NO: 170

Compound 0191

H-Aib-EGTFTSDVSSYLEGQAAREFIAWLVR-GRGQEP-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-GOAPASRLSTEALGRLSAELHELATLPRTETGSGSP-amide

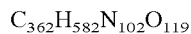

$C_{362}H_{582}N_{102}O_{119}$
Molecular weight (average) calculated: 8267.1065 g/mol
mono isotopic mass: 8262.2625 g/mol
LCMS34: found $(M+5H)^{5+}$1653.45 (mono isotopic)
The amino acid sequence of HXEGTFTSDVS-SYLEGQAAREFIAWLVRGRGQEPKGQAPASRL-STEALGRLSAELHELATLPRTETGSGSP has SEQ ID NO: 171

Compound 0202

H-Aib-EGTFTSDVSSYLEGQAA-K([2-[2-[2-[[2-[2-[2-g[(4S)-4-carboxy-4-(19-carboxynonadecanoylamino)butanoyl]amino]ethoxy]ethoxy]acetyl]amino]ethoxy]ethoxy]acetyl])-EFIAWLVRGRGQEPGOAPEASELSTAALGRL-SAELHELATLPRTETGSGSP-amide

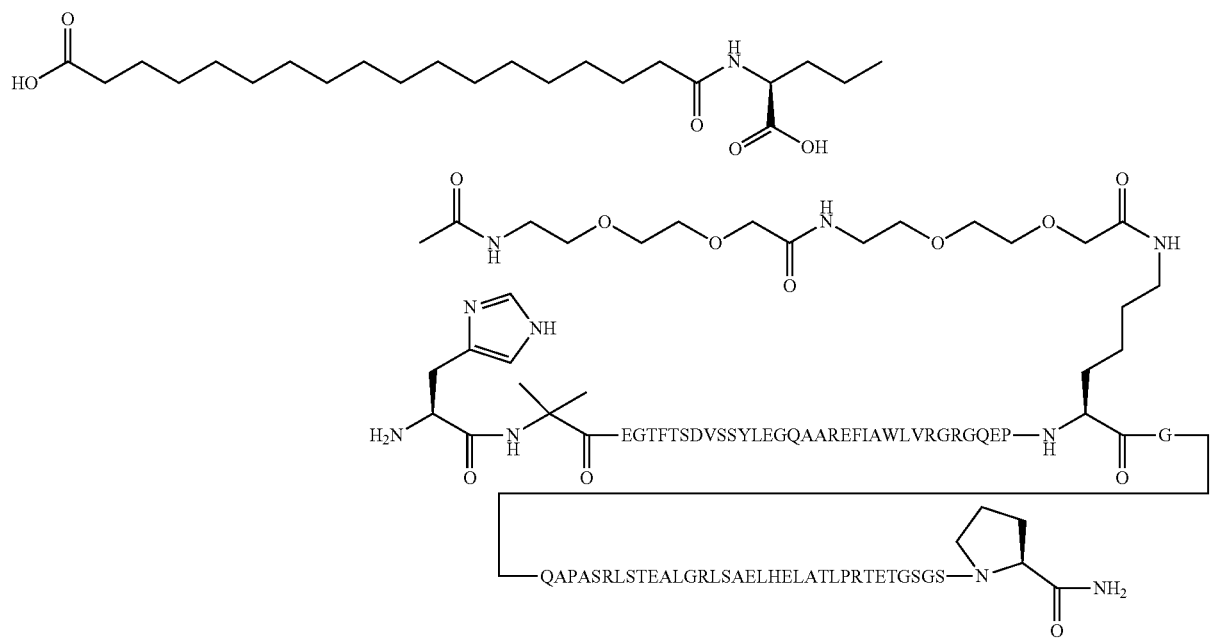

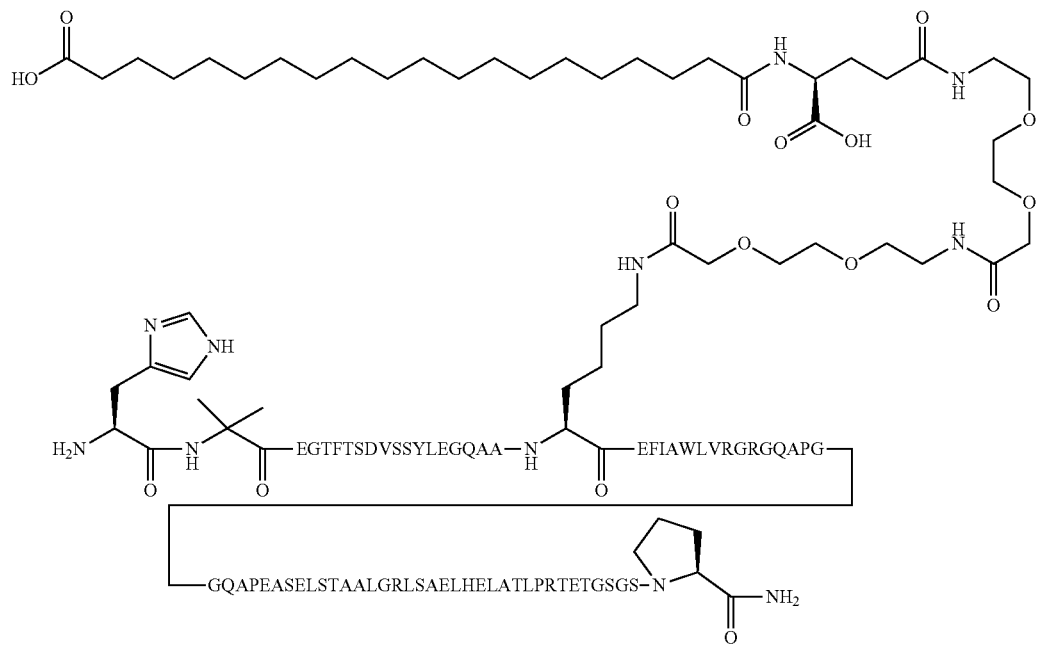

$C_{360}H_{574}N_{96}O_{121}$

Molecular weight (average) calculated: 8182.9802 g/mol
mono isotopic mass: 8178.1713 g/mol LCMS34: found $(M+5H)^{5+}$ 1636.67 (mono isotopic)

The amino acid sequence of HXEGTFTSDVSSVLEGQ-MAKEFIAWLVRGRGOEPGOAPEASELSTAALGRL-SAELHELATLPRTETGSGSP has SEQ ID NO: 121.

Compound 0231

HWEGTFTSDVSSYLEEQAAR-K([2-[2-[2-[[2-[2-[2-[[(4S)-4-carboxy-4-[10-(4-carboxyphenoxy)decanoy-lamino]butanoyl]amino]ethoxy]ethoxy]acetyl]amino]ethoxy]ethoxy]acetyl])-FIEWLVRGRGEGGGGGASELSTAALGRLS-K([2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl])-ELHELATLPRTETGSGSP-amide

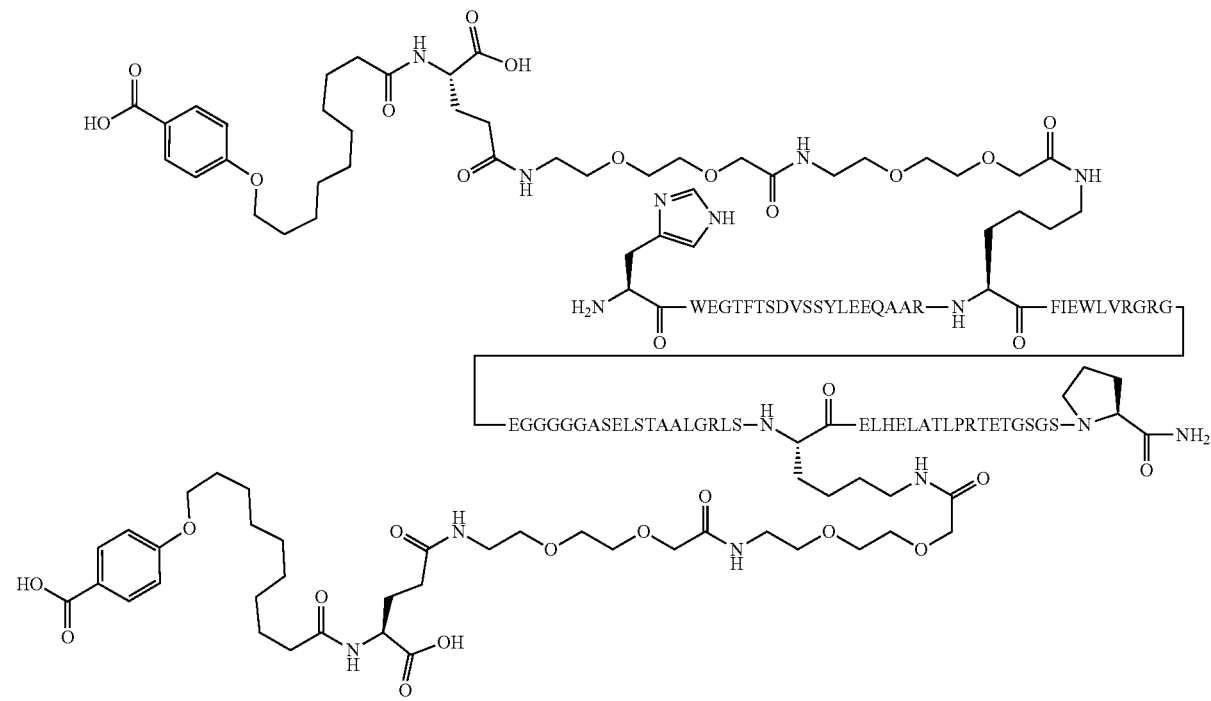

$C_{387}H_{602}N_{100}O_{131}$

Molecular weight (average) calculated: 8751.5122 g/mol mono isotopic mass: 8746.3519 g/mol LCMS34: found $(M+5H)^{5+}$1751.09 (most abundant)

The amino acid sequence of HWEGTFTSDVSSYLE-EQAARKFIEWLVRGRGEGGGGGASELSTAALGRL-SKELHELATLPRTETGSGSP has SEQ ID NO: 172.

Compound 0232

HWEGTFTSDVSSYLEEQAAR-K([2-[2-[2-[2-[2-[2-[[(4S)-4-carboxy-4-[10-(4-carboxyphenoxy)decanoyl-amino]butanoyl]amino]ethoxy]ethoxy]acetyl]amino]ethoxy]ethoxy]acetyl])-FIEWLVRGRGEGGGGGASELSTAALGRLSAELHEL-K([2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl])-TLPRTETGSGSP-amide

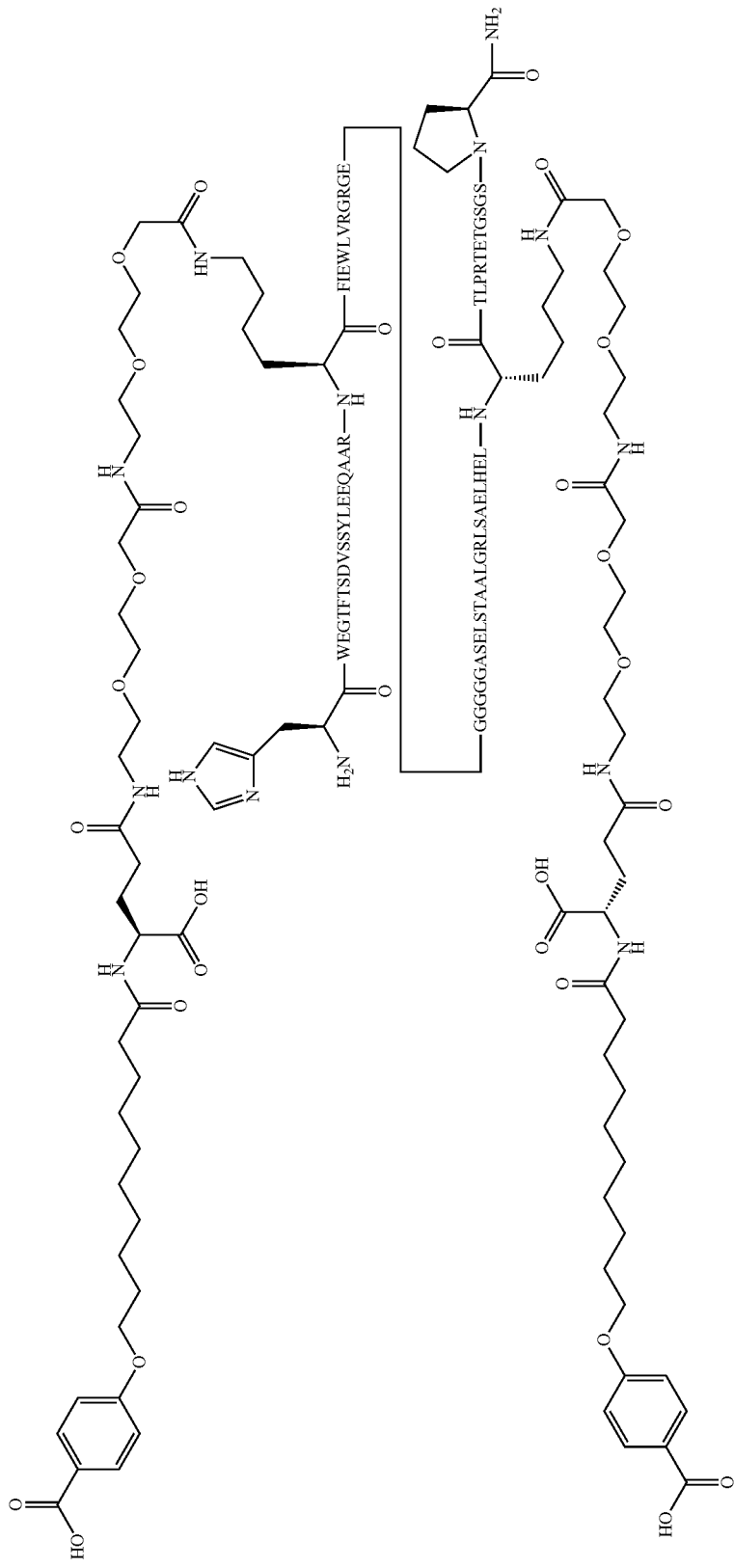

$C_{387}H_{602}N_{100}O_{131}$

Molecular weight (average) calculated: 8751.5122 g/mol mono isotopic mass: 8746.3519 g/mol LCMS34: found $(M+5H)^{5+}$1751.17 (most abundant)

The amino acid sequence of HWEGTFTSDVSSYLE-EQAARKFIEWLVRGRGEGGGGGASELSTAALGRL-SAELHELKTLPRTETGSGSP has SEQ ID NO: 173.

Compound 0233

HWEGTFTSDVSSYLEEQAAREFIEWLVRG-K([2-[2-[2-[[2-[2-[2-[[(4S)-4-carboxy-4-[10-(4-carboxyphenoxy) decanoylamino]butanoyl]amino]ethoxy]ethoxy]acetyl] amino]ethoxy]ethoxy]acetyl])-GEGGGGGASELSTAALGRLS-K([2-[2-[2-[[2-[2-[2-[(4S)-4-carboxy-4-[10-(4-carboxyphenoxy)decanoylamino] butanoyl]amino]ethoxy]ethoxy]acetyl]amino]ethoxy] ethoxy]acetyl])- ELHELATLPRTETGSGSP-amide

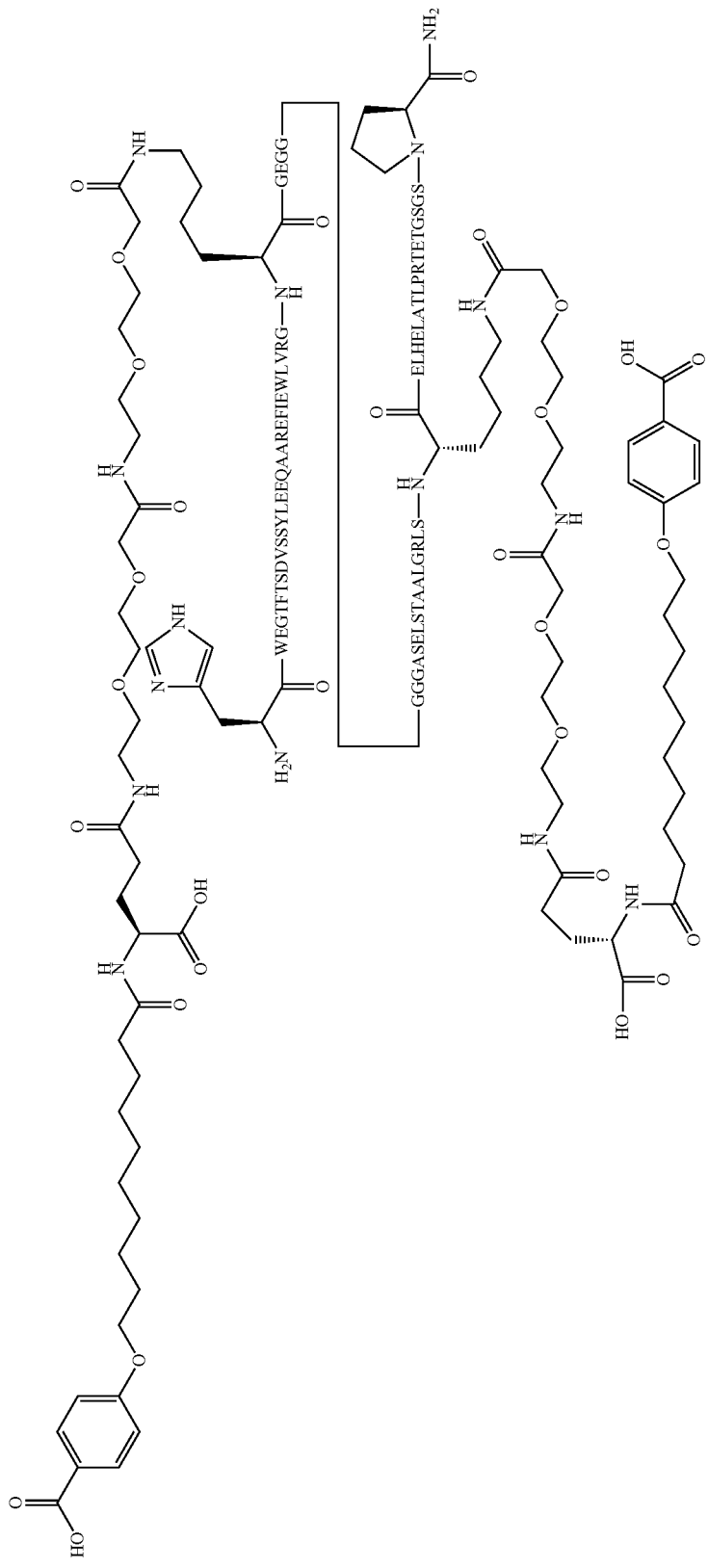

$C_{386}H_{597}N_{97}O_{133}$

Molecular weight (average) calculated: 8724.4405 g/mol mono isotopic mass: 8719.2933 g/mol LCMS34: found $(M+5H)^{5+}$1745.54 (most abundant)

The amino acid sequence of HWEGTFTSDVSSYLE-EQAAREFIEWLVRGKGEGGGGGASELSTAALGRL-SKELHELATLPRTETGSGSP has SEQ ID NO: 174

Compound 0234

HWEGTFTSDVSSYLEEQAAREFIEWLVRG-K([2-[2-[2-[[2-[2-[2-[[(4S)-4-carboxy-4-[10-(4-carboxyphenoxy) decanoylamino]butanoyl]amino]ethoxy]ethoxy]acetyl] amino]ethoxy]ethoxy]acetyl])-GEGGGGGASELSTAALGRLSAELHEL-K([2-[2-[2-[[2-[2-[2-[[(4S)-4-carboxy-4-[10-(4-carboxyphenoxy) decanoylamino]butanoyl]amino]ethoxy]ethoxy]acetyl] amino]ethoxy]ethoxy]acetyl])-TLPRTETGSGSP-amide

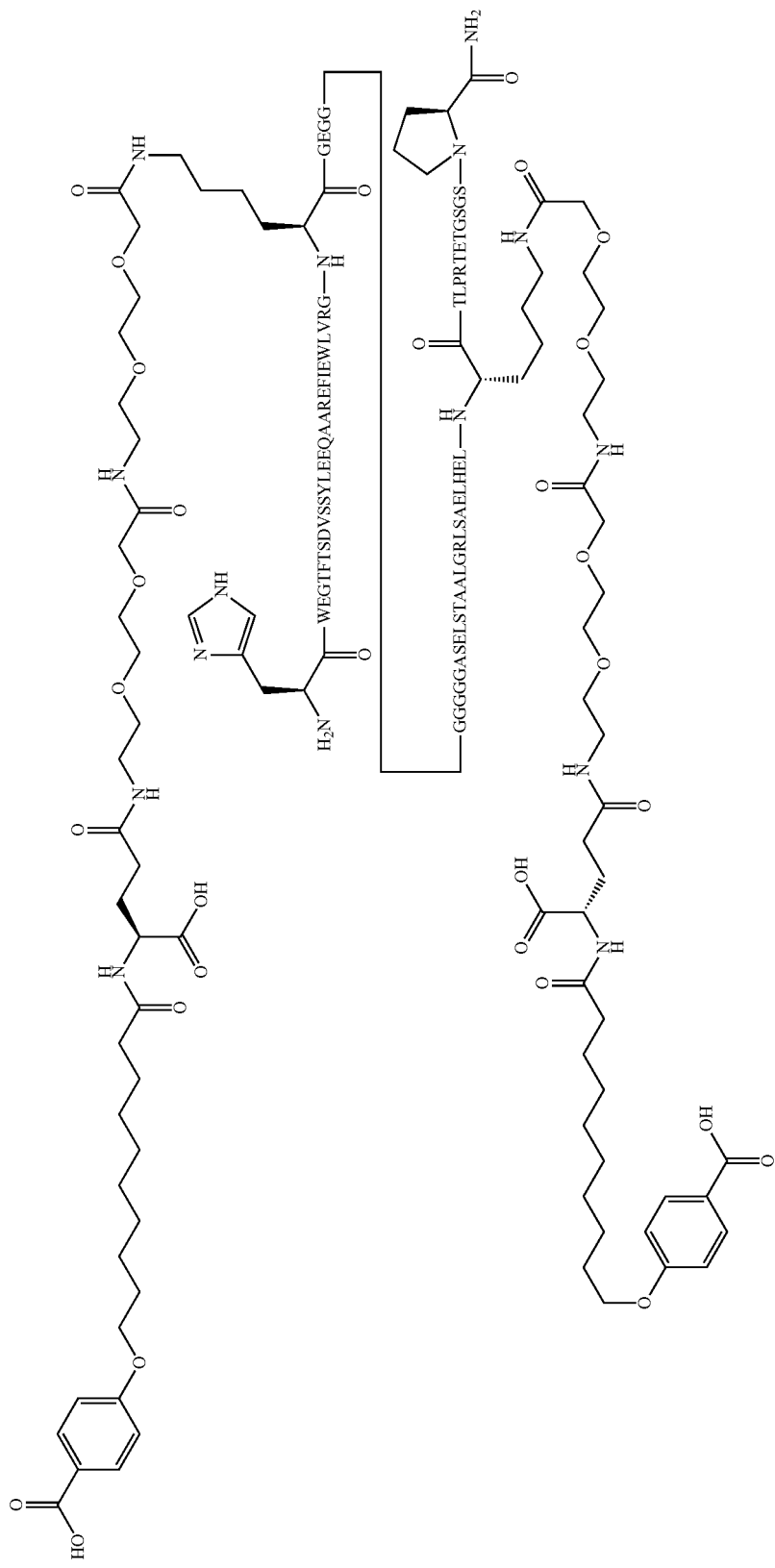

$C_{386}H_{597}N_{97}O_{133}$
Molecular weight (average) calculated: 8724.4405 g/mol
mono isotopic mass: 8719.2933 g/mol
LCMS34: found $(M+5H)^{5+}$ 1745.73 (most abundant)
The amino acid sequence of HWEGTFTSDVSSYLE-EQAAREFIEWLVRGKGEGGGGGASELSTAALGRL-SAELHELKTLPRTETGSGSP has SEQ ID NO: 175.
Compound 0235
H-Aib-EGTFTSDVSSYLEEQAAREFIAWLVRG-K([2-[2-[2-[2-[2-[2-[(4S)-4-carboxy-4-[10-(3-carboxyphenoxy)decanoylamino]butanoyl]amino]ethoxy]ethoxy]acetyl]amino]ethoxy]ethoxy]acetyl])-K([2-[2-[2-[[2-[2-[2-[[(4S)-4-carboxy-4-[10-(3-carboxyphenoxy)decanoylamino]butanoyl]amino]ethoxy]ethoxy]acetyl]amino]ethoxy]ethoxy]acetyl])-GGGGASELSTAALGRLSAELHELATLPRTETGSGSP-amide

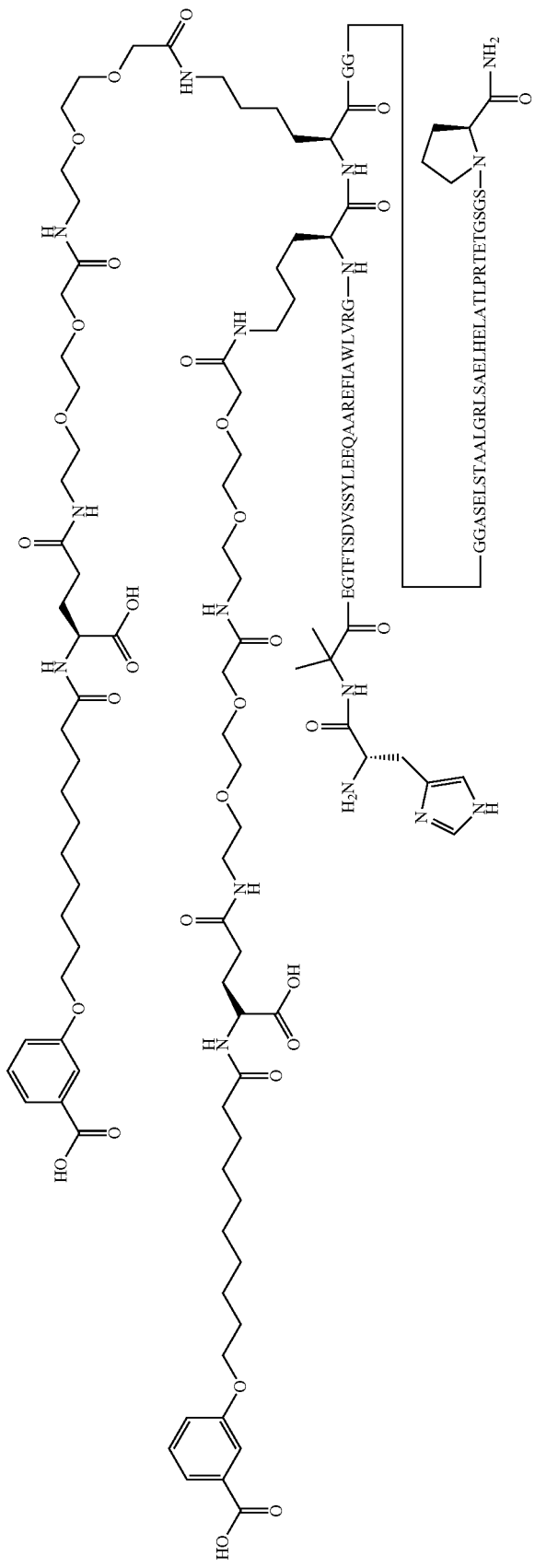

$C_{371}H_{584}N_{94}O_{127}$
Molecular weight (average) calculated: 8393.1603 g/mol
mono isotopic mass: 8388.2129 g/mol
LCMS34: found $(M+5H)^{5+}$1678.65 (mono isotopic)

The amino acid sequence of HXEGTFTSDVSSYLE-EQAAREFIAWLVRGKKGGGGASELSTAALGRLSAEL-HELATLPRTETGSGSP has SEQ ID NO: 176.

Compound 0254

HWEGTFTSDVSSYLEEQAAR-K([2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl)-FIEWLVRGRGEGGGGGASELSTAALGRLSAELHELATL-PRTETGSGSP-amide

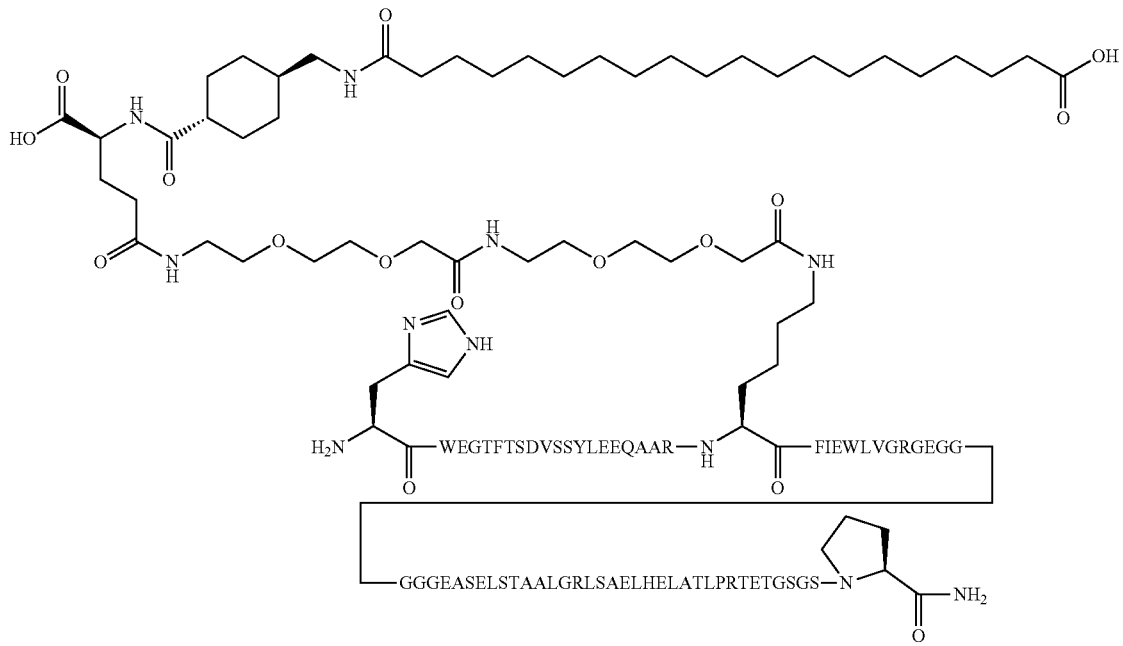

$C_{361}H_{571}N_{97}O_{118}$
Molecular weight (average) calculated: 8157.9755 g/mol
mono isotopic mass: 8153.1662 g/mol
LCMS34: found $(M+5H)^{5+}$1632.55 (most abundant)

The amino acid sequence of HWEGTFTSDVSSYLE-EQAARKFIEWLVRGRGEGGGGGASELSTAALGRL-SAELHELATLPRTETGSGSP has SEQ ID NO: 177.

Compound 0255

HWEGTFTSDVSSYLEEQAAR-K([2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl])-FIEWLVRGRGEGGGGGASELSTAALGRLS-K([2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl])-ELHELATLPRTETSS-amide

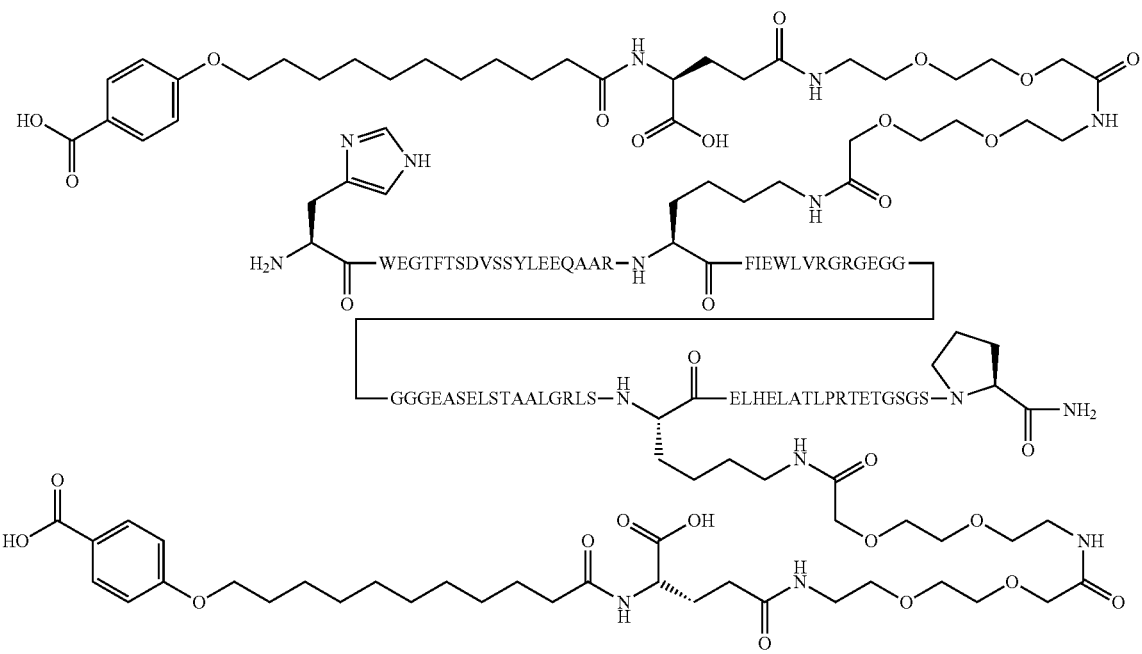

$C_{389}H_{606}N_{100}O_{131}$
Molecular weight (average) calculated: 8779.5653 g/mol
mono isotopic mass: 8774.3832 g/mol
LCMS34: found $(M+5H)^{5+}$ 1756.92 (most abundant)
The amino acid sequence of HWEGTFTSDVSSYLE-EQAARKFIEWLVRGRGEGGGGGASELSTAALGRL-SKELHELATLPRTETGSGSP has SEQ ID NO: 172.
Compound 0259
H-Aib-EGTFTSD-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-SSYLEEQAAREFIAWLVRGRGGGGGEASELSTAALGRL-SAELH-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-LATLPRTETGSGSP-amide

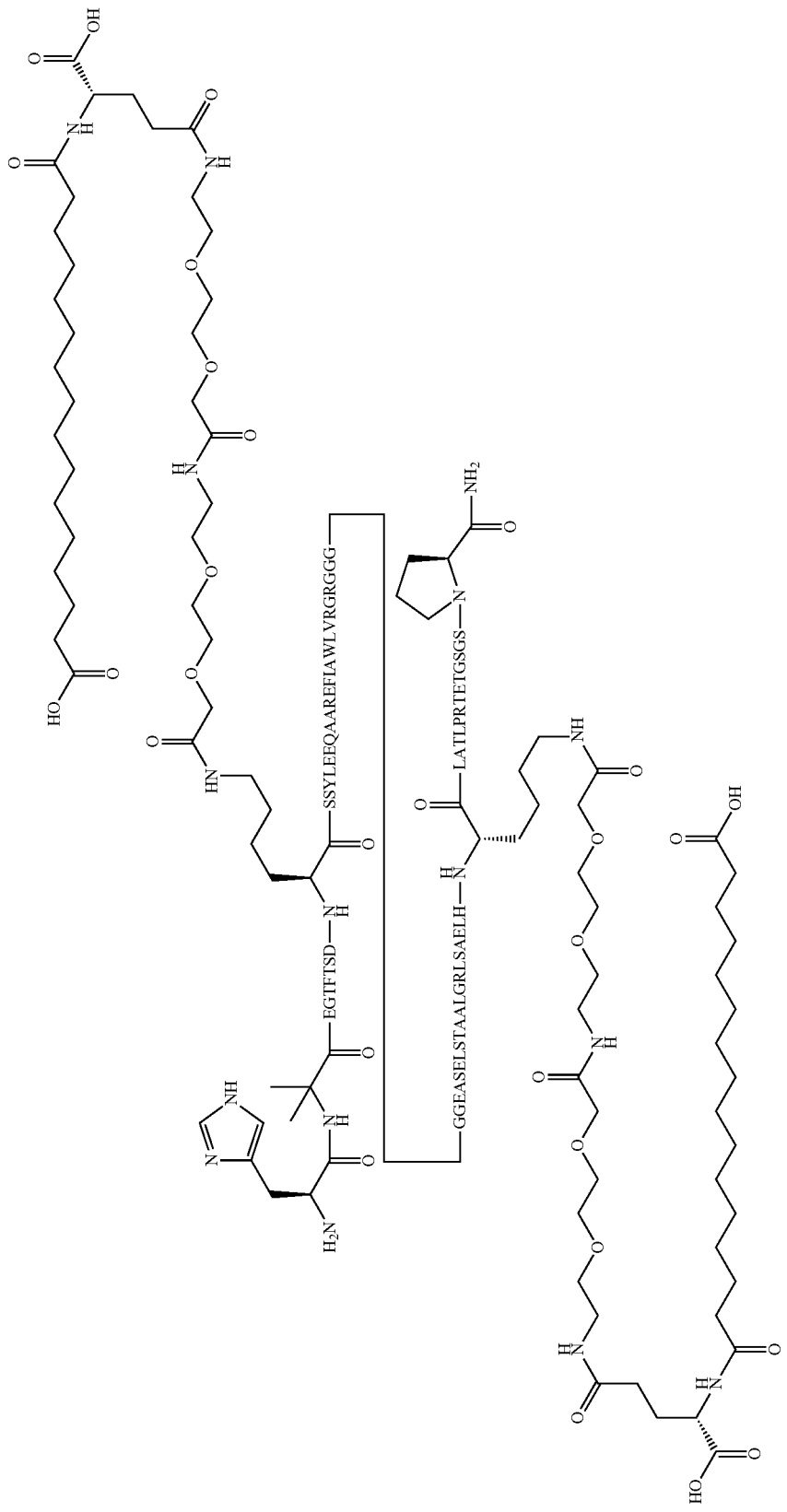

$C_{372}H_{602}N_{98}O_{126}$

Molecular weight (average) calculated: 8463.3413 g/mol mono isotopic mass: 8458.3711 g/mol LCMS_ZQ: found $(M+5H)^{5+}$ 1693.6 (most abundant)

The amino acid sequence of HXEGTFTSDKSSYLE-EQAAREFIAWLVRGRGGGGGEASELSTAALGRL-SAELHKLATLPRTETGSGSP has SEQ ID NO: 178.

Compound 0260

H-Aib-EGTFTSD-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-SSYLEEQAAREFIAWLVRGRGGGGGEASELSTAALGRL-SAELHEL-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]-TLPRTETGSGSP-amide

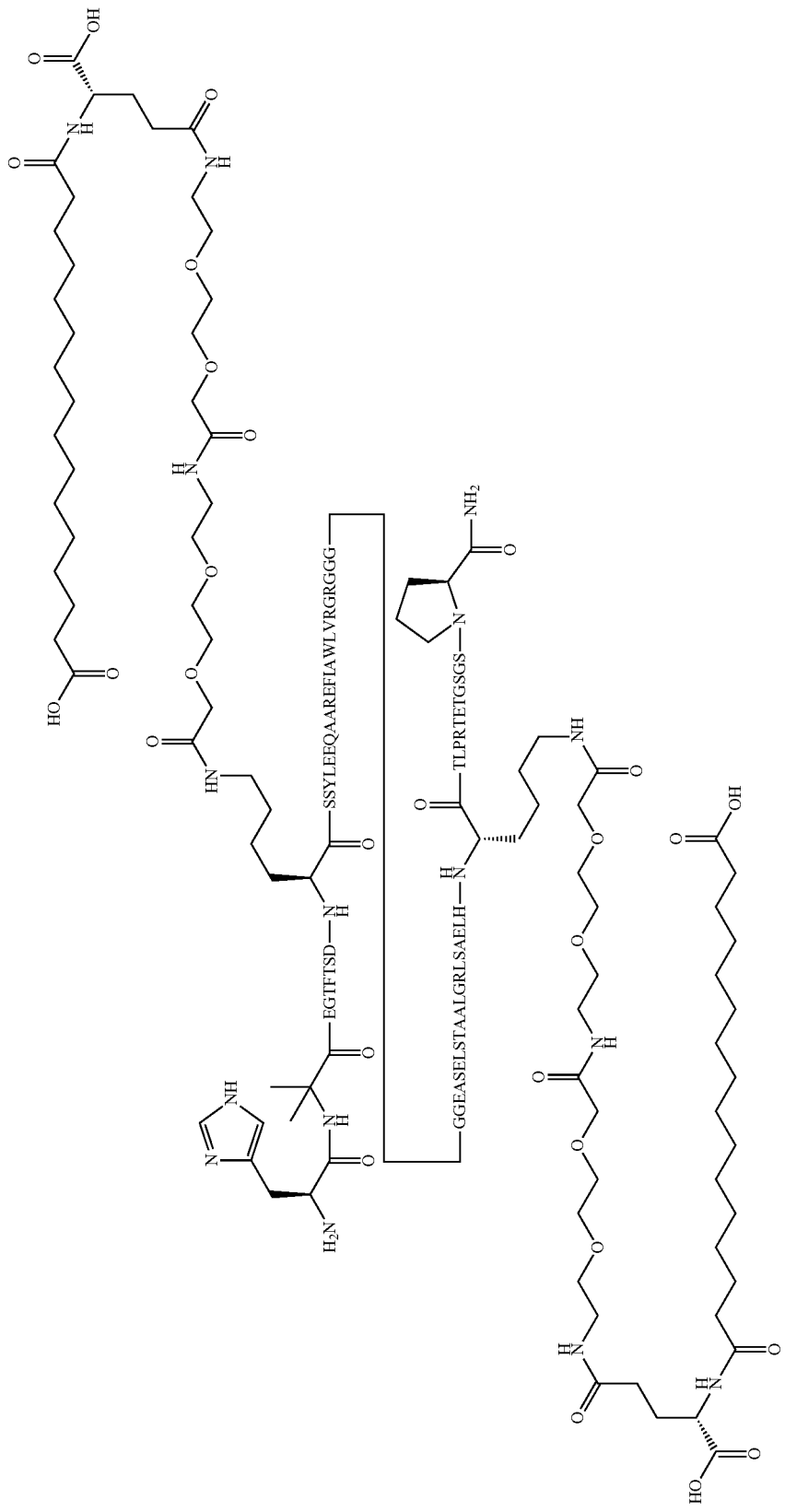

$C_{374}H_{604}N_{98}O_{128}$

Molecular weight (average) calculated: 8521.3774 g/mol mono isotopic mass: 8516.3766 g/mol LCMS_ZQ: found $(M+5H)^{5+}$ 1705.3 (most abundant)

The amino acid sequence of HXEGTFTSDKSSYLE-EQAAREFIAWLVRGRGGGGGEASELSTAALGRL-SAELHELKTLPRTETGSGSP has SEQ ID NO: 179.

Compound 0261

H-Aib-EGTFTSD-K([2-[2-[2-[[2-[2-[2-[[(4S)-4-carboxy-4-(15-carboxypentadecanoylamino)butanoyl]amino]ethoxy]ethoxyacetyl]amino]ethoxy]ethoxy]acetyl])-SSYLEEQAAREFIAWLVRGRGGGGEASELSTAALGRL-SAELHELATL-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-RTETGSGSP-amide

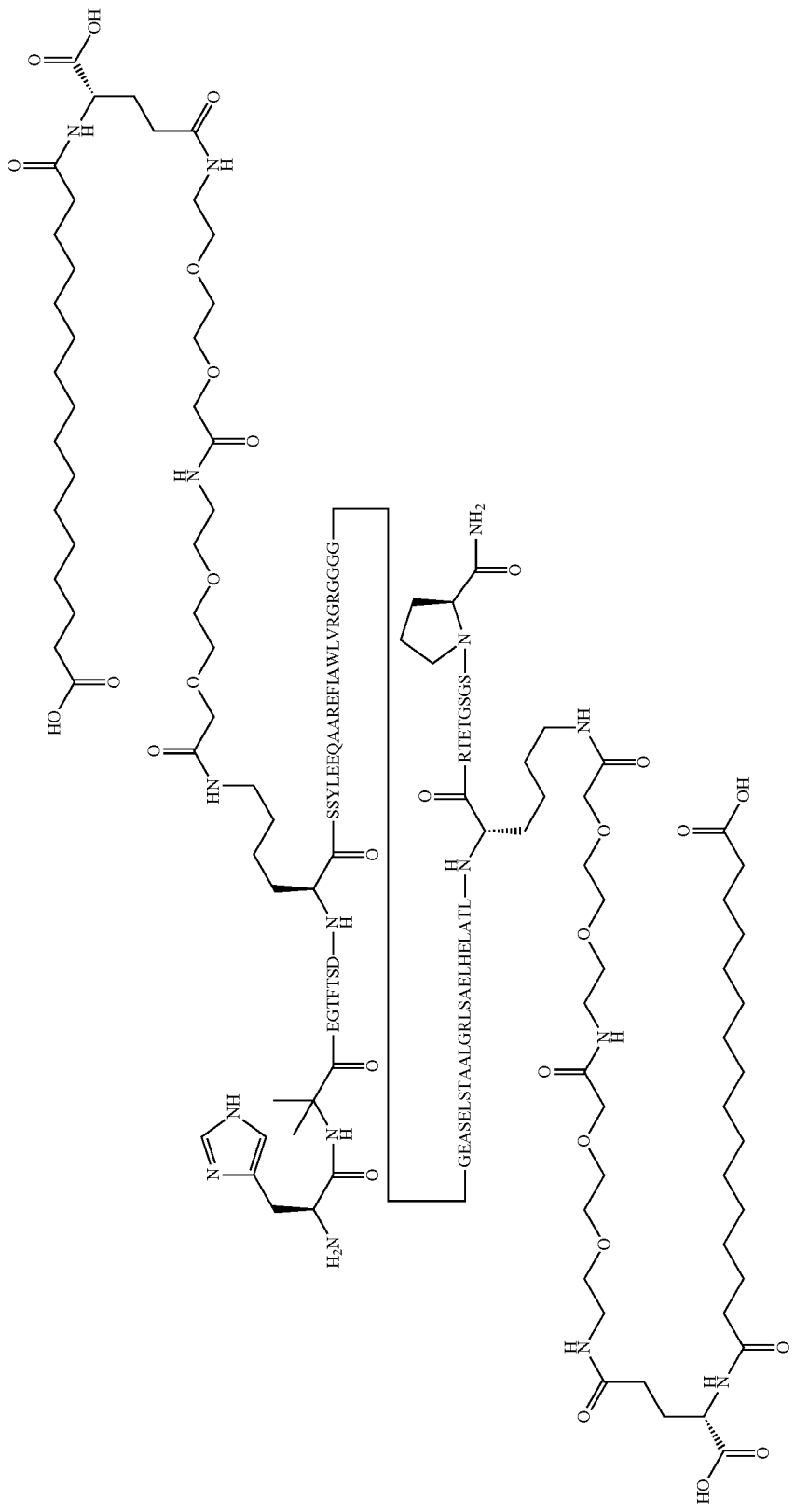

$C_{372}H_{602}N_{98}O_{128}$
Molecular weight (average) calculated: 8495.3401 g/mol
mono isotopic mass: 8490.3610 g/mol
LCMS_ZQ: found $(M+5H)^{5+}$1699.9 (most abundant)
The amino acid sequence of HXEGTFTSDKSSYLE-EQAAREFIAWLVRGRGGGGGEASELSTAALGRL-SAELHELATLKRTETGSGSP has SEQ ID NO: 180.

Compound 0263

H-Aib-EGTFTSDVSSYLEEQAAREFIAWLVRGR-K([2-[2-[2-[[2-[2-[2-[[(4S)-4-carboxy-4-[[4-[(19-carbxynonadecanoylamino)methyQcydohexanecarbonyl]amino]butanoyl]amino]ethoxy]ethoxy]acetyl]amino]ethoxy]ethoxy]acetyl])-EASELSTAALGRLSAELHELATLPRTETGSGSP-amide

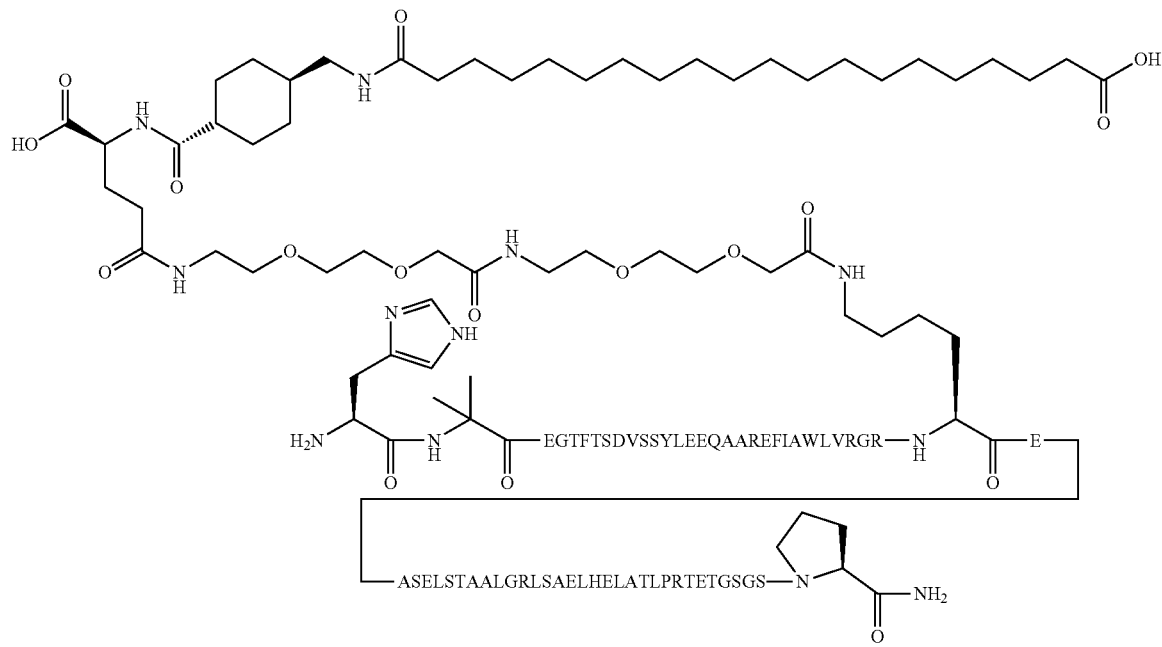

$C_{345}H_{555}N_{91}O_{113}$

Molecular weight (average) calculated: 7785.6401 g/mol mono isotopic mass: 7781.0480 g/mol LCMS_ZQ: found $(M+5H)^{5+}$1558.2 (most abundant)

The amino acid sequence of HXEGTFTSDVSSYLE-EQAAREFIAWLVRGRKEASELSTAALGRLSAEL-HELATLPRTETGSGSP has SEQ ID NO: 150.

Compound 0264

H-Aib-EGTFTSDVSSYLEEQAAREFIAWLVRG-K([2-[2-[2-[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl])-GGGGEASELSTAALGRLSAELHELATLPRTETGSGSP-amide

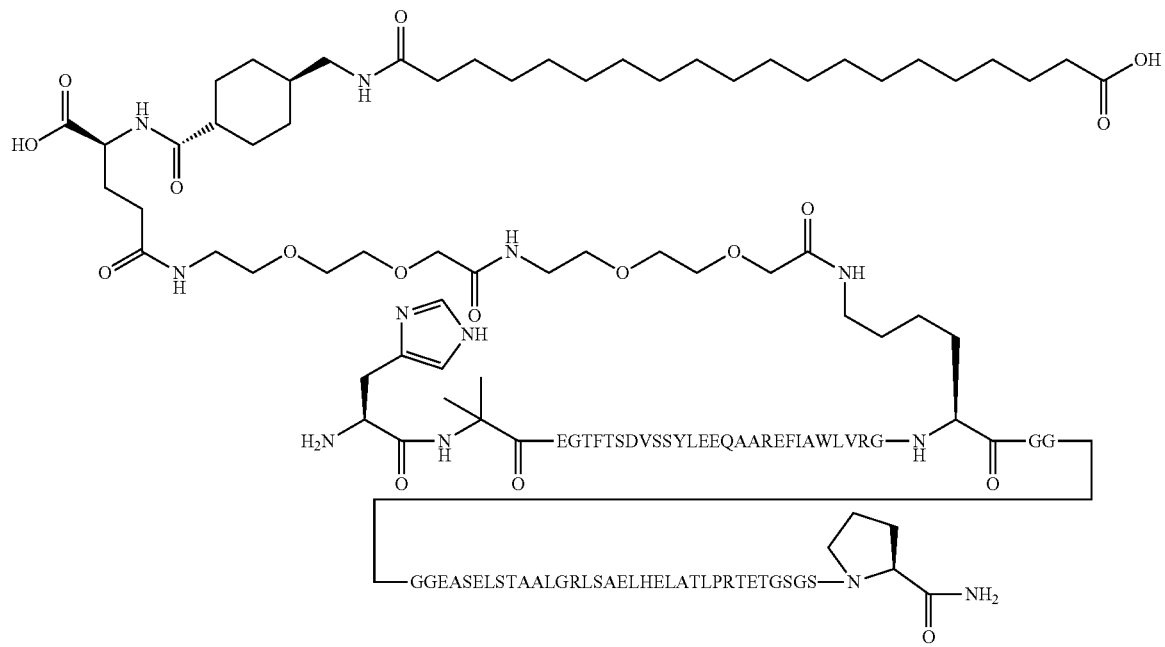

$C_{347}H_{555}N_{91}O_{116}$
Molecular weight (average) calculated: 7857.6597 g/mol
mono isotopic mass: 7853.0327 g/mol
LCMS_ZQ: found $(M+5H)^{5+}$ 1572.5 (most abundant)
The amino acid sequence of HXEGTFTSDVSSYLE-EQAAREFIAWLVRGKGGGGEASELSTAALGRLSAEL-HELATLPRTETGSGSP has SEQ ID NO: 181.
Compound 0265
H-Aib-EGTFTSDVSSYLEE-K([2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl])-AAREFIAWLVRGRGGGGEASELSTAALGRLSAE-LHELATLPRTETGSGSP-amide $C_{348}H_{559}N_{93}O_{115}$
Molecular weight (average) calculated: 7885.7162 g/mol
mono isotopic mass: 7881.0752 g/mol
LCMS_ZQ: found $(M+5H)^{5+}$ 1577.9 (most abundant)
The amino acid sequence of HXEGTFTSDVSSYLEE-KAAREFIAWLVRGRGGGGEASELSTAALGRLSAEL-HELATLPRTETGSGSP has SEQ ID NO: 182.
Compound 0266
H-Aib-EGTFTSD-K([2-[2-[2-[[2-[2-[2-[[(4S)-4-carboxy-4-[[4-[(19-carboxynonadecanoylamino)methyl]cyclohexanecarbonyl]amino]butanoylamino]ethoxy]ethoxy]acetyl]amino]ethoxy]ethoxy]acetyl])-SSYLEEQAAREFIAWLVRGRGGGGEASELSTAALGRL-SAELHELATLPRTETGSGSP-amide

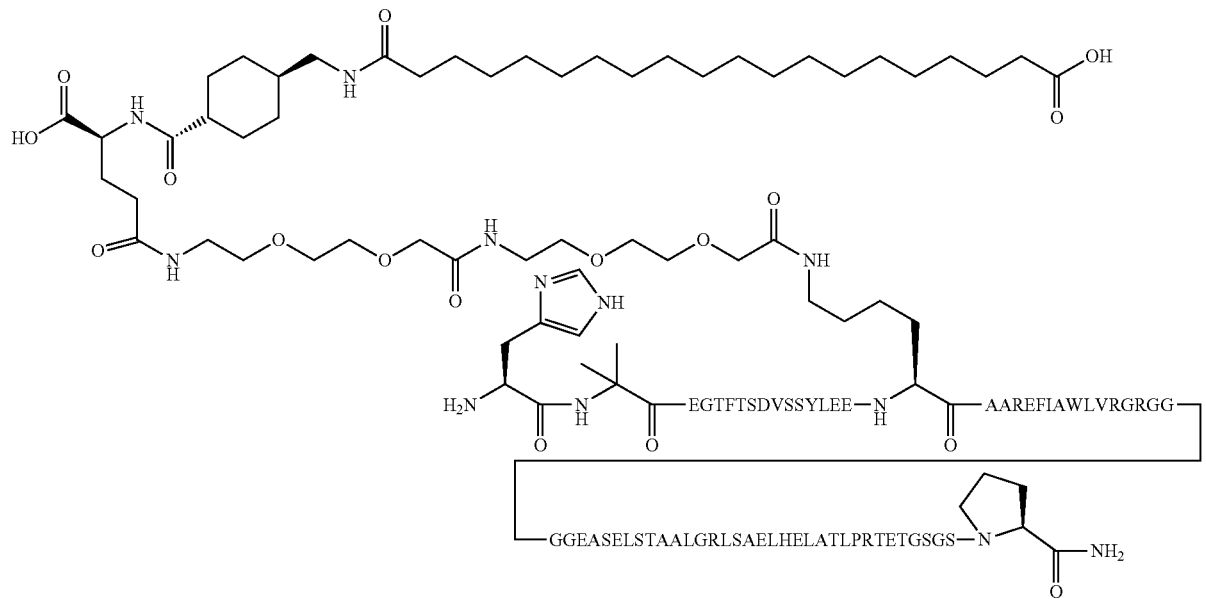

191  192 

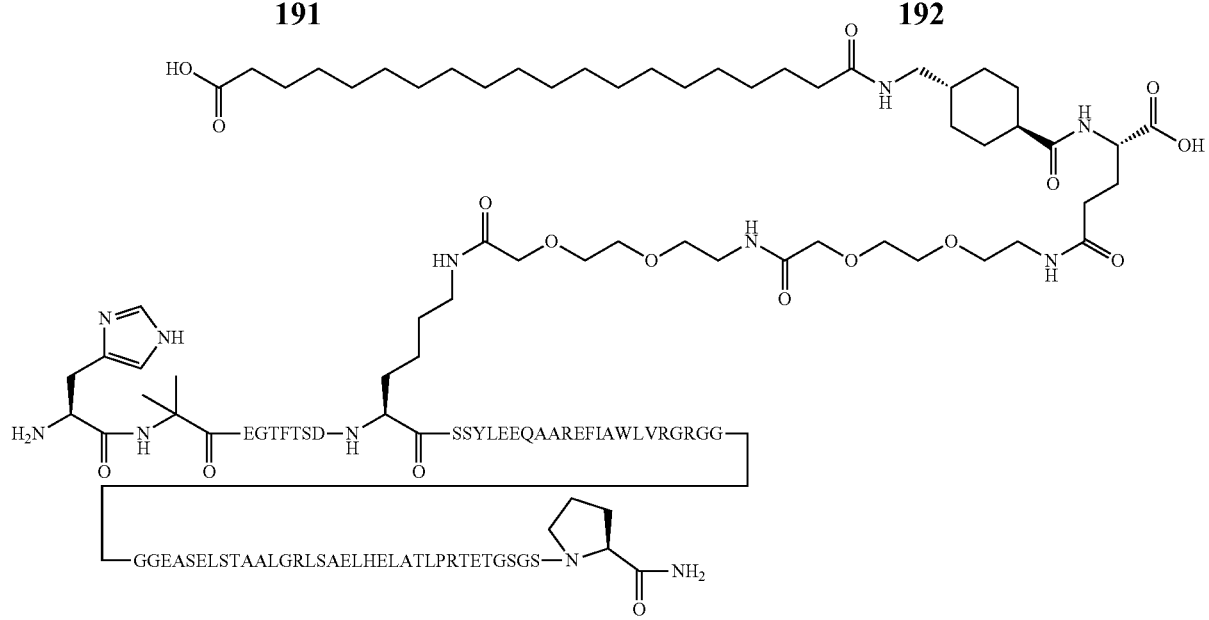

$C_{348}H_{558}N_{94}O_{116}$
Molecular weight (average) calculated: 7914.7143 g/mol
mono isotopic mass: 7910.0654 g/mol
LCMS_ZQ: found $(M+5H)^{5+}$1583.9 (most abundant)
The amino acid sequence of HXEGTFTSDKSSYLE-EQAAREFIAWLVRGRGGGGEASELSTAALGRLSAEL-HELATLPRTETGSGSP has SEQ ID NO: 183.
Compound 0267
HWEGTFTSDVSSYLEEQAAREFIEWLVRG-K([2-[2-[2-[[2-[2-[2-[[(4S)-4-carboxy-4-[[4-[(19-carboxynonade-canoylamino)methyl]cylohexanecarbonyl]amino]butanoyl]amino]ethoxy]ethoxy]acetyl]amino]ethoxy]ethoxy]acetyl])-GEASELSTAALGRLSAELHELATLPRTETGSGSP-amide $C_{350}H_{551}N_{89}O_{115}$
Molecular weight (average) calculated: 7845.6472 g/mol
mono isotopic mass: 7841.0003 g/mol
LCMS_ZQ: found $(M+5H)^{5+}$1570.1 (most abundant)
The amino acid sequence of HWEGTFTSDVS-SYLEEOAAREFIEWLVRGKGEASELSTAALGRL-SAELHELATLPRTETGSGSP has SEQ ID NO: 184.
Compound 0268
HWEGTFTSDVSSYLEEQAAREFIAWLVRGR-K([2-[2-[2-[[2-[2-(2-[[(4S)-4-carboxy-4-[[4-[(19-carboxynona-decanoylamino)methyl]cyclohexanecarbonyl]amino]butanoyl]amino]ethoxy]ethoxy]acetyl]amino]ethoxy]ethoxy]acetyl])-GGGGEASELSTAALGRLSAELHELATLPRTETGSGSP-amide

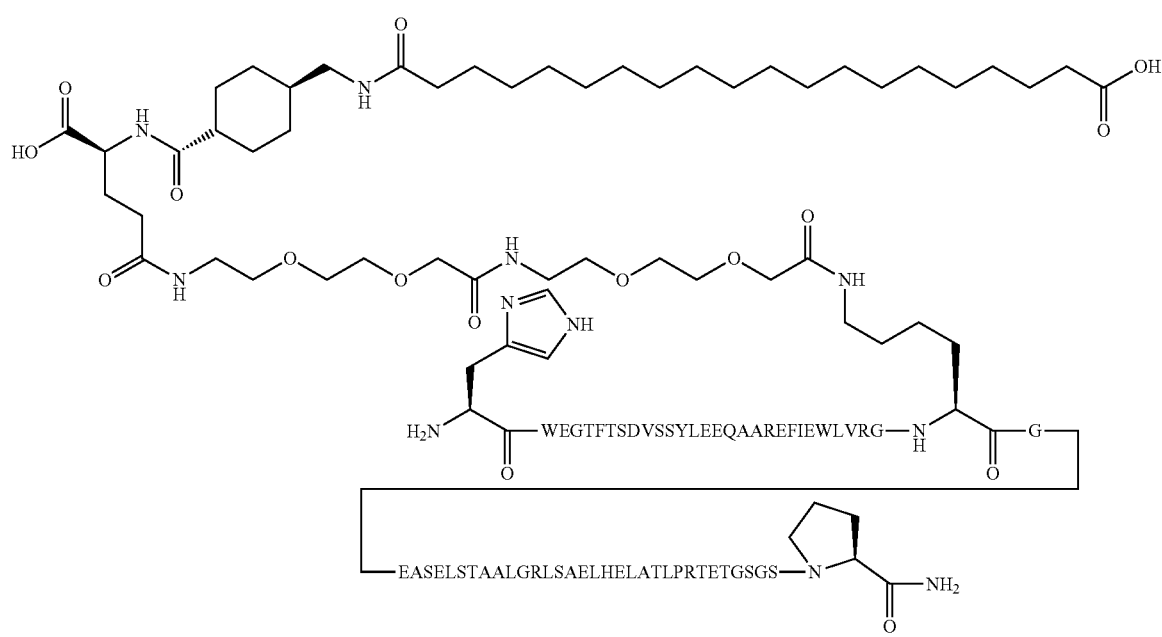

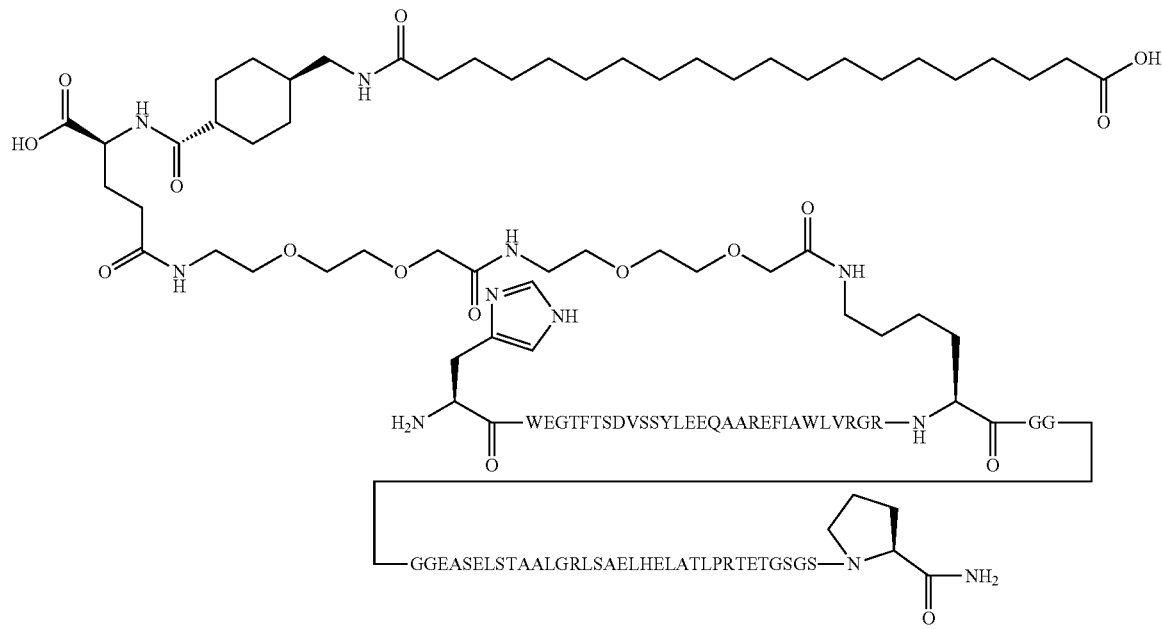

$C_{360}H_{570}N_{96}O_{117}$
Molecular weight (average) calculated: 8114.9508 g/mol
mono isotopic mass: 8110.1604 g/mol
LCMS_ZQ: found (M+5H)$^{5+}$1624.0 (most abundant)
The amino acid sequence of HWEGTFTSDVSSYLE-EQAAREFIAWLVRGRKGGGGEASELSTAALGRL-SAELHELATLPRTETGSGSP has SEQ ID NO: 185.

Compound 0269
HWEGTFTSDVSSYLEEQAAREFIEWLVRGR-K([2-[2-[2-[[2-[2-[2-[[(4S)-4-carboxy-4-[[4-[(19-carboxynona-decanoylamino)methyl]cyclohexanecarbonyl]amino]bu-tanoyl]amino]ethoxy]ethoxy]acetyl]amino]ethoxy]ethoxy]acetyl])-GGGGEASELSTAALGRLSAELHELATLPRTETGSGSP-amide

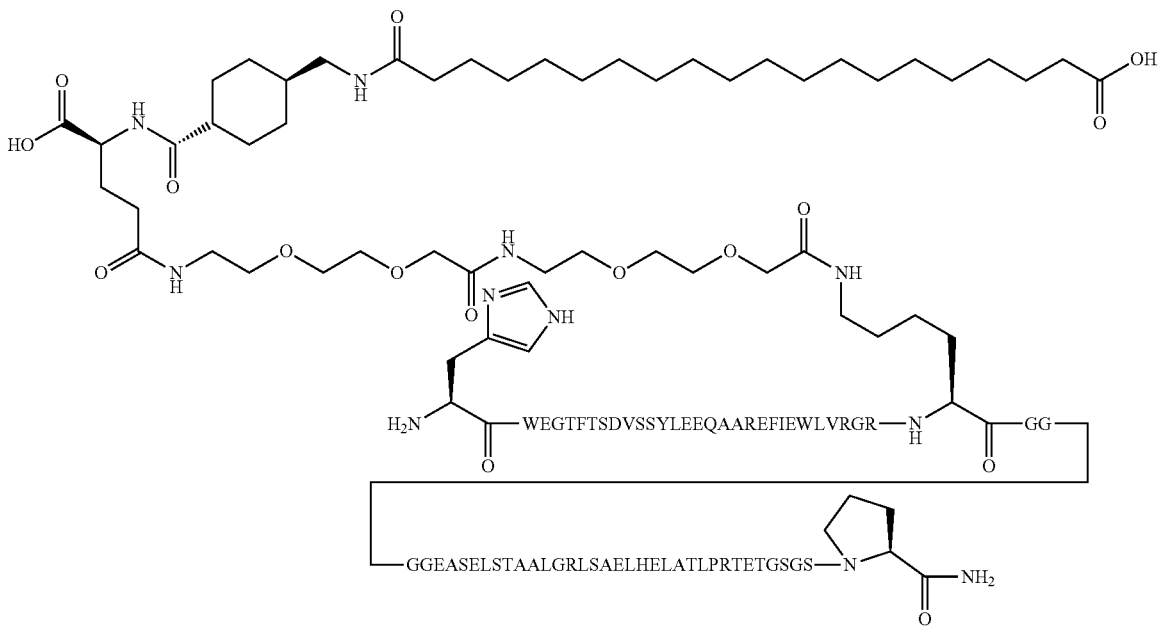

-continued

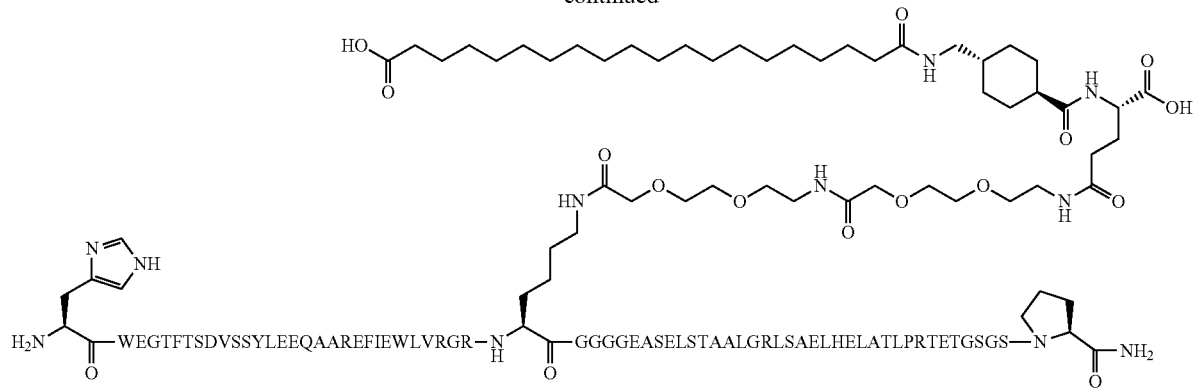

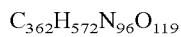

$C_{362}H_{572}N_{96}O_{119}$
Molecular weight (average) calculated: 8172.9869 g/mol
mono isotopic mass: 8168.1658 g/mol
LCMS_ZQ: found $(M+5H)^{5+}$ 1634.5 (mono isotopic)
The amino acid sequence of HWEGTFTSDVSSYLE-EQAAREFIEWLVRGRKGGGGEASELSTAALGRL-SAELHELATLPRTETGSGSP has SEQ ID NO: 186.
Compound 0270
HWEGTFTSDVSSYLEE-K([2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]-AAREFIEWLVRGRGEASELSTAALGRLSAELHELATL-PRTETGSGSP-amide

$C_{351}H_{555}N_{91}O_{114}$
Molecular weight (average) calculated: 7873.7037 g/mol
mono isotopic mass: 7869.0429 g/mol
LCMS_ZQ: found $(M+5H)^{5+}$ 1575.4 (most abundant)
The amino acid sequence of HWEGTFTSDVSSYLEE-KAAREFIEWLVRGRGEASELSTAALGRLSAEL-HELATLPRTETGSGSP has SEQ ID NO: 187.
Compound 0271
HWEGTFTSDVSSYLEE-K([2-[2-[2-[[2-[2-[2-[(4S)-4-carboxy-4-(17-carboxyheptadecanoylamino)butanoyl]amino]ethoxy]ethoxy]acetyl]amino]ethoxy]ethoxy]acetyl])-AAREFIEWLVRGRGEASELSTAALGRLSAELHELATL-PRTETGSGSP-amide

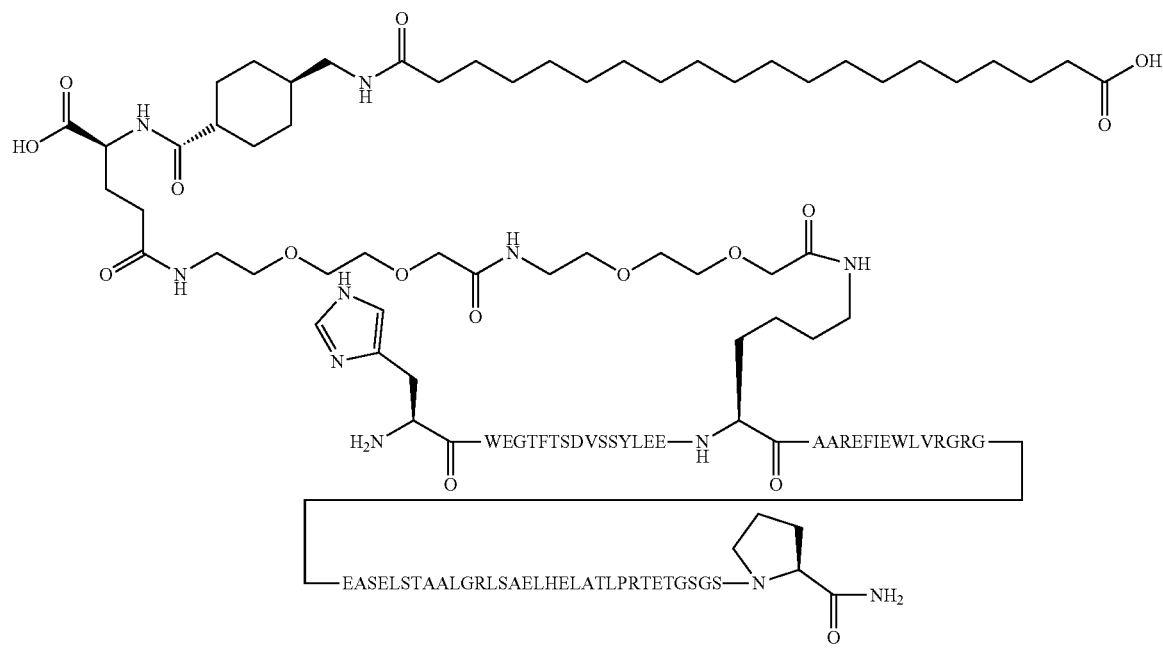

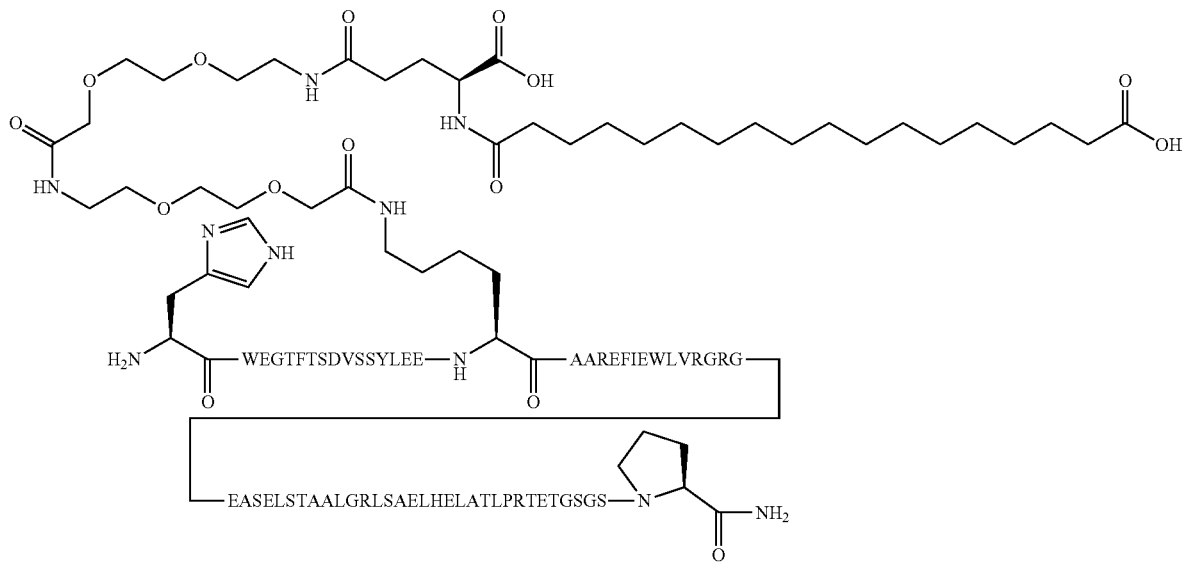

$C_{341}H_{538}N_{90}O_{113}$
Molecular weight (average) calculated: 7706.4556 g/mol
mono isotopic mass: 7701.9119 g/mol
LCMS_ZQ: found $(M+5H)^{5+}$ 1542.27 (most abundant)
The amino acid sequence of HWEGTFTSDVSSYLEE-KAAREFIEWLVRGRGEASELSTAALGRLSAEL-HELATLPRTETGSGSP has SEQ ID NO: 187.
Compound 0272
HWEGTFTSD-K([2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl])-SSYLEEQAAREFIEWLVRGRGEASELSTAALGR-LSAELHELATLPRTETGSGSP-amide $C_{351}H_{554}N_{92}O_{115}$
Molecular weight (average) calculated: 7902.7019 g/mol
mono isotopic mass: 7898.0330 g/mol
LCMS_ZQ: found $(M+5H)^{5+}$1581.4 (most abundant)
The amino acid sequence of HWEGTFTSDKSSYLE-EQAAREFIEWLVRGRGEASELSTAALGRLSAEL-HELATLPRTETGSGSP has SEQ ID NO: 188.
Compound 0273
HWEGTFTSD-K([2-[2-[2-[2-[2-[2-[[(4S)-4-carboxy-4-(17-carboxyheptadecanoylamino)butanoyl]amino]ethoxy]ethoxy]acetyl]aminoethoxy]ethoxy]acetyl])-SSYLE-EQAAREFIEWLVRGRGEASELSTAALGRLS-AELHELATLPRTETGSGSP-amide

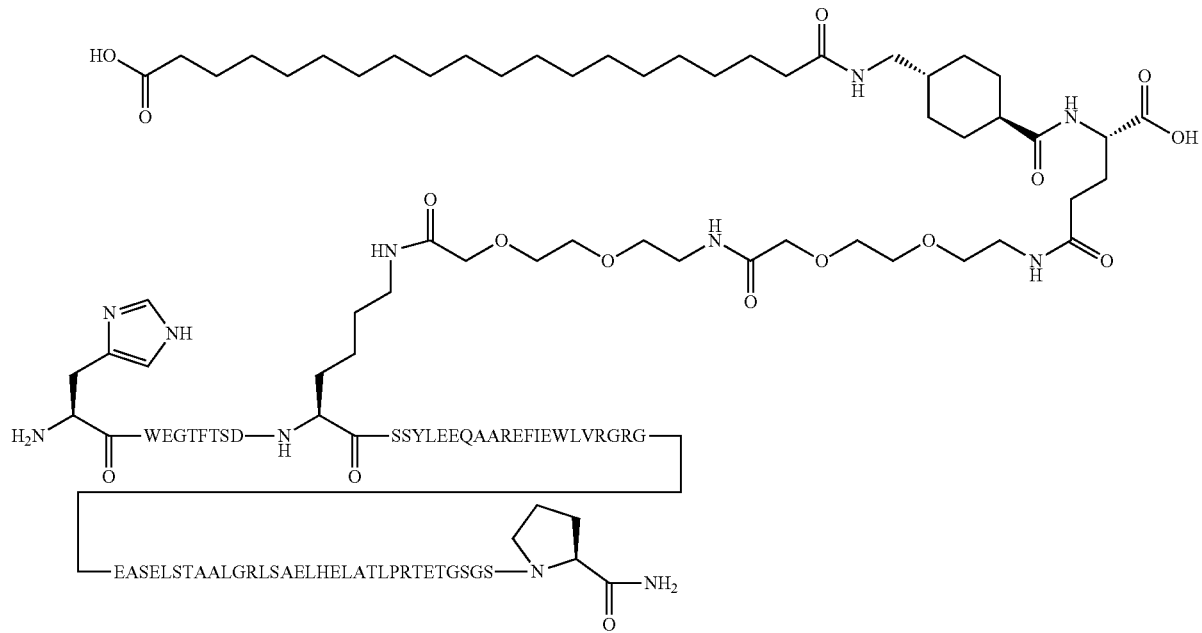

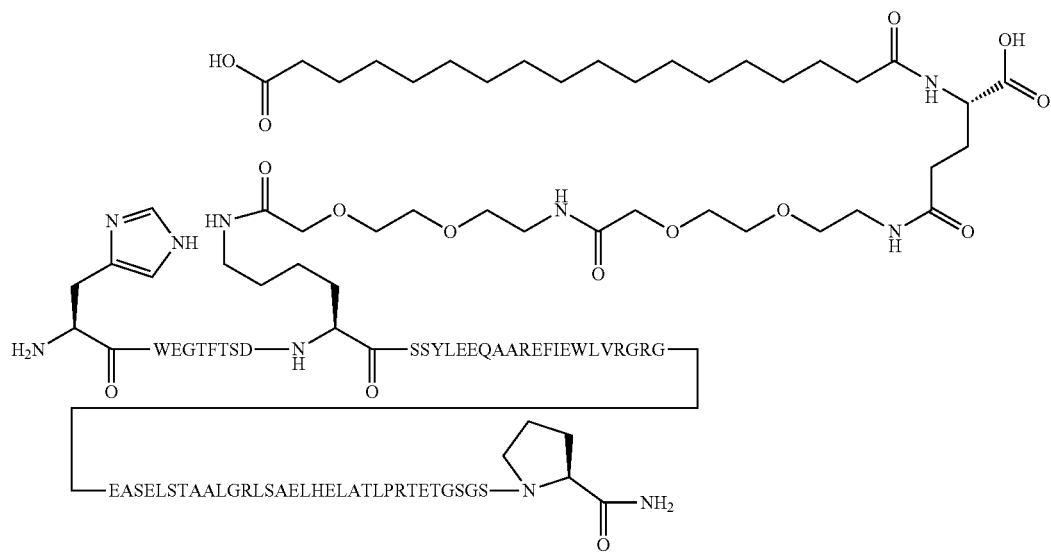

$C_{341}H_{537}N_{91}O_{114}$
Molecular weight (average) calculated: 7735.4538 g/mol
mono isotopic mass: 7730.9020 g/mol
LCMS_ZQ: found $(M+5H)^{5+}$ 1547.9 (most abundant)
The amino acid sequence of HWEGTFTSDKSSYLE-EQAAREFIEWLVRGRGEASELSTAALGRLSAEL-HELATLPRTETGSGSP has SEQ ID NO: 188.
Compound 0280
H-Aib-EGTFTSDVSSYLEEQAAREFIAWLVRG-K([2-[2-[2-[2-[2-[2-[[(4S)-4-carboxy-4-(15-carboxypentade-canoylamino)butanoyl]amino]ethoxy]ethoxy]acetyl]amino]ethoxy]ethoxy]acetyl])-GGGGGEASELSTAALGRLSAELH-K([2-[2-[2-[[2-[2-[2-[(4S)-4-carboxy-4-(15-carboxypentadecanoylamino)butanoyl]amino]ethoxy]ethoxy]acetyl]amino]ethoxy]ethoxy]acetyl])-LATLPRTETGSGSP-amide

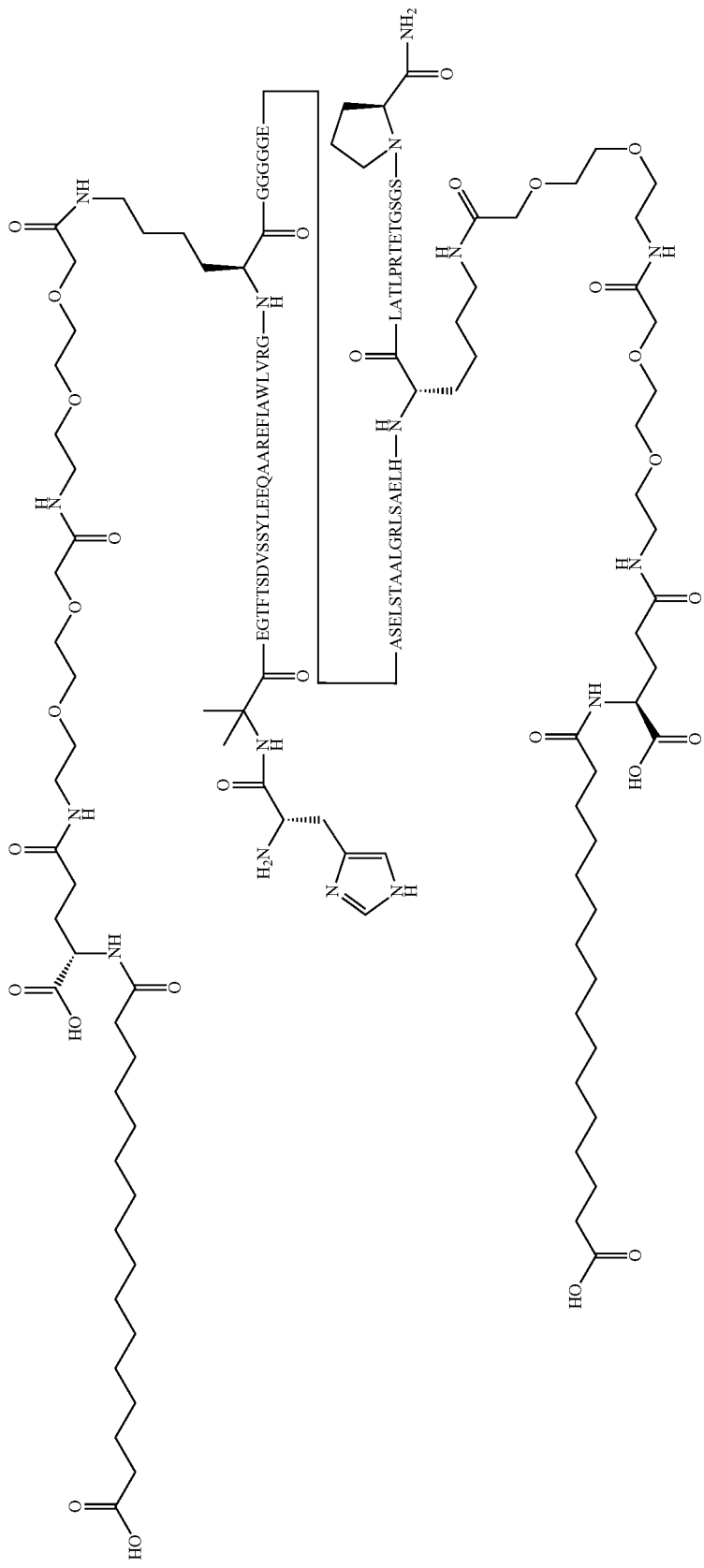

$C_{371}H_{599}N_{95}O_{126}$
Molecular weight (average) calculated: 8406.2867 g/mol
mono isotopic mass: 8401.3384 g/mol
LCMS34: found $(M+5H)^{5+}1682.1$ (most abundant)
The amino acid sequence of HXEGTFTSDVSSYLE-EQAAREFIAWLVRGKGGGGGEASELSTAALGRL-SAELHKLATLPRTETGSGSP has SEQ ID NO: 189.

Compound 0281

H-Aib-EGTFTSDVSSYLEEQAAREFIAWLVRG-K([2-[2-[2-[2-[2-[2-[[(4S)-4-caboxy-4-(15-carboxypentade-canoylamino)butanoyl]amino]ethoxy]ethoxy]acetyl]amino]ethoxy]ethoxy]acetyl])-GGGGGEASELSTAALGRLSAELHEL-K([2-[2-[2-Q[2-[2-[2-f[(4S)-4-carboxy-4-(15-carboxypentadecanoylamino)butanoyl]amino]ethoxy]ethoxy]acetyl]amino]ethoxy]ethoxy]acetyl])-TLPRTETGSGSP-amide

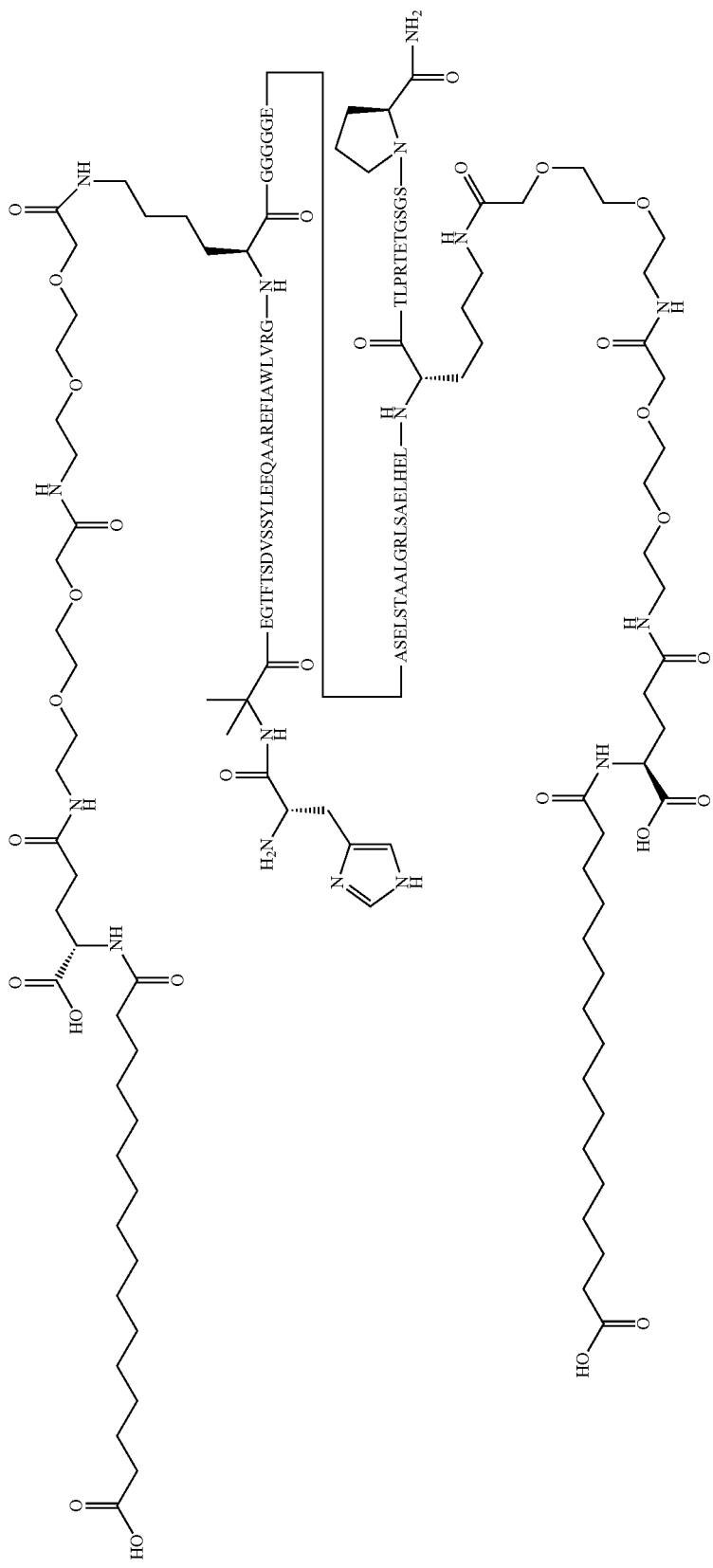

$C_{373}H_{601}N_{95}O_{128}$
Molecular weight (average) calculated: 8464.3227 g/mol
mono isotopic mass: 8459.3439 g/mol
LCMS34: found $(M+5H)^{5+}$1693.7 (most abundant)

The amino acid sequence of HXEGTFTSDVSSYLE-EQAAREFIAWLVRGKGGGGGEASELSTAALGRL-SAELHELKTLPRTETGSGSP has SEQ ID NO: 190.

Compound 0284

H-Aib-EGTFTSDVSSYLEEQAAREFIAWLVRG-K([2-[2-[2-[2-[2-[2-[(4S)-4-carboxy-4-(15-carboxypentade-canoylamino)butanoyl]amino]ethoxy]ethoxy]acetyl]amino]ethoxy]ethoxy]acetyl])-GGGGGEASELSTAALGRLSAELHELATL-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-RTETGSGSP-amide

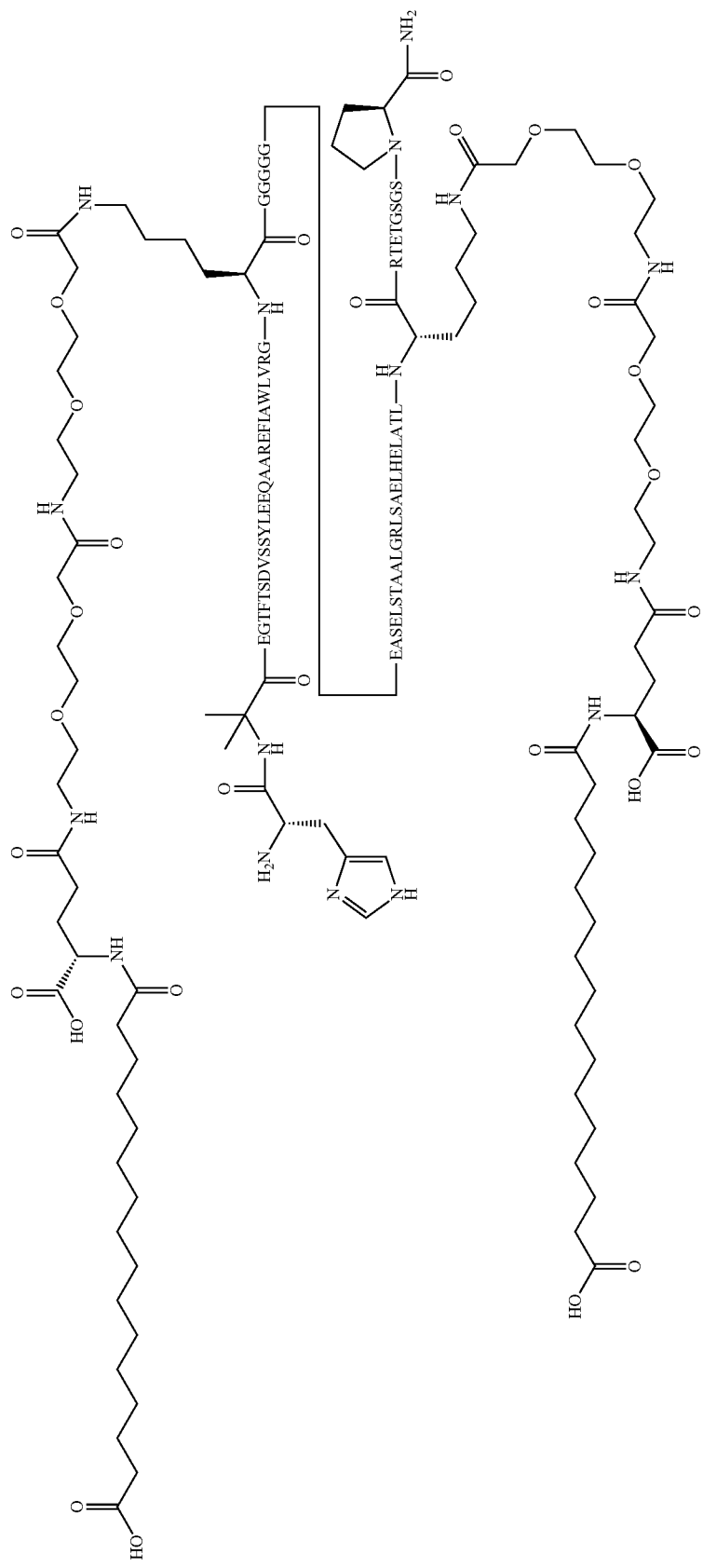

$C_{371}H_{599}N_{95}O_{128}$

Molecular weight (average) calculated: 8438.2855 g/mol mono isotopic mass: 8433.3283 g/mol LCMS34: found $(M+5H)^{5+}$ 1688.7 (most abundant)

The amino acid sequence of HXEGTFTSDVSSYLE-EQAAREFIAWLVRGKGGGGGEASELSTAALGRL-SAELHELATLKRTETGSGSP has SEQ ID NO: 191.

Compound 0285

H-Aib-EGTFTSDVSSYLEEQAAREFIAWLVRG-K([2-[2-[2-[[2-[2-[2-[[(4S)-4-carboxy-4-(15-carboxypentade-canoylamino)butanoyl]amino]ethoxy]ethoxy]acetyl]amino]ethoxy]ethoxy]acetyl])-GGGGGEASELSTAALGRLSAELHELATLPRTETG-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-GSP-amide

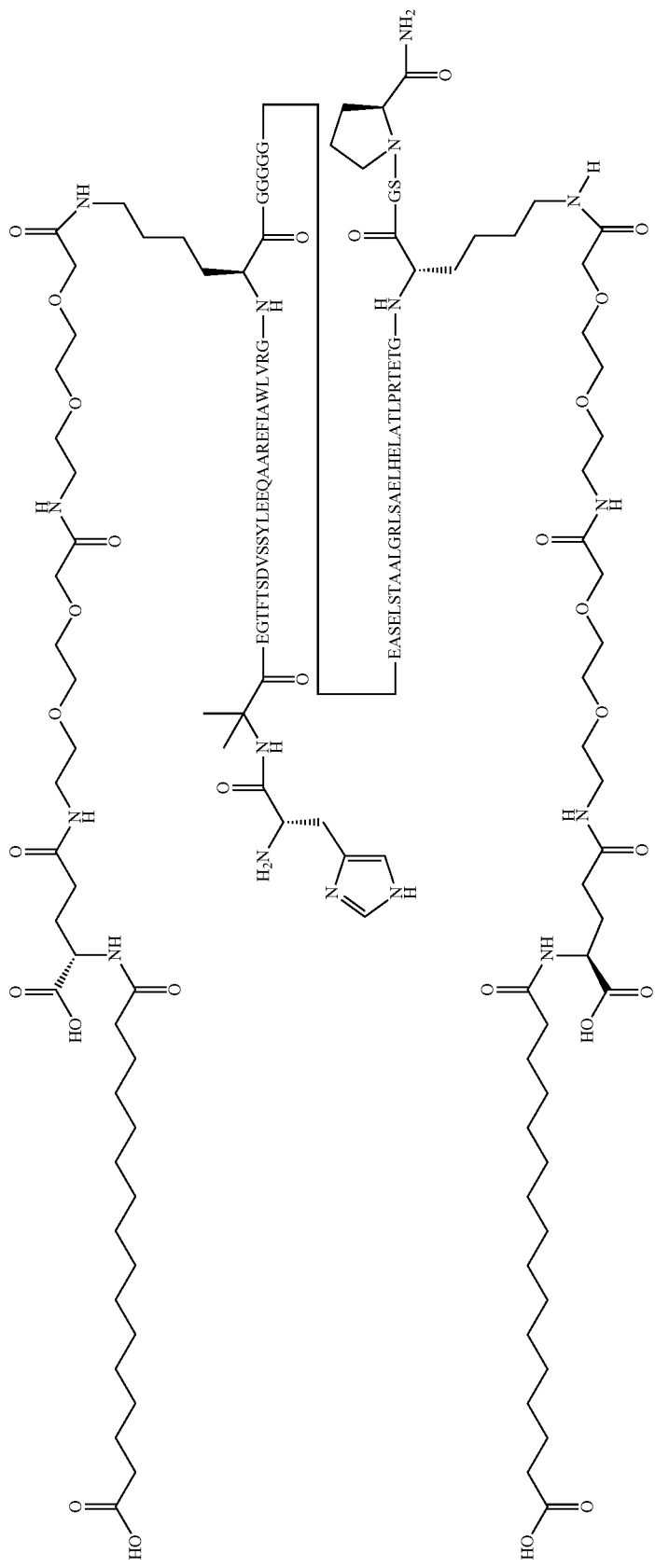

$C_{373}H_{601}N_{95}O_{127}$
Molecular weight (average) calculated: 8448.3233 g/mol
mono isotopic mass: 8443.3490 g/mol
LCMS34: found $(M+5H)^{5+}$1690.7 (most abundant)
The amino acid sequence of HXEGTFTSDVSSYLE-EQAAREFIAWLVRGKGGGGGEASELSTAALGRL-SAELHELATLPRTETGKGSP has SEQ ID NO: 192.

Compound 0292

H-Aib-EGTFTSD-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-SSYLEEQAAREFIAWLVRGRGGGGGASELSTAALGRLS-K([2-[2-[2-[2-[2-[2-[(4S)-4-carboxy-4-(15-carboxypentadecanoylamino)butanoyl]amino]ethoxy]ethoxy]acetyl]amino]ethoxy]ethoxy]acetyl])-ELHELATLPRTETGSS-amide

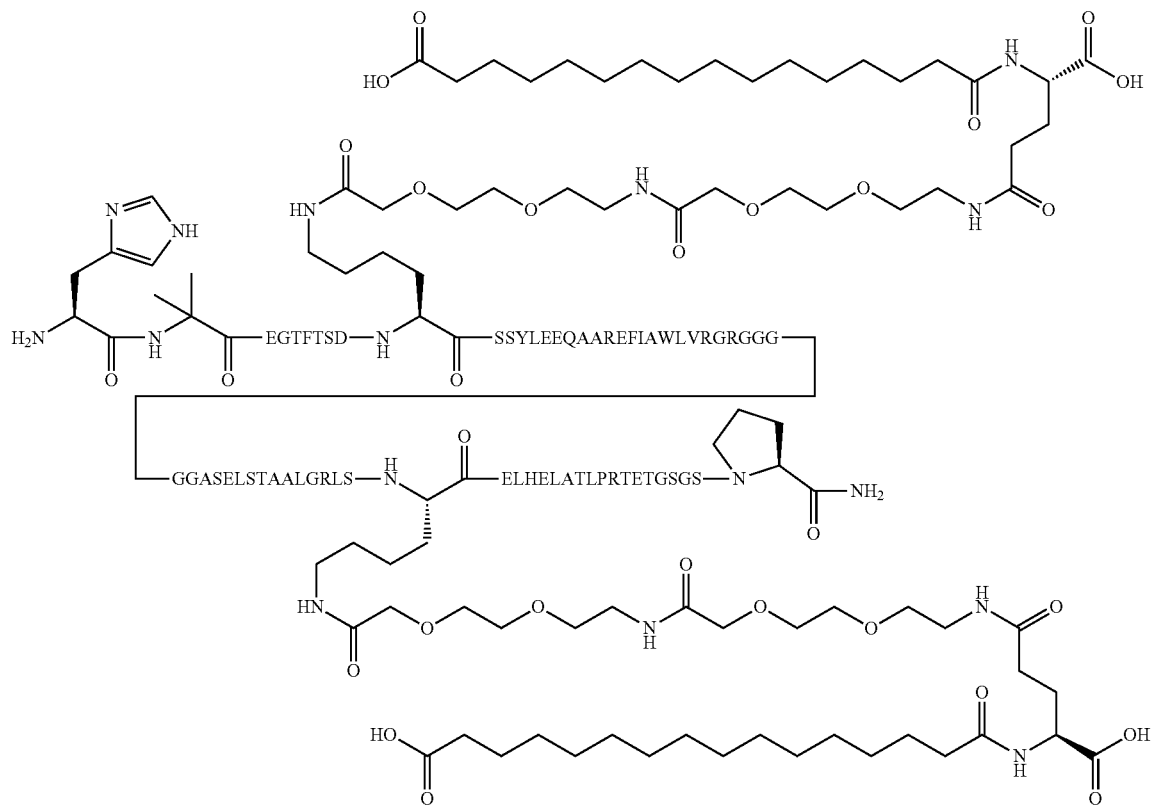

$C_{369}H_{597}N_{97}O_{125}$
Molecular weight (average) calculated: 8392.2634 g/mol
mono isotopic mass: 8387.3340 g/mol
LCMS34: found $(M+5H)^{5+}$1679.24 (most abundant)
The amino acid sequence of HXEGTFTSDKSSYLE-EQAAREFIAWLVRGRGGGGGASELSTAALGRLSKEL-HELATLPRTETGSGSP has SEQ ID NO: 193.

Compound 0294

H-Aib-EGTFTSDVSSYLE-K([2-[2-[2-[[2-[2-[2-[(4S)-4-carboxy-4-(15-carboxypentadecanoylamino)butanoyl]amino]ethoxy]ethoxy]acetyl]amino]ethoxy]ethoxy]acetyl])-QAAREFIAWLVRGRGGGGGASELSTAALGRLS-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-ELHELATLPRTETGSGSP-amide

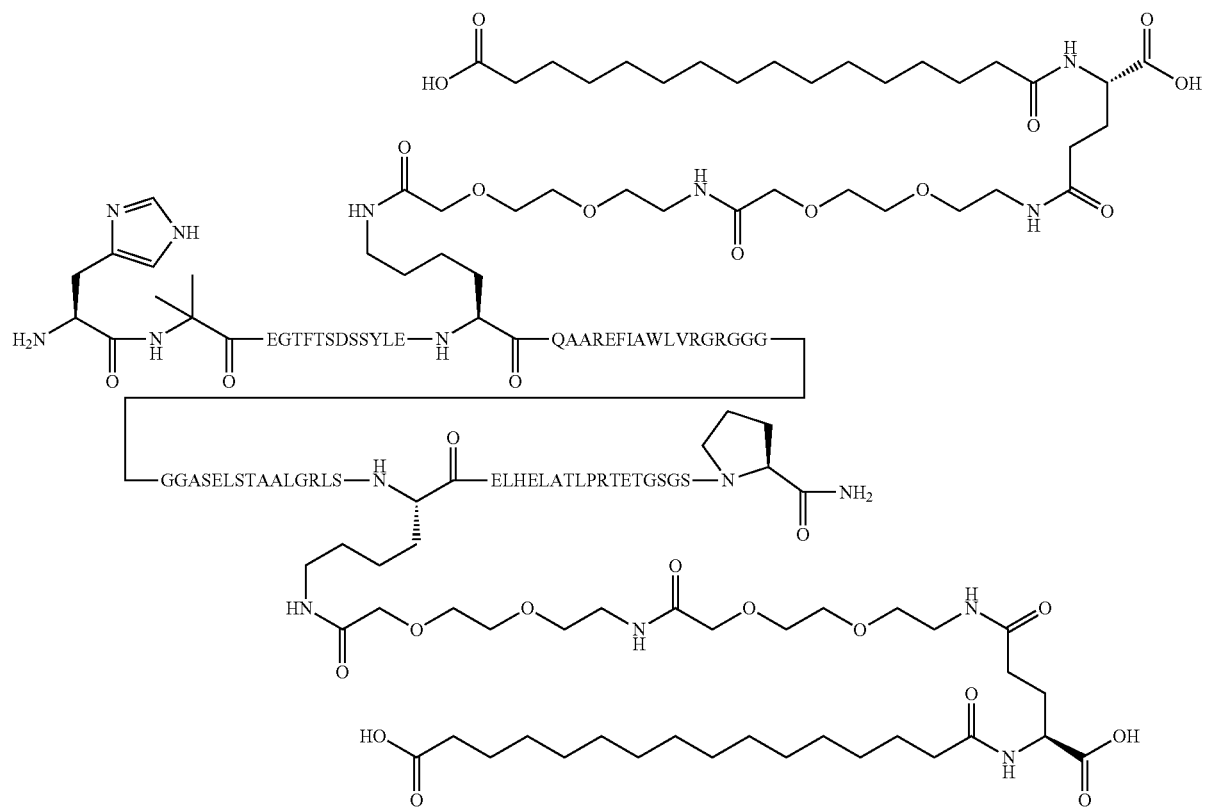

$C_{369}H_{599}N_{97}O_{123}$

Molecular weight (average) calculated: 8362.2805 g/mol mono isotopic mass: 8357.3598 g/mol LCMS34: found (M+5H)$^{5+}$1673.26 (most abundant)

The amino acid sequence of HXEGTFTSDVS-SYLEKOAAREFIAWLVRGRGGGGGASELSTAAL-GRLSKELHELATLPRTETGSGSP has SEQ ID NO: 194.

Compound 0295

H-Aib-EGTFTSDVSSYLEE-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-AAREFIAWLVRGRGGGGGASELSTAALGRLS-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-ELHELATLPRTETGSGSP-amide

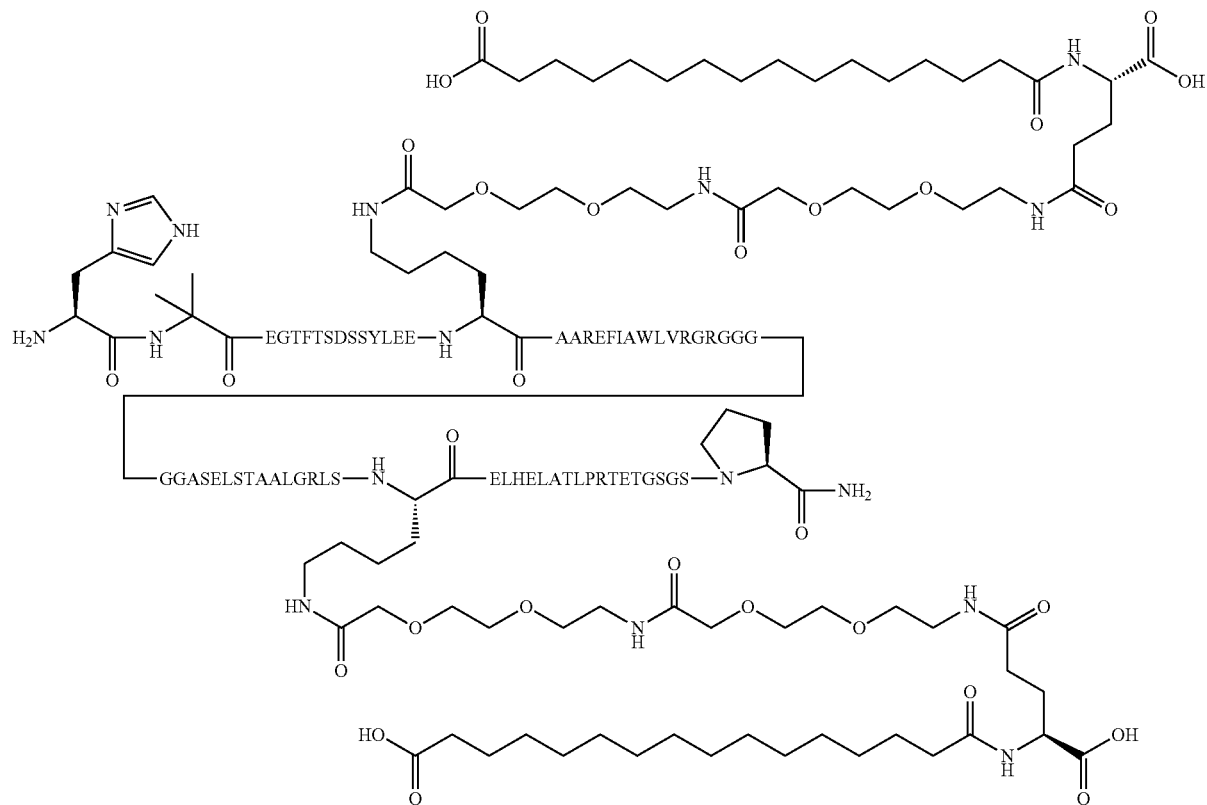

$C_{369}H_{598}N_{96}O_{124}$

Molecular weight (average) calculated: 8363.2652 g/mol mono isotopic mass: 8358.3439 g/mol LCMS34: found $(M+5H)^{5+}$ 1673.65 (most abundant)

The amino acid sequence of HXEGTFTSDVSSYLEE-KAAREFIAWLVRGRGGGGGASELSTAALGRLSKEL-HELATLPRTETGSGSP has SEQ ID NO: 195.

Compound 0296

H-Aib-EGTFTSDVSSYLEEQAAR-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-FIAWLVRGRGGGGGASELSTAALGRLS-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-ELHELATLPRTETGSGSP-amide

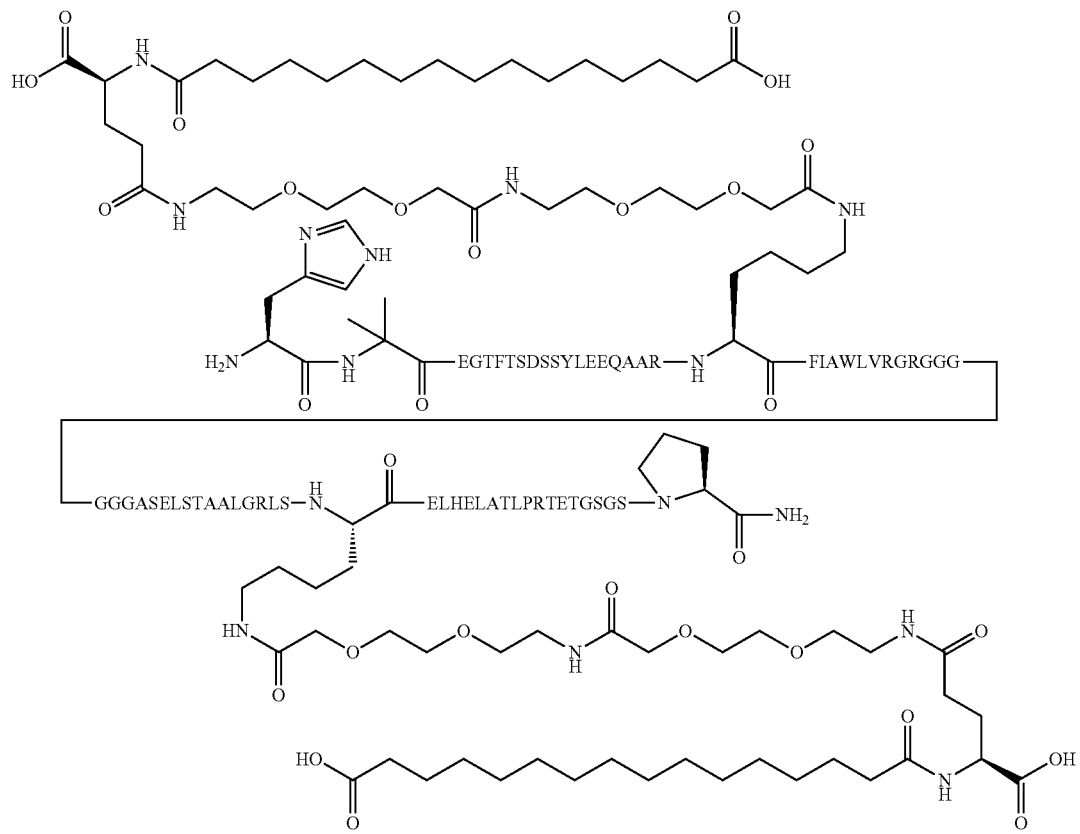

$C_{369}H_{599}N_{97}O_{123}$

Molecular weight (average) calculated: 8362.2805 g/mol mono isotopic mass: 8357.3598 g/mol LCMS34: found $(M+5H)^{5+}1673.46$ (most abundant)

The amino acid sequence of HXEGTFTSDVSSYLE-EQAARKFIAWLVRGRGGGGASELSTAALGRL-SKELHELATLPRTETGSGSP has SEQ ID NO: 196.

Compound 0297

H-Aib-EGTFTSDVSSYLEEQAAREFIAWLVR-K([2-[2-[2-[[2-[2-[2-[[(4S)-4-carboxy-4-(15-carboxypentade-canoylamino)butanoyl]amino]ethoxy]ethoxy]acetyl]amino]ethoxy]ethoxy]acetyl])-RGGGGGASELSTAALGRLS-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-ELHELATLPRTETGSGSP-amide

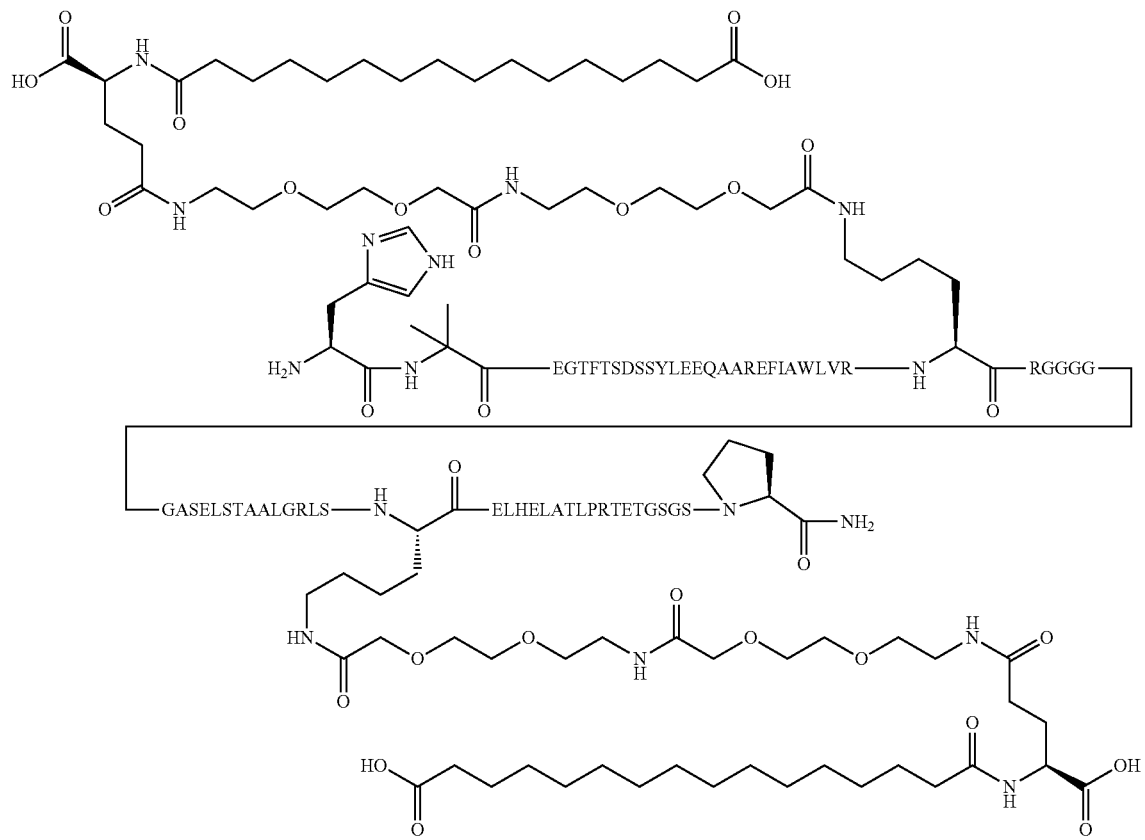

$C_{372}H_{603}N_{97}O_{125}$

Molecular weight (average) calculated: 8434.3431 g/mol mono isotopic mass: 8429.3810 g/mol LCMS34: found (M+5H)$^{5+}$1687.87 (most abundant)

The amino acid sequence of HXEGTFTSDVSSYLE-EQAAREFIAWLVRKRGGGGGASELSTAALGRLSKEL-HELATLPRTETGSGSP has SEQ ID NO: 197.

Compound 0299

H-Aib-EGTFTSDVSSYLEE-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-AAREFIAWLVRGRGGGGGEASELSTAALGRLSAELH-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-LATLPRTETGSGSP-amide

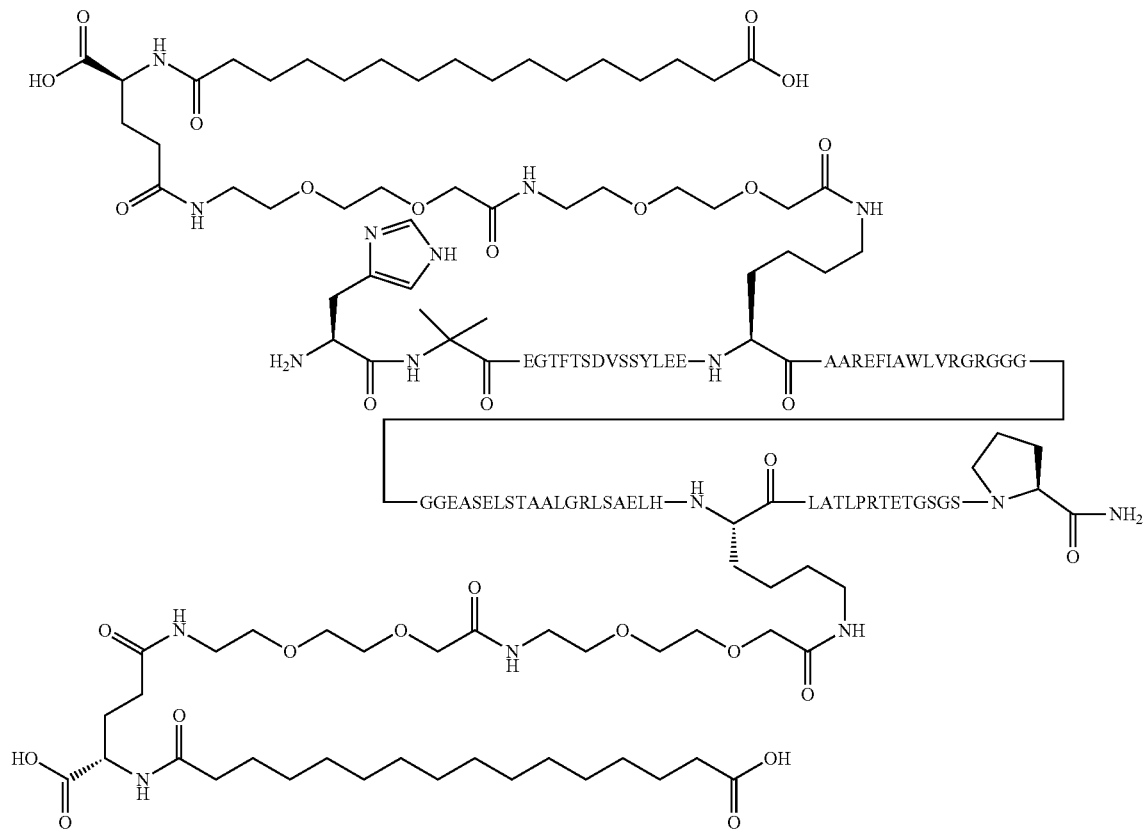

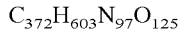

$C_{372}H_{603}N_{97}O_{125}$

Molecular weight (average) calculated: 8434.3431 g/mol mono isotopic mass: 8429.3810 g/mol LCMS34: found $(M+5H)^{5+}$1688 (most abundant)

The amino acid sequence of HXEGTFTSDVSSYLEE-KAAREFIAWLVRGRGGGGEASELSTAALGRLSAEL-HKLATLPRTETGSGSP has SEQ ID NO: 198.

Compound 0396

H-Aib-EGTFTSDVSSYLEE-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-AAREFIAWLVRGRGGGGEASELSTAALGRLSAELHEL-K([2-[2-[2-[[2-[2-[2-[(4S)-4-carboxy-4-(15-carboxypentadecanoylamino)butanoyl]amino]ethoxy]ethoxy]acetyl]amino]ethoxy]ethoxy]acetyl])-TLPRTETGSGSP-amide

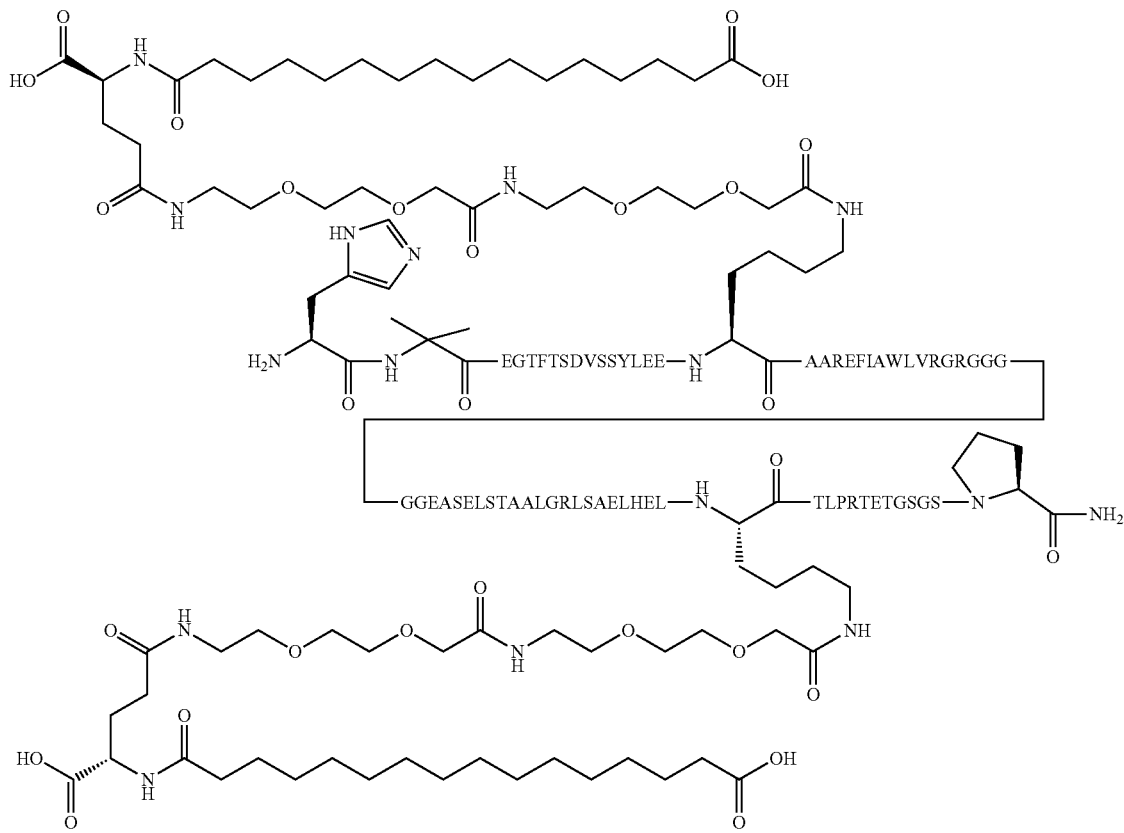

$C_{374}H_{605}N_{97}O_{127}$

Molecular weight (average) calculated: 8492.3792 g/mol
mono isotopic mass: 8487.3865 g/mol
LCMS34: found $(M+5H)^{5+}1699$ (most abundant)

The amino acid sequence of HXEGTFTSDVSSYLEE-KAAREFIAWLVRGRGGGGEASELSTAALGRLSAEL-HELKTLPRTETGSGSP has SEQ ID NO: 199.

Compound 0397

H-Aib-EGTFTSDVSSYLEE-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-AAREFIAWLVRGRGGGGEASELSTAALGRL-SAELHELATL-K([2-[2-[2-[[2-[2-[2-[[(4S)-4-carboxy-4-(15-carboxypentadecanoylamino)butanoyl]amino]ethoxyethoxyhacetyl]amino]ethoxy]ethoxy]acetyl])-RTETGSGSP-amide

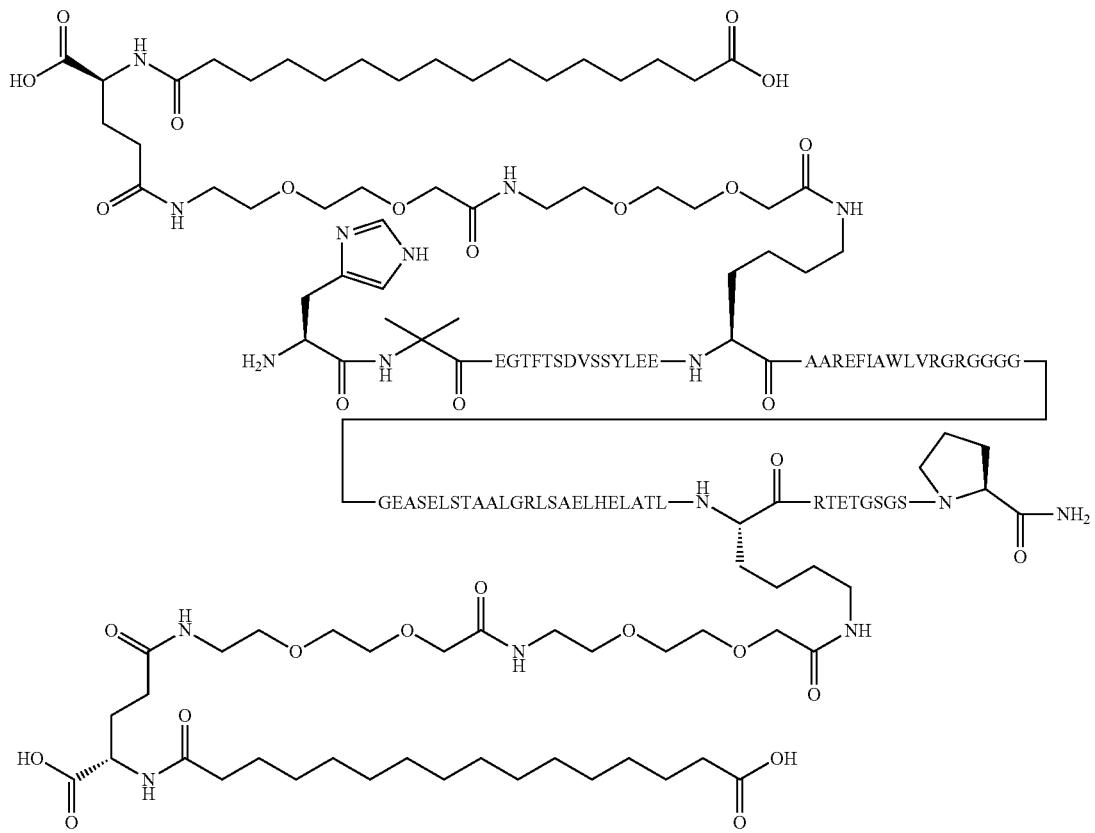

$C_{372}H_{603}N_{97}O_{127}$

Molecular weight (average) calculated: 8466.3419 g/mol mono isotopic mass: 8461.3708 g/mol LCMS34: found $(M+5H)^{5+}$ 1694 (most abundant)

The amino acid sequence of HXEGTFTSDVSSYLEE-KAAREFIAWLVRGRGGGGGEASELSTAALGRLSAEL-HELATLKRTETGSGSP has SEQ ID NO: 200.

Compound 0411

H-Aib-EGTFTSDVSSYLEE-K([2-[2-[2-[[2-[2-[2-[[(4S)-4-carboxy-4-(15-carboxypentadecanoylamino)bu-tanoyl]amino]ethoxy]ethoxy]acetyl]amino)ethoxy]ethoxy]acetyl])-AAREFIAWLVRGRGGGGGEASELSTAALGRLS-AELHELATLPRTETG-K([2-[2-[2-[[2-[2-[2-[[(4S)-4-carboxy-4-(15-carboxypentadecanoyvamino)butanoyl]amino]ethoxy]ethoxy]acetyl]amino]ethoxy]ethoxy]acetyl])-GSP-amide

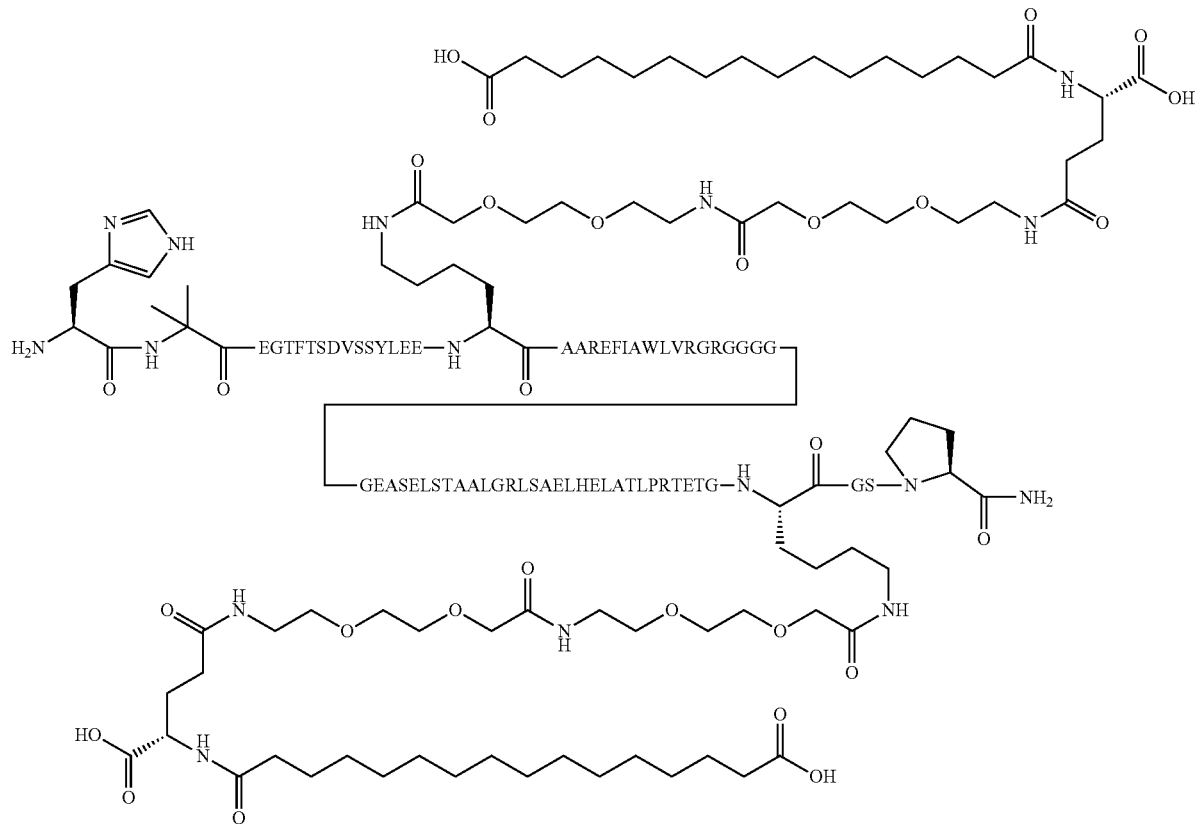

$C_{374}H_{605}N_{97}O_{126}$

Molecular weight (average) calculated: 8476.3798 g/mol mono isotopic mass: 8471.3915 g/mol LCMS34: found $(M+5H)^{5+}$ 1696 (most abundant)

The amino acid sequence of HXEGTFTSDVSSYLEE-KAAREFIAWLVRGRGGGGGEASELSTAALGRLSAEL-HELATLPRTETGKGSP has SEQ ID NO: 201.

Compound 0414

HAEGTFTSDVSSYLEE-K([2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl])-AAREFIEWLVRGRGEASELSTAALGRLSAELHELATL-PRTETGSGSP-amide

233

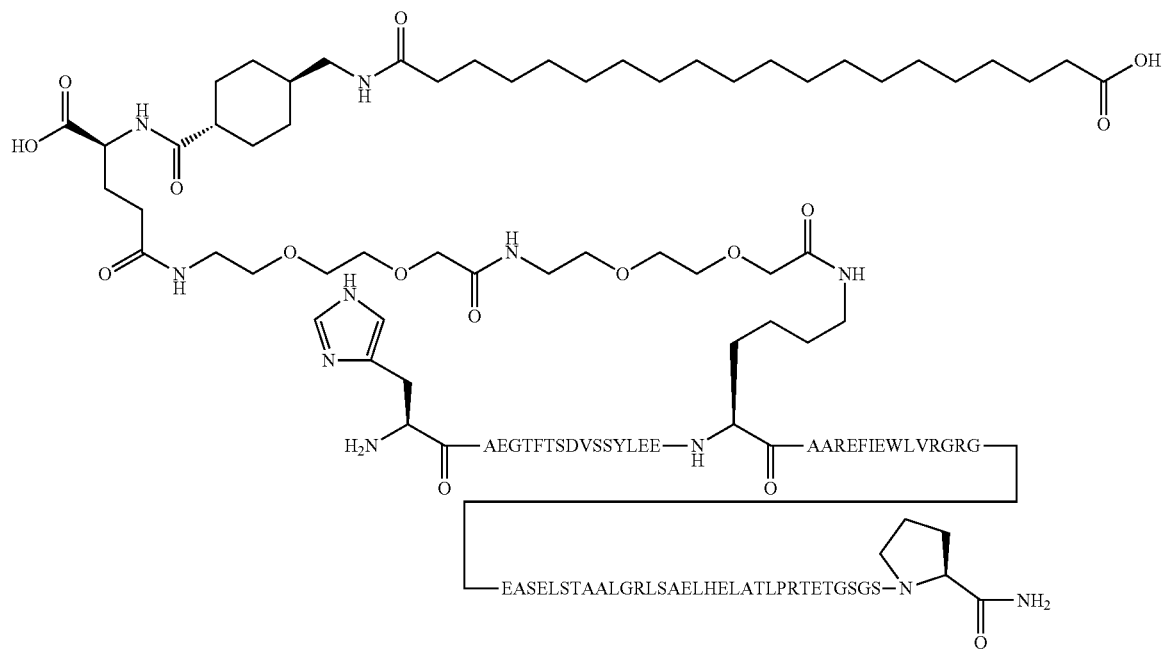

$C_{383}H_{619}N_{99}O_{130}$
Molecular weight (average) calculated: 7758.5717 g/mol
mono isotopic mass: 7754.0007 g/mol
LCMS34: found (M+5H)$^{5+}$1551.88 (mono isotopic)
The amino acid sequence of HAEGTFTSDVSSYLEE-KAAREFIEWLVRGRGEASELSTAALGRLSAEL-HELATLPRTETGSGSP has SEQ ID NO: 202.

234

Compound 0415
H-Aib-EGTFTSDVSSYLEE-K([2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl])-AAREFIEWLVRGRGEASELSTAALGRLSAELHELATLPRTETGSGSP-amide

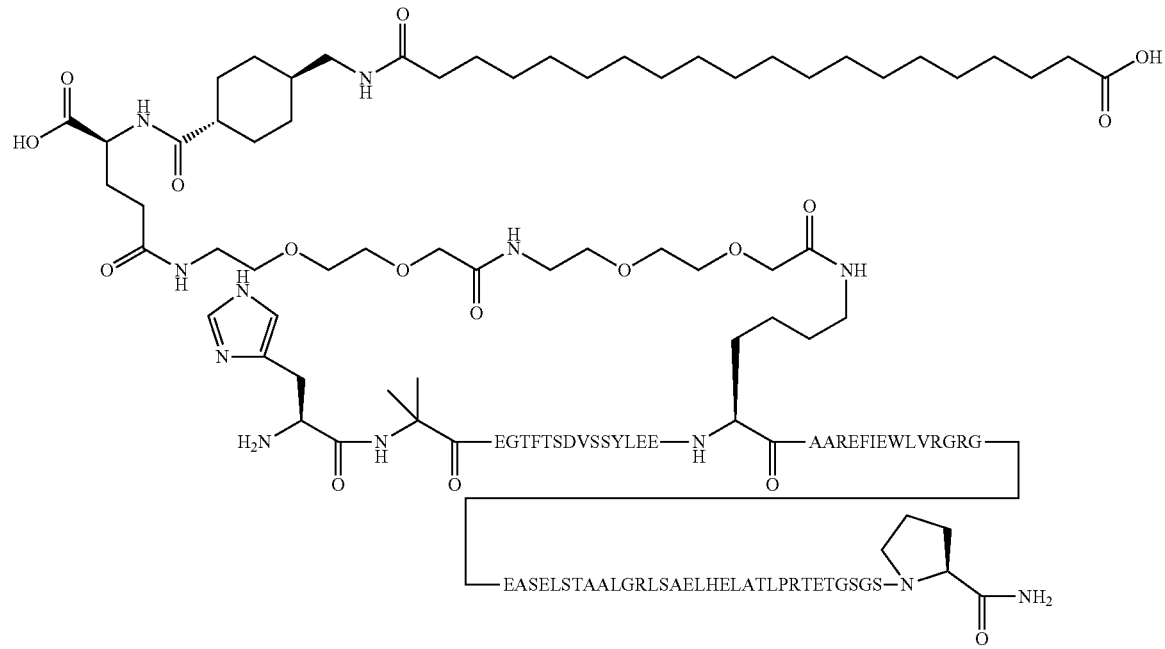

$C_{344}H_{552}N_{90}O_{114}$
Molecular weight (average) calculated: 7772.5983 g/mol
mono isotopic mass: 7768.0163 g/mol
LCMS34: found (M+5H)$^{5+}$ 1554.67 (mono isotopic)

The amino acid sequence of HXEGTFTSDVSSYLEE-KAAREFIEWLVRGRGEASELSTAALGRLSAEL-HELATLPRTETGSGSP has SEQ ID NO: 203.

Compound 0416

HAEGTFTS-K([2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl])-VSSYLEEQAAREFIEWLVRGRGEASELST-AALGRLSAELHELATLPRTETGSGSP-amide

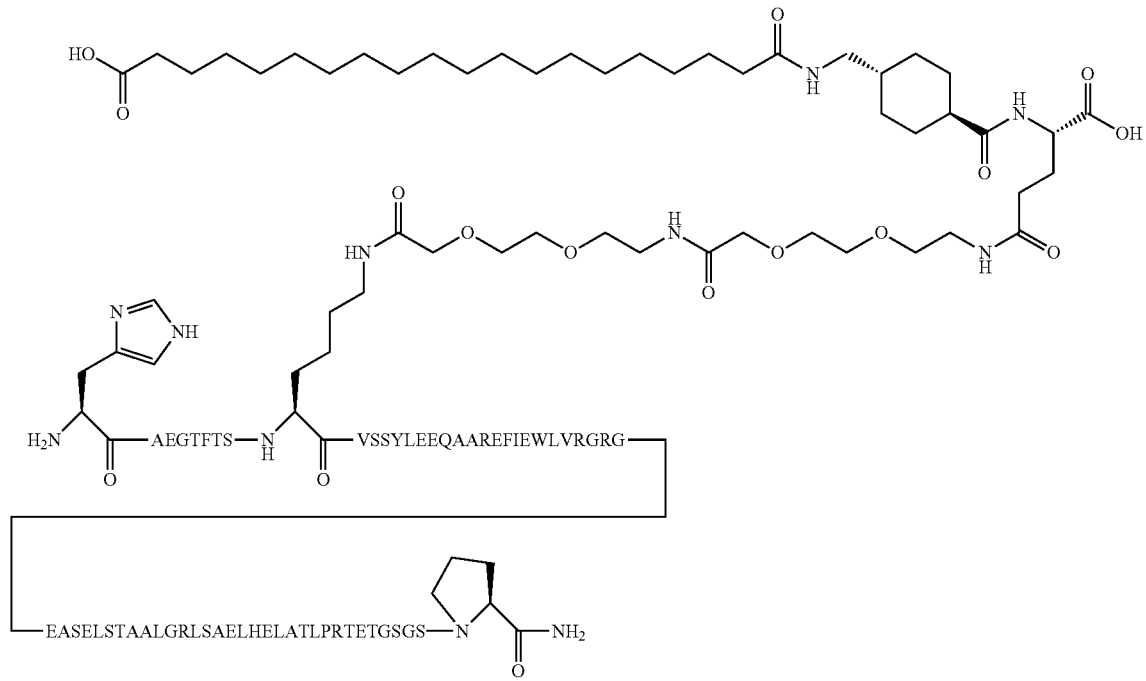

$C_{344}H_{553}N_{91}O_{113}$
Molecular weight (average) calculated: 7771.6135 g/mol
mono isotopic mass: 7767.0323 g/mol
LCMS_ZQ: found (M+5H)$^{5+}$1555.3 (most abundant)

The amino acid sequence of HAEGTFTSKVSSYLE-EQAAREFIEWLVRGRGEASELSTAALGRLSAEL-HELATLPRTETGSGSP has SEQ ID NO: 204.

Compound 0417

H-Aib-EGTFTS-K([2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]-VSSYLEEQAAREFIEWLVRGRGEASELSTAAL-GRLSAELHELATLPRTETGSGSP-amide

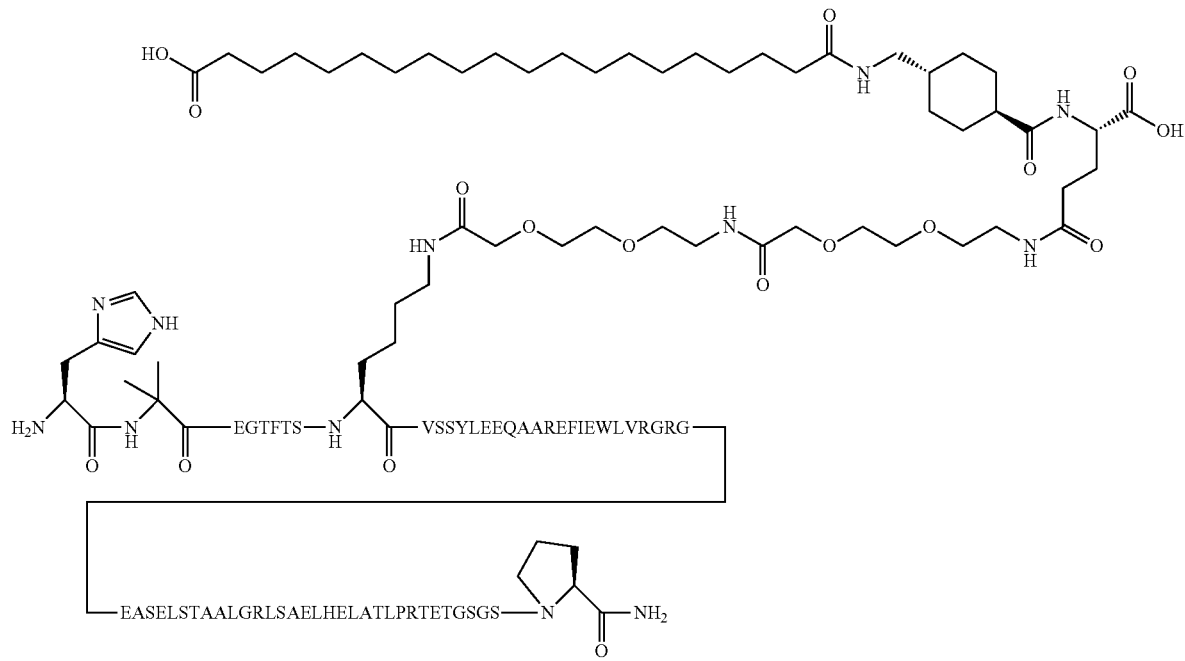

$C_{345}H_{555}N_{91}O_{113}$
Molecular weight (average) calculated: 7785.6401 g/mol
mono isotopic mass: 7781.0480 g/mol
LCMS_ZQ: found $(M+5H)^{5+}$ 1558.1 (most abundant)
The amino acid sequence of HXEGTFTSKVSSYLE-EQAAREFIEWLVRGRGEASELSTAALGRLSAEL-HELATLPRTETGSGSP has SEQ ID NO: 205.

Compound 0431
HAEGTFTSD-K([2-[2-[2-[[2-[2-[2-[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl])-SSYLEEQAAREFIEWLVRGRGEASELSTAALGRLSAEL-HELATLPRTETGSGSP-amide

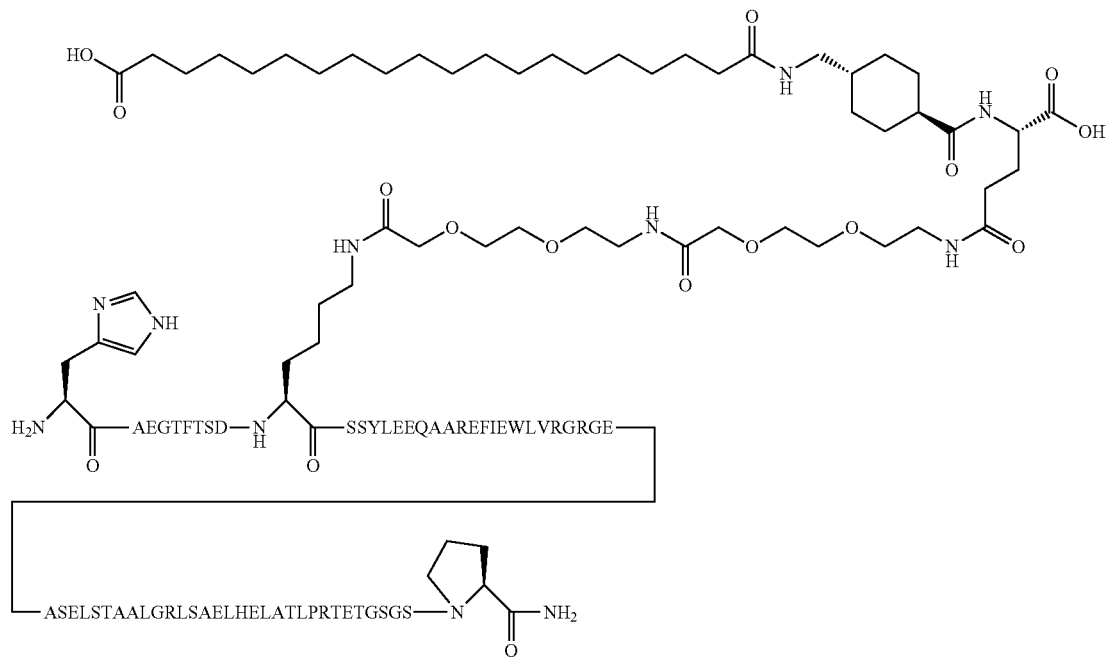

$C_{343}H_{549}N_{91}O_{115}$
Molecular weight (average) calculated: 7787.5699 g/mol
mono isotopic mass: 7782.9908 g/mol
LCMS_ZQ: found $(M+5H)^{5+}$ 1558.67 (most abundant)
The amino acid sequence of HAEGTFTSDKSSYLE-EQAAREFIEWLVRGRGEASELSTAALGRLSAEL-HELATLPRTETGSGSP has SEQ ID NO: 206.

Compound 0433

HWEGTFTSD-K([(2S)-2-amino-6-[[2-[2-[2-[[2-[2-[2-[[(4S)-4-carboxy-4-[[4-[(19-carboxynonadecanoylamino) methyl]cyclohexanecarbonyl]amino]butanoyl]amino] ethoxy]ethoxy]acetyl]amino]ethoxy]ethoxy]acetyl]amino] hex anoyl])-SSYLEEQAAREFIEWLVRGRGEASELSTAALGRL-SAELHELATLPRTETGSGSP-amide

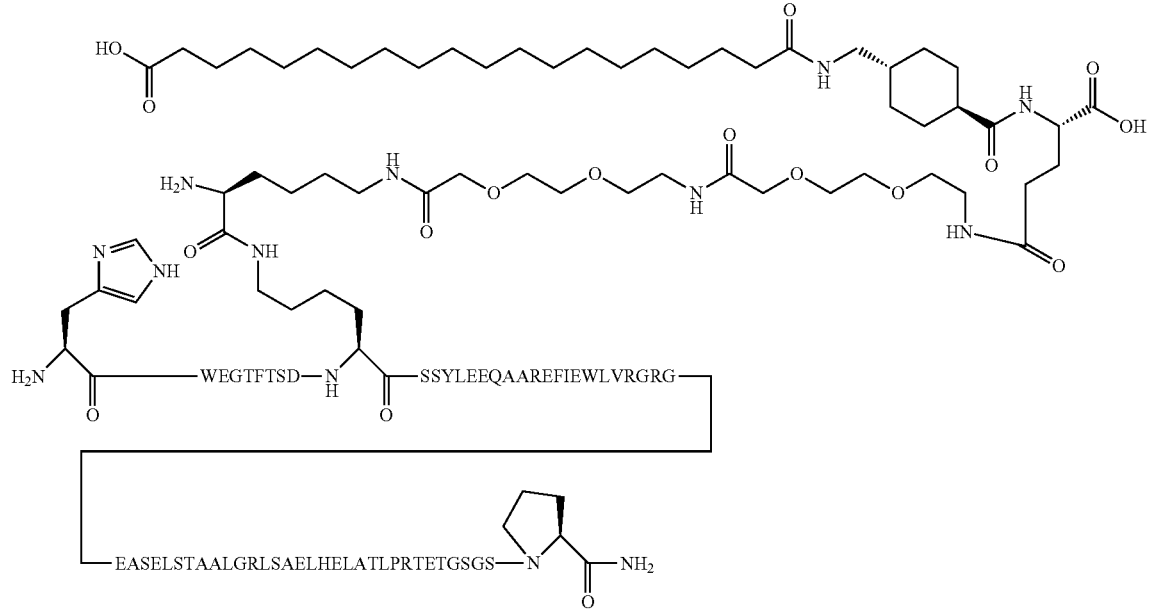

$C_{357}H_{566}N_{94}O_{116}$
Molecular weight (average) calculated: 8030.8741 g/mol
mono isotopic mass: 8026.1280 g/mol
LCMS34: found $(M+5H)^{5+}$ 1607.09 (most abundant)
The amino acid sequence of HWEGTFTSDKS-SYLEEQAAREFIEWLVRGRGEASELSTAALGRL-SAELHELATLPRTETGSGSP has SEQ ID NO: 188.

Compound 0434

HWEGTFTSDVSSYLEE-K([(2S)-2-amino-6-[[2-[2-[2-[[2-[2-[2-[[(4S)-4-carboxy-4-[[4-[(19-carboxynonadecanoylamino)methyl]cyclohexanecarbonyl)amino]butanoyl]amino]ethoxy]ethoxy]acetyl]amino]ethoxy]ethoxy] acetyl]amino]hex anoyl])-AAREFIEWLVRGRGEASELSTAALGRLSAELHELATL-PRTETGSGSP-amide

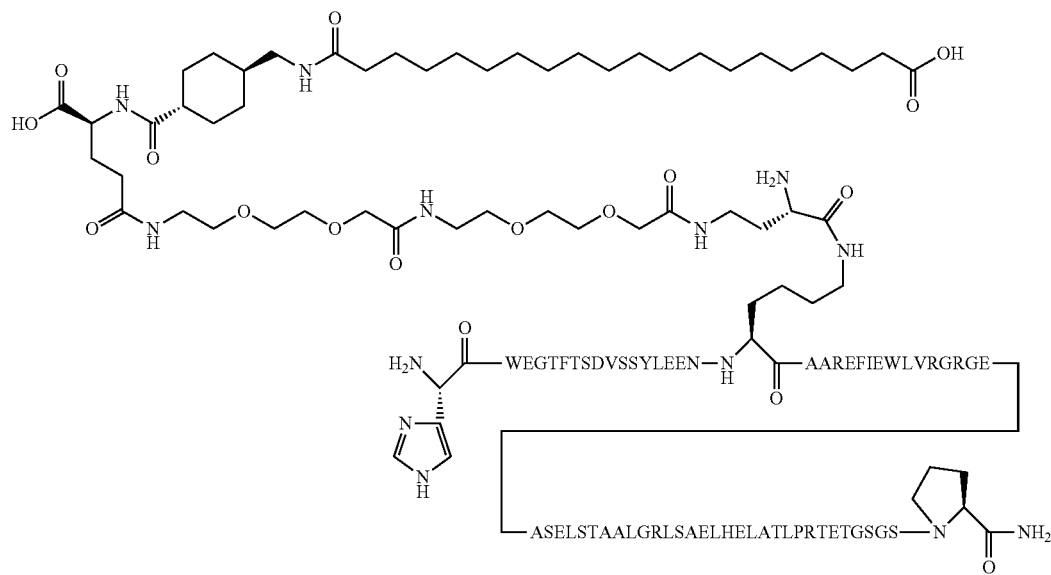

$C_{357}H_{567}N_{93}O_{115}$
Molecular weight (average) calculated: 8001.8760 g/mol
mono isotopic mass: 7997.1378 g/mol
LCMS34: found (M+5H)$^{5+}$1601.19 (most abundant)
The amino acid sequence of HWEGTFTSDVSSYLEE-KAAREFIEWLVRGRGEASELSTAALGRLSAEL-HELATLPRTETGSGSP has SEQ ID NO: 187.
Compound 0435
HWEGTFTSDVSSYLEEQAA-K([(2S)-2-amino-6-[[2-[2-[2-[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]hexanoyl])-EFIEWLVRGRGEASELSTAALGRLSAELHELATLPRTETGSGSP-amide $C_{356}H_{563}N_{91}O_{116}$
Molecular weight (average) calculated: 7973.8195 g/mol
mono isotopic mass: 7969.0953 g/mol
LCMS34: found (M+5H)$^{5+}$1595.67 (most abundant)
The amino acid sequence of HWEGTFTSDVSSYLE-EQAAKEFIEWLVRGRGEASELSTAALGRLSAEL-HELATLPRTETGSGSP has SEQ ID NO: 207.
Compound 0436
H-Aib-EGTFTSDVSSYLEEQAA-K([(2S)-2-amino-6-[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]hexanoyl])-EFIEWLVRGRGEASELSTAALGRLSAELHELATLPRTETGSGSP-amide

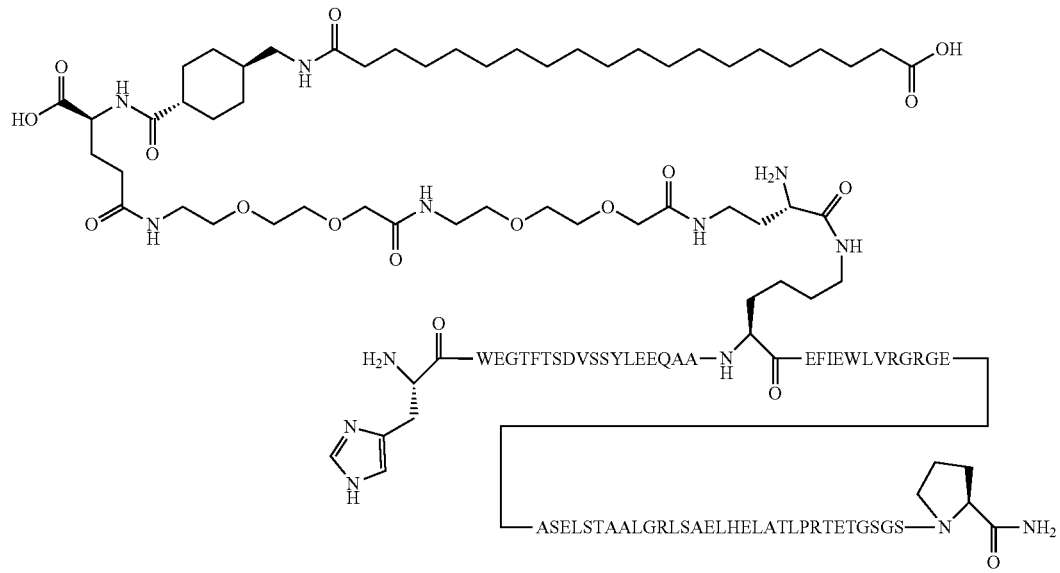

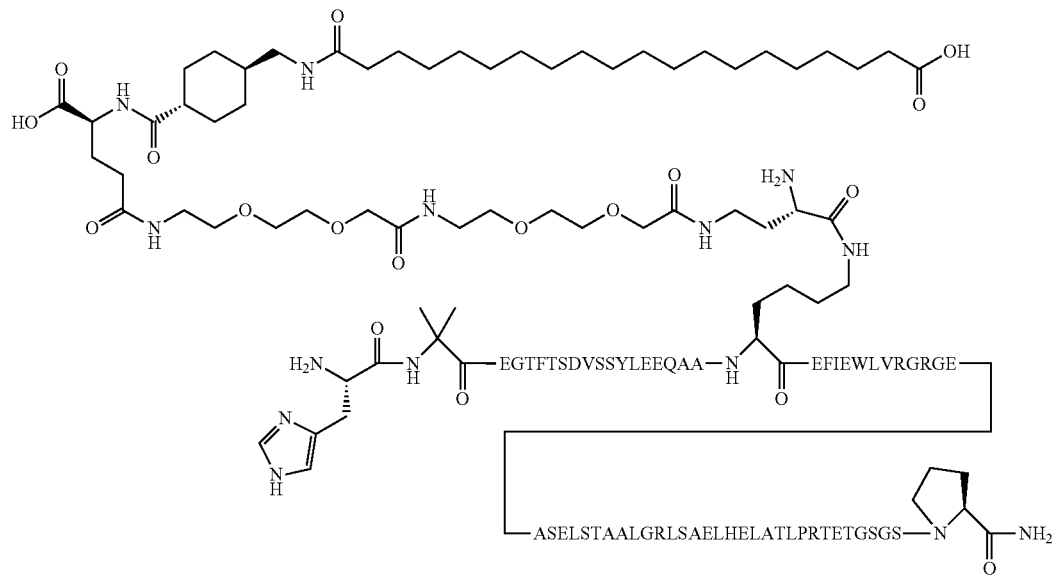

$C_{349}H_{560}N_{90}O_{116}$
Molecular weight (average) calculated: 7872.7141 g/mol
mono isotopic mass: 7868.0688 g/mol
LCMS34: found (M+5H)$^{5+}$ 1575.47 (most abundant)
The amino acid sequence of HXEGTFTSDVSSYLEEQAAKEFIEWLVRGRGEASELSTAALGRLSAELHELATLPRTETGSGSP has SEQ ID NO: 208.
Compound 0437
HWEGTFTSDVSSYLEEQAAR-K([(2S)-2-amino-6-[[2-[2-[2-[2-[2-[2-[(4S)-4-carboxy-4-[[4[(19-carboxynonadecanoylamino)methyl]cyclohexanecarbonyl]amino]butanoyl]amino]ethoxy]ethoxy]acetyl]amino]ethoxy]ethoxy]acetyl]amino]hexanoyl])-FIEWLVRGRGEASELSTAALGRLSAELHELATLPRTETGSGSP-amide $C_{357}H_{568}N_{94}O_{114}$
Molecular weight (average) calculated: 8000.8912 g/mol
mono isotopic mass: 7996.1538 g/mol
LCMS34: found (M+5H)$^{5+}$ 1601.06 (most abundant)
The amino acid sequence of HWEGTFTSDVSSYLEEQAARKFIEWLVRGRGEASELSTAALGRLSAELHELATLPRTETGSGSP has SEQ ID NO: 209.
Compound 0438
H-Aib-EGTFTSDVSSYLEEQAAREFIEWLVRGR-K([(2S)-2-amino-6-[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]hexanoyl])-EASELSTAALGRLSAELHELATLPRTETGSGSP-amide

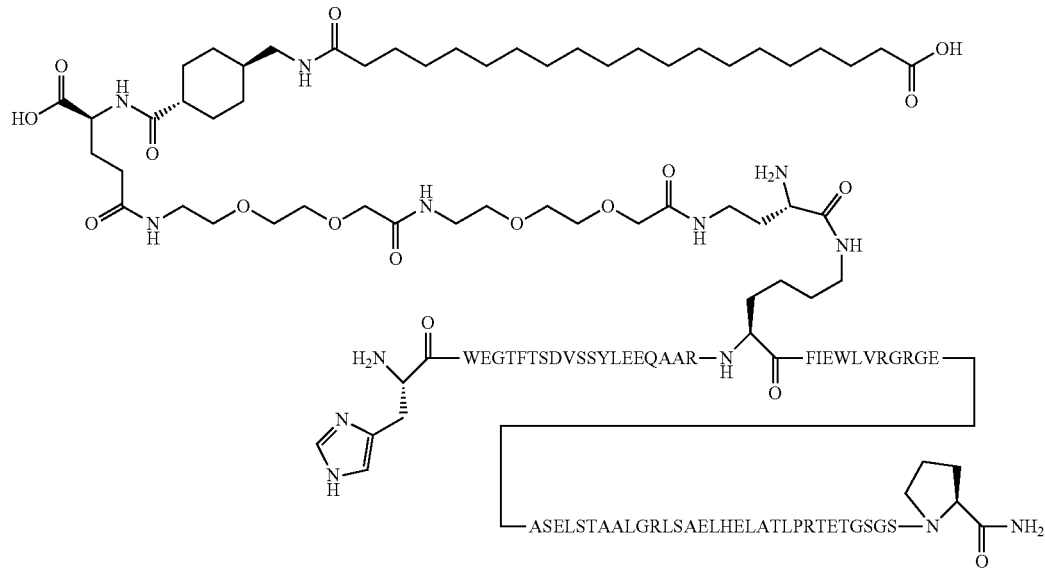

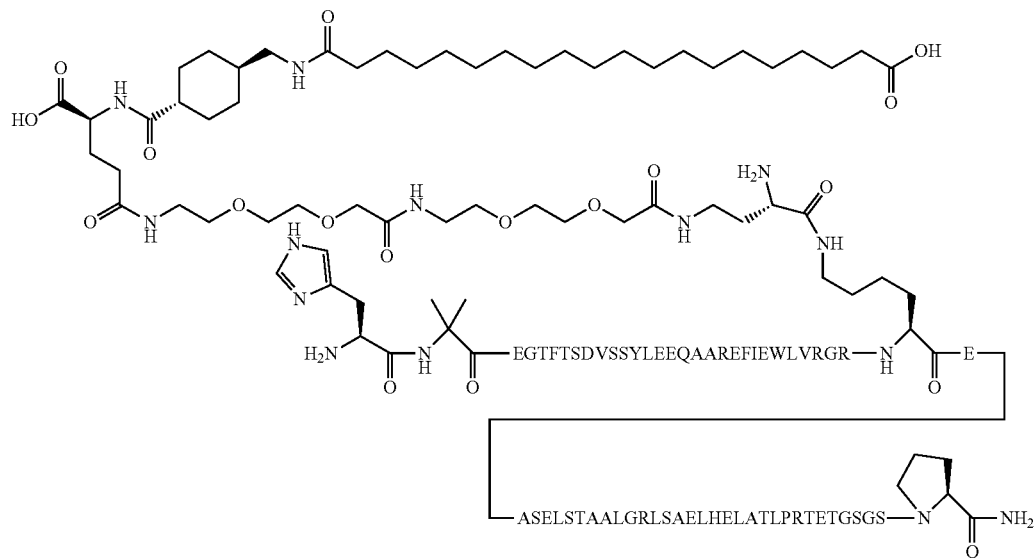

$C_{353}H_{569}N_{93}O_{116}$
Molecular weight (average) calculated: 7971.8485 g/mol
mono isotopic mass: 7967.1484 g/mol
LCMS34: found (M+5H)$^{5+}$1595.27 (most abundant)
The amino acid sequence of HXEGTFTSDVSSYLE-EQAAREFIEWLVRGRKEASELSTAALGRLSAEL-HELATLPRTETGSGSP has SEQ ID NO: 210
Compound 0439
H-Aib-EGTFTSDVSSYLEEQAAR-K([(2S)-2-amino-6-[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]hex anoyl])-FIEWLVRGRGEASELSTAALGRLSAELHELATLP-RTETGSGSP-amide $C_{350}H_{565}N_{93}O_{114}$
Molecular weight (average) calculated: 7899.7858 g/mol
mono isotopic mass: 7895.1273 g/mol
LCMS34: found (M+5H)$^{5+}$1580.88 (most abundant)
The amino acid sequence of HXEGTFTSDVSSYLE-EQAARKFIEWLVRGRGEASELSTAALGRLSAEL-HELATLPRTETGSGSP has SEQ ID NO: 211.
Compound 0440
H-Aib-EGTFTSD-K([2-[2-[2-[2[(2-[(2-2(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl])-SSYLEEQAAREFIEWLVRGRGEASELSTAALGRL-SAELHELATLPRTETGSGSP-amide

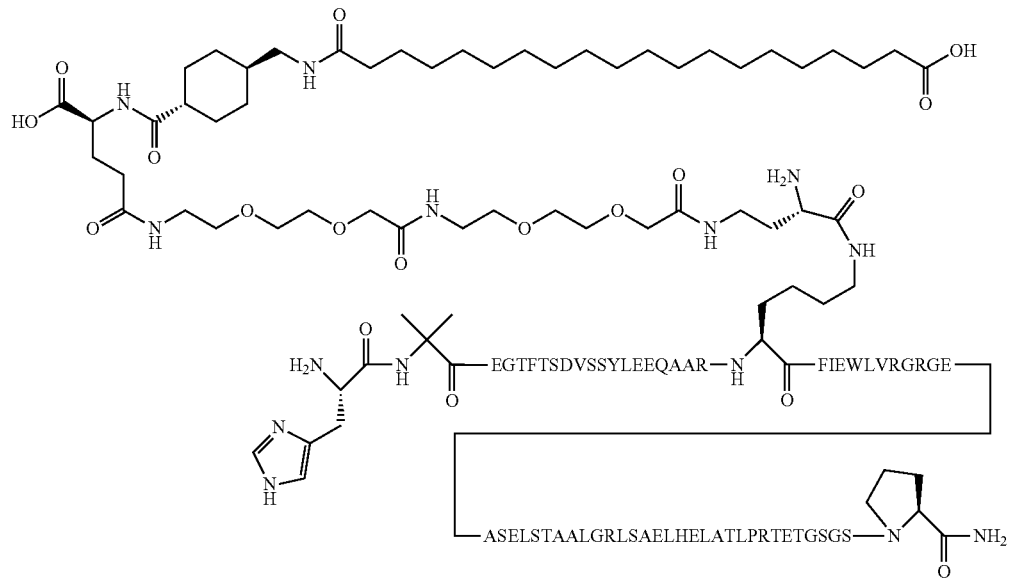

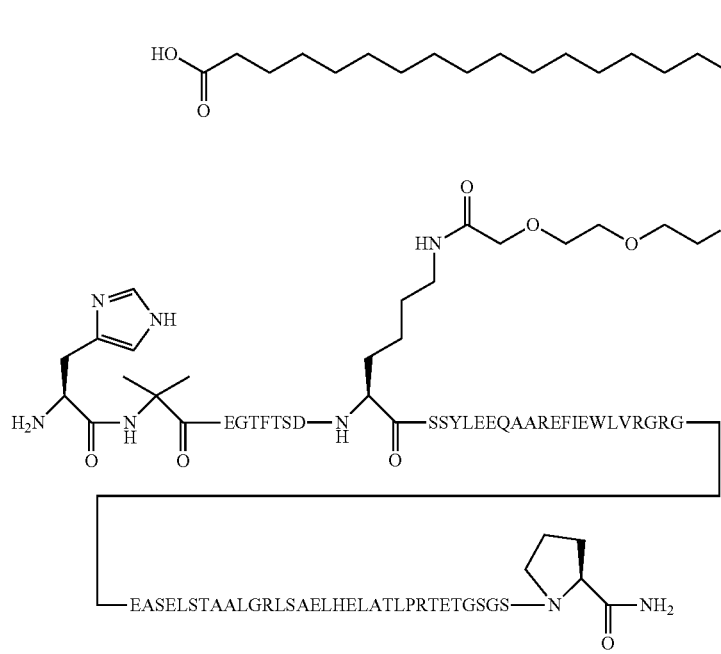

$C_{344}H_{551}N_{91}O_{115}$
Molecular weight (average) calculated: 7801.5964 g/mol
mono isotopic mass: 7797.0065 g/mol
LCMS34: found $(M+5H)^{5+}$ 1560.48 (mono isotopic)
The amino acid sequence of HXEGTFTSDKSSYLE-EQAAREFIEWLVRGRGEASELSTAALGRLSAEL-HELATLPRTETGSGSP has SEQ ID NO: 212.
Compound 0472
HAEGTFTSDVSSYLEE-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-AAREFIEWLVRGRGEASELSTAALGRLSAELHELATL-PRTETGSGSP-amide $C_{333}H_{533}N_{89}O_{113}$
Molecular weight (average) calculated: 7591.3236 g/mol
mono isotopic mass: 7586.8697 g/mol
LCMS34: found $(M+5H)^{5+}$ 1519.18 (most abundant)
The amino acid sequence of HAEGTFTSDVSSYLEE-KAAREFIEWLVRGRGEASELSTAALGRLSAEL-HELATLPRTETGSGSP has SEQ ID NO: 202.
Compound 0473
HWEGTFTSDVSSYLEE-K([2-[2-[2-[[2-[2-[2-[[(4S)-4-carboxy-4-(19-carboxynonadecanoylamino)butanoyl]amino)ethoxy]ethoxy]acetyl]amino]ethoxy]ethoxy]acetyl])-AAREFIEWLVRGRGEASELSTAALGRLSAELHELATL-PRTETGSGSP-amide

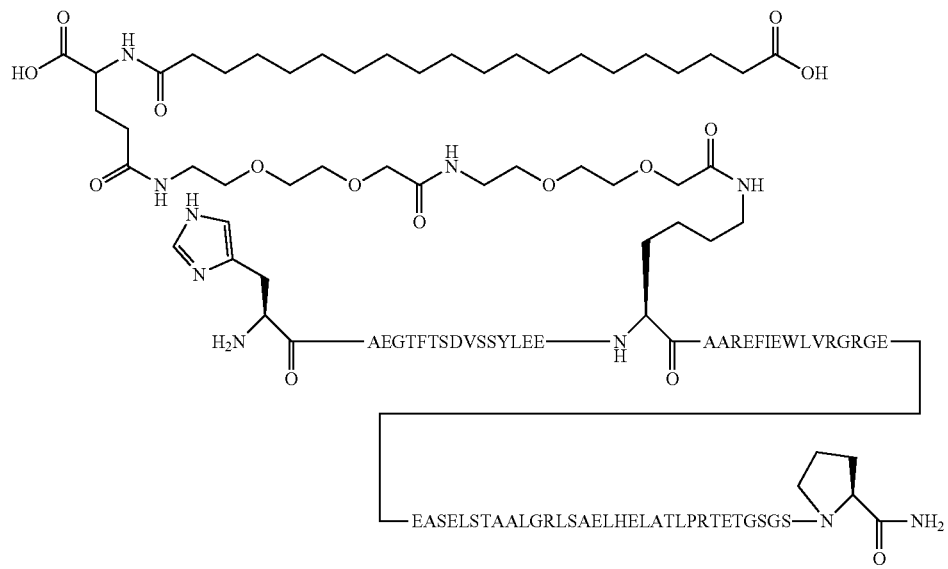

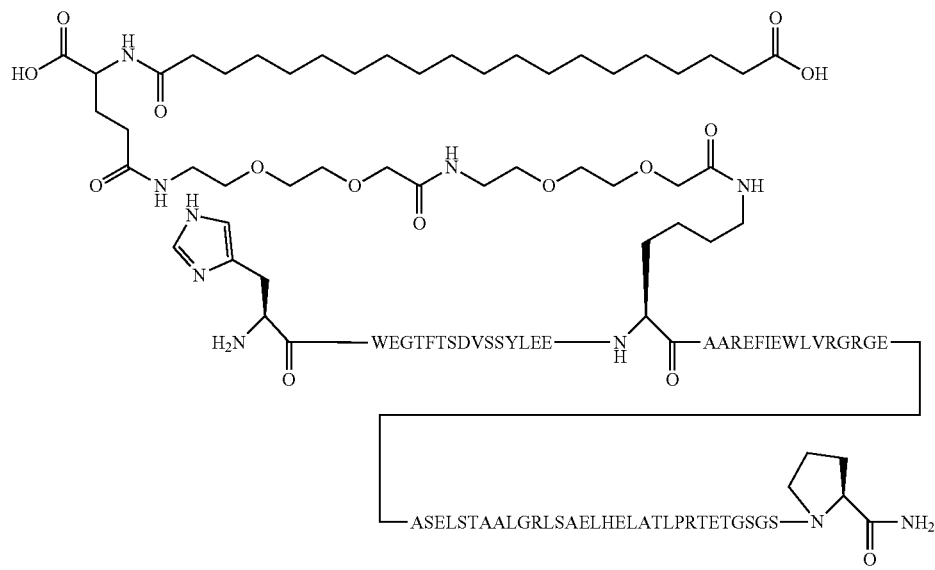

$C_{343}H_{542}N_{90}O_{113}$
Molecular weight (average) calculated: 7734.5088 g/mol
mono isotopic mass: 7729.9432 g/mol
LCMS34: found (M+5H)$^{5+}$1547.82 (most abundant)
The amino acid sequence of HWEGTFTSDVSSYLEE-KAAREFIEWLVRGRGEASELSTAALGRLSAEL-HELATLPRTETGSGSP has SEQ ID NO: 187.
Compound 0474
HAEGTFTSDVSSYLEE-K([2-[2-[2-[2-[2-[2-[[(4S)-4-carboxy-4-(19-carboxynonadecanoylamino)butanoyl]amino]ethoxy]ethoxy]acetyl]amino]ethoxy]ethoxy]acetyl])-AAREFIEWLVRGRGEASELSTAALGRLSAELHELATL-PRTETGSGSP-amide $C_{335}H_{537}N_{89}O_{113}$
Molecular weight (average) calculated: 7619.3768 g/mol
mono isotopic mass: 7614.9010 g/mol
LCMS34: found (M+5H)$^{5+}$1524.8 (most abundant)
The amino acid sequence of HAEGTFTSDVSSYLEE-KAAREFIEWLVRGRGEASELSTAALGRLSAEL-HELATLPRTETGSGSP has SEQ ID NO: 202.
Compound 0475
HAEGTFTSD-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-SSYLEE-K([2-[2-[2-[[2-[2-[2-[[(4S)-4-carboxy 4-(15-carboxypentadecanoylamino)butanoy]amino]ethoxy]ethoxy]acetyl]amino]ethoxy]ethoxy]acetyl])-AAREFIEWLVRGRGEASELSTAALGRLSAELHELATL-PRTETGSGSP-amide

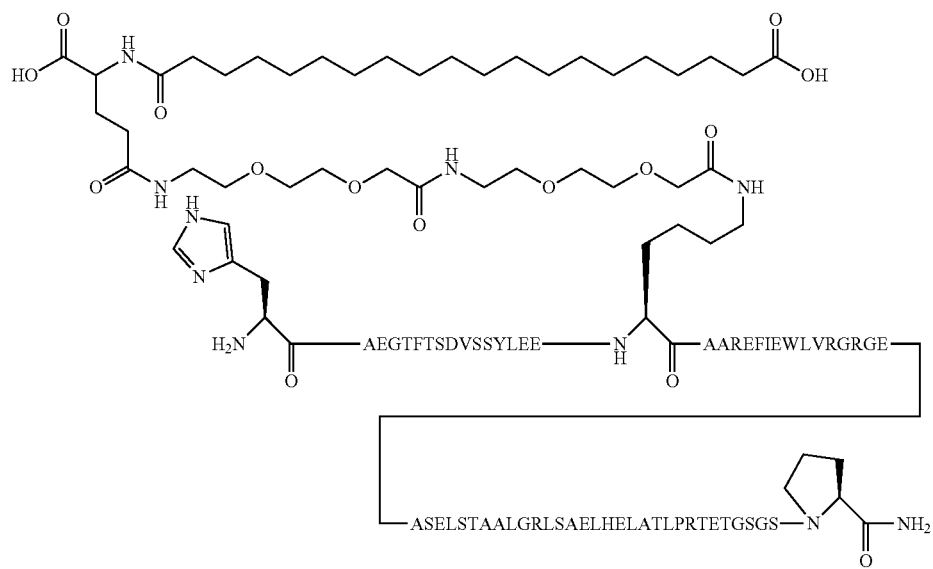

251

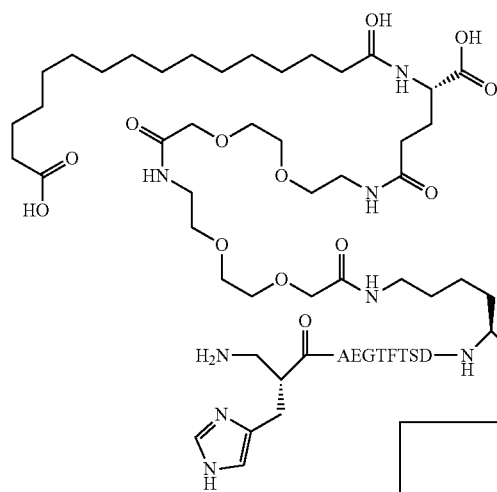

252

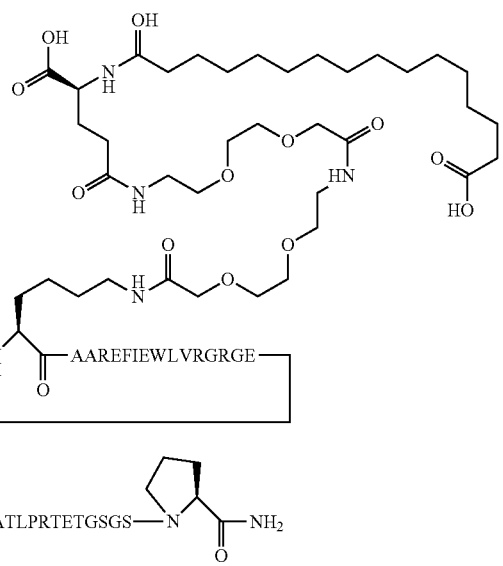

$C_{365}H_{589}N_{93}O_{125}$
Molecular weight (average) calculated: 8280.1303 g/mol
mono isotopic mass: 8275.2591 g/mol
LCMS34: found $(M+5H)^{5+}$ 1656.86 (most abundant)
The amino acid sequence of HAEGTFTSDKSSYLEE-KAAREFIEWLVRGRGEASELSTAALGRLSAEL-HELATLPRTETGSGSP has SEQ ID NO: 213.

Compound 0482

HAEGTFTSDVS-K([2-[2-[2-[[2-[2-[2-[(4S)-4-carboxy-4-(15-carboxypentadecanoylamino)butanyl]amino]ethoxy]ethoxy]acetylamino]ethoxy]ethoxy]acetyl])-YLEEQAVRE-FIA-K([2-[2-[2-[[2-[2-[2-[[(4S)-4-carboxy-4-(15-caoxypentadecanoylamino)butanoyl]amino]ethoxy]ethoxy]acetyl]amino]ethoxy]ethoxy]acetyl])-LVRGRGGGEASELSTAALGRLSAELHELAT-LPRTETGSGSP-amide

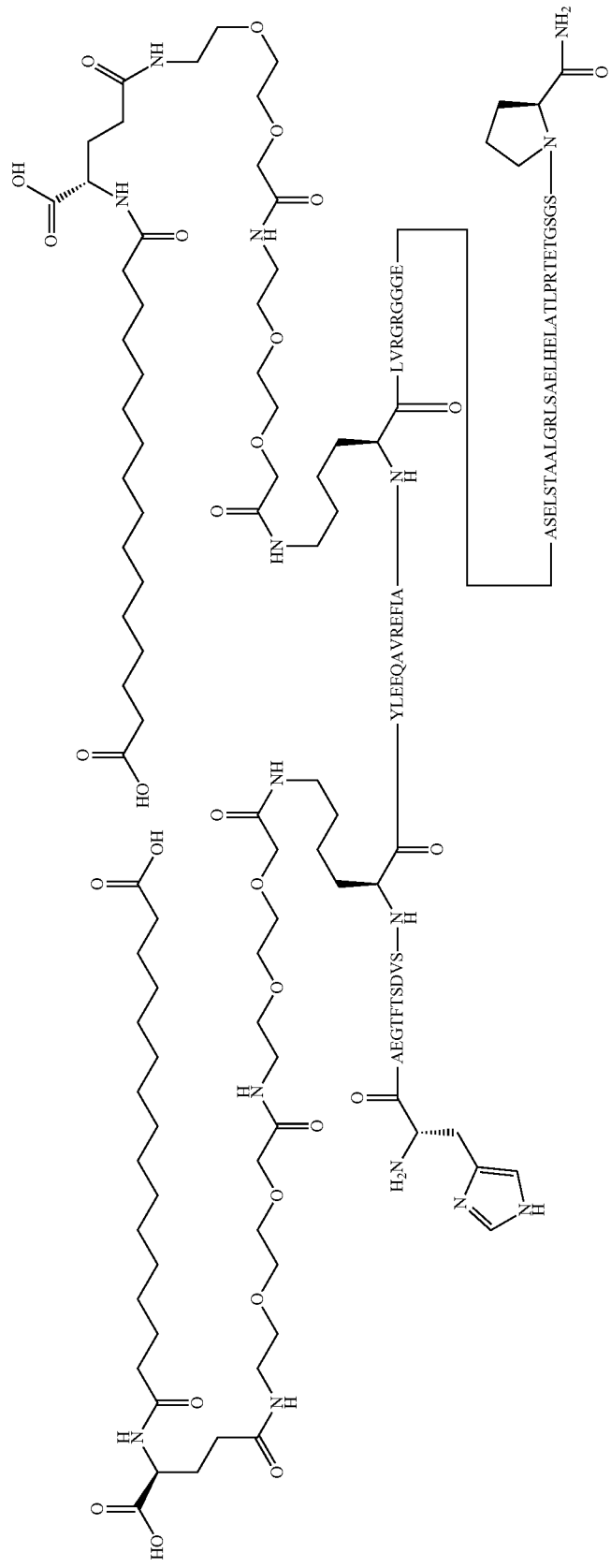

$C_{365}H_{599}N_{95}O_{125}$

Molecular weight (average) calculated: 8318.2231 g/mol mono isotopic mass: 8313.3435 g/mol LCMS_ZQ: found $(M+5H)^{5+}$ 1664.64 (most abundant)

The amino acid sequence of HAEGTFTSDVSKYLE-EQAVREFIAKLVRGRGGGEASELSTAALGRLSAEL-HELATLPRTETGSGSP has SEQ ID NO: 214.

Compound 0483

H-Aib-EGTFTSDVS-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-YLE-EQAVREFIA-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-LVRGRGGGEASELSTAALGRLSAELHELATLPR-TETGSGSP-amide

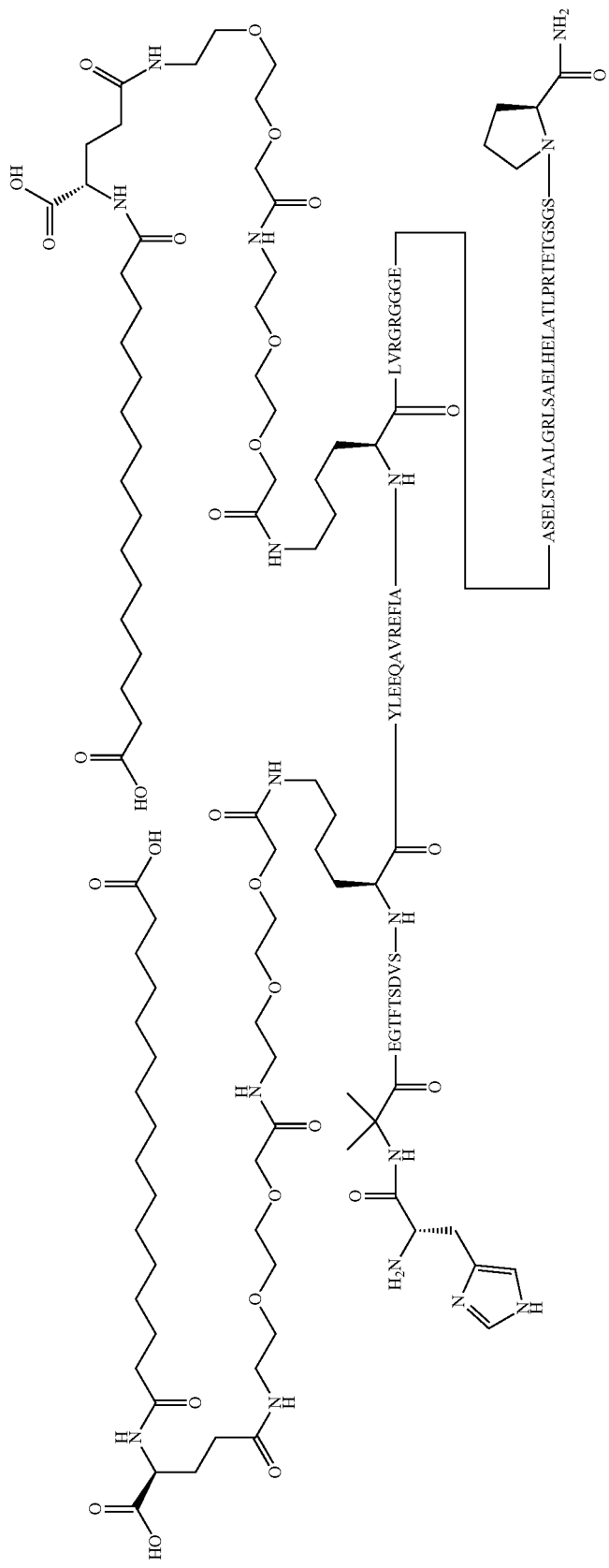

$C_{366}H_{601}N_{95}O_{125}$
Molecular weight (average) calculated: 8332.2496 g/mol
mono isotopic mass: 8327.3592 g/mol
LCMS34: found $(M+5H)^{5+}$ 1667.47 (most abundant)
The amino acid sequence of HXEGTFTSDVSKYLE-EQAVREFIAKLVRGRGGGEASELSTAALGRLSAEL-HELATLPRTETGSGSP has SEQ ID NO: 215.

Compound 0484

H-Aib-EGTFTSDVS-K([2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl])-YLEEGQAVREFIA-K([2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl])-LVRGRGGGEASELSTAALGRLSAELHELATLPR-TETGSGSP-amide

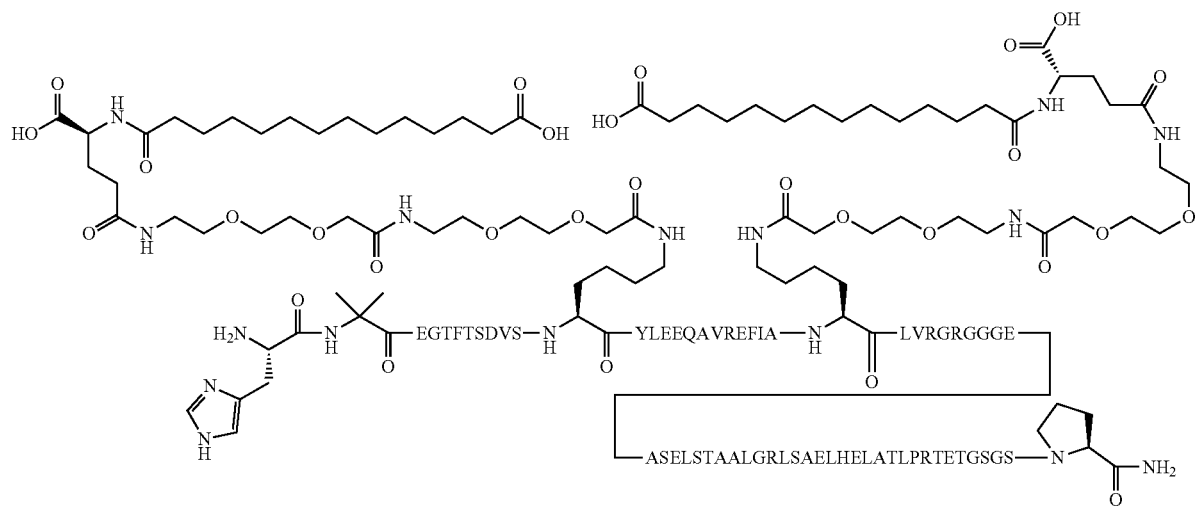

$C_{362}H_{593}N_{95}O_{125}$
Molecular weight (average) calculated: 8276.1433 g/mol
mono isotopic mass: 8271.2966 g/mol
LCMS34: found $(M+5H)^{5+}$ 1656.1 (most abundant)
The amino acid sequence of HXEGTFTSDVSKYLE-EQAVREFIAKLVRGRGGGEASELSTAALGRLSAEL-HELATLPRTETGSGSP has SEQ ID NO: 215.

Compound 0502

H-Aib-EGTFTSDVSSYLEEQAAREFIAWLVRGR-K([2-[2-[2-[[2-[2-[2-[(4S)-4-carboxy-4-(19-carboxynonadecanoylamino)butanoyl]amino]ethoxy]ethoxy]acetyl]amino]ethoxy]ethoxy]acetyl])-GGGGEASELSTAALGRLSAELHELATLPRTETGSGSP-amide

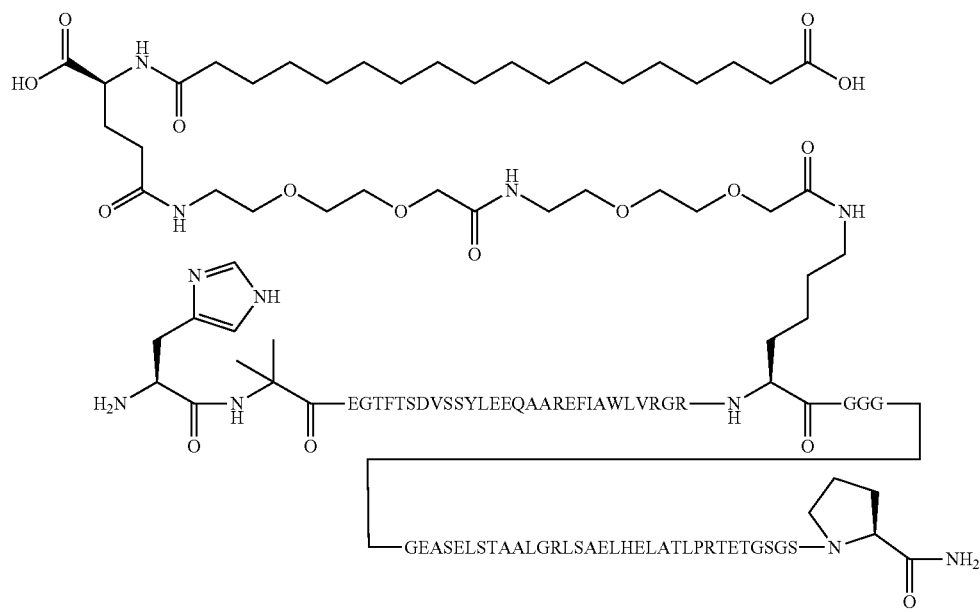

$C_{345}H_{554}N_{94}O_{116}$

Molecular weight (average) calculated: 7874.6505 g/mol
mono isotopic mass: 7870.0341 g/mol
LCMS34: found $(M+5H)^{5+}$ 1575.09 (mono isotopic)

The amino acid sequence of HXEGTFTSDVSSYLE-EQAAREFIAWLVRGRKGGGGEASELSTAALGRL-SAELHELATLPRTETGSGSP has SEQ ID NO: 153.

Compound 0503
H-Aib-EGTFTSDVSSYLEEQAAREFIEWLVRGR-K([2-[2-[2-[[2-[2-[2-[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl])-GGGGEASELSTAALGRLSAELHELATLPRTETGSGSP-amide

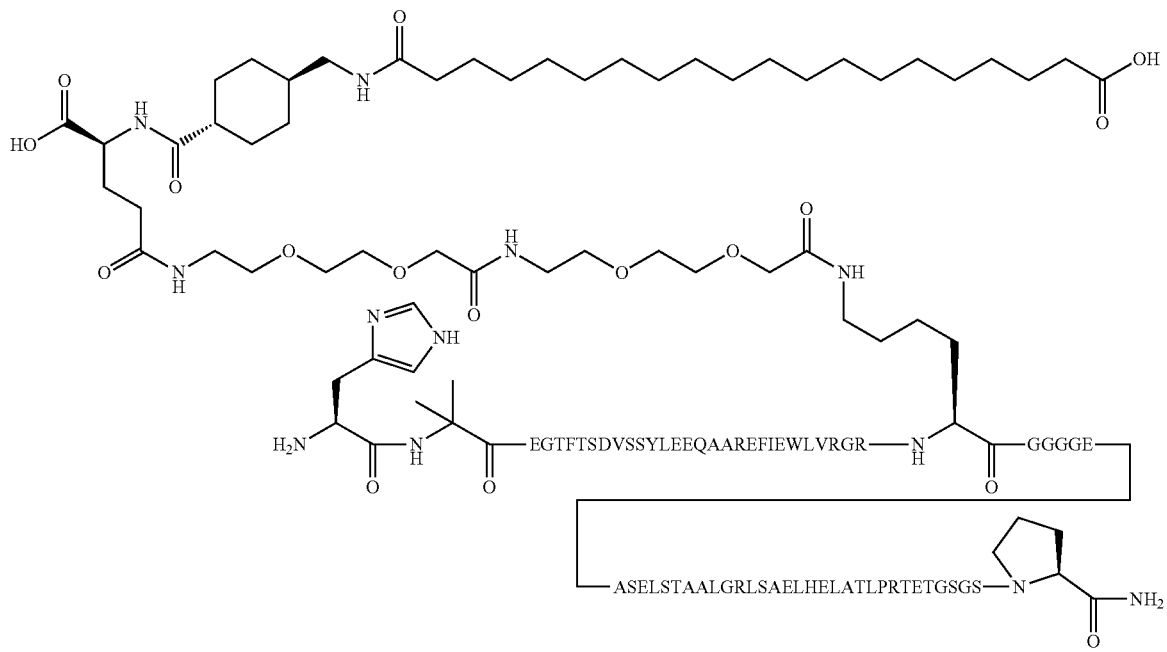

$C_{355}H_{569}N_{95}O_{119}$

Molecular weight (average) calculated: 8071.8815 g/mol mono isotopic mass: 8067.1393 g/mol LCMS34: found $(M+5H)^{5+}$ 1614.52 (mono isotopic)

The amino acid sequence of HXEGTFTSDVSSYLE-EQAAREFIEWLVRGRKGGGGEASELSTAALGRL-SAELHELATLPRTETGSGSP has SEQ ID NO: 216.

Compound 0504

H-Aib-EGTFTSDVSSYLEEQAAREFIAWLVRGRP-K([2-amino-6-[[2-[2-[2-[2-[2-[2-[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]acetyl])-GGGGEASELSTAALGRLSAELHELATLPRTETGSGSP-amide

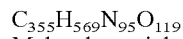

$C_{358}H_{574}N_{96}O_{118}$

Molecular weight (average) calculated: 8110.9606 g/mol mono isotopic mass: 8106.1866 g/mol LCMS34: found $(M+5H)^{5+}$ 1622.34 (most abundant)

The amino acid sequence of HXEGTFTSDVSSYLE-EQAAREFIAWLVRGRPKGGGGEASELSTAALGRL-SAELHELATLPRTETGSGSP has SEQ ID NO: 217.

Compound 0506

H-Aib-EGTFTSDVSSYLEEQAAREFIAWLVRGR-K([(2S)-2-amino-6-[[2-[2-[2-[2-[2-[2-[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]hexanoyl])-GGGGEASELSTAALGRLSAELHELATLPRTETGSGSP-amide

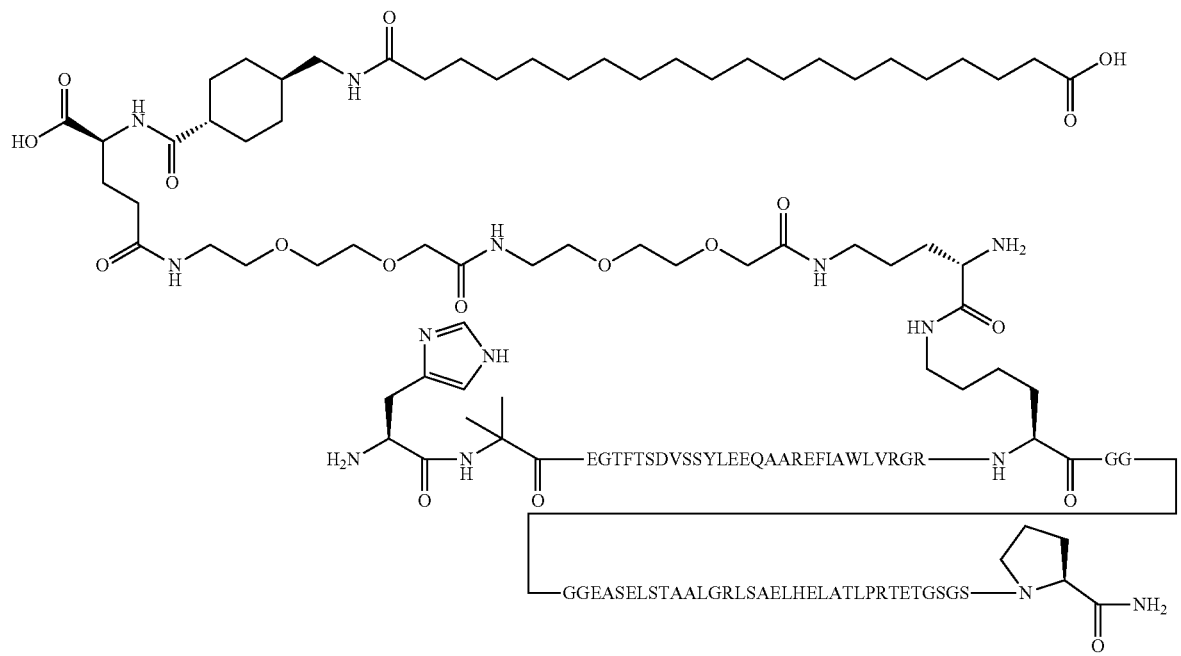

$C_{359}H_{579}N_{97}O_{118}$

Molecular weight (average) calculated: 8142.0177 g/mol mono isotopic mass: 8137.2288 g/mol LCMS34: found $(M+5H)^{5+}$1629.33 (most abundant)

The amino acid sequence of HXEGTFTSDVSSYLE-EQAAREFIAWLVRGRKGGGGEASELSTAALGRL-SAELHELATLPRTETGSGSP has SEQ ID NO: 153.

Compound 0509

H-Aib-EGTFTSDVSSYLEEQAAR-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-FIAWLVRGRGGGGGEASELSTAALGRLSAELH-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-LATLPRTETGSGSP-amide

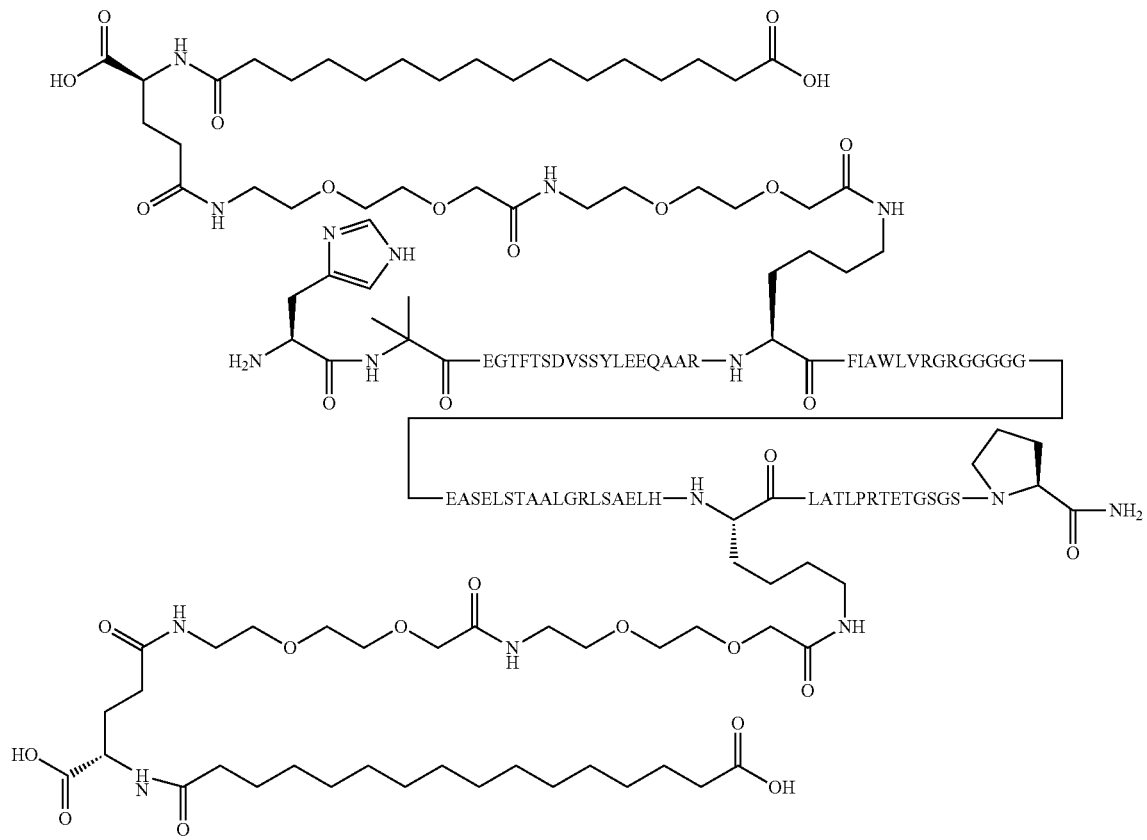

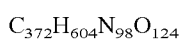

Molecular weight (average) calculated: 8140.9898 g/mol mono isotopic mass: 8428.3970 g/mol LCMS34: found $(M+5H)^{5+}$ 1687.55 (most abundant)

The amino acid sequence of HXEGTFTSDVS-SYLEEOAARKFIAWLVRGRGGGGGEASELSTAAL-GRLSAELHKLATLPRTETGSGSP has SEQ ID NO: 218.

Compound 0511

H-Aib-EGTFTSDVSRYLEEQAAREFIEWLVRGR-K([2-[2-[2-[[2-[2-[2-[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl])-GGGGEASELSTAALGRLSAELHELATLPRTETGSGSP-amide

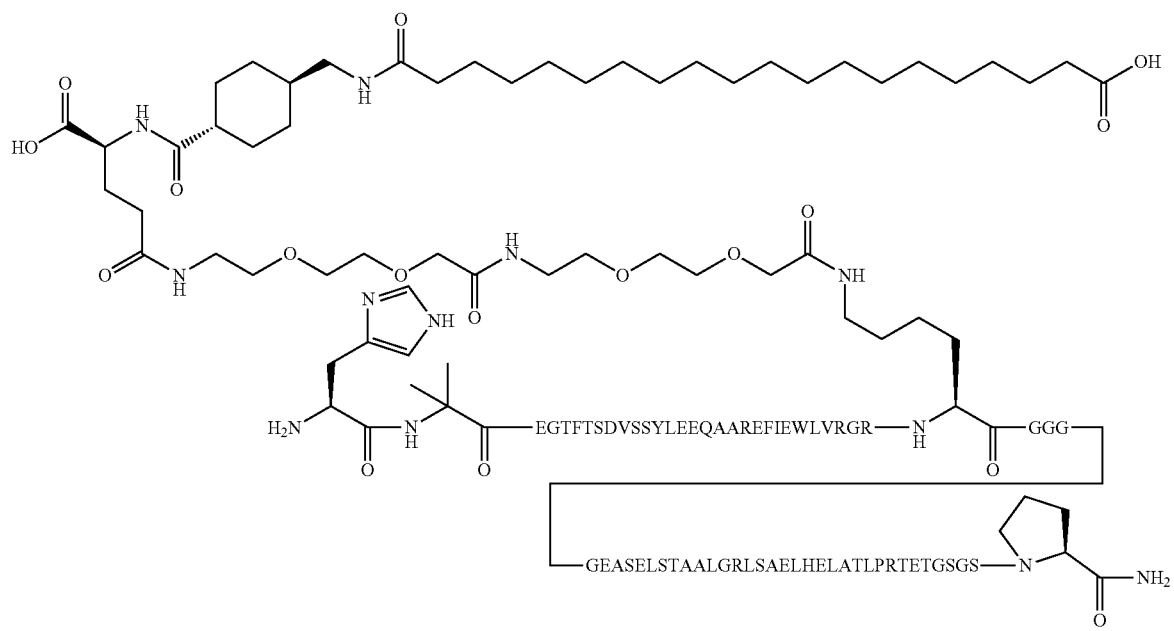

C₃₅₈H₅₇₆N₉₈O₁₁₈
Molecular weight (average) calculated: 8140.9898 g/mol
mono isotopic mass: 8136.2084 g/mol LCMS34: found (M+5H)⁵⁺1629.34 (most abundant)

The amino acid sequence of HXEGTFTSDVSRYLE-EQAAREFIEWLVRGRKGGGGEASELSTAALGRL-SAELHELATLPRTETGSGSP has SEQ ID NO: 219.

Compound 0512

H-Aib-EGTFTSDVSSYLEEQAAREFIAWLVRGR-K([2-[2-[2-[[2-[2-[2-[(4S)-4-carboxy-4-[4-[(19-carboxynona-decanoylamino)methyl]cyclohexanecarbonyl]amino]bu-tanoyl]amino]ethoxy]ethoxy]acetyl]amino]ethoxy]ethoxy] acetyl])-GGEASELSTAALGRLSAELHELATLPRTETGSGSP-amide

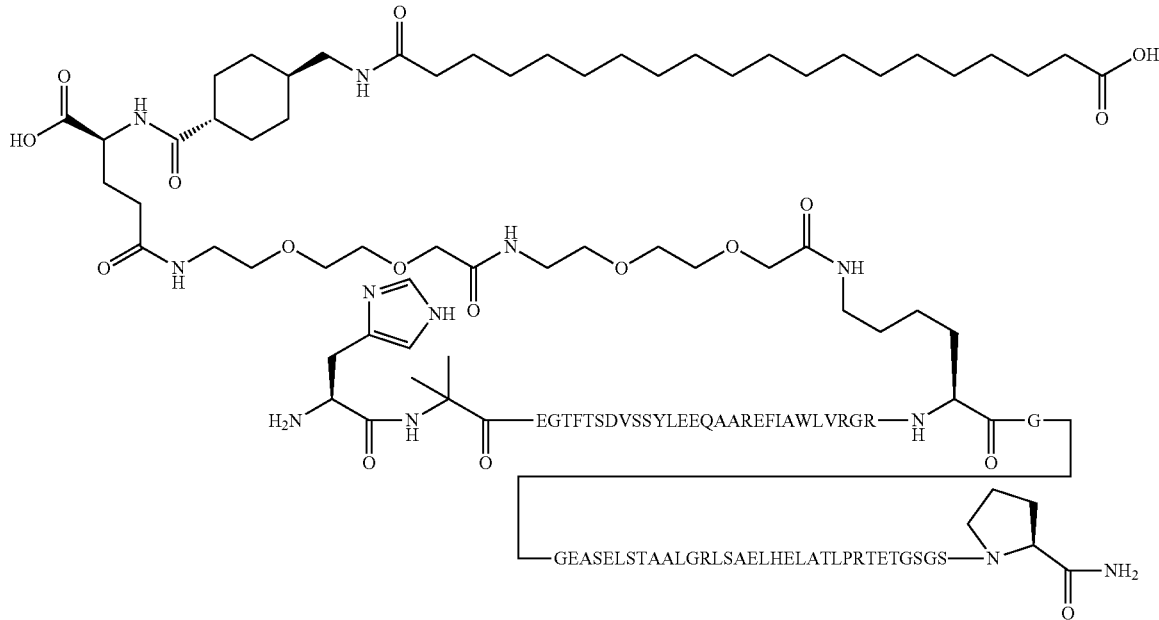

C₃₄₉H₅₆₁N₉₃O₁₁₅
Molecular weight (average) calculated: 7899.7427 g/mol
mono isotopic mass: 7895.0909 g/mol LCMS34: found (M+5H)⁵⁺1580.31 (most abundant)

The amino acid sequence of HXEGTFTSDVSSYLE-EQAAREFIAWLVRGRKGGEASELSTAALGRLSAEL-HELATLPRTETGSGSP has SEQ ID NO: 154.

Compound 0516

H-Aib-EGTFTSDVS-K([2-[2-[2-[2-[2-[2-[(4S)-4-car-boxy-4-(15-carboxypentadecanoylamino)butanoyl]amino]

ethoxy]ethoxy]acetyl]amino]ethoxy]ethoxy]acetyl])-YLE-EQAIAR-K([2-[2-[2-[2-[2-[2-[[(4S)-4-carboxy-4-(15-carboxypentadecanoylamino)butanoyl]amino]ethoxy]ethoxy]acetyl]amino]ethoxy]ethoxy]acetyl])-FIAWLVRGRGGGGEASELSTAALGRLSAELHELATL-PRTETGSGSP-amide

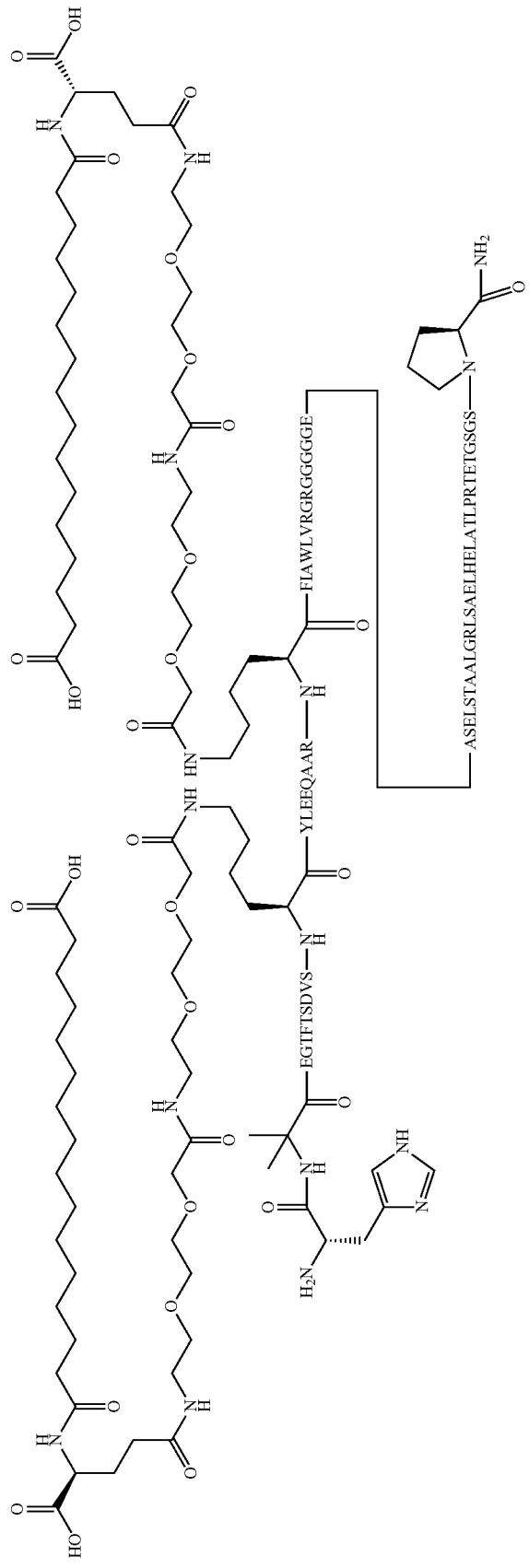

$C_{374}H_{606}N_{98}O_{125}$
Molecular weight (average) calculated: 8475.3950 g/mol
mono isotopic mass: 8470.4075 g/mol
LCMS34: found $(M+5H)^{5+}$ 1694.99 (mono isotopic)
The amino acid sequence of HXEGTFTSDVSKYLE-EQAARKFIAWLVRGRGGGGGEASELSTAALGRL-SAELHELATLPRTETGSGSP has SEQ ID NO: 220.

Compound 0518

H-Aib-EGTFTSDVS-K([2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl])-YLEEQAAREFIAWLVRGRGGGGGEASELSTAAL-GRLSAELHELATLPRTETGSGSP-amide

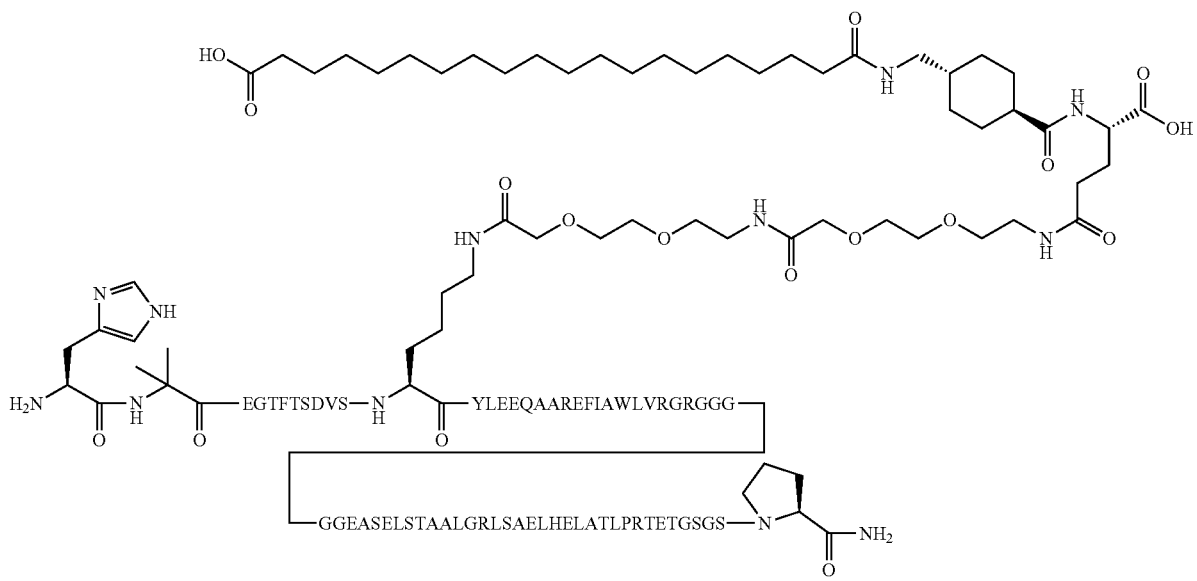

$C_{352}H_{565}N_{95}O_{116}$
Molecular weight (average) calculated: 7983.8194 g/mol
mono isotopic mass: 7979.1232 g/mol
LCMS34: found $(M+5H)^{5+}$ 1597.7 (most abundant)
The amino acid sequence of HXEGTFTSDVSKYLE-EQAAREFIAWLVRGRGGGGGEASELSTAALGRL-SAELHELATLPRTETGSGSP has SEQ ID NO: 221.

Compound 0528

H-Aib-EGTFTSDVS-K([2-[2-[2-[[2-[2-[2-[(4S)-4-carboxy-4-(15-carboxypentadecanoylamino)butanoyl]amino]ethoxy]ethoxy]acetyl]amino]ethoxy]ethoxy]acetyl])-YLE-EQAAREFIAWLVRGR-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-GGGGEASELSTAALGRLSAELHELATLPRTETGSGSP-amide

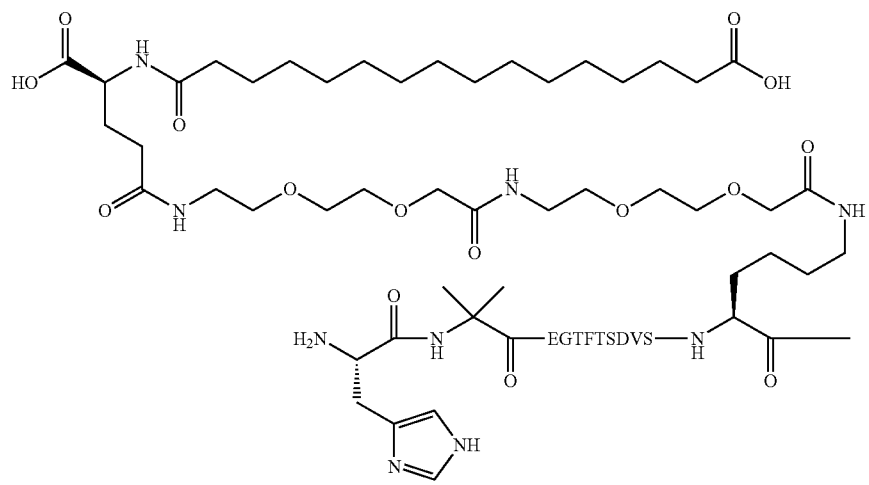

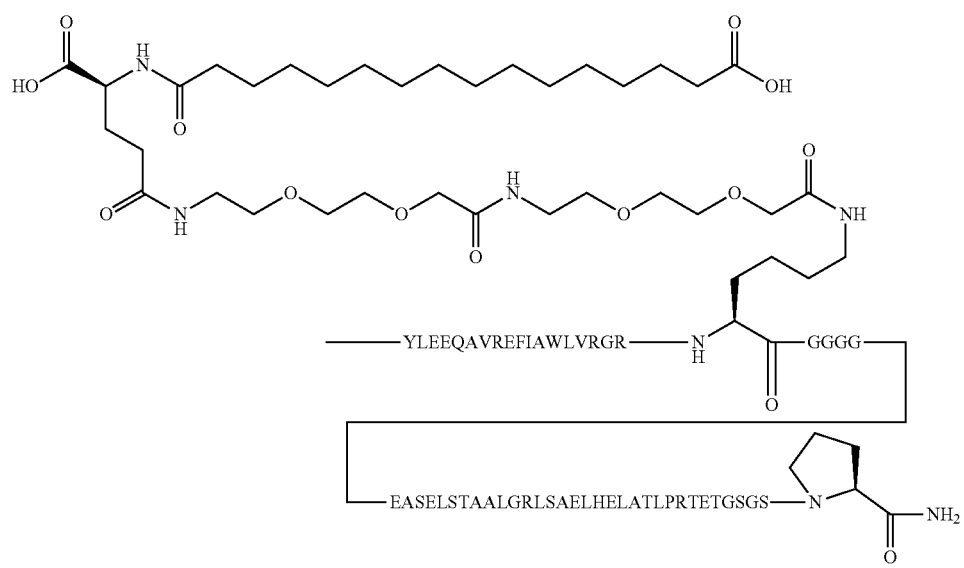

$C_{377}H_{610}N_{98}O_{127}$

Molecular weight (average) calculated: 8547.4577 g/mol mono isotopic mass: 8542.4287 g/mol LCMS34: found (M+5H)$^{5+}$1710.41 (most abundant)

The amino acid sequence of HXEGTFTSDVSKYLE-EQAAREFIAWLVRGRKGGGGEASELSTAALGRL-SAELHELATLPRTETGSGSP has SEQ ID NO: 222.

Compound 0529

H-Aib-EGTFTSDVSSYLEGQAAREFIAWLVR-GRGQEP-K([2-[2-[2-[[2-[2-[2-[(4S)-4-carboxy-4-(19-carboxynonadecanoylamino)butanoy]amino]ethoxy]ethoxy]acetyl]amino]ethoxy]ethoxy]acetyl])-GQAPEASELSTAALGRLSAELHELATLPRTETGSGSP-amide

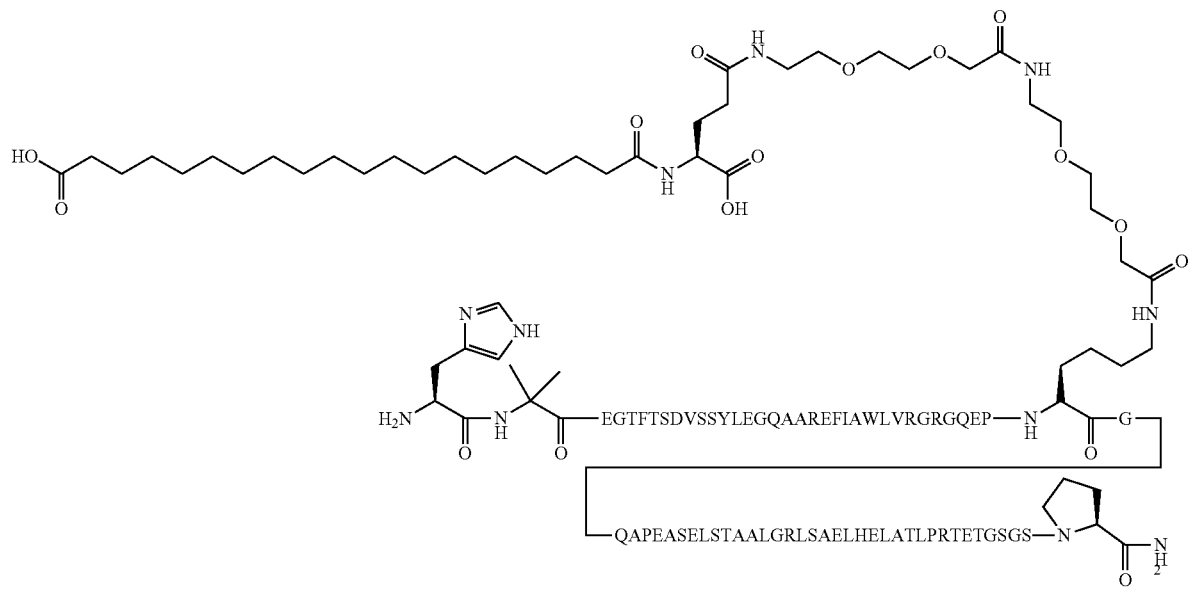

$C_{366}H_{586}N_{100}O_{122}$

Molecular weight (average) calculated: 8339.1658 g/mol mono isotopic mass: 8334.2724 g/mol LCMS34: found $(M+5H)^{5+}$ 1668.7 (mono abundant)

The amino acid sequence of HXEGTFTSDVS-SYLEGQAAREFIAWLVRGRGQEPKGQEASELSTAAL-GRLSAELHELATLPRTETGSGSP has SEQ ID NO: 137.

Compound 0539

H-Aib-EGTFTSDVSSYLEGOAAREFIAWLVRGR-GOEP-K([2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl])-GOAPEASELSTAALGRLSAELHELATLPRTETGSGSP-amide

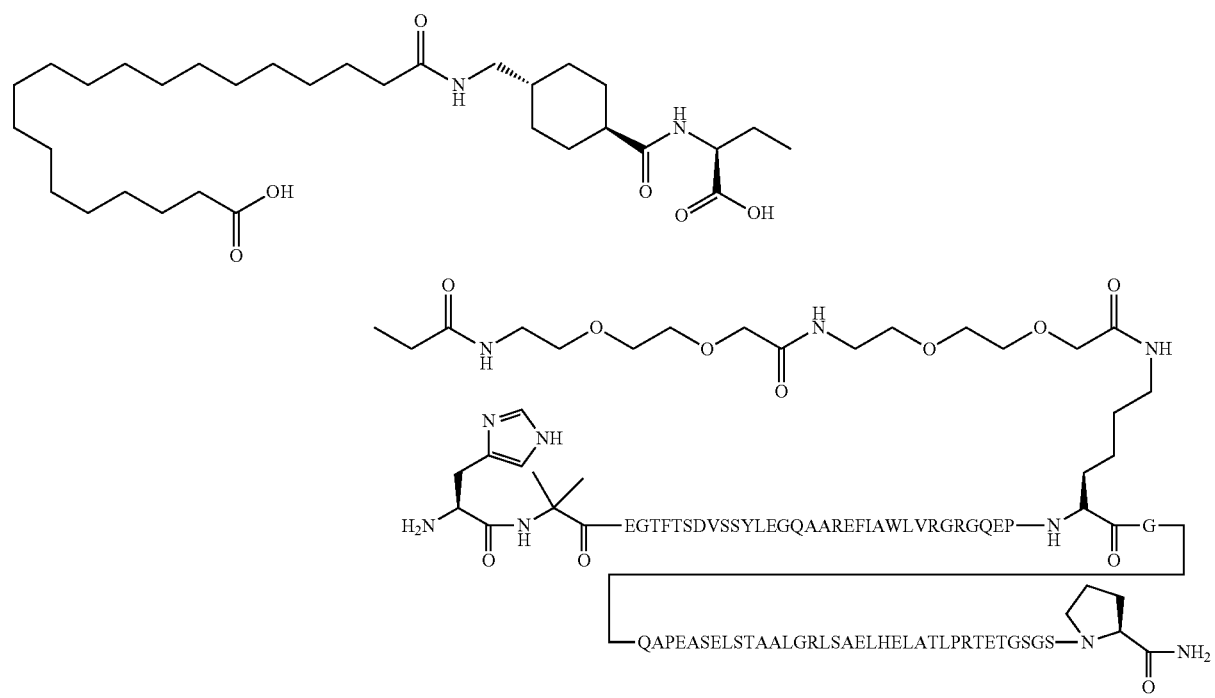

$C_{374}H_{599}N_{101}O_{123}$
Molecular weight (average) calculated: 8478.3608 g/mol
mono isotopic mass: 8473.3721 g/mol
LCMS34: found $(M+5H)^{5+}$ 1696.5011 (most abundant)

The amino acid sequence of HXEGTFTSDVS-SYLEGQAAREFIAWLVRGRGQEPKGQAPEASEL-STAALGRLSAELHELATLPRTETGSGSP has SEQ ID NO: 137.

Compound 0552

H-Aib-EGTFTSDVSSYLEEQAAREFIAWLVRGR-K([[(2S)-2-amino-6-[[2-[2-[2-[[2-[2-[2-[(4S)-4-carboxy-4-(19-carboxynonadecanoylamino)butanoyl]amino]ethoxy]ethoxy]acetyl]amino]ethoxy]ethoxyacetyl]amino]hexanoyl])-GGGGEASELSTAALGRLSAELHELATLPRTETGSGSP-amide

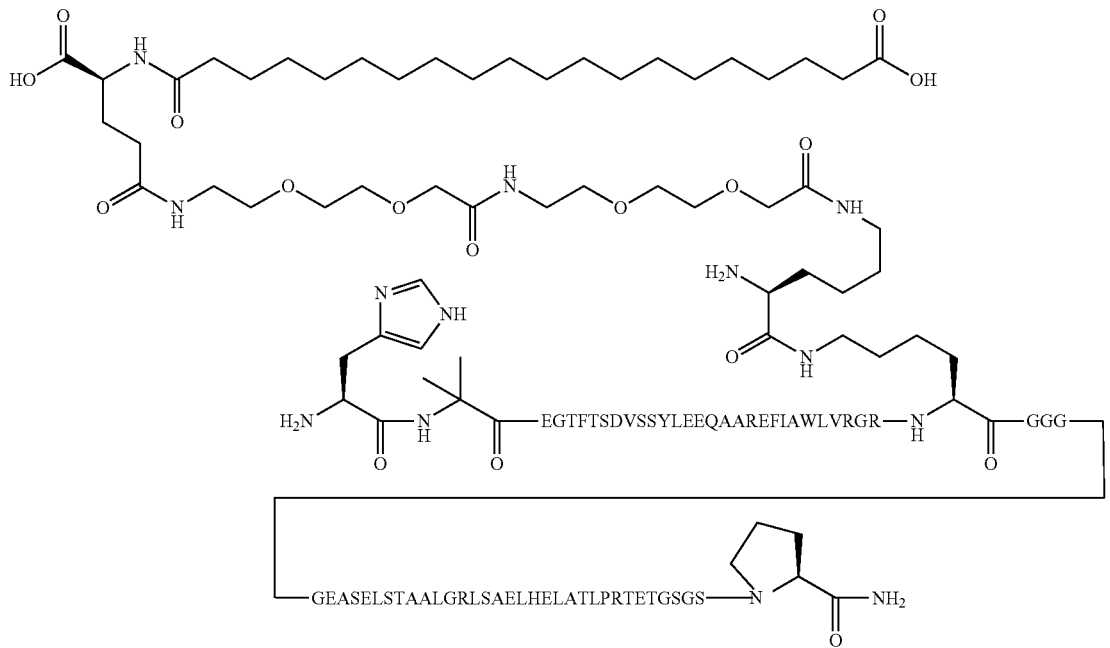

$C_{351}H_{566}N_{96}O_{117}$
Molecular weight (average) calculated: 8002.8227 g/mol
mono isotopic mass: 7998.1291 g/mol
LCMS34: found $(M+5H)^{5+}$ 1600.55 (mono isotopic)

The amino acid sequence of HXEGTFTSDVSSYLE-EQAAREFIAWLVRGRKGGGGEASELSTAALGRL-SAELHELATLPRTETGSGSP has SEQ ID NO: 153.

Compound 0560

HGEGTFTSDVSSYLEGQAA-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-EFIAWLVRGRGEASELSTAALGRLSAELHELA-TLPRTETGSGSP-amide

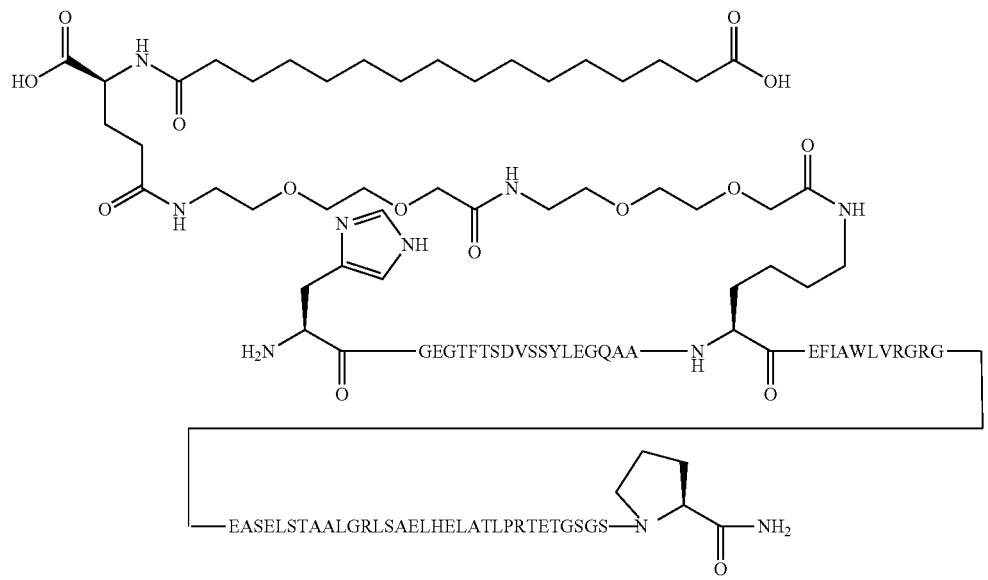

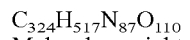

$C_{324}H_{517}N_{87}O_{110}$
Molecular weight (average) calculated: 7391.0887 g/mol
mono isotopic mass: 7386.7536 g/mol
LCMS34: found (M+5H)$^{5+}$ 1478.31 (mono isotopic)
The amino acid sequence of HGEGTFTSDVS-SYLEGQAAKEFIAWLVRGRGEASELSTAALGRL-SAELHELATLPRTETGSGSP has SEQ ID NO: 223.
Compound 0561
H-Aib-EGTFTSDVSSYLEEQAAR-K([2-[2-[2-[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl])-FIAWLVRGRGGGGGEASELSTAALGRLSAELHELATL-PRTETGSGSP-amide

$C_{350}H_{563}N_{95}O_{115}$
Molecular weight (average) calculated: 7941.7827 g/mol
mono isotopic mass: 7937.1127 g/mol
LCMS01: found (M+5H)$^{5+}$ 1589.3 (most abundant)
The amino acid sequence of HXEGTFTSDVSSYLE-EQAARKFIAWLVRGRGGGGGEASELSTAALGRL-SAELHELATLPRTETGSGSP has SEQ ID NO: 224.
Compound 0562
H-Aib-EGTFTSDVSSYLEEQAAR-K([2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl])-FIAWLVRGRGGGGGEASELSTAALGRLSAELHELATL-PRTETGSGSP-amide

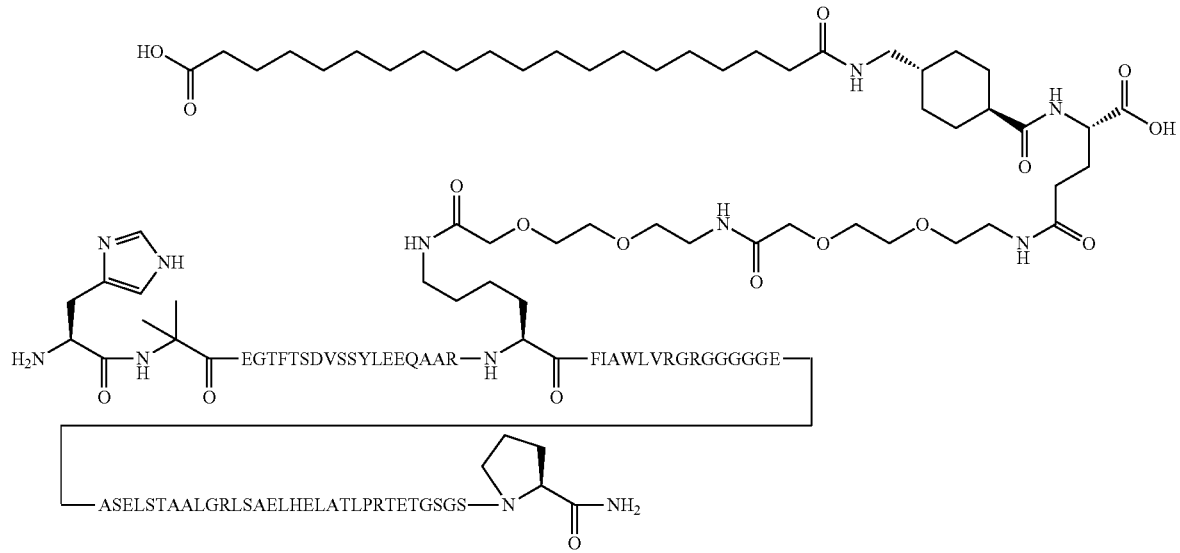

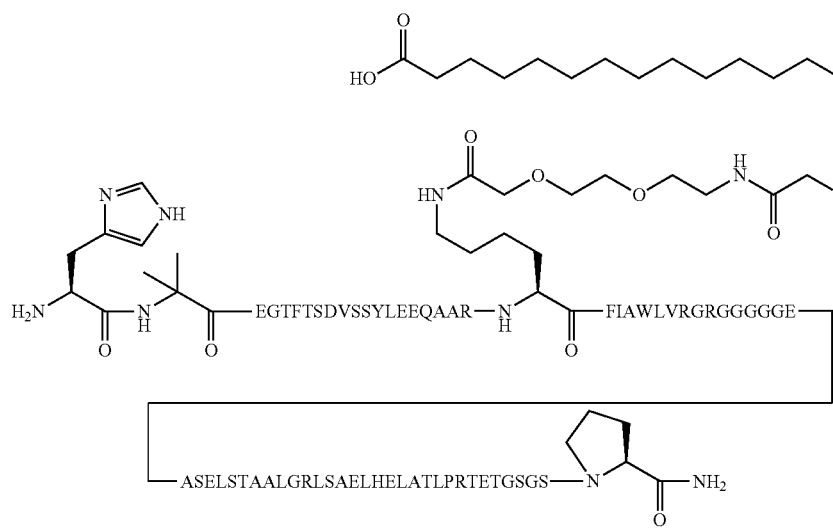

$C_{342}H_{550}N_{94}O_{114}$
Molecular weight (average) calculated: 7802.5878 g/mol
mono isotopic mass: 7798.0130 g/mol
LCMS01: found $(M+5H)^{5+}$1561.5 (most abundant)
The amino acid sequence of HXEGTFTSDVSSYLE-EQAARKFIAWLVRGRGGGGGEASELSTAALGRL-SAELHELATLPRTETGSGSP has SEQ ID NO: 224.
Compound 0564
H-Aib-EGTFTSDVS-K([2-[2-[2-[[(2S)-2,6-bis[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl]amino]hexanoyl]amino]ethoxy]ethoxy]acetyl])-YLEEQAAREFIAWLVRGRGGGGGEASELSTAA-LGRLSAELHELATLPRTETGSGSP-amide $C_{385}H_{624}N_{100}O_{131}$
Molecular weight (average) calculated: 8749.6655 g/mol
mono isotopic mass: 8744.5240 g/mol
LCMS34: found $(M+5H)^{5+}$1749.8 (mono isotopic)
The amino acid sequence of HXEGTFTSDVSKYLE-EQAAREFIAWLVRGRGGGGGEASELSTAALGRL-SAELHELATLPRTETGSGSP has SEQ ID NO: 221.
Compound 0565
H-Aib-EGTFTSDVS-K([2-[2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl])-YLE-EQAAREFIAWLVRGRGGGGGEASELSTAALGRLS-AELHELATLPRTETGSGSP-amide

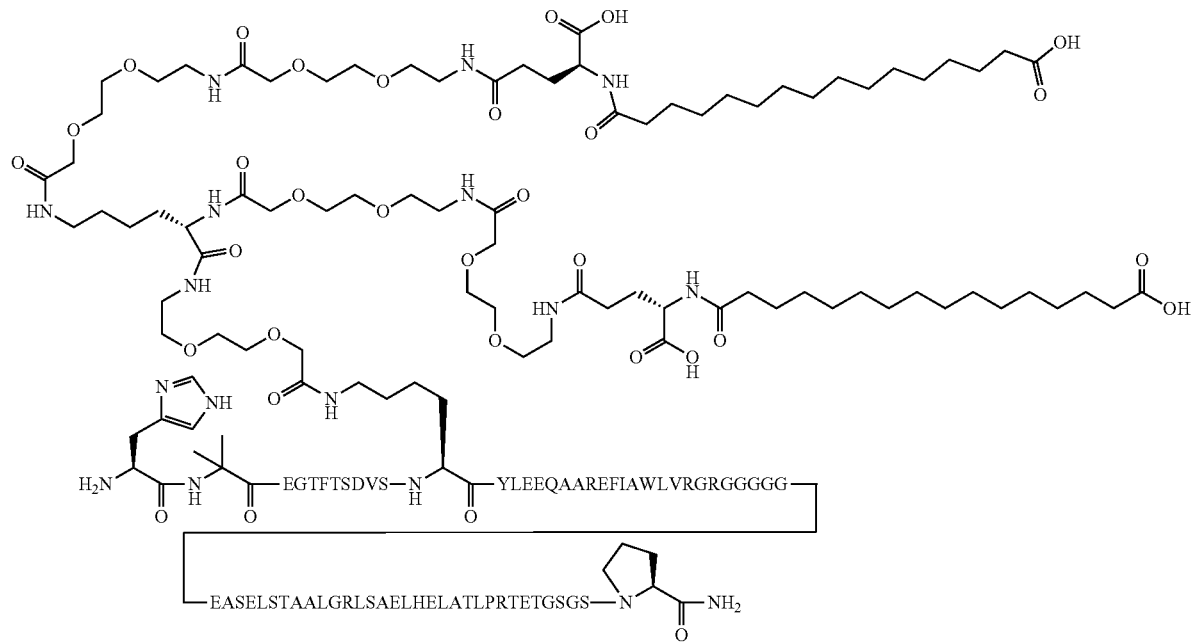

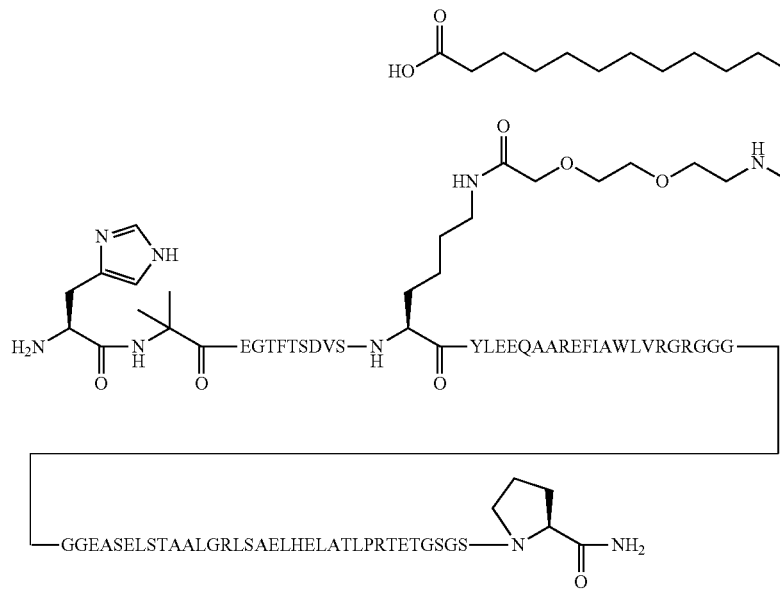
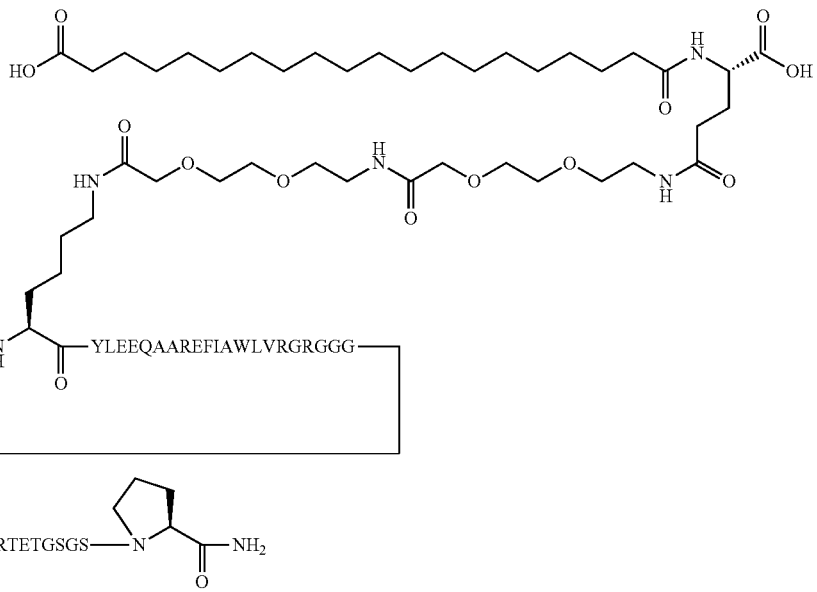

$C_{344}H_{552}N_{94}O_{115}$
Molecular weight (average) calculated: 7844.6245 g/mol
mono isotopic mass: 7840.0235 g/mol
LCMS34: found (M+5H)$^{5+}$1568.89 (mono isotopic)
The amino acid sequence of HXEGTFTSDVSKYLE-EQAAREFIAWLVRGRGGGGGEASELSTAALGRL-SAELHELATLPRTETGSGSP has SEQ ID NO: 221.
Compound 0575
H-Aib-EGTFTSDVS-K([2-[2-[2-[[2-[2-[2-[(4S)-4-carboxy-4-(15-carboxypentadecanoylamino)butanoyl]amino]ethoxy]ethoxy]acetyl]amino]ethoxy]ethoxy]acetyl])-YLE-EQAAR-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-FIAWLVRGROEGGGGGASELSTAALGRLSAELH-ELATLPRTETGSGSP-amide $C_{379}H_{614}N_{100}O_{127}$
Molecular weight (average) calculated: 8603.5243 g/mol
mono isotopic mass: 8598.4661 g/mol
LCMS34: found (M+5H)$^{5+}$1721.5 (most abundant)
The amino acid sequence of HXEGTFTSDVSKYLE-EQAARKFIAWLVRGRQEGGGGGASELSTAALGRL-SAELHELATLPRTETGSGSP has SEQ ID NO: 225.
Compound 0576
H-Aib-EGTFTSDVS-K([2-[2-[2-[[2-[2-[2-[(4S)-4-carboxy-4-(15-carboxypentadecanoylamino)butanoyl]amino]ethoxy]ethoxy]acetyl]amino]ethoxy]ethoxy]acetyl])-YLE-EQAAR-K([2-[2-[2-[[2-[2-[2-[[(4S)-4-carboxy-4-(15-carboxypentadecanoylamino)butanoyl]amino]ethoxy]ethoxy)acetyl]amino]ethoxy]ethoxy]acetyl])-FIEWLVRGRGEGGGGGASELSTAALGRLSAELHE-LATLPRTETGSGSP-amide

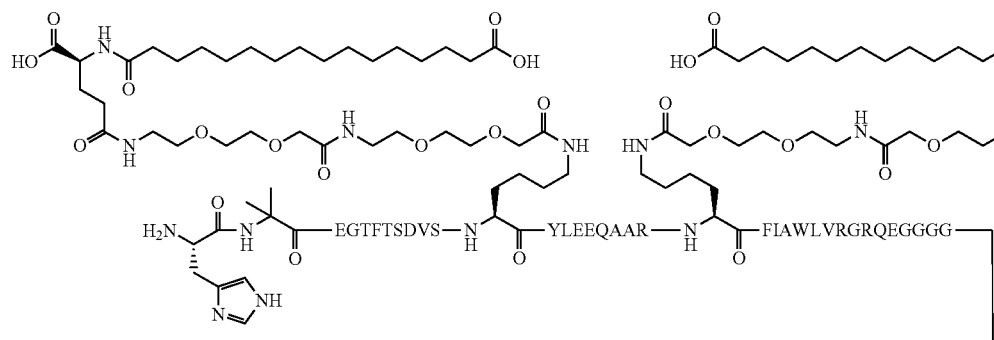
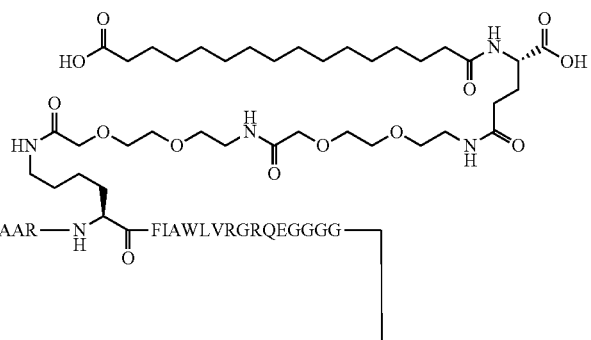

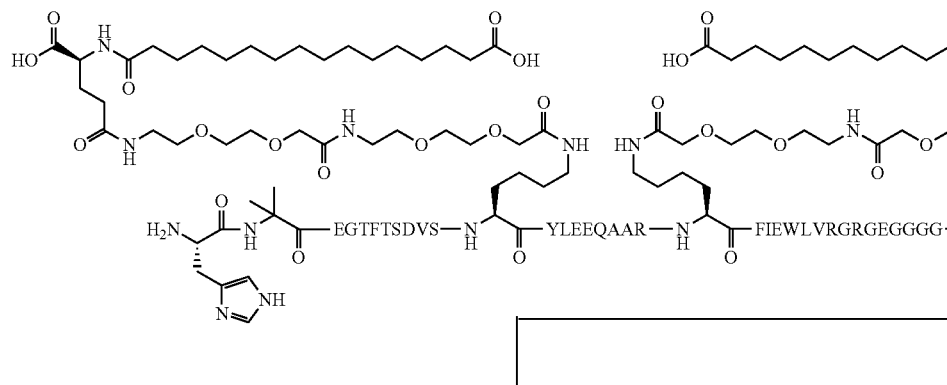

$C_{383}H_{619}N_{99}O_{130}$
Molecular weight (average) calculated: 8590.4824 g/mol
mono isotopic mass: 8585.4345 g/mol
LCMS34: found $(M+5H)^{5+}1719.1$ (most abundant)
The amino acid sequence of HXEGTFTSDVSKYLE-EQAARKFIEWLVRGRGEGGGGGASELSTAALGRL-SAELHELATLPRTETGSGSP has SEQ ID NO: 226.
Compound 0577
H-Aib-EGTFTSDVS-K([2-[2-[2-[[2-[2-[2-[(4S)-4-carboxy-4-(15-carboxypentadecanoylamino)butanoyl]amino]ethoxy]ethoxy]acetyl]amino]ethoxy]ethoxy]acetyl])-YLEEQAAR-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-FIEWLVRGRGEASELSTAALGRLSAELHELATLPRTETGSGSP-amide

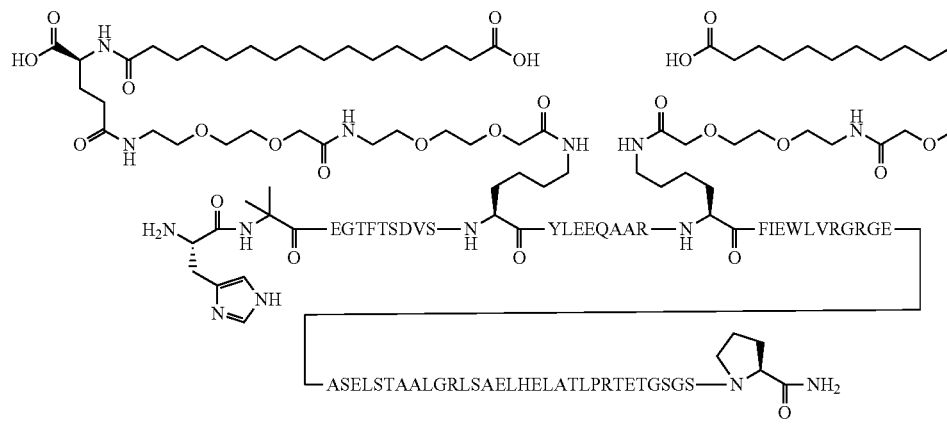

$C_{368}H_{596}N_{94}O_{123}$
Molecular weight (average) calculated: 8305.2258 g/mol
mono isotopic mass: 8300.3272 g/mol
LCMS34: found $(M+5H)^{5+}1661.9$ (most abundant)
The amino acid sequence of HXEGTFTSDVSKYLE-EQAARKFIEWLVRGRGEASELSTAALGRLSAEL-HELATLPRTETGSGSP has SEQ ID NO: 227.
Compound 0578
H-Aib-EGTFTSDVS-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-YLEEQAAR-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-FIAWLVRGRQEASELSTAALGRLSAELHELATLPRTETGSGSP-amide 291 292

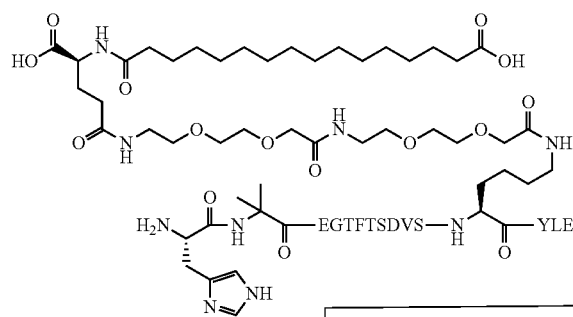
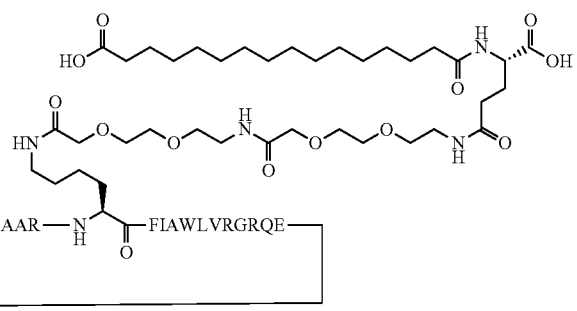

$C_{369}H_{599}N_{95}O_{122}$
Molecular weight (average) calculated: 8318.2677 g/mol
mono isotopic mass: 8313.3588 g/mol
LCMS34: found $(M+5H)^{5+}$1664.5 (most abundant)
The amino acid sequence of HXEGTFTSDVSKYLE-EQAARKFIAWLVRGROEASELSTAALGRLSAEL-HELATLPRTETGSGSP has SEQ ID NO: 228.
Compound 0580
H-Aib-EGTFTSDVSSYLEEQAAR-K([2-[2-[2-[[2-[2-[2-[[(4S)-4-carboxy-4-(19-carboxynonadecanoylamino)bu-tanoyl]amino]ethoxy]ethoxy]acetyl]amino]ethoxy]ethoxy]acetyl])-FIAWLVRGGASELSTAALGRLSAELHE-LATLPRTETGSGSP-amide $C_{323}H_{519}N_{85}O_{106}$
Molecular weight (average) calculated: 7289.0829 g/mol
mono isotopic mass: 7284.7834 g/mol
LCMS01: found $(M+5H)^{5+}$1458.76 (most abundant)
The amino acid sequence of H-Aib-EGTFTSDVSSYLE-EQAARKFIAWLVRGGASELSTAALGRLSAEL-HELATLPRTETGSGSP has SEQ ID NO: 229.
Compound 0581
H-Aib-EGTFTSDVSSYLEEQAAR-K([2-[2-[2-[2-[2-[2-[[(4S)-4-carboxy-4-(19-carboxynonadecanoylamino)bu-tanoyl]amino]ethoxy]ethoxy]acetyl]amino]ethoxy]ethoxy]acetyl])-FIEWLVRGASELSTAALGRLS-AELHELATLPRTETGSGSP-amide

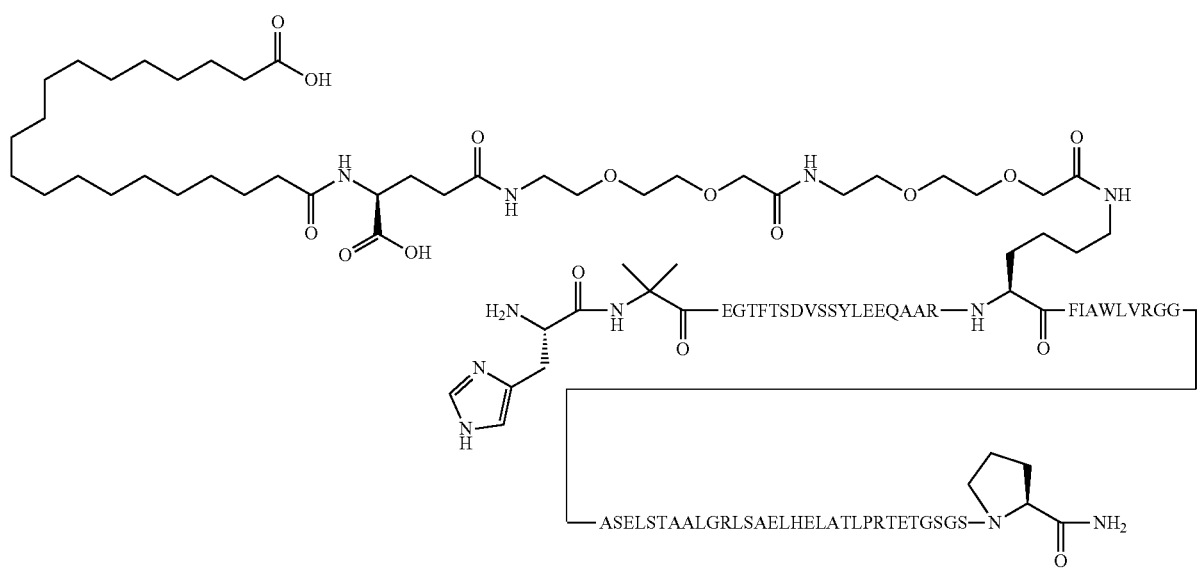

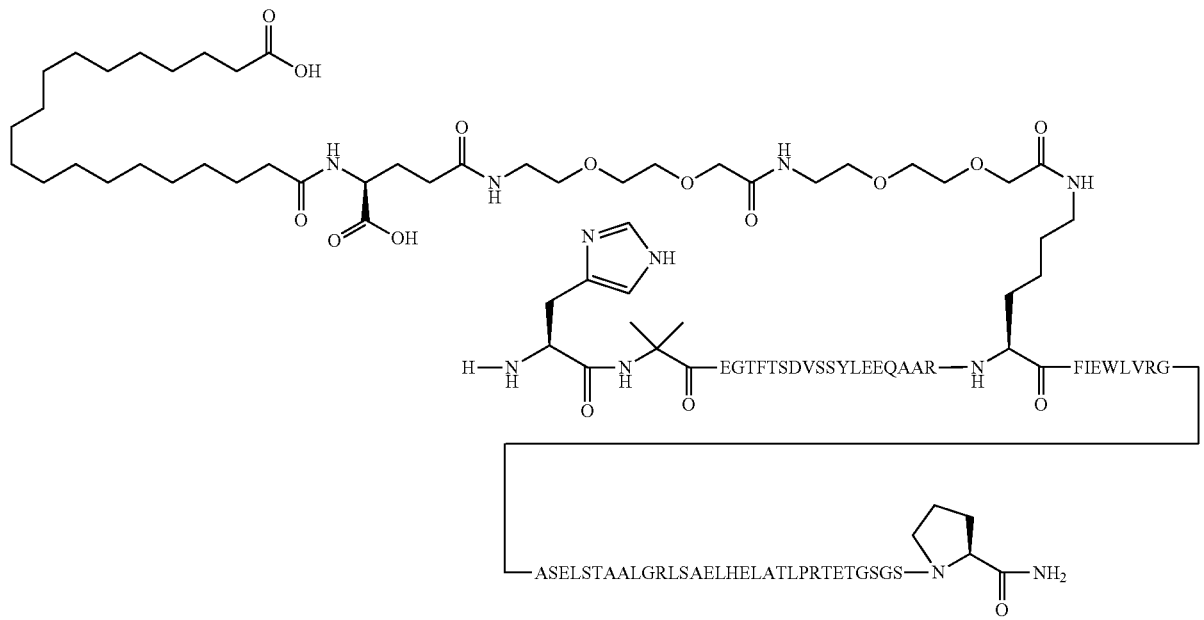

$C_{323}H_{518}N_{84}O_{107}$
Molecular weight (average) calculated: 7290.0676 g/mol
mono isotopic mass: 7285.7674 g/mol
LCMS01: found (M+5H)$^{5+}$1458.96 (most abundant)
The amino acid sequence of HXEGTFTSDVSSYLE-EQAARKFIEWLVRGASELSTAALGRLSAELHELATL-PRTETGSGSP has SEQ ID NO: 230.
Compound 0629
H-Aib-EGTFTSDVS-K([2-[2-[2-[[2-[2-[2-[(4S)-4-carboxy-4-(15-carboxypentadecanoylamino)butanoyl]amino]ethoxy]ethoxy]acetyl]amino]ethoxy]ethoxy]acetyl])-YLEEQAAR-K([2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]acetyl])-FIEWLVRGAAEASELSTAALGRLSAELHELATLPRTE-TGSGSP-amide $C_{383}H_{619}N_{99}O_{130}$
Molecular weight (average) calculated: 8234.1446 g/mol
mono isotopic mass: 8229.2788 g/mol
LCMS01: found (M+5H)$^{5+}$1647.55 (most abundant)
The amino acid sequence of HXEGTFTSDVSKYLE-EQAARKFIEWLVRGAAEASELSTAALGRLSAEL-HELATLPRTETGSGSP has SEQ ID NO: 231.
Compound 0630
H-Aib-EGTFTSDVS-K(6-[[(4S)-4-4-carboxy-4-[[4S)-4-(15-carboxypentadecanoylamino)butanoyl]amino]butanoyl]amino]hexanoyl)-YLEEQAAR-K(6-[[(4S)-4-carboxy-4-[[(4S)-4-carboxy-4-(15-carboxypentadecanoylamino)butanoyl]amino]butanoyl]amino]hexanoyl)-FIEWLVRGAAEASELSTAALGRLSAELHELAT-LPRTETGSGSP-amide

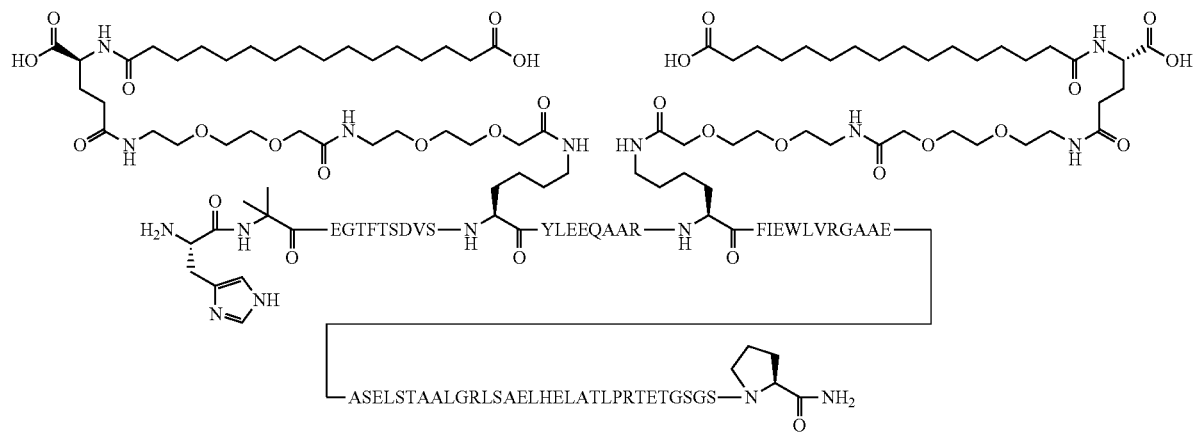

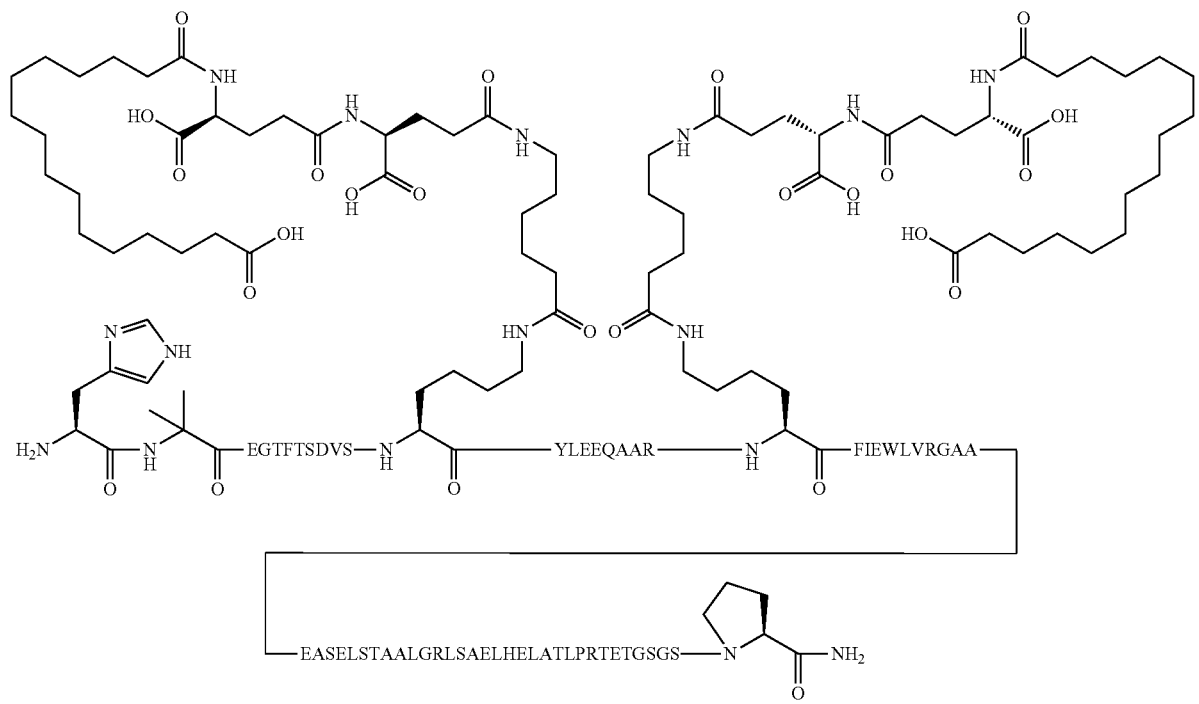

$C_{364}H_{583}N_{91}O_{119}$

Molecular weight (average) calculated: 8138.0621 g/mol mono isotopic mass: 8133.2365 g/mol LCMS01: found $(M+5H)^{5+}$ 1628.55 (most abundant)

The amino acid sequence of HXEGTFTSDVSKYLEEQAARKFIEWLVRGAAEASELSTAALGRLSAELHELATLPRTETGSGSP has SEQ ID NO: 231.

Compound 0631

H-Aib-EGTFTSDVS-K([(4S)-4-carboxy-4-[[(4S)-4-carboxy-4-[[(4S)-4-carboxy-4-[[(4S)-4-carboxy-4-(15-carboxypentadecanoylamino)butanoyl]amino]butanoyl]amino]butanoyl]amino]butanoyl])-YLEEQAAR-K([(4S)-4-carboxy-4-[[(4S)-4-carboxy-4-[[(4S)-4-carboxy-4-[[(4S)-4-carboxy-4-(15-carboxypentadecanoylamino)butanoyl]amino]butanoyl]amino]butanoyl])-FIEWLVRGAAEASELSTAALGRLSAELHELATLPRTETGSGSP- amide

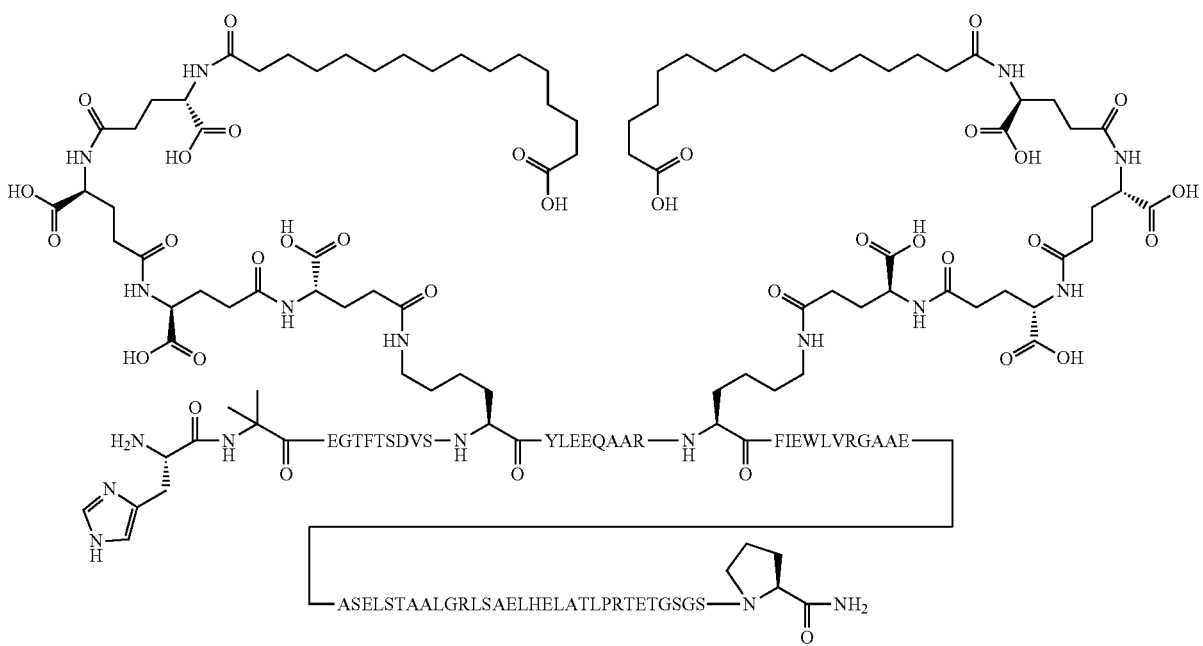

$C_{372}H_{589}N_{93}O_{129}$
Molecular weight (average) calculated: 8428.2028 g/mol
mono isotopic mass: 8423.2388 g/mol
LCMS34: found $(M+5H)^{5+}$1686.7 (most abundant)
The amino acid sequence of HXEGTFTSDVSKYLE-EQAARKFIEWLVRGAAEASELSTAALGRLSAEL-HELATLPRTETGSGSP has SEQ ID NO: 231.

Compound 0632

H-Aib-EGTFTSDVS-K([(4S)-4-carboxy-4[[(4S)-4-carboxy-4-[[(4S)-4-carboxy-4-[(4S)-4-carboxy-4(19-carboxynonadecanoylamino)butanoyl]amino]butanoyl]amino]butanoyl]amino]butanoyl])-YLEEQAAREFIEWLVRGAAEASELSTAALGRLSAE-LHELATLPRTETGSGSP-amide

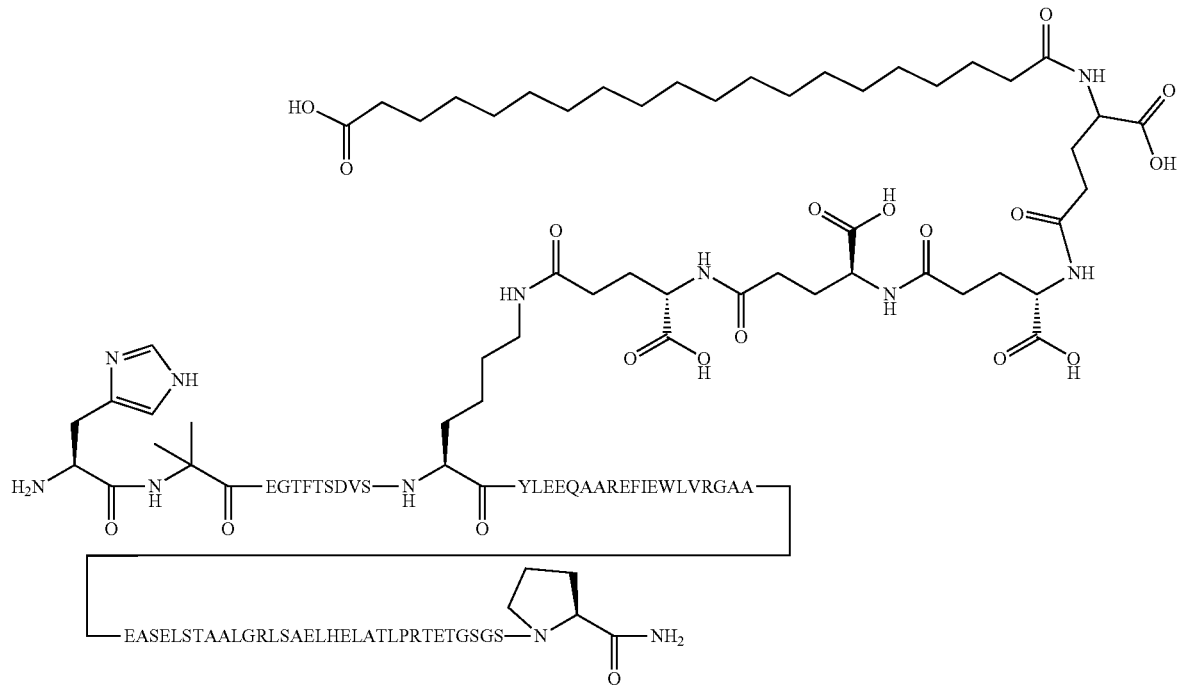

$C_{339}H_{536}N_{88}O_{116}$
Molecular weight (average) calculated: 7700.4031 g/mol
mono isotopic mass: 7695.8748 g/mol
LCMS34: found $(M+5H)^{5+}$1541.1 (most abundant)
The amino acid sequence of HXEGTFTSDVSKYLE-EQAAREFIEWLVRGAAEASELSTAALGRLSAEL-HELATLPRTETGSGSP has SEQ ID NO: 232.

Compound 0633

H-Aib-EGTFTSDVSSYLEEQAAR-K([(4S)-4-carboxy-4-[[(4S)-4-carboxy-4-[(4S)-4-carboxy-4-[[(4S)-4-carboxy-4-(19-carboxynonadecanoylamino)butanoyl]amino]butanoyl]amino]butanoyl]amino]butanoyl])-FIAWLVRGRGGGGGEASELSTAALGRLSAELH-ELATLPRTETGSGSP-amide

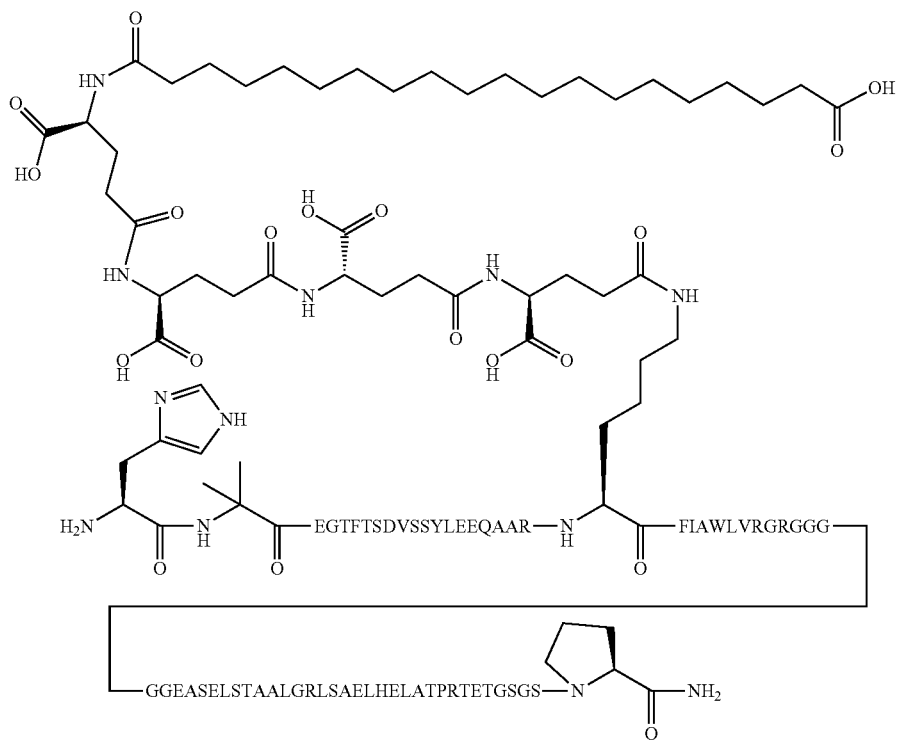

$C_{345}H_{549}N_{95}O_{117}$

Molecular weight (average) calculated: 7899.6169 g/mol mono isotopic mass: 7894.9930 g/mol LCMS34: found $(M+5H)^{5+}$ 1580.9 (most abundant)

The amino acid sequence of HXEGTFTSDVSSYLEEQAARKFIAWLVRGRGGGGGEASELSTAALGRLSAELHELATLPRTETGSGSP has SEQ ID NO: 224.

Compound 0634

H-Aib-EGTFTSDVS-K([(4S)-4-carboxy-4-[[(4S)-4-carboxy-4-[[(4S)-4-carboxy-4-[[(4S)-4-carboxy-4-(15-carboxypentadecanoylamino)butanoyl]amino]butanoyl]amino]butanoyl]amino]butanoyl])-YLEEQAAR-K([(4S)-4-carboxy-4-[[(4S)-4-carboxy-4-[[(4S)-4-carboxy-4-[[(4S)-4-carboxy-4-(15-carboxypentadecanoylamino)butanoyl]amino]butanoyl]amino]butanoyl])-FIAWLVRGRGEASELSTAALGRLSAELHELATLPRTETGSGSP-amide

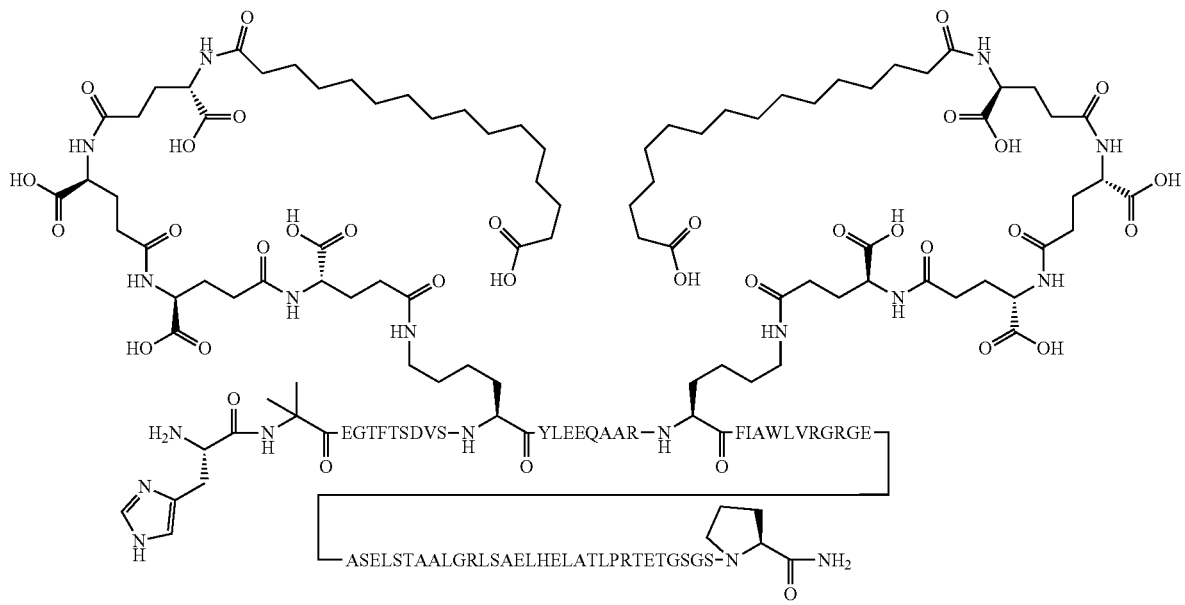

$C_{372}H_{592}N_{96}O_{127}$

Molecular weight (average) calculated: 8441.2479 g/mol mono isotopic mass: 8436.2817 g/mol LCMS34: found $(M+5H)^{5+}$1689.1 (most abundant)

The amino acid sequence of HXEGTFTSDVSKYLE-EQAARKFIAWLVRGRGEASELSTAALGRLSAEL-HELATLPRTETGSGSP has SEQ ID NO: 233.

Compound 0635

H-Aib-EGTFTSDVS-K([2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl])-YLE-EQAAR-K([2-[2-[2-[[2-[2-[2-[[4R)-4-carboxy 4-(13-carboxytridecanoylamino)butanoyl]amino]ethoxy]ethoxy]acetyl]amino]ethoxy]ethoxy]acetyl])-FIAWLVRGR-K([2-[2-[2-[[2-2[[(4S)-4-carboxy-4-(13-carboxytridecanoylamino)butanoyl]amino]ethoxy]ethoxy]acetyl]amino]ethoxy]ethoxy]acetyl])-GGEASELSTAALGRLSAELHELATLPRTETGSGSP-amide

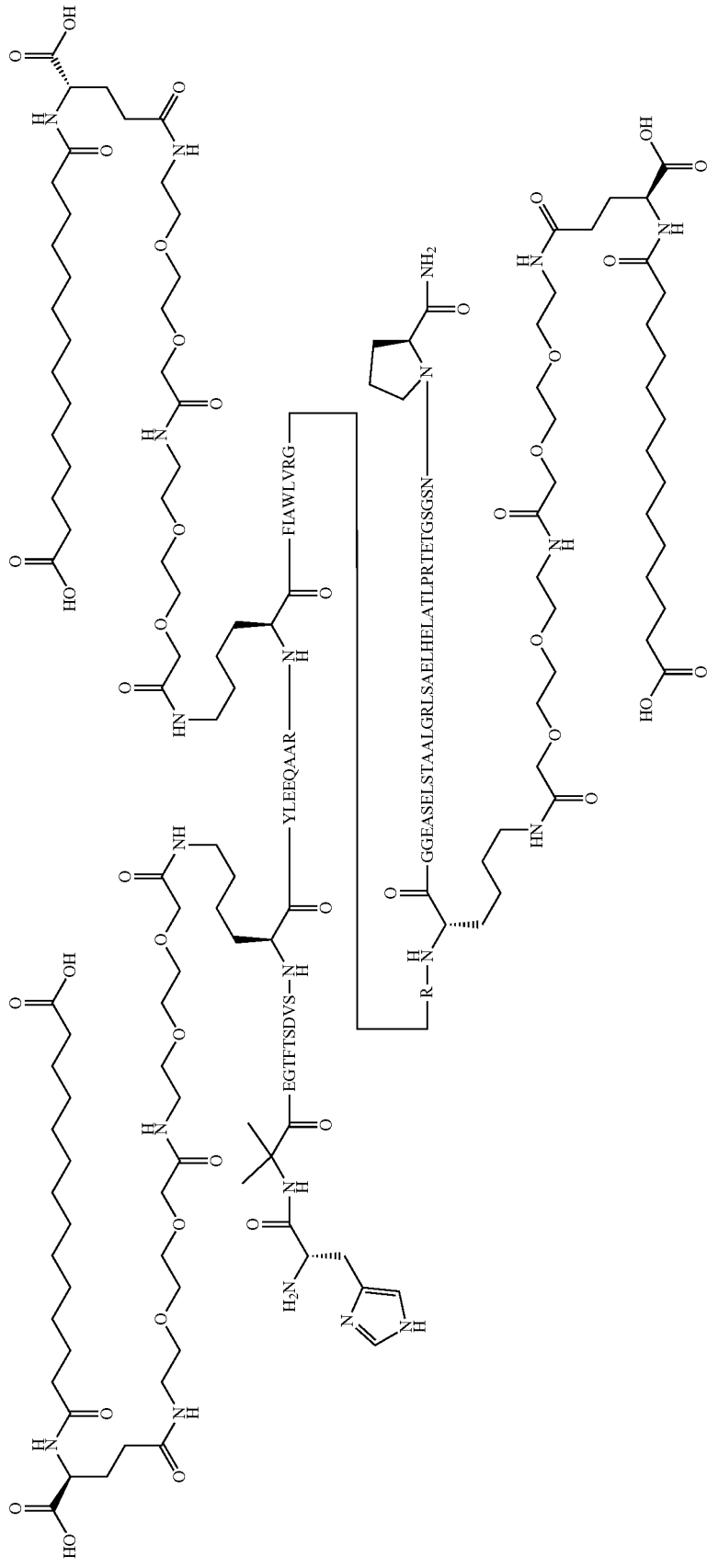

$C_{401}H_{654}N_{100}O_{135}$

Molecular weight (average) calculated: 9036.0725 g/mol mono isotopic mass: 9030.7384 g/mol LCMS34: found $(M+5H)^{5+}$ 1807.05 (mono isotopic)

The amino acid sequence of HXEGTFTSDVSKYLE-EQAARKFIAWLVRGRKGGEASELSTAALGRLSAEL-HELATLPRTETGSGSP has SEQ ID NO: 234.

Compound 0636

H-Aib-EGTFTSDVSSYLEEQAAR-K([2-[2-[2-[[2-[2-[2-[[(4S)-4-carboxy-4-[[(4S)-4-carboxy-4-[[(4S)-4-carboxy-4-(19-carboxynonadecanoylamino)butanoyl]amino]butanoyl]amino]butanoyl]amino]ethoxy]ethoxy]acetyl]amino]ethoxy]ethoxy]acetyl])-FIEWLVRGRQEAASELSTAALGRLSAELH-OLATLPRTETGSGSP-amide

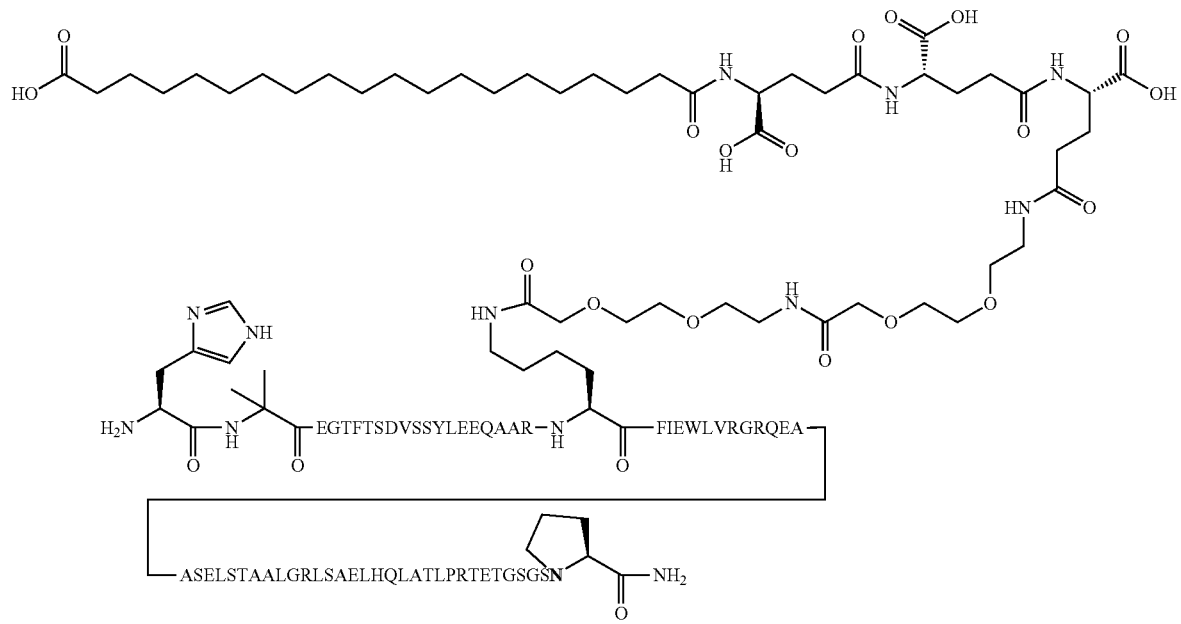

$C_{352}H_{565}N_{95}O_{119}$

Molecular weight (average) calculated: 8031.8176 g/mol mono isotopic mass: 8027.1080 g/mol LCMS34: found $(M+5H)^{5+}$ 1606.3 (mono isotopic)

The amino acid sequence of HXEGTFTSDVSSYLE-EQAARKFIEWLVRGRQEAASELSTAALGRLSAELHO-LATLPRTETGSGSP has SEQ ID NO: 235.

Compound 0637

H-Aib-EGTFTSDVSSYLEEQAAREFIAWLVRGR-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-GGGGSGGGEASELSTAALGRLSAELHELAT-LPRTETGSGSP-amide

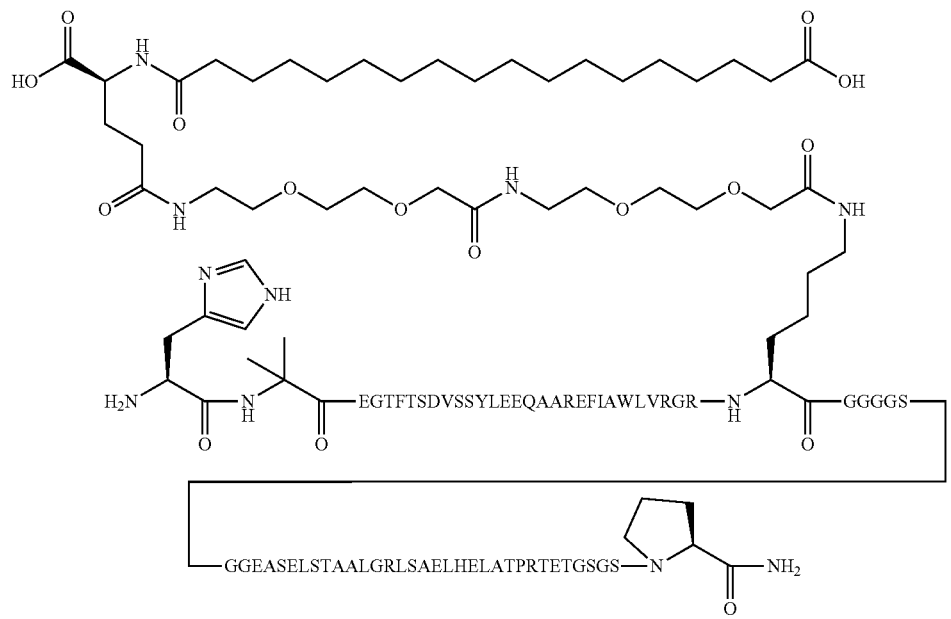

$C_{352}H_{564}N_{98}O_{121}$
Molecular weight (average) calculated: 8104.8286 g/mol
mono isotopic mass: 8100.0992 g/mol
LCMS_ZQ: found $(M+5H)^{5+}$1621.8 (most abundant)
The amino acid sequence of HXEGTFTSDVSSYLE-EQAAREFIAWLVRGRKGGGGSGGGEASELSTAAL-GRLSAELHELATLPRTETGSGSP has SEQ ID NO: 236.
Compound 0638
H-Aib-EGTFTSDVSSYLEEQAAREFIAWLVRGR-K([2-[2-[2-[[2-[2-[2-[(4S)-4-carboxy-4-(19-carboxynonade-canoylamino)butanoyl]amino]ethoxyethoxy]acetyl]amino]ethoxy]ethoxy]acetyl])-GGGGSGGGEASELSTAALGRLSAELHELATLP-RTETGSGSP-amide $C_{354}H_{568}N_{98}O_{121}$
Molecular weight (average) calculated: 8132.8817 g/mol
mono isotopic mass: 8128.1305 g/mol
LCMS_ZQ: found $(M+5H)^{5+}$1627.5 (most abundant)
The amino acid sequence of HXEGTFTSDVSSYLE-EQAAREFIAWLVRGRKGGGGSGGGEASELSTAAL-GRLSAELHELATLPRTETGSGSP has SEQ ID NO: 236.
Compound 0639
H-Aib-EGTFTSDVSSYLEEQAAR-K([2-[2-[2-[[2-[2-[2-[[(4S)-4-carboxy-4-(17-carboxyheptadecanoylamino)bu-tanoyl]amino]ethoxy]ethoxy]acetyl]amino]ethoxy]ethoxy]acetyl])-FIAWLVRGRGGGGEASELSTAALGRLSAELHELATL-PRTETGSGSP-amide

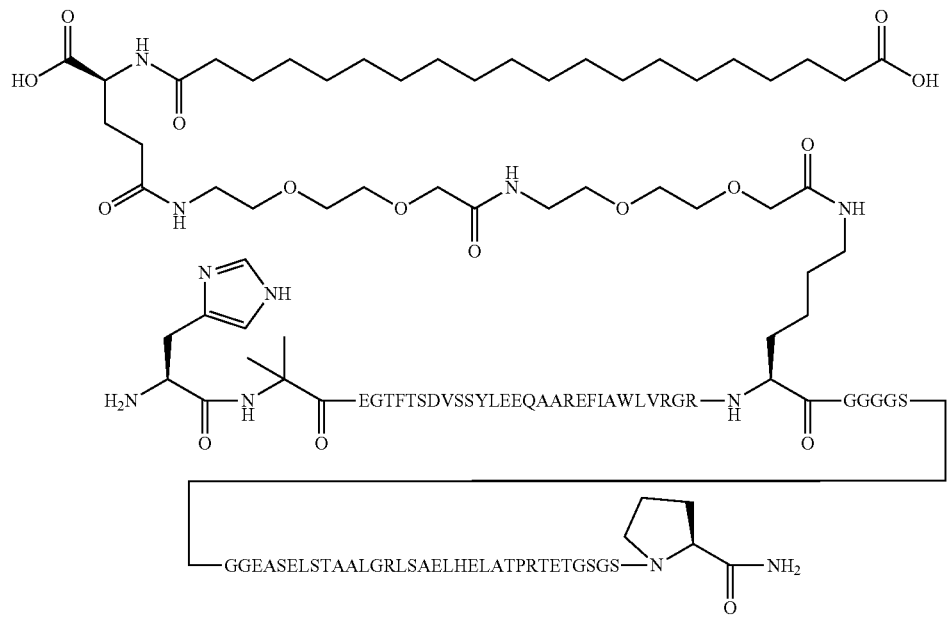

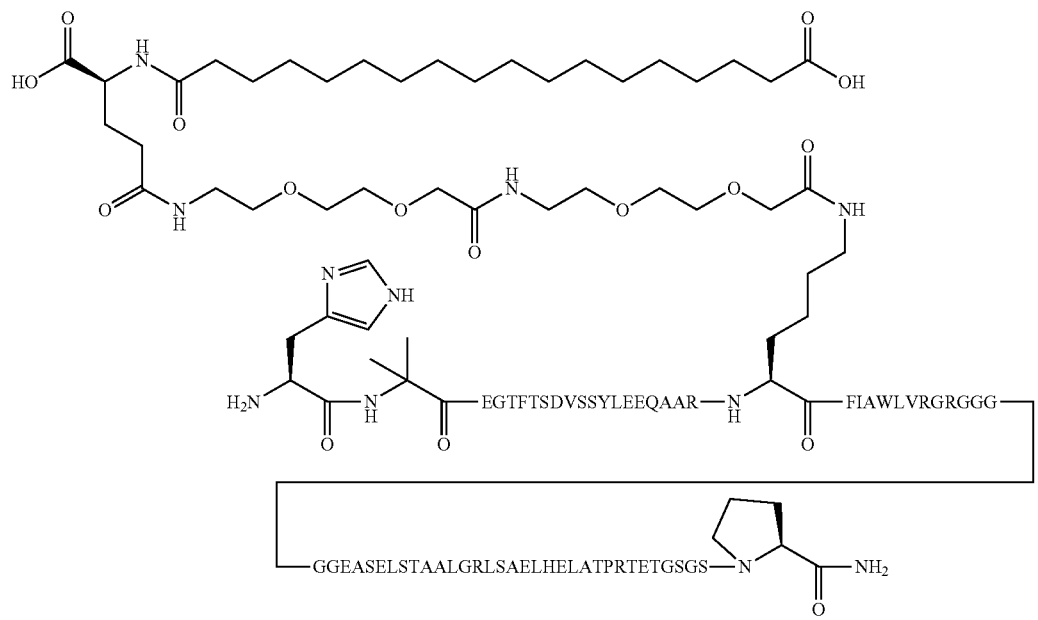

C<sub>340</sub>H<sub>564</sub>N<sub>94</sub>O<sub>114</sub>

$C_{340}H_{564}N_{94}O_{114}$

Molecular weight (average) calculated: 7774.5346 g/mol
mono isotopic mass: 7769.9817 g/mol
LCMS_ZQ: found (M+5H)$^{5+}$1556.0 (most abundant)
The amino acid sequence of HXEGTFTSDVSSYLE-EQAARKFIAWLVRGRGGGGGEASELSTAALGRL-SAELHELATLPRTETGSGSP has SEQ ID NO: 224.
Compound 0640
H-Aib-EGTFTSDVS-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-YLE-EQAAREFIAWLVRGRGGGGGEASELSTAALGRLSA-ELHELATLPRTETGSGSP-amide $C_{383}H_{619}N_{99}O_{130}$ Molecular weight (average) calculated: 7816.5713 g/mol
mono isotopic mass: 7811.9922 g/mol
LCMS34: found (M+5H)$^{5+}$1564.3 (most abundant)
The amino acid sequence of HXEGTFTSDVSKYLE-EQAAREFIAWLVRGRGGGGGEASELSTAALGRL-SAELHELATLPRTETGSGSP has SEQ ID NO: 221.
Compound 0648
HWEGTFTSDVSSYLEEQAAREFIAWLVRGR-K([2-[2-[2-[[2-[2-[2-[[(4S)-4-carboxy-4-(17-carboxyheptadecanoylamino)butanoyl]amino]ethoxy]ethoxy]acetyl]amino]ethoxyethoxy]acetyl])-GGGGEASELSTAALGRLSAELHELATLPRTETGSGSP-amide

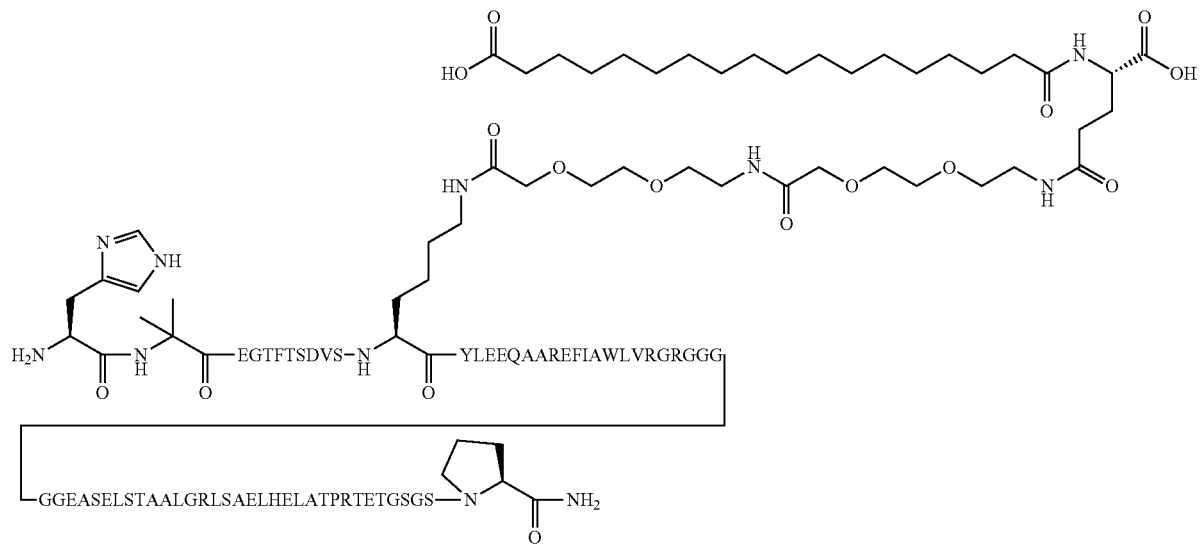

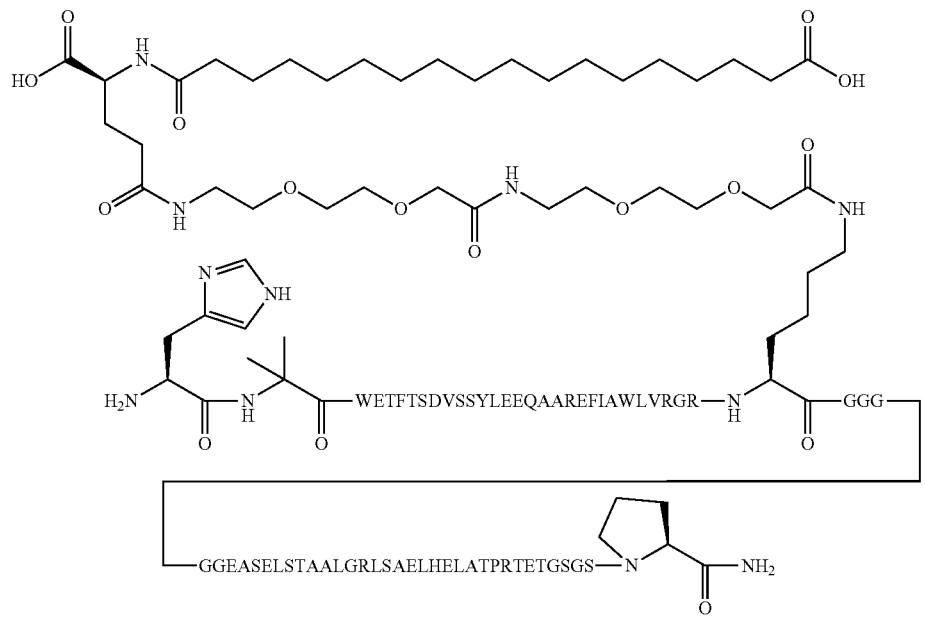

C₃₅₀H₅₅₃N₉₅O₁₁₆
Molecular weight (average) calculated: 7947.7027 g/mol
mono isotopic mass: 7943.0293 g/mol
LCMS34: found (M+5H)$^{5+}$1590.5 (most abundant)
The amino acid sequence of HWEGTFTSDVSSYLE-EQAAREFIAWLVRGRKGGGGEASELSTAALGRL-SAELHELATLPRTETGSGSP has SEQ ID NO: 185.
Compound 0654
H-Aib-EGTFTSDVSSYLEEQAAREFIAWLVRGR-K([2-[2-[2-[[2-[2-[2-[[(4S)-4-carboxy-4-(16-sulfohexadecanoylamino)butanoyl]amino]ethoxy]ethoxy]acetyl]amino]ethoxy]ethoxy]acetyl])-GGGGEASELSTAALGRLSAELHELATLPRTETGSGSP-amide C₃₄₁H₅₄₈N₉₄O₁₁₇ S
Molecular weight (average) calculated: 7868.6244 g/mol
mono isotopic mass: 7863.9541 g/mol
LCMS34: found (M+5H)$^{5+}$1573.79 (most isotopic)
The amino acid sequence of HXEGTFTSDVSSYLE-EQAAREFIAWLVRGRKGGGGEASELSTAALGRL-SAELHELATLPRTETGSGSP has SEQ ID NO: 153.
Compound 0655
H-Aib-EGTFTSDVSSYLEEQAAREFIAWLVRGR-K([2-[-2-[[2-[2-[2-[[(4S)-4-carboxy-4-[17-(1H-tetrazol-5-yl)heptadecanoylamino]butanoyl]amino]ethoxy]ethoxy]acetyl]amino]ethoxy]ethoxy]acetyl])-GGGGEASELSTAALGRLSAELHELATLPRTETGSGSP-amide

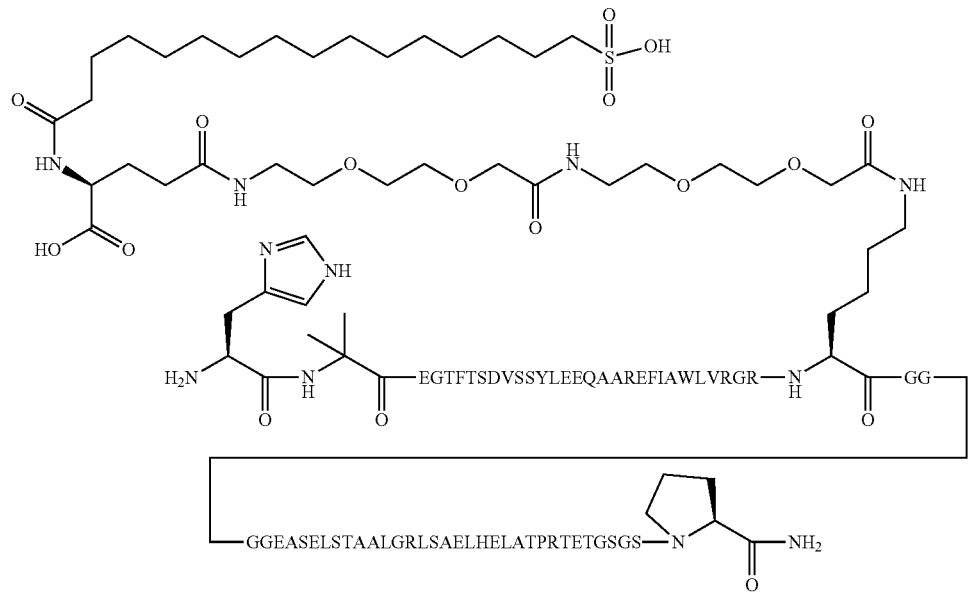

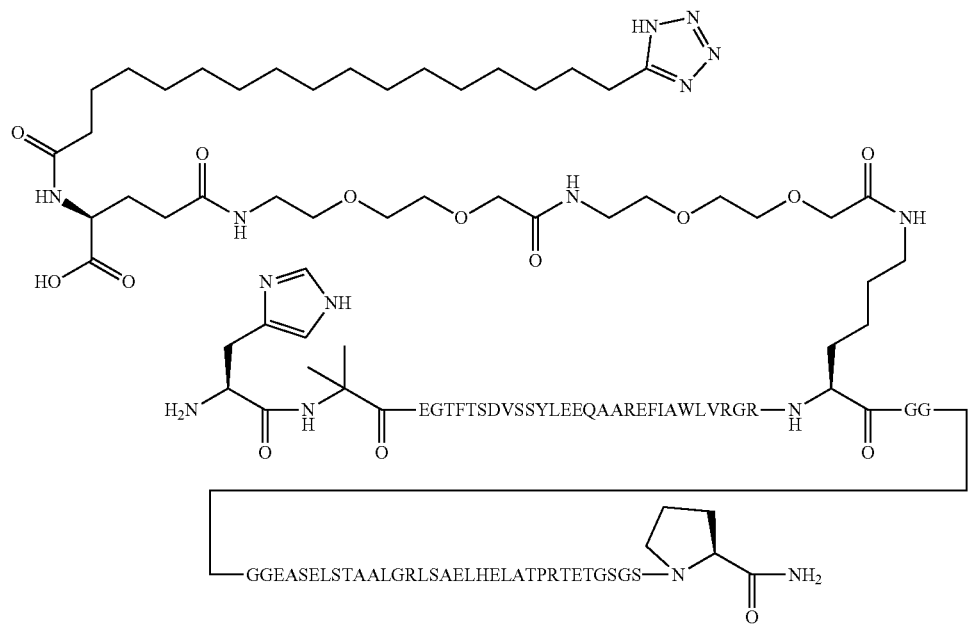

$C_{343}H_{550}N_{98}O_{114}$
Molecular weight (average) calculated: 7870.6253 g/mol
mono isotopic mass: 7866.0253 g/mol LCMS34: found $(M+5H)^{5+}$1574.2 (mono isotopic)

The amino acid sequence of HXEGTFTSDVSSYLE-EQAAREFIAWLVRGRKGGGGEASELSTAALGRL-SAELHELATLPRTETGSGSP has SEQ ID NO: 153.

Compound 0656

H-Aib-EGTFTSDVSSYLEEQAAREFIAWLVRGR-K ([(2S)-2-amino-6-[[(2S)-2-amino-6-[(4S)-4-carboxy-4-(17-carboxyheptadecanoylamino)butanoyl]amino]hexanoyl] amino]hexanoyl])-GGGGEASELSTAALGRLSAELHELATLPRTETGSGSP-amide

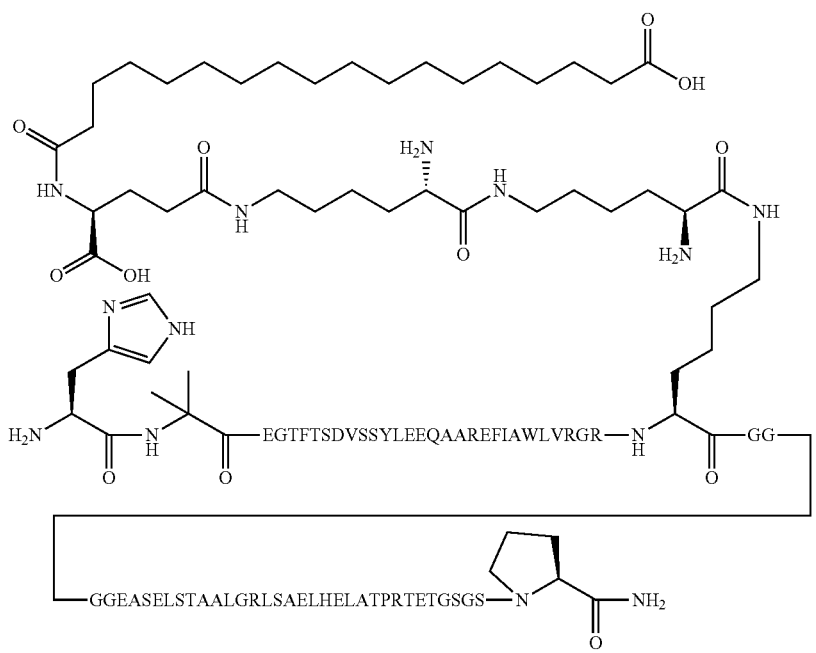

$C_{343}H_{552}N_{96}O_{112}$
Molecular weight (average) calculated: 7812.6290 g/mol
mono isotopic mass: 7808.0449 g/mol LCMS34: found $(M+5H)^{5+}$1562.61 (mono isotopic)

The amino acid sequence of HXEGTFTSDVSSYLE-EQAAREFIAWLVRGRKGGGGEASELSTAALGRL-SAELHELATLPRTETGSGSP has SEQ ID NO: 153.

Compound 0657

H-Aib-EGTFTSDVSSYLEEQAAREFIAWLVRGR-K([[(2S)-2-amino-6-[[(2S)-2-amino-6-[[(4S)-4-carboxy-4-(19-carboxynonadecanoylamino)butanoyl]amino]hexanoyl]amino]hexanoyl])-GGGGEASELSTAALGRLSAELHELATLPRTETGSGSP-amide

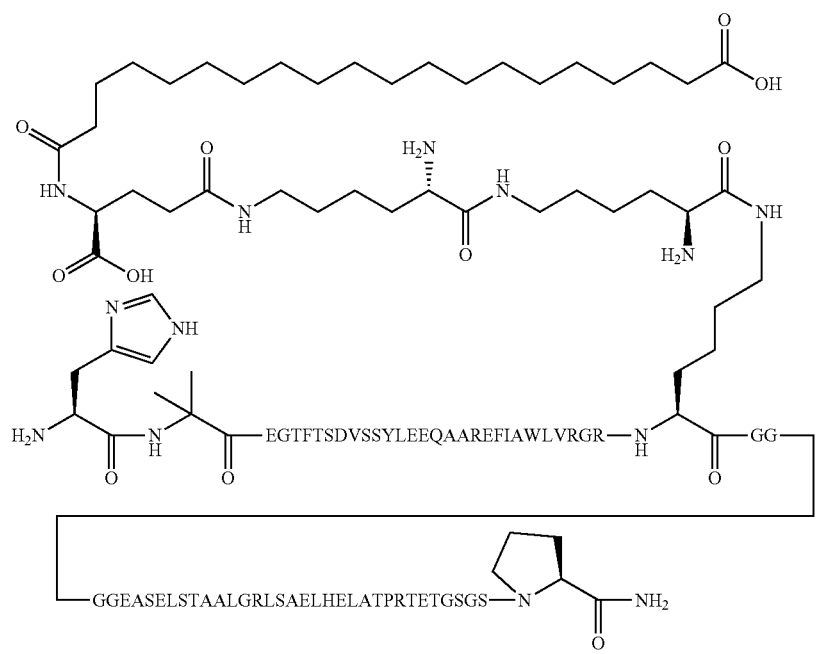

$C_{345}H_{556}N_{96}O_{112}$

Molecular weight (average) calculated: 7840.6821 g/mol mono isotopic mass: 7836.0762 g/mol LCMS34: found (M+5H)$^{5+}$1568.21 (mono isotopic)

The amino acid sequence of HXEGTFTSDVSSYLEEQAAREFIAWLVRGRKGGGGEASELSTAALGRLSAELHELATLPRTETGSGSP has SEQ ID NO: 153.

Compound 0658

H-Aib-EGTFTSDVSSYLEEQAAREFIAWLVRGR-K(6-[6-[[(4S)-4-carboxy-4-(17-carboxyheptadecanoylamino)butanoyl]amino]hexanoylamino]hexanoyl)-GGGGEASELSTAALGRLSAELHELATLPRTETGSGSP-amide

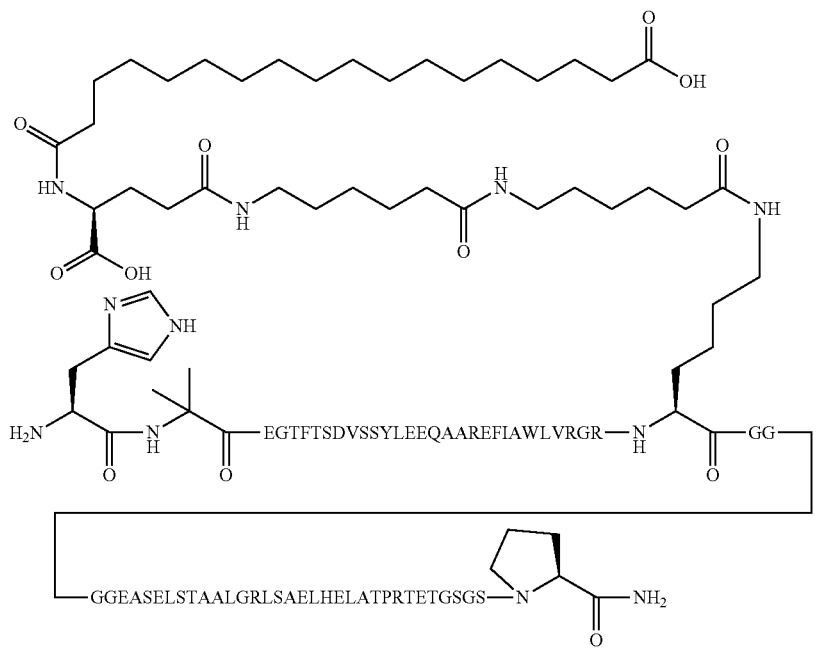

$C_{343}H_{550}N_{94}O_{112}$
Molecular weight (average) calculated: 7782.5997 g/mol
mono isotopic mass: 7778.0231 g/mol
LCMS34: found $(M+5H)^{5+}$1556.6 (mono isotopic)
The amino acid sequence of HXEGTFTSDVSSYLE-EQAAREFIAWLVRGRKGGGGEASELSTAALGRL-SAELHELATLPRTETGSGSP has SEQ ID NO: 153.
Compound 0659
H-Aib-EGTFTSDVSSYLEEQAAREFIAWLVRGR-K(6-[6-[[(4S)-4-carboxy-4-(19-carboxynonadecanoylamino)butanoyl]amino]hexanoylamino]hexanoyl)-GGGGEASEL-STAALGRLSAELHELATLPRTETGSGSP-amide $C_{345}H_{554}N_{94}O_{112}$
Molecular weight (average) calculated: 7810.6529 g/mol
mono isotopic mass: 7806.0544 g/mol
LCMS34: found $(M+5H)^{5+}$1562.21 (mono isotopic)
The amino acid sequence of HXEGTFTSDVSSYLE-EQAAREFIAWLVRGRKGGGGEASELSTAALGRL-SAELHELATLPRTETGSGSP has SEQ ID NO: 153.
Compound 0660
H-Aib-EGTFTSDVSSYLEEQAAREFIAWLVRGR-K([2-[2-[2-[[(4S)-4-carboxy-4-(17-carboxyheptadecanoylamino)butanoyl]amino]ethoxyethoxy]acetyl])-GGGGEA-SELSTAALGRLSAELHELATLPRTETGSGSP-amide

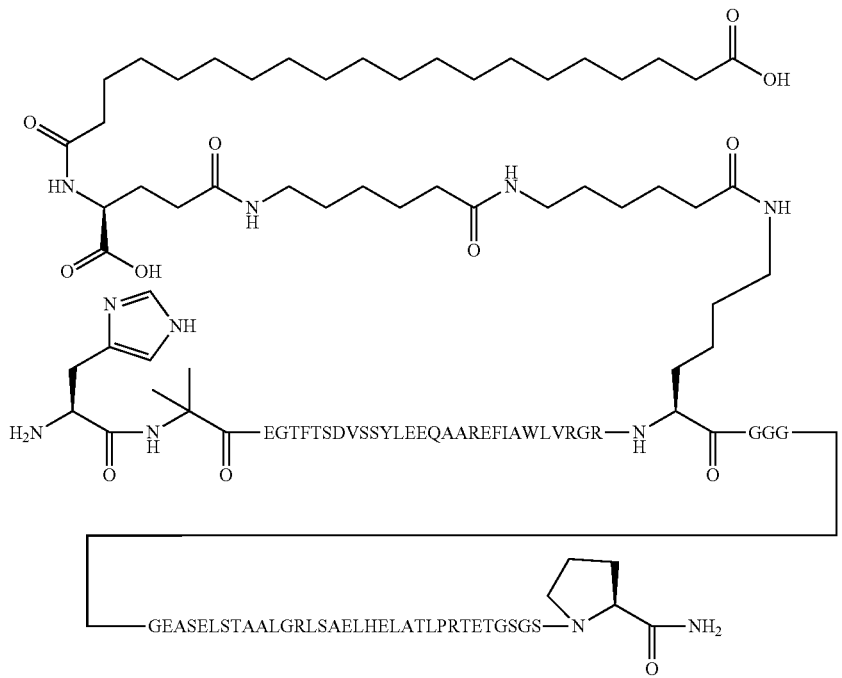

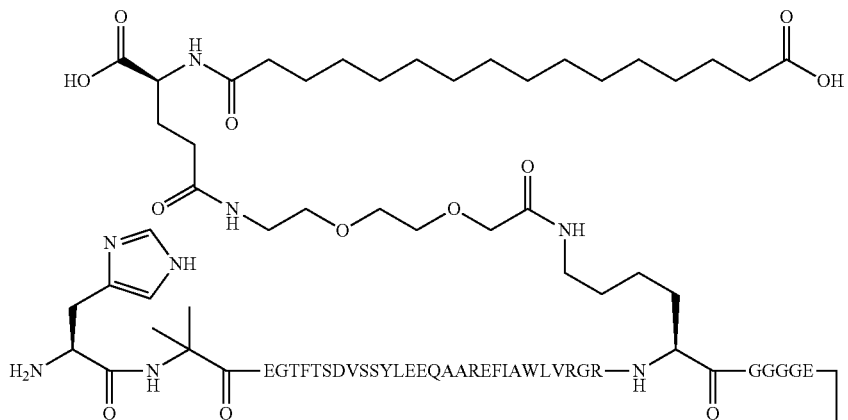

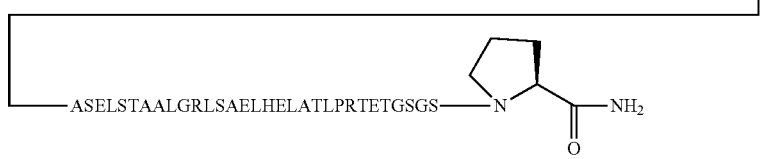

$C_{337}H_{539}N_{93}O_{113}$
Molecular weight (average) calculated: 7701.4409 g/mol
mono isotopic mass: 7696.9289 g/mol
LCMS34: found (M+5H)$^{5+}$1540.38 (mono isotopic)
The amino acid sequence of HXEGTFTSDVSSYLE-EQAAREFIAWLVRGRKGGGGEASELSTAALGRL-SAELHELATLPRTETGSGSP has SEQ ID NO: 153.
Compound 0661
H-Aib-EGTFTSDVSSYLEEQAAREFIAWLVRGR-K([2-[2-[2-[[2-[2-[2-[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]ethoxy]ethoxy]acetyl])-GGGGEASELSTAALGRLSAELHELATLPRTETGSGSP-amide $C_{349}H_{561}N_{95}O_{119}$
Molecular weight (average) calculated: 7991.7537 g/mol
mono isotopic mass: 7987.0767 g/mol
LCMS34: found (M+5H)$^{5+}$1598.41 (mono isotopic)
The amino acid sequence of HXEGTFTSDVSSYLE-EQAAREFIAWLVRGRKGGGGEASELSTAALGRL-SAELHELATLPRTETGSGSP has SEQ ID NO: 153.
Compound 0662
H-Aib-EGTFTSDVSSYLEEQAAREFIAWLVRGR-K([2-[2-[2-[[2-[2-[2-[2-[2-[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]ethoxy]ethoxy]etl xy]acetyl]-GGGGEASELSTAALGRLSAELHELATLPRTETGSGSP-amide

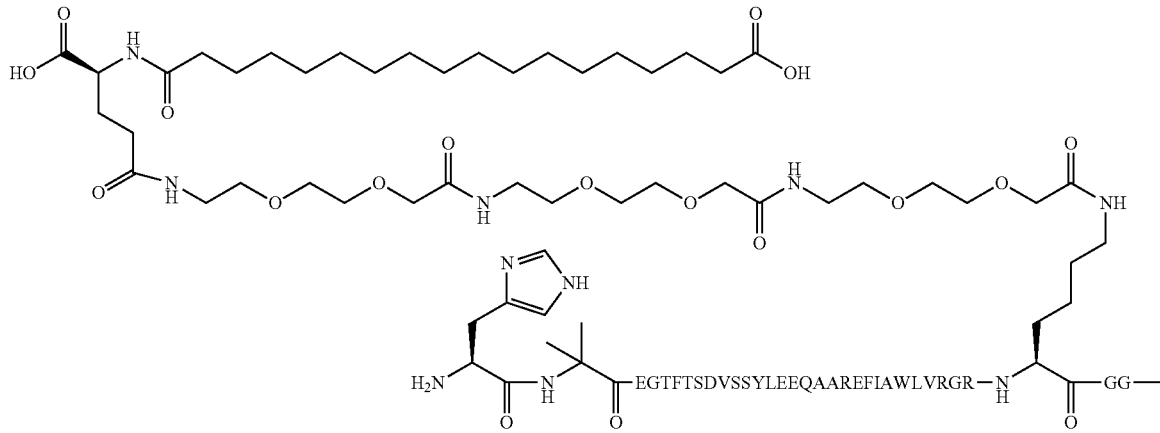

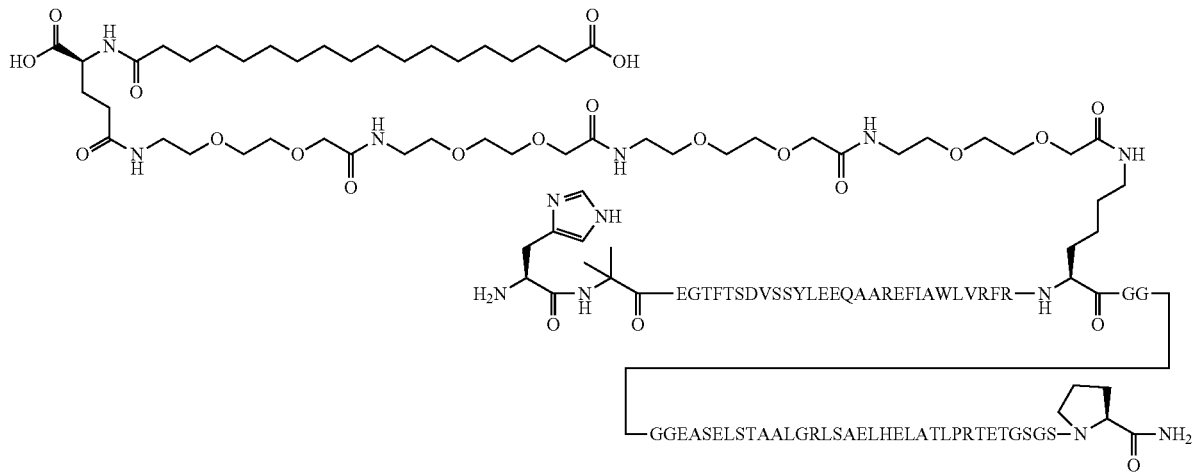

$C_{355}H_{572}N_{96}O_{122}$
Molecular weight (average) calculated: 8136.9102 g/mol
mono isotopic mass: 8132.1506 g/mol
LCMS34: found (M+5H)$^{5+}$1627.42 (mono isotopic)
The amino acid sequence of HXEGTFTSDVSSYLE-EQAAREFIAWLVRGRKGGGGEASELSTAALGRL-SAELHELATLPRTETGSGSP has SEQ ID NO: 153.

Compound 0663
H-Aib-EGTFTSDVSSYLEEAAREFIAWLVRGR-K([2-[2-[2-[[2-[2-[2-[[2-2-[2-[[2-[2-[2-[[(4S)-4-carboxy-4-(19-carboxynonadecanoylamino)butanoyl]amino]ethoxy]ethoxy]acetyl]amino]ethoxy]ethoxy]acetyl]amino]ethoxy]ethoxy]acetyl]amino]ethoxy]etho xy]acetyl])-GGGGEASELSTAALGRLSAELHELATLPRTETGSGSP-amide $C_{357}H_{576}N_{96}O_{122}$
Molecular weight (average) calculated: 8164.9633 g/mol
mono isotopic mass: 8160.1819 g/mol
LCMS34: found (M+5H)$^{5+}$1633.03 (mono isotopic)
The amino acid sequence of HXEGTFTSDVSSYLE-EQAAREFIAWLVRGRKGGGGEASELSTAALGRL-SAELHELATLPRTETGSGSP has SEQ ID NO: 153.

Example 1b: Comparator Compounds

Comparator Compound 0164
H-Aib-EGTFTSDVSSYLEGQAAKEIFAWLVRGR-K([(2S)-2-amino-6-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]hexanoyl])-GGEASELSTAALGRLSAELHELATLPRTETGSGSP-amide

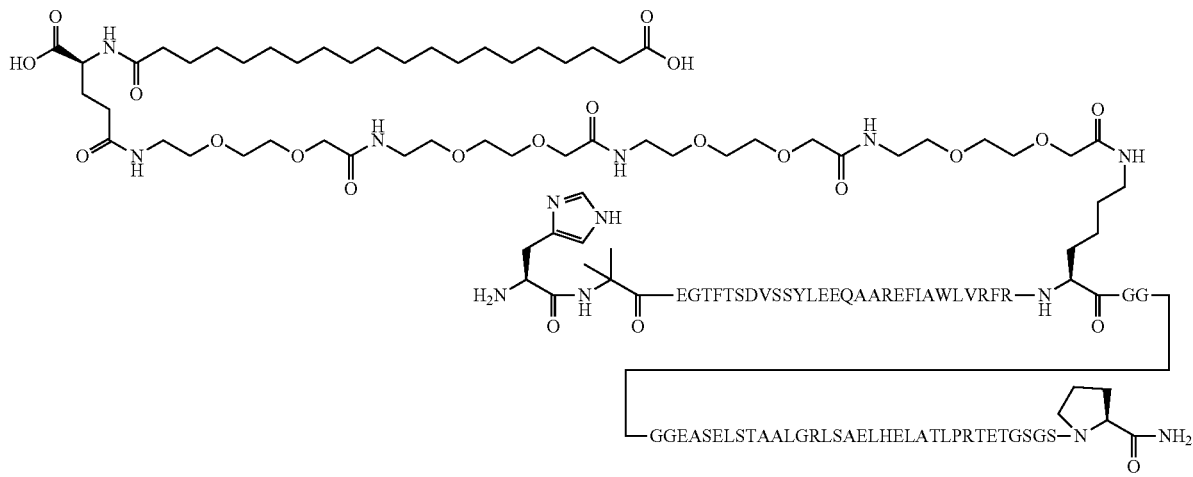

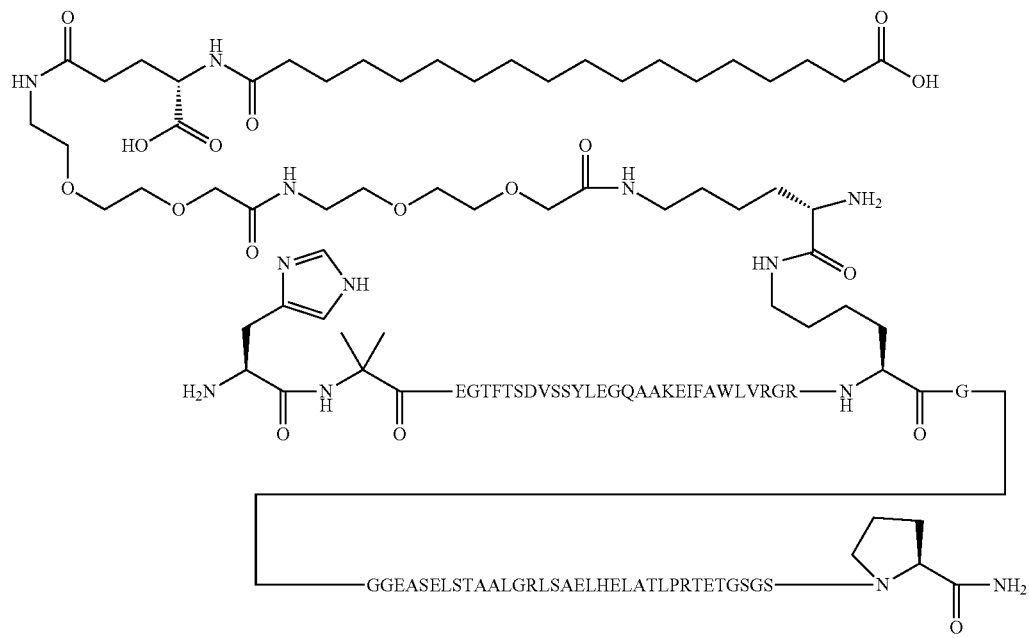

$C_{342}H_{552}N_{92}O_{113}$
Molecular weight (average) calculated: 7760.5909 g/mol
mono isotopic mass: 7756.0276 g/mol
LCMS34: found (M+5H)$^{5+}$1553.02 (most abundant).
The amino acid sequence of the peptide backbone in this comparator compound has SEQ ID NO: 241.
Comparator Compound 0185
H-Aib-EGTFTSDVSSYLEGQAAKEFIAWLVRGR-K([(2S)-2-amino-6-[[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]amino]hexanoyl])-GGEASELSTAALGRPSAELHELATLPRTETGSGSP-amide $C_{341}H_{548}N_{92}O_{113}$
Molecular weight (average) calculated: 7744.5484 g/mol
mono isotopic mass: 7739.9963 g/mol
LCMS34: found (M+5H)$^{5+}$1549.81 (most abundant)
The amino acid sequence of the peptide backbone in this comparator compound has SEQ ID NO: 242.
Comparator Compound 0015
H-Aib-EGTFTSDVSSYLEGQAA-K([2-[2-[2-[[2-[2-[2-Q[(4S)-4-carboxy-4-(17-carboxyheptadecanoylamino)butanoyl]amino]ethoxy]ethoxy]acetyl]amino]ethoxy]ethoxy]acetyl])-EFIAWLVRGRGGQEPGQEPCNTATCATORLA-EFLRHSSNNFGPILPPTNVGSNTP-amide

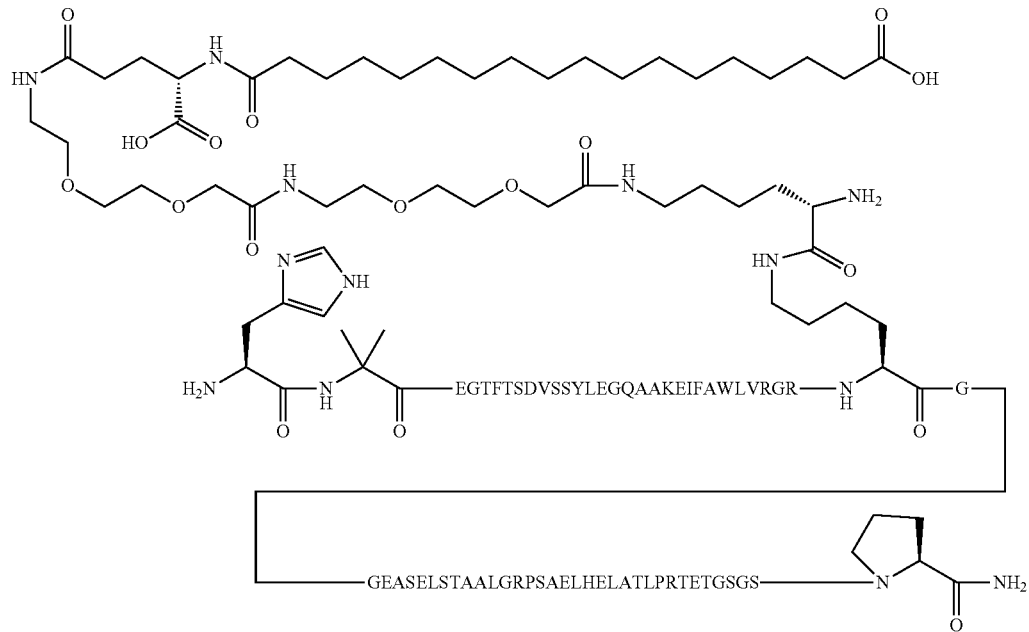

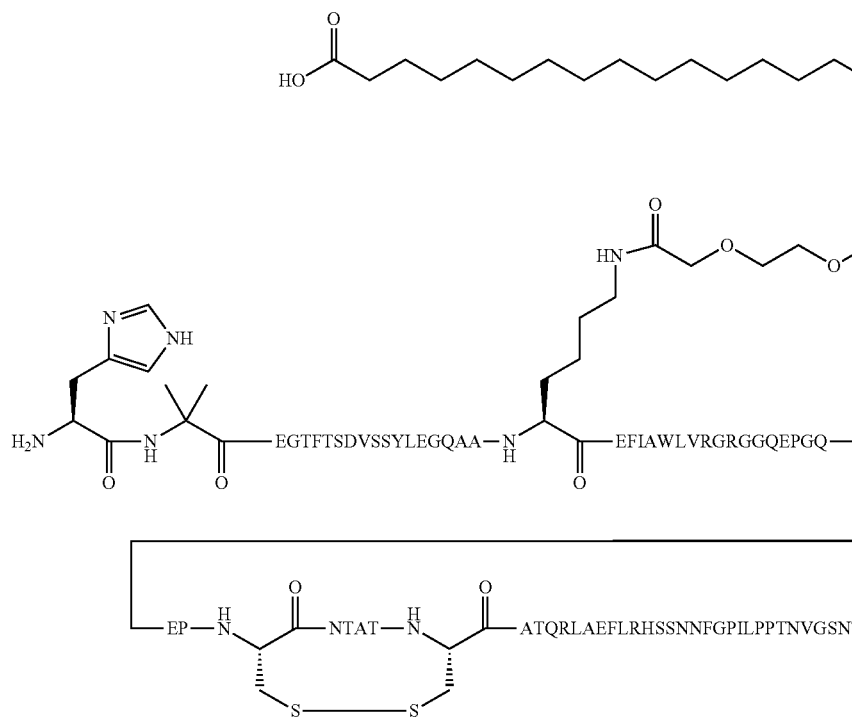
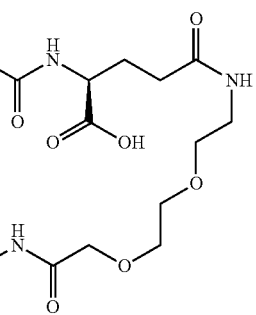

$C_{384}H_{596}N_{106}O_{124}S_2$

Molecular weight (average) calculated: 8745.6068 g/mol mono isotopic mass: 8740.3031 g/mol LCMS_ZQ: found $(M+5H)^{5+}$ 1749.9 (most abundant)

The amino acid sequence of the peptide backbone in this comparator compound has SEQ ID NO: 243.

Comparator Compound 0016

H-Aib-EGTFTSDVSSYLEGQAA-K([2-[2-[2-[2-[2-[2-[[(4S)-4-carboxy-4-(17-carboxyheptadecanoylamino)butanoyl]amino]ethoxy]ethoxy]acetyl]amino]ethoxy]ethoxy]acetyl])-EFIAWLVRGRGGOEPGQEP-K([2-[2-2[2 [2-[2-[[(4S)-4-carboxy-4-(17-carboxyheptadecanoylamino)butanoyl]amino]ethoxy]ethoxy]acetyl]amino]ethoxy]ethoxy]acetyl])-CNTATCATORLAEFLRHSSNNFGPILPPTNVGSNTP-amide

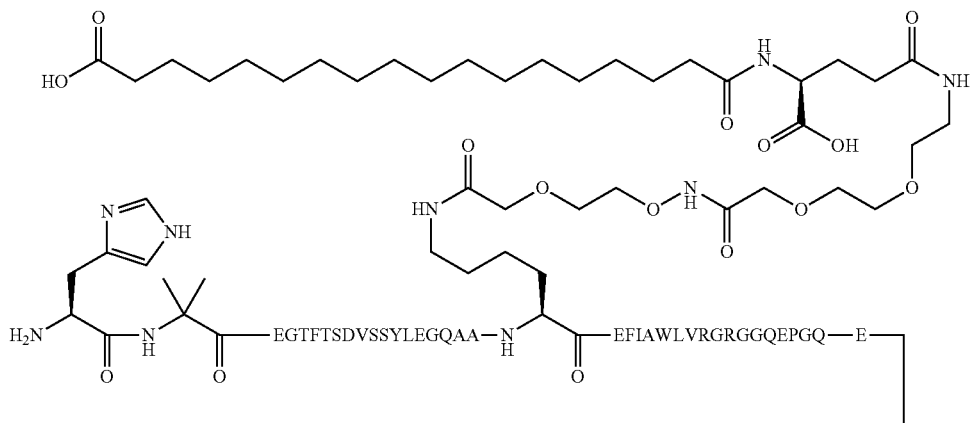
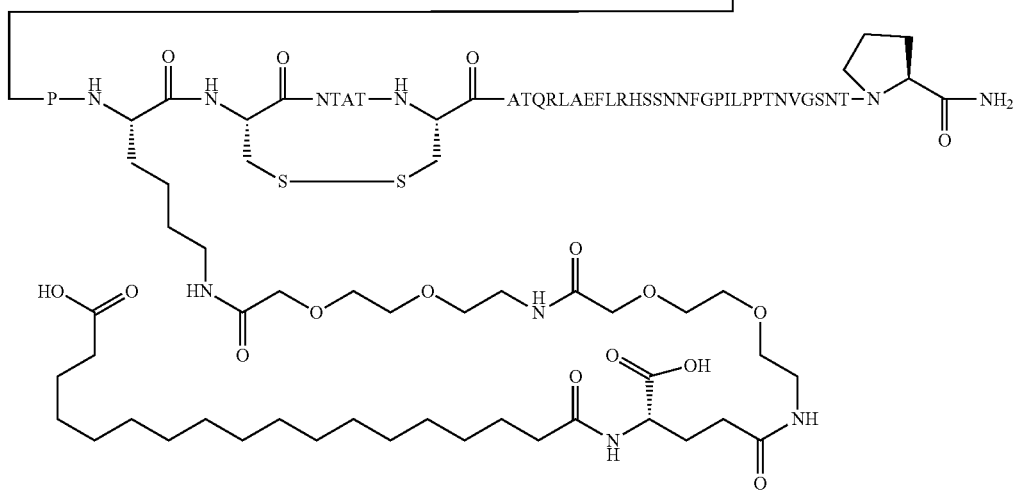

$C_{425}H_{669}N_{111}O_{137}S_2$

Molecular weight (average) calculated: 9589.6509 g/mol mono isotopic mass: 9583.8236 g/mol LCMS_ZQ: found $(M+5H)^{5+}$ 1918.9 (most abundant)

The amino acid sequence of the peptide backbone in this comparator compound has SEO ID NO: 244.

Comparator Compound 0668

H-Aib-EGTFTSDVSSYLEGOAA-K([2-[2-[2-[[2-[2-[2-[(4S)-4-carboxy-4-(17-carboxyheptadecanoylamino)bu-tanoyl]amino]ethoxy]ethoxy]acetyl]amino]ethoxy]ethoxy]acetyl])-EFIAWLVRGRGGOEPGOEP-K([[(4S)-4-carboxy-4-[[(4S)-4-carboxy-4-(15-carboxypentadecanoylamino)butanoyl]amino]butanoyl])-CNTATCATQRLADFLRHSSPNFGAIPSSTNVGSRTY-amide

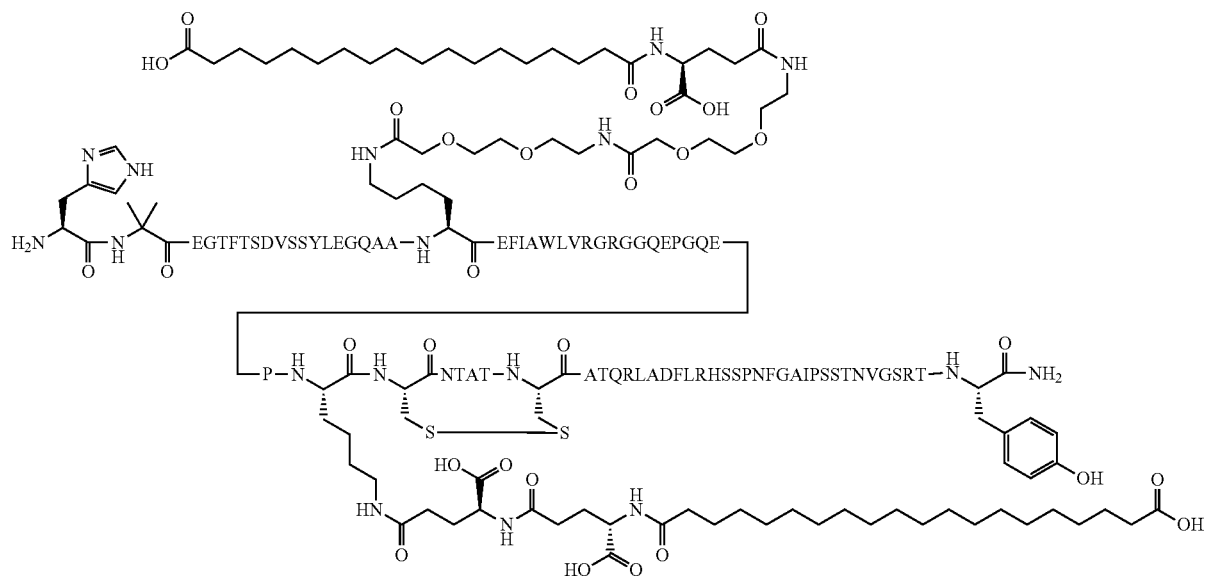

$C_{419}H_{655}N_{111}O_{135}S_2$
Molecular weight (average) calculated: 9471.4767 g/mol
mono isotopic mass: 9465.7242 g/mol
LCMS_ZQ: found $(M+5H)^{5+}$ 1895.2 (most abundant)
The amino acid sequence of the peptide backbone in this comparator compound has SEQ ID NO: 245.
Comparator Compound 0671
H-Aib-EGTFTSDVSSYLEEQAAREFIAWLVRGR-K([2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl])-GGGGEKCNTATCATQRLANFLVHSSNNFGPILPPT-NVGSNTY-amide $C_{378}H_{588}N_{104}O_{120}S_2$
Molecular weight (average) calculated: 8573.4681 g/mol
mono isotopic mass: 8568.2547 g/mol
LCMS_ZQ: found $(M+5H)^{5+}$ 1715.4 (most abundant)
The amino acid sequence of the peptide backbone in this comparator compound has SEQ ID NO: 251.
Comparator Compound 0672
H-Aib-EGTFTSDVSSYLEEQAAREFIAWLVRGR-K([2-[2-[2-[[2-[2-[2-[(4S)-4-carboxy-4-(17-carboxyheptadecanoylamino)butanoyl]amino]ethoxy]ethoxy]acetyl]amino]ethoxy]ethoxy]acetyl])-GGGGEKCNTATCATQRLAEFLRHSSNNFGPILPPT-NVGSNTP-amide

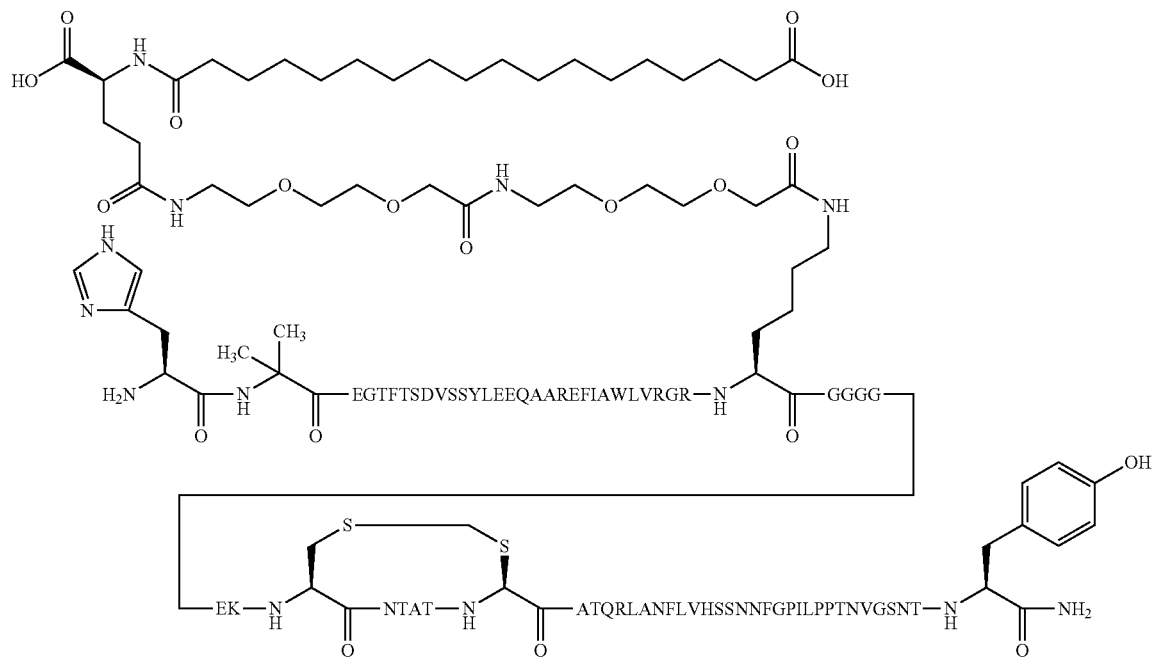

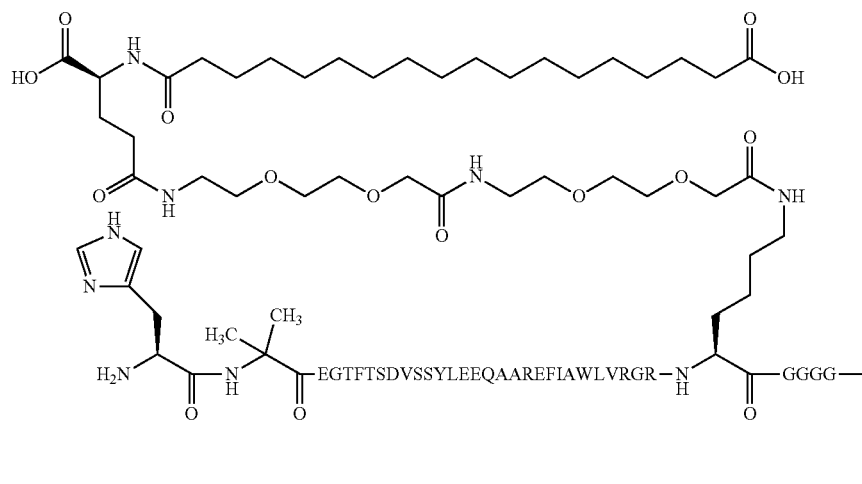

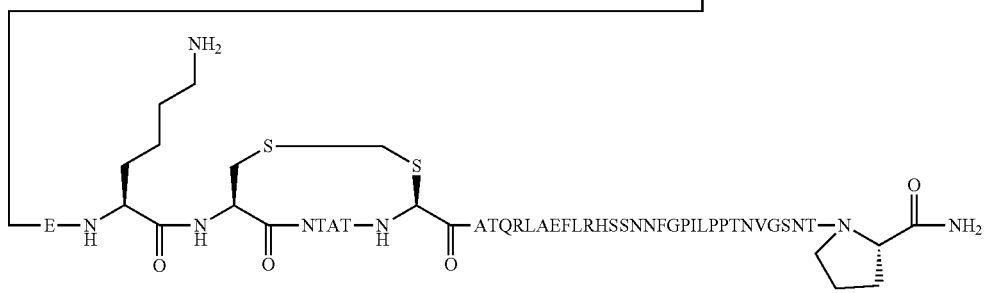

$C_{376}H_{590}N_{106}O_{120}S_2$

Molecular weight (average) calculated: 8579.4760 g/mol mono isotopic mass: 8574.2765 g/mol LCMS_ZQ: found $(M+5H)^{5+}$ 1716.8 (most abundant)

The amino acid sequence of the peptide backbone in this comparator compound has SEQ ID NO: 252.

Comparator Compound 0167

H-Aib-EGTFTSDVSSYLEEQAAREIFAWLVRGR-K([2-[2-[2-[[2-[2-[2-[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]acetyl])-GGGGEASELSTAALGRLSAELHELATLPRTETGSGSP-amide

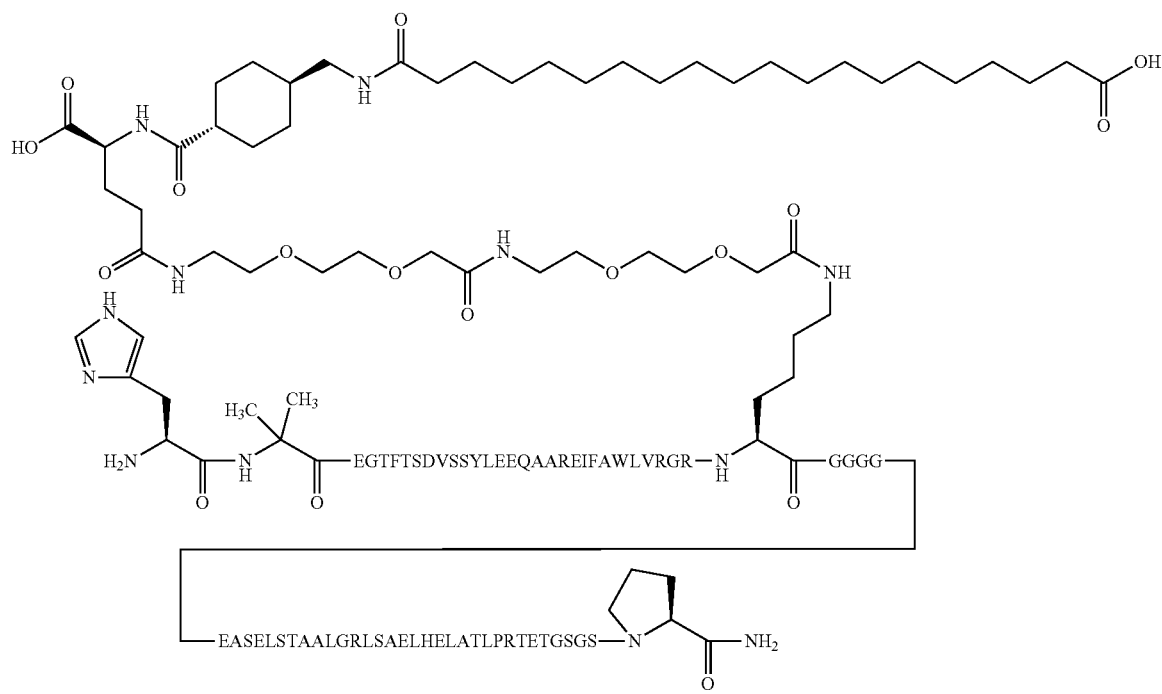

$C_{353}H_{567}N_{95}O_{117}$

Molecular weight (average) calculated: 8013.8454 g/mol mono isotopic mass: 8009.1338 g/mol LCMS34: found $(M+5H)^{5+}$ 1603.63 (most abundant)

The amino acid sequence of the peptide backbone in this comparator compound has SEQ ID NO: 253.

Comparator Compound 0192

H-Aib-EGTFTSDVSSYLEEQAAREFIAWLVRGR-K([2-[2-[2-[2-[2-[2-[(4S)-4-carboxy-4-[[4-[((19-carboxynona-decanoylamino)methyl]cyclohexanecarbonyl]amino]bu-tanoyl]amino]ethoxy]ethoxy]acetyl]amino]ethoxy]ethoxy]acetyl)-GGGGEASELSTAALGRPSAELHELATLPRTETGSGSP-amide

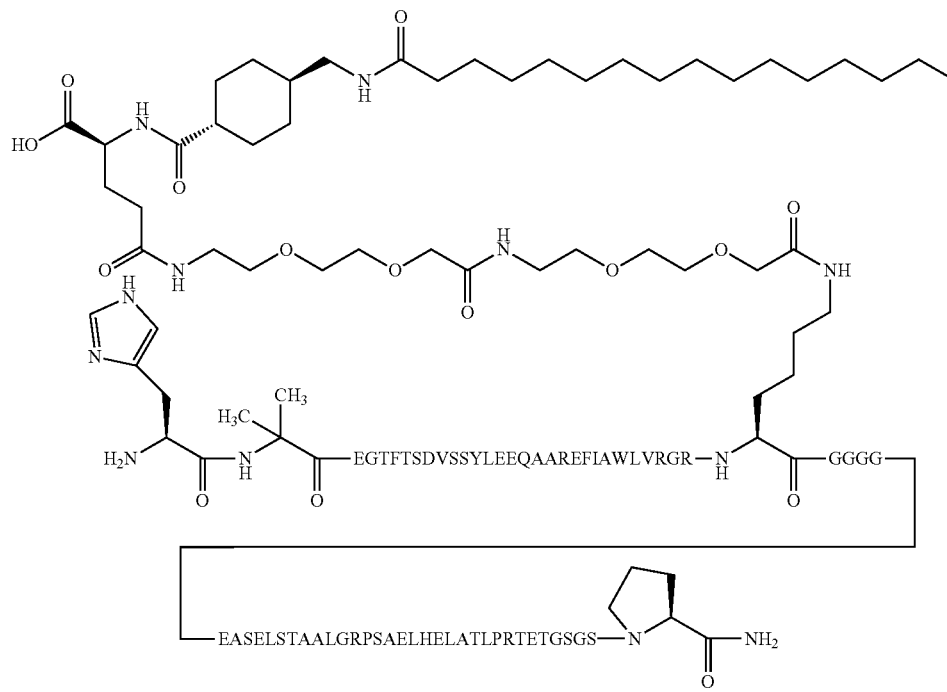

$C_{352}H_{563}N_{95}O_{117}$
Molecular weight (average) calculated: 7997.8029 g/mol
mono isotopic mass: 7993.1025 g/mol
LCMS34: found $(M+5H)^{5+}1600.63$ (most abundant)
The amino acid sequence of the peptide backbone in this comparator compound has SEQ ID NO: 254.

Example 1c: Amylin Receptor Agonist

Compound 1806
EASELSTAALGRLSAELHELATLPRTETGSGSP-amide

$C_{141}H_{236}N_{42}O_{52}$ Molecular weight (average) calculated: 3351.6327 g/mol
mono isotopic mass: 3349.7114 g/mol
LCMS_ZQ: found $(M+3H)^{3+}1118.4$ (most abundant).
The amino acid sequence of the peptide backbone in compound 1806 has SEQ ID NO: 250.

Example 2: Potencies of Compounds on the GLP-1 and Amylin Receptors

The potencies of compounds were tested as described in Assays 1 and 2.

Assay 1: Human GLP-1 Receptor In Vitro Potency Assay

To determine the ability of compounds to activate or agonise the GLP-1 receptor (GLP-1R), in vitro potency assays in cells expressing the human GLP-1 receptor were performed as described below.

Assay Principle

Activation of GLP-1 receptors leads to increased cellular concentrations of cyclic AMP (cAMP). Consequently, transcription is activated by promotors containing multiple copies of the cAMP response element (CRE). It is thus possible to measure GLP-1 receptor activity using a CRE-luciferase reporter gene introduced into Baby Hamster Kidney (BHK) cells co-expressing the GLP-1 receptor.

Cells and Assay Reagents

Cell stocks were prepared by culturing a stably transfected cell line expressing the human GLP-1 receptor and the CRE responsive luciferase (CRE-Luc) reporter gene (BHK 467-12A KZ-10, prepared according to methods known to the person skilled in the art) in growth medium consisting of DMEM (Gibco, 61965-026) supplemented with 10% FBS (Gibco, 16140-071), 1% Pen/Strep (Gibco, 15140-122), 1 mM Na-pyruvate (Gibco, 11360-039), 1 mg/mL G418 (Gibco, 10131-027) and 240 nM MTX (Pfizer, 15936). Cells at approximately 80-90% confluence were washed once in PBS and loosened from the cell flasks with Versene (Gibco, 15040-033). After centrifugation, the cell pellet was dissolved and diluted to 1.5×10E6 cells/mL in medium consisting of DMEM (Gibco, 61965-026) supplemented with 20% FBS (Gibco, 16140-071), 1% Pen/Strep (Gibco, 15140-122), 1 mM Na-Pyrovate (Gibco, 11360-039), 1 mg/mL G418 (Gibco, 10131-027), 240 nM MTX (Pfizer, 15936) and 10% DMSO (Sigma, D2650). Cells were aliquoted and stored at −180° C. until use.

The assay buffer consisted of DMEM without phenol red (Gibco, 11880-028) supplemented with 1× GlutaMAX (Gibco, 35050-038), 10 mM HEPES (Gibco, 15630-056), 1% (w/v) ovalbumin (Sigma, A5503) and 0.1% (v/v) Pluronic F-68 (Gibco, 24040-032).

Procedure

To perform the assay, serial dilutions (10-fold dilutions, 8 concentrations pr. compound) of comparator compounds and GLP-1 receptor-amylin receptor co-agonists were performed in assay buffer without HAS, often starting from approximately 100-200 nM in a 96-well plate. Frozen stocks of human GLP-1R/CRE-Luc cells were thawed in a 37° C. water bath, washed once in PBS and diluted to 100.000 cells/mL in assay buffer. For each dilution, 50 µL aliquots of comparator compounds or GLP-1 receptor-amylin receptor co-agonists were transferred to 96-well assay plates (ThermoFisher, 237105) to which 50 µL of the cell suspension was added (5.000 cells/well). The assay plates were incubated for 3 hours at 37° C. in 5% $CO_2$, left at room temperature for 5 minutes after which 100 µL SteadyLite Plus (PerkinElmer, 6066759) was added to each well. Plates were sealed and incubated at room temperature with gentle shaking for 30 minutes while protected from light. Luminescence was detected on a luminescence plate reader e.g. a Synergy 2 (BioTek). The $EC_{50}$-values [pM] were calculated by non-linear curve fitting applying a four-parameter logistic model (Hill slope=1) using GraphPad Prism or by means of TIBCO Enterprise Runtime for R (TIBCO Software, Palo Alto, CA, USA).

Assay 2: Hunan Amylin Receptor In Vitro Potency Assay

To determine the ability of compounds to activate or agonise the amylin receptor, in vitro potency assays on cells expressing the human amylin receptor (hAmyR3) can be performed as described below.

Assay Principle

Activation of hAmyR3 leads to increased cellular concentrations of cAMP. Consequently, transcription is activated by promotors containing multiple copies of the cAMP response element (CRE). It Is thus possible to measure hAmyR3 activity using a CRE-luciferase reporter gene introduced into Baby Hamster Kidney (BHK) cells co-expressing the hAmyR3.

Cells and Assay Reagents

A BHK cell line was stably transfected with the human calcitonin receptor (a) and a CRE-responsive luciferase (CRE-Luc) reporter gene according to methods known to the person skilled in the art (Hollex-1 cell line, obtained from Zymogentics described in U.S. Pat. No. 5,622,839). The cell line was further transfected with human receptor modifying protein 3 (RAMP3) using standard methods. This turns the human calcitonin receptor into a human amylin-3(a) receptor.

Cells stocks were prepared by culturing of the stably transfected BHK hAmyR3/CRE-Luc cell line in growth medium consisting of DMEM (Gibco, 31966-021) supplemented with 10% FBS (Gibco, 1640-071), 1% Pen/Strep (Gibco, 15140-122), 0.5 mg/mL Geneticin (Gibco, 10131-027), 0.4 mg/mL Hygromycin (Invitrogen, 1068701) and 250 nM Methotrexate (Sigma, A6770). Cells at approximately 80-90% confluence were washed once with PBS and loosened from the cell flasks with Versene (Gibco, 15040-033). After centrifugation, the cell pellet was dissolved and diluted to 2.5×10E6 cells/mL in Recovery™ Cell Culture Freezing Medium (Gibco, 12648-010). Cells were aliquoted and stored at −180° C. until use.

The assay buffer consisted of DMEM without phenol red (Gibco, 11880-028) supplemented with 1× GkutaMAX (Gibco, 35050-038), 10 mM HEPES (Gibco, 15630-056) and 0.1% (w/v) ovalbumin (Sigma, A5503).

Procedure

To perform the assay, BHK hAmyR3/CRE-Luc cells were thawed, washed once in PBS and seeded in 40 µL growth medium in a white 384-well culture plate (PerkinElmer, 6007688) at a cell density of 4.000 cells/well on the day before the experiment. The plate was incubated over night at 37° C. in 5% $CO_2$. On the day of the assay, cells were washed three times in assay buffer. Serial dilutions (7-fold dilutions, 7 concentrations pr. compound and one well containing only assay buffer) of comparator compounds and GLP-1 receptor-amylin receptor co-agonists were performed in assay buffer often starting from approximately 10-100 nM in 96-well plates and 30 µL of each concentration added to the 384-well assay plate with cells. The assay plate was incubated for 3 hours at 37° C. in 5% $CO_2$ after which 30 µL SteadyLite Plus (PerkinElmer, 6066759) was added to each well. The assay plate was sealed, incubated at room temperature with gentle shaking for 5 minutes followed by 30 minutes incubation without shaking while protected from light. Luminescence was detected on a luminescence plate reader e.g. a Synergy 2 (BioTek). The $EC_{50}$-values [pM] were calculated by non-linear curve fitting applying a four-parameter logistic model (Hill slope=1.5, shared bottom response within each plate) using GraphPad Prism or by means of TIBCO Enterprise Runtime for R (TIBCO Software, Palo Alto, CA, USA).

Example 2a: Potencies of GLP-1 Receptor-Amylin Receptor Co-Agonists on the GLP-1 and Amylin Receptors The potencies of compounds according to the invention were tested as described in Assays 1 and 2. The results are provided in Table 4a. Details regarding the compounds, such as IUPAC nomenclature, may be found in Example 1 and the Sequence Listing.

TABLE 4a

In vitro human AmyR3 and GLP-1R potencies of GLP-1 receptor-amylin receptor co-agonists.

| Compound no. | Human GLP-1R potency [EC50 (pM)] | Human AmyR3 potency [EC50 (pM)] |
|---|---|---|
| 0007 | 13.3 | 9.4 |
| 0009 | 7.9 | 49.5 |
| 0010 | 5.4 | 37.0 |
| 0019 | 13.7 | 26.5 |
| 0026 | 8.8 | 14.0 |
| 0035 | 16.7 | 16.0 |
| 0039 | 34.8 | 59.5 |
| 0040 | 20.7 | 7.7 |
| 0042 | 16.2 | 10.8 |
| 0044 | 16.0 | 9.1 |
| 0045 | 19.4 | 25.9 |
| 0051 | 14.3 | 19.5 |
| 0052 | 17.0 | 19.4 |
| 0056 | 41.4 | 120.0 |
| 0057 | 59.0 | 164.8 |
| 0071 | 69.4 | 158.9 |
| 0072 | 55.9 | 95.1 |
| 0073 | 1.6 | 34.7 |
| 0074 | 0.8 | 60.9 |
| 0075 | 84.5 | 43.9 |
| 0076 | 1.7 | 46.4 |
| 0077 | 2.1 | 25.7 |
| 0083 | 5.4 | 46.2 |
| 0084 | 2.5 | 14.0 |
| 0085 | 2.2 | 55.8 |
| 0086 | 3.9 | 78.3 |
| 0087 | 23.8 | 97.9 |
| 0089 | 5.7 | 65.5 |
| 0090 | 32.6 | 70.9 |
| 0092 | 18.5 | 10.9 |
| 0093 | 7.5 | 8.6 |

TABLE 4a-continued

In vitro human AmyR3 and GLP-1R potencies of GLP-1 receptor-amylin receptor co-agonists.

| Compound no. | Human GLP-1R potency [EC50 (pM)] | Human AmyR3 potency [EC50 (pM)] |
|---|---|---|
| 0094 | 7.5 | 11.3 |
| 0095 | 7.4 | 6.6 |
| 0097 | 10.0 | 93.1 |
| 0098 | 7.9 | 15.6 |
| 0099 | 9.6 | 44.9 |
| 0100 | 6.8 | 30.4 |
| 0101 | 7.1 | 10.2 |
| 0102 | 14.7 | 9.8 |
| 0103 | 28.1 | 11.6 |
| 0105 | 1.1 | 30.8 |
| 0106 | 5.5 | 28.4 |
| 0109 | 3.2 | 19.1 |
| 0110 | 2.7 | 40.7 |
| 0111 | 3.0 | 11.5 |
| 0114 | 1.0 | 17.5 |
| 0115 | 2.2 | 22.8 |
| 0116 | 1.5 | 21.7 |
| 0120 | 9.1 | 10.6 |
| 0124 | 27.9 | 24.4 |
| 0125 | 8.0 | 12.2 |
| 0127 | 7.1 | 63.9 |
| 0128 | 9.7 | 110.3 |
| 0129 | 1.2 | 23.5 |
| 0131 | 16.1 | 14.5 |
| 0132 | 3.0 | 34.9 |
| 0141 | 43.3 | 13.2 |
| 0142 | 88.2 | 15.4 |
| 0144 | 7.1 | 16.8 |
| 0145 | 11.9 | 16.5 |
| 0146 | 25.7 | 14.0 |
| 0147 | 36.8 | 33.7 |
| 0151 | 10.4 | 9.5 |
| 0156 | 22.6 | 22.6 |
| 0157 | 28.7 | 18.4 |
| 0159 | 30.3 | 19.3 |
| 0160 | 11.9 | 27.3 |
| 0179 | 8.8 | 35.9 |
| 0180 | 6.4 | 37.0 |
| 0191 | 5.9 | 54.8 |
| 0202 | 10.5 | 28.4 |
| 0231 | 5.6 | 68.0 |
| 0232 | 6.4 | 74.2 |
| 0233 | 46.4 | 182.5 |
| 0234 | 38.9 | 38.4 |
| 0235 | 10.4 | 24.0 |
| 0254 | 8.9 | 7.7 |
| 0255 | 2.5 | 28.6 |
| 0259 | 15.8 | 12.0 |
| 0260 | 11.9 | 41.8 |
| 0261 | 17.4 | 23.9 |
| 0263 | 13.8 | 25.2 |
| 0264 | 6.5 | 11.7 |
| 0265 | 6.0 | 8.1 |
| 0266 | 6.3 | 8.5 |
| 0267 | 28.5 | 45.3 |
| 0268 | 26.4 | 14.4 |
| 0269 | 7.7 | 7.5 |
| 0270 | 6.3 | 8.6 |
| 0271 | 4.6 | 15.2 |
| 0272 | 9.2 | 11.3 |
| 0273 | 24.9 | 18.0 |
| 0280 | 34.3 | 18.0 |
| 0281 | 35.2 | 114.5 |
| 0284 | 41.7 | 32.8 |
| 0285 | 19.0 | 78.9 |
| 0292 | 12.0 | 33.8 |
| 0294 | 13.7 | 34.3 |
| 0295 | 4.8 | 32.7 |
| 0296 | 4.0 | 29.9 |
| 0297 | 30.2 | 46.0 |
| 0299 | 6.0 | 11.5 |
| 0396 | 4.8 | 32.8 |
| 0397 | 3.8 | 18.5 |
| 0411 | 3.5 | 45.9 |
| 0414 | 11.2 | 17.7 |
| 0415 | 10.3 | 16.1 |
| 0416 | 104.6 | 18.3 |
| 0417 | 97.8 | 21.0 |
| 0431 | 10.9 | 11.9 |
| 0433 | 30.7 | 12.9 |
| 0434 | 11.8 | 13.9 |
| 0435 | 92.4 | 22.3 |
| 0436 | 15.2 | 12.3 |
| 0437 | 12.0 | 11.8 |
| 0438 | 11.8 | 27.5 |
| 0439 | 8.3 | 10.7 |
| 0440 | 5.7 | 10.4 |
| 0472 | 2.8 | 24.0 |
| 0473 | 3.1 | 16.2 |
| 0474 | 2.9 | 21.8 |
| 0475 | 70.4 | 66.8 |
| 0482 | 36.5 | 31.8 |
| 0483 | 33.7 | 36.8 |
| 0484 | 72.8 | 32.5 |
| 0502 | 8.4 | 9.0 |
| 0503 | 6.5 | 7.7 |
| 0504 | 8.3 | 6.0 |
| 0506 | 5.8 | 9.8 |
| 0509 | 7.1 | 29.9 |
| 0511 | 8.8 | 8.4 |
| 0512 | 7.6 | 10.8 |
| 0516 | 3.3 | 8.9 |
| 0518 | 3.4 | 4.4 |
| 0528 | 3.8 | 22.0 |
| 0529 | 6.4 | 14.1 |
| 0539 | 5.0 | 12.1 |
| 0552 | 4.7 | 6.9 |
| 0561 | 17.5 | 10.7 |
| 0562 | 19.3 | 4.1 |
| 0564 | 24.5 | 14.5 |
| 0565 | 6.4 | 6.2 |
| 0575 | 5.6 | 8.3 |
| 0576 | 2.9 | 10.1 |
| 0577 | 5.6 | 19.1 |
| 0578 | 2.5 | 26.9 |
| 0580 | 7.4 | 9.3 |
| 0581 | 17.0 | 26.4 |
| 0629 | 7.9 | 97.5 |
| 0630 | 7.1 | 109.7 |
| 0632 | 18.8 | 148.4 |
| 0633 | 28.2 | 5.3 |
| 0634 | 14.7 | 59.4 |
| 0635 | 7.3 | 78.9 |
| 0636 | 10.8 | 8.5 |
| 0637 | 1.9 | 14.1 |
| 0638 | 4.6 | 6.9 |
| 0639 | 1.5 | 4.6 |
| 0640 | 2.3 | 6.0 |
| 0648 | 17.0 | 9.2 |
| 0654 | 2.9 | 11.3 |
| 0655 | 3.0 | 11.4 |
| 0656 | 4.1 | 13.3 |
| 0657 | 9.9 | 10.4 |
| 0658 | 3.1 | 11.0 |
| 0659 | 4.7 | 11.5 |
| 0660 | 3.9 | 12.7 |
| 0661 | 2.8 | 14.4 |
| 0662 | 3.0 | 14.6 |
| 0663 | 3.2 | 12.6 |

Example 2b: Potencies of Compounds and Comparator Compounds on the GLP-1 and Amylin Receptors The GLP-1 receptor (GLP-1R) and amylin receptor (AmyR3) potencies of one compound according to the invention (compound 0111) were compared to the potencies of the GLP-1 and amylin receptor agonists from which it was derived, as well as the potencies of comparator compounds. The results are shown in Table 4b. Details regarding the compounds, such as IUPAC nomenclature, may be found in Example 1 and the Sequence Listing.

TABLE 4b

In vitro human AmyR3 and GLP-1R potencies of reference and comparator compounds.

| Compound no. or INN name | Description | Human GLP-1R potency [EC50 (pM)] | Human AmyR3 potency [EC50 (pM)] |
|---|---|---|---|
| Semaglutide | Active pharmaceutical ingredient (GLP-1 receptor agonist) in Ozempic®, Rybelsus® and Wegovy®. | 5.5 | — |
| Cagrilintide | Amylin receptor agonist (RA) in development. | — | 11 |
| Pramlintide | Active pharmaceutical ingredient (amylin RA) in Symlin®. | — | 7.8 |
| 1806 | Disulfide-free amylin RA. Amino acid sequence of amylin RA in compound 0111. | — | 5.0 |
| 0672 | Comparator compound derived from semaglutide and cagrilintide. | 2.2 | 606 |
| 0671 | Comparator compound derived from semaglutide and pramlintide. | 4.5 | 230 |
| 0111 | Compound derived from semaglutide and compound 1806. | 3.0 | 11.5 |

Comparator Compound 0672 comprises a GLP-1 RA having an amino acid sequence similar to that in semaglutide linked, via a short peptide linker, to an amylin RA having an amino acid sequence identical to that in cagrilintide. (in semaglutide, there is a lysine at position 20 (Lys20) and a glycine at position 31 (Gly31), relative to SEQ ID NO: 1 or SEQ ID NO: 238, and a protraction moiety attached to Lys20. The GLP-1 RA similar to semaglutide comprises an arginine at position 20 (Arg20) and a lysine residue at position 31 (Lys31), relative to SEQ ID NO: 1 or SEQ ID NO: 238, and a protraction moiety attached to Lys31.

Comparator Compound 0671 comprises the same GLP-1 RA as that in comparator compound 0672 linked, via a short peptide linker, to an amylin RA having an amino acid sequence identical to that within pramlintide.

Compound 0111 comprises the same GLP-1 sequence as that used in compound 0672 and compound 0671 linked, via a short peptide linker, to an amylin RA having an amino acid sequence identical to that in compound 1806).

Example 2c: Potencies of Compounds and Comparator Compounds on the GLP-1 and Amylin Receptors The GLP-1 receptor (GLP-1R) and amylin receptor (AmyR3) potencies of two compounds according to the invention (compounds 0045 and compound 0120) were compared to the potencies of comparator compounds having selected mutations in either their GLP-1 or amylin portion.

Comparator compounds 0164 and 0167 are identical to compounds 0045 and compound 0120, respectively, except for the fact that their GLP-1 portion comprises two sequence mutations: Phe22Ile and Ile23Phe, relative to the numbering in SEQ ID NO: 1, SEQ ID NO: 238 or SEQ ID NO: 255.

Comparator compounds 0185 and 0192 are identical to compounds 0045 and 0120, respectively, except for the fact that their amylin portion comprises a single mutation in the peptide backbone: Leu12Pro, relative to the numbering in SEQ ID NO: 79, SEQ ID NO: 240 or SEQ ID NO: 256.

Comparator compounds 0015, 0016 and 0668 are further examples of compounds comprising a GLP-1 receptor agonist similar to semaglutide (as detailed in Example 2b) and an amylin receptor agonist having the amino acid sequence of cagrilintide (compounds 0015 and 0016) or an alternative protracted amylin receptor agonist (compound 0668).

The results are shown in Table 4c. Details regarding the compounds, such as IUPAC nomenclature, may be found in Example 1 and the Sequence Listing.

TABLE 4c

In vitro human AmyR3 and GLP-1R potencies of further comparator compounds.

| Name or comparator compound no. | Special features | Human GLP-1R potency [EC50 (pM)] | Human AmyR3 potency [EC50 (pM)] |
|---|---|---|---|
| Semaglutide | | 5.5 | — |
| Human GLP-1 | | 10.8 | — |
| Cagrilintide | | — | 11.0 |
| Pramlintide | | — | 7.8 |
| Salmon calcitonin | | — | 3.5 |
| 0164 | Comparator to compound 0045 with potency impairing mutations in the GLP-1 receptor agonist. | 852.0 | 29.6 |
| 0167 | Comparator to compound 0120 with potency impairing mutations in the GLP-1 receptor agonist. | 10000.0 | 10.9 |
| 0185 | Comparator to compound 0045 with a potency impairing mutation in the amylin receptor agonist. | 13.1 | 5659.0 |
| 0192 | Comparator to compound 0120 with a potency impairing mutation in the amylin receptor agonist. | 10.8 | 10000 |
| 0015 | Compound comprising a GLP-1 RA similar to semaglutide, the amino acid sequence of cagrilintide and a single protraction moiety. | 45.0 | 312.0 |
| 0016 | Compound comprising a GLP-1 RA similar to semaglutide, the amino acid sequence of cagrilintide and two protraction moieties. | 509.5 | 1550.0 |
| 0668 | Compound comprising a GLP-1 RA similar to semaglutide and an acylated amylin agonist. | 455.0 | 10000.0 |

Results

The data in Table 4a show that all of the tested compounds agonise both the human AmyR3 and the GLP-1R, i.e., they are GLP-1 receptor-amylin receptor co-agonists. The compounds listed in Table 4a are all compounds according to the invention.

In contrast, the data in Table 4b show that linking the C-terminus of a potent GLP-1 receptor agonist (similar to semaglutide), via a peptide linker, to the N-terminus of a potent amylin receptor agonist (cagrilintide or pramlintide)

does not result in a compound that Is equally potent on these two receptors and that can necessarily function as a GLP-1 receptor-amylin receptor co-agonist (i.e., a compound according to the invention). A comparison of comparator compounds 0672 and 0671 with compound 0111 illustrates this point: compounds 0672 and 0671 both retained their potencies on the GLP-1 receptor but have impaired potency on the amylin receptor. Only compound 0111 retained full potency on both receptors and was similarly potent on both the GLP-1 and amylin receptors, relative to semaglutide and cagrilintide, respectively. Compound 0111 is considered a "balanced" compound.

The data in Table 4c show the comparator compounds' impaired ability to agonise (activate) the GLP-1 or the amylin receptor. The Phe22Ile and Ile23Phe mutations in comparator compounds 0164 and 0167 impaired their ability to agonise (activate) the GLP-1 receptor. The Leu12Pro mutation in comparator compounds 0185 and 0192 impaired their ability to agonise (activate) the amylin receptor. This impaired ability is further illustrated by the data provided in Table 6b. Further data in Table 4c highlight the difficulty of linking a GLP-1 receptor agonist to an amylin receptor agonist. Comparator compound 0015 was found to be a poor agonist of the amylin receptor. Comparator compounds 0016 and 0668 do not activate the amylin receptor.

Example 3: Preparation of Tablets for Pharmacokinetic Studies in Beagles

To be able to evaluate oral exposure following tablet dosing, tablet compositions comprising the test substance and SNAC (sodium N-(8-(2-hydroxybenzoyl)amino)caprylate) were prepared by mixing test substance with roller compacted SNAC and magnesium stearate as, e.g., described in WO 2019/149880. The amount of SNAC in the tablet composition was 100-300 mg, the amount of magnesium stearate in the tablet composition was 7.7 mg, and the target amount of each test substance in the tablet composition was 3-4 mg.

Example 4: Pharmacokinetic Studies in Beagle Dogs

Pharmacokinetic (PK) studies in Beagle dogs were conducted to determine the exposure of the GLP-1 receptor-amylin receptor co-agonist after peroral administration.

For the pharmacokinetic studies male Beagle dogs were used, 2-7, or 1 to 5, years of age and weighing approximately 10-15, such as 10-12, kg at the start of the studies. The dogs were group housed in pens (12 hours light: 12 hours dark), and fed individually and restrictedly once daily with Royal Canin Medium Adult dog (Royal Canin Products, China Branch, or Brogaarden A/S, Denmark). Exercise and group social were permitted daily, whenever possible. The dogs were used for repeated pharmacokinetic studies with a suitable wash-out period between successive dosing. An appropriate acclimatisation period was given prior to initiation of the first pharmacokinetic study. All handling, dosing and blood sampling of the animals were performed by trained and skilled staff. Before the studies the dogs were fasted overnight and from 0 to 4 h after dosing. Besides, the dogs were restricted to water 1 hour before dosing until 4 hours after dosing, but otherwise have ad libitum access to water during the whole period.

The tablets used for the p.o. studies described herein were immediate release SNAC-based tablets dosed orally.

The tablets were administered in the following manner: 10 min prior to tablet administration the dogs may be dosed subcutaneously with approximately 3 nmol/kg of SEQ ID NO: 237, tablets were placed in the back of the mouth of the dog to prevent chewing. The mouth was then closed, and 10 mL of tap water was given by a syringe or gavage to facilitate swallowing of the tablet.

Blood Sampling, Analysis and Pharmacokinetic Calculation

Blood was sampled at predefined time points for up till 240 hours, such as up till 10 hr, post dosing to adequately cover the full plasma concentration-time absorption profile of the GLP-1 agonist.

For each blood sampling time point approximately 0.8 mL of whole blood was collected in a 1.5 mL EDTA coated tube, and the tube was gently turned to allowing mixing of the sample with the EDTA. Blood samples (for example 0.8 mL) were collected in EDTA buffer (8 mM) and then centrifuged at 4° C. and 2000 G for 10 minutes. Plasma was pipetted into Micronic tubes on dry ice, and kept at −20° C. until analysis.

Blood samples were taken as appropriate, for example from a venflon in the cephalic vein in the front leg for the first 2 hours and then with syringe from the jugular vein for the rest of the time points (the first few drops were allowed to drain from the venflon to avoid heparin saline from the venflon in the sample).

Plasma concentration of the GLP-1 receptor-amylin receptor co-agonists were determined using LCMS. Individual plasma concentration-time profiles were analysed by a non-compartmental model in WinNonlin v. 5.0 or Phoenix v. 6.2 or 6.3 (Pharsight Inc., Mountain View, CA, USA), or other relevant software for PK analysis.

The individual plasma concentration-time profiles were analysed by non-compartmental analysis (NCA). The following PK parameters were calculated and reported: tmax, Cmax/Dose and t½, as shown in Table 5.

TABLE 5

Pharmacokinetic parameters in dogs after oral administration

| Compound no. | Tmax (hr) | Cmax/D (kg/L) | AUC/D (h * kg/L) | T½ (hr) |
|---|---|---|---|---|
| 0045 | 1.3 | 0.27 | 10.90 | 41 |
| 0084 | 1.5 | 0.36 | 15.16 | 47 |
| 0111 | 1.5 | 0.46 | 15.00 | 44 |
|  | 2.0 | 0.42 | 17.76 | 42 |
| 0120 | 2.0 | 0.24 | 7.3 | 24 |
|  | 2.0 | 0.44 | 14.45 | 22 |
| 0231 | 1.0 | 0.27 | 0.83 | 6 |
| 0232 | 0.8 | 0.51 | 2.00 | 4 |
| 0233 | 1.5 | 0.3 | 8.43 | 43 |
| 0234 | 1.0 | 0.35 | 8.00 | 31 |
| 0235 | 1.0 | 0.22 | 3.3 | 21 |
| 0254 | 1.8 | 0.36 | 19.54 | 40 |
| 0259 | 1.5 | 0.48 | 31.73 | 97 |
| 0265 | 2.0 | 0.16 | 5.68 | 16 |
| 0292 | 2.0 | 0.72 | 65.29 | 110 |
| 0431 | 1.5 | 0.29 | 9.75 | 34 |
| 0436 | 1.5 | 0.3 | 15.00 | 35 |
| 0439 | 2.0 | 0.21 | 5.36 | 24 |
| 0440 | 1.8 | 0.29 | 5.78 | 32 |
| 0502 | 2.0 | 0.14 | 9.8 | 66 |
|  | 2.0 | 0.24 | 13.92 | 61 |
|  | 4.0 | 0.33 | 22.46 | 74 |
| 0503 | 4.0 | 0.14 | 8.72 | 41 |
| 0504 | 3.0 | 0.12 | 3.25 | 25 |
| 0506 | 2.0 | 0.14 | 6.53 | 23 |
| 0511 | 2.0 | 0.14 | 3.80 | 25 |
| 0512 | 2.0 | 0.13 | 3.21 | 21 |
| 0516 | 2.0 | 0.67 | 43.92 | 99 |
|  | 2.0 | 0.39 | 34.57 | 103 |
| 0518 | 2.0 | 0.45 | 11.10 | 27 |

TABLE 5-continued

Pharmacokinetic parameters in dogs after oral administration

| Compound no. | Tmax (hr) | Cmax/D (kg/L) | AUC/D (h * kg/L) | T½ (hr) |
|---|---|---|---|---|
| 0528 | 1.5 | 0.5 | 37.01 | 107 |
| 0529 | 4.0 | 0.3 | 19.71 | 68 |
| 0539 | 3.0 | 0.22 | 8.71 | 30 |
| 0552 | 1.0 | 0.22 | 8.58 | 52 |
| 0575 | 1.5 | 0.34 | 27.60 | 91 |
| 0576 | 1.3 | 0.34 | 28.20 | 94 |
| 0577 | 1.3 | 0.45 | 37.60 | 93 |
| 0578 | 1.3 | 0.39 | 30.60 | 90 |
| 0580 | 2.0 | 0.38 | 12.77 | 39 |
| 0630 | 1.5 | 0.53 | 33.33 | 73 |
| 0640 | 1.5 | 0.37 | 7.57 | 29 |

Details regarding the compounds, such as IUPAC nomenclature, may be found in Example 1 and the Sequence Listing.

All of the compounds tested demonstrated oral bioavailability in this model, as concentrations of the compound in plasma were detected (Cmax/D>0 and AUC/D>0) following oral administration. Furthermore, the tested compounds had long half-lives (4-110 hrs), as compared to the half-lives of human GLP-1 and human amylin, measured in humans to be approximately 2-4 min and 15-20 min, respectively (Meier et al., Diabetes, 2004, 53(3): 654-662).

Example 5—Experimental Protocol for Efficacy Testing on Appetite Using an Ad Libitum Fed Rat Model Sprague Dawley (SD) rats from Taconic Europe, Denmark were used for the acute food intake experiments, wherein the principles of laboratory animal care were followed.

The rats had a body weight of 200-250 g at the start of the experiment. The rats arrived at least 10-14 days before the start of the experiment to allow acclimatisation to experimental settings. During this period, the animals were handled at least 2 times. Immediately upon arrival, rats were put on a reversed light cycle (dark from 11 am-11 pm) and put in the HM2 system and ID chipped. Three rats were housed in each cage. During the acclimatisation period, in which the rats get used to the new light cycle and diet (Research diet, LF 10% (D12450B), the animals had free access to food and water. Since rats are normally active and eat their major part of their daily food intake during the dark period, rats were dosed in the morning right before lights were turned off. Such a set-up results in the lowest data variation and highest test sensitivity. Each dose of GLP-amylin receptor co-agonist was tested in a group of 5-8 rats. A vehicle group of 6-8 rats was included in each set of testing. In each cage there were animals from three different treatment groups (this was done if one of the cages should malfunction). The rats were dosed once according to body weight with a 0.01-3 mg/kg solution administered subcutaneously (sc). The time of dosing was recorded for each group.

After dosing, the rats were returned to their home cages, where they had access to food and water. The food consumption was recorded individually and continuously by on-line registration (HM2 system) up to 72 h. At the end of the experimental session, the animals were euthanised.

Table 6 shows acute food intake in lean rats. The results allowed assessment of in vivo potency and provided an indication of the compounds' duration of action. Food intake was performed in rats up to 48 h.

TABLE 6a

Pharmacodynamic screening model: Acute food intake in rat after a single administration of a GLP-1-amylin co-agonist (10 nmol/kg).

| Compound No. (as provided in Example 1) | Food intake relative to vehicle (%) 0-24 hr, 10 nmol/kg | Food intake relative to vehicle (%) 24-48 hr, 10 nmol/kg |
|---|---|---|
| 0007 | 67 | 105 |
| 0035 | 76 | 95 |
| 0042 | 52 | 101 |
| 0044 | 40 | 82 |
| 0045 | 46 | 80 |
| 0052 | 42 | 86 |
| 0073 | 47 | 89 |
| 0084 | 44 | 50 |
| 0095 | 55 | 95 |
| 0100 | 85 | 86 |
| 0103 | 80 | 80 |
| 0111 | 28 | 75 |
| 0116 | 83 | 82 |
| 0120 | 53 | 55 |
| 0131 | 70 | 80 |
| 0151 | 29 | 70 |
| 0231 | 27 | 76 |
| 0232 | 61 | 95 |
| 0254 | 71 | 46 |
| 0411 | 81 | 88 |
| 0434 | 39 | 105 |
| 0439 | 43 | 41 |
| 0440 | 81 | 77 |
| 0502 | 61 | 72 |
| 0504 | 73 | 53 |
| 0506 | 47 | 44 |
| 0511 | 61 | 75 |
| 0516 | 87 | 82 |
| 0518 | 50 | 45 |
| 0552 | 56 | 55 |
| 0565 | 39 | 42 |
| 0640 | 28 | 66 |

Details regarding the compounds, such as IUPAC nomenclature, may be found in Example 1 and the Sequence Listing.

TABLE 6b

Pharmacodynamic screening model: Acute food intake in rats after a single administration of a GLP-1 receptor-amylin receptor co-agonist (compound 0120, 10 nmol/kg), compared to GLP-1-impaired compound 0167 and amylin-impaired compound 0192.

| Compound or comparator compound no. (as provided in Example 1) | Description | Food intake relative to vehicle (%) 0-24 hr, 10 nmol/kg | Food intake relative to vehicle (%) 24-48 hr, 10 nmol/kg |
|---|---|---|---|
| Vehicle | — | 100 | 100 |
| 0120 | GLP-1 receptor-amylin receptor co-agonist | 53 | 55 |
| 0167 | GLP-1 impaired comparator of compound 0120 | 85 | 73 |
| 0192 | Amylin-impaired comparator of compound 0120 | 71 | 67 |

Details regarding the compounds, such as IUPAC nomenclature, may be found in Example 1 and the Sequence Listing.

Following dosing of GLP-1 receptor-amylin receptor co-agonists to rats, it was observed that many of them induced a profound food intake inhibition, compared with vehicle treatment, as can be deduced from the data presented in Table 6a.

The data in Table 6b highlight the Importance of a compound being able to activate both the GLP-1 receptor and the amylin receptor. A comparison is made with three compounds: a GLP-1 receptor-amylin receptor co-agonist (compound 0120) which is fully potent on both receptors;

comparator compound 0167, which has impaired GLP-1 activity but full amylin potency, and comparator compound 0192, which has impaired amylin activity but full GLP-1 potency (See Table 4c for the in vitro data). When compound 0120 is administered to rats (10 nmol/kg), it results in significant inhibition of food intake within the first 48 hours. When either compound 0167 or compound 0192 Is administered to rats (10 nmol/kg), the rats' inhibition of food intake is, in both cases, significantly less than in the case of compound 0120. This indicates that both receptor systems are activated by compound 0120 and that it is a "balanced" compound.

While certain features of the invention have been Illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:
1. A Glucagon-Like Peptide-1 (GLP-1) receptor-amylin receptor co-agonist, selected from the group consisting of H-Aib-EGTFTSDVSSYLEEQAAREFIAWLVRGR-K([2-[2-[2-[[2-[2-[2-[(4S)-4-carboxy-4-(17-carboxyheptade-canoylamino)butanoyl]amino]ethoxy]ethoxy]acetyl]amino]ethoxy]ethoxy]acetyl])-GGGGEASELSTAALGRLSAELHELATLPRTETGSGSP-amide:

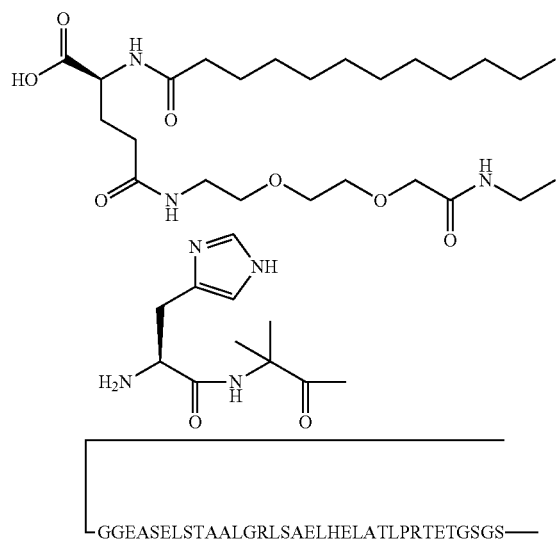

H-Aib-EGTFTSDVS-K([2-[2-[2-[2-[2-[2-[(4S)-4-car-boxy-4-(17-carboxyheptadecanoylamino)butanoyl]amino]ethoxy]ethoxy]acetyl]amino]ethoxy]ethoxy]acetyl])-YLEEQAAREFIAWLVRGRGGGGEASELS-TAALGRLSAELHELATLPRTETGSGSP-amide:

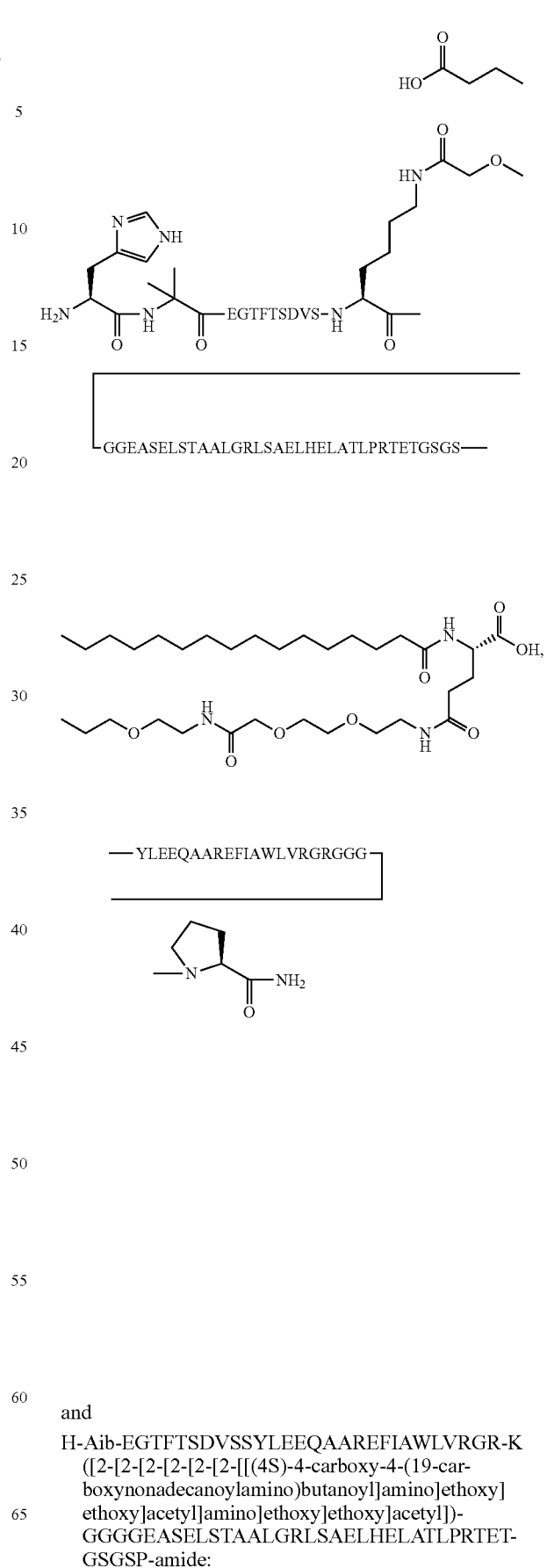

and
H-Aib-EGTFTSDVSSYLEEQAAREFIAWLVRGR-K([2-[2-[2-[2-[2-[2-[[(4S)-4-carboxy-4-(19-car-boxynonadecanoylamino)butanoyl]amino]ethoxy]ethoxy]acetyl]amino]ethoxy]ethoxy]acetyl])-GGGGEASELSTAALGRLSAELHELATLPRTET-GSGSP-amide:

429
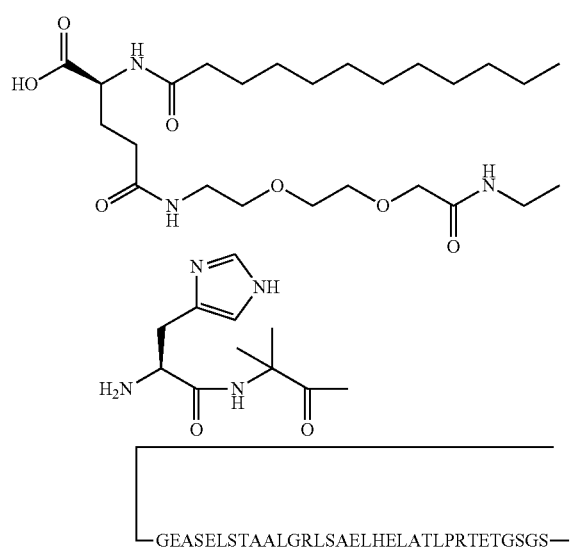
430
-continued
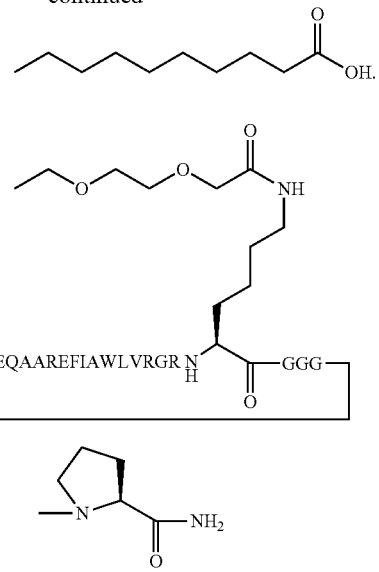
2. The GLP-1 receptor-amylin receptor co-agonist according to claim 1, which is H-Aib-EGTFTSDVSSYLE-EQAAREFIAWLVRGR-K([2-[2-[2-[2-[2-[2-[[(4S)-4-carboxy-4-(17-carboxyheptadecanoylamino)butanoyl]amino]ethoxy]ethoxy]acetyl]amino]ethoxy]ethoxy]acetyl])-GGGGEASELSTAALGRLSAELHELATLPRTETGSGSP-amide:
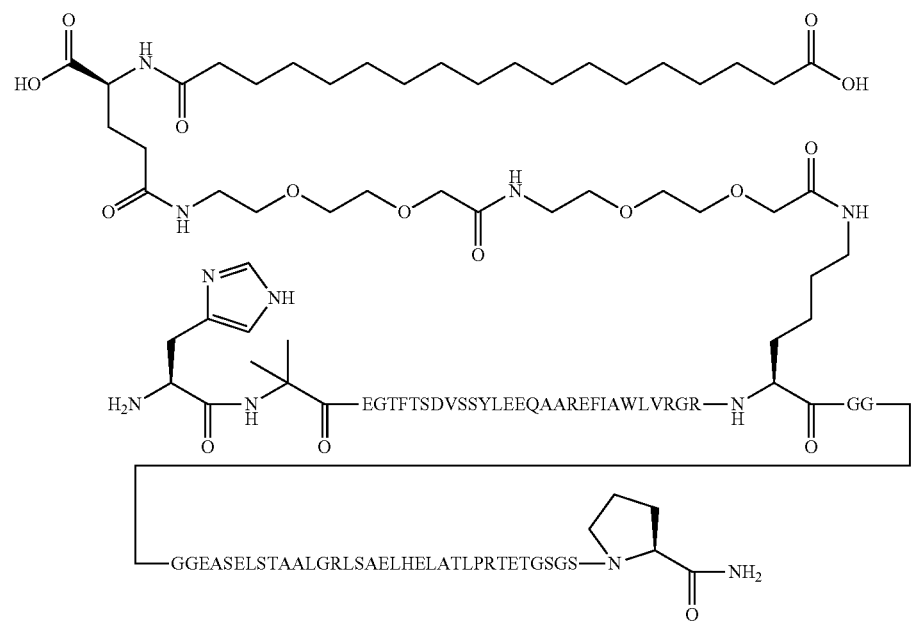

3. A pharmaceutical formulation comprising a GLP-1 receptor-amylin receptor co-agonist according to claim 2 and a pharmaceutically acceptable excipient.

4. A method of treating a human subject suffering from overweight, comprising administering to said human subject the pharmaceutical formulation according to claim 3.

5. The method of claim 4, wherein said human subject has an initial body mass index (BMI) of 27 or more.

6. The method of claim 5, wherein said human subject has at least one weight-related comorbidity selected from the group consisting of diabetes, hypertension, dyslipidaemia, high cholesterol and obstructive sleep apnoea.

7. The method of claim 5, wherein said human subject has cardiovascular disease, non-steroidal steatohepatitis or cognitive impairment.

8. A method of treating a human subject suffering from obesity, comprising administering to said human subject the pharmaceutical formulation according to claim 3.

9. The method of claim 8, wherein said human subject has an initial body mass index (BMI) of 30 or more.

10. The method of claim 9, wherein said human subject has at least one weight-related comorbidity selected from the group consisting of diabetes, hypertension, dyslipidemia, high cholesterol and obstructive sleep apnoea.

11. The method of claim 9, wherein said human subject has cardiovascular disease, non-steroidal steatohepatitis or cognitive impairment.

12. The GLP-1 receptor-amylin receptor co-agonist according to claim 1, which is H-Aib-EGTFTSDVS-K([2-[2-[2-[2-[2-[2-[[(4S)-4-carboxy-4-(17-carboxyheptadecanoylamino)butanoyl]amino]ethoxy]ethoxy]acetyl]amino]ethoxy]ethoxy]acetyl])-YLEEQAAREFIAWLVRGRGGGGEASELSTAALGRLSAELHELATLPRTETGSGSP-amide:

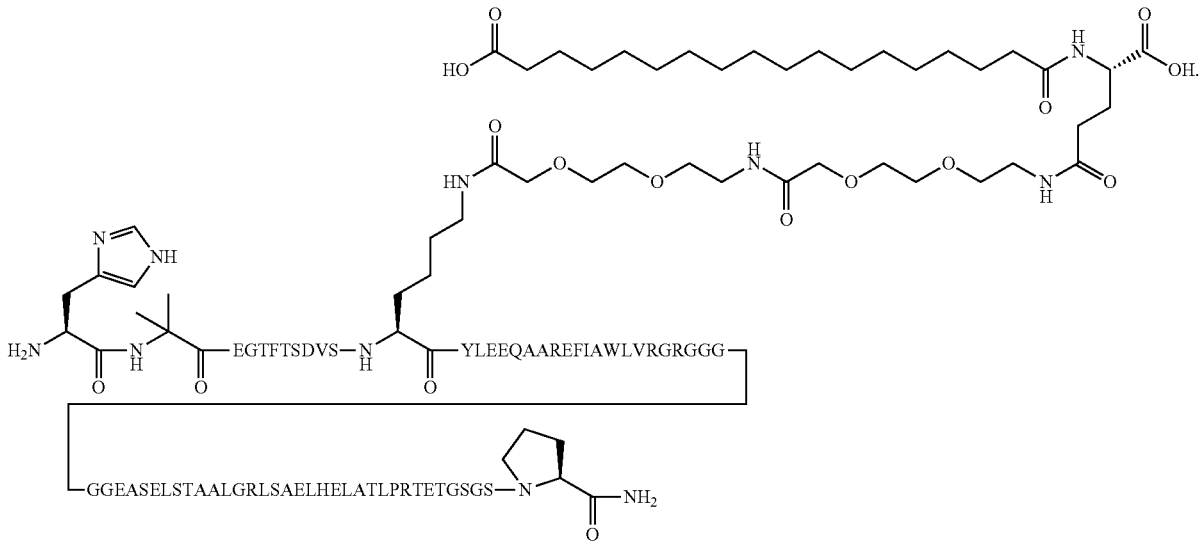

13. A pharmaceutical formulation comprising a GLP-1 receptor-amylin receptor co-agonist according to claim 12 and a pharmaceutically acceptable excipient.

14. A GLP-1 receptor-amylin receptor co-agonist according to claim 1, which is H-Aib-EGTFTSDVSSYLEEQAAREFIAWLVRGR-K([2-[2-[2-[2-[2-[2-[[(4S)-4-carboxy-4-(19-carboxynonadecanoylamino)butanoyl]amino]ethoxy]ethoxy]acetyl]amino]ethoxy]ethoxy]acetyl])-GGGGEASELSTAALGRLSAELHELATLPRTETGSGSP-amide:

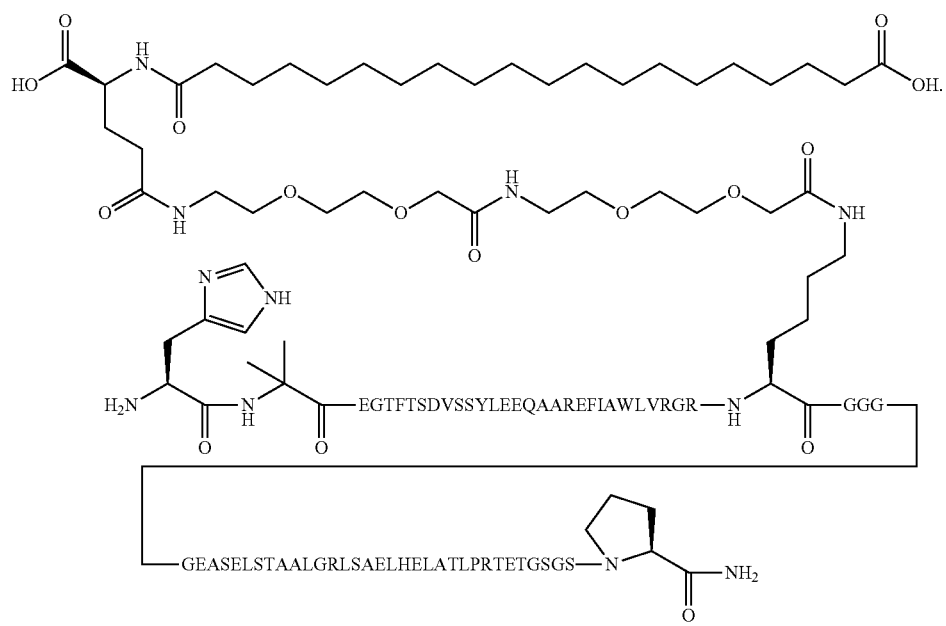

15. A pharmaceutical formulation comprising a GLP-1 receptor-amylin receptor co-agonist according to claim 14 and a pharmaceutically acceptable excipient.

16. A pharmaceutical formulation comprising a GLP-1 receptor-amylin receptor co-agonist according to claim 1 and a pharmaceutically acceptable excipient.

17. A method of treating a human subject suffering from overweight, comprising administering to said human subject the pharmaceutical formulation according to claim 16.

18. The method of claim 17, wherein said human subject has an initial body mass index (BMI) of 27 or more.

19. The method of claim 18, wherein said human subject has at least one weight-related comorbidity selected from the group consisting of diabetes, hypertension, dyslipidaemia, high cholesterol and obstructive sleep apnoea.

20. The method of claim 18, wherein said human subject has cardiovascular disease, non-steroidal steatohepatitis or cognitive impairment.

21. A method of treating a human subject suffering from obesity, comprising administering to said human subject the pharmaceutical formulation according to claim 16.

22. The method of claim 21, wherein said human subject has an initial body mass index (BMI) of 30 or more.

23. The method of claim 22, wherein said human subject has at least one weight-related comorbidity selected from the group consisting of diabetes, hypertension, dyslipidaemia, high cholesterol and obstructive sleep apnoea.

24. The method of claim 22, wherein said human subject has cardiovascular disease, non-steroidal steatohepatitis or cognitive impairment.

* * * * *

UNITED STATES PATENT AND TRADEMARK OFFICE
CERTIFICATE OF CORRECTION

| | | |
|---|---|---|
| PATENT NO. | : 12,054,528 B2 | |
| APPLICATION NO. | : 18/084088 | |
| DATED | : August 6, 2024 | |
| INVENTOR(S) | : Kruse | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 3 days.

Signed and Sealed this
Third Day of December, 2024

*Katherine Kelly Vidal*

Katherine Kelly Vidal
*Director of the United States Patent and Trademark Office*